US011505599B2

(12) United States Patent
Scheinberg et al.

(10) Patent No.: US 11,505,599 B2
(45) Date of Patent: Nov. 22, 2022

(54) T CELL RECEPTOR-LIKE ANTIBODIES SPECIFIC FOR FOXP3-DERIVED PEPTIDES

(71) Applicants: MEMORIAL SLOAN-KETTERING CANCER CENTER, New York, NY (US); EUREKA THERAPEUTICS, INC., Emeryville, CA (US)

(72) Inventors: David A. Scheinberg, New York, NY (US); Tao Dao, New York, NY (US); Cheng Liu, Emeryville, CA (US)

(73) Assignees: MEMORIAL SLOAN-KETTERING CANCER CENTER, New York, NY (US); EUREKA THERAPEUTICS, INC., Emeryville, CA (US)

( * ) Notice: Subject to any disclaimer, the term of this patent is extended or adjusted under 35 U.S.C. 154(b) by 390 days.

(21) Appl. No.: 16/069,999

(22) PCT Filed: Jan. 13, 2017

(86) PCT No.: PCT/US2017/013511

§ 371 (c)(1),
(2) Date: Jul. 13, 2018

(87) PCT Pub. No.: WO2017/124001

PCT Pub. Date: Jul. 20, 2017

(65) Prior Publication Data

US 2019/0284262 A1 Sep. 19, 2019

Related U.S. Application Data

(60) Provisional application No. 62/278,815, filed on Jan. 14, 2016.

(51) Int. Cl.

| | |
|---|---|
| ***C07K 16/30*** | (2006.01) |
| ***A61K 39/395*** | (2006.01) |
| ***C07K 16/18*** | (2006.01) |
| ***A61K 47/68*** | (2017.01) |
| ***A61P 35/00*** | (2006.01) |
| ***C07K 16/28*** | (2006.01) |
| ***C07K 16/46*** | (2006.01) |
| ***G01N 33/68*** | (2006.01) |
| *A61K 39/00* | (2006.01) |

(52) U.S. Cl.

CPC .......... *C07K 16/18* (2013.01); *A61K 47/6843* (2017.08); *A61K 47/6849* (2017.08); *A61P 35/00* (2018.01); *C07K 16/2833* (2013.01); *C07K 16/30* (2013.01); *C07K 16/468* (2013.01); *G01N 33/6854* (2013.01); *A61K 2039/505* (2013.01); *C07K 2317/31* (2013.01); *C07K 2317/32* (2013.01); *C07K 2317/33* (2013.01); *C07K 2317/34* (2013.01); *C07K 2317/565* (2013.01); *C07K 2317/622* (2013.01); *C07K 2317/73* (2013.01); *C07K 2317/732* (2013.01); *C07K 2317/76* (2013.01); *C07K 2317/92* (2013.01); *C07K 2319/03* (2013.01); *C07K 2319/33* (2013.01)

(58) Field of Classification Search

CPC .............. G01N 33/57484; C07K 16/30; A61K 39/39558

See application file for complete search history.

(56) References Cited

U.S. PATENT DOCUMENTS

| | | | |
|---|---|---|---|
| 4,956,778 | A | 9/1990 | Naito |
| 5,091,513 | A | 2/1992 | Huston et al. |
| 5,132,405 | A | 7/1992 | Huston et al. |
| 5,225,539 | A | 7/1993 | Winter |
| 5,530,101 | A | 6/1996 | Queen et al. |
| 5,585,089 | A | 12/1996 | Queen et al. |
| 5,677,425 | A | 10/1997 | Bodmer et al. |
| 5,693,762 | A | 12/1997 | Queen et al. |
| 5,714,350 | A | 2/1998 | Co et al. |
| 5,869,046 | A | 2/1999 | Presta et al. |
| 6,121,022 | A | 9/2000 | Presta et al. |
| 6,165,745 | A | 12/2000 | Ward et al. |
| 6,180,370 | B1 | 1/2001 | Queen et al. |
| 6,350,861 | B1 | 2/2002 | Co et al. |
| 2003/0059427 | A1 | 3/2003 | Force et al. |
| 2003/0153043 | A1 | 8/2003 | Carr et al. |
| 2005/0196754 | A1 | 9/2005 | Drmanac et al. |
| 2007/0072177 | A1 | 3/2007 | Bakker et al. |
| 2009/0137002 | A1 | 5/2009 | Petrul et al. |
| 2009/0324512 | A1 | 12/2009 | Silence et al. |
| 2009/0324579 | A1 | 12/2009 | Pandey et al. |
| 2010/0003253 | A1 | 1/2010 | Laeremans et al. |

(Continued)

FOREIGN PATENT DOCUMENTS

| | | | |
|---|---|---|---|
| EP | 0 154 316 | A2 | 9/1985 |
| EP | 0 401 384 | A1 | 12/1990 |

(Continued)

OTHER PUBLICATIONS

Schiffman et Al. (The New England Journal of Medicine, vol. 353, No. 20, p. 2101-2104, 2005) (Year: 2005).*
Cuzick et Al. (The Lancet, vol. 361, p. 296-300, 2003) (Year: 2003).*
Hernandez-Ledesma (Peptides, vol. 30, p. 426-430, 2009) (Year: 2009).*
Dao (Cancer Immunology Research, vol. 4, No. 11, Supplement 1, Abstract A058, 2016) (Year: 2016).*

(Continued)

*Primary Examiner* — Michael Allen
(74) *Attorney, Agent, or Firm* — Baker Botts L.L.P.

(57) ABSTRACT

The presently disclosed subject matter provides antigen-binding proteins (e.g., chimeric antigen receptors) and antibodies or antigen-binding portions thereof that bind to a Foxp3 peptide/MHC molecule complex. Such antibodies, fusion proteins and conjugates thereof are useful for inhibiting regulatory T cells and treating cancers.

11 Claims, 52 Drawing Sheets

Specification includes a Sequence Listing.

(56) References Cited

U.S. PATENT DOCUMENTS

2010/0092501 A1* 4/2010 Tsunoda ............ C07K 14/4713 424/185.1
2010/0143359 A1 6/2010 Ebert et al.
2010/0234578 A1 9/2010 Mikayama et al.
2011/0014211 A1 1/2011 Azuma et al.
2012/0005773 A1 1/2012 Aasen et al.
2012/0058906 A1 3/2012 Smider et al.
2012/0117685 A1 5/2012 Wu et al.
2013/0102031 A1 4/2013 King et al.
2013/0136744 A1 5/2013 Bouche et al.
2013/0287748 A1 10/2013 June et al.
2013/0323249 A1 12/2013 Zhou et al.
2013/0333068 A1 12/2013 Coffin
2014/0011982 A1 1/2014 Marasco et al.
2014/0030273 A1 1/2014 Verploegen et al.
2015/0224182 A1* 8/2015 Hunt ............. A61K 39/001182 424/85.2

FOREIGN PATENT DOCUMENTS

JP 2006/197930 A 8/2006
WO WO 00/42072 A2 7/2000
WO WO 2008/081581 A1 7/2008
WO WO 2009/003489 A1 1/2009
WO WO 2011/085343 A1 7/2011
WO WO 2015/070061 A1 5/2015
WO WO 2015/097536 A2 7/2015
WO WO 2015/189638 A2 12/2015

OTHER PUBLICATIONS

Johnson and Wu (Methods in Molecular Biology, Antibody Engineering: Methods and Protocols, vol. 248, p. 11-25, 2004) (Year: 2004).*
Komenaka et Al. (Clinics in Dermatology, 2004, vol. 22, p. 251-265) (Year: 2004).*
Evans et Al. (Q. J. Med 1999: 92: 299-307) (Year: 1999).*
Paul (Fundamental Immunology, 3rd Edition, 1993, pp. 292-295) (Year: 1993).*
Bendig M. M. (Methods: A Companion to Methods in Enzymology, 1995; 8:83-93) (Year: 1995).*
Rudikoff et al. (Proceedings of the National Academy of Sciences USA, vol. 79, p. 1979-1983, 1982) (Year: 1982).*
Baxevanis (Expert Opinion: Drug Discovery, vol. 3, No. 4, p. 441-452, 2008) (Year: 2008).*
Abdiche et al., "Probing the binding mechanism and affinity of tanezumab, a recombinant humanized anti-NGF monoclonal antibody, using a repertoire of biosensors," Protein Science 17:1326-1335 (2008).
Allen, "Ligand-Targeted Therapeutics in Anticancer Therapy," Nat. Rev. Cancer 2:750-763 (2002).
Altschul et al., "Basic Local Alignment Search Tool," J. Mol. Biol. 215:403-410 (1990).
Altschul et al., "Gapped BLAST and PSI-BLAST: a new generation of protein database search programs," Nucleic Acids Res. 25(17):3389-3402 (1997).
Arnon et al., "Monoclonal Antibodies for Immunotargeting Of Drugs in Cancer Therapy," in Monoclonal Antibodies and Cancer Therapy, Reisfeld et al. (eds.), pp. 243-256 (Alan R. Liss, Inc. 1985).
Asano et al., "Cytotoxic Enhancement of a Bispecific Diabody by Format Conversion to Tandem Single-chain Variable Fragment (taFv)," JBiol Chem 286(3):1812-1818 (2011).
Azinovic et al., "Survival benefit associated with human anti-mouse antibody (HAMA) in patients with B-cell malignancies," Cancer Immunol Immunother 55:1451-1458 (2006).
Baumgartner et al., "Melanoma Induces Immunosuppression by Upregulating Foxp3+ Regulatory T Cells," J. Surg. Res. 141:72-77 (2007).
Benton et al., "Screening Agt Recombinant Clones by Hybridization to Single Plaques in situ," Science 196(4286):180-182 (1977).
Bird et al., "Single-Chain Antigen-Binding Proteins," Science 242:423-426 (1988).
Bos et al., "Transient regulatory T cell ablation deters oncogene-driven breast cancer and enhances radiotherapy," J Exp. Med. 210(11):2435-2446 (2013).
Bregni, et al., "Human Peripheral Blood Hematopoietic Progenitors Are Optimal Targets of Retroviral-Mediated Gene Transfer," Blood 80(6):1418-1422 (1992).
Brennan et al., "Preparation of Bispecific Antibodies by Chemical Recombination of Monoclonal Immunoglobulin G${1}$ Fragments," Science 229(4708):81-83 (1985).
Brentjens et al., "Safety and persistence of adoptively transferred autologous CD19-targeted T cells in patients with relapsed or chemotherapy refractory B-cell leukemias," Blood 118(18):4817-4828 (2011).
Brigham et al., "Rapid Communication: In vivo Transfection of Murine Lungs with a Functioning Prokaryotic Gene Using a Liposome Vehicle," Am. J. Med. Sci. 298(4):278-281 (1989).
Brocks et al., "A TNF receptor antagonistic scFv, which is not secreted in mammalian cells, is expressed as a soluble mono- and bivalent scFv derivative in insect cells," Immunotechnology 3:173-184 (1997).
Caron et al., "Engineered Humanized Dimeric Forms of IgG Are More Effective Antibodies," J Exp Med 176:1191-1195 (1992).
Chames et al., "Direct selection of a human antibody fragment directed against the tumor T-cell epitope HLA-A1-MAGE-A1 from a nonimmunized phage-Fab library," PNAS USA 97(14):7969-7974 (2000).
Chen et al., "Selection and Analysis of an Optimized Anti-VEGF Antibody: Crystal Structure of an Affinity-matured Fab in Complex with Antigen," J. Mol. Biol. 293:865-881 (1999).
Cox et al., "A Directory of Human Germ-line Vϰ Segments Reveals a Strong Bias in their Usage," Eur. J. Immunol. 24:827-836 (1994).
Cuesta et al., "Multivalent antibodies: when design surpasses evolution," Trends in Biotechnology 28:355-362 (2010).
Curiel et al., "Specific recruitment of regulatory T cells in ovarian carcinoma fosters immune privilege and predicts reduced survival," Nat. Med. 10(9):942-949 (2004).
Dannull et al., "Enhancement of vaccine-mediated antitumor immunity in cancer patients after depletion of regulatory T cells," J Clin. Invest. 115(12):3623-3633 (2005).
Danos et al., "Safe and efficient generation of recombinant retroviruses with amphotropic and ecotropic host ranges," PNAS USA 85:6460-6464 (1988).
Dao et al., "Abstract A058: Selective targeting of T regulatory cells by a TCR-mimic monoclonal antibody specific for foxp3-derived epitopes [abstract]," In: Proceedings of the Second CRI-CIMT-EATI-AACR International Cancer Immunotherapy Conference: Translating Science into Survival; Sep. 25-28, 2016; New York, NY. Philadelphia (PA): AACR; Cancer Immunol Res 2016;4(11 Suppl): Abstract nr A058, 4 pages.
Dao et al., "Depleting T regulatory cells by targeting intracellular Foxp3 with a TCR mimic antibody," OncoImmunology, 8:7:1570778 (2019).
Dao et al., "Identification of a Human Cyclin Dl-Derived Peptide that Induces Human Cytotoxic CD4 T Cells," PLoS ONE 4(8):e6730 (2009).
Dao et al., "Targeting the Intracellular WT1 Oncogene Product with a Therapeutic Human Antibody," Sci Transl Med. 5(176): 176ra33 (2013).
Dao et al., "Therapeutic bispecific T-cell engager antibody targeting the intracellular oncoprotein WT1," Nat Biotechnol. 33(10):1079-1086 (2015).
Felgner et al., "Lipofection: A highly efficient, lipid-mediated DNA-transfection procedure," Proc. Natl. Acad. Sci. USA 84:7413-7417 (1987).
Fife et al., "Inhibition of T cell activation and autoimmune diabetes using a B cell surface-linked CTLA-4 agonist," J Clin Invest. 116(8):2252-2261 (2006).
Giomarelli et al., "Inhibition of thrombin-induced platelet aggregation using human single-chain Fv antibodies specific for TREM-like transcript-1," Thromb Haemost 97:955-963 (2007).

(56) References Cited

OTHER PUBLICATIONS

Glennie et al., "Preparation and performance of bispecific F(ab' gamma)2 antibody containing thioether-linked Fab' gamma fragments," J. Immunol. 139:2367-2375 (1987).
Godfrey et al., "In vitro-expanded human $CD4^+CD25^+$ T-regulatory cells can markedly inhibit allogeneic dendritic cell-stimulated MLR cultures," Blood 104(2):453-461 (2004).
GOMBP3, UniProtKB/TrEMBL Accession No. GOMBP3, Dec. 9, 2015 [online], [Retrieved on Aug. 13, 2020], Retrieved from the Internet <URL:https://www.uniprot.org/uniprot/GOMBP3,txt?version=12> entire document.
Grunstein et al., "Colony hybridization: A method for the isolation of cloned DNAs that contain a specific gene," PNAS USA 72(10):3961-3965 (1975).
Gunasekaran et al., "Enhancing Antibody Fc Heterodimer Formation through Electrostatic Steering Effects. Applications to Bispecific Molecules and Monovalent IgG," J. Biol. Chem. 285(25): 19637-19646 (2010).
Harris et al., "Crystallographic Structure of an Intact IgGl Monoclonal Antibody," Journal of Molecular Biology 275:861-872 (1998).
Heid et al., "Foxp3±CD25-Tumor Cells with Regulatory Function in Sezary Syndrome," J. Invest. Dermatol. 129:2875-2885 (2009).
Held et al., "Dissecting cytotoxic T cell responses towards the NY-ESO-1 protein by peptide/MHC-specific antibody fragments," Eur J. Immunol. 34:2919-2929 (2004).
Hellstrom et al., "Antibodies For Drug Delivery," in Controlled Drug Delivery (2nd Ed.), Robinson et al. (eds.), pp. 623-653 (Marcel Dekker, Inc. 1987).
Ho et al., "Inhibition of Cocaine Binding to the Human Dopamine Transporter by a Single Chain Anti-Idiotypic Antibody: Its Cloning, Expression and Functional Properties," BioChim Biophys Acta 1638(3):257-266 (2003).
Hughes et al., "Retroviral Gene Transfer to Primitive Normal and Leukemic Hematopoietic Cells Using Clinically Applicable Procedures," J. Clin. Invest. 89:1817-1824 (1992).
Huston et al., "Protein engineering of antibody binding sites: Recovery of specific activity in an anti-digoxin single-chain Fv analogue produced in *Escherichia coli*," PNAS 85:5879-5883 (1988).
International Search Report dated Jul. 17, 2017 in International Application No. PCT/US17/13511.
Jones et al., "Replacing the complementarity-determining regions in a human antibody with those from a mouse," Nature 321:522-525 (1986).
Kabat et al., Sequences of Proteins of Immunological Interest, 4th U. S. Department of Health and Human Services, National Institutes of Health (1987).
Kabat, E. A., et al. (1991) Sequences of Proteins of Immunological Interest, Fifth Edition, U.S. Department of Health and Human Services, NIH Publication No. 91-3242.
Karpovsky et al., "Production of Target-Specific Effector Cells Using Hetero—Cross-Linked Aggregates Containing Anti-Target Cell and Anti-Fcγ Receptor Antibodies," J. Exp. Med. 160:1686-1701 (1984).
Kimmel, "Identification and Characterization of Specific Clones: Strategy for Confirming the Validity of Presumptive Clones," Methods Enzymology 152:507-511 (1987).
Klechevsky et al., "Antitumor activity of immunotoxins with T cell receptor-like specificity against human melanoma xenografts," Cancer Res 68(15):6360-6367 (2008).
Kobayashi et al., "Defining MHC class II T helper epitopes for WT1 tumor antigen," Cancer Immunol. Immunother. 55:850-860 (2006).
Koneru et al., "IL-12 secreting tumor-targeted chimeric antigen receptor T cells eradicate ovarian tumors in vivo" Oncolmmunology 4(3):e994446 (2015), 12 pages.
Larsen et al., "Functional characterization of Foxp3-specific spontaneous immune responses," Leukemia 27:2332-2340 (2013).
Ledbetter et al., "Agonistic Activity of a CD40-Specific Single-Chain Fv Constructed from the Variable Regions of mAb G28-5," Crit Rev Immunol. 17:427-43 5 (1997).
Lev et al., "Isolation and Characterization of Human Recombinant Antibodies Endowed with the Antigen-specific, Major Histocompatibility Complex-restricted Specificity of T Cells Directed toward the Widely Expressed Tumor T-cell Epitopes of the Telomerase Catalytic Subunit," Cancer Res 62:3184-3194 (2002).
Levings et al., "Human C25+CD4+ T Suppressor Cells Clones Produce Transforming Growth Factor β, but not Interleukin 10, and Are Distinct from Type 1 T Regulator Cells," J. Exp. Med. 196(10): 1335-1346 (2002).
Litzinger et al., "IL-2 immunotoxin denileukin diftitox reduces regulatory T cells and enhances vaccine-mediated T-cell immunity," Blood 110(9):3192-3201 (2007).
Liu et al., "Heteroantibody duplexes target cells for lysis by cytotoxic T lymphocytes," PNAS USA 82:8648-8652 (1985).
Liyanage et al., "Prevalence of Regulatory T Cells is Increased in Peripheral Blood and Tumor Microenvironment of Patients with Pancreas or Breast Adenocarcinoma," J. Immunol. 169:2756-2761 (2002).
Loffler et al., "A recombinant bispecific single-chain antibody, CD19XCD3, induces rapid and high lymphoma-directed cytotoxicity by unstimulated T lymphocytes," Blood 95(6):2098-2103 (2000).
Lu et al., "Characterization of Protective Human CD4+CD25+ Foxp3+ Regulatory T Cells Generated with IL-2, TGF-β and Retinoic Acid," PLoS ONE 5(12):el5150 (2010).
Martin et al., "Application of $AIMe_3$-Mediated Amidation Reactions to Solution Phase Peptide Synthesis," Tetrahedron Letters 39:1517-1520 (1998).
May et al., "Peptide Epitopes from the Wilms' Tumor 1 Oncoprotein Stimulate $CD4^+$ and $CD8^+$ T Cells That Recognize and Kill Human Malignant Mesothelioma Tumor Cells," Clin. Cancer Res. 13(15):4547-4555 (2007).
McCafferty et al., "Phage antibodies: filamentous phage displaying antibody variable domains," Nature 348:552-554 (1990).
Miederer et al., "Realizing the potential of the Actinium-225 radionuclide generator in targeted alpha-particle therapy applications," Adv Drug Deliv Rev 60(12):1371-1382 (2008).
Miller et al., "Generation of Helper-Free Amphotropic Retroviruses That Transduce a Dominant-Acting, Methotrexate-Resistant Dihydrofolate Reductase Gene," Mol. Cell. Biol. 5(3):431-437 (1985).
Miller et al., "Redesign of Retrovirus Packaging Cell Lines to Avoid Recombination Leading to Helper Virus Production," Mol. Cell. Biol. 6(8):2895-2902 (1986).
MOJRF5, UniProtKB/TrEMBL Accession No. MOJRF5, May 27, 2015 [online], [Retrieved on Aug. 13, 2020], Retrieved from the internet <URL: https://www.uniprot.org/uniprot/MOJRF5 ,txt?version=4> entire document.
Moosmayer et al., "A single-chain TNF receptor antagonist is an effective inhibitor of TNF mediated cytotoxicity," Therapeutic Immunol. 2:31-40 (1995).
Muller, et al., "Improved Pharmacokinetics of Recombinant Bispecific Antibody Molecules by Fusion to Human Serum Albumin," JBiol Chem 282(17):12650-12660 (2007).
Myers et al., "Optimal alignments in linear space," CABIOS 4(1):11-17 (1988).
Nair et al., "Vaccination against the Forkhead Family Transcription Factor Foxp3 Enhances Tumor Immunity," Cancer Res. 67(1):371-380 (2007).
Needleman et al., "A General Method Applicable to the Search for Similarities in the Amino Acid Sequence of Two Proteins," J. Mol. Biol. 48:443-453 (1970).
NetMHC 4.0 Server (https://www.cbs.dtu.dk/services/NetMHC/), Oct. 24, 2017 [online], Retrieved on Aug. 13, 2020.
Noy et al., "T-cell receptor-like antibodies: novel reagents for clinical cancer immunology and immunotherapy," Expert Rev Anticancer Ther. 5(3):523-536 (2005).
Oka et al., "WT1 Peptide Cancer Vaccine for Patients with Hematopoietic Malignancies and Solid Cancers," The Scientific World Journal 7:649-665 (2007).
Ono et al., "Plasmid DNAs directly injected into mouse brain with lipofectin can be incorporated and expressed by brain cells," Neuroscience Letters 117:259-263 (1990).

(56) References Cited

OTHER PUBLICATIONS

Order, "Analysis, Results, and Future Prospective of the Therapeutic Use of Radiolabeled Antibody in Cancer Therapy," Monoclonal Antibodies for Cancer Detection and Therapy, Baldwin et al. (eds.), Chapter 15, pp. 303-315 (Academic Press 1985).
Park et al., "CD19-targeted CAR T-cell therapeutics for hematologic malignancies: interpreting clinical outcomes to date," Blood 127(26):3312-3320 (2016).
Parker et al., "Scheme for ranking potential HLA-A2 binding peptides based on independent binding of individual peptide side-chains," J. Immunol., 152:163 (1994).
Pastan et al., "Overview Immunotoxins in Cancer Therapy," Curr. Opin. Investig. Drugs 3(7):1089-1091 (2002).
Paulus, "Preparation and Biomedical Applications of Bispecific Antibodies," Behring Ins. Mitt. 78:118-132(1985).
Payne, "Progress in immunoconjugate cancer therapeutics," Cancer Cell 3:207-212 (2003).
Persic et al., "An integrated vector system for the eukaryotic expression of antibodies or their fragments after selection from phage display libraries," Gene 187:9-18 (1997).
Peter et al., "Protective effects of an anti-melanocortin-4 receptor scFv derivative in lipopolysaccharide-induced cachexia in rats," J Cachexia Sarcopenia Muscle 4:79-88 (2013).
Peter et al., "scFv Single Chain Antibody Variable Fragment as Inverse Agonist of the β2-Adrenergic Receptor," J Biol Chem 278(38):36740-36747 (2003).
Queen et al., "A humanized antibody that binds to the interleukin 2 receptor," PNAS USA 86:10029-10033 (1989).
Rafiq et al., "Optimized T-cell receptor-mimic chimeric antigen receptor T cells directed toward the intracellular Wilms Tumor 1 antigen," Leukemia 31:1788-1797 (2017).
Rech et al., "CD25 Blockade Depletes and Selectively Reprogram Regulatory T cells in Concert with Immunotherapy in Cancer Patients," Sci. Transl. Med. 4(134):134ra62 (2012).
Riechmann et al., "Reshaping human antibodies for therapy," Nature 332:323-327 (1988).
Ritter et al., "Serological Analysis of Human Anti-Human Antibody Responses in Colon Cancer Patients Treated with Repeated Doses of Humanized Monoclonal Antibody A33," Cancer Research 61:6851-6859 (2001).
Roberts et al., "Vaccination with CD20 peptides induces a biologically active, specific immune response in mice," Blood: 99:3748-3755) (2002).
Rossi et al., "Stably tethered multifunctional structures of defined composition made by the dock and lock method for use in cancer targeting," PNAS USA 103(18):6841-6846 (2006).
Saito et al., "Drug delivery strategy utilizing conjugation via reversible disulfide linkages: role and site of cellular reducing activities," Adv. Drug Deliv. Rev. 5 5:199-215 (2003).
Schuler et al., "SYFPEITHI: Database for Searching and T-Cell Epitope Prediction," Immunoinformatics Methods in Molecular Biology 409:75-93 (2007).
Schultz et al., "T Regulatory Cells Exhibit Surface Expression of FoxP3 Derived Peptides Presented within Class I MHC," Blood 126:2228 (2015), 5 pages.
Senter et al., "Selective activation of anticancer prodrugs by monoclonal antibodyenzyme conjugates," Adv. Drug Deliv. Rev. 53:247-264 (2001).
Shieh et al., "Transgenic Expression of Single-Chain Anti-CTLA-4 Fv on β Cells Protects Nonobese Diabetic Mice from Autoimmune Diabetes," J Immunol 183:2277-2285 (2009).
Singh et al., "ProPred: prediction of HLA-DR binding sites," Bioinformatics 17(12):1236-1237 (2001).
Straubinger et al., "Liposomes as Carriers for Intracellular Delivery of Nucleic Acids," Methods in Enzymology 101:512-527 (1983).
Sugiyama et al., "Anti-CCR4 mAb selectively depletes effector-type Foxp3±CD4+ regulator T cells, evoking antitumor immune responses in humans," PNAS 110(44):17945-17950 (2013).
Supplementary European Search Report dated Jun. 4, 2019 in Application No. EP 17739080.
Thorpe et al., "The Preparation and Cytotoxic Properties of Antibody-Toxin Conjugates," Immunol. Rev., 62:119-158 (1982).
Thorpe, "Antibody Carriers of Cytotoxic Agents in Cancer Therapy: A Review," in Monoclonal Antibodies '84: Biological and Clinical Applications, Pinchera et al. (eds.), pp. 475-506 (1985).
Tjandra et al., "Development of human anti-murine antibody (HAMA) response in patients," Immunol Cell Biol. 68:367-376 (1990).
Tomimatsu et al., "Production of Human Monoclonal Antibodies against FcεRIα by a Method Combining in Vitro Immunization with Phage Display," Biosci Biotechnol Biochem 73(7):1465-1469 (2009).
Tomlinson et al., "The Repertoire of Human Germline VH Sequences Reveals about Fifty Groups of VH Segments with Different Hypervariable Loops," J. Mol. Biol. 227:776-798 (1992).
Trail et al., "Monoclonal antibody drug immunoconjugates for targeted treatment of cancer," Cancer Immunol. Immunother. 52:328-337 (2003).
UniProtKB/TrEMBL Accession No. A0A0M3QYJ1, Dec. 9, 2015 [online], [Retrieved on Dec. 12, 2019], Retrieved from the Internet <URL: https://www.uniprot.org/uniprot/A0A0M3QYJ1 (entire document).
Wahl et al., "Improved Radioimaging and Tumor Localization with Monoclonal F(ab')2," J. Nucl. Med. 24:316-325 (1983).
Wahl et al., "Molecular Hybridization of Immobilized Nucleic Acids: Theoretical Concepts and Practical Considerations," Methods Enzymology 152:399-407 (1987).
Ward et al., "Binding activities of a repertoire of single immunoglobulin variable domains secreted from *Escherichia coli*," Nature 341:544-546 (1989).
Weiner et al., "The role of T cell activation in anti-CD3 x antitumor bispecific antibody therapy," J. Immunology 152:2385-2392 (1994).
Wolf et al., "Increase of Regulatory T Cells in the Peripheral Blood of Cancer Patients," Clin. Cancer. Res. 9:606-612 (2003).
Wolff et al., "Direct Gene Transfer into Mouse Muscle in Vivo," Science 247(4949):1465-1468 (1990).
Wu et al., "Receptor-mediated Gene Delivery and Expression in Vivo," Journal of Biological Chemistry 263(29):14621-14624 (1988).
Wu et al., "Targeting Genes: Delivery and Persistent Expression of a Foreign Gene Driven by Mammalian Regulatory Elements in Vivo," Journal of Biological Chemistry 264(29):16985-16987 (1989).
Xie et al., "Direct demonstration of MuSK involvement in acetylcholine receptor clustering through identification of agonist ScFv," Nat Biotech 15(8):768-771 (1997).
Xu et al., "Correction of the enzyme deficiency in hematopoietic cells of Gaucher patients using a clinically acceptable retroviral supernatant transduction protocol," Exp. Hemat. 22:223-230 (1994).
Yasmina, et al., "Probing the binding mechanism and affinity of tanezumab, a recombinant humanized anti-NGF monoclonal antibody, using a repertoire of biosensors," Protein Science 17:1326-1335 (2008).
Zhao et al., "Characteristics of an scFv Antibody Fragment that Binds to Immunoglobulin G of Graves' Disease Patients and Inhibits Autoantibody-Mediated Thyroid-Stimulating Activity," Hyrbidoma 27(6):445-451 (2008).

* cited by examiner

| | Sample | Median:FITC-A |
|---|---|---|
| (thick solid) | T2+FoxP7_#11.fcs | 454 |
| (thick dashed) | T2+FoxP7_#17.fcs | 745 |
| (thick dash-dot) | T2+FoxP7_#18.fcs | 761 |
| (thin dashed) | T2+FoxP7_#21.fcs | 428 |
| (dotted) | T2+FoxP7_#26.fcs | 410 |
| (thin solid) | T2+FoxP7_#27.fcs | 658 |
| (thin dashed) | T2+FoxP7_#28.fcs | 873 |
| (thin dash-dot) | T2+FoxP7_#32.fcs | 4069 |
| (solid) | T2+FoxP7_#9.fcs | 287 |
| (dashed) | T2+FoxP7_Pr435_#20.fcs | 140 |
| (dash-dot) | T2+FoxP7_2nd_GAM_F.fcs | 116 |
| (sparse dotted) | T2+FoxP7_uns.fcs | 93.8 |

| Sample | Median:FITC-A |
|---|---|
| T2_#11.fcs | 143 |
| T2_#17.fcs | 143 |
| T2_#18.fcs | 148 |
| T2_#21.fcs | 147 |
| T2_#26.fcs | 146 |
| T2_#27.fcs | 150 |
| T2_#28.fcs | 144 |
| T2_#32.fcs | 138 |
| T2_#9.fcs | 150 |
| T2_Pr435_#20.fcs | 149 |
| T2_2nd_GAM_F.fcs | 121 |
| T2_uns.fcs | 106 |

| | Sample | Median:FITC-A |
|---|---|---|
| | T2+R3_#11.fcs | 144 |
| | T2+R3_#17.fcs | 146 |
| | T2+R3_#18.fcs | 146 |
| | T2+R3_#21.fcs | 143 |
| | T2+R3_#26.fcs | 144 |
| | T2+R3_#27.fcs | 145 |
| | T2+R3_#28.fcs | 140 |
| | T2+R3_#32.fcs | 136 |
| | T2+R3_#9.fcs | 144 |
| | T2+R3_Pr435_#20.fcs | 145 |
| | T2+R3_2nd_GAM_F.fcs | 123 |
| | T2+R3_uns.fcs | 99.8 |

| | Sample | Median:FITC-A |
|---|---|---|
| | T2+FoxP7_Clone #24.fcs | 1041 |
| | T2+FoxP7_Clone #23.fcs | 982 |
| | T2+FoxP7_Clone #21.fcs | 1546 |
| | T2+FoxP7_Clone #20.fcs | 1223 |
| | T2+FoxP7_Clone #18.fcs | 1539 |
| | T2+FoxP7_Clone #17.fcs | 1757 |
| | T2+FoxP7_Clone #11.fcs | 1686 |
| | T2+FoxP7_Clone #10.fcs | 1131 |
| | T2+FoxP7_Clone #9.fcs | 1732 |
| | T2+FoxP7_Clone #5.fcs | 2052 |
| | T2+FoxP7_2nd GAM_F.fcs | 133 |
| | T2+FoxP7_uns.fcs | 103 |

| Sample | Median:FITC-A |
|---|---|
| T2_Clone #24.fcs | 146 |
| T2_Clone #23.fcs | 141 |
| T2_Clone #21.fcs | 138 |
| T2_Clone #20.fcs | 136 |
| T2_Clone #18.fcs | 139 |
| T2_Clone #17.fcs | 151 |
| T2_Clone #11.fcs | 142 |
| T2_Clone #10.fcs | 149 |
| T2_Clone #9.fcs | 149 |
| T2_Clone #5.fcs | 142 |
| T2_2nd GAM_F.fcs | 100 |
| T2_uns.fcs | 99.5 |

| Sample | Median:FITC-A |
|---|---|
| T2+EW_Clone #24.fcs | 141 |
| T2+EW_Clone #23.fcs | 144 |
| T2+EW_Clone #21.fcs | 143 |
| T2+EW_Clone #20.fcs | 139 |
| T2+EW_Clone #18.fcs | 139 |
| T2+EW_Clone #17.fcs | 144 |
| T2+EW_Clone #11.fcs | 143 |
| T2+EW_Clone #10.fcs | 151 |
| T2+EW_Clone #9.fcs | 151 |
| T2+EW_Clone #5.fcs | 149 |
| T2+EW_2nd GAM_F.fcs | 113 |
| T2+EW_uns.fcs | 94.7 |

| | Sample | Median:FITC-A |
|---|---|---|
| ------ | T2+FoxP7_#55.fcs | 405 |
| ········ | T2+FoxP7_#54.fcs | 732 |
| —— | T2+FoxP7_#53.fcs | 1051 |
| — — | T2+FoxP7_#34.fcs | 1046 |
| —·— | T2+FoxP7_#32.fcs | 1642 |
| —— | T2+FoxP7_#30.fcs | 1126 |
| — — — | T2+FoxP7_#29.fcs | 1007 |
| —·— | T2+FoxP7_#28.fcs | 1736 |
| —— | T2+FoxP7_#27.fcs | 1945 |
| — — — | T2+FoxP7_#26.fcs | 1876 |
| —·— | T2+FoxP7_#25.fcs | 1034 |
| —·— | T2+FoxP7_GAM_F.fcs | 318 |
| · · · · · | T2+FoxP7_uns.fcs | 95.8 |

| Sample | Median:FITC-A |
|---|---|
| T2+R3_#11.fcs | 119 |
| T2+R3_#17.fcs | 124 |
| T2+R3_#18.fcs | 117 |
| T2+R3_#20.fcs | 128 |
| T2+R3_#21.fcs | 123 |
| T2+R3_#27.fcs | 123 |
| T2+R3_#28.fcs | 118 |
| T2+R3_#32.fcs | 123 |
| T2+R3_#5.fcs | 129 |
| T2+R3_#53.fcs | 121 |
| T2+R3_#54.fcs | 122 |
| T2+R3_2nd_GAM_F.fcs | 109 |
| T2+R3_uns.fcs | 80.9 |

| | Sample | Median:FITC-A |
|---|---|---|
| ---- | T2+FoxP7_#11.fcs | 2619 |
| ········ | T2+FoxP7_#17.fcs | 2587 |
| ------ | T2+FoxP7_#18.fcs | 2791 |
| —— | T2+FoxP7_#20.fcs | 2301 |
| — — — | T2+FoxP7_#21.fcs | 2223 |
| —·— | T2+FoxP7_#27.fcs | 2819 |
| —— | T2+FoxP7_#28.fcs | 2791 |
| — — — | T2+FoxP7_#32.fcs | 3844 |
| —·— | T2+FoxP7_#5.fcs | 2457 |
| —— | T2+FoxP7_#53.fcs | 2704 |
| — — — | T2+FoxP7_#54.fcs | 4372 |
| —-— | T2+FoxP7_2nd_GAM_F.fcs | 104 |
| · · · · · | T2+FoxP7_uns.fcs | 81.7 |

| Sample | Median:FITC-A |
|---|---|
| T2+R3_#11.fcs | 119 |
| T2+R3_#17.fcs | 124 |
| T2+R3_#18.fcs | 117 |
| T2+R3_#20.fcs | 128 |
| T2+R3_#21.fcs | 123 |
| T2+R3_#27.fcs | 123 |
| T2+R3_#28.fcs | 118 |
| T2+R3_#32.fcs | 123 |
| T2+R3_#5.fcs | 129 |
| T2+R3_#53.fcs | 121 |
| T2+R3_#54.fcs | 122 |
| T2+R3_2nd_GAM_F.fcs | 109 |
| T2+R3_uns.fcs | 80.9 |

| | Sample | Median:FITC-A |
|---|---|---|
| ------ | T2_#55.fcs | 389 |
| ........ | T2_#54.fcs | 343 |
| —— | T2_#53.fcs | 355 |
| — — — | T2_#34.fcs | 361 |
| —·— | T2_#32.fcs | 356 |
| —— | T2_#30.fcs | 354 |
| — — — | T2_#29.fcs | 369 |
| —·— | T2_#28.fcs | 353 |
| —— | T2_#27.fcs | 355 |
| — — — | T2_#26.fcs | 385 |
| —·— | T2_#25.fcs | 386 |
| ---- | T2_GAM_F.fcs | 320 |
| ...... | T2_uns.fcs | 91.4 |

| Sample | Median:FITC-A |
|---|---|
| T2+EW_#55.fcs | 391 |
| T2+EW_#54.fcs | 364 |
| T2+EW_#53.fcs | 346 |
| T2+EW_#34.fcs | 386 |
| T2+EW_#32.fcs | 357 |
| T2+EW_#30.fcs | 378 |
| T2+EW_#29.fcs | 359 |
| T2+EW_#28.fcs | 338 |
| T2+EW_#27.fcs | 371 |
| T2+EW_#26.fcs | 375 |
| T2+EW_#25.fcs | 375 |
| T2+EW_GAM_F.fcs | 310 |
| T2+EW_uns.fcs | 93 |

| | Sample | Median:FITC-A |
|---|---|---|
| ——— | T2 (FoxP2)_#9.fcs | 140 |
| – – – | T2 (FoxP2)_#8.fcs | 141 |
| —·— | T2 (FoxP2)_#6.fcs | 146 |
| ——— | T2 (FoxP2)_#4.fcs | 147 |
| – – – | T2 (FoxP2)_#20.fcs | 149 |
| —·— | T2 (FoxP2)_#15.fcs | 145 |
| ——— | T2 (FoxP2)_#13.fcs | 143 |
| – – – | T2 (FoxP2)_#12.fcs | 151 |
| —··— | T2 (FoxP2)_#2nd.fcs | 118 |
| ········ | T2 (FoxP2)_uns.fcs | 95.2 |

| | Sample | Median:FITC-A |
|---|---|---|
| —— | T2+Foxp2 (Foxp2)_#12.fcs | 689 |
| – – – | T2+Foxp2 (Foxp2)_#9.fcs | 829 |
| —·— | T2+Foxp2 (Foxp2)_#8.fcs | 258 |
| —— | T2+Foxp2 (Foxp2)_#6.fcs | 291 |
| – – – | T2+Foxp2 (Foxp2)_#4.fcs | 652 |
| —·— | T2+Foxp2 (Foxp2)_#20.fcs | 801 |
| —— | T2+Foxp2 (Foxp2)_#15.fcs | 822 |
| – – – | T2+Foxp2 (Foxp2)_#13.fcs | 630 |
| –·–·– | T2+Foxp2 (Foxp2)_2nd.fcs | 125 |
| ········ | T2+Foxp2 (Foxp2)_uns.fcs | 95.2 |

| | Sample | Median:FITC-A |
|---|---|---|
| thin solid line | T2+R3 (FOXp2)_#9.fcs | 148 |
| thin dashed line | T2+R3 (FOXp2)_#8.fcs | 142 |
| thin dash-dot line | T2+R3 (FOXp2)_#6.fcs | 157 |
| solid line | T2+R3 (FOXp2)_#4.fcs | 145 |
| dashed line | T2+R3 (FOXp2)_#20.fcs | 148 |
| dash-dot line | T2+R3 (FOXp2)_#15.fcs | 145 |
| thick solid line | T2+R3 (FOXp2)_#13.fcs | 141 |
| thick dashed line | T2+R3 (FOXp2)_#12.fcs | 151 |
| long-dash line | T2+R3 (FOXp2)_2nd.fcs | 126 |
| dotted line | T2+R3 (FOXp2)_uns.fcs | 94.4 |

| | Sample | Median:FITC-A |
|---|---|---|
| —·— | T2 (FoxP4)_#5.fcs | 155 |
| —— | T2 (FoxP4)_#4.fcs | 155 |
| – – – | T2 (FoxP4)_#2.fcs | 157 |
| ----- | T2 (FoxP4)_2nd.fcs | 125 |
| ······· | T2 (FoxP4)_uns.fcs | 99.8 |

| | Sample | Median:FITC-A |
|---|---|---|
| —·— | T2+FoxP4 (FoxP4)_#5.fcs | 242 |
| —— | T2+FoxP4 (FoxP4)_#4.fcs | 160 |
| – – – | T2+FoxP4 (FoxP4)_#2.fcs | 160 |
| ---- | T2+FoxP4 (FoxP4)_2nd.fcs | 120 |
| ········ | T2+FoxP4 (FoxP4)_uns.fcs | 95.2 |

| | Sample | Median:FITC-A |
|---|---|---|
| —·— | T2+R3 (FoxP4)_#5.fcs | 143 |
| —— | T2+R3 (FoxP4)_#4.fcs | 148 |
| — — | T2+R3 (FoxP4)_#2.fcs | 147 |
| ---- | T2+R3 (FoxP4)_2nd.fcs | 118 |
| ········ | T2+R3 (FoxP4)_uns.fcs | 91.1 |

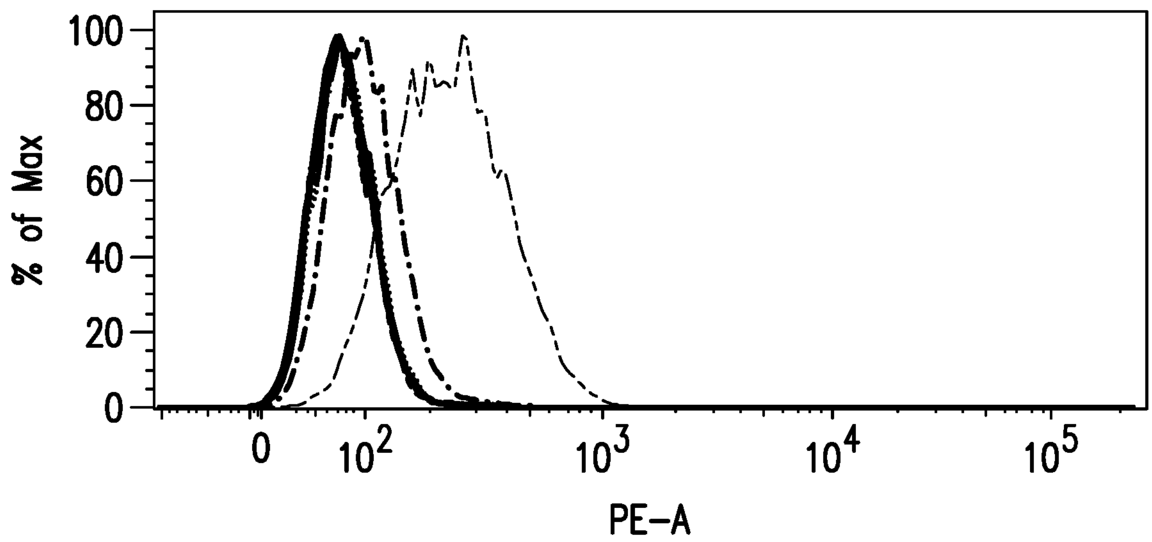

| | Sample | Median:FITC-A |
|---|---|---|
| ·········· | MAC1_FoxP7_#17_0;1ug_ml.fcs | 78 |
| ——— | MAC1_FoxP7_#17_1ug_ml.fcs | 76.2 |
| - - - - - | MAC1_FoxP7_#18_0;1ug_ml.fcs | 75.4 |
| —·— | MAC1_FoxP7_#18_1ug_ml.fcs | 78 |
| ——— | MAC1_FoxP7_#20_0;1ug_ml.fcs | 75.4 |
| - - - - - | MAC1_FoxP7_#20_1ug_ml.fcs | 75.4 |
| —·— | MAC1_FoxP7_#27_0;1ug_ml.fcs | 73.9 |
| ——— | MAC1_FoxP7_#27_1ug_ml.fcs | 74.6 |
| ——— | MAC1_FoxP7_#28_0;1ug_ml.fcs | 74.6 |
| - - - - - | MAC1_FoxP7_#28_1ug_ml.fcs | 74.6 |
| —·— | MAC1_FoxP7_#32_0;1ug_ml.fcs | 99.8 |
| - - - - | MAC1_FoxP7_#32_1ug_ml.fcs | 239 |
| ·········· | MAC1_FoxP7_#53_0;1ug_ml.fcs | 78 |
| ——— | MAC1_FoxP7_#53_1ug_ml.fcs | 78 |
| - - - - - | MAC1_FoxP7_#54_0;1ug_ml.fcs | 76.2 |
| —·— | MAC1_FoxP7_#54_1ug_ml.fcs | 75.4 |
| ——— | MAC1_GA6xHIS_PE.fcs | 77 |
| - - - - - | MAC1_NC16-BiTE_0;1ug_ml.fcs | 75.4 |
| —·— | MAC1_NC16-BiTE_1ug_ml.fcs | 75.4 |
| ——— | MAC1_uns.fcs | 77 |

FIG. 7A

| | Sample | Median:FITC-A |
|---|---|---|
| —— | MAC1_mIso_F.fcs | 93.6 |
| —— | MAC1_BB7_F.fcs | 35013 |

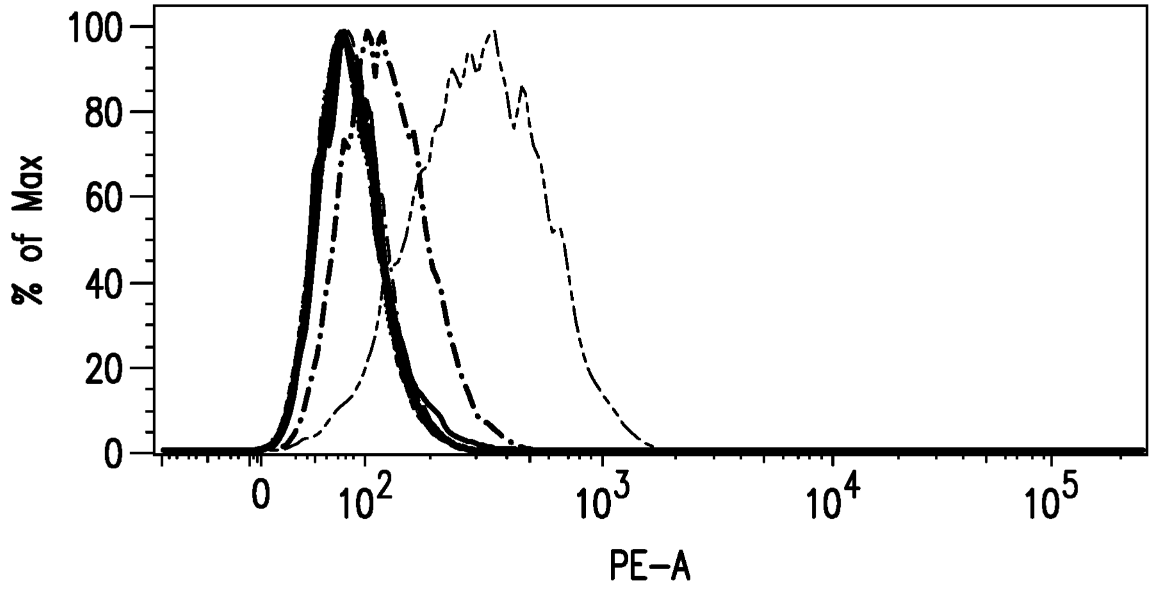

| | Sample | Median:FITC-A |
|---|---|---|
| | MAC2A_FoxP7_#17_0;1ug_ml.fcs | 76.2 |
| | MAC2A_FoxP7_#17_1ug_ml.fcs | 78.8 |
| | MAC2A_FoxP7_#18_0;1ug_ml.fcs | 78 |
| | MAC2A_FoxP7_#18_1ug_ml.fcs | 78 |
| | MAC2A_FoxP7_#20_0;1ug_ml.fcs | 77 |
| | MAC2A_FoxP7_#20_1ug_ml.fcs | 77 |
| | MAC2A_FoxP7_#27_0;1ug_ml.fcs | 80.1 |
| | MAC2A_FoxP7_#27_1ug_ml.fcs | 80.9 |
| | MAC2A_FoxP7_#28_0;1ug_ml.fcs | 78.8 |
| | MAC2A_FoxP7_#28_1ug_ml.fcs | 76.2 |
| | MAC2A_FoxP7_#32_0;1ug_ml.fcs | 118 |
| | MAC2A_FoxP7_#32_1ug_ml.fcs | 302 |
| | MAC2A_FoxP7_#53_0;1ug_ml.fcs | 77 |
| | MAC2A_FoxP7_#53_1ug_ml.fcs | 78 |
| | MAC2A_FoxP7_#54_0;1ug_ml.fcs | 79.3 |
| | MAC2A_FoxP7_#54_1ug_ml.fcs | 78 |
| | MAC2A_NC16-BiTE_0;1ug_ml.fcs | 74.6 |
| | MAC2A_NC16-BiTE_1ug_ml.fcs | 73.9 |
| | MAC2A_GA6xHIS_PE.fcs | 78 |
| | MAC2A_uns.fcs | 78 |

FIG. 7B

| | Sample | Median:FITC-A |
|---|---|---|
| —— (thick) | MAC2A_BB7_F.fcs | 44050 |
| —— (thin) | MAC2A_mIso_F.fcs | 86.2 |

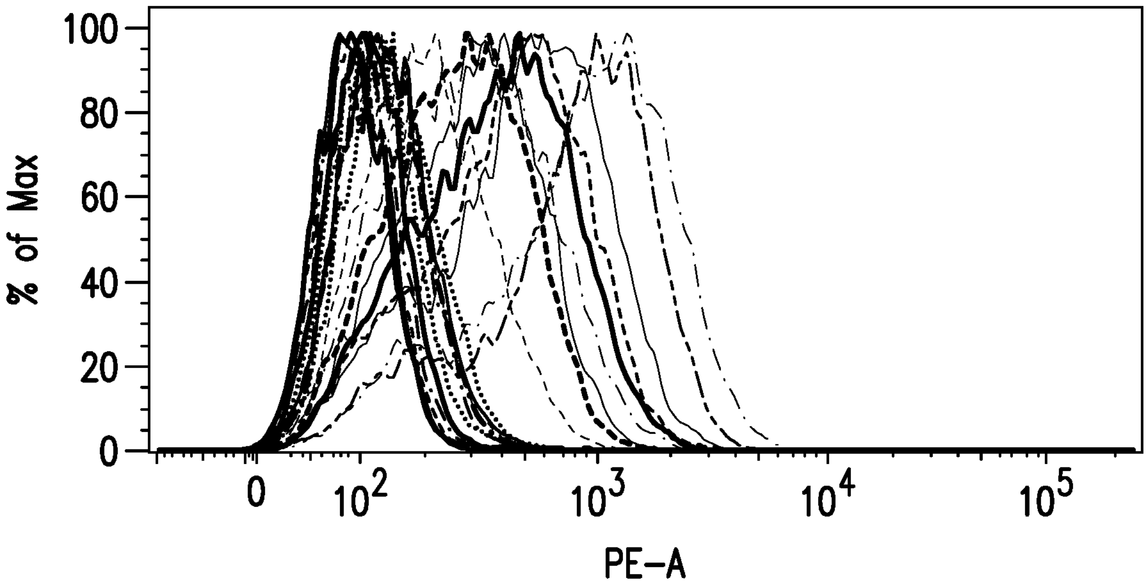

| | Sample | Median:FITC-A |
|---|---|---|
| ·········· | Jurkat_FoxP7_#17_0;1ug_ml.fcs | 135 |
| ——— | Jurkat_FoxP7_#17_1ug_ml.fcs | 507 |
| - - - - | Jurkat_FoxP7_#18_0;1ug_ml.fcs | 189 |
| —·— | Jurkat_FoxP7_#18_1ug_ml.fcs | 928 |
| ——— | Jurkat_FoxP7_#20_0;1ug_ml.fcs | 126 |
| - - - - | Jurkat_FoxP7_#20_1ug_ml.fcs | 438 |
| —·— | Jurkat_FoxP7_#27_0;1ug_ml.fcs | 122 |
| ——— | Jurkat_FoxP7_#27_1ug_ml.fcs | 377 |
| ——— | Jurkat_FoxP7_#28_0;1ug_ml.fcs | 103 |
| - - - - | Jurkat_FoxP7_#28_1ug_ml.fcs | 263 |
| —·— | Jurkat_FoxP7_#32_0;1ug_ml.fcs | 126 |
| - - - - | Jurkat_FoxP7_#32_1ug_ml.fcs | 847 |
| ·········· | Jurkat_FoxP7_#53_0;1ug_ml.fcs | 112 |
| ——— | Jurkat_FoxP7_#53_1ug_ml.fcs | 298 |
| - - - - | Jurkat_FoxP7_#54_0;1ug_ml.fcs | 123 |
| —·— | Jurkat_FoxP7_#54_1ug_ml.fcs | 283 |
| ——— | Jurkat_GA6xHIS_PE.fcs | 86.5 |
| - - - - | Jurkat_NC16-BiTE_0;1ug_ml.fcs | 89.4 |
| —·— | Jurkat_NC16-BiTE_1ug_ml.fcs | 96.6 |
| ——— | Jurkat_uns.fcs | 85.6 |

FIG. 7C

| | Sample | Median:FITC-A |
|---|---|---|
| (thick line) | Jurkat_mIso_F.fcs | 93.6 |
| (thin line) | Jurkat_BB7_F.fcs | 101 |

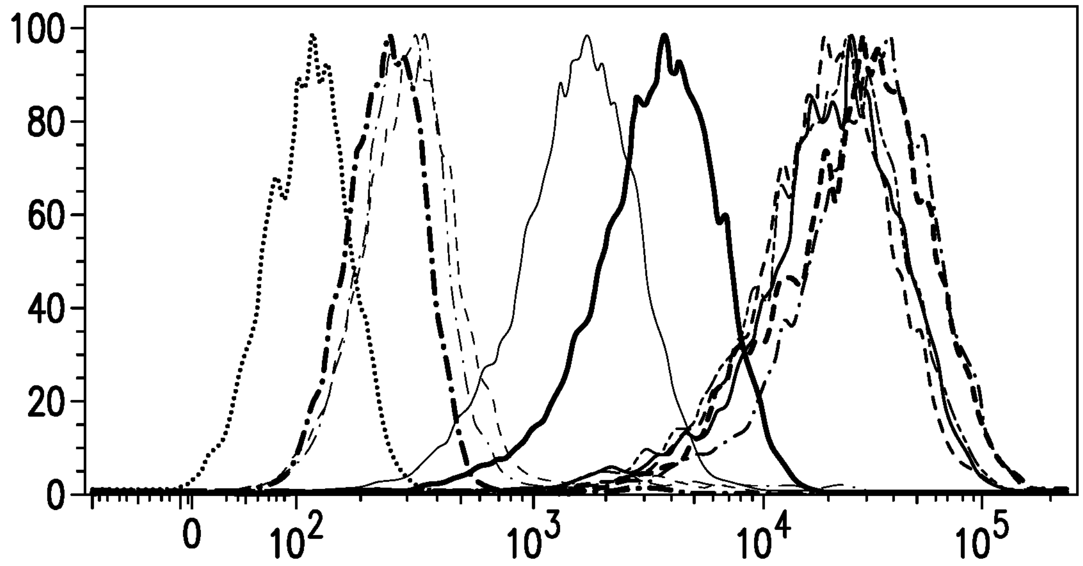

| Sample | Median:FITC-A |
|---|---|
| T2+FoxP7-G10_FoxP7#32-BiTE_1ug.fcs | 1607 |
| T2+FoxP7-A9_FoxP7#32-BiTE_1ug.fcs | 316 |
| T2+FoxP7-A8_FoxP7#32-BiTE_1ug.fcs | 296 |
| T2+FoxP7-A7_FoxP7#32-BiTE_1ug.fcs | 22412 |
| T2+FoxP7-A5_FoxP7#32-BiTE_1ug.fcs | 20522 |
| T2+FoxP7-A3_FoxP7#32-BiTE_1ug.fcs | 32380 |
| T2+FoxP7-A2_FoxP7#32-BiTE_1ug.fcs | 3614 |
| T2+FoxP7-A1_FoxP7#32-BiTE_1ug.fcs | 29053 |
| T2+CT_FoxP7#32-BiTE_1ug.fcs | 252 |
| T2+FoxP7_FoxP7#32-BiTE_1ug.fcs | 21800 |
| T2_FoxP7#32-BiTE_1ug.fcs | 117 |

WT: TLIRWAILEA

A1: ALIRWAILEA
A2: TAIRWAILEA
A3: TLARWAILEA
A4: TLIAWAILEA
A5: TLIRAAILEA
A7: TLIRWAALEA
A8: TLIRWAIAEA
A9: TLIRWAILAA
G10: TLIRWAILEG

FIG. 8A

| | Sample | Median:FITC-A |
|---|---|---|
| — — — (thin) | T2+FoxP7-G10_BB7_F.fcs | 34141 |
| —·— | T2+FoxP7-A9_BB7_F.fcs | 10388 |
| ——— | T2+FoxP7-A8_BB7_F.fcs | 16487 |
| ——— (thick) | T2+FoxP7-A7_BB7_F.fcs | 18650 |
| — — — (thick) | T2+FoxP7-A5_BB7_F.fcs | 10362 |
| ——— (thin) | T2+FoxP7-A3_BB7_F.fcs | 35102 |
| —·— (thin) | T2+FoxP7-A2_BB7_F.fcs | 11199 |
| — — — | T2+FoxP7-A1_BB7_F.fcs | 29570 |
| —·— (thick) | T2+FoxP7_BB7_F.fcs | 17959 |
| ········· | T2_BB7_F.fcs | 6944 |

WT: TLIRWAILEA

A1: ALIRWAILEA
A2: TAIRWAILEA
A3: TLARWAILEA
A4: TLIAWAILEA
A5: TLIRAAILEA
A7: TLIRWAALEA
A8: TLIRWAIAEA
A9: TLIRWAILAA
G10: TLIRWAILEG

#32 on CD4+CD25+CD127^hi T cells

| Sample Name | Median, PE-A |
|---|---|
| EXT017-17 + T2.fcs | 92.9 |
| EXT017-17 + T2-EXT017.fcs | 2.36E4 |
| EXT017-17 + T2-017mut1.fcs | 7884 |
| EXT017-17 + T2-017mut2.fcs | 99.8 |
| EXT017-17 + T2-017mut3.fcs | 741 |
| EXT017-17 + T2-017mut4.fcs | 103 |
| EXT017-17 + T2-017mut5.fcs | 98.1 |
| EXT017-17 + T2-017mut7.fcs | 97.8 |
| EXT017-17 + T2-017mut8.fcs | 3587 |
| EXT017-17 + T2-017mut9.fcs | 94.7 |

Sensitive to positions: 4, 5, 7, 9

| Sample Name | Median, PE-A |
|---|---|
| ············ EXT017−18 + T2.fcs | 90.6 |
| ———— EXT017−18 + T2−EXT017.fcs | 2.59E4 |
| - - - - - EXT017−18 + T2−017mut1.fcs | 143 |
| −·−·− EXT017−18 + T2−017mut2.fcs | 97.3 |
| ———— EXT017−18 + T2−017mut3.fcs | 5152 |
| - - - - - EXT017−18 + T2−017mut4.fcs | 99.1 |
| −·−·− EXT017−18 + T2−017mut5.fcs | 95.8 |
| ———— EXT017−18 + T2−017mut7.fcs | 95.4 |
| - - - - - EXT017−18 + T2−017mut8.fcs | 6603 |
| −·−·− EXT017−18 + T2−017mut9.fcs | 386 |

Sensitive to positions: 1, 4, 5, 7, 9

| Sample Name | Median, PE-A |
|---|---|
| EXT017-20 + T2.fcs | 91.3 |
| EXT017-20 + T2-EXT017.fcs | 1.71E4 |
| EXT017-20 + T2-017mut1.fcs | 4074 |
| EXT017-20 + T2-017mut2.fcs | 96.0 |
| EXT017-20 + T2-017mut3.fcs | 96.4 |
| EXT017-20 + T2-017mut4.fcs | 93.7 |
| EXT017-20 + T2-017mut5.fcs | 95.0 |
| EXT017-20 + T2-017mut7.fcs | 94.9 |
| EXT017-20 + T2-017mut8.fcs | 1.11E4 |
| EXT017-20 + T2-017mut9.fcs | 95.6 |

Sensitive to positions: 3, 4, 5, 7, 9

| Sample Name | Median, PE-A |
|---|---|
| ·············· EXT017-27 + T2.fcs | 90.4 |
| ——— EXT017-27 + T2-EXT017.fcs | 2.12E4 |
| - - - - - EXT017-27 + T2-017mut1.fcs | 222 |
| -·-·- EXT017-27 + T2-017mut2.fcs | 98.2 |
| ——— EXT017-27 + T2-017mut3.fcs | 2257 |
| - - - - - EXT017-27 + T2-017mut4.fcs | 99.0 |
| -·-·- EXT017-27 + T2-017mut5.fcs | 95.4 |
| ——— EXT017-27 + T2-017mut7.fcs | 96.3 |
| - - - - - EXT017-27 + T2-017mut8.fcs | 6405 |
| -·-·- EXT017-27 + T2-017mut9.fcs | 131 |

Sensitive to positions: 1, 4, 5, 7, 9

| Sample Name | Median, PE-A |
|---|---|
| EXT017-28 + T2.fcs | 93.9 |
| EXT017-28 + T2-EXT017.fcs | 3.95E4 |
| EXT017-28 + T2-017mut1.fcs | 2.01E4 |
| EXT017-28 + T2-017mut2.fcs | 102 |
| EXT017-28 + T2-017mut3.fcs | 1.34E4 |
| EXT017-28 + T2-017mut4.fcs | 108 |
| EXT017-28 + T2-017mut5.fcs | 107 |
| EXT017-28 + T2-017mut7.fcs | 96.4 |
| EXT017-28 + T2-017mut8.fcs | 2.75E4 |
| EXT017-28 + T2-017mut9.fcs | 5891 |

Sensitive to positions: 4, 5, 7

| Sample Name | Median, PE-A |
|---|---|
| EXT017-32 + T2.fcs | 91.8 |
| EXT017-32 + T2-EXT017.fcs | 2.75E4 |
| EXT017-32 + T2-017mut1.fcs | 1.51E4 |
| EXT017-32 + T2-017mut2.fcs | 103 |
| EXT017-32 + T2-017mut3.fcs | 2.10E4 |
| EXT017-32 + T2-017mut4.fcs | 2.08E4 |
| EXT017-32 + T2-017mut5.fcs | 2713 |
| EXT017-32 + T2-017mut7.fcs | 99.6 |
| EXT017-32 + T2-017mut8.fcs | 96.7 |
| EXT017-32 + T2-017mut9.fcs | 93.6 |

Sensitive to positions: 7, 8, 9

| Sample Name | Median, PE-A |
|---|---|
| EXT017-53 + T2.fcs | 89.5 |
| EXT017-53 + T2-EXT017.fcs | 2.58E4 |
| EXT017-53 + T2-017mut1.fcs | 1102 |
| EXT017-53 + T2-017mut2.fcs | 95.3 |
| EXT017-53 + T2-017mut3.fcs | 5779 |
| EXT017-53 + T2-017mut4.fcs | 95.8 |
| EXT017-53 + T2-017mut5.fcs | 98.5 |
| EXT017-53 + T2-017mut7.fcs | 98.9 |
| EXT017-53 + T2-017mut8.fcs | 1.21E4 |
| EXT017-53 + T2-017mut9.fcs | 149 |

Sensitive to positions: 4, 5, 7, 9

| Sample Name | Median, PE-A |
|---|---|
| EXT017−54 + T2.fcs | 89.9 |
| EXT017−54 + T2−EXT017.fcs | 3.04E4 |
| EXT017−54 + T2−017mut1.fcs | 2.35E4 |
| EXT017−54 + T2−017mut2.fcs | 94.7 |
| EXT017−54 + T2−017mut3.fcs | 7776 |
| EXT017−54 + T2−017mut4.fcs | 374 |
| EXT017−54 + T2−017mut5.fcs | 91.2 |
| EXT017−54 + T2−017mut7.fcs | 91.1 |
| EXT017−54 + T2−017mut8.fcs | 5846 |
| EXT017−54 + T2−017mut9.fcs | 3535 |

Sensitive to positions: 4, 5, 7

T CELL RECEPTOR-LIKE ANTIBODIES SPECIFIC FOR FOXP3-DERIVED PEPTIDES

CROSS-REFERENCE TO RELATED APPLICATIONS

This application is a U.S. National Stage Patent Application under 35 U.S.C. § 371 of International Application No. PCT/US2017/013511, filed Jan. 13, 2017, which claims priority to U.S. Provisional Patent Application Ser. No. 62/278,815, filed Jan. 14, 2016, to each of which priority is claimed and the contents of each of which are incorporated herein in their entireties.

GRANT INFORMATION

This invention was made with government support under CA008748, CA055349 and CA023766 awarded by the National Institutes of Health. The government has certain rights in the invention.

SEQUENCE LISTING

The specification further incorporates by reference the Sequence Listing submitted herewith via EFS on Jul. 13, 2018. Pursuant to 37 C.F.R. § 1.52(e)(5), the Sequence Listing text file, identified as 0727340755SL.txt, is 256,130 bytes and was created on Jul. 13, 2018. The Sequence Listing, electronically filed herewith, does not extend beyond the scope of the specification and thus does not contain new matter.

TECHNICAL FIELD

The presently disclosed subject matter relates generally to antibodies against forkhead box P3 ("Foxp3"), specifically antibodies that recognize a Foxp3 peptide in conjunction with a major histocompatibility complex ("MHC") molecule.

BACKGROUND OF THE PRESENTLY DISCLOSED SUBJECT MATTER

For induction of cytotoxic T cell ("CTL") responses, intracellular proteins are usually degraded by the proteasome or endo/lysosomes, and the resulting peptide fragments bind to MHC class I or II molecules. These peptide-MHC complexes are displayed at the cell surface where they provide targets for T cell recognition via a peptide-MHC (pMHC)-T cell receptor ("TCR") interaction (Oka et al., The Scientific World Journal 2007; 7: 649-665; Kobayashi et al., Cancer Immunol. Immunother. 2006; 55 (7): 850-860).

To improve efficacy, cell marker antigens can be targeted with monoclonal antibody ("mAb") therapy. Mab therapy has been shown to exert powerful antitumor effects by multiple mechanisms, including complement-dependent cytotoxicity ("CDC"), antibody-dependent cellular cytotoxicity ("ADCC") and direct cell inhibition or apoptosis-inducing effects on cells which express target molecules and have the functions of suppressing anti-tumor immune responses and favoring tumor progression. Furthermore, mAb can be used as carriers to specifically deliver a cytotoxic moiety such as a radionuclide, cytotoxic drug or toxin to the target cells (Miederer et al., Adv Drug Deliv Rev 2008; 60 (12): 1371-1382).

A tremendous benefit would exist if, in addition to a cellular immunotherapy approach, a humoral immunotherapy approach was available to target non-cell surface antigens. Therefore, a mAb that mimics a T cell receptor in that it is specific for a target comprising a fragment of an intracellular protein in conjunction with an MHC molecule, for example, a Foxp3 peptide/HLA-A2 complex, would be a novel and effective therapeutic agent alone or as a vehicle capable of delivering potent anti-cancer reagents, such as drugs, toxins and radioactive elements. Such mAbs would also be useful as diagnostic or prognostic tools.

Regulatory T (Treg) cells expressing Foxp3 play a central role in maintaining self tolerance and immune homeostasis. Treg cells can suppress activation, proliferation and function of a wide variety of immune cells, including $CD4^+$, $CD8^+$ T cells, Natural killer ("NK") cells, NK-T cells, B cells, and antigen-presenting cells (APCs) in vitro and in vivo. The dysfunction of Treg cells, leads to autoimmune diseases, allergy and maintenance of allo-graft tolerance. On the other hand, Treg cells can also suppress anti-tumor immune responses and favor tumor progression, and thus immunosuppression by tumor-induced regulatory T (Treg) cells presents a major obstacle for successful immunotherapy. Treg cells are considered the most powerful inhibitors of anti-tumor immunity and the greatest barrier to successful immunotherapy. Treg expansion and their negative prognostic implications for tumor growth are general phenomena seen in many types of cancers Therefore, developing strategies to deplete Treg could help reactivate or stimulate immune responses against cancer cells. A number of strategies for depletion or interference with Treg function have been attempted, e.g., depletion of Treg by monoclonal antibodies (mAb) specific for CD25, glucorticoid-induced TNF-related protein (GITR) and ligand-directed toxins targeted to cell surface receptor CD25 (such as Dennileukin diftitox). However, both CD25 and GITR are expressed not only in Treg cells, but also in activated CD4 and CD8 effector T cells. The problem with these strategies is a lack of specificity of currently available agents, resulting in depletion of the beneficial anti-tumor effector T cells. The transcription factor forkhead box P3 (Foxp3) is essential to the establishment and suppressive function of Tregs and therefore would be a highly specific and ideal target for eliminating Treg cells. However, Foxp3 is an undruggable intracellular protein. Therefore, there is a large unmet need for drugs that selectively inhibit Treg cells.

SUMMARY OF THE PRESENTLY DISCLOSED SUBJECT MATTER

The presently disclosed subject matter identifies and characterizes antigen-binding proteins, such as antibodies and chimeric antigen receptors, that are able to target Foxp3 transcription factor. The presently disclosed antibodies target a peptide/MHC complex as it would typically appear on the surface of a cell following antigen processing of Foxp3 protein and presentation by the cell. In certain embodiments, a presently disclosed antibody is a T Cell Receptor mimics (TCRm) antibody. In certain embodiments, a TCRm antibody mimics T-cell receptors in that the antibodies have the ability to specifically recognize and bind to a peptide in an MHC-restricted fashion, that is, when the peptide is bound to an MHC antigen (e.g., a human MHC molecule). The peptide/MHC complex recapitulates the antigen as it would typically appear on the surface of a cell following antigen processing and presentation of the Foxp3 protein to a T-cell. In certain embodiments, TCRm antibodies are soluble antibodies that function like a T-Cell receptor in that they recognize the peptide presented in the HLA groove (versus the 3D topology of the complete protein from which the peptide comes) and can elicit the downstream T-cell immune effectors.

In certain non-limiting embodiments, the antibody or antigen-binding portion thereof either does not bind to its target Foxp3 peptide in the absence of its partner MHC molecule. In certain non-limiting embodiments, the antibody or antigen-binding portion thereof bind to its target Foxp3 peptide in the absence of its partner MHC molecule with a binding affinity which is at least 10-fold, or at least 100-fold, or at least 1000-fold less than the binding affinity of the antibody or antigen-binding portion thereof to the peptide/MHC complex.

The antibodies disclosed herein specifically recognize and bind to epitopes of a peptide/MHC complex (e.g., a Foxp3/HLA complex, more specifically, a Foxp3/HLA class I complex, more specifically, a Foxp3/HLA-A complex, and more specifically, a Foxp3/HLA-A2 complex, even more specifically, a Foxp3/HLA-A*02:01 complex). Examples of Foxp3 peptides that are recognized by the antigen-binding proteins of the presently disclosed subject matter as part of a human MHC-peptide complex include, but are not limited to, Foxp3-1 having the amino acid sequence set forth in SEQ ID NO: 2 or a portion thereof, Foxp3-2 having the amino acid sequence set forth in SEQ ID NO: 3 or a portion thereof, Foxp3-3 having the amino acid sequence set forth in SEQ ID NO: 4 or a portion thereof, Foxp3-4 having the amino acid sequence set forth in SEQ ID NO: 5 or a portion thereof, Foxp3-5 having the amino acid sequence set forth in SEQ ID NO: 6 or a portion thereof, Foxp3-6 having the amino acid sequence set forth in SEQ ID NO: 7 or a portion thereof, and Foxp3-7 having the amino acid sequence set forth in SEQ ID NO: 8 or a portion thereof.

In certain embodiments, therefore, the presently disclosed subject matter provides for an isolated antibody, or an antigen-binding portion thereof, which binds to a Foxp3 peptide bound to a human MHC molecule. The Foxp3 peptide binds to the MHC molecule to form a Foxp3/MHC complex. In certain embodiments, the MHC molecule is an HLA class I molecule. In certain embodiments, the HLA class I molecule is HLA-A. In certain embodiments, the HLA-A is HLA-A2. In certain embodiments, the HLA-A2 is HLA-A*02:01.

In certain embodiments, the Foxp3 peptide is a portion of a human Foxp3 polypeptide comprising the amino acid sequence set forth in SEQ ID NO: 1. In certain embodiments, the Foxp3 peptide has a length of 8-12 amino acids. In certain embodiments, the Foxp3 peptide has a length of 9 amino acids. In certain embodiments, the Foxp3 peptide has a length of 10 amino acids.

In certain embodiments, the antibody or antigen-binding portion binds to Foxp3-7 having the amino acid sequence set forth in SEQ ID NO: 8. In certain embodiments, the antibody or antigen-binding portion binds to a portion of Foxp3-7. In certain embodiments, the antibody or antigen-binding portion thereof that binds to Foxp3-7 or a portion thereof comprises a heavy chain variable region CDR3 sequence and a light chain variable region CDR3 sequence selected from the group consisting of (a) a heavy chain variable region CDR3 sequence comprising amino acid sequence set forth in SEQ ID NO: 11 or a modification thereof, and a light chain variable region CDR3 sequence comprising amino acid sequence set forth in SEQ ID NO: 14 or a modification thereof, (b) a heavy chain variable region CDR3 sequence comprising an amino acid sequence set forth in SEQ ID NO: 17 or a modification thereof, and a light chain variable region CDR3 sequence comprising amino an acid sequence set forth in SEQ ID NO: 20 or a modification thereof; (c) a heavy chain variable region CDR3 sequence comprising an amino acid sequence set forth in SEQ ID NO: 23 or a modification thereof, and a light chain variable region CDR3 sequence comprising an amino acid sequence set forth in SEQ ID NO: 26 or a modification thereof; (d) a heavy chain variable region CDR3 sequence comprising an amino acid sequence set forth in SEQ ID NO: 29 or a modification thereof, and a light chain variable region CDR3 sequence comprising an amino acid sequence set forth in SEQ ID NO: 32 or a modification thereof, (e) a heavy chain variable region CDR3 sequence comprising an amino acid sequence set forth in SEQ ID NO: 35 or a modification thereof, and a light chain variable region CDR3 sequence comprising an amino acid sequence set forth in SEQ ID NO: 38 or a modification thereof, (f) a heavy chain variable region CDR3 sequence comprising an amino acid sequence set forth in SEQ ID NO: 41 or a modification thereof, and a light chain variable region CDR3 sequence comprising an amino acid sequence set forth in SEQ ID NO: 44 or a modification thereof; (g) a heavy chain variable region CDR3 sequence comprising an amino acid sequence set forth in SEQ ID NO: 47 or a modification thereof, and a light chain variable region CDR3 sequence comprising an amino acid sequence set forth in SEQ ID NO: 50 or a modification thereof, and (h) a heavy chain variable region CDR3 sequence comprising an amino acid sequence set forth in SEQ ID NO: 53 or a modification thereof, and a light chain variable region CDR3 sequence comprising an amino acid sequence set forth in SEQ ID NO: 56 or a modification thereof. In certain embodiments, the antibody or antigen-binding portion thereof that binds to Foxp3-7 or a portion thereof further comprises a heavy chain variable region CDR2 sequence and a light chain variable region CDR2 sequence selected from the group consisting of: (a) a heavy chain variable region CDR2 sequence comprising an amino acid sequence set forth in SEQ ID NO: 10 or a modification thereof, and a light chain variable region CDR2 sequence comprising an amino acid sequence set forth in SEQ ID NO: 13 or a modification thereof, (b) a heavy chain variable region CDR2 sequence comprising an amino acid sequence set forth in SEQ ID NO: 16 or a modification thereof, and a light chain variable region CDR2 sequence comprising an amino acid sequence set forth in SEQ ID NO: 19 or a modification thereof; (c) a heavy chain variable region CDR2 sequence comprising an amino acid sequence set forth in SEQ ID NO: 22 or a modification thereof, and a light chain variable region CDR2 sequence comprising an amino acid sequence set forth in SEQ ID NO: 25 or a modification thereof; (d) a heavy chain variable region CDR2 sequence comprising an amino acid sequence set forth in SEQ ID NO: 28 or a modification thereof, and a light chain variable region CDR2 sequence comprising an amino acid sequence set forth in SEQ ID NO: 31 or a modification thereof; (e) a heavy chain variable region CDR2 sequence comprising an amino acid sequence set forth in SEQ ID NO: 34 or a modification thereof, and a light chain variable region CDR2 sequence comprising an amino acid sequence set forth in SEQ ID NO: 37 or a modification thereof; (f) a heavy chain variable region CDR2 sequence comprising an amino acid sequence set forth in SEQ ID NO: 40 or a modification thereof, and a light chain variable region CDR2 sequence comprising an amino acid sequence set forth in SEQ ID NO: 43 or a modification thereof; (g) a heavy chain variable region CDR2 sequence comprising an amino acid sequence set forth in SEQ ID NO: 46 or a modification thereof, and a light chain variable region CDR2 sequence comprising an amino acid sequence set forth in SEQ ID NO: 49 or a modification thereof; and (h) a heavy chain variable region CDR2 sequence comprising an amino acid sequence set forth in SEQ ID NO: 52 or a modification thereof, and a light chain variable region CDR2 sequence comprising an amino acid sequence set forth in SEQ ID NO: 55 or a modification thereof. In certain embodiments, the antibody or antigen-binding portion thereof that binds to Foxp3-7 or a portion thereof further comprises a heavy chain variable region CDR1 sequence and a light chain variable region CDR1 sequence selected from the group consisting of: (a) a heavy chain variable region CDR1 sequence comprising an amino acid sequence set forth in SEQ ID NO: 9 or a modification thereof, and a light chain variable region CDR1 sequence comprising an amino acid sequence set forth in SEQ ID NO: 12 or a modification thereof; (b) a heavy chain variable region CDR1 sequence comprising an amino acid sequence set forth in SEQ ID NO: 15 or a modification thereof, and a light chain variable region CDR1 sequence comprising an amino acid sequence set forth in SEQ ID NO: 18 or a modification thereof; (c) a heavy chain variable region CDR1 sequence comprising an amino acid sequence set forth in SEQ ID NO: 21 or a modification thereof, and a light chain variable region CDR1 sequence comprising an amino acid sequence set forth in SEQ ID NO: 24 or a modification thereof, (d) a heavy chain variable region CDR1 sequence comprising an amino acid sequence set forth in SEQ ID NO: 27 or a modification thereof, and a light chain variable region CDR1 sequence comprising an amino acid sequence set forth in SEQ ID NO: 30 or a modification thereof; (e) a heavy chain variable region CDR1 sequence comprising an amino acid sequence set forth in SEQ ID NO: 33 or a modification thereof, and a light chain variable region CDR1 sequence comprising an amino acid sequence set forth in SEQ ID NO: 36 or a modification thereof; (f) a heavy chain variable region CDR1 sequence comprising an amino acid sequence set forth in SEQ ID NO: 39 or a modification thereof, and a light chain variable region CDR1 sequence comprising an amino acid sequence set forth in SEQ ID NO: 42 or a modification thereof, (g) a heavy chain variable region CDR1 sequence comprising an amino acid sequence set forth in SEQ ID NO: 45 or a modification thereof, and a light chain variable region CDR1 sequence comprising an amino acid sequence set forth in SEQ ID NO: 48 or a modification thereof, and (h) a heavy chain variable region CDR1 sequence comprising an amino acid sequence set forth in SEQ ID NO: 51 or a modification thereof, and a light chain variable region CDR1 sequence comprising an amino acid sequence set forth in SEQ ID NO: 54 or a modification thereof.

In certain embodiments, the antibody or antigen-binding portion thereof that binds to Foxp3-7 or a portion thereof comprises (a) a heavy chain variable region CDR1 comprising an amino acid sequence set forth in SEQ ID NO: 9; a heavy chain variable region CDR2 comprising an amino acid sequence set forth in SEQ ID NO: 10; a heavy chain variable region CDR3 comprising an amino acid sequence set forth in SEQ ID NO: 11; a light chain variable region CDR1 comprising an amino acid sequence set forth in SEQ ID NO: 12; a light chain variable region CDR2 comprising an amino acid sequence set forth in SEQ ID NO: 13; and a light chain variable region CDR3 comprising an amino acid sequence set forth in SEQ ID NO: 14; (b) a heavy chain variable region CDR1 comprising an amino acid sequence set forth in SEQ ID NO: 15; a heavy chain variable region CDR2 comprising an amino acid sequence set forth in SEQ ID NO: 16; a heavy chain variable region CDR3 comprising an amino acid sequence set forth in SEQ ID NO: 17; a light chain variable region CDR1 comprising an amino acid sequence set forth in SEQ ID NO: 18; a light chain variable region CDR2 comprising an amino acid sequence set forth in SEQ ID NO: 19; and a light chain variable region CDR3 comprising an amino acid sequence set forth in SEQ ID NO: 20; (c) a heavy chain variable region CDR1 comprising an amino acid sequence set forth in SEQ ID NO: 21; a heavy chain variable region CDR2 comprising an amino acid sequence set forth in SEQ ID NO: 22; a heavy chain variable region CDR3 comprising an amino acid sequence set forth in SEQ ID NO: 23; a light chain variable region CDR1 comprising an amino acid sequence set forth in SEQ ID NO: 24; a light chain variable region CDR2 comprising an amino acid sequence set forth in SEQ ID NO: 25; and a light chain variable region CDR3 comprising an amino acid sequence set forth in SEQ ID NO: 26; (d) a heavy chain variable region CDR1 comprising an amino acid sequence set forth in SEQ ID NO: 27; a heavy chain variable region CDR2 comprising an amino acid sequence set forth in SEQ ID NO: 28; a heavy chain variable region CDR3 comprising an amino acid sequence set forth in SEQ ID NO: 29; a light chain variable region CDR1 comprising an amino acid sequence set forth in SEQ ID NO: 30; a light chain variable region CDR2 comprising an amino acid sequence set forth in SEQ ID NO: 31; and a light chain variable region CDR3 comprising an amino acid sequence set forth in SEQ ID NO: 32; (e) a heavy chain variable region CDR1 comprising an amino acid sequence set forth in SEQ ID NO: 33; a heavy chain variable region CDR2 comprising an amino acid sequence set forth in SEQ ID NO: 34; a heavy chain variable region CDR3 comprising an amino acid sequence set forth in SEQ ID NO: 35; a light chain variable region CDR1 comprising an amino acid sequence set forth in SEQ ID NO: 36; a light chain variable region CDR2 comprising an amino acid sequence set forth in SEQ ID NO: 37; and a light chain variable region CDR3 comprising an amino acid sequence set forth in SEQ ID NO: 38; (f) a heavy chain variable region CDR1 comprising an amino acid sequence set forth in SEQ ID NO: 39; a heavy chain variable region CDR2 comprising an amino acid sequence set forth in SEQ ID NO: 40; a heavy chain variable region CDR3 comprising an amino acid sequence set forth in SEQ ID NO: 41; a light chain variable region CDR1 comprising an amino acid sequence set forth in SEQ ID NO: 42; a light chain variable region CDR2 comprising an amino acid sequence set forth in SEQ ID NO: 43; and a light chain variable region CDR3 comprising an amino acid sequence set forth in SEQ ID NO: 44; (g) a heavy chain variable region CDR1 comprising an amino acid sequence set forth in SEQ ID NO: 45; a heavy chain variable region CDR2 comprising an amino acid sequence set forth in SEQ ID NO: 46; a heavy chain variable region CDR3 comprising an amino acid sequence set forth in SEQ ID NO: 47; a light chain variable region CDR1 comprising an amino acid sequence set forth in SEQ ID NO: 48; a light chain variable region CDR2 comprising an amino acid sequence set forth in SEQ ID NO: 49; and a light chain variable region CDR3 comprising an amino acid sequence set forth in SEQ ID NO: 50; or (h) a heavy chain variable region CDR1 comprising an amino acid sequence set forth in SEQ ID NO: 51; a heavy chain variable region CDR2 comprising an amino acid sequence set forth in SEQ ID NO: 52; a heavy chain variable region CDR3 comprising an amino acid sequence set forth in SEQ ID NO: 53; a light chain variable region CDR1 comprising an amino acid sequence set forth in SEQ ID NO: 54; a light chain variable region CDR2 comprising an amino acid sequence set forth in SEQ ID NO:

55; and a light chain variable region CDR3 comprising an amino acid sequence set forth in SEQ ID NO: 56. In certain embodiments, the antibody or antigen-binding portion thereof that binds to Foxp3-7 or a portion thereof comprises a heavy chain variable region CDR1 comprising an amino acid sequence set forth in SEQ ID NO: 39; a heavy chain variable region CDR2 comprising an amino acid sequence set forth in SEQ ID NO: 40; a heavy chain variable region CDR3 comprising an amino acid sequence set forth in SEQ ID NO: 41; a light chain variable region CDR1 comprising an amino acid sequence set forth in SEQ ID NO: 42; a light chain variable region CDR2 comprising an amino acid sequence set forth in SEQ ID NO: 43; and a light chain variable region CDR3 comprising an amino acid sequence set forth in SEQ ID NO: 44.

In certain embodiments, the antibody or antigen-binding portion thereof that binds to Foxp3-7 or a portion thereof comprises a heavy chain variable region that comprises an amino acid sequence that is at least about 80% homologous, or at least about 90% homologous, or at least about 95% homologous, or at least about 98% homologous, to the sequence selected from the group consisting of SEQ ID NOS: 93, 95, 97, 99, 101, 103, 105, and 107, and/or a light chain variable region that comprises an amino acid sequence that is at least about 80% homologous, or at least about 90% homologous, or at least about 95% homologous, or at least about 98% homologous, to the sequence selected from the group consisting of SEQ ID NOS: 94, 96, 98, 100, 102, 104, 106, and 108. Such antibody or antigen-binding portion thereof comprises (a) a heavy chain variable region comprising an amino acid sequence set forth in SEQ ID NO: 93, and a light chain variable region that comprising an amino acid sequence set forth in SEQ ID NO: 94; (b) a heavy chain variable region comprising an amino acid sequence set forth in SEQ ID NO: 95, and a light chain variable region that comprising an amino acid sequence set forth in SEQ ID NO: 96; (c) a heavy chain variable region comprising an amino acid sequence set forth in SEQ ID NO: 97, and a light chain variable region that comprising an amino acid sequence set forth in SEQ ID NO: 98; (d) a heavy chain variable region comprising an amino acid sequence set forth in SEQ ID NO: 99, and a light chain variable region that comprising an amino acid sequence set forth in SEQ ID NO: 100; (e) a heavy chain variable region comprising an amino acid sequence set forth in SEQ ID NO: 101, and a light chain variable region that comprising an amino acid sequence set forth in SEQ ID NO: 102; (f) a heavy chain variable region comprising an amino acid sequence set forth in SEQ ID NO: 103, and a light chain variable region that comprising an amino acid sequence set forth in SEQ ID NO: 104; (g) a heavy chain variable region comprising an amino acid sequence set forth in SEQ ID NO: 105, and a light chain variable region that comprising an amino acid sequence set forth in SEQ ID NO: 106; or (h) a heavy chain variable region comprising an amino acid sequence set forth in SEQ ID NO: 107, and a light chain variable region that comprising an amino acid sequence set forth in SEQ ID NO: 108. In certain embodiments, the antibody or antigen-binding portion thereof that binds to Foxp3-7 or a portion thereof comprises a heavy chain variable region comprising an amino acid sequence set forth in SEQ ID NO: 103, and a light chain variable region that comprising an amino acid sequence set forth in SEQ ID NO: 104.

In certain embodiments, the antibody or antigen-binding portion binds to Foxp3-2 having the amino acid sequence set forth in SEQ ID NO: 3 or a portion thereof. In certain embodiments, the antibody or antigen-binding portion thereof that binds to Foxp3-2 or a portion thereof comprises a heavy chain variable region CDR3 sequence and a light chain variable region CDR3 sequence selected from the group consisting of: (a) a heavy chain variable region CDR3 sequence comprising an amino acid sequence set forth in SEQ ID NO: 59 or a modification thereof, and a light chain variable region CDR3 sequence comprising an amino acid sequence set forth in SEQ ID NO: 62 or a modification thereof (b) a heavy chain variable region CDR3 sequence comprising an amino acid sequence set forth in SEQ ID NO: 65 or a modification thereof, and a light chain variable region CDR3 sequence comprising an amino acid sequence set forth in SEQ ID NO: 68 or a modification thereof; (c) a heavy chain variable region CDR3 sequence comprising an amino acid sequence set forth in SEQ ID NO: 71 or a modification thereof, and a light chain variable region CDR3 sequence comprising an amino acid sequence set forth in SEQ ID NO: 74 or a modification thereof, (d) a heavy chain variable region CDR3 sequence comprising an amino acid sequence set forth in SEQ ID NO: 77 or a modification thereof, and a light chain variable region CDR3 sequence comprising an amino acid sequence set forth in SEQ ID NO: 80 or a modification thereof, and (e) a heavy chain variable region CDR3 sequence comprising an amino acid sequence set forth in SEQ ID NO: 83 or a modification thereof, and a light chain variable region CDR3 sequence comprising an amino acid sequence set forth in SEQ ID NO: 86 or a modification thereof. In certain embodiments, the antibody or antigen-binding portion thereof that binds to Foxp3-2 or a portion thereof further comprises a heavy chain variable region CDR2 sequence and a light chain variable region CDR2 sequence selected from the group consisting of: (a) a heavy chain variable region CDR2 sequence comprising an amino acid sequence set forth in SEQ ID NO: 58 or a modification thereof, and a light chain variable region CDR2 sequence comprising an amino acid sequence set forth in SEQ ID NO: 61 or a modification thereof; (b) a heavy chain variable region CDR2 sequence comprising an amino acid sequence set forth in SEQ ID NO: 64 or a modification thereof, and a light chain variable region CDR2 sequence comprising an amino acid sequence set forth in SEQ ID NO: 67 or a modification thereof; (c) a heavy chain variable region CDR2 sequence comprising an amino acid sequence set forth in SEQ ID NO: 70 or a modification thereof, and a light chain variable region CDR2 sequence comprising an amino acid sequence set forth in SEQ ID NO: 73 or a modification thereof; (d) a heavy chain variable region CDR2 sequence comprising an amino acid sequence set forth in SEQ ID NO: 76 or a modification thereof, and a light chain variable region CDR2 sequence comprising an amino acid sequence set forth in SEQ ID NO: 79 or a modification thereof, and (e) a heavy chain variable region CDR2 sequence comprising an amino acid sequence set forth in SEQ ID NO: 82 or a modification thereof, and a light chain variable region CDR2 sequence comprising an amino acid sequence set forth in SEQ ID NO: 85 or a modification thereof. In certain embodiments, the antibody or antigen-binding portion thereof that binds to Foxp3-2 or a portion thereof further comprises a heavy chain variable region CDR1 sequence and a light chain variable region CDR1 sequence selected from the group consisting of: (a) a heavy chain variable region CDR1 sequence comprising an amino acid sequence set forth in SEQ ID NO: 57 or a modification thereof, and a light chain variable region CDR1 sequence comprising an amino acid sequence set forth in SEQ ID NO: 60 or a modification thereof, (b) a heavy chain variable region CDR1 sequence comprising an amino acid sequence set forth in SEQ ID NO: 63 or a modification thereof, and a light chain variable region CDR1 sequence comprising an amino acid sequence set forth in SEQ ID NO: 66 or a modification thereof; (c) a heavy chain variable region CDR1 sequence comprising an amino acid sequence set forth in SEQ ID NO: 69 or a modification thereof, and a light chain variable region CDR1 sequence comprising an amino acid sequence set forth in SEQ ID NO: 71 or a modification thereof, (d) a heavy chain variable region CDR1 sequence comprising an amino acid sequence set forth in SEQ ID NO: 75 or a modification thereof, and a light chain variable region CDR1 sequence comprising an amino acid sequence set forth in SEQ ID NO: 78 or a modification thereof; and (e) a heavy chain variable region CDR1 sequence comprising an amino acid sequence set forth in SEQ ID NO: 81 or a modification thereof, and a light chain variable region CDR1 sequence comprising an amino acid sequence set forth in SEQ ID NO: 84 or a modification thereof.

In certain embodiments, the antibody or antigen-binding portion thereof that binds to Foxp3-2 or a portion thereof comprises (a) a heavy chain variable region CDR1 comprising an amino acid sequence set forth in SEQ ID NO: 57; a heavy chain variable region CDR2 comprising an amino acid sequence set forth in SEQ ID NO: 58; a heavy chain variable region CDR3 comprising an amino acid sequence set forth in SEQ ID NO: 59; a light chain variable region CDR1 comprising an amino acid sequence set forth in SEQ ID NO: 60; a light chain variable region CDR2 comprising an amino acid sequence set forth in SEQ ID NO: 61; and a light chain variable region CDR3 comprising an amino acid sequence set forth in SEQ ID NO: 62; (b) a heavy chain variable region CDR1 comprising an amino acid sequence set forth in SEQ ID NO: 63; a heavy chain variable region CDR2 comprising an amino acid sequence set forth in SEQ ID NO: 64; a heavy chain variable region CDR3 comprising an amino acid sequence set forth in SEQ ID NO: 65; a light chain variable region CDR1 comprising an amino acid sequence set forth in SEQ ID NO: 66; a light chain variable region CDR2 comprising an amino acid sequence set forth in SEQ ID NO: 67; and a light chain variable region CDR3 comprising an amino acid sequence set forth in SEQ ID NO: 68; (c) a heavy chain variable region CDR1 comprising an amino acid sequence set forth in SEQ ID NO: 69; a heavy chain variable region CDR2 comprising an amino acid sequence set forth in SEQ ID NO: 70; a heavy chain variable region CDR3 comprising an amino acid sequence set forth in SEQ ID NO: 71; a light chain variable region CDR1 comprising an amino acid sequence set forth in SEQ ID NO: 72; a light chain variable region CDR2 comprising an amino acid sequence set forth in SEQ ID NO: 73; and a light chain variable region CDR3 comprising an amino acid sequence set forth in SEQ ID NO: 74; (d) a heavy chain variable region CDR1 comprising an amino acid sequence set forth in SEQ ID NO: 75; a heavy chain variable region CDR2 comprising an amino acid sequence set forth in SEQ ID NO: 76; a heavy chain variable region CDR3 comprising an amino acid sequence set forth in SEQ ID NO: 77; a light chain variable region CDR1 comprising an amino acid sequence set forth in SEQ ID NO: 78; a light chain variable region CDR2 comprising an amino acid sequence set forth in SEQ ID NO: 79; and a light chain variable region CDR3 comprising an amino acid sequence set forth in SEQ ID NO: 80; or (e) a heavy chain variable region CDR1 comprising an amino acid sequence set forth in SEQ ID NO: 81; a heavy chain variable region CDR2 comprising an amino acid sequence set forth in SEQ ID NO: 82; a heavy chain variable region CDR3 comprising an amino acid sequence set forth in SEQ ID NO: 83; a light chain variable region CDR1 comprising an amino acid sequence set forth in SEQ ID NO: 84; a light chain variable region CDR2 comprising an amino acid sequence set forth in SEQ ID NO: 85; and a light chain variable region CDR3 comprising an amino acid sequence set forth in SEQ ID NO: 86.

In certain embodiments, the antibody or antigen-binding portion thereof that binds to Foxp3-2 or a portion thereof comprises a heavy chain variable region that comprises an amino acid sequence that is at least about 80% homologous to the sequence selected from the group consisting of SEQ ID NOS: 109, 111, 113, 115, and 117, and/or a light chain variable region that comprises an amino acid sequence that is at least about 80% homologous, or at least about 90% homologous, or at least about 95% homologous, or at least about 98% homologous, to the sequence selected from the group consisting of SEQ ID NOS: 110, 112, 114, 116, and 118. Such antibody or antigen-binding portion thereof comprises (a) a heavy chain variable region comprising an amino acid sequence set forth in SEQ ID NO: 109, and a light chain variable region that comprising an amino acid sequence set forth in SEQ ID NO: 110; (b) a heavy chain variable region comprising an amino acid sequence set forth in SEQ ID NO: 111, and a light chain variable region that comprising an amino acid sequence set forth in SEQ ID NO: 112; (c) a heavy chain variable region comprising an amino acid sequence set forth in SEQ ID NO: 113, and a light chain variable region that comprising an amino acid sequence set forth in SEQ ID NO: 114; (d) a heavy chain variable region comprising an amino acid sequence set forth in SEQ ID NO: 115, and a light chain variable region that comprising an amino acid sequence set forth in SEQ ID NO: 116; or (e) a heavy chain variable region comprising an amino acid sequence set forth in SEQ ID NO: 117, and a light chain variable region that comprising an amino acid sequence set forth in SEQ ID NO: 118.

In certain embodiments, the antibody or antigen-binding portion binds to Foxp3-4 having the amino acid sequence set forth in SEQ ID NO: 5 or a portion thereof. In certain embodiments, the antibody or antigen-binding portion thereof that binds to Foxp3-2 or a portion thereof comprises a heavy chain variable region CDR1 comprising an amino acid sequence set forth in SEQ ID NO: 87 or a modification thereof; a heavy chain variable region CDR2 comprising an amino acid sequence set forth in SEQ ID NO: 88 or a modification thereof; a heavy chain variable region CDR3 comprising an amino acid sequence set forth in SEQ ID NO: 89 or a modification thereof; a light chain variable region CDR1 comprising an amino acid sequence set forth in SEQ ID NO: 90 or a modification thereof; a light chain variable region CDR2 comprising an amino acid sequence set forth in SEQ ID NO: 91 or a modification thereof, and a light chain variable region CDR3 comprising an amino acid sequence set forth in SEQ ID NO: 92 or a modification thereof.

In certain embodiments, the antibody or antigen-binding portion thereof that binds to Foxp3-4 or a portion thereof comprises a heavy chain variable region that comprises an amino acid sequence that is at least about 80% homologous, or at least about 90% homologous, or at least about 95% homologous, or at least about 98% homologous, to the sequence of SEQ ID NO: 119, and/or a light chain variable region that comprises an amino acid sequence that is at least about 80% homologous to the sequence of SEQ ID NOS: 120. In certain embodiments, the antibody or antigen-binding portion thereof that binds to Foxp3-4 or a portion thereof comprises a heavy chain variable region that comprises the amino acid sequence set forth in SEQ ID NO: 119, and/or a light chain variable region that comprises the amino acid sequence set forth in SEQ ID NOS: 120

The modification can be one or more deletions, insertions, and/or substitutions. The modification thereof can comprise no more than 2, no more than 3, no more than 4, or no more than 5 modifications. The modification can be a conservative modification or non-a conservative modification.

In certain embodiments, the antibody or antigen-binding portion thereof binds to the N-terminal of the Foxp3 peptide. In certain embodiments, the antibody or antigen-binding portion thereof binds to C-terminal of the Foxp3 peptide. The antibody or antigen-binding portion thereof specifically binds to the Foxp3 peptide, e.g., binds to the Foxp3 peptide with a binding affinity ($K_D$) of $1\times10^{-7}$ M or less.

The presently disclosed subject matter also provides for isolated antibodies or antigen-binding portions thereof, which (i) cross-compete for binding to a Foxp3 peptide bound to a human MHC molecule with any of the antibodies or antigen-binding portions thereof disclosed herein, and (ii) specifically bind to the Foxp3 peptide with a binding affinity ($K_D$) of about $5\times10^{-7}$ M or less.

In certain non-limiting embodiments, the antibody or antigen-binding portion thereof either does not bind to its target Foxp3 peptide in the absence of its partner MHC molecule, or does so with an affinity which is at least 10-fold, or at least 100-fold, or at least 1000-fold less.

The presently disclosed subject matter further provides for isolated antibodies or antigen-binding portions thereof, which bind to the same or a substantially overlapping equivalent epitope on Foxp3 peptide bound to a human MHC molecule with any of the antibodies or antigen-binding portions thereof disclosed herein.

In certain embodiments, the antibody or antigen-binding portion thereof is a fully human antibody or an antigen-binding portion thereof. In certain embodiments, the antibody or antigen-binding portion thereof is a chimeric antibody or an antigen-binding portion thereof. In certain embodiments, the antibody or antigen-binding portion thereof is a humanized antibody or an antigen-binding portion thereof. In certain embodiments, the antigen-binding portion of the antibody is an Fab, Fab', F(ab')2, Fv or single chain Fv (scFv). In certain embodiments, the antibody or antigen-binding portion thereof is of an IgG1, IgG2, IgG3, or IgG4 isotype. In certain embodiments, the antibody or antigen-binding portion thereof is of an IgG1 isotype. In certain embodiments, an antigen binding portion is comprised in a fusion protein with one or more non-immunoglobulin component.

In certain embodiments, the above-described antibody comprises one or more post-translational modifications. In certain non-limiting embodiments, the one or more post-translational modifications comprise afucosylation. For example, the antibody comprises an afucosylated Fc region.

In another aspect, the presently disclosed subject matter provides for an immunoconjugate comprising a first component which is an antigen-binding protein, antibody or antigen-binding portion thereof as disclosed herein. The immunoconjugate comprises a second component that is a cytotoxin, a detectable label, a radioisotope, a therapeutic agent, a binding protein or a molecule having a second amino acid sequence. Where the second component is a binding protein or second antibody, the binding protein or second antibody has binding specificity for a target that is different from the HLA-peptide complex for which the first is specific.

In a related aspect, therefore, the presently disclosed subject matter provides for a bispecific antibody comprising an antigen-binding protein or functional fragment thereof as described herein. In certain embodiments, the bispecific antibody recognizes the Foxp3 peptide bound to the MHC molecule (Foxp3/MHC complex), and a cell surface protein. In certain embodiments, the cell surface protein is CD3 or CD16.

In yet another aspect, the presently disclosed subject matter provides for antigen-binding proteins, including antibodies and chimeric antigen receptors (CARs) specific for a Foxp3 peptide/HLA complex, e.g., a Foxp3/HLA class I complex, more specifically, a Foxp3/HLA-A complex, and more specifically, a Foxp3/HLA-A2 complex, even more specifically, a Foxp3/HLA-A*02:01 complex. The presently disclosed subject matter also provides for nucleic acid encoding the presently disclosed CARs, vectors comprising such nucleic acids, including vectors to facilitate expression and/or secretion of an antigen-binding protein (e.g., an antibody or CAR) in accordance with the presently disclosed subject matter.

In another related aspect, the presently disclosed subject matter provides for host cells comprising the nucleic acids or antigen-binding proteins disclosed herein, including recombinant immune effector cells, such as, T-cells genetically modified to express a CAR comprising an antigen-binding region in accordance with the presently disclosed subject matter. In certain embodiments, the host cell is a T cell. In certain embodiments, the host cell is a Treg cell. Cells that have been engineered to produce antibodies in accordance with the disclosure are also encompassed by the presently disclosed subject matter.

In a related aspect, the presently disclosed subject matter provides for pharmaceutical compositions comprising the antigen-binding proteins, antibodies, nucleic acids, vectors, or cells comprising the nucleic acids or antigen-binding proteins disclosed herein, together with a pharmaceutically acceptable carrier.

In another aspect, the presently disclosed subject matter provides for a method for detecting Foxp3/MHC on the surface of cells or tissues using Foxp3 antibodies of the presently disclosed subject matter.

In another aspect, the presently disclosed subject matter provides for methods of killing a Foxp3-expressing cell in a subject. In certain embodiments, the method comprises administering to the subject an antibody or antigen-binding portion thereof (including bispecific antibody), an antigen-binding protein (including CAR), an immunoconjugate, nucleic acid encoding the antigen-binding protein or antibody or a cell comprising the nucleic acids or proteins as disclosed herein.

In another aspect, the presently disclosed subject matter provides for methods of inducing an immune response in a subject. In certain embodiments, the method comprises administering to the subject an antibody or antigen-binding portion thereof (including bispecific antibody), an antigen-binding protein (including CAR), an immunoconjugate, nucleic acid encoding the antigen-binding protein or antibody or a cell comprising the nucleic acids or proteins as disclosed herein.

In another aspect, the presently disclosed subject matter provides for methods of selectively inhibiting (e.g., inactivating, inhibiting the proliferation of or killing) regulatory T cells in a subject. In certain embodiments, the method comprises administering to the subject an antibody or antigen-binding portion thereof (including bispecific antibody), an antigen-binding protein (including CAR), an immunoconjugate, nucleic acid encoding the antigen-binding protein or antibody or a cell comprising the nucleic acids or proteins as disclosed herein. In certain embodiments, the method reduces number of regulatory T cells, depletes regulatory T cells, inhibits immunosuppressive activity of regulatory T cells, and/or blocks regulatory T cells trafficking into lymph nodes or tumors.

In yet another aspect, the presently disclosed subject matter provides for methods for treating cancer, comprising administering to a subject suffering cancer a therapeutically effective amount of an antibody or antigen-binding portion thereof (including bispecific antibody), an antigen-binding protein (e.g., a CAR), an immunoconjugate, nucleic acid encoding the antigen-binding protein or antibody or a cell comprising the nucleic acids or proteins as disclosed herein, thereby inducing the death of the cancer cell in the subject. In certain embodiments, the cancer is selected from the group consisting of breast cancer, ovarian cancer, melanoma, lung cancer, pancreatic cancer, gastric cancer, colon cancer, glioblastoma, kidney cancer, liver cancer, lymphoma, leukemia, myeloma, sarcoma, and combinations thereof. In certain embodiments, the subject is a human. In certain embodiments, the subject is a non-human animal such as but not limited to a non-human primate, a dog, a cat, a horse, a cow, a pig, a mouse, a rat, a hamster, a rabbit, etc. In certain embodiments, the cancer cell expresses Foxp3.

Furthermore, the presently disclosed subject matter provides for kits for treating cancer comprising an antibody or antigen-binding portion thereof (including bispecific antibody), an antigen-binding protein (including CAR), an immunoconjugate, nucleic acid encoding the antigen-binding protein or antibody or a cell comprising the nucleic acids or proteins as disclosed herein.

BRIEF DESCRIPTION OF THE DRAWINGS

FIGS. 8A-8B represent epitope specificity. (A) The Foxp3-TLI peptide sequence was substituted with alanine at positions 1, 2, 3, 4, 5, 7, 8, 9 or with glycine (G10) at position ten (sequences in FIGS. 8A-8B). T2 cells were pulsed with indicated peptides at 50 ug/ml and the binding of #32-BITE was measured by flow cytometry. FIG. 8A discloses SEQ ID NOS: 8 and 144-152, respectively, in order of appearance. (B) Cells were simultaneously stained with anti-HLA-A2 mAb, clone BB7.2, to measure the relative binding of the peptides to HLA-A2 molecule. FIG. 8B discloses SEQ ID NOS: 8 and 144-152, respectively, in order of appearance.

DETAILED DESCRIPTION

I. Definitions

Figure 1A:
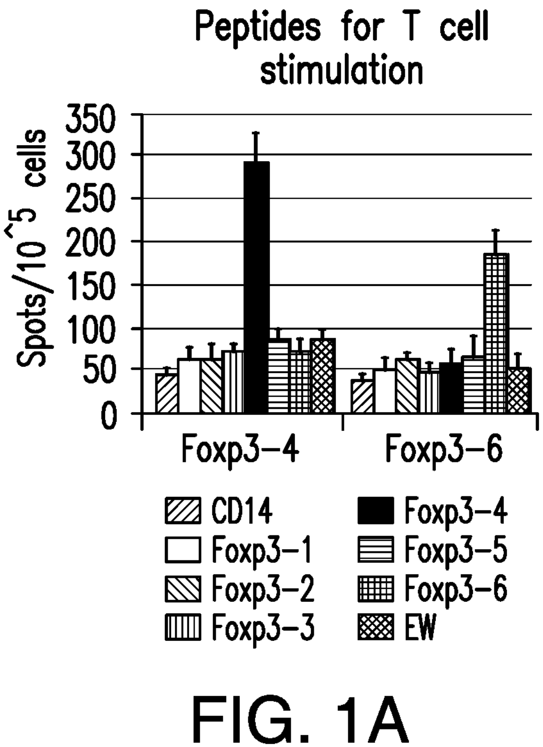
FIGS. 1A-1D represent peptide-specific T-cell response of Foxp3 peptides. (A) CD3 T cells from HLA-A*02:01 (also referred to as "HLA-A0201" or "HLA-A*0201") donors were stimulated with Foxp3-4 or Foxp3-6 peptides for 3 rounds and T cell response was tested against Foxp3-1, -2, -3, -4, -5 or -6 peptides by IFN-g elispot assay. (B) T cells from the same donor were further stimulated another 2 rounds with the Foxp3-4 or -6 peptide and tested against Foxp3-4 or Foxp3-6 peptide. (C and D) T cells from a different HLA-A2$^+$ donor were stimulated with Foxp3-1 or -3 (3 rounds), or Foxp3-2 or -5 peptide (5 rounds) and the peptide-specific T cell response was tested against the stimulating peptide. Controls: CD14$^+$ APCs and CD14$^+$ cells pulsed with irrelevant peptide EW. Data represent the mean value+/−SD from triplicate micro-well cultures.
Figure 1C:
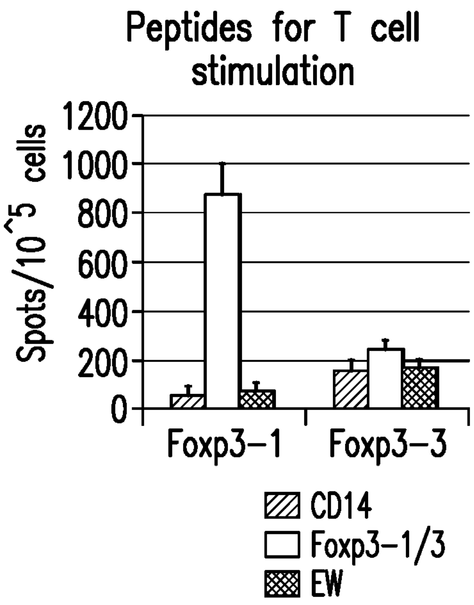
Figure 1B:
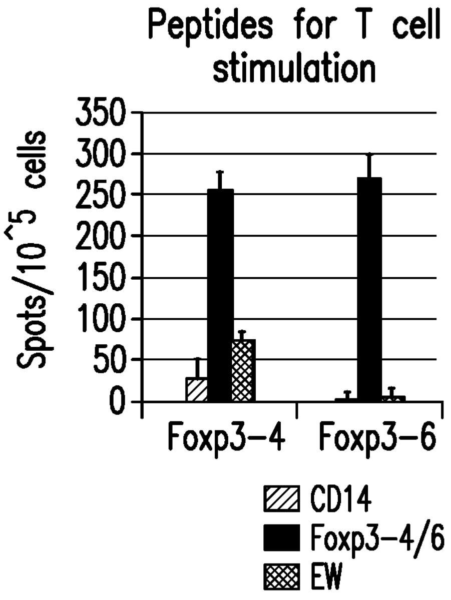
Figure 1D:
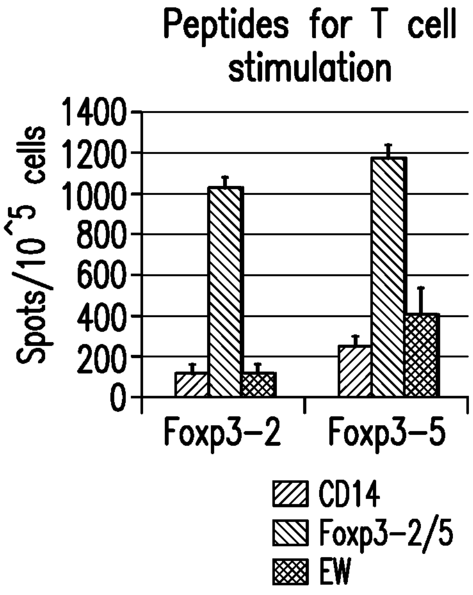

Unless defined otherwise, all technical and scientific terms used herein have the meaning commonly understood by a person skilled in the art to which this invention belongs. The following references provide one of ordinary skill in the art with a general definition of many of the terms used in the presently disclosed subject matter: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991); Molecular Cloning: a Laboratory Manual 3rd edition, J. F. Sambrook and D. W. Russell, ed. Cold Spring Harbor Laboratory Press 2001; Recombinant Antibodies for Immunotherapy, Melvyn Little, ed. Cambridge University Press 2009; "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988); "Phage Display: A Laboratory Manual" (Barbas et al., 2001). The contents of these references and other references containing standard protocols, widely known to and relied upon by those of skill in the art, including manufacturers' instructions are hereby incorporated by reference as part of the presently disclosed subject matter. As used herein, the following terms have the meanings ascribed to them below, unless specified otherwise.

The following abbreviations are used throughout the present application:

Ab: Antibody
ADCC: Antibody-dependent cellular cytotoxicity
ALL: Acute lymphocytic leukemia
AML: Acute myeloid leukemia
APC: Antigen presenting cell
132M: Beta-2-microglobulin
BITE: Bi-specific T cell engaging antibody
CAR: Chimeric antigen receptor
CDC: Complement dependent cytotoxicity CMC: Complement mediated cytotoxicity
CDR: Complementarity determining region
$C_L$: Constant domain of the light chain
$CH_1$: 1st constant domain of the heavy chain
$CH_{1, 2, 3}$: 1st, 2nd and 3rd constant domains of the heavy chain
$CH_{2, 3}$: 2nd and 3rd constant domains of the heavy chain
CHO: Chinese hamster ovary
CTL: Cytotoxic T cell
E:T Ratio: Effector:Target ratio
Fab: Antibody binding fragment
FACS: Flow assisted cytometric cell sorting
FBS: Fetal bovine serum
FR: Framework region
HC: Heavy chain
HLA: Human leukocyte antigen
Ig: Immunoglobulin
IRES: Internal ribosome entry site
$K_D$: Dissociation constant
$k_{off}$: Dissociation rate
$k_{on}$: Association rate
MHC: Major histocompatibility complex
MM: Multiple myeloma
scFv: Single-chain variable fragment
TCR: T cell receptor
TIL: Tumor infiltration lymphocyte
TLI: Foxp3-7 peptide (sequence TLIRWAILEA (SEQ ID NO: 8))
$V_H$: Variable heavy chain includes heavy chain hypervariable region and heavy chain variable framework region
$V_L$: Variable light chain includes light chain hypervariable region and light chain variable framework region
Foxp3: Foxhead box P3

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, e.g., up to 10%, up to 5%, or up to 1% of a given value. Alternatively, particularly with respect to biological systems or processes, the term can mean within an order of magnitude, e.g., within 5-fold, or within 2-fold, of a value.

As used herein, the term "cell population" refers to a group of at least two cells expressing similar or different phenotypes. In non-limiting examples, a cell population can include at least about 10, at least about 100, at least about 200, at least about 300, at least about 400, at least about 500, at least about 600, at least about 700, at least about 800, at least about 900, at least about 1000 cells expressing similar or different phenotypes.

As used herein, the term "antigen-binding protein" refers to a protein or polypeptide that comprises an antigen-binding region or antigen-binding portion, that is, has a strong affinity to another molecule to which it binds. Antigen-binding proteins encompass antibodies, chimeric antigen receptors (CARs) and fusion proteins.

The terms "antibody" and "antibodies" refer to antigen-binding proteins of the immune system. As used herein, the term "antibody" includes whole, full length antibodies having an antigen-binding region, and any fragment thereof in which the "antigen-binding portion" or "antigen-binding region" is retained, or single chains, for example, single chain variable fragment (scFv), thereof. The term "antibody" means not only intact antibody molecules, but also fragments of antibody molecules that retain immunogen-binding ability. Such fragments are also well known in the art and are regularly employed both in vitro and in vivo. Accordingly, as used herein, the term "antibody" means not only intact immunoglobulin molecules but also the well-known active fragments $F(ab')_2$, and Fab. $F(ab')_2$, and Fab fragments that lack the Fc fragment of intact antibody, clear more rapidly from the circulation, and may have less non-specific tissue binding of an intact antibody (Wahl et al., *J. Nucl. Med.* 24:316-325 (1983). In certain embodiments, an antibody is a glycoprotein comprising at least two heavy (H) chains and two light (L) chains inter-connected by disulfide bonds. Each heavy chain is comprised of a heavy chain variable region (abbreviated herein as $V_H$) and a heavy chain constant ($C_H$) region. The heavy chain constant region is comprised of three domains, CH1, CH2 and CH3. Each light chain is comprised of a light chain variable region (abbreviated herein as $V_L$) and a light chain constant $C_L$ region. The light chain constant region is comprised of one domain, $C_L$. The $V_H$ and $V_L$ regions can be further sub-divided into regions of hypervariability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1 q) of the classical complement system.

The term "antigen-binding portion", "antigen-binding fragment", or "antigen-binding region" of an antibody, as used herein, refers to that region or portion of an antibody that binds to the antigen and which confers antigen specificity to the antibody; fragments of antigen-binding proteins, for example, antibodies includes one or more fragments of an antibody that retain the ability to specifically bind to an antigen (e.g., an peptide/HLA complex). It has been shown that the antigen-binding function of an antibody can be performed by fragments of a full-length antibody. Examples of antigen-binding portions encompassed within the term "antibody fragments" of an antibody include a Fab fragment, a monovalent fragment consisting of the $V_L$, $V_H$, $C_L$ and CH1 domains; a $F(ab)_2$ fragment, a bivalent fragment comprising two Fab fragments linked by a disulfide bridge at the hinge region; a Fd fragment consisting of the $V_H$ and CH1 domains; a Fv fragment consisting of the $V_L$ and $V_H$ domains of a single arm of an antibody; a dAb fragment (Ward et al., 1989 Nature 341:544-546), which consists of a $V_H$ domain; and an isolated complementarity determining region (CDR).

Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules. These are known as single chain Fv (scFv); see e.g., Bird et al., 1988 Science 242:423-426; and Huston et al., 1988 Proc. Natl. Acad. Sci. 85:5879-5883. These antibody fragments are obtained using conventional techniques known to those of ordinary skill in the art, and the fragments are screened for utility in the same manner as are intact antibodies.

An "isolated antibody" or "isolated antigen-binding protein" is one which has been identified and separated and/or recovered from a component of its natural environment. "Synthetic antibodies" or "recombinant antibodies" are generally generated using recombinant technology or using peptide synthetic techniques known to those of skill in the art.

As used herein, the term "single-chain variable fragment" or "scFv" is a fusion protein of the variable regions of the heavy ($V_H$) and light chains ($V_L$) of an immunoglobulin (e.g., mouse or human) covalently linked to form a $V_H$::$V_L$ heterodimer. The heavy ($V_H$) and light chains ($V_L$) are either joined directly or joined by a peptide-encoding linker (e.g., 10, 15, 20, 25 amino acids), which connects the N-terminus of the $V_H$ with the C-terminus of the $V_L$, or the C-terminus of the $V_H$ with the N-terminus of the $V_L$. The linker is usually rich in glycine for flexibility, as well as serine or threonine for solubility. Despite removal of the constant regions and the introduction of a linker, scFv proteins retain the specificity of the original immunoglobulin. Single chain Fv polypeptide antibodies can be expressed from a nucleic acid comprising $V_H$- and $V_L$-encoding sequences as described by Huston, et al. (Proc. Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754. Antagonistic scFvs having inhibitory activity have been described (see, e.g., Zhao et al., Hyrbidoma (Larchmt) 2008 27(6):455-51; Peter et al., J Cachexia Sarcopenia Muscle 2012 Aug. 12; Shieh et al., J Imuno12009 183(4):2277-85; Giomarelli et al., Thromb Haemost 2007 97(6):955-63; Fife eta., J Clin Invst 2006 116(8):2252-61; Brocks et al., Immunotechnology 1997 3(3):173-84; Moosmayer et al., Ther Immunol 1995 2(10: 31-40). Agonistic scFvs having stimulatory activity have been described (see, e.g., Peter et al., J Bioi Chern 2003 25278(38):36740-7; Xie et al., Nat Biotech 1997 15(8):768-71; Ledbetter et al., Crit Rev Immunol 1997 17(5-6):427-55; Ho et al., BioChim Biophys Acta 2003 1638(3):257-66).

As used herein, "F(ab)" refers to a fragment of an antibody structure that binds to an antigen but is monovalent and does not have a Fc portion, for example, an antibody digested by the enzyme papain yields two F(ab) fragments and an Fc fragment (e.g., a heavy (H) chain constant region; Fc region that does not bind to an antigen).

As used herein, "F(ab')2" refers to an antibody fragment generated by pepsin digestion of whole IgG antibodies, wherein this fragment has two antigen binding (ab') (bivalent) regions, wherein each (ab') region comprises two separate amino acid chains, a part of a H chain and a light (L) chain linked by an S—S bond for binding an antigen and where the remaining H chain portions are linked together. A "F(ab')2" fragment can be split into two individual Fab' fragments.

As used herein, the term "vector" refers to any genetic element, such as a plasmid, phage, transposon, cosmid, chromosome, virus, virion, etc., which is capable of replication when associated with the proper control elements and which can transfer gene sequences into cells. Thus, the term includes cloning and expression vehicles, as well as viral vectors and plasmid vectors.

As used herein, the term "expression vector" refers to a recombinant nucleic acid sequence, e.g., a recombinant DNA molecule, containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used herein, "CDRs" are defined as the complementarity determining region amino acid sequences of an antibody which are the hypervariable regions of immunoglobulin heavy and light chains. See, e.g., Kabat et al., Sequences of Proteins of Immunological Interest, 4th U. S. Department of Health and Human Services, National Institutes of Health (1987). Generally, antibodies comprise three heavy chain and three light chain CDRs or CDR regions in the variable region. CDRs provide the majority of contact residues for the binding of the antibody to the antigen or epitope. In certain embodiments, the CDRs regions are delineated using the Kabat system (Kabat, E. A., et al. (1991) Sequences of Proteins of Immunological Interest, Fifth Edition, U.S. Department of Health and Human Services, NIH Publication No. 91-3242).

As used herein, the term "affinity" is meant a measure of binding strength. Without being bound to theory, affinity depends on the closeness of stereochemical fit between antibody combining sites and antigen determinants, on the size of the area of contact between them, and on the distribution of charged and hydrophobic groups. Affinity also includes the term "avidity," which refers to the strength of the antigen-antibody bond after formation of reversible complexes. Methods for calculating the affinity of an antibody for an antigen are known in the art, comprising use of binding experiments to calculate affinity. Antibody activity in functional assays (e.g., flow cytometry assay) is also reflective of antibody affinity. Antibodies and affinities can be phenotypically characterized and compared using functional assays (e.g., flow cytometry assay).

Nucleic acid molecules useful in the presently disclosed subject matter include any nucleic acid molecule that encodes an antibody or an antigen-binding portion thereof. Such nucleic acid molecules need not be 100% identical with an endogenous nucleic acid sequence. Polynucleotides having "substantial homology" or "substantial identity" to an endogenous sequence are typically capable of hybridizing with at least one strand of a double-stranded nucleic acid molecule. Homology and the percent homology can be determined by standard software programs such as BLAST or FASTA. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152: 507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Rogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

As used herein, the term "cross-compete" or "compete" refers to the situation where binding of a presently disclosed antibody or an antigen-binding portion thereof to a given antigen, e.g., a Foxp3 peptide or a Foxp3/HLA class I complex (e.g., a Foxp3/HLA-A complex, e.g., a Foxp3/HLA-A2 complex, e.g., a Foxp3/HLA-A*02:01 complex), decreases or reduces binding of a reference antibody or an antigen-binding portion thereof, e.g., that comprises the $V_H$ and $V_L$ CDR1, CDR2, and CDR3 sequences or $V_H$ and $V_L$ sequences of any of the presently disclosed antibodies or antigen-binding portions thereof to the same antigen. The term "cross-compete" or "compete" also refers to the situation where binding of a reference antibody or an antigen-binding portion thereof to a given antigen, e.g., a Foxp3 peptide or a Foxp3/HLA class I complex (e.g., a Foxp3/HLA-A complex, e.g., a Foxp3/HLA-A2 complex, e.g., a Foxp3/HLA-A*02:01 complex), decreases or reduces binding of a presently disclosed antibody or an antigen-binding portion thereof to the same antigen. The "cross-competing" or "competing" antibodies or antigen-binding portions thereof bind to the same or substantially the same epitope, an overlapping or substantially overlapping epitope, or an adjacent epitope on the antigen (e.g., a Foxp3 peptide or a Foxp3/HLA class I complex (e.g., a Foxp3/HLA-A complex, e.g., a Foxp3/HLA-A2 complex, e.g., a Foxp3/HLA-A*02:01 complex)) as the reference antibody or antigen-binding portion thereof.

As used herein, an "effective amount" or "therapeutically effective amount" is an amount sufficient to affect a beneficial or desired clinical result upon treatment. An effective amount can be administered to a subject in one or more doses. In terms of treatment, an effective amount is an amount that is sufficient to palliate, ameliorate, stabilize, reverse or slow the progression of the disease, or otherwise reduce the pathological consequences of the disease. The effective amount is generally determined by the physician on a case-by-case basis and is within the skill of one in the art. Several factors are typically taken into account when determining an appropriate dosage to achieve an effective amount. These factors include age, sex and weight of the subject, the condition being treated, the severity of the condition and the form and effective concentration of the immunoresponsive cells administered.

As used herein, the term "heterologous nucleic acid molecule or polypeptide" refers to a nucleic acid molecule (e.g., a cDNA, DNA or RNA molecule) or polypeptide that is not normally present in a cell or sample obtained from a cell. This nucleic acid may be from another organism, or it may be, for example, an mRNA molecule that is not normally expressed in a cell or sample.

As used herein, the term "increase" refers to alter positively by at least about 5%, including, but not limited to, alter positively by about 5%, by about 10%, by about 25%, by about 30%, by about 50%, by about 75%, or by about 100%.

As used herein, the term "reduce" refers to alter negatively by at least about 5% including, but not limited to, alter negatively by about 5%, by about 10%, by about 25%, by about 30%, by about 50%, by about 75%, or by about 100%.

As used herein, the term "isolated," "purified," or "biologically pure" refers to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or polypeptide of the presently disclosed subject matter is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

As used herein, the term "specifically binds" or "specifically binds to" or "specifically target" is meant a polypeptide or fragment thereof (including an antibody or an antigen-binding portion thereof) that recognizes and binds a biological molecule of interest (e.g., a Foxp3/MHC complex, (e.g., a Foxp3/HLA complex, more specifically, a Foxp3/HLA class I complex, more specifically, a Foxp3/HLA-A complex, more specifically, a Foxp3/HLA-A2 complex, or more specifically, a Foxp3/HLA-A*02:01 complex), but which does not substantially recognize and bind other molecules in a sample, for example, a biological sample. In certain embodiments, an antibody or an antigen-binding portion thereof that "specifically binds to a Foxp3/MHC complex" refers to an antibody or an antigen-binding portion thereof that binds to a Foxp3/MHC complex with a $K_D$ of $5\times10^{-7}$ M or less, $1\times10^{-7}$ M or less, $5\times10^{-8}$ M or less, $1\times10^{-8}$ M or less, $5\times10^{-9}$ M or less, $1\times10^{-9}$ M or less, $5\times10^{-10}$ M or less, $1\times10^{-10}$ M or less, $5\times10^{-11}$M or less, or $1\times10^{-11}$ M or less.

As used herein, the term "treating" or "treatment" refers to clinical intervention in an attempt to alter the disease course of the individual or cell being treated, and can be performed either for prophylaxis or during the course of clinical pathology. Therapeutic effects of treatment include, without limitation, preventing occurrence or recurrence of disease, alleviation of symptoms, diminishment of any direct or indirect pathological consequences of the disease, preventing metastases, decreasing the rate of disease progression, amelioration or palliation of the disease state, and remission or improved prognosis. By preventing progression of a disease or disorder, a treatment can prevent deterioration due to a disorder in an affected or diagnosed subject or a subject suspected of having the disorder, but also a treatment may prevent the onset of the disorder or a symptom of the disorder in a subject at risk for the disorder or suspected of having the disorder.

As used herein, the term "subject" refers to any animal (e.g., a mammal), including, but not limited to, humans, and non-human animals (including, but not limited to, non-human primates, dogs, cats, rodents, horses, cows, pigs, mouses, rats, hamsters, rabbits, and the like (e.g., which is to be the recipient of a particular treatment, or from whom cells are harvested). In certain embodiments, the subject is a human.

II. Foxp3 and Treg Cells

Foxp3 has been identified as a key player in Treg function, and is the most definitive marker of $CD4^+CD25^+$ Treg cells. Foxp3 is required for Treg cell lineage differentiation, maintenance and suppressive function. Apart from naturally occurring Treg cells that arise in the thymus, inducible Treg cells have been identified, with predominance in infection and cancer. Extrathymic generation of Treg cells requires Foxp3 induction by suboptimal antigen stimulation of $CD4^+$ T cells in the presence of transforming growth factor (TGF)-β. Analysis of Foxp3 expression in tumor-infiltrating lymphocytes (TILs) has shown that the accumulation of Treg cells correlates with poor prognosis in many cancer types, including breast, lung, melanoma, ovarian and pancreatic cancers (1-4). Therapeutically targeting the Treg population promote antitumor immunity and tumor rejection in mouse models of various types of cancer (5, 6). It has also been shown in patients that depletion of Treg cells enhances vaccine-mediated anti-tumor immunity in pancreatic cancer and induces regression of melanoma metastasis (7-9). These studies demonstrate a prominent tumor-promoting role of Treg cells in cancer by suppression of immune response.

In addition to the accumulation of $Foxp3^+$ Treg cells in tumor infiltrating lymphocytes (TIL)s, local lymph nodes and the blood of cancer patients, which confers growth and metastatic advantage of cancer cells by inhibiting anti-tumor immunity, the expression of Foxp3 has also been shown in some cancer cells. Foxp3-expressing pancreatic carcinoma cells and cutaneous T cell lymphoma cells have been shown to suppress T cell proliferation (2, 11). Therefore, cancer cells may share suppressive effects with regulatory T (Treg) cells, and that mimicking Treg function may represent a new mechanism of immune evasion in cancer.

Overall, Treg cells are considered the most powerful inhibitors of anti-tumor immunity and the greatest barrier to successful immunotherapy. A number of strategies for depletion or interference with Treg function have been attempted. These include: depletion of Treg by monoclonal antibodies (mAb) specific for CD25, glucorticoid-induced TNF-related protein (GITR) and ligand-directed toxins targeted to cell surface receptor CD25 (such as Dennileukin diftitox). However, both CD25 and GITR are expressed not only in Treg cells, but also in activated CD4 and CD8 effector T cells. In addition, disruption of tumor homing by Treg, and modulation of T cell plasticity have all been attempted. The problem with these strategies is a lack of specificity, resulting in depletion of the beneficial anti-tumor effector T cells.

Hence there is a need for drugs that could selectively inhibit Treg cells. To the best knowledge of the inventors, no drugs could selectively inhibit Treg cells, no effective targets for Treg cells on the cell surface that could be or are currently being used to suppress Treg cells or to kill Treg cells, and no selective drugs that can deplete Treg cells.

Foxp3 is an ideal target except that it is no druggable by small molecules and it is inside the cell so antibody therapy is not feasible. However, peptides from Foxp3 protein that are degraded and processed for cell surface presentation can serve as a target of a TCR mimic antibody. TCR-mimic antibodies specific for Foxp3-derived epitopes specifically and directly deplete $Foxp3^+$ Treg cells and tumor cells. The depletion of Treg cells can greatly unleash anti-tumor immunity by removing immunosuppression caused by both Treg cells and tumor cells.

Tregs can be identified using various surface cell markers, such as CD4 (cluster of differentiation 4) and CD25 (alpha chain of IL-2 receptor). Additionally, it is known that activated conventional T cells can transiently express Foxp3. The expression of CD127 can be used as a cell marker to distinguish activated conventional T cells from Tregs. CD127 is also known as the alpha chain of IL-7 receptor. It has been found that Tregs express low CD127, whereas activated T cells express high CD127.

In certain embodiments, Tregs are identified by one or more of presence of CD4 ($CD4^+$), low expression level of CD127 ($CD127^{low}$), high expression level of CD25 ($CD25^{high}$), and high expression level of Foxp3 ($Foxp3^{high}$). In certain embodiments, Tregs are identified by the presence of CD4 and high expression level of CD25, e.g., $CD4^+$ $CD25^{high}$ T cells. In certain embodiments, Tregs are identified by the presence of CD4, and low expression level of CD127, e.g., $CD4^+CD127^{low}$ T cells. In certain embodiments, Tregs are identified by the presence of CD4, high expression level of CD25 and low expression level of CD127, e.g., $CD4^+$ $CD25^{high}CD127^{low}$ T cells.

In certain embodiments, a presently disclosed antibody or antigen-binding portion thereof binds to one or more Treg cell. In certain embodiments, a presently disclosed antibody or antigen-binding portion thereof binds to one or more T cell selected from the group consisting of $CD4^+$ T cells, $CD127^{low}$ T cells, $CD25^{high}$ T cells, $Foxp3^{high}$ T cells, and combinations thereof. The combinations include all possible combinations including $CD4^+$ T cells, $CD127^{low}$ T cells, $CD25^{high}$ T cells, and $Foxp3^{high}$ T cells: e.g., any two of $CD4^+$ T cells, $CD127^{low}$ T cells, $CD25^{high}$ T cells, and $Foxp3^{high}$ T cells (e.g., $CD4^+CD127^{low}$ T cells, $CD4^+$ $CD25^{high}$ T cells, $CD4^+$ $Foxp3^{high}$ T cells, $CD127^{low}$ $CD25^{high}$ T cells, $D127^{low}$ $Foxp3^{high}$ T cells, or $CD25^{high}$ $Foxp3^{high}$ T cells), any three of $CD4^+$ T cells, $CD127^{low}$ T cells, $CD25^{high}$ T cells, and $Foxp3^{high}$ T cells (e.g., $CD4^+$ $CD127^{low}$ $CD25^{high}$ T cells, $CD4^+CD127^{low}$ $Foxp3^{high}$ T cells, $CD4^+CD25^{high}$ $Foxp3^{high}$ T cells, or $CD127^{low}$ $CD25^{high}$ $Foxp3^{high}$ T cells), and all four of $CD4^+$ T cells, $CD127^{low}$ T cells, $CD25^{high}$ T cells, and $Foxp3^{high}$ T cells (e.g., $CD4^+CD127^{low}$ $CD25^{high}$ $Foxp3^{high}$ T cells).

In certain embodiments, a presently disclosed antibody or antigen-binding portion thereof binds to one or more $CD127^{low}$ T cell. In certain embodiments, a presently disclosed antibody or antigen-binding portion thereof binds to one or more $Foxp3^{high}$ T cell. In certain embodiments, a presently disclosed antibody or antigen-binding portion thereof binds to one or more $CD25^{high}$ T cell. In certain embodiments, a presently disclosed antibody or antigen-binding portion thereof binds to one or more $CD4^+$ T cell. In certain embodiments, a presently disclosed antibody or antigen-binding portion thereof binds to one or more $CD4^+$ $CD25^{high}$ T cell. In certain embodiments, a presently disclosed antibody or antigen-binding portion thereof binds to one or more $CD4^+CD127^{low}$ T cell. In certain embodiments, a presently disclosed antibody or antigen-binding portion thereof binds to one or more $CD4^+CD25^{high}CD127^{low}$ T cell.

III. Anti-Foxp3 Antibodies Targeting Foxp3/MHC Peptide Complex

The presently disclosed subject matter employs an approach to obtaining therapeutic antibodies to any protein, including those proteins that are inaccessible because they are not expressed on the cell surface, e.g., Foxp3.

In order to target antigens derived from intracellular or nuclear proteins, development of a therapeutic antibody an uncommon approach is required. This approach is to generate recombinant antibodies (Abs, e.g., monoclonal Abs (mAb)) that recognize the peptide/MHC complex expressed on the cell surface, with the same specificity as a T-cell receptor (TCR). Such Abs share functional homology with TCRs regarding target recognition, but confer higher affinity and capabilities of arming with potent cytotoxic agents that antibodies feature. Technically, TCR-like mAbs may be generated by conventional hybridoma techniques or by in vitro antibody library techniques known to those of skill in the art, to produce human, humanized or chimeric antibodies.

Only 10% of a cell's proteins are destined for expression on the cell surface. Therefore, monoclonal antibodies do not exist for the vast majority of proteins. In contrast, nearly all proteins within the cell are processed and presented on the cell surface as peptides within the context of MHC molecules for recognition by T cell receptors. Traditionally, the MHC-peptide complex could only be recognized by a T-cell receptor (TCR), limiting the ability to detect an epitope of interest using T cell-based readout assays. Phage display methodology now has enabled the reliable generation of monoclonal antibodies to these unique epitopes, thus opening the door to a new universe of antigens that were previously inaccessible. The use of phage display libraries has made it possible to select large numbers of antibody repertoires for unique and rare antibodies against very defined epitopes (for more details on phage display (see McCafferty et al., *Nature,* 348: 552-554.). The rapid identification of human Fab or scFv fragments highly specific for tumor antigen-derived peptide-MHC complex molecules has thus become possible (Noy, *Expert Rev Anticancer Ther* 2005:5 (3): 523-536. Chames et al., *Proc Natl Acad Sci USA* 2000; 97: 7969-7974; Held et al., *Eur J. Immunol.* 2004: 34:2919-2929; Lev et al., *Cancer Res* 2002; 62: 3184-3194). Immuno-toxins, generated by fusing TCR-like Fab specific for melanoma Ag MART-1 26-35/A2 or gp100 280-288/A2 to a truncated form of *Pseudomonas* endotoxin, have been shown to inhibit human melanoma growth both in vitro and in vivo (Klechevsky et al., *Cancer Res* 2008; 68 (15): 6360-6367). The presently disclosed subject matter involves the development of a TCR-like, fully human Ab (e.g., mAb) that recognizes, for example, the Foxp3 peptide/HLA-A2 complex for cancer therapy. Therefore, the presently disclosed subject matter provides for methods and compositions to construct phage-antibody reagents that will recognize specific MHC/peptide complexes on the cell surface in order to vastly expand Treg specific targets. The presently disclosed subject matter provides for antibodies (e.g., monoclonal antibodies) to the neo-epitopes of peptide/MHC complexes derived from the prototypical intracellular Treg marker, Foxp3.

In certain embodiments, a presently disclosed antibody or antigen-binding portion thereof binds to a Foxp3 peptide/MHC complex with a high binding affinity, for example with a $K_D$ of about $5\times10^{-7}$ M or less, e.g., about $1\times10^{-7}$ M or less, about $5\times10^{-8}$ M or less, about $1\times10^{-8}$ M or less, about $5\times10^{-9}$M or less about $1\times10^{-9}$M or less, about $5\times10^{-10}$ M or less, about $1\times10^{-10}$ M or less, about $5\times10^{-11}$M or less, or about $1\times10^{-11}$ M or less. In certain embodiments, a presently disclosed antibody or antigen-binding portion thereof binds to a Foxp3 peptide/MHC complex with a $K_D$ of from about $1\times10^{-11}$ M to about $5\times10^{-7}$ M, e.g., from about $1\times10^{-11}$M to about $1\times10^{-10}$ M, from about $1\times10^{-11}$M to about $5\times10^{-11}$ M, from about $5\times10^{-11}$M to about $1\times10^{-10}$ M, from about $1\times10^{-10}$ M to about $1\times10^{-9}$ M, from about $1\times10^{-1o}$ M to about $5\times10^{-10}$ M, from about $5\times10^{-10}$ M to about $1\times10^{-9}$ M, from $1\times10^{-9}$M to about $1\times10^{-8}$ M, from $1\times10^{-9}$ M to about $5\times10^{-9}$ M, from $5\times10^{-9}$M to about $1\times10^{-8}$ M, from about $1\times10^{-8}$M to about $1\times10^{-7}$ M, from about $1\times10^{-8}$M to about $5\times10^{-8}$ M, or from about $5\times10^{-8}$M to about $1\times10^{-7}$ M. In certain embodiments, a presently disclosed antibody or antigen-binding portion thereof binds to a Foxp3 peptide/MHC complex with a $K_D$ of from about $1\times10^{-7}$ M to about $2.5\times10^{-7}$ M, e.g., from about $1\times10^{-7}$M to about $1.5\times10^{-7}$ M, from about $1.5\times10^{-7}$M to about $2\times10^{-7}$ M, or from about $2\times10^{-7}$M to about $2.5\times10^{-7}$ M. In certain embodiments, a presently disclosed antibody or antigen-binding portion thereof binds to a Foxp3 peptide/MHC complex with a $K_D$ of about $1.4\times10^{-7}$ M. In certain embodiments, a presently disclosed antibody or antigen-binding portion thereof binds to a Foxp3 peptide/MHC complex with a $K_D$ of about $1.9\times10^{-7}$ M. In certain embodiments, a presently disclosed antibody or antigen-binding portion thereof binds to a Foxp3 peptide/MHC complex with a $K_D$ of about $2.2\times10^{-7}$ M. In certain embodiments, a presently disclosed antibody or antigen-binding portion thereof binds to a Foxp3 peptide/MHC complex with a $K_D$ of from about $3\times10^{-7}$ M to about $7\times10^{-8}$ M, e.g., from about $3\times10^{-8}$ M to about $4\times10^{-8}$ M, from about $4\times10^{-8}$ M to about $5\times10^{-8}$ M, from about $5\times10^{-8}$ M to about $6\times10^{-8}$ M, or from about $6\times10^{-8}$ M to about $7\times10^{-8}$ M. In certain embodiments, a presently disclosed antibody or antigen-binding portion thereof binds to a Foxp3 peptide/MHC complex with a $K_D$ of about $3.3\times10^{-8}$ M. In certain embodiments, a presently disclosed antibody or antigen-binding portion thereof binds to a Foxp3 peptide/MHC complex with a $K_D$ of about $3.5\times10^{-8}$ M. In certain embodiments, a presently disclosed antibody or antigen-binding portion thereof binds to a Foxp3 peptide/MHC complex with a $K_D$ of about $4.8\times10^{-8}$ M. In certain embodiments, a presently disclosed antibody or antigen-binding portion thereof binds to a Foxp3 peptide/MHC complex with a $K_D$ of about $4.9\times10^{-8}$ M. In certain embodiments, a presently disclosed antibody or antigen-binding portion thereof binds to a Foxp3 peptide/MHC complex with a $K_D$ of about $5\times10^{-8}$ M. In certain embodiments, a presently disclosed antibody or antigen-binding portion thereof binds to a Foxp3 peptide/MHC complex with a $K_D$ of about $7\times10^{-8}$ M. In certain embodiments, a presently disclosed antibody or antigen-binding portion thereof binds to a Foxp3 peptide/MHC complex with a $K_D$ of about $7.2\times10^{-8}$ M. In certain embodiments, a presently disclosed antibody or antigen-binding portion thereof binds to a Foxp3 peptide/MHC complex with a $K_D$ of from about $1\times10^{-10}$ M to about $5\times10^{-10}$ M, e.g., from about $1\times10^{-10}$ M to about $2\times10^{-10}$ M, from about $2\times10^{-10}$ M to about $3\times10^{-10}$ M, from about $3\times10^{-10}$ M to about $4\times10^{-10}$ M or $4\times10^{-10}$ M to about $5\times10^{-10}$ M. In certain embodiments, a presently disclosed antibody or antigen-binding portion thereof binds to a Foxp3 peptide/MHC complex with a $K_D$ of about $2\times10^{-10}$ M. In certain embodiments, a presently disclosed antibody or antigen-binding portion thereof binds to a Foxp3 peptide/MHC complex with a $K_D$ of about $5\times10^{-10}$ M. In certain embodiments, a presently disclosed antibody or antigen-binding portion thereof binds to a Foxp3 peptide/MHC complex with a $K_D$ of about $4.6\times10^{-10}$ M.

In the presently disclosed subject matter, antigen-binding proteins, including antibodies, having an antigen-binding region based on scFvs that are selected from human scFv phage display libraries using recombinant HLA-peptide complexes are described. These molecules demonstrated exquisite specificity, for example as shown with anti-Foxp3 antibodies that recognize only Foxp3/MHC complexes (e.g., Foxp3/HLA complexes, more specifically, Foxp3/HLA class I complexes, more specifically, Foxp3/HLA-A complexes, more specifically, Foxp3/HLA-A2 complexes, and more specifically, Foxp3/HLA-A*02:01 complexes). In addition, along with their inability to bind to MHC-complexes containing other peptides, the molecules are also unable to bind to the peptides themselves, further demonstrating their TCR-like specificity.

Recombinant antibodies with TCR-like specificity represent a new and valuable tool for research and therapeutic applications in tumor immunology and immunotherapy. Foxp3 is a well-established and validated Treg marker.

The presently disclosed antigen-binding portion can be a Fab, Fab', $F(ab')_2$, Fv or a single chain variable fragment (scFv). In certain non-limiting embodiments, the presently disclosed antigen-binding portion thereof is a scFv. In certain embodiments, the scFv is a human scFv. The scFvs of the presently disclosed subject matter selected by phage display are initially tested for their ability to bind to peptide presented on the surface of HLA-positive cells. After T2 cells are incubated in the presence of peptide, fluorescently labeled antibodies can be used to selectively recognize the antigen pulsed cells using flow cytometry.

In certain embodiments, the presently disclosed subject matter provides for antibodies that have the scFv sequence fused to one or more constant domains of the heavy or light chain variable region of the antibodies to form an antibody with an Fc region of a human immunoglobulin to yield a bivalent protein, increasing the overall avidity and stability of the antibody. In addition, the Fc portion allows the direct conjugation of other molecules, including but not limited to fluorescent dyes, cytotoxins, radioisotopes, etc. to the antibody for example, for use in antigen quantitation studies, to immobilize the antibody for affinity measurements, for targeted delivery of a therapeutic agent, and/or to test for Fc-mediated cytotoxicity using immune effector cells and many other applications.

The molecules of the presently disclosed subject matter are based on the identification and selection of scFv using phage display, the amino acid sequence of which confers the molecules' specificity for the MHC restricted peptide of interest and forms the basis of all antigen-binding proteins of the disclosure. The scFv, therefore, can be used to design a diverse array of "antibody" molecules, including, for example, full length antibodies, fragments thereof, such as Fab and $F(ab')_2$, minibodies, fusion proteins, including scFv-Fc fusions, multivalent antibodies, that is, antibodies that have more than one specificity for the same antigen or different antigens, for example, bispecific T-cell engaging antibodies (BITE), tribodies, etc. (see Cuesta et al., Multivalent antibodies: when design surpasses evolution. *Trends in Biotechnology* 28:355-362 2010).

In constructing a recombinant immunoglobulin, appropriate amino acid sequences for constant regions of various immunoglobulin isotypes and methods for the production of a wide array of antibodies are known to those of ordinary skill in the art.

Phage display technology allows for the rapid selection and production of antigen-specific scFv and Fab fragments, which are useful in and of themselves, or which can be further developed to provide complete antibodies, antigen binding proteins or antigen binding fragments thereof. Complete Abs with Fc domains have a number of advantages over the scFv and Fab antibodies. First, only full length Abs exert immunological function such as CDC and ADCC mediated via Fc domain. Second, bivalent mAbs offer stronger antigen-binding affinity than monomeric Fab Abs. Third, plasma half-life and renal clearance will be different with the Fab and bivalent mAb. The particular features and advantages of each can be matched to the planned effector strategy. Fourth, bivalent mAb may be internalized at different rates than scFv and Fab, altering immune function or carrier function. Alpha emitters, for example, do not need to be internalized to kill the targets, but many drugs and toxins will benefit from internalization of the immune complex. In certain embodiments, therefore, once scFv clones specific for a Foxp3 peptide-HLA complex are obtained from phage display libraries, a full length IgG Ab (e.g., mAb) using the scFv fragments is produced.

To produce recombinant human monoclonal IgG in HEK293 or Chinese hamster ovary (CHO) cell lines cells, a full length IgG mAb can be engineered based on a method known to those of skill in the art (Tomomatsu et al., Production of human monoclonal antibodies against FceRIa by a method combining in vitro immunization with phage display. Biosci Biotechnol Biochem 73(7): 1465-1469 2009). Briefly, antibody variable regions can be sub-cloned into mammalian expression vectors, with matching Lambda or Kappa light chain constant sequences and IgG1 subclass Fc (for example) (Lidija P, et al. An integrated vector system for the eukaryotic expression of antibodies or their fragments after selection from phage display libraries. Gene 1997; 187(1): 9-18; Lisa J H, et al. Crystallographic structure of an intact lgG1 monoclonal antibody. Journal of Molecular Biology 1998; 275 (5): 861-872). Kinetic binding analysis (Yasmina N A, et al. Probing the binding mechanism and affinity of tanezumab, a recombinant humanized anti-NGF monoclonal antibody, using a repertoire of biosensors. Protein Science 2008; 17(8): 1326-1335) can be used to confirm specific binding of full length IgG to a Foxp3/HLA class I complex with a $K_D$ in nanomolar range.

In certain embodiments, the presently disclosed subject matter provides for an antigen-binding protein that is a full length antibody (anti-Foxp3 antibody), the heavy and light chains of an antibody of the presently disclosed subject matter may be full-length (e.g., an antibody including at least one, and preferably two, complete heavy chains, and at least one, and preferably two, complete light chains). The antibody can be of an IgG1, IgG2, IgG3, IgG4, IgM, IgA1, IgA2, IgD, or IgE isotype. In certain embodiments, an antigen binding portion is comprised in a fusion protein with one or more non-immunoglobulin component. In certain embodiments, the antibody is of an IgG1, IgG2, IgG3, or IgG4 isotype. In one non-limiting embodiment, the antibody is of an IgG1 isotype (e.g., a human IgG1 antibody). The choice of antibody type may depend on the immune effector function that the antibody is designed to elicit. The light chain constant region can be a kappa or lambda constant region, preferably is a kappa constant region.

In certain embodiments, a presently disclosed antibody or other antigen-binding protein specifically binds to a Foxp3 peptide bound to an MHC molecule, e.g., a HLA molecule, more specifically, a HLA class I molecule, more specifically, a HLA-A molecule, more specifically, a HLA-A2, even more specifically, HLA-A*02:01. The Foxp3 peptide can include 6-20 amino acids, e.g., 8-12 amino acids, e.g., 8, 9, 10, 11, or 12 amino acids. In certain embodiments, the Foxp3 peptide is a 9-mer peptide. In certain embodiments, the Foxp3 peptide is a 10-mer peptide. The Foxp3 peptide can be one known in the art.

In certain embodiments, the Foxp3 peptide is a portion of a Foxp3 protein. In certain embodiments, the Foxp3 peptide is a portion of a human Foxp3 protein. In certain embodiments, the human Foxp3 protein has an amino acid sequence set forth in SEQ ID NO: 1 (Genbank Accession No. ABQ15210.1), which is provided below.

```
                                                    [SEQ ID NO: 1]
  1mpnprpgkps apslalgpsp gaspswraap kasdllgarg pggtfqgrdl rggahassss

 61lnpmppsqlq lptlplvmva psgarlgplp hlqallqdrp hfmhqlstvd ahartpvlqv

121hplespamis ltppttatgv fslkarpglp pginvaslew vsrepallct fpnpsaprkd

181stlsavpqss ypllangvck wpgcekvfee pedflkhcqa dhlldekgra qcllqremvq

241sleqqlvlek eklsamqahl agkmaltkas svassdkgsc civaagsqgp vvpawsgpre

301apdslfavrr hlwgshgnst fpeflhnmdy fkfhnmrppf tyatlirwai leapekqrtl

361neiyhwftrm faffrnhpat wknairhnls lhkcfvrves ekgavwtvde lefrkkrsqr

421psrcsnptpg p
```

In certain embodiments, the Foxp3 peptide is selected from the group consisting of Foxp3-1 having the amino acid sequence set forth in SEQ ID NO: 2 (which is amino acid sequences 252-260 of SEQ ID NO:1) or a portion thereof, Foxp3-2 having the amino acid sequence set forth in SEQ ID NO: 3 (which is amino acid sequences 390-398 of SEQ ID NO:1) or a portion thereof, Foxp3-3 having the amino acid sequence set forth in SEQ ID NO: 4 (which is amino acid sequences 304-312 of SEQ ID NO:1) or a portion thereof, Foxp3-4 having the amino acid sequence set forth in SEQ ID NO: 5 (which is amino acid sequences 388-396 of SEQ ID NO:1) or a portion thereof, Foxp3-5 having the amino acid sequence set forth in SEQ ID NO: 6 (which is amino acid sequences 95-103 of SEQ ID NO:1) or a portion thereof, Foxp3-6 having the amino acid sequence set forth in SEQ ID NO: 7 (which is amino acid sequences 69-77 of SEQ ID NO:1) or a portion thereof, and Foxp3-7 having the amino acid sequence set forth in SEQ ID NO: 8 (which is amino acid sequences 344-353 of SEQ ID NO:1) or a portion thereof. The sequences of SEQ ID NOS: 2-8 are provided below.

```
                          (SEQ ID NO: 2)
KLSAMQAHL
                          (SEQ ID NO: 3)
SLHKCFVRV,
                          (SEQ ID NO: 4)
SLFAVRRHL
                          (SEQ ID NO: 5)
NLSLHKCFV
                          (SEQ ID NO: 6)
LLQDRPHFM
                          (SEQ ID NO: 7)
LQLPTLPLV
                          (SEQ ID NO: 8)
TLIRWAILEA
```

In certain embodiments, the Foxp3 peptide is Foxp3-7. In certain embodiments, the Foxp3 peptide is Foxp3-2. In certain embodiments, the Foxp3 peptide is Foxp3-4. In certain embodiments, the antibody or other antigen-binding protein binds to the C-terminal of the Foxp3 peptide in the Foxp3/MHC complex. In certain embodiments, the antibody or other antigen-binding protein binds to the N-terminal of the Foxp3 peptide in the Foxp3/MHC complex. The epitope mapping data shown in Example 2 below demonstrate that the certain antibodies bind to the C terminal of the amino acid sequence in the MHC molecule.

In certain embodiments, the antibody or other antigen-binding protein binds to Foxp3-7 in conjunction with HLA-A*02:01. Non-limiting examples of scFvs that bind to Foxp3-7 include EXT017-5, EXT017-9, EXT017-10, EXT017-11, EXT017-17, EXT017-18, EXT017-20, EXT017-21, EXT017-23, EXT017-24, EXT017-25, EXT017-26, EXT017-27, EXT017-28, EXT017-29, EXT017-30, EXT017-32, EXT017-34, EXT017-53, EXT017-54, and EXT017-55.

In certain embodiments, a presently disclosed antibody or antigen-binding portion thereof binds to at least one portion of Foxp3-1, Foxp3-2, Foxp3-3, Foxp3-4, Foxp3-5, Foxp3-6, or Foxp3-7. More specifically, in certain embodiments, a presently disclosed antibody or antigen-binding portion thereof binds to at least one portion of Foxp3-7 (SEQ ID NO: 8).

The heavy chain and light chain variable region CDR1, CDR2, and CDR3 sequences of EXT017-17, EXT017-18, EXT017-20, EXT017-27, EXT017-28, EXT017-32, EXT017-53, and EXT017-54 are shown in Table 1 below. The CDR regions are delineated using the Kabat system (Kabat, E. A., et al. (1991) Sequences of Proteins of Immunological Interest, Fifth Edition, U.S. Department of Health and Human Services, NIH Publication No. 91-3242). The full length amino acid sequences and nucleotides encoding thereof, the heavy chain variable region sequences and nucleotides encoding thereof, and the light chain variable region sequences and nucleotides encoding thereof, of EXT017-17, EXT017-18, EXT017-20, EXT017-27, EXT017-28, EXT017-32, EXT017-53, and EXT017-54 are shown in Appendix A.

TABLE 1

| clones | HCDR1 | HCDR2 | HCDR3 | LCDR1 | LCDR2 | LCDR3 |
|---|---|---|---|---|---|---|
| EXT017-17 | GDTFSRYA (SEQ ID NO: 9) | IIPIFGTP (SEQ ID NO: 10) | ARSIYRYSEYDH (SEQ ID NO: 11) | SSNIGAGYD (SEQ ID NO: 12) | GNS (SEQ ID NO: 13) | QSYDSSLSGYV (SEQ ID NO: 14) |
| EXT017-18 | GYTFSNYY (SEQ ID NO: 15) | INPSVGTT (SEQ ID NO: 16) | ARDWWGQMMYDG (SEQ ID NO: 17) | SSNIGSNT (SEQ ID NO: 18) | SNN (SEQ ID NO: 19) | AAWDDSLNGQGV (SEQ ID NO: 20) |
| EXT017-20 | GGTFSSYA (SEQ ID NO: 21) | IIPIFGTA (SEQ ID NO: 22) | ARYSYKYGELDT (SEQ ID NO: 23) | SSNIGAGYD (SEQ ID NO: 24) | GNS (SEQ ID NO: 25) | QSYDSSLSGSV (SEQ ID NO: 26) |
| EXT017-27 | GYTFTNYY (SEQ ID NO: 27) | IRPSGGIT (SEQ ID NO: 28) | ARSWDYFASNDF (SEQ ID NO: 29) | NIGSES (SEQ ID NO: 30) | DDD (SEQ ID NO: 31) | QVWDRSSDHWF (SEQ ID NO: 32) |
| EXT017-28 | GGTFSTYA (SEQ ID NO: 33) | IIPIFGTA (SEQ ID NO: 34) | ARAEYVYGEYDQ (SEQ ID NO: 35) | SSNIGAGYD (SEQ ID NO: 36) | GNS (SEQ ID NO: 37) | QSYDSSLSGYV (SEQ ID NO: 38) |
| EXT017-32 | GFTFNNHA (SEQ ID NO: 39) | ISFDGDD K (SEQ ID NO: 40) | SRDPYHFASGSYSYFDY (SEQ ID NO: 41) | NIGSKS (SEQ ID NO: 42) | YDS (SEQ ID NO: 43) | QVWDSSSDHYV (SEQ ID NO: 44) |
| EXT017-53 | GYTFTNYY (SEQ ID NO: 45) | IRPSGGNT (SEQ ID NO: 46) | ARSWNSRDVDS (SEQ ID NO: 47) | SGSIASHY(SEQ ID NO: 48) | ENN (SEQ ID NO: 49) | QSYDRSNHVV (SEQ ID NO: 50 |
| EXT017-54 | GGTFSSYA (SEQ ID NO: 51) | IIPIFGTA (SEQ ID NO: 52) | ARPSYYSIKSAWDH (SEQ ID NO: 53) | TSNIGKNG (SEQ ID NO: 54) | NDH (SEQ ID NO: 55) | ATWDDTLDLPL (SEQ ID NO: 56) |

The heavy chain and light chain variable region CDR1, CDR2, and CDR3 sequences of EXT017-5, EXT017-9, EXT017-10, EXT017-11, EXT017-21, EXT017-23, EXT017-24, EXT017-25, EXT017-26, EXT017-29, EXT017-30, EXT017-34, and EXT017-55 are shown in Appendix B. The full length amino acid sequences and nucleotides encoding thereof, the heavy chain variable region sequences and nucleotides encoding thereof, and the light chain variable region sequences and nucleotides encoding thereof, of EXT017-5, EXT017-9, EXT017-10, EXT017-11, EXT017-21, EXT017-23, EXT017-24, EXT017-25, EXT017-26, EXT017-29, EXT017-30, EXT017-34, and EXT017-55 are shown in Appendix C.

In certain embodiments, the antibody or other antigen-binding protein binds to Foxp3-2 in conjunction with HLA-A*02:01. Non-limiting examples of scFvs that bind to Foxp3-2 include EXT019-6, EXT019-12, EXT019-9, EXT019-15, EXT019-20, EXT019-4, EXT019-13, and EXT019-8. The heavy chain and light chain variable region CDR1, CDR2, and CDR3 sequences of EXT019-6, EXT019-9, EXT019-12, EXT019-15, and EXT019-20 are shown in Table 2 below. The full length amino acid sequences and nucleotides encoding thereof, the heavy chain variable region sequences and nucleotides encoding thereof, and the light chain variable region sequences and nucleotides encoding thereof, of EXT019-6, EXT019-9, EXT019-12, EXT019-15, and EXT019-20 are shown in Appendix D.

TABLE 2

| | VH CDR1 | VHCDR2 | VH CDR3 | VL CDR1 | VL CDR2 | VL CDR3 |
|---|---|---|---|---|---|---|
| EXT019-06 | GYNFASEW (SEQ ID NO: 57) | IYPAESEI (SEQ ID NO: 58) | ARAWDANYIYMDI (SEQ ID NO: 59) | SSNIGAGYD (SEQ ID NO: 60) | GNN (SEQ ID NO: 61) | QSYDSSLSDVV (SEQ ID NO: 62) |
| EXT019-09 | GFAFSGSS (SEQ ID NO: 63) | ITSKAYNYAT (SEQ ID NO: 64) | TQTGDSSAY (SEQ ID NO: 65) | NIGSKS (SEQ ID NO: 66) | YDS (SEQ ID NO: 67) | QVWDSSSDHWV (SEQ ID NO: 68) |

TABLE 2-continued

| clones | VH CDR1 | VHCDR2 | VH CDR3 | VL CDR1 | VL CDR2 | VL CDR3 |
|---|---|---|---|---|---|---|
| EXT019-12 | GFTFSSYW (SEQ ID NO: 69) | IKQDGSEK (SEQ ID NO: 70) | ARYGGGPYDS (SEQ ID NO: 71) | NIGSKS (SEQ ID NO: 72) | YDS (SEQ ID NO: 73) | QVWDSSSDHRV (SEQ ID NO: 74) |
| EXT019-15 | GFSFSNYA (SEQ ID NO: 75) | ISGRGGSI (SEQ ID NO: 76) | AKSSEDYYFYHMDA (SEQ ID NO: 77) | NIGSES (SEQ ID NO: 78) | YDS (SEQ ID NO: 79) | QVWDHINDHYV (SEQ ID NO: 80) |
| EXT019-20 | SISSKSAAWN (SEQ ID NO: 81) | YRSKWYY (SEQ ID NO: 82) | ARSTGTFDY (SEQ ID NO: 83) | NIGSKS (SEQ ID NO: 84) | YDS (SEQ ID NO: 85) | QVWDSSSDRVV (SEQ ID NO: 86) |

The heavy chain and light chain variable region CDR1, CDR2, and CDR3 sequences of EXT019-4, EXT019-13, and EXT019-8 are shown in Appendix E. The full length amino acid sequences and nucleotides encoding thereof, the heavy chain variable region sequences and nucleotides encoding thereof, and the light chain variable region sequences and nucleotides encoding thereof, of EXT019-4, EXT019-13, and EXT019-8 are shown in Appendix D.

In certain embodiments, the antibody or other antigen-binding protein binds to Foxp3-4 in conjunction with HLA-A*02:01. Non-limiting examples of scFvs that bind to Foxp3-4 include EXT018-5, EXT018-2, and EXT018-4. The heavy chain and light chain variable region CDR1, CDR2, and CDR3 sequences of EXT018-5 are shown in Table 3 below. The full length amino acid sequences and nucleotides encoding thereof, the heavy chain variable region sequences and nucleotides encoding thereof, and the light chain variable region sequences and nucleotides encoding thereof, of EXT018-5 shown in Appendix F.

TABLE 3

| clones | HCDR1 | HCDR2 | HCDR3 | LCDR1 | LCDR2 | LCDR3 |
|---|---|---|---|---|---|---|
| EXT018-5 | GFTFSSYA (SEQ ID NO: 87) | ISYDGSNK (SEQ ID NO: 88) | ARDRHDYVMDV (SEQ ID NO: 89) | NIGSKT (SEQ ID NO: 90) | YDS (SEQ ID NO: 91) | QVWDGSSDHVI (SEQ ID NO: 92) |

The heavy chain and light chain variable region CDR1, CDR2, and CDR3 sequences of EXT018-2, and EXT018-4 are shown in Appendix G. The full length amino acid sequences and nucleotides encoding thereof, the heavy chain variable region sequences and nucleotides encoding thereof, and the light chain variable region sequences and nucleotides encoding thereof, of EXT018-2, and EXT018-4 are shown in Appendix F.

Given that each of EXT017-5, EXT017-9, EXT017-10, EXT017-11, EXT017-17, EXT017-18, EXT017-20, EXT017-21, EXT017-23, EXT017-24, EXT017-25, EXT017-26, EXT017-27, EXT017-28, EXT017-29, EXT017-30, EXT017-32, EXT017-34, EXT017-53, EXT017-54, and EXT017-55 can bind to Foxp3-7 in conjunction with HLA-A*02:01, the $V_H$ and $V_L$ sequences of EXT017-5, EXT017-9, EXT017-10, EXT017-11, EXT017-17, EXT017-18, EXT017-20, EXT017-21, EXT017-23, EXT017-24, EXT017-25, EXT017-26, EXT017-27, EXT017-28, EXT017-29, EXT017-30, EXT017-32, EXT017-34, EXT017-53, EXT017-54, and EXT017-55 can be "mixed and matched" to create other antibodies or other antigen-binding proteins that bind to Foxp3-7 in conjunction with HLA-A*02:01.

Similarly, given that each of EXT019-6, EXT019-12, EXT019-9, EXT019-15, EXT019-20, EXT019-4, EXT019-13, and EXT019-8 can bind to Foxp3-2 in conjunction with HLA-A*02:01, the $V_H$ and $V_L$ sequences of EXT019-6, EXT019-12, EXT019-9, EXT019-15, EXT019-20, EXT019-4, EXT019-13, and EXT019-8 can be "mixed and matched" to create other antibodies or other antigen-binding proteins that bind to Foxp3-2 in conjunction with HLA-A*02:01.

Similarly, given that each of EXT018-5, EXT018-2, and EXT018-4 can bind to Foxp3-4 in conjunction with HLA-A*02:01, the $V_H$ and $V_L$ sequences of EXT018-5, EXT018-2, and EXT018-4 can be "mixed and matched" to create other antibodies or other antigen-binding proteins that bind to Foxp3-4 in conjunction with HLA-A*02:01.

Such "mixed and matched" antibodies can be tested using the binding assays known in the art, including for example, ELISAs, Western blots, RIAs, Biacore analysis. Preferably, when $V_H$ and $V_L$ chains are mixed and matched, a $V_H$ sequence from a particular $V_H/V_L$ pairing is replaced with a structurally similar $V_H$ sequence. Likewise, a $V_L$ sequence from a particular $V_H/V_L$ pairing is replaced with a structurally similar $V_L$ sequence.

In certain embodiments, a presently disclosed antibody or other antigen-binding protein comprises: (a) the $V_H$ of EXT017-5, EXT017-9, EXT017-10, EXT017-11, EXT017-17, EXT017-18, EXT017-20, EXT017-21, EXT017-23, EXT017-24, EXT017-25, EXT017-26, EXT017-27, EXT017-28, EXT017-29, EXT017-30, EXT017-32, EXT017-34, EXT017-53, EXT017-54, or EXT017-55, as shown in Appendices A and C, and/or (b) the $V_L$ of EXT017-5, EXT017-9, EXT017-10, EXT017-11, EXT017-17, EXT017-18, EXT017-20, EXT017-21, EXT017-23, EXT017-24, EXT017-25, EXT017-26, EXT017-27, EXT017-28, EXT017-29, EXT017-30, EXT017-32, EXT017-34, EXT017-53, EXT017-54, or EXT017-55, as shown in Appendices A and C.

In certain embodiments, the antibody or other antigen-binding protein comprises (a) a $V_H$ comprising an amino acid sequence selected from the group consisting of SEQ ID NOS: 93, 95, 97, 99, 101, 103, 105, and 107; and/or (b) a $V_L$ comprising an amino acid sequence selected from the group consisting of SEQ ID NOS: 94, 96, 98, 100, 102, 104, 106, and 108.

Preferred heavy and light chain combinations include:

(a) a heavy chain variable region comprising an amino acid sequence set forth in SEQ ID NO: 93, and a light chain variable region that comprising an amino acid sequence set forth in SEQ ID NO: 94;

(b) a heavy chain variable region comprising an amino acid sequence set forth in SEQ ID NO: 95, and a light chain variable region that comprising an amino acid sequence set forth in SEQ ID NO: 96;

(c) a heavy chain variable region comprising an amino acid sequence set forth in SEQ ID NO: 97, and a light chain variable region that comprising an amino acid sequence set forth in SEQ ID NO: 98;

(d) a heavy chain variable region comprising an amino acid sequence set forth in SEQ ID NO: 99, and a light chain variable region that comprising an amino acid sequence set forth in SEQ ID NO: 100;

(e) a heavy chain variable region comprising an amino acid sequence set forth in SEQ ID NO: 101, and a light chain variable region that comprising an amino acid sequence set forth in SEQ ID NO: 102;

(f) a heavy chain variable region comprising an amino acid sequence set forth in SEQ ID NO: 103, and a light chain variable region that comprising an amino acid sequence set forth in SEQ ID NO: 104;

(g) a heavy chain variable region comprising an amino acid sequence set forth in SEQ ID NO: 105, and a light chain variable region that comprising an amino acid sequence set forth in SEQ ID NO: 106; or (h) a heavy chain variable region comprising an amino acid sequence set forth in SEQ ID NO: 107, and a light chain variable region that comprising an amino acid sequence set forth in SEQ ID NO: 108.

In certain embodiments, a presently disclosed antibody or other antigen-binding protein comprises: (a) the $V_H$ of EXT019-6, EXT019-12, EXT019-9, EXT019-15, EXT019-20, EXT019-4, EXT019-13, and EXT019-8 as shown in Appendix D, and/or (b) the $V_L$ of EXT019-6, EXT019-12, EXT019-9, EXT019-15, EXT019-20, EXT019-4, EXT019-13, and EXT019-8, as shown in Appendix D.

For example, the antibody or other antigen-binding protein comprises (a) a VH comprising an amino acid sequence selected from the group consisting of SEQ ID NOS: 109, 111, 113, 115, and 117; and/or (b) a $V_L$ comprising an amino acid sequence selected from the group consisting of SEQ ID NOS: 110, 112, 114, 116, and 118.

Preferred heavy and light chain combinations include:

(a) a heavy chain variable region comprising an amino acid sequence set forth in SEQ ID NO: 109, and a light chain variable region that comprising an amino acid sequence set forth in SEQ ID NO: 110;

(b) a heavy chain variable region comprising an amino acid sequence set forth in SEQ ID NO: 111, and a light chain variable region that comprising an amino acid sequence set forth in SEQ ID NO: 112;

(c) a heavy chain variable region comprising an amino acid sequence set forth in SEQ ID NO: 113, and a light chain variable region that comprising an amino acid sequence set forth in SEQ ID NO: 114;

(d) a heavy chain variable region comprising an amino acid sequence set forth in SEQ ID NO: 115, and a light chain variable region that comprising an amino acid sequence set forth in SEQ ID NO: 116; or (e) a heavy chain variable region comprising an amino acid sequence set forth in SEQ ID NO: 117, and a light chain variable region that comprising an amino acid sequence set forth in SEQ ID NO: 118.

In certain embodiments, a presently disclosed antibody or other antigen-binding protein comprises: (a) the $V_H$ of EXT018-5, EXT018-2, and EXT018-4 as shown in Appendix F, and/or (b) the $V_L$ of EXT018-5, EXT018-2, and EXT018-4, as shown in Appendicx F.

For example, the antibody or other antigen-binding protein comprises (a) a $V_H$ comprising the amino acid sequence set forth in SEQ ID NO: 119; and/or (b) a $V_L$ comprising the amino acid sequence set forth in SEQ ID NOS: 120.

In certain embodiments, the presently disclosed antibody or other antigen-binding protein comprises the heavy chain and light chain CDR1s, CDR2s and CDR3s of EXT017-5, EXT017-9, EXT017-10, EXT017-11, EXT017-17, EXT017-18, EXT017-20, EXT017-21, EXT017-23, EXT017-24, EXT017-25, EXT017-26, EXT017-27, EXT017-28, EXT017-29, EXT017-30, EXT017-32, EXT017-34, EXT017-53, EXT017-54, or EXT017-55, as shown in Table 1 and Appendix B.

Given that each of EXT017-5, EXT017-9, EXT017-10, EXT017-11, EXT017-17, EXT017-18, EXT017-20, EXT017-21, EXT017-23, EXT017-24, EXT017-25, EXT017-26, EXT017-27, EXT017-28, EXT017-29, EXT017-30, EXT017-32, EXT017-34, EXT017-53, EXT017-54, or EXT017-55 can bind to Foxp3-7 in conjunction with HLA-A*02:01 and that antigen-binding specificity is provided primarily by the CDR1, CDR2, and CDR3 regions, the $V_H$ CDR1, CDR2, and CDR3 sequences and $V_L$ CDR1, CDR2, and CDR3 sequences of each of EXT017-5, EXT017-9, EXT017-10, EXT017-11, EXT017-17, EXT017-18, EXT017-20, EXT017-21, EXT017-23, EXT017-24, EXT017-25, EXT017-26, EXT017-27, EXT017-28, EXT017-29, EXT017-30, EXT017-32, EXT017-34, EXT017-53, EXT017-54, or EXT017-55 can be "mixed and matched" (i.e., CDRs from different antibodies can be mixed and match, although each antibody must contain a $V_H$ CDR1, CDR2, and CDR3 and a V L CDR1, CDR2, and CDR3) to create other antibodies or other antigen-binding proteins that bind to Foxp3-7 in conjunction with HLA-A*02:01.

Similarly, given that each of EXT019-6, EXT019-12, EXT019-9, EXT019-15, EXT019-20, EXT019-4, EXT019-13, and EXT019-8 can bind to Foxp3-2 in conjunction with HLA-A*02:01 and that antigen-binding specificity is provided primarily by the CDR1, CDR2, and CDR3 regions, the $V_H$ CDR1, CDR2, and CDR3 sequences and $V_L$ CDR1, CDR2, and CDR3 sequences of each of EXT019-6, EXT019-12, EXT019-9, EXT019-15, EXT019-20, EXT019-4, EXT019-13, and EXT019-8 can be "mixed and matched" to create other antibodies or other antigen-binding proteins that bind to Foxp3-2 in conjunction with HLA-A*02:01. Such "mixed and matched" antibodies can be tested using the binding assays described above.

Similarly, given that each of EXT018-5, EXT018-2, and EXT018-4 can bind to Foxp3-4 in conjunction with HLA-A*02:01 and that antigen-binding specificity is provided primarily by the CDR1, CDR2, and CDR3 regions, the $V_H$ CDR1, CDR2, and CDR3 sequences and $V_L$ CDR1, CDR2, and CDR3 sequences of each of EXT018-5, EXT018-2, and EXT018-4 can be "mixed and matched" to create other antibodies or other antigen-binding proteins that bind to Foxp3-4 in conjunction with HLA-A*02:01. Such "mixed and matched" antibodies can be tested using the binding assays described above.

When $V_H$ CDR sequences are mixed and matched, the CDR1, CDR2 and/or CDR3 sequence from a particular $V_H$ sequence is replaced with a structurally similar CDR sequence(s). Likewise, when $V_L$ CDR sequences are mixed and matched, the CDR1, CDR2 and/or CDR3 sequence from a particular $V_L$ sequence preferably is replaced with a structurally similar CDR sequence(s). It will be readily apparent to the ordinarily skilled artisan that novel $V_H$ and $V_L$ sequences can be created by substituting one or more $V_H$ and/or $V_L$ CDR region sequences with structurally similar sequences from the CDR sequences of the antibodies or antigen-binding portions thereof disclosed herein.

In certain embodiments, a presently disclosed antibody, or antigen-binding portion thereof comprises:

(a) the $V_H$ CDR1 of EXT017-5, EXT017-9, EXT017-10, EXT017-11, EXT017-17, EXT017-18, EXT017-20, EXT017-21, EXT017-23, EXT017-24, EXT017-25, EXT017-26, EXT017-27, EXT017-28, EXT017-29, EXT017-30, EXT017-32, EXT017-34, EXT017-53, EXT017-54, or EXT017-55, as shown in Table 1 and Appendix B;

(b) the $V_H$ CDR2 of EXT017-5, EXT017-9, EXT017-10, EXT017-11, EXT017-17, EXT017-18, EXT017-20, EXT017-21, EXT017-23, EXT017-24, EXT017-25, EXT017-26, EXT017-27, EXT017-28, EXT017-29, EXT017-30, EXT017-32, EXT017-34, EXT017-53, EXT017-54, or EXT017-55, as shown in Table 1 and Appendix B;

(c) the $V_H$ CDR3 of EXT017-5, EXT017-9, EXT017-10, EXT017-11, EXT017-17, EXT017-18, EXT017-20, EXT017-21, EXT017-23, EXT017-24, EXT017-25, EXT017-26, EXT017-27, EXT017-28, EXT017-29, EXT017-30, EXT017-32, EXT017-34, EXT017-53, EXT017-54, or EXT017-55, as shown in Table 1 and Appendix B;

(d) the $V_L$ CDR1 of EXT017-5, EXT017-9, EXT017-10, EXT017-11, EXT017-17, EXT017-18, EXT017-20, EXT017-21, EXT017-23, EXT017-24, EXT017-25, EXT017-26, EXT017-27, EXT017-28, EXT017-29, EXT017-30, EXT017-32, EXT017-34, EXT017-53, EXT017-54, or EXT017-55, as shown in Table 1 and Appendix B;

(e) the $V_L$ CDR2 of EXT017-5, EXT017-9, EXT017-10, EXT017-11, EXT017-17, EXT017-18, EXT017-20, EXT017-21, EXT017-23, EXT017-24, EXT017-25, EXT017-26, EXT017-27, EXT017-28, EXT017-29, EXT017-30, EXT017-32, EXT017-34, EXT017-53, EXT017-54, or EXT017-55, as shown in Table 1 and Appendix B; and (f) the $V_L$ CDR3 of EXT017-5, EXT017-9, EXT017-10, EXT017-11, EXT017-17, EXT017-18, EXT017-20, EXT017-21, EXT017-23, EXT017-24, EXT017-25, EXT017-26, EXT017-27, EXT017-28, EXT017-29, EXT017-30, EXT017-32, EXT017-34, EXT017-53, EXT017-54, or EXT017-55, as shown in Table 1 and Appendix B.

For example, a presently disclosed antibody, or antigen-binding portion thereof comprises:

(a) a heavy chain variable region CDR1 comprising an amino acid sequence selected from the group consisting of SEQ ID NOs: 9, 15, 21, 27, 33, 39, 45, and 51;

(b) a heavy chain variable region CDR2 comprising an amino acid sequence selected from the group consisting of SEQ ID NOs: 10, 16, 22, 28, 34, 40, 46, 52;

(c) a heavy chain variable region CDR3 comprising an amino acid sequence selected from the group consisting of SEQ ID NOs: 11, 17, 23, 29, 35, 41, 47, and 53;

(d) a light chain variable region CDR1 comprising an amino acid sequence selected from the group consisting of SEQ ID NOs: 12, 18, 24, 30, 36, 40, 42, 48, and 54;

(e) a light chain variable region CDR2 comprising an amino acid sequence selected from the group consisting of SEQ ID NOs: 13, 19, 25, 31, 37, 43, 49, and 55; and (f) a light chain variable region CDR3 comprising an amino acid sequence selected from the group consisting of SEQ ID NOs: 14, 20, 26, 32, 38, 44, 50, and 56.

In certain embodiments, a presently disclosed antibody, or antigen-binding portion thereof comprises: a heavy chain variable region CDR1 comprising an amino acid sequence set forth in SEQ ID NO: 9; a heavy chain variable region CDR2 comprising an amino acid sequence set forth in SEQ ID NO: 10; a heavy chain variable region CDR3 comprising an amino acid sequence set forth in SEQ ID NO: 11; a light chain variable region CDR1 comprising an amino acid sequence set forth in SEQ ID NO: 12; a light chain variable region CDR2 comprising an amino acid sequence set forth in SEQ ID NO: 13; and a light chain variable region CDR3 comprising an amino acid sequence set forth in SEQ ID NO: 14. The antibody comprising this combination of CDR1, CDR2, and CDR3 is referred to as "EXT017-17".

In certain embodiments, a presently disclosed antibody, or antigen-binding portion thereof comprises: a heavy chain variable region CDR1 comprising an amino acid sequence set forth in SEQ ID NO: 15; a heavy chain variable region CDR2 comprising an amino acid sequence set forth in SEQ ID NO: 16; a heavy chain variable region CDR3 comprising an amino acid sequence set forth in SEQ ID NO: 17; a light chain variable region CDR1 comprising an amino acid sequence set forth in SEQ ID NO: 18; a light chain variable region CDR2 comprising an amino acid sequence set forth in SEQ ID NO: 19; and a light chain variable region CDR3 comprising an amino acid sequence set forth in SEQ ID NO: 20. The antibody comprising this combination of CDR1, CDR2, and CDR3 is referred to as "EXT017-18".

In certain embodiments, a presently disclosed antibody, or antigen-binding portion thereof comprises: a heavy chain variable region CDR1 comprising an amino acid sequence set forth in SEQ ID NO: 21; a heavy chain variable region CDR2 comprising an amino acid sequence set forth in SEQ ID NO: 22; a heavy chain variable region CDR3 comprising an amino acid sequence set forth in SEQ ID NO: 23; a light chain variable region CDR1 comprising an amino acid sequence set forth in SEQ ID NO: 24; a light chain variable region CDR2 comprising an amino acid sequence set forth in SEQ ID NO: 25; and a light chain variable region CDR3 comprising an amino acid sequence set forth in SEQ ID NO: 26. The antibody comprising this combination of CDR1, CDR2, and CDR3 is referred to as "EXT017-20".

In certain embodiments, a presently disclosed antibody, or antigen-binding portion thereof comprises: a heavy chain variable region CDR1 comprising an amino acid sequence set forth in SEQ ID NO: 27; a heavy chain variable region CDR2 comprising an amino acid sequence set forth in SEQ ID NO: 28; a heavy chain variable region CDR3 comprising an amino acid sequence set forth in SEQ ID NO: 29; a light chain variable region CDR1 comprising an amino acid sequence set forth in SEQ ID NO: 30; a light chain variable region CDR2 comprising an amino acid sequence set forth in SEQ ID NO: 31; and a light chain variable region CDR3 comprising an amino acid sequence set forth in SEQ ID NO: 32. The antibody comprising this combination of CDR1, CDR2, and CDR3 is referred to as "EXT017-27".

In certain embodiments, a presently disclosed antibody, or antigen-binding portion thereof comprises: a heavy chain variable region CDR1 comprising an amino acid sequence set forth in SEQ ID NO: 33; a heavy chain variable region CDR2 comprising an amino acid sequence set forth in SEQ ID NO: 34; a heavy chain variable region CDR3 comprising an amino acid sequence set forth in SEQ ID NO: 35; a light chain variable region CDR1 comprising an amino acid sequence set forth in SEQ ID NO: 36; a light chain variable region CDR2 comprising an amino acid sequence set forth in SEQ ID NO: 37; and a light chain variable region CDR3 comprising an amino acid sequence set forth in SEQ ID NO: 38. The antibody comprising this combination of CDR1, CDR2, and CDR3 is referred to as “EXT017-28”.

In certain embodiments, a presently disclosed antibody, or antigen-binding portion thereof comprises: a heavy chain variable region CDR1 comprising an amino acid sequence set forth in SEQ ID NO: 39; a heavy chain variable region CDR2 comprising an amino acid sequence set forth in SEQ ID NO: 40; a heavy chain variable region CDR3 comprising an amino acid sequence set forth in SEQ ID NO: 41; a light chain variable region CDR1 comprising an amino acid sequence set forth in SEQ ID NO: 42; a light chain variable region CDR2 comprising an amino acid sequence set forth in SEQ ID NO: 43; and a light chain variable region CDR3 comprising an amino acid sequence set forth in SEQ ID NO: 44. The antibody comprising this combination of CDR1, CDR2, and CDR3 is referred to as “EXT017-32”.

In certain embodiments, a presently disclosed antibody, or antigen-binding portion thereof comprises: a heavy chain variable region CDR1 comprising an amino acid sequence set forth in SEQ ID NO: 45; a heavy chain variable region CDR2 comprising an amino acid sequence set forth in SEQ ID NO: 46; a heavy chain variable region CDR3 comprising an amino acid sequence set forth in SEQ ID NO: 47; a light chain variable region CDR1 comprising an amino acid sequence set forth in SEQ ID NO: 48; a light chain variable region CDR2 comprising an amino acid sequence set forth in SEQ ID NO: 49; and a light chain variable region CDR3 comprising an amino acid sequence set forth in SEQ ID NO: 50. The antibody comprising this combination of CDR1, CDR2, and CDR3 is referred to as “EXT017-53”.

In certain embodiments, a presently disclosed antibody, or antigen-binding portion thereof comprises: a heavy chain variable region CDR1 comprising an amino acid sequence set forth in SEQ ID NO: 51; a heavy chain variable region CDR2 comprising an amino acid sequence set forth in SEQ ID NO: 52; a heavy chain variable region CDR3 comprising an amino acid sequence set forth in SEQ ID NO: 53; a light chain variable region CDR1 comprising an amino acid sequence set forth in SEQ ID NO: 54; a light chain variable region CDR2 comprising an amino acid sequence set forth in SEQ ID NO: 55; and a light chain variable region CDR3 comprising an amino acid sequence set forth in SEQ ID NO: 56. The antibody comprising this combination of CDR1, CDR2, and CDR3 is referred to as “EXT017-54”.

In certain embodiments, a presently disclosed antibody, or antigen-binding portion thereof comprises:

(a) the $V_H$ CDR1 of EXT019-6, EXT019-12, EXT019-9, EXT019-15, EXT019-20, EXT019-4, EXT019-13, and EXT019-8, as shown in Table 2 and Appendix E;

(b) the $V_H$ CDR2 of EXT019-6, EXT019-12, EXT019-9, EXT019-15, EXT019-20, EXT019-4, EXT019-13, and EXT019-8, as shown in Table 2 and Appendix E;

(c) the $V_H$ CDR3 of EXT019-6, EXT019-12, EXT019-9, EXT019-15, EXT019-20, EXT019-4, EXT019-13, and EXT019-8, as shown in Table 2 and Appendix E;

(d) the $V_L$ CDR1 of EXT019-6, EXT019-12, EXT019-9, EXT019-15, EXT019-20, EXT019-4, EXT019-13, and EXT019-8, as shown in Table 2 and Appendix E;

(e) the $V_L$ CDR2 of EXT019-6, EXT019-12, EXT019-9, EXT019-15, EXT019-20, EXT019-4, EXT019-13, and EXT019-8, as shown in Table 2 and Appendix E; and (f) the $V_L$ CDR3 of EXT019-6, EXT019-12, EXT019-9, EXT019-15, EXT019-20, EXT019-4, EXT019-13, and EXT019-8, as shown in Table 2 and Appendix E.

For example, a presently disclosed antibody, or antigen-binding portion thereof comprises:

(a) a heavy chain variable region CDR1 comprising an amino acid sequence selected from the group consisting of SEQ ID NOs: 57, 63, 69, 75, and 81;

(b) a heavy chain variable region CDR2 comprising an amino acid sequence selected from the group consisting of SEQ ID NOs: 58, 64, 70, 76, and 82;

(c) a heavy chain variable region CDR3 comprising an amino acid sequence selected from the group consisting of SEQ ID NOs: 59, 65, 71, 77, and 83;

(d) a light chain variable region CDR1 comprising an amino acid sequence selected from the group consisting of SEQ ID NOs: 60, 66, 72, 78, and 84;

(e) a light chain variable region CDR2 comprising an amino acid sequence selected from the group consisting of SEQ ID NOs: 61, 67, 73, 79, and 85; and (f) a light chain variable region CDR3 comprising an amino acid sequence selected from the group consisting of SEQ ID NOs: 62, 68, 74, 80, and 86.

In certain embodiments, a presently disclosed antibody, or antigen-binding portion thereof comprises: a heavy chain variable region CDR1 comprising an amino acid sequence set forth in SEQ ID NO: 57; a heavy chain variable region CDR2 comprising an amino acid sequence set forth in SEQ ID NO: 58; a heavy chain variable region CDR3 comprising an amino acid sequence set forth in SEQ ID NO: 59; a light chain variable region CDR1 comprising an amino acid sequence set forth in SEQ ID NO: 60; a light chain variable region CDR2 comprising an amino acid sequence set forth in SEQ ID NO: 61; and a light chain variable region CDR3 comprising an amino acid sequence set forth in SEQ ID NO: 62. The antibody comprising this combination of CDR1, CDR2, and CDR3 is referred to as “EXT019-6”.

In certain embodiment, a presently disclosed antibody, or antigen-binding portion thereof comprises: a heavy chain variable region CDR1 comprising an amino acid sequence set forth in SEQ ID NO: 63; a heavy chain variable region CDR2 comprising an amino acid sequence set forth in SEQ ID NO: 64; a heavy chain variable region CDR3 comprising an amino acid sequence set forth in SEQ ID NO: 65; a light chain variable region CDR1 comprising an amino acid sequence set forth in SEQ ID NO: 66; a light chain variable region CDR2 comprising an amino acid sequence set forth in SEQ ID NO: 67; and a light chain variable region CDR3 comprising an amino acid sequence set forth in SEQ ID NO: 68. The antibody comprising this combination of CDR1, CDR2, and CDR3 is referred to as “EXT019-9”.

In certain embodiment, a presently disclosed antibody, or antigen-binding portion thereof comprises: a heavy chain variable region CDR1 comprising an amino acid sequence set forth in SEQ ID NO: 69; a heavy chain variable region CDR2 comprising an amino acid sequence set forth in SEQ ID NO: 70; a heavy chain variable region CDR3 comprising an amino acid sequence set forth in SEQ ID NO: 71; a light chain variable region CDR1 comprising an amino acid sequence set forth in SEQ ID NO: 72; a light chain variable region CDR2 comprising an amino acid sequence set forth in SEQ ID NO: 73; and a light chain variable region CDR3 comprising an amino acid sequence set forth in SEQ ID NO:

74. The antibody comprising this combination of CDR1, CDR2, and CDR3 is referred to as "EXT019-12".

In certain embodiment, a presently disclosed antibody, or antigen-binding portion thereof comprises: a heavy chain variable region CDR1 comprising an amino acid sequence set forth in SEQ ID NO: 75; a heavy chain variable region CDR2 comprising an amino acid sequence set forth in SEQ ID NO: 76; a heavy chain variable region CDR3 comprising an amino acid sequence set forth in SEQ ID NO: 77; a light chain variable region CDR1 comprising an amino acid sequence set forth in SEQ ID NO: 78; a light chain variable region CDR2 comprising an amino acid sequence set forth in SEQ ID NO: 79; and a light chain variable region CDR3 comprising an amino acid sequence set forth in SEQ ID NO: 80. The antibody comprising this combination of CDR1, CDR2, and CDR3 is referred to as "EXT019-15".

In certain embodiment, a presently disclosed antibody, or antigen-binding portion thereof comprises: a heavy chain variable region CDR1 comprising an amino acid sequence set forth in SEQ ID NO: 81; a heavy chain variable region CDR2 comprising an amino acid sequence set forth in SEQ ID NO: 82; a heavy chain variable region CDR3 comprising an amino acid sequence set forth in SEQ ID NO: 83; a light chain variable region CDR1 comprising an amino acid sequence set forth in SEQ ID NO: 84; a light chain variable region CDR2 comprising an amino acid sequence set forth in SEQ ID NO: 85; and a light chain variable region CDR3 comprising an amino acid sequence set forth in SEQ ID NO: 86. The antibody comprising this combination of CDR1, CDR2, and CDR3 is referred to as "EXT019-20".

In certain embodiments, a presently disclosed antibody, or antigen-binding portion thereof comprises:

(a) the $V_H$ CDR1 of EXT018-5, EXT018-2, and EXT018-4, as shown in Table 3 and Appendix G;

(b) the $V_H$ CDR2 of EXT018-5, EXT018-2, and EXT018-4, as shown in Table 3 and Appendix G;

(c) the $V_H$ CDR3 of EXT018-5, EXT018-2, and EXT018-4, as shown in Table 3 and Appendix G;

(d) the $V_L$ CDR1 of EXT018-5, EXT018-2, and EXT018-4, as shown in Table 3 and Appendix G;

(e) the $V_L$ CDR2 of EXT018-5, EXT018-2, and EXT018-4, as shown in Table 3 and Appendix G; and (f) the $V_L$ CDR3 of EXT018-5, EXT018-2, and EXT018-4, as shown in Table 3 and Appendix G.

In certain embodiments, a presently disclosed antibody, or antigen-binding portion thereof comprises: a heavy chain variable region CDR1 comprising an amino acid sequence set forth in SEQ ID NO: 87; a heavy chain variable region CDR2 comprising an amino acid sequence set forth in SEQ ID NO: 88; a heavy chain variable region CDR3 comprising an amino acid sequence set forth in SEQ ID NO: 89; a light chain variable region CDR1 comprising an amino acid sequence set forth in SEQ ID NO: 90; a light chain variable region CDR2 comprising an amino acid sequence set forth in SEQ ID NO: 91; and a light chain variable region CDR3 comprising an amino acid sequence set forth in SEQ ID NO: 92. The antibody comprising this combination of CDR1, CDR2, and CDR3 is referred to as "EXT018-5".

The constant region/framework region of the presently disclosed antibodies can be altered, for example, by amino acid substitution, to modify the properties of the antibody (e.g., to increase or decrease one or more of: antigen binding affinity, Fc receptor binding, antibody carbohydrate, for example, glycosylation, fucosylation, etc, the number of cysteine residues, effector cell function, effector cell function, complement function or introduction of a conjugation site).

In certain embodiments, a presently disclosed antibody is a fully-human antibody. In certain embodiments, a presently disclosed antibody is a fully-human monoclonal antibody (mAb). Fully-human mAbs are preferred for therapeutic use in humans because murine antibodies cause an immunogenicity reaction, known as the HAMA (human anti-mouse antibodies) response (Azinovic I, et al. Survival benefit associated with human anti-mouse antibody (HAMA) in patients with B-cell malignancies. Cancer Immunol Immunother 2006; 55(12):1451-8; Tjandra J J, et al. Development of human anti-murine antibody (HAMA) response in patients. Immunol Cell Biol 1990; 68(6):367-76), when administered to humans, causing serious side effects, including anaphylaxis and hypersensitivity reactions. This immunogenicity reaction is triggered by the human immune system recognizing the murine antibodies as foreign because of slightly different amino acid sequences from natural human antibodies. Humanization methods known in the art (Riechmann L, et al. Reshaping human antibodies for therapy. Nature 1988; 332 (6162): 332:323; Queen C, et al. A humanized antibody that binds to the interleukin 2 receptor. Proc Natl Acad Sci USA 1989; 86 (24): 10029-33) can be employed to reduce the immunogenicity of murine-derived antibodies (Gerd R, et al. Serological Analysis of Human Anti-Human Antibody Responses in Colon Cancer Patients Treated with Repeated Doses of Humanized Monoclonal Antibody A33. Cancer Res 2001; 61, 6851-6859).

The use of phage display libraries has made it possible to select large numbers of antibodies repertoires for unique and rare antibodies against very defined epitopes (for more details on phage display see McCafferty et al., Phage antibodies: filamentous phage displaying antibody variable domains. Nature, 348: 552-554.) The rapid identification of human Fab or scFvs highly specific for tumor antigen-derived peptide-MHC complex molecules has thus become possible. Immuno-toxins, generated by fusing TCR-like Fab specific for melanoma Ag MART-1 26-35/A2 or gp100 280-288/A2 to a truncated form of *Pseudomonas* endotoxin, have been shown to inhibit human melanoma growth both in vitro and in vivo (Klechevsky E, et al. Antitumor activity of immunotoxins with T-cell receptor-like specificity against human melanoma xenografts. Cancer Res 2008; 68 (15): 6360-6367). In addition, by engineering full-length monoclonal antibodies (mAbs) using the Fab fragments, it is possible to directly generate a therapeutic human mAbs, bypassing months of time-consuming work, normally needed for developing therapeutic mAbs, e.g., for treating cancers, or immune diseases.

Homologous Antibodies

In certain embodiments, a presently disclosed antibody or antigen-binding portion thereof comprises heavy and light chain variable regions comprising amino acid sequences that are homologous to the amino acid sequences of the antibodies or antigen-binding portions thereof (e.g., scFvs) described herein (e.g., EXT017-5, EXT017-9, EXT017-10, EXT017-11, EXT017-17, EXT017-18, EXT017-20, EXT017-21, EXT017-23, EXT017-24, EXT017-25, EXT017-26, EXT017-27, EXT017-28, EXT017-29, EXT017-30, EXT017-32, EXT017-34, EXT017-53, EXT017-54, EXT017-55, EXT019-6, EXT019-12, EXT019-9, EXT019-15, EXT019-20, EXT019-4, EXT019-13, EXT019-8, EXT018-5, EXT018-2, or EXT018-4), and wherein the antibodies or antigen-binding portions thereof retain the desired functional properties of the anti-Foxp3 antibodies or antigen-binding portions thereof of the presently disclosed subject matter.

For example, a presently disclosed antibody or antigen-binding portion thereof comprises a heavy chain variable region comprising an amino acid sequence that is at least about 80% homologous (e.g., at least about 81% homologous, at least about 82% homologous, at least about 83% homologous, at least about 84% homologous, at least about 85% homologous, at least about 86% homologous, at least about 87% homologous, at least about 88% homologous, at least about 89% homologous, at least about 90% homologous, at least about 91% homologous, at least about 92% homologous, at least about 93% homologous, at least about 94% homologous, at least about 95% homologous, at least about 96% homologous, at least about 97% homologous, at least about 98% homologous, at least about 99% homologous, or about 100% homologous) to the $V_H$ sequence of EXT017-5, EXT017-9, EXT017-10, EXT017-11, EXT017-17, EXT017-18, EXT017-20, EXT017-21, EXT017-23, EXT017-24, EXT017-25, EXT017-26, EXT017-27, EXT017-28, EXT017-29, EXT017-30, EXT017-32, EXT017-34, EXT017-53, EXT017-54, EXT017-55, EXT019-6, EXT019-12, EXT019-9, EXT019-15, EXT019-20, EXT019-4, EXT019-13, EXT019-8, EXT018-5, EXT018-2, or EXT018-4 (as shown in Appendices A, C, D, and F), and a light chain variable region comprising an amino acid sequence that is at least 80% homologous (e.g., at least about 81% homologous, at least about 82% homologous, at least about 83% homologous, at least about 84% homologous, at least about 85% homologous, at least about 86% homologous, at least about 87% homologous, at least about 88% homologous, at least about 89% homologous, at least about 90% homologous, at least about 91% homologous, at least about 92% homologous, at least about 93% homologous, at least about 94% homologous, at least about 95% homologous, at least about 96% homologous, at least about 97% homologous, at least about 98% homologous, at least about 99% homologous, or about 100% homologous) to the $V_L$ sequence of EXT017-5, EXT017-9, EXT017-10, EXT017-11, EXT017-17, EXT017-18, EXT017-20, EXT017-21, EXT017-23, EXT017-24, EXT017-25, EXT017-26, EXT017-27, EXT017-28, EXT017-29, EXT017-30, EXT017-32, EXT017-34, EXT017-53, EXT017-54, EXT017-55, EXT019-6, EXT019-12, EXT019-9, EXT019-15, EXT019-20, EXT019-4, EXT019-13, EXT019-8, EXT018-5, EXT018-2, or EXT018-4 (as shown in Appendices A, C, D, and F), and the antibody or antigen-binding portion thereof binds to a Foxp3 peptide in conjunction with HLA-A*02:01 with a $K_D$ of about $5\times10^{-7}$M or less.

For example, a presently disclosed antibody or antigen-binding portion thereof comprises:

(a) a heavy chain variable region comprising an amino acid sequence that is at least about 80% homologous to an amino acid sequence selected from the group consisting of SEQ ID NOs: 93, 95, 97, 99, 101, 103, 105, 107, 109, 111, 113, 115, 117, and 119;

(b) a light chain variable region comprising an amino acid sequence that is at least about 80% homologous to an amino acid sequence selected from the group consisting of SEQ ID NOs: 94, 96, 98, 100, 102, 104, 106, 108, 110, 112, 114, 116, 118, and 120; and wherein the antibody or antigen-binding portion thereof binds to a Foxp3 peptide in conjunction with HLA-A*02:01 with a $K_D$ of about $5\times10^{-7}$ M or less.

In certain embodiments, the $V_H$ and/or $V_L$ amino acid sequences can be about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% homologous to the sequences set forth above. An antibody having $V_H$ and $V_L$ regions having high (i.e., about 80% or greater) homology to the $V_H$ and $V_L$ regions of the sequences set forth above, can be obtained by mutagenesis (e.g., site-directed or PCR-mediated mutagenesis), followed by testing of the encoded altered antibody for retained function (i.e., the binding affinity) using the binding assays described herein.

The comparison of sequences and determination of homology between two sequences can be accomplished using a mathematical algorithm and is standard in the art.

As one non-limiting example, the percent homology between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percent homology between two amino acid sequences can be determined using the Needleman and Wunsch (J. Mol. Biol. 48:444-453 (1970)) algorithm which has been incorporated into the GAP program in the GCG software package (available at gcg.com), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the presently disclosed subject matter can further be used as a "query sequence" to perform a search against public databases to, for example, identify related sequences. Such searches can be performed using the XBLAST program (version 2.0) of Altschul, et al. (1990) J. Mol. Biol. 215: 403-10. BLAST protein searches can be performed with the XBLAST program, score=50, wordlength=3 to obtain amino acid sequences homologous to the antibody molecules of the invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and NBLAST) can be used. (See ncbi.nlm.nih.gov).

Antibodies with Modifications

In certain embodiments, a presently disclosed antibody or antigen-binding portion thereof comprises a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on the antibodies or antigen-binding portions thereof (e.g., scFvs) described herein (e.g., EXT017-5, EXT017-9, EXT017-10, EXT017-11, EXT017-17, EXT017-18, EXT017-20, EXT017-21, EXT017-23, EXT017-24, EXT017-25, EXT017-26, EXT017-27, EXT017-28, EXT017-29, EXT017-30, EXT017-32, EXT017-34, EXT017-53, EXT017-54, EXT017-55, EXT019-6, EXT019-12, EXT019-9, EXT019-15, EXT019-20, EXT019-4, EXT019-13, EXT019-8, EXT018-5, EXT018-2, or EXT018-4, as shown in Tables 1-3 and Appendices B, E and G), or modifications thereof, and wherein the antibodies or antigen-binding portions thereof retain the desired functional properties of the anti-Foxp3 antibodies or antigen-binding portions thereof of the presently disclosed subject matter.

The presently disclosed subject matter provides an isolated antibody, or antigen-binding portion thereof, comprising a heavy chain variable region comprising CDR1, CDR2, and CDR3 sequences and a light chain variable region comprising CDR1, CDR2, and CDR3 sequences, wherein:

(a) the heavy chain variable region CDR3 sequence comprises an amino acid sequence selected from the group consisting of SEQ ID NOs: 11, 17, 23, 29, 35, 41, 47, 53, 59, 65, 71, 77, 83, and 89, or a conservative modification thereof;

(b) the light chain variable region CDR3 sequence comprises an amino acid sequence selected from the group consisting of SEQ ID NOs: 14, 20, 26, 32, 38, 44, 50, 56, 62, 68, 74, 80, 86, and 92, or a modification thereof, and the antibody or antigen-binding portion thereof specifically binds to a Foxp3 peptide bound to a MHC molecule.

In certain embodiments, the heavy chain variable region CDR2 sequence comprises an amino acid sequence selected from the group consisting of SEQ ID NOs: 10, 16, 22, 28, 34, 40, 46, 52, 58, 64, 70, 76, 82, and 88, or a modification thereof; and the light chain variable region CDR2 sequence comprises an amino acid sequence selected from the group consisting of SEQ ID NOs: 13, 19, 25, 31, 37, 43, 49, 55, 61, 67, 73, 79, 85, and 91, or a modification thereof.

In certain embodiments, the heavy chain variable region CDR1 sequence comprises an amino acid sequence selected from the group consisting of SEQ ID NOs: 9, 15, 21, 27, 33, 39, 45, 51, 57, 63, 69, 75, 81, and 87, and a modification thereof; and the light chain variable region CDR1 sequence comprises an amino acid sequence selected from the group consisting of SEQ ID NOs: 12, 18, 24, 30, 36, 42, 48, 54, 60, 66, 72, 78, 84, and 90, or a modification thereof.

In certain embodiments, the modification(s) do not significantly affect or alter the binding characteristics of the antibody containing the amino acid sequence. Such modifications include amino acid substitutions, additions and deletions. Modifications can be introduced into the presently antibody or antigen-binding portion by standard techniques known in the art, such as site-directed mutagenesis and PCR-mediated mutagenesis.

The modifications can be conservative modifications, non-conservative modifications, or mixtures of conservative and non-conservative modifications. Conservative amino acid substitutions are ones in which the amino acid residue is replaced with an amino acid residue having a similar side chain. Families of amino acid residues having similar side chains have been defined in the art. Exemplary conservative amino acid substitutions are shown in Table 4. Amino acid substitutions may be introduced into an antibody of interest and the products screened for a desired activity, e.g., retained/improved antigen binding, decreased immunogenicity, or improved ADCC or CDC.

TABLE 4

| Original Residue | Exemplary conservative amino acid Substitutions |
|---|---|
| Ala (A) | Val; Leu; Ile |
| Arg (R) | Lys; Gln; Asn |
| Asn (N) | Gln; His; Asp, Lys; Arg |
| Asp (D) | Glu; Asn |
| Cys (C) | Ser; Ala |
| Gln (Q) | Asn; Glu |
| Glu (E) | Asp; Gln |
| Gly (G) | Ala |
| His (H) | Asn; Gln; Lys; Arg |
| Ile (I) | Leu; Val; Met; Ala; Phe |
| Leu (L) | Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |

TABLE 4-continued

| Original Residue | Exemplary conservative amino acid Substitutions |
|---|---|
| Pro (P) | Ala |
| Ser (S) | Thr |
| Thr (T) | Val; Ser |
| Trp (W) | Tyr; Phe |
| Tyr (Y) | Trp; Phe; Thr; Ser |
| Val (V) | Ile; Leu; Met; Phe; Ala |

Amino acids may be grouped according to common side-chain properties:

hydrophobic: Norleucine, Met, Ala, Val, Leu, Ile;

neutral hydrophilic: Cys, Ser, Thr, Asn, Gln;

acidic: Asp, Glu;

basic: His, Lys, Arg;

residues that influence chain orientation: Gly, Pro;

aromatic: Trp, Tyr, Phe.

Thus, one or more amino acid residues within a CDR region can be replaced with other amino acid residues from the same group and the altered antibody can be tested for retained function using the functional assays described herein.

Non-conservative substitutions entail exchanging a member of one of these classes for another class.

In certain embodiments, no more than one, no more than two, no more than three, no more than four, no more than five residues within a specified sequence or a CDR region are altered.

Cross-Competing Antibodies

The presently disclosed subject matter provides antibodies or antigen-binding portions thereof that cross-compete for binding to a Foxp3 peptide/HLA complex (e.g., a Foxp3 peptide/HLA class I complex, a Foxp3 peptide/HLA-A2 complex, or a Foxp3 peptide/HLA-A*02:01 complex) with any of the anti-Foxp3 antibodies or antigen-binding portions thereof (e.g., scFvs) of the presently disclosed subject matter (e.g., EXT017-5, EXT017-9, EXT017-10, EXT017-11, EXT017-17, EXT017-18, EXT017-20, EXT017-21, EXT017-23, EXT017-24, EXT017-25, EXT017-26, EXT017-27, EXT017-28, EXT017-29, EXT017-30, EXT017-32, EXT017-34, EXT017-53, EXT017-54, EXT017-55, EXT019-6, EXT019-12, EXT019-9, EXT019-15, EXT019-20, EXT019-4, EXT019-13, EXT019-8, EXT018-5, EXT018-2, or EXT018-4), and specifically binds to a Foxp3 peptide with a binding affinity ($K_D$) of about $5\times10^{-7}$ M or less, e.g., about $1\times10^{-7}$ M or less, about $5\times10^{-8}$ M or less, about $1\times10^{-8}$ M or less, about $5\times10^{-9}$ M or less, about $1\times10^{-9}$ M or less, about $5\times10^{-10}$ M or less, about $1\times10^{-10}$ M or less, about $5\times10^{-11}$ M or less, or about $1\times10^{-11}$M or less. The cross-competing antibodies or antigen-binding portions thereof bind to the same epitope region, e.g., same epitope, adjacent epitope, or overlapping as any of the anti-Foxp3 antibodies or antigen-binding portions thereof described herein. In certain embodiments, the cross-competing antibodies or antigen-binding portions thereof bind to the same epitope on the Foxp3 peptide as any of the anti-Foxp3 antibodies or antigen-binding portions thereof described herein.

Such cross-competing antibodies can be identified based on their ability to cross-compete with any one of the presently disclosed anti-Foxp3 antibodies or antigen-binding portions thereof in standard Foxp3 binding assays. For example, Biacore analysis, ELISA assays or flow cytometry can be used to demonstrate cross-competition with the antibodies or antigen-binding portions thereof of the presently disclosed subject matter. The ability of a test antibody to inhibit the binding of, for example, any one of the presently disclosed anti-Foxp3 antibodies or antigen-binding portions thereof to a Foxp3 peptide/MHC (e.g., a Foxp3/HLA complex more specifically, a Foxp3/HLA class I complex, more specifically, a Foxp3/HLA-A2 complex, and more specifically, a Foxp3/HLA-A*02:01 complex) demonstrates that the test antibody can compete with any one of the presently disclosed anti-Foxp3 antibodies or antigen-binding portions thereof for binding to such Foxp3 peptide/MHC complex.

Characterization of Antibody Binding to Antigen

Antibodies of the presently disclosed subject can be tested for binding to a Foxp3 peptide/HLA complex by, for example, standard ELISA. To determine the isotype of purified antibodies, isotype ELISAs can be performed using reagents specific for antibodies of a particular isotype. Anti-Foxp3 human IgGs can be further tested for reactivity with the Foxp3 peptide/MHC complex by Western blotting.

In certain embodiments, $K_D$ is measured by a radiolabeled antigen binding assay (RIA). In certain embodiments, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881 (1999)).

In certain embodiments, $K_D$ is measured using a BIACORE® surface plasmon resonance assay. For example, an assay using a BIACORE®-2000 or a BIACORE®-3000 (BIAcore, Inc., Piscataway, N.J.)

Immunoconjugates

The presently disclosed subject provides for an anti-Foxp3 antibody or an antigen-binding portion thereof conjugated to a therapeutic moiety, such as a cytotoxin, a drug (e.g., an immunosuppressant) or a radiotoxin. Such conjugates are referred to herein as "immunoconjugates". Immunoconjugates that include one or more cytotoxins are referred to as "immunotoxins." A cytotoxin or cytotoxic agent includes any agent that is detrimental to (e.g., kills) cells. Examples include taxol (such as ricin, diphtheria, gelonin), cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, calecheamicin, aureastatin, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other examples of therapeutic cytotoxins that can be conjugated to an anti-Foxp3 antibody or an antigen-binding portion thereof disclosed herein include duocarmycins, calicheamicins, maytansines and auristatins, and derivatives thereof. An example of a calicheamicin antibody conjugate is commercially available (Mylotarg™; Wyeth-Ayerst).

Cytoxins can be conjugated to anti-Foxp3 antibody or an antigen-binding portion thereof disclosed herein using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D). For further discussion of types of cytotoxins, linkers and methods for conjugating therapeutic agents to antibodies, see also Saito, G. et al. (2003) Adv. Drug Deliv. Rev. 55:199-215; Trail, P. A. et al. (2003) Cancer Immunol. Immunother. 52:328-337; Payne, G. (2003) Cancer Cell 3:207-212; Allen, T. M. (2002) Nat. Rev. Cancer 2:750-763; Pastan, I. and Kreitman, R. J. (2002) Curr. Opin. Investig. Drugs 3:1089-1091; Senter, P. D. and Springer, C. J. (2001) Adv. Drug Deliv. Rev. 53:247-264.

Anti-Foxp3 antibodies of the presently disclosed subject matter also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, $^{90}$Y, $^{131}$I, $^{225}$Ac, $^{213}$Bi, $^{223}$Ra, $^{177}$Lu, and $^{227}$Th. a Method for preparing radioimmunconjugates are established in the art. Examples of radioimmunoconjugates are commercially available, including Zevalin™ (IDEC Pharmaceuticals) and Bexxar™ (Corixa Pharmaceuticals), and similar methods can be used to prepare radioimmunoconjugates using the antibodies of the invention.

The antibody conjugates of the presently disclosed subject matter can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor (TNF) or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Bispecific Molecules

The presently disclosed subject matter provides for bispecific molecules comprising an anti-Foxp3 antibody or an antigen-binding portion thereof disclosed herein. An antibody or an antigen-binding portion thereof of the presently disclosed subject matter, can be derivatized or linked to another functional molecule, e.g., another peptide or protein (e.g., another antibody or ligand for a receptor) to generate a bispecific molecule that binds to at least two different binding sites or target molecules. The antibody of the presently disclosed subject matter can in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule, a presently disclosed anti-Foxp3 antibody or an antigen-binding portion thereof can be functionally linked (e.g., by chemical coupling, genetic fusion, noncovalent association or otherwise) to one or more other binding molecules, such as another antibody, antibody fragment, peptide or binding mimetic, such that a bispecific molecule results.

The presently disclosed subject matter provides bispecific molecules comprising at least one first binding specificity for a first target epitope or antigen and a second binding specificity for a second target epitope or antigen. The second target epitope or antigen can be different from the first epitope or antigen. In certain embodiments, the bispecific molecule is multispecific, the molecule can further include a third binding specificity. Where a first portion of a bispecific antibody binds to an antigen on a tumor cell for example and a second portion of a bispecific antibody recognizes an antigen on the surface of a human immune effector cell, the antibody is capable of recruiting the activity of that effector cell by specifically binding to the effector antigen on the human immune effector cell. In certain embodiments, bispecific antibodies, therefore, are able to form a link between effector cells, for example, T cells and tumor cells, thereby enhancing effector function.

The bispecific molecules of the presently disclosed subject matter can be prepared by conjugating the constituent binding specificities using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5, 5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC) (see e.g., Karpovsky et al. (1984) J. Exp. Med. 160:1686; Liu, M A et al. (1985) Proc. Natl. Acad. Sci. USA 82:8648). Other methods include those described in Paulus (1985) Behring Ins. Mitt. No. 78, 118-132; Brennan et al. (1985) Science 229:81-83), and Glennie et al. (1987) J. Immunol. 139: 2367-2375). Preferred conjugating agents are SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains. In one non-limiting embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')$_2$ or ligand x Fab fusion protein.

Binding of the bispecific molecules to their specific targets can be confirmed by, for example, enzyme-linked immunosorbent assay (ELISA), radioimmunoassay (RIA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest. Alternatively, the complexes can be detected using any of a variety of other immunoassays. For example, the antibody can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a γ counter or a scintillation counter or by autoradiography.

In certain embodiments, the bispecific antibodies recognize both Foxp3/MHC complex and a cell surface protein on a T cell, a NK cell, a NK T cell, neutrophil, monocyte, or macrophage. Non-limiting examples of cell surface protein include CD3 and CD16. In certain embodiments, the bispecific antibodies recognize both Foxp3/MHC complex and CD3 on immune T cells as described (Yan, et al., *J. Biol. Chem.* 2010; 285: 19637-19646; Rossi, et al., *Proc Natl Aca Sci USA* 2006; 103:6841-6) with a human IgG1 Fc. Bispecific antibodies recruit and target cytotoxic T cells to Foxp3/MHC positive cancer cells, while maintaining Fc effector functions and long half life in vivo. Three mechanisms are involved in the specific killing of cancer cells mediated by bispecific antibodies: i) killing by activated T cells; ii) ADCC activity; iii) CDC activity. Other formats of bispecific antibodies can be constructed, such tandem scFv molecules (taFv), diabodies (db), or single chain diabodies (scDb), and fusion protein with human serum albumin (Ryutaro, et al., *J Biol Chem* 2011; 286: 1812-1818; Anja, et al., *Blood* 2000; 95(6): 2098-2103; Weiner, et al., *J Immunology* 1994; 152(5): 2385-2392; Dafne, et al., *J Biol Chem* 2007; 282: 12650-12660), but are devoid of Fc effector functions with distinct pharmacokinetic profiles.

Engineered and Modified Antibodies

An antibody of the presently disclosed subject matter further can be prepared using an antibody or an antigen-binding portion thereof having one or more of the $V_H$ and/or $V_L$ sequences disclosed herein as starting material to engineer a modified antibody, which modified antibody may have altered properties from the starting antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain CDRs. For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) Nature 332:323-327; Jones, P. et al. (1986) Nature 321:522-525; Queen, C. et al. (1989) Proc. Natl. Acad. See. U.S.A. 86:10029-10033; U.S. Pat. No. 5,225,539 to Winter, and U.S. Pat. Nos. 5,530,101; 5,585,089; 5,693,762 and 6,180,370 to Queen et al.)

Framework sequences can be obtained from public DNA databases or published references that include germline antibody gene sequences. For example, germline DNA sequences for human heavy and light chain variable region genes can be found in the IMGT human germline sequence database (available on the Internet at imgt.org), as well as in Kabat, E. A., et al. (1991) Sequences of Proteins of Immunological Interest, Fifth Edition, U.S. Department of Health and Human Services, NIH Publication No. 91-3242; Tomlinson, I. M., et al. (1992) "The Repertoire of Human Germline $V_H$ Sequences Reveals about Fifty Groups of $V_H$ Segments with Different Hypervariable Loops" J. Mol. Biol. 227:776-798; and Cox, J. P. L. et al. (1994) "A Directory of Human Germ-line $V_H$ Segments Reveals a Strong Bias in their Usage" Eur. J. Immunol. 24:827-836; the contents of each of which are expressly incorporated herein by reference. As another example, the germline DNA sequences for human heavy and light chain variable region genes can be found in the GenBank database.

The $V_H$ CDR1, CDR2, and CDR3 sequences, and the $V_L$ CDR1, CDR2, and CDR3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al).

Another type of variable region modification is to mutate amino acid residues within the $V_H$ and/or $V_L$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays. Preferably conservative modifications (as discussed above) are introduced. The mutations may be amino acid substitutions, additions or deletions. For example, no more than one, two, three, four or five residues within a CDR region are altered.

Accordingly, the presently disclosed subject matter provides for isolated anti-Foxp3 monoclonal antibodies or antigen-binding portions thereof comprising a heavy chain variable region comprising: (a) the $V_H$ CDR1 sequence of the antibodies and antigen-bindingn portions thereof (e.g., scFvs) disclosed herein (e.g., #9, #11, #17, #18, #20, #21, #26, #27, #28, #32, #53, #54, #6, #9, #12, #15, or #5), or an amino acid sequence having at least one (e.g., no more than one, no more than two, no more than three, no more than four or no more than five) amino acid modification (e.g., substitution, deletion and/or addition) as compared to the $V_H$ CDR1 sequence of any one of the antibodies or antigen-binding portions thereof disclosed herein; (b) the $V_H$ CDR2 sequence of any one of the antibodies or antigen-binding portions thereof disclosed herein, or an amino acid sequence having at least one (e.g., no more than one, no more than two, no more than three, no more than four or no more than five) amino acid modification (e.g., substitution, deletion and/or addition) as compared to the $V_H$ CDR2 of any one of the antibodies or antigen-binding portions thereof disclosed herein; (c) the $V_H$ CDR3 sequence of any one of the antibodies or antigen-binding portions thereof disclosed herein, or an amino acid sequence having at least one (e.g., no more than one, no more than two, no more than three, no more than four or no more than five) amino acid modification (e.g., substitution, deletion and/or addition) as compared to the $V_H$ CDR3 of any one of the antibodies or antigen-binding portions thereof disclosed herein; (d) the $V_L$ CDR1 sequence of any one of the antibodies or antigen-binding portions thereof disclosed herein, or an amino acid sequence having at least one (e.g., no more than one, no more than two, no more than three, no more than four or no more than five) amino acid modification (e.g., substitution, deletion and/or addition) as compared to the $V_L$ CDR1 of any one of the antibodies or antigen-binding portions thereof disclosed herein; (e) the $V_L$ CDR2 sequence of any one of the antibodies or antigen-binding portions thereof disclosed herein, or an amino acid sequence having at least one (e.g., no more than one, no more than two, no more than three, no more than four or no more than five) amino acid modification (e.g., substitution, deletion and/or addition) as compared to the $V_L$ CDR2 of any one of the antibodies or antigen-binding portions thereof disclosed herein; and (f) the $V_L$ CDR3 sequence of any one of the antibodies or antigen-binding portions thereof disclosed herein, or an amino acid sequence having at least one (e.g., no more than one, no more than two, no more than three, no more than four or no more than five) amino acid modification (e.g., substitution, deletion and/or addition) as compared to the $V_L$ CDR3 of any one of the antibodies or antigen-binding portions thereof disclosed herein.

For example, the presently disclosed subject matter provides for isolated anti-Foxp3 monoclonal antibodies or antigen-binding portions thereof comprising a heavy chain variable region comprising: (a) a $V_H$ CDR1 region comprising the amino acid sequence set forth in SEQ ID NOS: 9, 15, 21, 27, 33, 39, 45, 51, 57, 63, 69, 75, 81, or 87, or an amino acid sequence having at least one (e.g., no more than one, no more than two, no more than three, no more than four or no more than five) amino acid modification (e.g., substitution, deletion and/or addition) as compared to SEQ ID NOS: 9, 15, 21, 27, 33, 39, 45, 51, 57, 63, 69, 75, 81, or 87; (b) a $V_H$ CDR2 region comprising the amino acid sequence set forth in SEQ ID NOs: 10, 16, 22, 28, 34, 40, 46, 52, 58, 64, 70, 76, 82, or 88, or an amino acid sequence having at least one (e.g., no more than one, no more than two, no more than three, no more than four or no more than five) amino acid modification (e.g., substitution, deletion and/or addition) as compared to SEQ ID NOs: 10, 16, 22, 28, 34, 40, 46, 52, 58, 64, 70, 76, 82, or 88; (c) a $V_H$ CDR3 region comprising the amino acid sequence set forth in SEQ ID NOs: 11, 17, 23, 29, 35, 41, 47, 53, 59, 65, 71, 77, 83, or 89, or an amino acid sequence having at least one (e.g., no more than one, no more than two, no more than three, no more than four or no more than five) amino acid modification (e.g., substitution, deletion and/or addition) as compared to SEQ ID NOs: 11, 17, 23, 29, 35, 41, 47, 53, 59, 65, 71, 77, 83, or 89; (d) a $V_L$ CDR1 region comprising the amino acid sequence set forth in SEQ ID NOs: 12, 18, 24, 30, 36, 40, 42, 48, 54, 60, 66, 72, 78, 84, or 90, or an amino acid sequence having at least one (e.g., no more than one, no more than two, no more than three, no more than four or no more than five) amino acid modification (e.g., substitution, deletion and/or addition) as compared to SEQ ID NOs: 12, 18, 24, 30, 36, 40, 42, 48, 54, 60, 66, 72, 78, 84, or 90; (e) a $V_L$ CDR2 region comprising the amino acid sequence set forth in SEQ ID NOs: 13, 19, 25, 31, 37, 43, 49, 55, 61, 67, 73, 79, 85, or 91, or an amino acid sequence having at least one (e.g., no more than one, no more than two, no more than three, no more than four or no more than five) amino acid modification (e.g., substitution, deletion and/or addition) as compared to SEQ ID NOs: 13, 19, 25, 31, 37, 43, 49, 55, 61, 67, 73, 79, 85, or 91; and (f) a $V_L$ CDR3 region comprising the amino acid sequence set forth in SEQ ID NOs: 14, 20, 26, 32, 38, 44, 50, 56, 62, 68, 74, 80, 86, or 92, or an amino acid sequence having at least one (e.g., no more than one, no more than two, no more than three, no more than four or no more than five) amino acid modification (e.g., substitution, deletion and/or addition) as compared to SEQ ID NOs: 14, 20, 26, 32, 38, 44, 50, 56, 62, 68, 74, 80, 86, or 92.

Engineered antibodies of the presently disclosed subject matter include those in which modifications are made to framework residues within $V_H$ and/or $V_K$, e.g., to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, anti-Foxp3 antibodies or antigen-binding portions thereof of the presently disclosed subject matter may be engineered to include modifications within the Fc region, typically to alter one or more functional properties of the antibody, such as serum half-life, complement fixation, Fc receptor binding, and/or antigen-dependent cellular cytotoxicity. Furthermore, a presently disclosed anti-Foxp3 antibody may be chemically modified (e.g., one or more chemical moieties can be attached to the antibody) or be modified to alter its glycosylation, again to alter one or more functional properties of the antibody. The hinge region of CH1 may be modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody. The Fc hinge region of an antibody may be mutated to decrease the biological half life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al. The antibody may be modified to increase its biological half life, e.g., the antibody may be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al. Furthermore, the Fc region may be altered by replacing at least one amino acid residue with a different amino acid residue to alter the effector function(s) of the antibody. The Fc region may be modified to increase the ability of the antibody to mediate antibody dependent cellular cytotoxicity (ADCC) and/or to increase the affinity of the antibody for an Fcγ receptor, e.g., as described in WO 00/42072 by Presta. In certain embodiments, a presently disclosed anti-Foxp3 antibody comprises an afucosylated Fc region. Removal of the fucose residue from the N-glycans of the Fc portion of immunoglobulin G (IgG) can result in a dramatic enhancement of ADCC through improved affinity for Fcγ receptor IIIc (FcγRIIIa).

Additionally or alternatively, the glycosylation of an antibody may be modified. For example, an aglycoslated antibody can be made (i.e., the antibody lacks glycosylation). Glycosylation can be altered to, for example, increase the affinity of the antibody for antigen, see e.g., U.S. Pat. Nos. 5,714,350 and 6,350,861. Such carbohydrate modifications can be accomplished by, for example, altering one or more sites of glycosylation within the antibody sequence. For example, one or more amino acid substitution can be made that result in elimination of one or more variable region framework glycosylation sites to thereby eliminate glycosylation at that site.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery.

Another modification of the antibodies may be pegylation. An antibody can be pegylated to, for example, increase the biological (e.g., serum) half life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation may be carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono ($C_1$-$C_{10}$) alkoxy- or aryloxy-polyethylene glycol or polyethylene glycol-maleimide. The antibody to be pegylated may be an aglycosylated antibody. Methods for pegylating proteins are known in the art and can be applied to the antibodies disclosed herein, see e.g., EP 0 154 316 and EP 0 401 384.

III. Methods of Preparation

1. Identification of Peptides with High Predictive Binding to MHC Molecules

The presently disclosed subject matter provides for a method for the generation of antibodies that specifically bind to MHC-restricted peptides, which, when presented as part of a peptide/MHC complex are able to elicit a specific cytotoxic T-cell response. HLA class I molecules present endogenous derived peptides of about 8-12 amino acids in length to $CD8^+$ cytotoxic T lymphocytes. Peptides to be used in the presently disclosed method are generally about 6-22 amino acids in length, and in some embodiments, between about 9 and 20 amino acids (more specifically, between 8-12 amino acids, e.g., 9 amino acids or 10 amino acids) and comprise an amino acid sequence derived from a protein of interest, for example, human Foxp3 protein having an amino acid sequence set forth in SEQ ID NO: 1 (Genbank Accession No. ABQ15210.1, provided below) or an analog thereof.

```
                                                              [SEQ ID NO: 1]
  1 mpnprpgkps apslalgpsp gaspswraap kasdllgarg pggtfqgrdl rggahasssss

 61 lnpmppsqlq lptlplvmva psgarlgplp hlqallqdrp hfmhqlstvd ahartpvlqv

121 hplespamis ltppttatgv fslkarpglp pginvaslew vsrepallct fpnpsaprkd

181 stlsavpqss ypllangvck wpgcekvfee pedflkhcqa dhlldekgra qcllqremvq

241 sleqqlvlek eklsamqahl agkmaltkas svassdkgsc civaagsqgp vvpawsgpre

301 apdslfavrr hlwgshgnst fpeflhnmdy fkfhnmrppf tyatlirwai leapekqrtl

361 neiyhwftrm faffrnhpat wknairhnls lhkcfvrves ekgavwtvde lefrkkrsqr

421 psrcsnptpg p
```

Peptides suitable for use in generating antibodies in accordance with the presently disclosed method can be determined based on the presence of MHC molecule (e.g., HLA molecule, more specifically, HLA class I molecule, more specifically, HLA-A, more specifically, HLA-A2, and more specifically, HLA-A*02:01) binding motifs and the cleavage sites for proteasomes and immune-proteasomes using computer prediction models known to those of skill in the art. For predicting MHC class I binding sites, such models include, but are not limited to, ProPred1 (described in more detail in Singh and Raghava, *Bioinformatics* 17(12): 1236-1237 2001), SYFPEITHI (see Schuler et al. *Immunoinformatics Methods in Molecular Biology*, vol 409(1): 75-93 2007), Net MHC (cbs.dtu.dk), and BIMAS (bimas.cit.nih.gov).

HLA-A*02:01 is expressed in 39-46% of all caucasians and therefore, represents a suitable choice of MHC antigen for use in the present method. For identification of one embodiment of a Foxp3 peptide antigen, amino acid sequences and predicted binding of putative Foxp3 epitopes to HLA-A*02:01 molecules were identified using the predictive algorithm of the SYFPEITHI database (syfpeithi.de; see Schuler (2007)). For identification of one embodiment of a Foxp3 peptide antigen, amino acid sequences and predicted binding of putative Foxp3 epitopes to HLA-A*02:01 molecules were identified using the predictive algorithm of the BIMAS (bimas.cit.nih.gov). For identification of one embodiment of a Foxp3 peptide antigen, amino acid sequences and predicted binding of putative Foxp3 epitopes to HLA-A*02:01 molecules were identified using the predictive algorithm of RANKPEP (bio.dfci.harvard.edu).

Once appropriate peptides are identified, peptide synthesis can be done in accordance with protocols well known to those of ordinary skill in the art. Because of their relatively small size, the peptides of the presently disclosed subject matter can be directly synthesized in solution or on a solid support in accordance with conventional peptide synthesis techniques. Various automatic synthesizers are commercially available and can be used in accordance with known protocols. The synthesis of peptides in solution phase has become a well-established procedure for large-scale production of synthetic peptides and as such is a suitable alternative method for preparing the peptides of the invention. (See e.g., Stewart et al., *Tetrahedron Letters* Vol. 39, pages 1517-1520 1998.)

Each of the peptides used in the protocols described herein was purchased and synthesized by Genemed Synthesis, Inc. (San Antonio, Tex.). The quality of the peptides was assessed by high-performance liquid chromatography analysis, and the expected molecular weight was observed using matrix-assisted laser desorption mass spectrometry. Peptides were sterile and 80% to >90% pure. The peptides were dissolved in DMSO and diluted in saline at 5 mg/mL and stored at -80 OC.

Subsequent to peptide selection, binding activity of selected peptides is tested using the antigen-processing-deficient T2 cell line, which increases expression of HLA-A when stabilized by a peptide in the antigen-presenting groove. Briefly, T2 cells are pulsed with peptide for a time sufficient to induce HLA-A expression. HLA-A expression of T2 cells is then measured by immunostaining with a fluorescently labeled monoclonal antibody specific for HLA-A (for example, BB7.2) and flow cytometry. Fluorescence index (FI) is calculated as the mean fluorescence intensity (MFI) of HLA-A*02:01 on T2 cells as determined by fluorescence-activated cell-sorting analysis, using the formula FI=(MFI [T2 cells with peptide]/MFI [T2 cells without peptide]-1.

Fully human T-cell receptor (TCR)-like antibodies to Foxp3 were produced using the method disclosed herein. TCR-like anti-Foxp3 antibodies generated by phage display technology are specific for a Foxp3 peptide/HLA complex similar to that which induces HLA-restricted cytotoxic CD8 T-cells.

Once a suitable peptide has been identified, the target antigen to be used for phage display library screening, that is, a peptide/MHC complex (for example, Foxp3/HLA complex, e.g., Foxp3 peptide/HLA-A*02:01) is prepared by bringing the peptide and the histocompatibility antigen together in solution to form the complex.

2. Selecting a High Affinity scFv Against a Foxp3 Peptide

The next step is the selection of phage that binds to the target antigen of interest with high affinity, from phage in a human phage display library that either does not bind or that binds with lower affinity. This is accomplished by iterative binding of phage to the antigen, which is bound to a solid support, for example, beads or mammalian cells followed by removal of non-bound phage and by elution of specifically bound phage. In certain embodiments, antigens are first biotinylated for immobilization to, for example, streptavidin-conjugated Dynabeads M-280. The phage library is incubated with the cells, beads or other solid support and non binding phage is removed by washing. Clones that bind are selected and tested.

Once selected, positive scFv clones are tested for their binding to HLA-A2/peptide complexes on live T2 cell surfaces by indirect flow cytometry. Briefly, phage clones are incubated with T2 cells that have been pulsed with a Foxp3 peptide, or an irrelevant peptide (control). The cells are washed and then with a mouse anti-M13 coat protein mAb. Cells are washed again and labeled with a FITC-goat (Fab)2 anti-mouse Ig prior to flow cytometry.

In other embodiments, the anti-Foxp3 antibodies may comprise one or more framework region amino acid substitutions designed to improve protein stability, antibody binding, expression levels or to introduce a site for conjugation of therapeutic agents. These scFv are then used to produce recombinant human monoclonal Igs in accordance with methods known to those of skill in the art.

Methods for reducing the proliferation of leukemia cells is also included, comprising contacting leukemia cells with a presently disclosed Foxp3 antibody. In a related aspect, the presently disclosed antibodies can be used for the prevention or treatment of leukemia. Administration of therapeutic antibodies is known in the art.

IV. Chimeric Antigen Receptors

Chimeric antigen receptors (CARs) are engineered receptors, which graft or confer a specificity of interest onto an immune effector cell. CARs can be used to graft the specificity of a monoclonal antibody onto a T cell; with transfer of their coding sequence facilitated by retroviral vectors.

There are three generations of CARs. "First generation" CARs are typically composed of an extracellular antigen binding domain (e.g., a scFv fused to a transmembrane domain, fused to cytoplasmic/intracellular domain of the T cell receptor chain. "First generation" CARs typically have the intracellular domain from the CD3-chain, which is the primary transmitter of signals from endogenous TCRs. "First generation" CARs can provide de novo antigen recognition and cause activation of both $CD4^+$ and $CD8^+$ T cells through their CD3 chain signaling domain in a single fusion molecule, independent of HLA-mediated antigen presentation. "Second generation" CARs add intracellular domains from various co-stimulatory molecules (e.g., CD28, 4-1BB, ICOS, OX40) to the cytoplasmic tail of the CAR to provide additional signals to the T cell. "Second generation" CARs comprise those that provide both co-stimulation (e.g., CD28 or 4-1BB) and activation (CD3). Preclinical studies have indicated that "Second Generation" CARs can improve the anti-tumor activity of T cells. For example, robust efficacy of "Second Generation" CAR modified T cells was demonstrated in clinical trials targeting the CD19 molecule in patients with chronic lymphoblastic leukemia (CLL) and acute lymphoblastic leukemia (ALL). "Third generation" CARs comprise those that provide multiple co-stimulation (e.g., CD28 and 4-1BB) and activation (CD3).

In accordance with the presently disclosed subject matter, the CARs comprise an extracellular antigen-binding domain, a transmembrane domain and an intracellular domain, where the extracellular antigen-binding domain binds to a Foxp3 peptide bound to an MHC molecule (e.g., a HLA molecule, more specifically, a HLA class I molecule). In certain embodiments, the extracellular antigen-binding domain is a scFv. In certain embodiments, the scFv is a human scFv. Non-limiting example of scFv include EXT017-5, EXT017-9, EXT017-10, EXT017-11, EXT017-17, EXT017-18, EXT017-20, EXT017-21, EXT017-23, EXT017-24, EXT017-25, EXT017-26, EXT017-27, EXT017-28, EXT017-29, EXT017-30, EXT017-32, EXT017-34, EXT017-53, EXT017-54, EXT017-55 EXT019-6, EXT019-12, EXT019-9, EXT019-15, EXT019-20, EXT019-4, EXT019-13, EXT019-8, EXT018-5, EXT018-2, and EXT018-4.

In certain embodiments, the extracellular antigen-binding domain is a Fab, which is optionally crosslinked. In a certain embodiments, the extracellular binding domain is a $F(ab)_2$. In certain embodiments, any of the foregoing molecules may be comprised in a fusion protein with a heterologous sequence to form the extracellular antigen-binding domain.

In certain non-limiting embodiments, an extracellular antigen-binding domain of a presently disclosed CAR can comprise a linker connecting the heavy chain variable region and light chain variable region of the extracellular antigen-binding domain. As used herein, the term "linker" refers to a functional group (e.g., chemical or polypeptide) that covalently attaches two or more polypeptides or nucleic acids so that they are connected to one another. As used herein, a "peptide linker" refers to one or more amino acids used to couple two proteins together (e.g., to couple $V_H$ and $V_L$ domains). In certain embodiments, the linker comprises amino acids having the sequence set forth in SEQ ID NO: 135, which is provided below. In certain embodiments, the nucleotide sequence encoding the amino acid sequence of SEQ ID NO: 135 is set forth in SEQ ID NO: 136, which is provided below.

```
                                        (SEQ ID NO: 135)
SRGGGGSGGGGSGGGGSLEMA

                                        (SEQ ID NO: 136)
TCTAGAGGTGGTGGTGGTAGCGGCGGCGGCGGCTCTGGTGGTGGTGG

ATCCCTCGAGATGGCC
```

In certain embodiments, the extracellular antigen-binding domain is a scFv, which comprises a $V_H$ comprising the amino acid sequence set forth in SEQ ID NO: 93, 95, 97, 99, 101, 103, 105, 107, 109, 111, 113, 115, 117, or 119, or an amino acid sequence that is at least 80% homologous to SEQ ID NO: 93, 95, 97, 99, 101, 103, 105, 107, 109, 111, 113, 115, 117, or 119, and a $V_L$ comprising the amino acid sequence set forth in SEQ ID NO: 94, 96, 98, 100, 102, 104, 106, and 108, 110, 112, 114, 116, 118, or 120, or an amino acid sequence that is at least 80% homologous to SEQ ID NO: 94, 96, 98, 100, 102, 104, 106, and 108, 110, 112, 114, 116, 118, or 120, and optionally a linker comprising the amino acid sequence set forth in SEQ ID NO: 135.

In certain embodiments, the extracellular antigen-binding domain is a scFv, which comprises (a) a $V_H$ CDR1 region comprising the amino acid sequence set forth in SEQ ID NOS: 9, 15, 21, 27, 33, 39, 45, 51, 57, 63, 69, 75, 81, or 87, or an amino acid sequence having at least one (e.g., no more than one, no more than two, no more than three, no more than four or no more than five) amino acid modification (e.g., substitution, deletion and/or addition) as compared to SEQ ID NOS: 9, 15, 21, 27, 33, 39, 45, 51, 57, 63, 69, 75, 81, or 87; (b) a $V_H$ CDR2 region comprising the amino acid sequence set forth in SEQ ID NOs: 10, 16, 22, 28, 34, 40, 46, 52, 58, 64, 70, 76, 82, or 88, or an amino acid sequence having at least one (e.g., no more than one, no more than two, no more than three, no more than four or no more than five) amino acid modification (e.g., substitution, deletion and/or addition) as compared to SEQ ID NOs: 10, 16, 22, 28, 34, 40, 46, 52, 58, 64, 70, 76, 82, or 88; (c) a $V_H$ CDR3 region comprising the amino acid sequence set forth in SEQ ID NOs: 11, 17, 23, 29, 35, 41, 47, 53, 59, 65, 71, 77, 83, or 89, or an amino acid sequence having at least one (e.g., no more than one, no more than two, no more than three, no more than four or no more than five) amino acid modification (e.g., substitution, deletion and/or addition) as compared to SEQ ID NOs: 11, 17, 23, 29, 35, 41, 47, 53, 59, 65, 71, 77, 83, or 89; (d) a $V_L$ CDR1 region comprising the amino acid sequence set forth in SEQ ID NOs: 12, 18, 24, 30, 36, 40, 42, 48, 54, 60, 66, 72, 78, 84, or 90, or an amino acid sequence having at least one (e.g., no more than one, no more than two, no more than three, no more than four or no more than five) amino acid modification (e.g., substitution, deletion and/or addition) as compared to SEQ ID NOs: 12, 18, 24, 30, 36, 40, 42, 48, 54, 60, 66, 72, 78, 84, or 90; (e) a $V_L$ CDR2 region comprising the amino acid sequence set forth in SEQ ID NOs: 13, 19, 25, 31, 37, 43, 49, 55, 61, 67, 73, 79, 85, or 91, or an amino acid sequence having at least one (e.g., no more than one, no more than two, no more than three, no more than four or no more than five) amino acid modification (e.g., substitution, deletion and/or addition) as compared to SEQ ID NOs: 13, 19, 25, 31, 37, 43, 49, 55, 61, 67, 73, 79, 85, or 91; and (f) a $V_L$ CDR3 region comprising the amino acid sequence set forth in SEQ ID NOs: 14, 20, 26, 32, 38, 44, 50, 56, 62, 68, 74, 80, 86, or 92, or an amino acid sequence having at least one (e.g., no more than one, no more than two, no more than three, no more than four or no more than five) amino acid modification (e.g., substitution, deletion and/or addition) as compared to SEQ ID NOs: 14, 20, 26, 32, 38, 44, 50, 56, 62, 68, 74, 80, 86, or 92, and optionally a linker comprising the amino acid sequence set forth in SEQ ID NO: 135. In certain embodiments, the scFv further comprises a His-tag and a HA-tag. In certain embodiments, the amino acid sequence of the His-tag and HA-tag comprises the amino acid sequence of SEQ ID NO: 141, as provided below. The nucleotide sequence encoding SEQ ID NO: 141 is SEQ ID NO: 142.

[SEQ ID NO: 141]
TSGQAGQHHHHHHGAYPYDVPDYAS

[SEQ ID NO: 142]
CTAGTGGCCAGGCCGGCCAGCACCATCACCATCACCATGGCGCATAC

CCGTACGACGTTCCGGACTACGCTTCT

In certain embodiments, the extracellular antigen-binding domain is a scFv comprising an amino acid sequence selected from the group consisting of SEQ ID NOS: 121, 122, 123, 124, 125, 126, 127, 128, 129, 130, 131, 132, 133, and 134.

In certain embodiments, the extracellular antigen-binding domain is a scFv comprising a $V_H$ comprising the amino acid sequence set forth in SEQ ID NO: 93 or an amino acid sequence that is at least 80% homolgous to SEQ ID NO: 93, a $V_L$ comprising the amino acid sequence set forth in SEQ ID NO: 94 or an amino acid sequence that is at least 80% homolgous to SEQ ID NO: 94, a linker comprising the amino acid sequence set forth in SEQ ID NO: 135, and a His-tag and a HA-tag comprising the amino acid sequence set forth in SEQ ID NO: 141. In certain embodiments, the extracellular antigen-binding domain is a scFv comprising a heavy chain variable region CDR1 comprising an amino acid sequence set forth in SEQ ID NO: 9; a heavy chain variable region CDR2 comprising an amino acid sequence set forth in SEQ ID NO: 10; a heavy chain variable region CDR3 comprising an amino acid sequence set forth in SEQ ID NO: 11; a light chain variable region CDR1 comprising an amino acid sequence set forth in SEQ ID NO: 12; a light chain variable region CDR2 comprising an amino acid sequence set forth in SEQ ID NO: 13; and a light chain variable region CDR3 comprising an amino acid sequence set forth in SEQ ID NO: 14, a linker comprising the amino acid sequence set forth in SEQ ID NO: 135, and a His-tag and a HA-tag comprising the amino acid sequence set forth in SEQ ID NO: 141. In certain embodiments, the scFv comprises the amino acid sequence set forth in SEQ ID NO: 121.

In certain embodiments, the extracellular antigen-binding domain is a scFv comprising a $V_H$ comprising the amino acid sequence set forth in SEQ ID NO: 95 or an amino acid sequence that is at least 80% homolgous to SEQ ID NO: 95, a $V_L$ comprising the amino acid sequence set forth in SEQ ID NO: 96 or an amino acid sequence that is at least 80% homolgous to SEQ ID NO: 96, a linker comprising the amino acid sequence set forth in SEQ ID NO: 135, and a His-tag and a HA-tag comprising the amino acid sequence set forth in SEQ ID NO: 141. In certain embodiments, the extracellular antigen-binding domain is a scFv comprising a heavy chain variable region CDR1 comprising an amino acid sequence set forth in SEQ ID NO: 15; a heavy chain variable region CDR2 comprising an amino acid sequence set forth in SEQ ID NO: 16; a heavy chain variable region CDR3 comprising an amino acid sequence set forth in SEQ ID NO: 17; a light chain variable region CDR1 comprising an amino acid sequence set forth in SEQ ID NO: 18; a light chain variable region CDR2 comprising an amino acid sequence set forth in SEQ ID NO: 19; and a light chain variable region CDR3 comprising an amino acid sequence set forth in SEQ ID NO: 20, a linker comprising the amino acid sequence set forth in SEQ ID NO: 135, and a His-tag and a HA-tag comprising the amino acid sequence set forth in SEQ ID NO: 141. In certain embodiments, the scFv comprises the amino acid sequence set forth in SEQ ID NO: 122.

In certain embodiments, the extracellular antigen-binding domain is a scFv comprising a $V_H$ comprising the amino acid sequence set forth in SEQ ID NO: 97 or an amino acid sequence that is at least about 80% homolgous to SEQ ID NO: 97, a $V_L$ comprising the amino acid sequence set forth in SEQ ID NO: 98 or an amino acid sequence that is at least about 80% homolgous to SEQ ID NO: 98, a linker comprising the amino acid sequence set forth in SEQ ID NO: 135, and a His-tag and a HA-tag comprising the amino acid sequence set forth in SEQ ID NO: 141. In certain embodiments, the extracellular antigen-binding domain is a scFv comprising a heavy chain variable region CDR1 comprising an amino acid sequence set forth in SEQ ID NO: 21; a heavy chain variable region CDR2 comprising an amino acid sequence set forth in SEQ ID NO: 22; a heavy chain variable region CDR3 comprising an amino acid sequence set forth in SEQ ID NO: 23; a light chain variable region CDR1 comprising an amino acid sequence set forth in SEQ ID NO: 24; a light chain variable region CDR2 comprising an amino acid sequence set forth in SEQ ID NO: 25; and a light chain variable region CDR3 comprising an amino acid sequence set forth in SEQ ID NO: 26, a linker comprising the amino acid sequence set forth in SEQ ID NO: 135, and a His-tag and a HA-tag comprising the amino acid sequence set forth in SEQ ID NO: 141. In certain embodiments, the scFv comprises the amino acid sequence set forth in SEQ ID NO: 123.

In certain embodiments, the extracellular antigen-binding domain is a scFv comprising a $V_H$ comprising the amino acid sequence set forth in SEQ ID NO: 99 or an amino acid sequence that is at least about 80% homolgous to SEQ ID NO: 99, a $V_L$ comprising the amino acid sequence set forth in SEQ ID NO: 100 or an amino acid sequence that is at least about 80% homolgous to SEQ ID NO: 100, a linker comprising the amino acid sequence set forth in SEQ ID NO: 135, and a His-tag and a HA-tag comprising the amino acid sequence set forth in SEQ ID NO: 141. In certain embodiments, the extracellular antigen-binding domain is a scFv comprising a heavy chain variable region CDR1 comprising an amino acid sequence set forth in SEQ ID NO: 27; a heavy chain variable region CDR2 comprising an amino acid sequence set forth in SEQ ID NO: 28; a heavy chain variable region CDR3 comprising an amino acid sequence set forth in SEQ ID NO: 29; a light chain variable region CDR1 comprising an amino acid sequence set forth in SEQ ID NO: 30; a light chain variable region CDR2 comprising an amino acid sequence set forth in SEQ ID NO: 31; and a light chain variable region CDR3 comprising an amino acid sequence set forth in SEQ ID NO: 32, a linker comprising the amino acid sequence set forth in SEQ ID NO: 135, and a His-tag and a HA-tag comprising the amino acid sequence set forth in SEQ ID NO: 141. In certain embodiments, the scFv comprises the amino acid sequence set forth in SEQ ID NO: 124.

In certain embodiments, the extracellular antigen-binding domain is a scFv comprising a $V_H$ comprising the amino acid sequence set forth in SEQ ID NO: 101 or an amino acid sequence that is at least about 80% homolgous to SEQ ID NO: 101, a $V_L$ comprising the amino acid sequence set forth in SEQ ID NO: 102 or an amino acid sequence that is at least about 80% homolgous to SEQ ID NO: 102, a linker comprising the amino acid sequence set forth in SEQ ID NO: 135, and a His-tag and a HA-tag comprising the amino acid sequence set forth in SEQ ID NO: 141. In certain embodiments, the extracellular antigen-binding domain is a scFv comprising a heavy chain variable region CDR1 comprising an amino acid sequence set forth in SEQ ID NO: 33; a heavy chain variable region CDR2 comprising an amino acid sequence set forth in SEQ ID NO: 34; a heavy chain variable region CDR3 comprising an amino acid sequence set forth in SEQ ID NO: 35; a light chain variable region CDR1 comprising an amino acid sequence set forth in SEQ ID NO: 36; a light chain variable region CDR2 comprising an amino acid sequence set forth in SEQ ID NO: 37; and a light chain variable region CDR3 comprising an amino acid sequence set forth in SEQ ID NO: 38, a linker comprising the amino acid sequence set forth in SEQ ID NO: 135, and a His-tag and a HA-tag comprising the amino acid sequence set forth in SEQ ID NO: 141. In certain embodiments, the scFv comprises the amino acid sequence set forth in SEQ ID NO: 125.

In certain embodiments, the extracellular antigen-binding domain is a scFv comprising a $V_H$ comprising the amino acid sequence set forth in SEQ ID NO: 103 or an amino acid sequence that is at least about 80% homolgous to SEQ ID NO: 103, a $V_L$ comprising the amino acid sequence set forth in SEQ ID NO: 104 or an amino acid sequence that is at least about 80% homolgous to SEQ ID NO: 104, a linker comprising the amino acid sequence set forth in SEQ ID NO: 135, and a His-tag and a HA-tag comprising the amino acid sequence set forth in SEQ ID NO: 141. In certain embodiments, the extracellular antigen-binding domain is a scFv comprising a heavy chain variable region CDR1 comprising an amino acid sequence set forth in SEQ ID NO: 39; a heavy chain variable region CDR2 comprising an amino acid sequence set forth in SEQ ID NO: 40; a heavy chain variable region CDR3 comprising an amino acid sequence set forth in SEQ ID NO: 41; a light chain variable region CDR1 comprising an amino acid sequence set forth in SEQ ID NO: 42; a light chain variable region CDR2 comprising an amino acid sequence set forth in SEQ ID NO: 43; and a light chain variable region CDR3 comprising an amino acid sequence set forth in SEQ ID NO: 44, a linker comprising the amino acid sequence set forth in SEQ ID NO: 135, and a His-tag and a HA-tag comprising the amino acid sequence set forth in SEQ ID NO: 141. In certain embodiments, the scFv comprises the amino acid sequence set forth in SEQ ID NO: 126.

In certain embodiments, the extracellular antigen-binding domain is a scFv comprising a $V_H$ comprising the amino acid sequence set forth in SEQ ID NO: 105 or an amino acid sequence that is at least about 80% homolgous to SEQ ID NO: 105, a $V_L$ comprising the amino acid sequence set forth in SEQ ID NO: 106 or an amino acid sequence that is at least about 80% homolgous to SEQ ID NO: 106, a linker comprising the amino acid sequence set forth in SEQ ID NO: 135, and a His-tag and a HA-tag comprising the amino acid sequence set forth in SEQ ID NO: 141. In certain embodiments, the extracellular antigen-binding domain is a scFv comprising a heavy chain variable region CDR1 comprising an amino acid sequence set forth in SEQ ID NO: 45; a heavy chain variable region CDR2 comprising an amino acid sequence set forth in SEQ ID NO: 46; a heavy chain variable region CDR3 comprising an amino acid sequence set forth in SEQ ID NO: 47; a light chain variable region CDR1 comprising an amino acid sequence set forth in SEQ ID NO: 48; a light chain variable region CDR2 comprising an amino acid sequence set forth in SEQ ID NO: 49; and a light chain variable region CDR3 comprising an amino acid sequence set forth in SEQ ID NO: 50, a linker comprising the amino acid sequence set forth in SEQ ID NO: 135, and a His-tag and a HA-tag comprising the amino acid sequence set forth in SEQ ID NO: 141. In certain embodiments, the scFv comprises the amino acid sequence set forth in SEQ ID NO: 127.

In certain embodiments, the extracellular antigen-binding domain is a scFv comprising a $V_H$ comprising the amino acid sequence set forth in SEQ ID NO: 107 or an amino acid sequence that is at least about 80% homolgous to SEQ ID NO: 107, a $V_L$ comprising the amino acid sequence set forth in SEQ ID NO: 108 or an amino acid sequence that is at least 80% homolgous to SEQ ID NO: 108, a linker comprising the amino acid sequence set forth in SEQ ID NO: 135, and a His-tag and a HA-tag comprising the amino acid sequence set forth in SEQ ID NO: 141. In certain embodiments, the extracellular antigen-binding domain is a scFv comprising a heavy chain variable region CDR1 comprising an amino acid sequence set forth in SEQ ID NO: 51; a heavy chain variable region CDR2 comprising an amino acid sequence set forth in SEQ ID NO: 52; a heavy chain variable region CDR3 comprising an amino acid sequence set forth in SEQ ID NO: 53; a light chain variable region CDR1 comprising an amino acid sequence set forth in SEQ ID NO: 54; a light chain variable region CDR2 comprising an amino acid sequence set forth in SEQ ID NO: 55; and a light chain variable region CDR3 comprising an amino acid sequence set forth in SEQ ID NO: 56, a linker comprising the amino acid sequence set forth in SEQ ID NO: 135, and a His-tag and a HA-tag comprising the amino acid sequence set forth in SEQ ID NO: 141. In certain embodiments, the scFv comprises the amino acid sequence set forth in SEQ ID NO: 128.

In certain embodiments, the extracellular antigen-binding domain is a scFv comprising a $V_H$ comprising the amino acid sequence set forth in SEQ ID NO: 109 or an amino acid sequence that is at least about 80% homolgous to SEQ ID NO: 109, a $V_L$ comprising the amino acid sequence set forth in SEQ ID NO: 110 or an amino acid sequence that is at least about 80% homolgous to SEQ ID NO: 110, a linker comprising the amino acid sequence set forth in SEQ ID NO: 135, and a His-tag and a HA-tag comprising the amino acid sequence set forth in SEQ ID NO: 141. In certain embodiments, the extracellular antigen-binding domain is a scFv comprising a heavy chain variable region CDR1 comprising an amino acid sequence set forth in SEQ ID NO: 57; a heavy chain variable region CDR2 comprising an amino acid sequence set forth in SEQ ID NO: 58; a heavy chain variable region CDR3 comprising an amino acid sequence set forth in SEQ ID NO: 59; a light chain variable region CDR1 comprising an amino acid sequence set forth in SEQ ID NO: 60; a light chain variable region CDR2 comprising an amino acid sequence set forth in SEQ ID NO: 61; and a light chain variable region CDR3 comprising an amino acid sequence set forth in SEQ ID NO: 62, a linker comprising the amino acid sequence set forth in SEQ ID NO: 135, and a His-tag and a HA-tag comprising the amino acid sequence set forth in SEQ ID NO: 141. In certain embodiments, the scFv comprises the amino acid sequence set forth in SEQ ID NO: 129.

In certain embodiments, the extracellular antigen-binding domain is a scFv comprising a $V_H$ comprising the amino acid sequence set forth in SEQ ID NO: 111 or an amino acid sequence that is at least about 80% homolgous to SEQ ID NO: 111, a $V_L$ comprising the amino acid sequence set forth in SEQ ID NO: 112 or an amino acid sequence that is at least about 80% homolgous to SEQ ID NO: 112, a linker comprising the amino acid sequence set forth in SEQ ID NO: 135, and a His-tag and a HA-tag comprising the amino acid sequence set forth in SEQ ID NO: 141. In certain embodiments, the extracellular antigen-binding domain is a scFv comprising a heavy chain variable region CDR1 comprising an amino acid sequence set forth in SEQ ID NO: 63; a heavy chain variable region CDR2 comprising an amino acid sequence set forth in SEQ ID NO: 64; a heavy chain variable region CDR3 comprising an amino acid sequence set forth in SEQ ID NO: 65; a light chain variable region CDR1 comprising an amino acid sequence set forth in SEQ ID NO: 66; a light chain variable region CDR2 comprising an amino acid sequence set forth in SEQ ID NO: 67; and a light chain variable region CDR3 comprising an amino acid sequence set forth in SEQ ID NO: 68, a linker comprising the amino acid sequence set forth in SEQ ID NO: 135, and a His-tag and a HA-tag comprising the amino acid sequence set forth in SEQ ID NO: 141. In certain embodiments, the scFv comprises the amino acid sequence set forth in SEQ ID NO: 130.

In certain embodiments, the extracellular antigen-binding domain is a scFv comprising a $V_H$ comprising the amino acid sequence set forth in SEQ ID NO: 113 or an amino acid sequence that is at least about 80% homolgous to SEQ ID NO: 113, a $V_L$ comprising the amino acid sequence set forth in SEQ ID NO: 114 or an amino acid sequence that is at least about 80% homolgous to SEQ ID NO: 114, a linker comprising the amino acid sequence set forth in SEQ ID NO: 135, and a His-tag and a HA-tag comprising the amino acid sequence set forth in SEQ ID NO: 141. In certain embodiments, the extracellular antigen-binding domain is a scFv comprising a heavy chain variable region CDR1 comprising an amino acid sequence set forth in SEQ ID NO: 69; a heavy chain variable region CDR2 comprising an amino acid sequence set forth in SEQ ID NO: 70; a heavy chain variable region CDR3 comprising an amino acid sequence set forth in SEQ ID NO: 71; a light chain variable region CDR1 comprising an amino acid sequence set forth in SEQ ID NO: 72; a light chain variable region CDR2 comprising an amino acid sequence set forth in SEQ ID NO: 73; and a light chain variable region CDR3 comprising an amino acid sequence set forth in SEQ ID NO: 74, a linker comprising the amino acid sequence set forth in SEQ ID NO: 135, and a His-tag and a HA-tag comprising the amino acid sequence set forth in SEQ ID NO: 141. In certain embodiments, the scFv comprises the amino acid sequence set forth in SEQ ID NO: 131.

In certain embodiments, the extracellular antigen-binding domain is a scFv comprising a $V_H$ comprising the amino acid sequence set forth in SEQ ID NO: 115 or an amino acid sequence that is at least about 80% homolgous to SEQ ID NO: 115, a $V_L$ comprising the amino acid sequence set forth in SEQ ID NO: 116 or an amino acid sequence that is at least about 80% homolgous to SEQ ID NO: 116, a linker comprising the amino acid sequence set forth in SEQ ID NO: 135, and a His-tag and a HA-tag comprising the amino acid sequence set forth in SEQ ID NO: 141. In certain embodiments, the extracellular antigen-binding domain is a scFv comprising a heavy chain variable region CDR1 comprising an amino acid sequence set forth in SEQ ID NO: 75; a heavy chain variable region CDR2 comprising an amino acid sequence set forth in SEQ ID NO: 76; a heavy chain variable region CDR3 comprising an amino acid sequence set forth in SEQ ID NO: 77; a light chain variable region CDR1 comprising an amino acid sequence set forth in SEQ ID NO: 78; a light chain variable region CDR2 comprising an amino acid sequence set forth in SEQ ID NO: 79; and a light chain variable region CDR3 comprising an amino acid sequence set forth in SEQ ID NO: 80, a linker comprising the amino acid sequence set forth in SEQ ID NO: 135, and a His-tag and a HA-tag comprising the amino acid sequence set forth in SEQ ID NO: 141. In certain embodiments, the scFv comprises the amino acid sequence set forth in SEQ ID NO: 132.

In certain embodiments, the extracellular antigen-binding domain is a scFv comprising a $V_H$ comprising the amino acid sequence set forth in SEQ ID NO: 117 or an amino acid sequence that is at least about 80% homolgous to SEQ ID NO: 117, a $V_L$ comprising the amino acid sequence set forth in SEQ ID NO: 118 or an amino acid sequence that is at least about 80% homolgous to SEQ ID NO: 118, a linker comprising the amino acid sequence set forth in SEQ ID NO: 135, and a His-tag and a HA-tag comprising the amino acid sequence set forth in SEQ ID NO: 141. In certain embodiments, the extracellular antigen-binding domain is a scFv comprising a heavy chain variable region CDR1 comprising an amino acid sequence set forth in SEQ ID NO: 81; a heavy chain variable region CDR2 comprising an amino acid sequence set forth in SEQ ID NO: 82; a heavy chain variable region CDR3 comprising an amino acid sequence set forth in SEQ ID NO: 83; a light chain variable region CDR1 comprising an amino acid sequence set forth in SEQ ID NO: 84; a light chain variable region CDR2 comprising an amino acid sequence set forth in SEQ ID NO: 85; and a light chain variable region CDR3 comprising an amino acid sequence set forth in SEQ ID NO: 86, a linker comprising the amino acid sequence set forth in SEQ ID NO: 135, and a His-tag and a HA-tag comprising the amino acid sequence set forth in SEQ ID NO: 141. In certain embodiments, the scFv comprises the amino acid sequence set forth in SEQ ID NO: 133.

In certain embodiments, the extracellular antigen-binding domain is a scFv comprising a $V_H$ comprising the amino acid sequence set forth in SEQ ID NO: 119 or an amino acid sequence that is at least about 80% homolgous to SEQ ID NO: 119, a $V_L$ comprising the amino acid sequence set forth in SEQ ID NO: 120 or an amino acid sequence that is at least about 80% homolgous to SEQ ID NO: 120, a linker comprising the amino acid sequence set forth in SEQ ID NO: 135, and a His-tag and a HA-tag comprising the amino acid sequence set forth in SEQ ID NO: 141. In certain embodiments, the extracellular antigen-binding domain is a scFv comprising a heavy chain variable region CDR1 comprising an amino acid sequence set forth in SEQ ID NO: 87; a heavy chain variable region CDR2 comprising an amino acid sequence set forth in SEQ ID NO: 88; a heavy chain variable region CDR3 comprising an amino acid sequence set forth in SEQ ID NO: 89; a light chain variable region CDR1 comprising an amino acid sequence set forth in SEQ ID NO: 90; a light chain variable region CDR2 comprising an amino acid sequence set forth in SEQ ID NO: 91; and a light chain variable region CDR3 comprising an amino acid sequence set forth in SEQ ID NO: 92, a linker comprising the amino acid sequence set forth in SEQ ID NO: 135, and a His-tag and a HA-tag comprising the amino acid sequence set forth in SEQ ID NO: 141. In certain embodiments, the scFv comprises the amino acid sequence set forth in SEQ ID NO: 134.

In addition, the extracellular antigen-binding domain can comprise a leader or a signal peptide that directs the nascent protein into the endoplasmic reticulum. Signal peptide or leader can be essential if the CAR is to be glycosylated and anchored in the cell membrane. The signal sequence or leader can be a peptide sequence (about 5, about 10, about 15, about 20, about 25, or about 30 amino acids long) present at the N-terminus of newly synthesized proteins that directs their entry to the secretory pathway. In non-limiting examples, the signal peptide is covalently joined to the 5' terminus of the extracellular antigen-binding domain.

In certain non-limiting embodiments, the transmembrane domain of the CAR comprises a hydrophobic alpha helix that spans at least a portion of the membrane. Different transmembrane domains result in different receptor stability. After antigen recognition, receptors cluster and a signal is transmitted to the cell. In accordance with the presently disclosed subject matter, the transmembrane domain of the CAR can comprise a CD8 polypeptide, a CD28 polypeptide, a CD3 polypeptide, a CD4 polypeptide, a 4-1BB polypeptide, an OX40 polypeptide, an ICOS polypeptide, a CTLA-4 polypeptide, a PD-1 polypeptide, a LAG-3 polypeptide, a 2B4 polypeptide, a BTLA polypeptide, a synthetic peptide (not based on a protein associated with the immune response), or a combination thereof.

In certain embodiments, the transmembrane domain of a presently disclosed CAR comprises a CD28 polypeptide. In certain embodiments, the transmembrane domain of a presently disclosed CAR comprises a CD8 polypeptide.

In certain non-limiting embodiments, an intracellular domain of the CAR can comprise a CD3zeta (CD3) polypeptide, which can activate or stimulate a cell (e.g., a cell of the lymphoid lineage, e.g., a T cell). CD3 comprises 3 ITAMs, and transmits an activation signal to the cell (e.g., a cell of the lymphoid lineage, e.g., a T cell) after antigen is bound. The CD3 polypeptide can have an amino acid sequence that is at least about 85%, about 90%, about 95%, about 96%, about 97%, about 98%, about 99% or about 100% homologous to the sequence having a NCBI Reference No: NP_932170 (SEQ ID No: 137), or fragments thereof, and/or may optionally comprise up to one or up to two or up to three conservative amino acid substitutions. In non-limiting embodiments, the CD3ζ polypeptide can have an amino acid sequence that is a consecutive portion of SEQ ID NO: 137 which is at least 20, or at least 30, or at least 40, or at least 50, and up to 164 amino acids in length. Alternatively or additionally, in non-limiting various embodiments, the CD3ζ polypeptide has an amino acid sequence of amino acids 1 to 164, 1 to 50, 50 to 100, 100 to 150, or 150 to 164 of SEQ ID NO: 137. In certain embodiments, the CD3ζ polypeptide has an amino acid sequence of amino acids 52 to 121 of SEQ ID NO: 137.

SEQ ID NO: 137 is provided below:

```
                                                         [SEQ ID NO: 137]
  1 MKWKALFTAA ILQAQLPITE AQSFGLLDPK LCYLLDGILF IYGVILTALF LRVKFSRSAD

 61 APAYQQGQNQ LYNELNLGRR EEYDVLDKRR GRDPEMGGKP QRRKNPQEGL YNELQKDKMA

121 EAYSEIGMKG ERRRGKGHDG LYQGLSTATK DTYDALHMQA LPPR
```

In certain embodiments, the CD3 polypeptide has the amino acid sequence set forth in SEQ ID NO: 138, which is provided below.

```
                                          [SEQ ID NO: 138]
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR
```

In certain non-limiting embodiments, an intracellular domain of the CAR further comprises at least one co-stimulatory signaling region comprising at least one co-stimulatory molecule, which can provide optimal lymphocyte activation. As used herein, “co-stimulatory molecules” refer to cell surface molecules other than antigen receptors or their ligands that are required for an efficient response of lymphocytes to antigen. The at least one co-stimulatory signaling region can include a CD28 polypeptide, a 4-1BB polypeptide, an OX40 polypeptide, an ICOS polypeptide, a synthetic peptide (not based on a protein associated with the immune response), or a combination thereof. The co-stimulatory molecule can bind to a co-stimulatory ligand, which is a protein expressed on cell surface that upon binding to its receptor produces a co-stimulatory response, i.e., an intracellular response that effects the stimulation provided when an antigen binds to its CAR molecule. In certain embodiments, the intracellular domain of the CAR comprises a co-stimulatory signaling region that comprises a CD28 polypeptide. In one non-limiting embodiment, the CAR comprises a CD28 transmembrane domain and a CD28 co-stimulatory signaling domain, where CD28 polypeptide comprised in the transmembrane domain and the co-stimulatory signaling region has the amino acid sequence set forth in SEQ ID NO: 139, which is provided below.

(SEQ ID NO: 139)
IEVMYPPPYLDNEKSNGTIIHVKGKHLCPSPLFPGPSKPFWVLVVVGGVL

ACYSLLVTVAFIIFWVRSKRSRLLHSDYMNMTPRRPGPTRKHYQPYAPPR

DFAAYRS

In addition, the presently disclosed subject matter provides immunoresponsive cells expressing a presently disclosed CAR. The immunoresponsive cells can be transduced with a presently disclosed CAR such that the cells express the CAR. The presently disclosed subject matter also provides methods of using such cells for the treatment of a tumor or Foxp3-associated pathologic condition. The immunoresponsive cells of the presently disclosed subject matter can be cells of the lymphoid lineage. The lymphoid lineage, comprising B, T and natural killer (NK) cells, provides for the production of antibodies, regulation of the cellular immune system, detection of foreign agents in the blood, detection of cells foreign to the host, and the like. Non-limiting examples of immunoresponsive cells of the lymphoid lineage include T cells, Natural Killer (NK) cells, embryonic stem cells, and pluripotent stem cells (e.g., those from which lymphoid cells may be differentiated).

In certain embodiments, the immunoresponsive cell is a T cell. T cells can be lymphocytes that mature in the thymus and are chiefly responsible for cell-mediated immunity. T cells are involved in the adaptive immune system. T cells of the presently disclosed subject matter can be any type of T cells, including, but not limited to, T helper cells, cytotoxic T cells, memory T cells (including central memory T cells, stem-cell-like memory T cells (or stem-like memory T cells), and two types of effector memory T cells: e.g., TEM cells and TEMRA cells), Regulatory T cells (also known as suppressor T cells), Natural killer T cells, Mucosal associated invariant T cells, and γδ T cells. Cytotoxic T cells (CTL or killer T cells) are a subset of T lymphocytes capable of inducing the death of infected somatic or tumor cells. In certain embodiments, the CAR-expressing T cells express Foxp3 to achieve and maintain a T regulatory phenotype.

Natural killer (NK) cells can be lymphocytes that are part of cell-mediated immunity and act during the innate immune response. NK cells do not require prior activation in order to perform their cytotoxic effect on target cells.

Genetic modification of immunoresponsive cells (e.g., T cells, NK cells) can be accomplished by transducing a substantially homogeneous cell composition with a recombinant DNA or RNA construct. The vector can be a retroviral vector (e.g., gamma retroviral), which is employed for the introduction of the DNA or RNA construct into the host cell genome. For example, a polynucleotide encoding a presently disclosed CAR can be cloned into a retroviral vector and expression can be driven from its endogenous promoter, from the retroviral long terminal repeat, or from an alternative internal promoter.

Non-viral vectors or RNA may be used as well. Random chromosomal integration, or targeted integration (e.g., using a nuclease, transcription activator-like effector nucleases (TALENs), Zinc-finger nucleases (ZFNs), and/or clustered regularly interspaced short palindromic repeats (CRISPRs), or transgene expression (e.g., using a natural or chemically modified RNA) can be used.

For initial genetic modification of the cells to provide cells expressing a presently disclosed CAR, a retroviral vector is generally employed for transduction, however any other suitable viral vector or non-viral delivery system can be used. For subsequent genetic modification of the cells to provide cells comprising an antigen presenting complex comprising at least two co-stimulatory ligands, retroviral gene transfer (transduction) likewise proves effective. Combinations of retroviral vector and an appropriate packaging line are also suitable, where the capsid proteins will be functional for infecting human cells. Various amphotropic virus-producing cell lines are known, including, but not limited to, PA12 (Miller, et al. (1985) *Mol. Cell. Biol.* 5:431-437); PA317 (Miller, et al. (1986)*Mol. Cell. Biol.* 6:2895-2902); and CRIP (Danos, et al. (1988) *Proc. Natl. Acad. Sci. USA* 85:6460-6464). Non-amphotropic particles are suitable too, e.g., particles pseudotyped with VSVG, RD114 or GALV envelope and any other known in the art.

Possible methods of transduction also include direct co-culture of the cells with producer cells, e.g., by the method of Bregni, et al. (1992) Blood 80:1418-1422, or culturing with viral supernatant alone or concentrated vector stocks with or without appropriate growth factors and polycations, e.g., by the method of Xu, et al. (1994) *Exp. Hemat.* 22:223-230; and Hughes, et al. (1992) *J Clin. Invest.* 89:1817.

Non-viral approaches can also be employed for the expression of a protein in cell. For example, a nucleic acid molecule can be introduced into a cell by administering the nucleic acid in the presence of lipofection (Feigner et al., Proc. Natl. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., Journal of Biological Chemistry 263:14621, 1988; Wu et al., Journal of Biological Chemistry 264:16985, 1989), or by micro-injection under surgical conditions (Wolff et al., Science 247:1465, 1990). Other non-viral means for gene transfer include transfection in vitro using calcium phosphate, DEAE dextran, electroporation, and protoplast fusion. Liposomes can also be potentially beneficial for delivery of DNA into a cell. Transplantation of normal genes into the affected tissues of a subject can also be accomplished by transferring a normal nucleic acid into a cultivatable cell type ex vivo (e.g., an autologous or heterologous primary cell or progeny thereof), after which the cell (or its descendants) are injected into a targeted tissue or are injected systemically. Recombinant receptors can also be derived or obtained using transposases or targeted nucleases (e.g. Zinc finger nucleases, meganucleases, or TALE nucleases). Transient expression may be obtained by RNA electroporation.

cDNA expression for use in polynucleotide therapy methods can be directed from any suitable promoter (e.g., the human cytomegalovirus (CMV), simian virus 40 (SV40), or metallothionein promoters), and regulated by any appropriate mammalian regulatory element or intron (e.g., the elongation factor 1a enhancer/promoter/intron structure). For example, if desired, enhancers known to preferentially direct gene expression in specific cell types can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

The resulting cells can be grown under conditions similar to those for unmodified cells, whereby the modified cells can be expanded and used for a variety of purposes.

V. Pharmaceutical Compositions and Methods of Use

Antibodies (including bispecific antibodies and engineered antibodies disclosed herein) and compositions comprising thereof, antigen binding proteins (including CARs) and compositions comprising thereof, and immunoconjugates and compositions comprising thereof of the presently disclosed subject matter can be used to kill Foxp3-expressing cells. Antibodies (including bispecific antibodies and engineered antibodies disclosed herein) and compositions comprising thereof, antigen binding proteins (including CARs) and compositions comprising thereof, and immunoconjugates and compositions comprising thereof of the presently disclosed subject matter can be used to induce an immune response in a subject. Furthermore, antibodies (including bispecific antibodies and engineered antibodies disclosed herein) and compositions comprising thereof, antigen binding proteins (including CARs) and compositions comprising thereof, and immunoconjugates and compositions comprising thereof of the presently disclosed subject matter can be used to selectively inhibit (e.g., inactivate, inhibit the proflieration of or kill) certain T cells, e.g., $CD4^+$ T cells, $CD127^{low}$ T cells, $CD25^{high}$ T cells, $Foxp3^{high}$ T cells, and combinations thereof, e.g., regulatory T (Treg) cells. Foxp3 has been identified as a key player in Treg function, and is the most definitive marker of $CD4^+CD25^+$ Treg cells. The presently disclosed antibodies and antigen binding proteins specifically target Treg cells and selectively inhibit Treg cells. In certain embodiments, the methods comprise administering a presently disclosed antibody or antigen binding protein to a subject. Antibodies and antigen binding proteins of the presently disclosed subject matter can reduce number of T cells (e.g., Tregs), deplete T cells (e.g., Tregs), inhibit immunosuppressive activity of T cells (e.g., Tregs), block T cells (e.g., Tregs) trafficking into lymph nodes or tumors, inhibit (inactivat and/or kill T cells (e.g., Tregs); and/or induce death of cancer cells.

Additionally, a presently disclosed antibody (including a bispecific antibody and an engineered antibody disclosed herein) or a composition comprising thereof, antigen binding protein (including CAR) or a composition comprising thereof, or immunoconjugate or a composition comprising thereof can be used to treat cancer. Most tumor-associated antigens are self-proteins, which elicit weak natural or induced T cell responses after immunotherapy. Treg cells have been shown to be able to recognize tumor-associated self-antigens and control T cell responses against various cancer antigens. In certain embodiments, the method comprise administering a presently disclosed antibody (including a bispecific antibody and an engineered antibody disclosed herein) or a composition comprising thereof, antigen binding protein (including CAR) or a composition comprising thereof, or immunoconjugate or a composition comprising thereof to a subject suffering from cancer, thereby inducing death of a cancer cell in the subject. In certain embodiments, the cancer cell expresses Foxp3. In certain embodiments, a presently disclosed antibody (including a bispecific antibody and an engineered antibody disclosed herein) or a composition comprising thereof, antigen binding protein (including CAR) or a composition comprising thereof, or immunoconjugate or a composition comprising thereof is administered to the subject in an amount sufficient to prevent, inhibit, or reduce the progression of the cancer or tumor. Progression includes, e.g., the growth, invasiveness, metastases and/or recurrence of the cancer or tumor. Amounts effective for this use will depend upon the severity of the disease and the general state of the patient's own immune system. Dosing schedules will also vary with the disease state and status of the patient, and will typically range from a single bolus dosage or continuous infusion to multiple administrations per day (e.g., every 4-6 hours), or as indicated by the treating physician and the patient's condition.

The identification of medical conditions treatable by the antibodies (including bispecific antibodies and engineered antibodies disclosed herein) and compositions comprising thereof, antigen binding proteins (including CARs) and compositions comprising thereof, and immunoconjugates and compositions comprising thereof of the presently disclosed subject matter is well within the ability and knowledge of one skilled in the art. A clinician skilled in the art can readily determine, for example, by the use of clinical tests, physical examination and medical/family history, if an individual is a candidate for such treatment.

Non-limiting examples of cancers include various solid tumors, including, but not limited to, melanoma, ovarian cancer, breast cancer, lung cancer, pancreatic cancer, gastric cancer, colon cancer, glioblastoma, kidney cancer, liver cancer, lymphoma, leukemia, myeloma, and sarcoma.

Anticancer immunotherapies can be improved by concomitant Treg blockade. In certain embodiments, the cancer subject receives or has received one or more anticancer immunotherapy. Non-limiting examples of anticancer immunotherapy include antibody therapy, cellular therapy (T cells, NK cells, etc.), CAR therapy, bone marrow transplantation and donor leukocyte infusions, immune T cell regulatory therapies (immune checkpoint therapy, e. g., anti-PD-1 antibodies, anti-PD-L1 antibodies, anti-LAG3 antibodies, anti-CTLA-4 antibodies, and anti-CD47 antibodies), and vaccination-based drugs and variants thereof. In certain embodiments, the method comprises administering a presently disclosed Foxp3 antibody (including bispecific antibody and engineered antibody) or a composition comprising thereof, antigen binding protein (including a CAR) or a composition comprising thereof, or an immunoconjugate or a composition comprising thereof in combination with one or more other agents, including, but not limited to, anti-PD-1 antibodies, anti-PD-L1 antibodies, anti-LAG3 antibodies, anti-CTLA-4 antibodies, and anti-CD47 antibodies. For example, an embodiment of the presently disclosed subject matter provides a method of treating a medical condition by administering a presently disclosed antibody or antigen binding protein with an antineoplastic agent. Treg blockade may also benefit the therapeutic effects of a wide variety of other cancer therapies, including, but not limited to, chemotherapy, targeted therapy (e.g., a tyrosine kinase inhibitor), hormonal therapy, radiation therapy, surgery, hyperthermia, topical therapy, light-activated therapy, and therapies where an activated immune system may be needed to enhance killing, to reduce residual tumor or leukemia cells, or to act synergistically or additively with such therapies. The antibody can be chemically or biosynthetically linked to one or more of the antineoplastic agents to make an antibody drug conjugate as well.

Any suitable method or route can be used to administer a presently disclosed antibody or antigen binding protein (e.g., a CAR), and optionally, to co-administer antineoplastic agents and/or antagonists of other receptors. Routes of administration include, for example, intravenous, intraperitoneal, intra arterial, subcutaneous, intrathecal, topical, or intramuscular administration. Co administered agents may be given by these routes and also orally. It should be emphasized, however, that the presently disclosed subject matter is not limited to any particular method or route of administration.

It is noted that a presently disclosed antibody (including bispecific antibody and engineered antibody) or antigen binding protein (including a CAR) can be administered as a conjugate, which binds specifically to the receptor and delivers a toxic, lethal payload following ligand-toxin internalization.

It is understood that antibodies (including bispecific antibodies and engineered antibodies), antigen binding proteins (including CARs) or immunoconjugates of the presently disclosed subject matter can be administered in the form of a composition, e.g., a pharmaceutical composition comprising a pharmaceutically acceptable carrier. Suitable pharmaceutically acceptable carriers include, for example, one or more of water, saline, phosphate buffered saline, dextrose, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the binding proteins. The compositions of the injection may, as is well known in the art, be formulated so as to provide quick, sustained or delayed release of the active ingredient after administration to the mammal.

Other aspects of the presently disclosed subject matter include without limitation, the use of antibodies and nucleic acids that encode them as research tools for the detection of Foxp3 in cells and tissues. The presently disclosed subject matter provides methods for detecting Foxp3 in a whole cell or tissue. In certain embodiments, the method comprises (a) contacting a cell or tissue with a presently disclosed antibody or antigen-binding portion thereof comprising a detectable label; and (b) determining the amount of the labeled antibody or antigen-binding portion thereof bound to the cell or tissue by measuring the amount of detectable label associated with the cell or tissue, wherein the amount of bound antibody or antigen-binding portion thereof indicates the amount of Foxp3 in the cell or tissue.

Pharmaceutical compositions comprising the disclosed antibodies and nucleic acids are encompassed by the presently disclosed subject matter. Vectors comprising the nucleic acids of the presently disclosed subject matter for antibody-based treatment by vectored immunotherapy are also contemplated by the presently disclosed subject matter. Vectors include expression vectors which enable the expression and secretion of antibodies, as well as vectors which are directed to cell surface expression of the antigen-binding proteins, such as chimeric antigen receptors.

Cells comprising the nucleic acids, for example cells that have been transfected with the vectors of the presently disclosed subject matter are also encompassed by the disclosure.

For use in diagnostic and research applications, kits are also provided that contain a presently disclosed anti-Foxp3 antibody or nucleic acids of the presently disclosed subject matter, assay reagents, buffers, and the like.

VI. Kits

The presently disclosed subject matter provides kits for the treatment or prevention of cancer. In certain embodiments, the kit comprises a therapeutic composition containing an effective amount of a presently disclosed antibody (including a bispecific antibody or an engineered antibody), antigen binding protein (including a CAR), or an immunoconjugate in unit dosage form. In certain embodiments, the kit comprises a sterile container which contains a therapeutic or prophylactic vaccine; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

If desired, a presently disclosed antibody (including a bispecific antibody or an engineered antibody), antigen binding protein (including a CAR), or an immunoconjugate is provided together with instructions for administering the cell to a subject having or at risk of developing a cancer. The instructions will generally include information about the use of the composition for the treatment or prevention of cancer. In other embodiments, the instructions include at least one of the following: description of the therapeutic agent; dosage schedule and administration for treatment or prevention of cancer or symptoms thereof; precautions; warnings; indications; counter-indications; over-dosage information; adverse reactions; animal pharmacology; clinical studies; and/or references. The instructions may be printed directly on the container (when present), or as a label applied to the container, or as a separate sheet, pamphlet, card, or folder supplied in or with the container.

VII. Methods

1. Flow Cytometry Analysis.

For cell surface staining, cells were incubated with appropriate mAbs for 30 minutes on ice, washed, and incubated with secondary antibody reagents when necessary. For #32-BITE staining, human T cells or cancer cells were incubated with different concentrations of #32-BITE or control BITE for 30 minutes on ice, washed, and incubated with secondary mAb against His-Tag. Flow cytometry data were collected on a FACS Calibur (Becton Dickinson) or LSRFortessa (BD Biosciences) and analyzed with FlowJo V8.7.1 and 9.4.8 software.

2. Selection and Characterization of scFv Specific for Foxp3 Peptide/HLA-A*02:01 Complexes.

Well established phage display libraries and screening methods known to those of skill in the art were used to select scFv fragments highly specific for a Foxp3 peptide/HLA-A2 complex. In certain embodiments, a human scFv antibody phage display library was used for the selection of mAb clones. In order to reduce the conformational change of MHC1 complex introduces by immobilizing onto plastic surfaces, a solution panning method was used in place of conventional plate panning. In brief, biotinylated antigens were first mixed with the human scFv phage library, then the antigen-scFv antibody complexes were pulled down by streptavidin-conjugated Dynabeads M-280 through a magnetic rack.

Bound clones were then eluted and were used to infect *E. Coli* XL1-Blue. The scFv phage clones expressed in the bacteria were purified (Yasmina, et al., *Protein Science* 2008; 17(8): 1326-1335; Roberts et al., *Blood* 2002: 99 (10): 3748-3755). Panning was performed for 3-4 cycles to enrich scFv phage clones binding to HLA-A*02:01/Foxp3 complex specifically. Positive clones were determined by standard ELISA method against biotinylated single chain HLA-A*02:01/Foxp3 peptide complexes. Positive clones were further tested for their binding to HLA-A2/peptide complexes on live cell surfaces by flow cytometry, using a TAP-deficient, HLA-A*02:01$^+$ cell line, T2. T2 cells were pulsed with peptides (50 μg/ml) in the serum-free RPMI1640 medium, in the presence of 20 μg/ml 132 M overnight. The cells were washed, and the staining was performed as follows.

The cells were first stained with purified scFv phage clones, and followed by staining with a mouse anti-M13 mAb, and finally the goat $F(ab)_2$ anti-mouse Ig's conjugate to FITC. Each step of the staining was done between 30-60 minutes on ice and the cells were washed twice between each step of the staining.

3. Engineering Full Length mAb Using the Selected ScFv Fragments.

Phage display technology allows for the rapid selection and production of antigen-specific scFv and Fab fragments, which are useful in and of themselves, or which can be further developed to provide complete antibodies, antigen-binding proteins or antigen-binding portions thereof. Complete mAbs with Fc domains have a number of advantages over the scFv and Fab antibodies. First, only full length Abs exert immunological function such as CDC and ADCC mediated via Fc domain. Second, bivalent mAbs offer stronger antigen-binding affinity than monomeric Fab Abs. Third, plasma half-life and renal clearance will be different with the Fab and bivalent mAb. The particular features and advantages of each can be matched to the planned effector strategy. Fourth, bivalent mAb may be internalized at different rates than scFv and Fab, altering immune function or carrier function. Alpha emitters, for example, do not need to be internalized to kill the targets, but many drugs and toxins will benefit from internalization of the immune complex. In certain embodiments, therefore, once scFv clones specific for Foxp3/HLA-A2 were obtained from phage display libraries, a full length IgG mAb using the scFv fragments was produced.

Full-length human IgG1 of the selected phage clones were produced in HEK293 and Chinese hamster ovary (CHO) cell lines, as described (Caron et al., *J Exp Med* 176:1191-1195. 1992). In brief, antibody variable regions were sub-cloned into mammalian expression vectors, with matching human lambda or kappa light chain constant region and human IgG1 subclass Fc. Molecular weight of the purified full length IgG antibodies were measured under both reducing and non-reducing conditions by electrophoresis.

4. Engineering Chimeric Antigen Receptors and Immune Effector Cells.

Nucleic acids that encode antibodies and antigen-binding proteins identified herein can be used engineer recombinant immune effector cells. Methods and vectors to generate genetically modified T-cells, for example, are known in the art (See Brentjens et al., *Safety and persistence of adoptively transferred autologous CD19-targeted T cells in patients with relapsed or chemotherapy refractory B-cell leukemias in Blood* 118(18):4817-4828, November 2011).

5. Characterization of the Full-Length Human IgG1 for the Foxp3/A0201 Complex.

Initially, specificities of the fully human IgG1 mAbs for the Foxp3 peptide/A0201 complex were determined by staining T2 cells pulsed with or without a Foxp3 peptide (e.g., Foxp3-7), or irrelevant EW or RHAMM-R3 control peptides, followed by secondary goat $F(ab)_2$ anti-human IgG mAb conjugate to PE or FITC, using indirect or direct staining. The fluorescence intensity was measured by flow cytometry.

The same method was used to determine the binding of the mAbs to fresh tumor cells and cell lines.

Exemplary Embodiments

1. An isolated antibody, or an antigen-binding portion thereof, which binds to a Foxp3 peptide bound to a human major histocompatibility complex (MHC) molecule.

2. The antibody or antigen-binding portion thereof of embodiment 1, wherein the human MHC molecule is a human leukocyte antigen (HLA) molecule.

3. The antibody or antigen-binding portion thereof of embodiment 2, wherein the HLA molecule is a HLA class I molecule.

4. The antibody or antigen-binding portion thereof of embodiment 3, wherein the HLA class I molecule is HLA-A.

5. The antibody or antigen-binding portion thereof of embodiment 4, wherein the HLA-A is HLA-A2.

6. The antibody or antigen-binding portion thereof of embodiment 5, wherein the HLA-A2 is HLA-A*02:01.

7. The antibody or antigen-binding portion thereof of any one of embodiments 1-6, wherein the Foxp3 peptide is a portion of a human Foxp3 polypeptide comprising the amino acid sequence set forth in SEQ ID NO: 1.

8. The antibody or antigen-binding portion thereof of any one of embodiments 1-7, wherein the Foxp3 peptide has a length of 8-12 amino acids.

9. The antibody or antigen-binding portion thereof of embodiment 8, wherein the Foxp3 peptide has a length of 9 amino acids.

10. The antibody or antigen-binding portion thereof of embodiment 8, wherein the Foxp3 peptide has a length of 10 amino acids.

11. The antibody or antigen-binding portion thereof of any one of embodiments 1-10, wherein the Foxp3 peptide is selected from the group consisting of Foxp3-7 having the amino acid sequence set forth in SEQ ID NO: 8 or a portion thereof, Foxp3-1 having the amino acid sequence set forth in SEQ ID NO: 2 or a portion thereof, Foxp3-2 having the amino acid sequence set forth in SEQ ID NO: 3 or a portion thereof, Foxp3-3 having the amino acid sequence set forth in SEQ ID NO: 4 or a portion thereof, Foxp3-4 having the amino acid sequence set forth in SEQ ID NO: 5 or a portion thereof, Foxp3-5 having the amino acid sequence set forth in SEQ ID NO: 6 or a portion thereof, and Foxp3-6 having the amino acid sequence set forth in SEQ ID NO: 7 or a portion thereof.

12. The antibody or antigen-binding portion thereof of embodiment 11, wherein the Foxp3 peptide is Foxp3-7 having the amino acid sequence set forth in SEQ ID NO: 8.

13. The antibody or antigen-binding portion thereof of any one of embodiments 1-8, and 10-12, comprising a heavy chain variable region CDR3 sequence and a light chain variable region CDR3 sequence selected from the group consisting of:

(a) a heavy chain variable region CDR3 sequence comprising amino acid sequence set forth in SEQ ID NO: 11 or a modification thereof, and a light chain variable region CDR3 sequence comprising amino acid sequence set forth in SEQ ID NO: 14 or a modification thereof.

(b) a heavy chain variable region CDR3 sequence comprising an amino acid sequence set forth in SEQ ID NO: 17 or a modification thereof, and a light chain variable region CDR3 sequence comprising amino an acid sequence set forth in SEQ ID NO: 20 or a modification thereof.

(c) a heavy chain variable region CDR3 sequence comprising an amino acid sequence set forth in SEQ ID NO: 23 or a modification thereof, and a light chain variable region CDR3 sequence comprising an amino acid sequence set forth in SEQ ID NO: 26 or a modification thereof (d) a heavy chain variable region CDR3 sequence comprising an amino acid sequence set forth in SEQ ID NO: 29 or a modification thereof, and a light chain variable region CDR3 sequence comprising an amino acid sequence set forth in SEQ ID NO: 32 or a modification thereof.

(e) a heavy chain variable region CDR3 sequence comprising an amino acid sequence set forth in SEQ ID NO: 35 or a modification thereof, and a light chain variable region CDR3 sequence comprising an amino acid sequence set forth in SEQ ID NO: 38 or a modification thereof.

(f) a heavy chain variable region CDR3 sequence comprising an amino acid sequence set forth in SEQ ID NO: 41 or a modification thereof, and a light chain variable region CDR3 sequence comprising an amino acid sequence set forth in SEQ ID NO: 44 or a modification thereof.

(g) a heavy chain variable region CDR3 sequence comprising an amino acid sequence set forth in SEQ ID NO: 47 or a modification thereof, and a light chain variable region CDR3 sequence comprising an amino acid sequence set forth in SEQ ID NO: 50 or a modification thereof and (h) a heavy chain variable region CDR3 sequence comprising an amino acid sequence set forth in SEQ ID NO: 53 or a modification thereof, and a light chain variable region CDR3 sequence comprising an amino acid sequence set forth in SEQ ID NO: 56 or a modification thereof.

14. The antibody or antigen-binding portion thereof of any one of embodiments 1-8 and 10-13, comprising a heavy chain variable region CDR2 sequence and a light chain variable region CDR2 sequence selected from the group consisting of:

(a) a heavy chain variable region CDR2 sequence comprising an amino acid sequence set forth in SEQ ID NO: 10 or a modification thereof, and a light chain variable region CDR2 sequence comprising an amino acid sequence set forth in SEQ ID NO: 13 or a modification thereof.

(b) a heavy chain variable region CDR2 sequence comprising an amino acid sequence set forth in SEQ ID NO: 16 or a modification thereof, and a light chain variable region CDR2 sequence comprising an amino acid sequence set forth in SEQ ID NO: 19 or a modification thereof.

(c) a heavy chain variable region CDR2 sequence comprising an amino acid sequence set forth in SEQ ID NO: 22 or a modification thereof, and a light chain variable region CDR2 sequence comprising an amino acid sequence set forth in SEQ ID NO: 25 or a modification thereof.

(d) a heavy chain variable region CDR2 sequence comprising an amino acid sequence set forth in SEQ ID NO: 28 or a modification thereof, and a light chain variable region CDR2 sequence comprising an amino acid sequence set forth in SEQ ID NO: 31 or a modification thereof.

(e) a heavy chain variable region CDR2 sequence comprising an amino acid sequence set forth in SEQ ID NO: 34 or a modification thereof, and a light chain variable region CDR2 sequence comprising an amino acid sequence set forth in SEQ ID NO: 37 or a modification thereof.

(f) a heavy chain variable region CDR2 sequence comprising an amino acid sequence set forth in SEQ ID NO: 40 or a modification thereof, and a light chain variable region CDR2 sequence comprising an amino acid sequence set forth in SEQ ID NO: 43 or a modification thereof.

(g) a heavy chain variable region CDR2 sequence comprising an amino acid sequence set forth in SEQ ID NO: 46 or a modification thereof, and a light chain variable region CDR2 sequence comprising an amino acid sequence set forth in SEQ ID NO: 49 or a modification thereof and (h) a heavy chain variable region CDR3 sequence comprising an amino acid sequence set forth in SEQ ID NO: 52 or a modification thereof, and a light chain variable region CDR3 sequence comprising an amino acid sequence set forth in SEQ ID NO: 55 or a modification thereof.

15. The antibody or antigen-binding portion thereof of any one of embodiments 1-8 and 10-14, comprising a heavy chain variable region CDR1 sequence and a light chain variable region CDR1 sequence selected from the group consisting of:

(a) a heavy chain variable region CDR1 sequence comprising an amino acid sequence set forth in SEQ ID NO: 9 or a modification thereof, and a light chain variable region CDR1 sequence comprising an amino acid sequence set forth in SEQ ID NO: 12 or a modification thereof.

(b) a heavy chain variable region CDR1 sequence comprising an amino acid sequence set forth in SEQ ID NO: 15 or a modification thereof, and a light chain variable region CDR1 sequence comprising an amino acid sequence set forth in SEQ ID NO: 18 or a modification thereof (c) a heavy chain variable region CDR1 sequence comprising an amino acid sequence set forth in SEQ ID NO: 21 or a modification thereof, and a light chain variable region CDR1 sequence comprising an amino acid sequence set forth in SEQ ID NO: 24 or a modification thereof and (d) a heavy chain variable region CDR1 sequence comprising an amino acid sequence set forth in SEQ ID NO: 27 or a modification thereof, and a light chain variable region CDR1 sequence comprising an amino acid sequence set forth in SEQ ID NO: 30 or a modification thereof.

(e) a heavy chain variable region CDR1 sequence comprising an amino acid sequence set forth in SEQ ID NO: 33 or a modification thereof, and a light chain variable region CDR1 sequence comprising an amino acid sequence set forth in SEQ ID NO: 36 or a modification thereof.

(f) a heavy chain variable region CDR1 sequence comprising an amino acid sequence set forth in SEQ ID NO: 39 or a modification thereof, and a light chain variable region CDR1 sequence comprising an amino acid sequence set forth in SEQ ID NO: 42 or a modification thereof.

(g) a heavy chain variable region CDR1 sequence comprising an amino acid sequence set forth in SEQ ID NO: 45 or a modification thereof, and a light chain variable region CDR1 sequence comprising an amino acid sequence set forth in SEQ ID NO: 48 or a modification thereof and (h) a heavy chain variable region CDR1 sequence comprising an amino acid sequence set forth in SEQ ID NO: 51 or a modification thereof, and a light chain variable region CDR1 sequence comprising an amino acid sequence set forth in SEQ ID NO: 54 or a modification thereof.

16. The antibody or antigen-binding portion thereof of any one of embodiments 1-8 and 10-15, comprising:

(a) a heavy chain variable region CDR1 comprising an amino acid sequence set forth in SEQ ID NO: 9; a heavy chain variable region CDR2 comprising an amino acid sequence set forth in SEQ ID NO: 10; a heavy chain variable region CDR3 comprising an amino acid sequence set forth in SEQ ID NO: 11; a light chain variable region CDR1 comprising an amino acid sequence set forth in SEQ ID NO: 12; a light chain variable region CDR2 comprising an amino acid sequence set forth in SEQ ID NO: 13; and a light chain variable region CDR3 comprising an amino acid sequence set forth in SEQ ID NO: 14;

(b) a heavy chain variable region CDR1 comprising an amino acid sequence set forth in SEQ ID NO: 15; a heavy chain variable region CDR2 comprising an amino acid sequence set forth in SEQ ID NO: 16; a heavy chain variable region CDR3 comprising an amino acid sequence set forth in SEQ ID NO: 17; a light chain variable region CDR1 comprising an amino acid sequence set forth in SEQ ID NO: 18; a light chain variable region CDR2 comprising an amino acid sequence set forth in SEQ ID NO: 19; and a light chain variable region CDR3 comprising an amino acid sequence set forth in SEQ ID NO: 20;

(c) a heavy chain variable region CDR1 comprising an amino acid sequence set forth in SEQ ID NO: 21; a heavy chain variable region CDR2 comprising an amino acid sequence set forth in SEQ ID NO: 22; a heavy chain variable region CDR3 comprising an amino acid sequence set forth in SEQ ID NO: 23; a light chain variable region CDR1 comprising an amino acid sequence set forth in SEQ ID NO: 24; a light chain variable region CDR2 comprising an amino acid sequence set forth in SEQ ID NO: 25; and a light chain variable region CDR3 comprising an amino acid sequence set forth in SEQ ID NO: 26;

(d) a heavy chain variable region CDR1 comprising an amino acid sequence set forth in SEQ ID NO: 27; a heavy chain variable region CDR2 comprising an amino acid sequence set forth in SEQ ID NO: 28; a heavy chain variable region CDR3 comprising an amino acid sequence set forth in SEQ ID NO: 29; a light chain variable region CDR1 comprising an amino acid sequence set forth in SEQ ID NO: 30; a light chain variable region CDR2 comprising an amino acid sequence set forth in SEQ ID NO: 31; and a light chain variable region CDR3 comprising an amino acid sequence set forth in SEQ ID NO: 32;

(e) a heavy chain variable region CDR1 comprising an amino acid sequence set forth in SEQ ID NO: 33; a heavy chain variable region CDR2 comprising an amino acid sequence set forth in SEQ ID NO: 34; a heavy chain variable region CDR3 comprising an amino acid sequence set forth in SEQ ID NO: 35; a light chain variable region CDR1 comprising an amino acid sequence set forth in SEQ ID NO: 36; a light chain variable region CDR2 comprising an amino acid sequence set forth in SEQ ID NO: 37; and a light chain variable region CDR3 comprising an amino acid sequence set forth in SEQ ID NO: 38;

(f) a heavy chain variable region CDR1 comprising an amino acid sequence set forth in SEQ ID NO: 39; a heavy chain variable region CDR2 comprising an amino acid sequence set forth in SEQ ID NO: 40; a heavy chain variable region CDR3 comprising an amino acid sequence set forth in SEQ ID NO: 41; a light chain variable region CDR1 comprising an amino acid sequence set forth in SEQ ID NO: 42; a light chain variable region CDR2 comprising an amino acid sequence set forth in SEQ ID NO: 43; and a light chain variable region CDR3 comprising an amino acid sequence set forth in SEQ ID NO: 44;

(g) a heavy chain variable region CDR1 comprising an amino acid sequence set forth in SEQ ID NO: 45; a heavy chain variable region CDR2 comprising an amino acid sequence set forth in SEQ ID NO: 46; a heavy chain variable region CDR3 comprising an amino acid sequence set forth in SEQ ID NO: 47; a light chain variable region CDR1 comprising an amino acid sequence set forth in SEQ ID NO: 48; a light chain variable region CDR2 comprising an amino acid sequence set forth in SEQ ID NO: 49; and a light chain variable region CDR3 comprising an amino acid sequence set forth in SEQ ID NO: 50; or (h) a heavy chain variable region CDR1 comprising an amino acid sequence set forth in SEQ ID NO: 51; a heavy chain variable region CDR2 comprising an amino acid sequence set forth in SEQ ID NO: 52; a heavy chain variable region CDR3 comprising an amino acid sequence set forth in SEQ ID NO: 53; a light chain variable region CDR1 comprising an amino acid sequence set forth in SEQ ID NO: 54; a light chain variable region CDR2 comprising an amino acid sequence set forth in SEQ ID NO: 55; and a light chain variable region CDR3 comprising an amino acid sequence set forth in SEQ ID NO: 56.

17. The antibody or antigen-binding portion thereof of embodiment 16, comprising: a heavy chain variable region CDR1 comprising an amino acid sequence set forth in SEQ ID NO: 39; a heavy chain variable region CDR2 comprising an amino acid sequence set forth in SEQ ID NO: 40; a heavy chain variable region CDR3 comprising an amino acid sequence set forth in SEQ ID NO: 41; a light chain variable region CDR1 comprising an amino acid sequence set forth in SEQ ID NO: 42; a light chain variable region CDR2 comprising an amino acid sequence set forth in SEQ ID NO: 43; and a light chain variable region CDR3 comprising an amino acid sequence set forth in SEQ ID NO: 44.

18. The antibody or antigen-binding portion thereof of any one of embodiments 1-8, and 10-16, comprising a heavy chain variable region that comprises an amino acid sequence that is at least about 80% homologous to the sequence selected from the group consisting of SEQ ID NOS: 93, 95, 97, 99, 101, 103, 105, and 107.

19. The antibody or antigen-binding portion thereof of embodiment 18, comprising a heavy chain variable region that comprises an amino acid sequence selected from the group consisting of SEQ ID NOS: 93, 95, 97, 99, 101, 103, 105, and 107.

20. The antibody or antigen-binding portion thereof of any one of embodiments 1-8, and 10-16, comprising a light chain variable region that comprises an amino acid sequence that is at least about 80% homologous to the sequence selected from the group consisting of SEQ ID NOS: 94, 96, 98, 100, 102, 104, 106, and 108.

21. The antibody or antigen-binding portion thereof of embodiment 20, comprising a light chain variable region that comprises an amino acid sequence selected from the group consisting of SEQ ID NOS: 94, 96, 98, 100, 102, 104, 106, and 108.

22. The antibody or antigen-binding portion thereof of any one of embodiments 18-21, comprising:

(a) a heavy chain variable region comprising an amino acid sequence that is at least about 80% homologous to the amino acid sequence set forth in SEQ ID NO: 93, and a light chain variable region that comprising an amino acid sequence that is at least about 80% homologous to the amino acid sequence set forth in SEQ ID NO: 94;

(b) a heavy chain variable region comprising an amino acid sequence that is at least about 80% homologous to the amino acid sequence set forth in SEQ ID NO: 95, and a light chain variable region that comprising an amino acid sequence that is at least about 80% homologous to the amino acid sequence set forth in SEQ ID NO: 96;

(c) a heavy chain variable region comprising an amino acid sequence that is at least about 80% homologous to the amino acid sequence set forth in SEQ ID NO: 97, and a light chain variable region that comprising an amino acid sequence that is at least about 80% homologous to the amino acid sequence set forth in SEQ ID NO: 98;

(d) a heavy chain variable region comprising an amino acid sequence that is at least about 80% homologous to the amino acid sequence set forth in SEQ ID NO: 99, and a light chain variable region that comprising an amino acid sequence that is at least about 80% homologous to the amino acid sequence set forth in SEQ ID NO: 100;

(e) a heavy chain variable region comprising an amino acid sequence that is at least about 80% homologous to the amino acid sequence set forth in SEQ ID NO: 101, and a light chain variable region that comprising an amino acid sequence that is at least about 80% homologous to the amino acid sequence set forth in SEQ ID NO: 102;

(f) a heavy chain variable region comprising an amino acid sequence that is at least about 80% homologous to the amino acid sequence set forth in SEQ ID NO: 103, and a light chain variable region that comprising an amino acid sequence that is at least about 80% homologous to the amino acid sequence set forth in SEQ ID NO: 104;

(g) a heavy chain variable region comprising an amino acid sequence that is at least about 80% homologous to the amino acid sequence set forth in SEQ ID NO: 105, and a light chain variable region that comprising an amino acid sequence that is at least about 80% homologous to the amino acid sequence set forth in SEQ ID NO: 106; or (h) a heavy chain variable region comprising an amino acid sequence that is at least about 80% homologous to the amino acid sequence set forth in SEQ ID NO: 107, and a light chain variable region that comprising an amino acid sequence that is at least about 80% homologous to the amino acid sequence set forth in SEQ ID NO: 108.

23. The antibody or antigen-binding portion thereof of embodiment 22, comprising:

(a) a heavy chain variable region comprising an amino acid sequence set forth in SEQ ID NO: 93, and a light chain variable region that comprising an amino acid sequence set forth in SEQ ID NO: 94;

(b) a heavy chain variable region comprising an amino acid sequence set forth in SEQ ID NO: 95, and a light chain variable region that comprising an amino acid sequence set forth in SEQ ID NO: 96;

(c) a heavy chain variable region comprising an amino acid sequence set forth in SEQ ID NO: 97, and a light chain variable region that comprising an amino acid sequence set forth in SEQ ID NO: 98;

(d) a heavy chain variable region comprising an amino acid sequence set forth in SEQ ID NO: 99, and a light chain variable region that comprising an amino acid sequence set forth in SEQ ID NO: 100;

(e) a heavy chain variable region comprising an amino acid sequence set forth in SEQ ID NO: 101, and a light chain variable region that comprising an amino acid sequence set forth in SEQ ID NO: 102;

(f) a heavy chain variable region comprising an amino acid sequence set forth in SEQ ID NO: 103, and a light chain variable region that comprising an amino acid sequence set forth in SEQ ID NO: 104;

(g) a heavy chain variable region comprising an amino acid sequence set forth in SEQ ID NO: 105, and a light chain variable region that comprising an amino acid sequence set forth in SEQ ID NO: 106; or (h) a heavy chain variable region comprising an amino acid sequence set forth in SEQ ID NO: 107, and a light chain variable region that comprising an amino acid sequence set forth in SEQ ID NO: 108.

24. The antibody or antigen-binding portion thereof of embodiment 23, comprising: a heavy chain variable region comprising an amino acid sequence set forth in SEQ ID NO: 103, and a light chain variable region that comprising an amino acid sequence set forth in SEQ ID NO: 104.

25. The antibody or antigen-binding portion thereof of embodiment 11, wherein the Foxp3 peptide is Foxp3-2 having the amino acid sequence set forth in SEQ ID NO: 3.

26. The antibody or antigen-binding portion thereof of embodiment 25, comprising a heavy chain variable region CDR3 sequence and a light chain variable region CDR3 sequence selected from the group consisting of:

(a) a heavy chain variable region CDR3 sequence comprising an amino acid sequence set forth in SEQ ID NO: 59 or a modification thereof, and a light chain variable region CDR3 sequence comprising an amino acid sequence set forth in SEQ ID NO: 62 or a modification thereof;

(b) a heavy chain variable region CDR3 sequence comprising an amino acid sequence set forth in SEQ ID NO: 65 or a modification thereof, and a light chain variable region CDR3 sequence comprising an amino acid sequence set forth in SEQ ID NO: 68 or a modification thereof;

(c) a heavy chain variable region CDR3 sequence comprising an amino acid sequence set forth in SEQ ID NO: 71 or a modification thereof, and a light chain variable region CDR3 sequence comprising an amino acid sequence set forth in SEQ ID NO: 74 or a modification thereof;

(d) a heavy chain variable region CDR3 sequence comprising an amino acid sequence set forth in SEQ ID NO: 77 or a modification thereof, and a light chain variable region CDR3 sequence comprising an amino acid sequence set forth in SEQ ID NO: 80 or a modification thereof and (e) a heavy chain variable region CDR3 sequence comprising an amino acid sequence set forth in SEQ ID NO: 83 or a modification thereof, and a light chain variable region CDR3 sequence comprising an amino acid sequence set forth in SEQ ID NO: 86 or a modification thereof.

27. The antibody or antigen-binding portion thereof of embodiments 25 or 26, comprising a heavy chain variable region CDR2 sequence and a light chain variable region CDR2 sequence selected from the group consisting of:

(a) a heavy chain variable region CDR2 sequence comprising an amino acid sequence set forth in SEQ ID NO: 58 or a modification thereof, and a light chain variable region CDR2 sequence comprising an amino acid sequence set forth in SEQ ID NO: 61 or a modification thereof.

(b) a heavy chain variable region CDR2 sequence comprising an amino acid sequence set forth in SEQ ID NO: 64 or a modification thereof, and a light chain variable region CDR2 sequence comprising an amino acid sequence set forth in SEQ ID NO: 67 or a modification thereof.

(c) a heavy chain variable region CDR2 sequence comprising an amino acid sequence set forth in SEQ ID NO: 70 or a modification thereof, and a light chain variable region CDR2 sequence comprising an amino acid sequence set forth in SEQ ID NO: 73 or a modification thereof.

(d) a heavy chain variable region CDR2 sequence comprising an amino acid sequence set forth in SEQ ID NO: 76 or a modification thereof, and a light chain variable region CDR2 sequence comprising an amino acid sequence set forth in SEQ ID NO: 79 or a modification thereof and (e) a heavy chain variable region CDR2 sequence comprising an amino acid sequence set forth in SEQ ID NO: 82 or a modification thereof, and a light chain variable region CDR2 sequence comprising an amino acid sequence set forth in SEQ ID NO: 85 or a modification thereof.

28. The antibody or antigen-binding portion thereof of embodiment 25, 26 or 27, comprising a heavy chain variable region CDR1 sequence and a light chain variable region CDR1 sequence selected from the group consisting of:

(a) a heavy chain variable region CDR1 sequence comprising an amino acid sequence set forth in SEQ ID NO: 57 or a modification thereof, and a light chain variable region CDR1 sequence comprising an amino acid sequence set forth in SEQ ID NO: 60 or a modification thereof;

(b) a heavy chain variable region CDR1 sequence comprising an amino acid sequence set forth in SEQ ID NO: 63 or a modification thereof, and a light chain variable region CDR1 sequence comprising an amino acid sequence set forth in SEQ ID NO: 66 or a modification thereof;

(c) a heavy chain variable region CDR1 sequence comprising an amino acid sequence set forth in SEQ ID NO: 69 or a modification thereof, and a light chain variable region CDR1 sequence comprising an amino acid sequence set forth in SEQ ID NO: 71 or a modification thereof;

(d) a heavy chain variable region CDR1 sequence comprising an amino acid sequence set forth in SEQ ID NO: 75 or a modification thereof, and a light chain variable region CDR1 sequence comprising an amino acid sequence set forth in SEQ ID NO: 78 or a modification thereof; and (e) a heavy chain variable region CDR1 sequence comprising an amino acid sequence set forth in SEQ ID NO: 81 or a modification thereof, and a light chain variable region CDR1 sequence comprising an amino acid sequence set forth in SEQ ID NO: 84 or a modification thereof.

29. The antibody or antigen-binding portion thereof of any one of embodiments 25-28, comprising:

(a) a heavy chain variable region CDR1 comprising an amino acid sequence set forth in SEQ ID NO: 57; a heavy chain variable region CDR2 comprising an amino acid sequence set forth in SEQ ID NO: 58; a heavy chain variable region CDR3 comprising an amino acid sequence set forth in SEQ ID NO: 59; a light chain variable region CDR1 comprising an amino acid sequence set forth in SEQ ID NO: 60; a light chain variable region CDR2 comprising an amino acid sequence set forth in SEQ ID NO: 61; and a light chain variable region CDR3 comprising an amino acid sequence set forth in SEQ ID NO: 62;

(b) a heavy chain variable region CDR1 comprising an amino acid sequence set forth in SEQ ID NO: 63; a heavy chain variable region CDR2 comprising an amino acid sequence set forth in SEQ ID NO: 64; a heavy chain variable region CDR3 comprising an amino acid sequence set forth in SEQ ID NO: 65; a light chain variable region CDR1 comprising an amino acid sequence set forth in SEQ ID NO: 66; a light chain variable region CDR2 comprising an amino acid sequence set forth in SEQ ID NO: 67; and a light chain variable region CDR3 comprising an amino acid sequence set forth in SEQ ID NO: 68;

(c) a heavy chain variable region CDR1 comprising an amino acid sequence set forth in SEQ ID NO: 69; a heavy chain variable region CDR2 comprising an amino acid sequence set forth in SEQ ID NO: 70; a heavy chain variable region CDR3 comprising an amino acid sequence set forth in SEQ ID NO: 71; a light chain variable region CDR1 comprising an amino acid sequence set forth in SEQ ID NO: 72; a light chain variable region CDR2 comprising an amino acid sequence set forth in SEQ ID NO: 73; and a light chain variable region CDR3 comprising an amino acid sequence set forth in SEQ ID NO: 74;

(d) a heavy chain variable region CDR1 comprising an amino acid sequence set forth in SEQ ID NO: 75; a heavy chain variable region CDR2 comprising an amino acid sequence set forth in SEQ ID NO: 76; a heavy chain variable region CDR3 comprising an amino acid sequence set forth in SEQ ID NO: 77; a light chain variable region CDR1 comprising an amino acid sequence set forth in SEQ ID NO: 78; a light chain variable region CDR2 comprising an amino acid sequence set forth in SEQ ID NO: 79; and a light chain variable region CDR3 comprising an amino acid sequence set forth in SEQ ID NO: 80; or (e) a heavy chain variable region CDR1 comprising an amino acid sequence set forth in SEQ ID NO: 81; a heavy chain variable region CDR2 comprising an amino acid sequence set forth in SEQ ID NO: 82; a heavy chain variable region CDR3 comprising an amino acid sequence set forth in SEQ ID NO: 83; a light chain variable region CDR1 comprising an amino acid sequence set forth in SEQ ID NO: 84; a light chain variable region CDR2 comprising an amino acid sequence set forth in SEQ ID NO: 85; and a light chain variable region CDR3 comprising an amino acid sequence set forth in SEQ ID NO: 86.

30. The antibody or antigen-binding portion thereof of any one of embodiments 25-29, comprising a heavy chain variable region that comprises an amino acid sequence that is at least about 80% homologous to the sequence selected from the group consisting of SEQ ID NOS: 109, 111, 113, 115, and 117.

31. The antibody or antigen-binding portion thereof of embodiment 30, comprising a heavy chain variable region that comprises an amino acid sequence set forth in SEQ ID NO: 109, SEQ ID NO: 111, SEQ ID NO: 113, SEQ ID NO: 115, or SEQ ID NO: 117.

32. The antibody or antigen-binding portion thereof of any one of embodiments 25-31, comprising a light chain variable region that comprises an amino acid sequence that is at least about 80% homologous to the sequence selected from the group consisting of SEQ ID NOS: 110, 112, 114, 116, and 118.

33. The antibody or antigen-binding portion thereof of embodiment 32, comprising a light chain variable region that comprises an amino acid sequence set forth in SEQ ID NO: 110, SEQ ID NO: 112, SEQ ID NO: 114, SEQ ID NO: 116, or SEQ ID NO: 118.

34. The antibody or antigen-binding portion thereof of any one of embodiments 30-33, comprising:

(a) a heavy chain variable region comprising an amino acid sequence that is at least about 80% homologous the amino acid sequence set forth in SEQ ID NO: 109, and a light chain variable region that comprising an amino acid sequence that is at least about 80% homologous the amino acid sequence set forth in SEQ ID NO: 110;

(b) a heavy chain variable region comprising an amino acid sequence that is at least about 80% homologous the amino acid sequence set forth in SEQ ID NO: 111, and a light chain variable region that comprising an amino acid sequence s that is at least about 80% homologous the amino acid sequence et forth in SEQ ID NO: 112;

(c) a heavy chain variable region comprising an amino acid sequence that is at least about 80% homologous the amino acid sequence set forth in SEQ ID NO: 113, and a light chain variable region that comprising an amino acid sequence that is at least about 80% homologous the amino acid sequence set forth in SEQ ID NO: 114;

(d) a heavy chain variable region comprising an amino acid sequence that is at least about 80% homologous the amino acid sequence set forth in SEQ ID NO: 115, and a light chain variable region that comprising an amino acid sequence that is at least about 80% homologous the amino acid sequence set forth in SEQ ID NO: 116; or (e) a heavy chain variable region comprising an amino acid sequence that is at least about 80% homologous the amino acid sequence set forth in SEQ ID NO: 117, and a light chain variable region that comprising an amino acid sequence that is at least about 80% homologous the amino acid sequence set forth in SEQ ID NO: 118.

35. The antibody or antigen-binding portion thereof of embodiment 34, comprising:

(a) a heavy chain variable region comprising an amino acid sequence set forth in SEQ ID NO: 109, and a light chain variable region that comprising an amino acid sequence set forth in SEQ ID NO: 110;

(b) a heavy chain variable region comprising an amino acid sequence set forth in SEQ ID NO: 111, and a light chain variable region that comprising an amino acid sequence set forth in SEQ ID NO: 112;

(c) a heavy chain variable region comprising an amino acid sequence set forth in SEQ ID NO: 113, and a light chain variable region that comprising an amino acid sequence set forth in SEQ ID NO: 114;

(d) a heavy chain variable region comprising an amino acid sequence set forth in SEQ ID NO: 115, and a light chain variable region that comprising an amino acid sequence set forth in SEQ ID NO: 116; or (e) a heavy chain variable region comprising an amino acid sequence set forth in SEQ ID NO: 117, and a light chain variable region that comprising an amino acid sequence set forth in SEQ ID NO: 118.

36. The antibody or antigen-binding portion thereof of embodiment 11, wherein the Foxp3 peptide is Foxp3-4 having the amino acid sequence set forth in SEQ ID NO: 5.

37. The antibody or antigen-binding portion thereof of embodiment 36, comprising a heavy chain variable region CDR3 sequence comprising an amino acid sequence set forth in SEQ ID NO: 89 or a modification thereof, and a light chain variable region CDR3 sequence comprising an amino acid sequence set forth in SEQ ID NO: 92 or a modification thereof.

38. The antibody or antigen-binding portion thereof of embodiment 36 or 37, comprising a heavy chain variable region CDR2 sequence comprising an amino acid sequence set forth in SEQ ID NO: 88 or a modification thereof, and a light chain variable region CDR2 sequence comprising an amino acid sequence set forth in SEQ ID NO: 91 or a modification thereof.

39. The antibody or antigen-binding portion thereof of embodiment 36, 37 or 38, comprising a heavy chain variable region CDR1 sequence comprising an amino acid sequence set forth in SEQ ID NO: 87 or a modification thereof, and a light chain variable region CDR2 sequence comprising an amino acid sequence set forth in SEQ ID NO: 90 or a modification thereof.

40. The antibody or antigen-binding portion thereof of any one of embodiments 36-39, comprising a heavy chain variable region CDR1 comprising an amino acid sequence set forth in SEQ ID NO: 87; a heavy chain variable region CDR2 comprising an amino acid sequence set forth in SEQ ID NO: 88; a heavy chain variable region CDR3 comprising an amino acid sequence set forth in SEQ ID NO: 89; a light chain variable region CDR1 comprising an amino acid sequence set forth in SEQ ID NO: 90; a light chain variable region CDR2 comprising an amino acid sequence set forth in SEQ ID NO: 91; and a light chain variable region CDR3 comprising an amino acid sequence set forth in SEQ ID NO: 92.

41. The antibody or antigen-binding portion thereof of any one of embodiments 36-40, comprising a heavy chain variable region that comprises an amino acid sequence that is at least about 80% homologous the amino acid sequence set forth in SEQ ID NO: 119.

42. The antibody or antigen-binding portion thereof of embodiment 41, comprising a heavy chain variable region that comprises an amino acid sequence set forth in SEQ ID NO: 119.

43. The antibody or antigen-binding portion thereof of any one of embodiments 36-42, comprising a light chain variable region that comprises an amino acid sequence that is at least about 80% homologous the amino acid sequence set forth in SEQ ID NO: 120.

44. The antibody or antigen-binding portion thereof of embodiment 43, comprising a light chain variable region that comprises an amino acid sequence set forth in SEQ ID NO: 120.

45. The antibody or antigen-binding portion thereof of any one of embodiments 41-44, comprising a heavy chain variable region comprising an amino acid sequence that is at least about 80% homologous the amino acid sequence set forth in SEQ ID NO: 119, and a light chain variable region that comprising an amino acid sequence that is at least about 80% homologous the amino acid sequence set forth in SEQ ID NO: 120.

46. The antibody or antigen-binding portion thereof of embodiment 45, comprising a heavy chain variable region comprising an amino acid sequence set forth in SEQ ID NO: 119, and a light chain variable region that comprising an amino acid sequence set forth in SEQ ID NO: 120.

47. The antibody or antigen-binding portion thereof of any one of embodiments 13-15, 26-28 and 37-39, wherein the modification is selected from deletions, insertions, substitutions, and combinations thereof.

48. The antibody or antigen-binding portion thereof of any one of embodiments 13-15, 26-28 and 37-39, wherein the modification thereof consists of no more than 2, no more than 3, no more than 4, or no more than 5 modifications.

49. The antibody or antigen-binding portion thereof of any one of embodiments 1-48, which binds to the N-terminal of the Foxp3 peptide that is bound to the human MHC molecule.

50. The antibody or antigen-binding portion thereof of any one of embodiments 1-48, which binds to the C-terminal of the Foxp3 peptide that is bound to the human MHC molecule.

51. The antibody or antigen-binding portion thereof of any one of embodiments 1-50, which binds to the Foxp3 peptide/MHC complex with a binding affinity (KD) of about 1×10-7 M or less.

52. An isolated antibody, or an antigen-binding portion thereof, which cross-competes for binding to a Foxp3 peptide bound to a human MHC molecule with a reference antibody or antigen-binding portion comprising:

(a) a heavy chain variable region CDR1 comprising an amino acid sequence set forth in SEQ ID NO: 9; a heavy chain variable region CDR2 comprising an amino acid sequence set forth in SEQ ID NO: 10; a heavy chain variable region CDR3 comprising an amino acid sequence set forth in SEQ ID NO: 11; a light chain variable region CDR1 comprising an amino acid sequence set forth in SEQ ID NO: 12; a light chain variable region CDR2 comprising an amino acid sequence set forth in SEQ ID NO: 13; and a light chain variable region CDR3 comprising an amino acid sequence set forth in SEQ ID NO: 14;

(b) a heavy chain variable region CDR1 comprising an amino acid sequence set forth in SEQ ID NO: 15; a heavy chain variable region CDR2 comprising an amino acid sequence set forth in SEQ ID NO: 16; a heavy chain variable region CDR3 comprising an amino acid sequence set forth in SEQ ID NO: 17; a light chain variable region CDR1 comprising an amino acid sequence set forth in SEQ ID NO: 18; a light chain variable region CDR2 comprising an amino acid sequence set forth in SEQ ID NO: 19; and a light chain variable region CDR3 comprising an amino acid sequence set forth in SEQ ID NO: 20;

(c) a heavy chain variable region CDR1 comprising an amino acid sequence set forth in SEQ ID NO: 21; a heavy chain variable region CDR2 comprising an amino acid sequence set forth in SEQ ID NO: 22; a heavy chain variable region CDR3 comprising an amino acid sequence set forth in SEQ ID NO: 23; a light chain variable region CDR1 comprising an amino acid sequence set forth in SEQ ID NO: 24; a light chain variable region CDR2 comprising an amino acid sequence set forth in SEQ ID NO: 25; and a light chain variable region CDR3 comprising an amino acid sequence set forth in SEQ ID NO: 26;

(d) a heavy chain variable region CDR1 comprising an amino acid sequence set forth in SEQ ID NO: 27; a heavy chain variable region CDR2 comprising an amino acid sequence set forth in SEQ ID NO: 28; a heavy chain variable region CDR3 comprising an amino acid sequence set forth in SEQ ID NO: 29; a light chain variable region CDR1 comprising an amino acid sequence set forth in SEQ ID NO: 30; a light chain variable region CDR2 comprising an amino acid sequence set forth in SEQ ID NO: 31; and a light chain variable region CDR3 comprising an amino acid sequence set forth in SEQ ID NO: 32;

(e) a heavy chain variable region CDR1 comprising an amino acid sequence set forth in SEQ ID NO: 33; a heavy chain variable region CDR2 comprising an amino acid sequence set forth in SEQ ID NO: 34; a heavy chain variable region CDR3 comprising an amino acid sequence set forth in SEQ ID NO: 35; a light chain variable region CDR1 comprising an amino acid sequence set forth in SEQ ID NO: 36; a light chain variable region CDR2 comprising an amino acid sequence set forth in SEQ ID NO: 37; and a light chain variable region CDR3 comprising an amino acid sequence set forth in SEQ ID NO: 38;

(f) a heavy chain variable region CDR1 comprising an amino acid sequence set forth in SEQ ID NO: 39; a heavy chain variable region CDR2 comprising an amino acid sequence set forth in SEQ ID NO: 40; a heavy chain variable region CDR3 comprising an amino acid sequence set forth in SEQ ID NO: 41; a light chain variable region CDR1 comprising an amino acid sequence set forth in SEQ ID NO: 42; a light chain variable region CDR2 comprising an amino acid sequence set forth in SEQ ID NO: 43; and a light chain variable region CDR3 comprising an amino acid sequence set forth in SEQ ID NO: 44;

(g) a heavy chain variable region CDR1 comprising an amino acid sequence set forth in SEQ ID NO: 45; a heavy chain variable region CDR2 comprising an amino acid sequence set forth in SEQ ID NO: 46; a heavy chain variable region CDR3 comprising an amino acid sequence set forth in SEQ ID NO: 47; a light chain variable region CDR1 comprising an amino acid sequence set forth in SEQ ID NO: 48; a light chain variable region CDR2 comprising an amino acid sequence set forth in SEQ ID NO: 49; and a light chain variable region CDR3 comprising an amino acid sequence set forth in SEQ ID NO: 50;

(h) a heavy chain variable region CDR1 comprising an amino acid sequence set forth in SEQ ID NO: 51; a heavy chain variable region CDR2 comprising an amino acid sequence set forth in SEQ ID NO: 52; a heavy chain variable region CDR3 comprising an amino acid sequence set forth in SEQ ID NO: 53; a light chain variable region CDR1 comprising an amino acid sequence set forth in SEQ ID NO: 54; a light chain variable region CDR2 comprising an amino acid sequence set forth in SEQ ID NO: 55; and a light chain variable region CDR3 comprising an amino acid sequence set forth in SEQ ID NO: 56;

(i) a heavy chain variable region CDR1 comprising an amino acid sequence set forth in SEQ ID NO: 57; a heavy chain variable region CDR2 comprising an amino acid sequence set forth in SEQ ID NO: 58; a heavy chain variable region CDR3 comprising an amino acid sequence set forth in SEQ ID NO: 59; a light chain variable region CDR1 comprising an amino acid sequence set forth in SEQ ID NO: 60; a light chain variable region CDR2 comprising an amino acid sequence set forth in SEQ ID NO: 61; and a light chain variable region CDR3 comprising an amino acid sequence set forth in SEQ ID NO: 62;

(j) a heavy chain variable region CDR1 comprising an amino acid sequence set forth in SEQ ID NO: 63; a heavy chain variable region CDR2 comprising an amino acid sequence set forth in SEQ ID NO: 64; a heavy chain variable region CDR3 comprising an amino acid sequence set forth in SEQ ID NO: 65; a light chain variable region CDR1 comprising an amino acid sequence set forth in SEQ ID NO: 66; a light chain variable region CDR2 comprising an amino acid sequence set forth in SEQ ID NO: 67; and a light chain variable region CDR3 comprising an amino acid sequence set forth in SEQ ID NO: 68;

(k) a heavy chain variable region CDR1 comprising an amino acid sequence set forth in SEQ ID NO: 69; a heavy chain variable region CDR2 comprising an amino acid sequence set forth in SEQ ID NO: 70; a heavy chain variable region CDR3 comprising an amino acid sequence set forth in SEQ ID NO: 71; a light chain variable region CDR1 comprising an amino acid sequence set forth in SEQ ID NO: 72; a light chain variable region CDR2 comprising an amino acid sequence set forth in SEQ ID NO: 73; and a light chain variable region CDR3 comprising an amino acid sequence set forth in SEQ ID NO: 74;

(l) a heavy chain variable region CDR1 comprising an amino acid sequence set forth in SEQ ID NO: 75; a heavy chain variable region CDR2 comprising an amino acid sequence set forth in SEQ ID NO: 76; a heavy chain variable region CDR3 comprising an amino acid sequence set forth in SEQ ID NO: 77; a light chain variable region CDR1 comprising an amino acid sequence set forth in SEQ ID NO: 78; a light chain variable region CDR2 comprising an amino acid sequence set forth in SEQ ID NO: 79; and a light chain variable region CDR3 comprising an amino acid sequence set forth in SEQ ID NO: 80;

(m) a heavy chain variable region CDR1 comprising an amino acid sequence set forth in SEQ ID NO: 81; a heavy chain variable region CDR2 comprising an amino acid sequence set forth in SEQ ID NO: 82; a heavy chain variable region CDR3 comprising an amino acid sequence set forth in SEQ ID NO: 83; a light chain variable region CDR1 comprising an amino acid sequence set forth in SEQ ID NO: 84; a light chain variable region CDR2 comprising an amino acid sequence set forth in SEQ ID NO: 85; and a light chain variable region CDR3 comprising an amino acid sequence set forth in SEQ ID NO: 86; or (n) a heavy chain variable region CDR1 comprising an amino acid sequence set forth in SEQ ID NO: 87; a heavy chain variable region CDR2 comprising an amino acid sequence set forth in SEQ ID NO: 88; a heavy chain variable region CDR3 comprising an amino acid sequence set forth in SEQ ID NO: 89; a light chain variable region CDR1 comprising an amino acid sequence set forth in SEQ ID NO: 90; a light chain variable region CDR2 comprising an amino acid sequence set forth in SEQ ID NO: 91; and a light chain variable region CDR3 comprising an amino acid sequence set forth in SEQ ID NO: 92, and wherein the cross-competing antibody or antigen-binding portion thereof specifically binds to the Foxp3 peptide/MHC complex with a binding affinity (KD) of about 5×10-7 M or less.

53. An isolated antibody, or an antigen-binding portion thereof, which binds to the same epitope on a Foxp3 peptide bound to an MHC molecule with a reference antibody or antigen-binding portion comprising:

(a) a heavy chain variable region CDR1 comprising an amino acid sequence set forth in SEQ ID NO: 9; a heavy chain variable region CDR2 comprising an amino acid sequence set forth in SEQ ID NO: 10; a heavy chain variable region CDR3 comprising an amino acid sequence set forth in SEQ ID NO: 11; a light chain variable region CDR1 comprising an amino acid sequence set forth in SEQ ID NO: 12; a light chain variable region CDR2 comprising an amino acid sequence set forth in SEQ ID NO: 13; and a light chain variable region CDR3 comprising an amino acid sequence set forth in SEQ ID NO: 14;

(b) a heavy chain variable region CDR1 comprising an amino acid sequence set forth in SEQ ID NO: 15; a heavy chain variable region CDR2 comprising an amino acid sequence set forth in SEQ ID NO: 16; a heavy chain variable region CDR3 comprising an amino acid sequence set forth in SEQ ID NO: 17; a light chain variable region CDR1 comprising an amino acid sequence set forth in SEQ ID NO: 18; a light chain variable region CDR2 comprising an amino acid sequence set forth in SEQ ID NO: 19; and a light chain variable region CDR3 comprising an amino acid sequence set forth in SEQ ID NO: 20;

(c) a heavy chain variable region CDR1 comprising an amino acid sequence set forth in SEQ ID NO: 21; a heavy chain variable region CDR2 comprising an amino acid sequence set forth in SEQ ID NO: 22; a heavy chain variable region CDR3 comprising an amino acid sequence set forth in SEQ ID NO: 23; a light chain variable region CDR1 comprising an amino acid sequence set forth in SEQ ID NO: 24; a light chain variable region CDR2 comprising an amino acid sequence set forth in SEQ ID NO: 25; and a light chain variable region CDR3 comprising an amino acid sequence set forth in SEQ ID NO: 26;

(d) a heavy chain variable region CDR1 comprising an amino acid sequence set forth in SEQ ID NO: 27; a heavy chain variable region CDR2 comprising an amino acid sequence set forth in SEQ ID NO: 28; a heavy chain variable region CDR3 comprising an amino acid sequence set forth in SEQ ID NO: 29; a light chain variable region CDR1 comprising an amino acid sequence set forth in SEQ ID NO: 30; a light chain variable region CDR2 comprising an amino acid sequence set forth in SEQ ID NO: 31; and a light chain variable region CDR3 comprising an amino acid sequence set forth in SEQ ID NO: 32;

(e) a heavy chain variable region CDR1 comprising an amino acid sequence set forth in SEQ ID NO: 33; a heavy chain variable region CDR2 comprising an amino acid sequence set forth in SEQ ID NO: 34; a heavy chain variable region CDR3 comprising an amino acid sequence set forth in SEQ ID NO: 35; a light chain variable region CDR1 comprising an amino acid sequence set forth in SEQ ID NO: 36; a light chain variable region CDR2 comprising an amino acid sequence set forth in SEQ ID NO: 37; and a light chain variable region CDR3 comprising an amino acid sequence set forth in SEQ ID NO: 38;

(f) a heavy chain variable region CDR1 comprising an amino acid sequence set forth in SEQ ID NO: 39; a heavy chain variable region CDR2 comprising an amino acid sequence set forth in SEQ ID NO: 40; a heavy chain variable region CDR3 comprising an amino acid sequence set forth in SEQ ID NO: 41; a light chain variable region CDR1 comprising an amino acid sequence set forth in SEQ ID NO: 42; a light chain variable region CDR2 comprising an amino acid sequence set forth in SEQ ID NO: 43; and a light chain variable region CDR3 comprising an amino acid sequence set forth in SEQ ID NO: 44;

(g) a heavy chain variable region CDR1 comprising an amino acid sequence set forth in SEQ ID NO: 45; a heavy chain variable region CDR2 comprising an amino acid sequence set forth in SEQ ID NO: 46; a heavy chain variable region CDR3 comprising an amino acid sequence set forth in SEQ ID NO: 47; a light chain variable region CDR1 comprising an amino acid sequence set forth in SEQ ID NO: 48; a light chain variable region CDR2 comprising an amino acid sequence set forth in SEQ ID NO: 49; and a light chain variable region CDR3 comprising an amino acid sequence set forth in SEQ ID NO: 50;

(h) a heavy chain variable region CDR1 comprising an amino acid sequence set forth in SEQ ID NO: 51; a heavy chain variable region CDR2 comprising an amino acid sequence set forth in SEQ ID NO: 52; a heavy chain variable region CDR3 comprising an amino acid sequence set forth in SEQ ID NO: 53; a light chain variable region CDR1 comprising an amino acid sequence set forth in SEQ ID NO: 54; a light chain variable region CDR2 comprising an amino acid sequence set forth in SEQ ID NO: 55; and a light chain variable region CDR3 comprising an amino acid sequence set forth in SEQ ID NO: 56;

(i) a heavy chain variable region CDR1 comprising an amino acid sequence set forth in SEQ ID NO: 57; a heavy chain variable region CDR2 comprising an amino acid sequence set forth in SEQ ID NO: 58; a heavy chain variable region CDR3 comprising an amino acid sequence set forth in SEQ ID NO: 59; a light chain variable region CDR1 comprising an amino acid sequence set forth in SEQ ID NO: 60; a light chain variable region CDR2 comprising an amino acid sequence set forth in SEQ ID NO: 61; and a light chain variable region CDR3 comprising an amino acid sequence set forth in SEQ ID NO: 62;

(j) a heavy chain variable region CDR1 comprising an amino acid sequence set forth in SEQ ID NO: 63; a heavy chain variable region CDR2 comprising an amino acid sequence set forth in SEQ ID NO: 64; a heavy chain variable region CDR3 comprising an amino acid sequence set forth in SEQ ID NO: 65; a light chain variable region CDR1 comprising an amino acid sequence set forth in SEQ ID NO: 66; a light chain variable region CDR2 comprising an amino acid sequence set forth in SEQ ID NO: 67; and a light chain variable region CDR3 comprising an amino acid sequence set forth in SEQ ID NO: 68;

(k) a heavy chain variable region CDR1 comprising an amino acid sequence set forth in SEQ ID NO: 69; a heavy chain variable region CDR2 comprising an amino acid sequence set forth in SEQ ID NO: 70; a heavy chain variable region CDR3 comprising an amino acid sequence set forth in SEQ ID NO: 71; a light chain variable region CDR1 comprising an amino acid sequence set forth in SEQ ID NO: 72; a light chain variable region CDR2 comprising an amino acid sequence set forth in SEQ ID NO: 73; and a light chain variable region CDR3 comprising an amino acid sequence set forth in SEQ ID NO: 74;

(l) a heavy chain variable region CDR1 comprising an amino acid sequence set forth in SEQ ID NO: 75; a heavy chain variable region CDR2 comprising an amino acid sequence set forth in SEQ ID NO: 76; a heavy chain variable region CDR3 comprising an amino acid sequence set forth in SEQ ID NO: 77; a light chain variable region CDR1 comprising an amino acid sequence set forth in SEQ ID NO: 78; a light chain variable region CDR2 comprising an amino acid sequence set forth in SEQ ID NO: 79; and a light chain variable region CDR3 comprising an amino acid sequence set forth in SEQ ID NO: 80;

(m) a heavy chain variable region CDR1 comprising an amino acid sequence set forth in SEQ ID NO: 81; a heavy chain variable region CDR2 comprising an amino acid sequence set forth in SEQ ID NO: 82; a heavy chain variable region CDR3 comprising an amino acid sequence set forth in SEQ ID NO: 83; a light chain variable region CDR1 comprising an amino acid sequence set forth in SEQ ID NO: 84; a light chain variable region CDR2 comprising an amino acid sequence set forth in SEQ ID NO: 85; and a light chain variable region CDR3 comprising an amino acid sequence set forth in SEQ ID NO: 86; or (n) a heavy chain variable region CDR1 comprising an amino acid sequence set forth in SEQ ID NO: 87; a heavy chain variable region CDR2 comprising an amino acid sequence set forth in SEQ ID NO: 88; a heavy chain variable region CDR3 comprising an amino acid sequence set forth in SEQ ID NO: 89; a light chain variable region CDR1 comprising an amino acid sequence set forth in SEQ ID NO: 90; a light chain variable region CDR2 comprising an amino acid sequence set forth in SEQ ID NO: 91; and a light chain variable region CDR3 comprising an amino acid sequence set forth in SEQ ID NO: 92.

54. An isolated antibody, or an antigen-binding portion thereof, which cross-competes for binding to a Foxp3 peptide bound to an MHC molecule with a reference antibody or antigen-binding portion comprising:

(a) a heavy chain variable region comprising an amino acid sequence set forth in SEQ ID NO: 93, and a light chain variable region that comprising an amino acid sequence set forth in SEQ ID NO: 94;

(b) a heavy chain variable region comprising an amino acid sequence set forth in SEQ ID NO: 95, and a light chain variable region that comprising an amino acid sequence set forth in SEQ ID NO: 96;

(c) a heavy chain variable region comprising an amino acid sequence set forth in SEQ ID NO: 97, and a light chain variable region that comprising an amino acid sequence set forth in SEQ ID NO: 98;

(d) a heavy chain variable region comprising an amino acid sequence set forth in SEQ ID NO: 99, and a light chain variable region that comprising an amino acid sequence set forth in SEQ ID NO: 100;

(e) a heavy chain variable region comprising an amino acid sequence set forth in SEQ ID NO: 101, and a light chain variable region that comprising an amino acid sequence set forth in SEQ ID NO: 102;

(f) a heavy chain variable region comprising an amino acid sequence set forth in SEQ ID NO: 103, and a light chain variable region that comprising an amino acid sequence set forth in SEQ ID NO: 104;

(g) a heavy chain variable region comprising an amino acid sequence set forth in SEQ ID NO: 105, and a light chain variable region that comprising an amino acid sequence set forth in SEQ ID NO: 106;

(h) a heavy chain variable region comprising an amino acid sequence set forth in SEQ ID NO: 107, and a light chain variable region that comprising an amino acid sequence set forth in SEQ ID NO: 108;

(i) a heavy chain variable region comprising an amino acid sequence set forth in SEQ ID NO: 109, and a light chain variable region that comprising an amino acid sequence set forth in SEQ ID NO: 110;

(j) a heavy chain variable region comprising an amino acid sequence set forth in SEQ ID NO: 111, and a light chain variable region that comprising an amino acid sequence set forth in SEQ ID NO: 112;

(k) a heavy chain variable region comprising an amino acid sequence set forth in SEQ ID NO: 113, and a light chain variable region that comprising an amino acid sequence set forth in SEQ ID NO: 114;

(l) a heavy chain variable region comprising an amino acid sequence set forth in SEQ ID NO: 115, and a light chain variable region that comprising an amino acid sequence set forth in SEQ ID NO: 116;

(m) a heavy chain variable region comprising an amino acid sequence set forth in SEQ ID NO: 117, and a light chain variable region that comprising an amino acid sequence set forth in SEQ ID NO: 118; or (n) a heavy chain variable region comprising an amino acid sequence set forth in SEQ ID NO: 119, and a light chain variable region that comprising an amino acid sequence set forth in SEQ ID NO: 120, and wherein the cross-competing antibody or antigen-binding portion thereof specifically binds to the Foxp3 peptide/MHC complex with a binding affinity (KD) of about 5×10-7 M or less.

55. An isolated antibody, or an antigen-binding portion thereof, which binds to the same epitope on a Foxp3 peptide bound to an MHC molecule with a reference antibody or antigen-binding portion comprising:

(a) a heavy chain variable region comprising an amino acid sequence set forth in SEQ ID NO: 93, and a light chain variable region that comprising an amino acid sequence set forth in SEQ ID NO: 94;

(b) a heavy chain variable region comprising an amino acid sequence set forth in SEQ ID NO: 95, and a light chain variable region that comprising an amino acid sequence set forth in SEQ ID NO: 96;

(c) a heavy chain variable region comprising an amino acid sequence set forth in SEQ ID NO: 97, and a light chain variable region that comprising an amino acid sequence set forth in SEQ ID NO: 98;

(d) a heavy chain variable region comprising an amino acid sequence set forth in SEQ ID NO: 99, and a light chain variable region that comprising an amino acid sequence set forth in SEQ ID NO: 100;

(e) a heavy chain variable region comprising an amino acid sequence set forth in SEQ ID NO: 101, and a light chain variable region that comprising an amino acid sequence set forth in SEQ ID NO: 102;

(f) a heavy chain variable region comprising an amino acid sequence set forth in SEQ ID NO: 103, and a light chain variable region that comprising an amino acid sequence set forth in SEQ ID NO: 104;

(g) a heavy chain variable region comprising an amino acid sequence set forth in SEQ ID NO: 105, and a light chain variable region that comprising an amino acid sequence set forth in SEQ ID NO: 106;

(h) a heavy chain variable region comprising an amino acid sequence set forth in SEQ ID NO: 107, and a light chain variable region that comprising an amino acid sequence set forth in SEQ ID NO: 108;

(i) a heavy chain variable region comprising an amino acid sequence set forth in SEQ ID NO: 109, and a light chain variable region that comprising an amino acid sequence set forth in SEQ ID NO: 110;

(j) a heavy chain variable region comprising an amino acid sequence set forth in SEQ ID NO: 111, and a light chain variable region that comprising an amino acid sequence set forth in SEQ ID NO: 112;

(k) a heavy chain variable region comprising an amino acid sequence set forth in SEQ ID NO: 113, and a light chain variable region that comprising an amino acid sequence set forth in SEQ ID NO: 114;

(l) a heavy chain variable region comprising an amino acid sequence set forth in SEQ ID NO: 115, and a light chain variable region that comprising an amino acid sequence set forth in SEQ ID NO: 116;

(m) a heavy chain variable region comprising an amino acid sequence set forth in SEQ ID NO: 117, and a light chain variable region that comprising an amino acid sequence set forth in SEQ ID NO: 118; or (n) a heavy chain variable region comprising an amino acid sequence set forth in SEQ ID NO: 119, and a light chain variable region that comprising an amino acid sequence set forth in SEQ ID NO: 120.

56. The antibody or antigen-binding portion thereof of any one of embodiments 52-55, wherein the human MHC molecule is a HLA molecule.

57. The antibody or antigen-binding portion thereof of embodiment 56, wherein the HLA molecule is a HLA class I molecule.

58. The antibody or antigen-binding portion thereof of embodiment 57, wherein the HLA class I molecule is HLA-A.

59. The antibody or antigen-binding portion thereof of embodiment 58, wherein the HLA-A is HLA-A2.

60. The antibody or antigen-binding portion thereof of embodiment 59, wherein the HLA-A2 is HLA-A*02:01.

61. The antibody or antigen-binding portion thereof of any one of embodiments 52-60, wherein the Foxp3 peptide is selected from the group consisting of Foxp3-7 having the amino acid sequence set forth in SEQ ID NO: 8 or a portion thereof; Foxp3-1 having the amino acid sequence set forth in SEQ ID NO: 2 or a portion thereof, Foxp3-2 having the amino acid sequence set forth in SEQ ID NO: 3 or a portion thereof, Foxp3-3 having the amino acid sequence set forth in SEQ ID NO: 4 or a portion thereof, Foxp3-4 having the amino acid sequence set forth in SEQ ID NO: 5 or a portion thereof, Foxp3-5 having the amino acid sequence set forth in SEQ ID NO: 6 or a portion thereof, and Foxp3-6 having the amino acid sequence set forth in SEQ ID NO: 7 or a portion thereof.

62. The antibody or antigen-binding portion thereof of embodiment 61, wherein the Foxp3 peptide is Foxp3-7 or a portion thereof.

63. The antibody or antigen-binding portion thereof of any one of embodiments 52-62, wherein the reference antibody or antigen-binding portion thereof comprises a heavy chain variable region comprising an amino acid sequence set forth in SEQ ID NO: 103, and a light chain variable region that comprising an amino acid sequence set forth in SEQ ID NO: 104.

64. The antibody or antigen-binding portion thereof of embodiment 61, wherein the Foxp3 peptide is Foxp3-2 or a portion thereof.

65. The antibody or antigen-binding portion thereof of embodiment 61, wherein the Foxp3 peptide is Foxp3-4 or a portion thereof.

66. The antibody or antigen-binding portion thereof of any one of the preceding embodiments, wherein the antibody comprises a human variable region framework region.

67. The antibody or antigen-binding portion thereof of any one of the preceding embodiments, which is a fully human antibody or an antigen-binding portion thereof.

68. The antibody or antigen-binding portion thereof of any one of embodiments 1-66, which is a chimeric antibody or an antigen-binding portion thereof.

69. The antibody or antigen-binding portion thereof of any one of embodiments 1-66, which is a humanized antibody or an antigen-binding portion thereof.

70. The antibody or antigen-binding portion thereof of any one of the preceding embodiments, wherein the antigen-binding portion of the antibody is an Fab, Fab', F(ab')2, Fv or single chain Fv (scFv).

71. The antibody or antigen-binding portion thereof of any one of the preceding embodiments, which is of an IgG1, IgG2, IgG3, or IgG4 isotype.

72. The antibody or antigen-binding portion thereof of embodiment 71, which is of an IgG1 isotype.

73. The antibody or antigen-binding portion thereof of any one of the preceding embodiments, comprising one or more post-translational modifications.

74. The antibody or antigen-binding portion thereof of embodiment 73, wherein the one or more post-translational modifications comprise afucosylation.

75. The antibody or antigen-binding portion thereof of embodiment 74, comprising an afucosylated Fc region.

76. A composition comprising the antibody or antigen-binding portion thereof of any one of the preceding embodiments, and a pharmaceutically acceptable carrier.

77. An immunoconjugate comprising the antibody or antigen-binding portion thereof of any one of embodiments 1-75 linked to a therapeutic agent.

78. The immunoconjugate of embodiment 77, wherein said therapeutic agent is a drug, cytotoxin, or a radioactive isotope.

79. A composition comprising the immunoconjugate of embodiment 77 or 78 and a pharmaceutically acceptable carrier.

80. A bispecific molecule comprising the antibody or antigen-binding portion thereof of any one of embodiments 1-75, linked to a second functional moiety.

81. The bispecific molecule of embodiment 80, wherein the second functional moiety has a different binding specificity than said antibody or antigen binding portion thereof.

82. The bispecific molecule of embodiment 80 or 81, which recognizes a Foxp3 peptide bound to the MHC molecule and a cell surface protein.

83. The bispecific molecule of embodiment 82, wherein the cell surface protein is CD3 or CD16.

84. A composition comprising the bispecific molecule of any one of embodiments 80-83 and a pharmaceutically acceptable carrier.

85. An isolated nucleic acid that encodes an antibody or antigen-binding portion thereof of any one of embodiments 1-75.

86. An expression vector comprising the nucleic acid molecule of embodiment 85.

87. A host cell comprising the expression vector of embodiment 86.

88. A method for detecting Foxp3 in a whole cell or tissue, comprising:

(a) contacting a cell or tissue with an antibody or an antigen-binding portion thereof that binds to a Foxp3 peptide that is bound to a human MHC molecule, wherein the antibody or antigen-binding portion thereof comprises a detectable label; and (b) determining the amount of the labeled antibody or antigen-binding portion thereof bound to the cell or tissue by measuring the amount of detectable label associated with the cell or tissue, wherein the amount of bound antibody or antigen-binding portion thereof indicates the amount of Foxp3 in the cell or tissue.

89. The method of embodiment 88, wherein the human MHC molecule is a HLA molecule.

90. The method of embodiment 89, wherein the HLA molecule is a HLA class I molecule.

91. The method of embodiment 90, wherein the HLA class I molecule is HLA-A.

92. The method of embodiment 91, wherein the HLA-A is HLA-A2.

93. The method of embodiment 92, wherein the HLA-A2 is HLA-A*02:01.

94. The method of any one of embodiments 88-93, wherein the Foxp3 peptide is selected from the group consisting of Foxp3-7 having the amino acid sequence set forth in SEQ ID NO: 8 or a portion thereof; Foxp3-1 having the amino acid sequence set forth in SEQ ID NO: 2 or a portion thereof, Foxp3-2 having the amino acid sequence set forth in SEQ ID NO: 3 or a portion thereof, Foxp3-3 having the amino acid sequence set forth in SEQ ID NO: 4 or a portion thereof, Foxp3-4 having the amino acid sequence set forth in SEQ ID NO: 5 or a portion thereof, Foxp3-5 having the amino acid sequence set forth in SEQ ID NO: 6 or a portion thereof, and Foxp3-6 having the amino acid sequence set forth in SEQ ID NO: 7 or a portion thereof.

95. The method of embodiment 94, wherein the Foxp3 peptide is Foxp3-7 or a portion thereof.

96. The method of embodiment 94, wherein the Foxp3 peptide is Foxp3-2 or a portion thereof.

97. The method of embodiment 94, wherein the Foxp3 peptide is Foxp3-4 or a portion thereof.

98. The method of any one of embodiments 88-97, wherein the antibody or antigen-binding portion thereof is the antibody or antigen-binding portion thereof of any one of embodiments 1-75.

99. A chimeric antigen receptor (CAR) specific for a Foxp3 peptide bound to a human MHC molecule.

100. The CAR of embodiment 99, wherein the human MHC molecule is a HLA molecule.

101. The CAR of embodiment 100, wherein the HLA molecule is a HLA class I molecule.

102. The CAR of embodiment 101, wherein the HLA class I molecule is HLA-A.

103. The CAR of embodiment 102, wherein the HLA-A is HLA-A2.

104. The CAR of embodiment 103, wherein the HLA-A2 is HLA-A*02:01.

105. The CAR of any one of embodiments 99-104, wherein the Foxp3 peptide is selected from the group consisting of Foxp3-7 having the amino acid sequence set forth in SEQ ID NO: 8 or a portion thereof; Foxp3-1 having the amino acid sequence set forth in SEQ ID NO: 2 or a portion thereof, Foxp3-2 having the amino acid sequence set forth in SEQ ID NO: 3 or a portion thereof, Foxp3-3 having the amino acid sequence set forth in SEQ ID NO: 4 or a portion thereof, Foxp3-4 having the amino acid sequence set forth in SEQ ID NO: 5 or a portion thereof, Foxp3-5 having the amino acid sequence set forth in SEQ ID NO: 6 or a portion thereof, and Foxp3-6 having the amino acid sequence set forth in SEQ ID NO: 7 or a portion thereof.

106. The CAR of embodiment 105, wherein the Foxp3 peptide is Foxp3-7 or a portion thereof.

107. The CAR of embodiment 105, wherein the Foxp3 peptide is Foxp3-2 or a portion thereof.

108. The CAR of embodiment 105, wherein the Foxp3 peptide is Foxp3-4 or a portion thereof.

109. The CAR of any one of embodiments 99-108, wherein the CAR comprises an antigen-binding portion comprising a heavy chain variable region and a light chain variable region.

110. The CAR of embodiment 109, wherein the CAR comprises a linker between the heavy chain variable region and the light chain variable region.

111. The CAR of embodiment 110, wherein the linker comprises the amino acid sequence set forth in SEQ ID NO: 135.

112. The CAR of any one of embodiments 99-111, wherein the CAR comprises the antigen-binding portion of any one of embodiments 1-75.

113. The CAR of any one of embodiments 109-112, wherein the antigen-binding portion comprises a single-chain variable fragment (scFv).

114. The CAR of embodiment 113, wherein the scFv is a human scFv.

115. The CAR of embodiment 114, wherein the human scFv comprises the amino acid sequence selected from the group consisting of SEQ ID NOS: 121, 122, 123, 124, 125, 126, 127, 128, 129, 130, 131, 132, 133, and 134.

116. The CAR of embodiment 115, wherein the human scFv comprises the amino acid sequence set forth in SEQ ID NO: 126.

117. The CAR of any one of embodiments 109-112, wherein the antigen-binding portion comprises a Fab, which is optionally crosslinked.

118. The CAR of any one of embodiments 109-112, wherein the antigen-binding portion comprises a F(ab)2.

119. An isolated nucleic acid encoding the CAR of any one of embodiments 99-118.

120. A vector comprising the isolated nucleic acid of embodiment 119.

121. A host cell comprising the nucleic acid of embodiment 119.

122. The host cell of embodiment 121, wherein the host cell is a T cell.

123. A method of killing a Foxp3-expressing cell, comprising contacting a Foxp3-expressing cell with the antibody or antigen-binding portion thereof of any one of embodiments 1-75 or a composition comprising thereof.

124. Use of the antibody or antigen-binding portion thereof of any one of embodiments 1-75 or a composition comprising thereof to kill a Foxp3-expressing cell.

125. The antibody or antigen-binding portion thereof of any one of embodiments 1-75 or a composition comprising thereof for use in killing a Foxp3-expressing cell.

126. A method of killing a Foxp3-expressing cell, comprising contacting a Foxp3-expressing cell with the CAR of any one of embodiments 99-118 or a composition comprising thereof.

127. Use of the CAR of any one of embodiments 99-118 or a composition comprising thereof to kill a Foxp3-expressing cell.

128. The CAR of any one of embodiments 99-118 or a composition comprising thereof for use in killing a Foxp3-expressing cell.

129. A method of killing a Foxp3-expressing cell, comprising contacting a Foxp3-expressing cell with the bispecific antibody of any one of embodiments 80-83 or a composition comprising thereof.

130. Use of the bispecific antibody of any one of embodiments 80-83 or a composition comprising thereof to kill a Foxp3-expressing cell.

131. The bispecific antibody of any one of embodiments 80-83 or a composition comprising thereof for use in killing a Foxp3-expressing cell.

132. A method of killing a Foxp3-expressing cell, comprising contacting a Foxp3-expressing cell with the immunoconjugate of embodiment 77 or 78 or a composition comprising thereof.

133. Use of the immunoconjugate of embodiment 77 or 78 or a composition comprising thereof to kill a Foxp3-expressing cell.

134. The immunoconjugate of embodiment 77 or 78 or a composition comprising thereof for use in killing a Foxp3-expressing cell.

135. The method of any one of embodiments 123, 126, 129, and 132, wherein the Foxp3-expressing cell is a T cell is selected from the group consisting of $CD4^+$ T cells, $CD25^{high}$ T cells, $CD127^{low}$ T cells, Foxp3high T cells, and combinations thereof.

136. The use of any one of embodiments 124, 127, 130, and 133, wherein the Foxp3-expressing cell is a T cell selected from the group consisting of $CD4^+$ T cells, $CD25^{high}$ T cells, $CD127^{low}$ T cells, Foxp3high T cells, and combinations thereof.

137. The antibody of embodiment 125, wherein the Foxp3-expressing cell is a T cell is selected from the group consisting of $CD4^+$ T cells, $CD25^{high}$ T cells, $CD127^{low}$ T cells, Foxp3high T cells, and combinations thereof.

138. The bispecific antibody of embodiment 131, wherein the Foxp3-expressing cell is a T cell is selected from the group consisting of $CD4^+$ T cells, $CD25^{high}$ T cells, $CD127^{low}$ T cells, Foxp3high T cells, and combinations thereof.

139. The immunoconjugate of embodiment 134, wherein the Foxp3-expressing cell is a T cell is selected from the group consisting of $CD4^+$ T cells, $CD25^{high}$ T cells, $CD127^{low}$ T cells, Foxp3high T cells, and combinations thereof.

140. A method of inducing an immune response in a subject, comprising administering the antibody or antigen-binding portion thereof of any one of embodiments 1-75 or a composition comprising thereof to the subject.

141. Use of the antibody or antigen-binding portion thereof of any one of embodiments 1-75 or a composition comprising thereof to induce an immune response in a subject.

142. The antibody or antigen-binding portion thereof of any one of embodiments 1-75 or a composition comprising thereof for use in inducing an immune response.

143. A method of inducing an immune response in a subject, comprising administering the CAR of any one of embodiments 99-118 or a composition comprising thereof to the subject.

144. Use of the CAR of any one of embodiments 99-118 or a composition comprising thereof to induce an immune response in a subject.

145. The CAR of any one of embodiments 99-118 or a composition comprising thereof for use in inducing an immune response.

146. A method of inducing an immune response in a subject, comprising administering the bispecific antibody of any one of embodiments 80-83 or a composition comprising thereof to the subject.

147. Use of the bispecific antibody of any one of embodiments 80-83 or a composition comprising thereof to induce an immune response in a subject.

148. The bispecific antibody of any one of embodiments 80-83 or a composition comprising thereof for use in inducing an immune response.

149. A method of inducing an immune response in a subject, comprising administering the immunoconjugate of embodiment 77 or 78 or a composition comprising thereof to the subject.

150. Use of the immunoconjugate of embodiment 77 or 78 or a composition comprising thereof to induce an immune response in a subject.

151. The immunoconjugate of embodiment 77 or 78 or a composition comprising thereof for use in inducing an immune response.

152. A method of selectively inhibiting a T cell in a subject, comprising administering the antibody or antigen-binding portion thereof of any one of embodiments 1-75 or a composition comprising thereof to the subject, wherein the T cell is selected from the group consisting of $CD4^+$ T cells, $CD25^{high}$ T cells, $CD127^{low}$ T cells, Foxp3high T cells, and combinations thereof.

153. Use of the antibody or antigen-binding portion thereof of any one of embodiments 1-75 or a composition comprising thereof to selectively inhibit a T cell in a subject, wherein the T cell is selected from the group consisting of $CD4^+$ T cells, $CD25^{high}$ T cells, $CD127^{low}$ T cells, Foxp3high T cells, and combinations thereof.

154. The antibody or antigen-binding portion thereof of any one of embodiments 1-75 or a composition comprising thereof for use in selective inhibition of a T cell, wherein the T cell is selected from the group consisting of $CD4^+$ T cells, $CD25^{high}$ T cells, $CD127^{low}$ T cells, Foxp3high T cells, and combinations thereof.

155. A method of selectively inhibiting a T cell in a subject, comprising administering the CAR of any one of embodiments 99-118 or a composition comprising thereof to the subject, wherein the T cell is selected from the group consisting of $CD4^+$ T cells, $CD25^{high}$ T cells, $CD127^{low}$ T cells, Foxp3high T cells, and combinations thereof.

156. Use of the CAR of any one of embodiments 99-118 or a composition comprising thereof to selectively inhibit a T cell in a subject, wherein the T cell is selected from the group consisting of $CD4^+$ T cells, $CD25^{high}$ T cells, $CD127^{low}$ T cells, $Foxp3^{high}$ T cells, and combinations thereof.

157. The CAR of any one of embodiments 99-118 or a composition comprising thereof for use in selective inhibition of a T cell that is selected from the group consisting of $CD4^+$ T cells, $CD25^{high}$ T cells, $CD127^{low}$ T cells, $Foxp3^{high}$ T cells, and combinations thereof.

158. A method of selectively inhibiting a T cell in a subject, comprising administering the bispecific antibody of any one of embodiments 80-83 or a composition comprising thereof to the subject.

159. Use of the bispecific antibody of any one of embodiments 80-83 or a composition comprising thereof to selectively inhibit a T cell in a subject, wherein the T cell is selected from the group consisting of $CD4^+$ T cells, $CD25^{high}$ T cells, $CD127^{low}$ T cells, $Foxp3^{high}$ T cells, and combinations thereof.

160. The bispecific antibody of any one of embodiments 80-83 or a composition comprising thereof for use in selective inhibition of a T cell that is selected from the group consisting of $CD4^+$ T cells, $CD25^{high}$ T cells, $CD127^{low}$ T cells, $Foxp3^{high}$ T cells, and combinations thereof.

161. A method of selectively inhibiting a T cell in a subject, comprising administering the immunoconjugate of embodiment 77 or 78 or a composition comprising thereof to the subject, wherein the T cell is selected from the group consisting of $CD4^+$ T cells, $CD25^{high}$ T cells, $CD127^{low}$ T cells, $Foxp3^{high}$ T cells, and combinations thereof.

162. Use of the immunoconjugate of embodiment 77 or 78 or a composition comprising thereof to selectively inhibit a T cell in a subject, wherein the T cell is selected from the group consisting of $CD4^+$ T cells, $CD25^{high}$ T cells, $CD127^{low}$ T cells, $Foxp3^{high}$ T cells, and combinations thereof.

163. The immunoconjugate of embodiment 77 or 78 or a composition comprising thereof for use in selective inhibition of a T cell that is selected from the group consisting of $CD4^+$ T cells, $CD25^{high}$ T cells, $CD127^{low}$ T cells, $Foxp3^{high}$ T cells, and combinations thereof.

164. The method of any one of embodiments 152, 155, 158, and 161, wherein the subject suffers from cancer.

165. The use of any one of embodiments 153, 154, 159, and 162, wherein the subject suffers from cancer.

166. The antibody or antigen-binding portion there of embodiment 154, wherein the subject suffers from cancer.

167. The CAR of embodiment 157, wherein the subject suffers from cancer.

168. The bispecific antibody of embodiment 160, wherein the subject suffers from cancer.

169. The immunoconjugate of embodiment 163, wherein the subject suffers from cancer.

170. The method of any one of embodiments 152, 155, 158, and 161, comprising one or more of the followings:
(i) reducing number of a T cell,
(ii) depleting the T cell,
(iii) inhibiting immunosuppressive activity of the T cell, and
(iv) blocking the T cell trafficking into lymph nodes.

171. The method of any one of embodiments 152, 155, 158, 161 and 170, wherein the T cell is a regulatory T cell.

172. The use of any one of embodiments 153, 156, 159, and 162, comprising one or more of the followings:
(i) reducing number of the T cell,
(ii) depleting the T cell,
(iii) inhibiting immunosuppressive activity of the T cell, and
(iv) blocking the T cell trafficking into lymph nodes.

173. The use of any one of embodiments 153, 156, 159, 162, and 172, wherein the T cell is a regulatory T cell.

174. The antibody or antigen-binding portion there of embodiment 154, which
(i) reduces number of the T cell,
(ii) depletes the T cell,
(iii) inhibits immunosuppressive activity of the T cell, and/or
(iv) blocks regulatory T cells trafficking into lymph nodes.

175. The antibody or antigen-binding portion there of embodiment 154 or 173, wherein the T cell is a regulatory T cell.

176. The CAR of embodiment 157, which
(i) reduces number of the T cell,
(ii) depletes the T cell,
(iii) inhibiting immunosuppressive activity of the T cell, and/or
(iv) blocking the T cell trafficking into lymph nodes.

177. The CAR of embodiment 157 or 176. wherein the T cell is a regulatory T cell.

178. The bispecific antibody of embodiment 160, which
(i) reduces number of the T cell,
(ii) depletes the T cell,
(iii) inhibits immunosuppressive activity of the T cell, and/or
(iv) blocks the T cell trafficking into lymph nodes.

179. The bispecific antibody of embodiment 160 or 178, wherein the T cell is a regulatory T cell.

180. The immunoconjugate of embodiment 163, which
(i) reduces number of the T cell,
(ii) depletes the T cell,
(iii) inhibits immunosuppressive activity of the T cell, and/or
(iv) blocks the T cell trafficking into lymph nodes.

181. The immunoconjugate of embodiment 163 or 179, wherein the T cell is a regulatory T cell.

182. A method of treating cancer, comprising administering an effective amount of the antibody or antigen-binding portion thereof of any one of embodiments 1-75 or a composition comprising thereof to a subject suffering from cancer, thereby inducing death of a cancer cell in the subject.

183. A method of treating cancer, comprising administering an effective amount of the CAR of any one of embodiments 99-118 or a composition comprising thereof to a subject suffering from cancer, thereby inducing death of a cancer cell in the subject.

184. A method of treating cancer, comprising administering an effective amount of the bispecific antibody of any one of embodiments 80-83 or a composition comprising thereof to a subject suffering from cancer, thereby inducing death of a cancer cell in the subject.

185. A method of treating cancer, comprising administering an effective amount of the immunoconjugate of embodiment 77 or 78 or a composition comprising thereof to a subject suffering from cancer, thereby inducing death of a cancer cell in the subject.

186. A method of treating cancer, comprising administering an effective amount of the antibody or antigen-binding portion thereof of any one of embodiments 1-75, the CAR of any one of embodiments 99-118, the bispecific antibody of any one of embodiments 80-83, the immunoconjugate of embodiment 77 or 78, or a composition comprising thereof to a subject suffering from cancer, thereby inhibiting a T cell in the subject.

187. The method of embodiment 186, wherein the T cell that is inhibited is a T regulatory cell.

188. The method of embodiment 186 or 187, wherein the T cell that is inhibited is a $CD4^+$ T cells, $CD25^{high}$ T cells, $CD127^{low}$ T cells, $Foxp3^{high}$ T cell, or a T cell exhibiting two or more of said markers.

189. The method of any one of embodiments 182-189, wherein the cancer is selected from the group consisting of breast cancer, ovarian cancer, melanoma, lung cancer, pancreatic cancer, gastric cancer, colon cancer, glioblastoma, kidney cancer, liver cancer, lymphoma, leukemia, myeloma, sarcoma, and combinations thereof.

190. The method of any one of embodiments 182-189, wherein the subject is a human.

191. The method of any one of embodiments 182-190, wherein the subject receives an anticancer immunotherapy.

192. The method of any one of embodiments 182-191, wherein the cancer cell and/or the T cell expresses Foxp3.

193. Use of the antibody or antigen-binding portion thereof of any one of embodiments 1-75 or a composition comprising thereof for treating cancer.

194. Use of the CAR of any one of embodiments 99-118 or a composition comprising thereof for treating cancer.

195. Use of the bispecific antibody of any one of embodiments 80-83 or a composition comprising thereof for treating cancer.

196. Use of the immunoconjugate of embodiment 77 or 78 or a composition comprising thereof for treating cancer.

197. The use of any one of embodiments 193-195, wherein the cancer is selected from the group consisting of breast cancer, ovarian cancer, melanoma, lung cancer, pancreatic cancer, gastric cancer, colon cancer, glioblastoma, kidney cancer, liver cancer, lymphoma, leukemia, myeloma, sarcoma, and combinations thereof.

198. The use of any one of embodiments 193-197, wherein the subject is a human.

199. The use of any one of embodiments 193-198, wherein the subject receives an anticancer immunotherapy.

200. The use of any one of embodiments 193-199, wherein the cancer cell expresses Foxp3.

201. The antibody or antigen-binding portion thereof of any one of embodiments 1-75 or a composition comprising thereof for use in treating cancer in a subject.

202. The antibody or antigen-binding portion thereof of embodiment 188, wherein the cancer is selected from the group consisting of breast cancer, ovarian cancer, melanoma, lung cancer, pancreatic cancer, gastric cancer, colon cancer, glioblastoma, kidney cancer, liver cancer, lymphoma, leukemia, myeloma, sarcoma, and combinations thereof.

203. The antibody or antigen-binding portion thereof of embodiment 201 or 202, wherein the subject is a human.

204. The antibody or antigen-binding portion thereof of any one of embodiments 201-203, wherein the subject receives an anticancer immunotherapy.

205. The antibody or antigen-binding portion thereof of any one of embodiments 198-201, wherein the cancer cell expresses Foxp3.

206. The CAR of any one of embodiments 99-118 or a composition comprising thereof for use in treating cancer in a subject.

207. The CAR of embodiment 206, wherein the cancer is selected from the group consisting of breast cancer, ovarian cancer, melanoma, lung cancer, pancreatic cancer, gastric cancer, colon cancer, glioblastoma, kidney cancer, liver cancer, lymphoma, leukemia, myeloma, sarcoma, and combinations thereof.

208. The CAR of embodiment 206 or 207, wherein the subject is a human.

209. The CAR of any one of embodiments 206-208, wherein the subject receives an anticancer immunotherapy.

210. The CAR of any one of embodiments 206-209, wherein the cancer cell expresses Foxp3.

211. The bispecific antibody of any one of embodiments 80-83 or a composition comprising thereof for use in treating cancer in a subject.

212. The bispecific antibody of embodiment 211, wherein the cancer is selected from the group consisting of breast cancer, ovarian cancer, melanoma, lung cancer, pancreatic cancer, gastric cancer, colon cancer, glioblastoma, kidney cancer, liver cancer, lymphoma, leukemia, myeloma, sarcoma, and combinations thereof.

213. The bispecific antibody of embodiment 211 or 212, wherein the subject is a human.

214. The bispecific antibody of any one of embodiments 211-213, wherein the subject receives an anticancer immunotherapy.

215. The bispecific antibody of any one of embodiments 211-214, wherein the cancer cell expresses Foxp3.

216. The immunoconjugate of embodiment 77 or 78 or a composition comprising thereof for use in treating cancer in a subject.

217. The immunoconjugate of embodiment 216, wherein the cancer is selected from the group consisting of breast cancer, ovarian cancer, melanoma, lung cancer, pancreatic cancer, gastric cancer, colon cancer, glioblastoma, kidney cancer, liver cancer, lymphoma, leukemia, myeloma, sarcoma, and combinations thereof.

218. The immunoconjugate of embodiment 216 or 217, wherein the subject is a human.

219. The immunoconjugate of any one of embodiments 216-218, wherein the subject receives an anticancer immunotherapy.

220. The immunoconjugate of any one of embodiments 216-219, wherein the cancer cell expresses Foxp3.

221. A kit for treating cancer, comprising the antibody or antigen-binding portion thereof of any one of embodiments 1-75.

222. A kit for treating cancer, comprising the CAR of any one of embodiments 99-118.

223. A kit for treating cancer, comprising the bispecific antibody of any one of embodiments 80-83.

224. A kit for treating cancer, comprising the immunoconjugate of embodiment 77 or 78.

225. The kit of any one of embodiments 221-224, wherein the cancer is selected from the group consisting of breast cancer, ovarian cancer, melanoma, lung cancer, pancreatic cancer, gastric cancer, colon cancer, glioblastoma, kidney cancer, liver cancer, lymphoma, leukemia, myeloma, sarcoma, and combinations thereof.

EXAMPLES

The following examples are put forth so as to provide those of ordinary skill in the art with a complete disclosure and description of how to make and use the antibodies, bispecific antibodies, compositions comprising thereof, screening, and therapeutic methods of the presently disclosed subject matter, and are not intended to limit the scope of what the inventors regard as their presently disclosed subject matter. It is understood that various other embodiments may be practiced, given the general description provided above.

Example 1—TCR-Mimic Monoclonal Antibodies Specific for Fox3p-Derived Epitopes Introduction Effector T cell checkpoint blockade therapy has emerged as an effective therapy for several cancers by activating dormant or exhausted T cells to kill cancer cells in patients. Regulatory T cells (Tregs) expressing CD4, CD25 and Foxp3 are found abundantly in tumor tissues and are considered powerful inhibitors of anti-tumor immunity and a critical barrier to successful immunotherapy. Decreased ratios of $CD8^+$ T cells to Tregs in tumor-infiltrating lymphocytes (TILs) is an indicator of poor prognosis in various human cancers. Depletion of Tregs has been shown to enhance spontaneous and vaccine-induced anti-tumor immune responses in animal models and in cancer patients in some cases. These studies demonstrate a prominent tumor-promoting role of Tregs in cancer and provide an opportunity for cancer immunotherapy in which modulation of Treg function could activate effector T cells to kill cancer cells.

Although depletion of Tregs in patients with cancer has received intense interest, effective applications have been hampered because Tregs do not express a specific cell surface molecule which can be targeted by a mAb nor a selectively druggable intracytoplasmic pathway. Various strategies have been attempted for depletion or interference with Treg function, which typically have focused on targeting CD25 (the IL-2 receptor) using mAbs specific for CD25 (Daclizumab) and Dennileukin difitox, a fusion protein of IL-2 and diphtheria toxin. In addition, elimination of Tregs by a mAb to glucorticoid-induced TNF-related protein (GITR) and suppression of Treg function by use of anti-CTLA4 antibodies, disruption of tumor homing by T-regs, or modulation of T cell plasticity, have also been attempted. Clinical studies with various cancers, in which Daclizumab and Dennileukin difitox were combined with vaccines, have demonstrated conflicting results. These data could be best explained because CD25 and GITR are both expressed not only in Tregs, but also in activated CD4 and CD8 effector T cells. A potential benefit of Treg depletion by targeting these molecules could be lost by concurrently elimination of activated effector lymphocytes. Therefore, there is no additional clinical evidence supports the broader applicability of these approaches. A recent in vitro study showed that a mAb specific for C—C chemokine receptor-4 (CCR4) could selectively deplete effector Tregs expressing a higher level of Foxp3 resulting in augmentation of CD8 T cell response specific for the NY-ESO-1 peptide. A defucosylated, humanized anti-CCR4 mAb, Mogamulizumab, has been in clinical trials for various cancers. While the results await more studies, there are some data that showed complex results[8-10]. In addition to Tregs, CCR4 is known to be expressed on activated T cells, T helper 2, NK cells, macrophages and dendritic cells and the effects of the mAb could be complicated. Cyclophosamide has been shown to selectively suppress Tregs but the mechanisms are unknown. Cyclophosamide is well-known for its cytotoxicity to tumor cells and therefore, the clinical effects are difficult to attribute to only Treg depletion. Clearly, there is a great need for more specific approaches targeting Tregs and eliminating their suppressive function.

Foxp3 has been identified as a key player in Treg function, and is the most definitive marker of $CD4^+CD25^+$ Tregs. It is required for Treg cell lineage differentiation, maintenance and importantly suppressive function. Apart from naturally occurring Tregs that arise in the thymus, inducible Treg cells have been identified, with predominance in infection and cancer. Interestingly, in addition to the critical role of Foxp3 in Tregs, many cancer cells also express Foxp3. Foxp3-expressing pancreatic carcinoma cells and cutaneous T cell lymphoma cells have been shown to suppress T cell proliferation. These studies suggest that cancer cells may share suppressive effects with Tregs, and that mimicking Treg function may represent a new mechanism of immune evasion in cancer.

As such, there are no selective drugs that can deplete Tregs. Foxp3 would be an ideal target except that it is no druggable by small molecules and it is an intracellular protein so antibody therapy is not feasible. Theoretically, peptides from Foxp3 protein that are degraded and processed for cell surface presentation can serve as a target of a TCR recognition. In a melanoma mouse model, Nair et al vaccinated mice with dendritic cells (DCs) electroporated with Foxp3-encoding mRNA. The vaccination elicited Foxp3-specific CTL response leading to preferential depletion of $Foxp3^+$ Tregs in tumors. Simultaneously vaccinate mice with well-defined TRP2 melanoma antigen (Ag) and Foxp3 enhanced the vaccine-induced protection against highly metastatic B6/F10.9 melanoma. Although no Foxp3-derived epitopes were identified in this study, it demonstrated the possibility of using T cell approach to target Foxp3 protein. Encouragingly, a recent in vitro human study has shown the results of identifying Foxp3-derived epitopes by human CD8 T cells in the context of HLA-A0201 molecule. Thus, a TCR-mimic mAb specific for Foxp3-derived epitopes should be able to specifically and directly deplete both Tregs and tumor cells expressing Foxp3 with double sword effects. Using a TCRm mAb, it was demonstrated that a TCRm mAb specific for human Foxp3, #32, can specifically binds and kill Foxp3-expressing Tregs and tumor cells. The depletion of Tregs should greatly unleash anti-tumor immunity by removing immunosuppression caused by both Tregs and tumor cells.

Methods and Materials

1. Peptide Synthesis

All peptides were purchased and synthesized by Genemed Synthesis, Inc. (San Antonio, Tex.). Peptides were sterile and 80% to >90% pure. The peptides were dissolved in DMSO and diluted in saline at 5 mg/mL and stored at −80° C. Control peptides used for HLA-A*02:01: Ewing sarcoma-derived peptide EW (QLQNPSYDK [SEQ ID NO:140]). Biotinylated single chain Foxp3p/HLA-A0201 complexes were synthesized by refolding the peptides with recombinant HLA-A*02 and beta2 microglobulin (β2M) at Eureka Therapeutics Inc. (Berkely, Calif.).

2. Cytokines, Antibodies and Cell Lines

Human granulocyte-macrophage colony-stimulating factor (GM-CSF), interleukin (IL)-1β, IL-4, IL-6, IL-15, tumor necrosis factor (TNF)-α and prostaglandin E2 (PGE2) were purchased from R&D Systems (Minneapolis, Minn.). Beta 2-microglobulin (β2-m) and human IFN-γ were purchased from Sigma (St. Louis, Mo.). Cell isolation kits for CD14 and CD3 were purchased from Miltenyi Biotec. (Bergisch Gladbach, Germany). Human IL-2 and TGF-β were purchased from R&D Systems. Human Treg isolation kit was purchased from Stem cell Technology (Canada). $Foxp-3^+$ and $HLA-A*0201^+$ cutaneous T lymphoma cell lines MAC-1 and MAC-2A were kindly provided by Dr. Mad H. Anderson, at University of Denmark. TAP-deficient T2 cells, T leukemia cell line JURKAT, and tumor cells were HLA typed by the Laboratory of Cellular Immunology at Memorial Sloan-Kettering Cancer Center. The cell lines were cultured in RPMI 1640 supplemented with 5% to 10% FCS, penicillin, streptomycin, 2 mmol/1 glutamine, and 2-mercaptoethanol at 37 C/5% CO2. Cells were checked regularly for mycoplasma. Cell identities were confirmed by phenotype or genotype.

Foxp3-#32 Fc-enhanced human IgG1, mouse IgG1, or BITE formats and their respect controls were produced by Eureka Therapeutics Inc. APC conjugation to mouse IgG1 form of #32 and its control was done by using lightening-link APC antibody labeling kit according to the instructions of the manufacturer (Novus Biologicals). Mabs against human HLA A*02 (clone BB7.2), its isotype control mouse IgG2b (clone MPC-11), human CD3 (clone HIT3A and OKT3), CD4 (clone RPA-T4), CD8 (clone RPA-T8). CD19 (clone HIB19), CD25 (clone 2A3), CD33 (clone WM53), CD45RA (clone HI100), mouse anti-His tag mAb (clone F24-796) conjugated to FITC or PE, were purchased from BD Biosciences, (San Diego, Calif.). Mabs specific for human Foxp3 clone PCH101, its isotype control rat IgG2a kappa, clone 236A/E7 and its isotype control mouse IgG1 kappa, CD4 (clone OKT4), CD14 (clone 61D3), CD127 (clone HIL-7R-M21), were purchased from eBioscience. Fixation and permeabilization kit for intracellular staining was also purchased from eBioscience. Luciferase substrate luciferine was purchased from Promega (Madison, Mich.).

3. In Vitro Stimulation and Human T-Cell Cultures

While many sequences can be predicted by the algorithms, these models do not predict binding to MHC when tested on live cells in 30% of cases, so in vitro testing is necessary. In addition, even if binding is demonstrated, a cytotoxic T cell response may not occur, requiring additional in vitro study.

After informed consent on Memorial Sloan-Kettering Cancer Center Institutional Review Board approved protocols, peripheral blood mononuclear cells (PBMC) from HLA-A*24:02 healthy donors were obtained by Ficoll density centrifugation. $CD14^+$ monocytes were isolated by positive selection using mAb to human CD14 coupled with magnetic beads and were used for the first stimulation of T cells. The $CD14^-$ fraction of PBMC was used for isolation of CD3, by negative immunomagnetic cell separation using a pan T cell isolation kit. The purity of the cells was always more than 98%. T cells were stimulated for 7 days in the presence of RPMI 1640 supplemented with 5% autologous plasma (AP), 20 ug/mL synthetic peptides, 2 ug/mL (32-m, and 5-10 ng/mL IL-15. Monocyte-derived dendritic cells (DCs) were generated from $CD14^+$ cells, by culturing the cells in RPMI 1640 medium supplemented with 1% AP, 500 units/mL recombinant IL-4, and 1,000 units/mL GM-CSF. On days 2 and 4 of incubation, fresh medium with IL-4 and GM-CSF was either added or replaced half of the culture medium. On day 5, 20 ug/mL class II peptide was added to the immature DCs. On day 6, maturation cytokine cocktail was added (IL-4, GM-CSF, 500 IU/mL IL-1, 1,000 IU/mL IL-6, 10 ng/ml TNF-α, and 1 ug/mL PGE-2). On day 7 or 8, T cells were re-stimulated with mature DCs at a 30:1, T:APC ratio, with IL-15. T cells were stimulated 3 to 5 times in the same manner, using either autologous DCs or $CD14^+$ cells as antigen-presenting cells (APCs). A week after final stimulation, the peptide-specific T cell response was examined by IFN-γ enzyme-linked immunospot (ELISPOT) assay.

4. IFN-γ ELISPOT Assay Measuring Peptide-Specific T Cell Response

HA-Multiscreen plates (Millipore) were coated with 100 uL of mouse anti-human IFN-γ antibody (10 μg/mL; clone 1-D1K; Mabtech) in PBS, incubated overnight at 4° C., washed with PBS to remove unbound antibody, and blocked with RPMI 1640/10% autologous plasma (AP) for 2 h at 37° C. $CD3^+$ T cells were plated with either autologous $CD14^+$ (10:1 E: APC ratio) or autologous DCs (30:1 E: APC ratio). Various test peptides were added to the wells at 20 μg/mL. Negative control wells contained APCs and T cells without peptides or with irrelevant peptides. Positive control wells contained T cells plus APCs plus 20 ug/ml phytohemagglutinin (PHA, Sigma). All conditions were done in triplicates. Microtiter plates were incubated for 20 h at 37° C. and then extensively washed with PBS/0.05% Tween® (polyoxyethylenesorbitan monolaurate) and 100 μl/well biotinylated detection antibody against human IFN-γ (2 μg/mL; clone 7-B6-1; Mabtech) was added. Plates were incubated for an additional 2 h at 37° C. and spot development was done as described (12, 13). Spot numbers were automatically determined with the use of a computer-assisted video image analyzer with KS ELISPOT 4.0 software (Carl Zeiss Vision).

5. $^{51}$Chromium Release Assay.

The presence of specific CTLs was measured in a standard chromium release assay as described (12, 13). Briefly, target cells alone, or pulsed with 50 μg/mL of synthetic peptides for 2 hours (in some cases for over night) at 37° C., are labeled with 50 uCi/million cells of $Na_2{}^{51}CrO_4$ (NEN Life Science Products, Inc.). After extensive washing, target cells are incubated with T cells at various E: T ratios. All conditions were done in triplicates. Plates were incubated for 4-5 hrs at 37° C. in 5% CO2. Supernatant fluids were harvested and radioactivity was measured in a gamma counter. Percentage specific lysis was determined from the following formula: [(experimental release−spontaneous release)/(maximum release−spontaneous release)]×100%. Maximum release was determined by lysis of radiolabeled targets in 1% SDS[12,13].

6. Treg Generation.

$CD4^+$ T cells or $CD4^+CD25^+$ T cells were purified from PBMCs by FACS sorting, and were stimulated with allo-PBMCs as stimulator/feeder cells at ratios of effector: stimulator (E:S) 10-20:1, in the presence of recombinant human IL-1 (100 unit) and TGF-β (long/ml) for a week and the same stimulation was repeated in a weekly basis to maintain the Treg cells. The phenotype of Treg was determined by surface staining of the cells with mAbs to CD4, $CD25^+$ and intracellular staining with foxp3. In certain embodiments, the mAb #32 (EXT017-32) was conjugated to APC and the specific recognition of the Treg cells was determined by binding of the mAb to the $CD4^+CD25^+$ $Foxp3^+$ cell population.

7. Phage Screening, Selection and Characterization of scFv Specific for Foxp3 Derived Epitopes A human ScFv antibody phage display library (7×1010 clones) was used for the selection of mAb clones as described previously[18]. In brief, biotinylated irrelevant peptide/HLA-A0201 complexes were used to remove any clones that potentially bind to HLA-A0201. Remaining clones were screened for the Foxp3p/HLA-A0201 complex. The selected clones were enriched by 3-4 rounds of panning processes. Positive clones were determined by standard ELISA method against biotinylated single chain Foxp3/HLA-A*0201 complexes.

The positive scFv clones were further tested for their binding to HLA-A2/peptide complexes on live cell surfaces by indirect flow cytometry on: (i) a TAP deficient HLA-A*02:01$^+$ cell line, T2, that are defective in presentation of endogenous HLA-associated peptides. T2 cells were pulsed with Foxp3 peptides or irrelevant peptide; (ii) $Foxp3^+$ HLA-A*02:01$^+$ cell lines such as MAC-1, MAC-2A and control cell lines Jurkat (HLA-A02$^-$), without pulsing with the peptide. The latter determine the recognition and binding affinity of the scFv to the naturally processed Foxp3-7p/A2 complex on tumor cells.

A total of 21 phage clones for Foxp3-7, 8 phage clones for Foxp3-2 and 3 phage clones for Foxp3-4 were screened for their ability to produce mAb specific for their respective Foxp3 peptide/A2 complex. The recognition of the Foxp3/A2 complex on live cells was measured by the binding of the phage scFv to T2 cells pulsed with the Foxp3 peptides and the other HLA-A2-binding peptides (50 ug/ml) in the serum-free RPMI1640 medium, in the presence of 20 ug/ml 132M overnight. These include: T2 cells alone; T2 cells pulsed with Foxp3-7, -2 or -3 peptides; T2 cells pulsed with HLA-A2-binding irrelevant EW or RHAMM 3(R3) peptide. The cells in the above groups were washed, then stained with 3 steps:

Step 1: Phage staining: T2 cell suspensions (10 μl) were incubated with puried scFv phage clones, 90 μl, on ice, 60 minutes, followed by a wash.

Step 2: Mouse mAb against M13 coat protein (1 mg/ml) at 1:100 dilution, on ice, 30 minutes, then washed.

Step 3: Goat (Fab)2 anti-mouse Ig conjugated to FITC or PE (1:100 dilution), on ice, 30 minutes, then wash.

The cells were washed twice between each step of the staining. Controls for flow cytometry included: Unstained cells and cells stained with only goat anti-mouse Ig (Fab)/FITC or PE.

8. Construction, Expression and Purification of Foxp3-BITE

Foxp3-#32 BITE was engineered as previously described[19]. N-terminal end of mAb #32 scFv was linked to the C-terminal end of an anti-human CD3E scFv of a mouse monoclonal antibody by a flexible linker. The DNA fragments encoding for the scFv of two mAbs were synthesized by GeneArt (InVitrogen) and subcloned into Eureka's mammalian expression vector pGSN-Hyg using standard DNA technology. A hexahistamine (His) tag (SEQ ID NO: 143) was inserted downstream of the #32 BITE at the C-terminal end for the detection and purification of the BITE.

Chinese hamster ovary (CHO) cells were transfected with the Foxp3-BITE expression vector and stable expression was achieved by standard drug selection with methionine sulfoximine (MSX), a glutamine synthetase (GS)-based method. CHO cell supernatants containing secreted Foxp3-BITE molecules were collected. Foxp3-#32BITE was purified using HisTrap HP column (GE healthcare) by FPLC AKTA system. Briefly, CHO cell culture was clarified and loaded onto the column with low imidazole concentration (20 mM), and then an isocratic high imidazole concentration elution buffer (500 mM) was used to elute the bound Foxp3-BITE protein. A negative control BITE antibody, was constructed from an irrelevant human IgG1 antibody (Cat #ET901, Eureka Therapeutics,) replacing Fox3-#32 scFv.

9. Treg Generation, Phenotypic Analysis and Foxp3-#32 mAb Binding $CD4^+$ T cells were purified from PBMCs of healthy HLA-A*0201 positive donors by FACS sorting, and were stimulated with allo-PBMCs (HLA-A*0201 negative) as stimulator/feeder cells at ratios of effector: stimulator (E:S) 1:5-10, or with tumor cells in the presence of recombinant human IL-2 (100 unit) and TGF-β (10 ng/ml) for one to two weeks and the same stimulation was repeated to maintain the Treg cells[15-17]. The phenotype of Tregs was determined by surface staining of the cells with mAbs to CD4, $CD25^+$, CD127, Foxp3 mAb #32 conjugated to APC, for 30 minutes on ice, washed. Foxp3 expression was measured by intracellular protein staining using mAb to human Foxp3 and Cytofix/CytoPerm kit (eBiosciences), according to the instructions of the manufacture. Analysis was done by flow cytometry on a Beckman Dickinson Fortesa.

10. SvFv Bi-Specific Antibody (BsAb) Constructs Mediated T Cell Cytotoxicity Against and Treg Cells in the Context of HLA-A*0201

Two methods were used to measure the killing of Tregs by Foxp3 #32 BITE. Since natural Tregs only represent a few percentage of $CD4^+$ T cells, and therefore, in order to obtain sufficient readout on Treg killing, in vitro-generated Tregs were used as targets and the killing of Tregs was determined by reduction of Treg population by flow cytometry. In brief, purified CD3 T cells by negative selection from HLA-A*02:01 negative donor (effectors) were incubated with Treg cells from HLA-A*02:$01^+$ donor at an E: T ratio 5:1, in the presence or absence of specific BsAb (also referred to as "BITE") construct (1 ug/ml) (e.g., BsAb-#32) or its control BsAb overnight. The cells were washed and stained with mAbs to CD4, CD25, foxp3 and HLA-A02. HLA-$A2^+$ cells were gated (Tregs as target) and the killing of Tregs was determined by the reduction of percentage of $CD4^+CD25^+$ $Foxp3^+$ cells in the HLA-A*$0201^+$ cells, compared to control cultures with effectors alone or with effectors plus control BITE. In addition, Treg-like T lymphoma cell lines MAC-1 and MAC-2A ($Foxp3^+$/HLAA*$0201^+$) were used as targets in ADCC assay by a standard $^{51}$Cr-release assay.

11. Antibody-Dependent Cellular Cytotoxicity (ADCC)

Target cells used for ADCC were T2 cells pulsed with or without Foxp3-TLI peptide or EW control peptide, and $Foxp3^+$ MAC-1 and MAC2A cell lines without peptide pulsing (see list in above "Cytokines, antibodies and cell lines" section). The Foxp3 #32 Fc-enhanced IgG1 or its isotype control, at various concentrations were incubated with target cells and fresh PBMCs at different effector: target (E:T) ratio for 4-5 hrs. Cytotoxicity was measured by standard $^{51}$Cr-release assay.

Results

The present study targets Foxp3 positive cells selectively by use of a T cell receptor mimic (TCRm) mAb, named mAb #32, which recognizes a human Foxp3-derived CD8 T cell epitope, presented by HLA-A*0201 molecules on the cell surface. The results show that mAb #32 specifically bound to $CD4^+CD25^{high}CD127^{l}$'$Foxp3^+$ Treg cells from HLA-A*0201 positive donors, and tumor cell lines co-expressing Foxp3 and HLA-A*0201. Both afucosylated Fc enhanced human IgG1 and bispecific T cell engager formats of the Foxp3 mAb are able to kill in vitro generated Treg clones from HLA-$A0201^+$ donos and "Treg-like" cutaneous lymphoma cells (HLA-A*02:$01^+$) that have a high level expression of CD4, CD25 and $Fox3^+$. This TCRm mAb may allow another approach to immunotherapy of human cancers or for other settings in which selective immune-stimulation is warranted. In addition, Fox3-targeting antibodies could be a novel approach in cancer immunotherapy by overcoming immunosuppresion caused by T-regs and tumor cells expressing Foxp3.

1. Selection of Foxp3-Derived Epitopes in the Context of HLA-A*0201

Unlike other well-defined epitopes derived from tumor antigens such as WT1, there has been little information on the epitopes derived from Foxp-3 that induces T cell responses. Therefore, the immunogenic epitopes that can generate cytotoxic CD8 T cells against Foxp3 were first identified. The entire human Foxp3 protein sequence was screened using three computer-based predictive algorithms BIMAS (bimas.cit.nih.gov), SYFPEITHI (syfpeithi.de) and RANKPEP (bio.dfci.harvard.edu). The potential epitopes derived from human Foxp3 for CD8 T cells in the context of HLA-A*02:01 molecule (Foxp3-1 having an amino acid sequence set forth in SEQ ID NO:2, Foxp3-2 having an amino acid sequence set forth in SEQ ID NO:3, Foxp3-3 having an amino acid sequence set forth in SEQ ID NO:4, Foxp3-4 having an amino acid sequence set forth in SEQ ID NO:5, Foxp3-5 having an amino acid sequence set forth in SEQ ID NO:6, Foxp3-6 having an amino acid sequence set forth in SEQ ID NO:7, and Foxp3-7 having an amino acid sequence set forth in SEQ ID NO: 8) were selected to test if these peptides are able to induce specific CD8 T cell response from HLA-A*02:$01^+$ donors. Importantly, all the selected HLA-A*0201-binding peptides were predicted to be cleaved at C-terminal, suggesting a higher probability of being processed by proteosomes.

2. Peptide-Specific T Cell Response in the Context of HLA-A*02:01 Molecule

While many sequences can be predicted by the algorithms, these models do not predict binding to MHC when tested on live cells in some cases, so in vitro testing is necessary. In addition, even if binding is demonstrated, a cytotoxic T cell response may not occur, requiring additional in vitro study. A number of Foxp-3-derived peptides were selected to test if they were able to stimulate CD8 T cell response from HLA-HLA-A*$0201^+$ donors. After testing T cell responses from multiple donors with multiple peptides derived from human Foxp3, Foxp3-7 (amino acid sequence set forth in SEQ ID NO: 8) was selected for further study. Interestingly, this peptide has also been shown to induce strong peptide-specific CD8 T cellresponse which recognizes $Foxp3^+$/HLA-A*0201$^+$ cutaneous T lymphoma cells [14].

CD3 T cells from multiple donors were stimulated with Foxp3-derived peptides for 3-5 rounds and the peptide-specific T cell response was measured by IFN-γ elispot assay and $^{51}$Cr-release assays. All the peptides, except for Foxp3-3 peptide, induced peptide-specific T cell response in multiple HAL-A*02:01$^+$ donors.

Figure 2A:
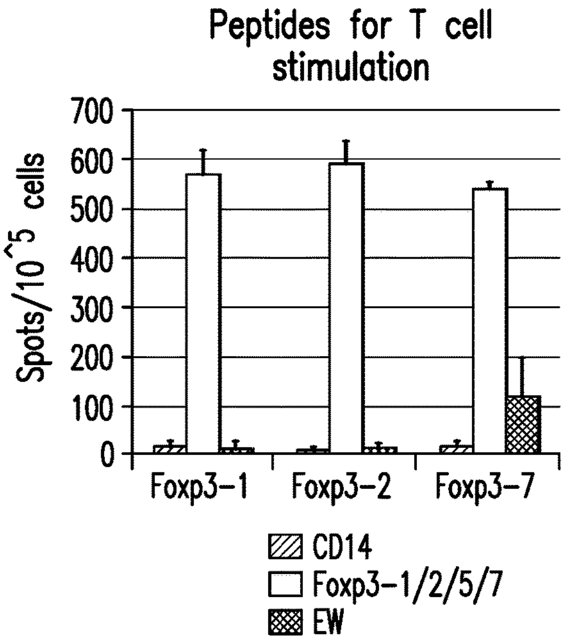
FIGS. 2A-2D represent peptide-specific T-cell response of Foxp3 peptides. (A and B) CD3 T cells from a third HLA-A*02:01$^+$ donor were stimulated with indicated Foxp3 peptides for 5 rounds and tested against the stimulating peptides. In a different experiment, T cells stimulated with Foxp3-4, 6 or -7 peptide were tested against the stimulating peptide pulsed onto autologous CD14$^+$ APCs (C), Un-pulsed Foxp3$^+$ HLA-A2$^+$ cell lines MAC-1, MAC2A, Foxp3$^+$ HLA-A2-cell line Jurkat or CD4$^+$CD25$^+$/HLA-A2$^+$ Treg cells generated in vitro were used as target cells (D).
Figure 2C:
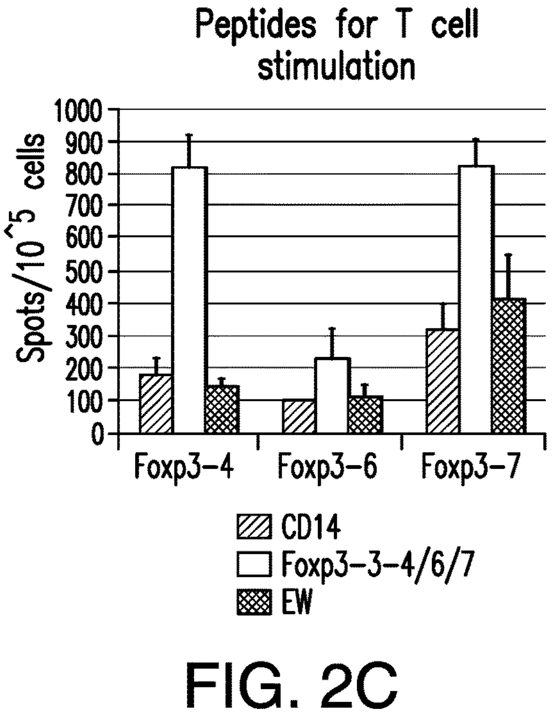
Figure 2B:
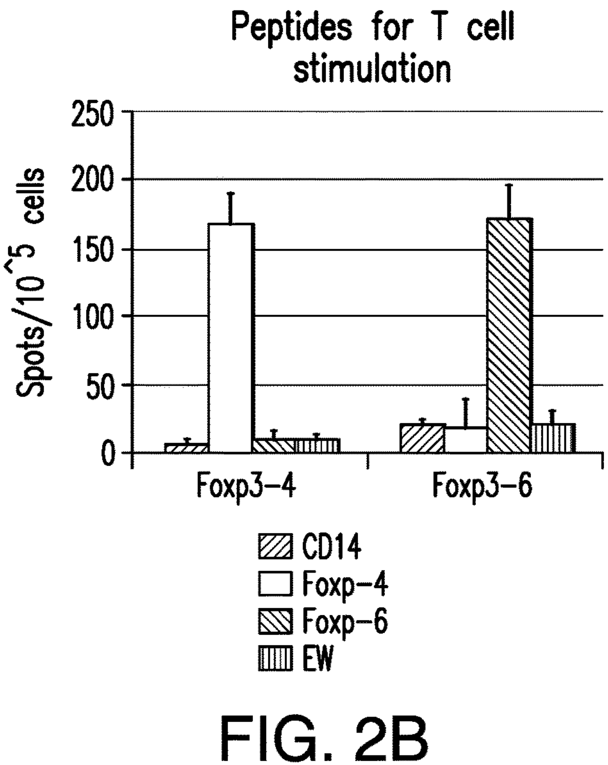
Figure 2D:
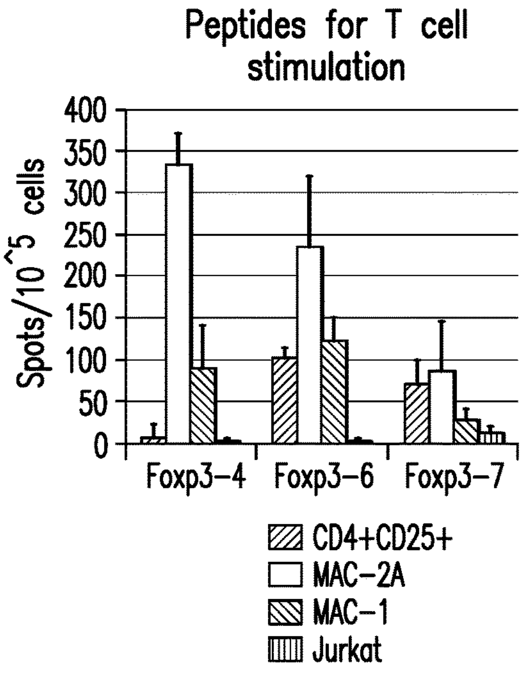

T cells stimulated with Foxp3-1 to 6 peptides elicited peptide-specific response against only the stimulating peptides, but not other peptides, nor the controls including $CD14^+$ antigen-presenting cells (APCs) or APCs pulsed with irrelevant peptide EW without Peptides (FIGS. 1A-1D and FIG. 2A). Peptide-specific T cell response was reproducible in multiple HLA-$A2^+$ donors (FIGS. 2A-2C) and no cross-reactivity among the peptides were ever detected, as another example shown in FIG. 2B.

Figure 3:
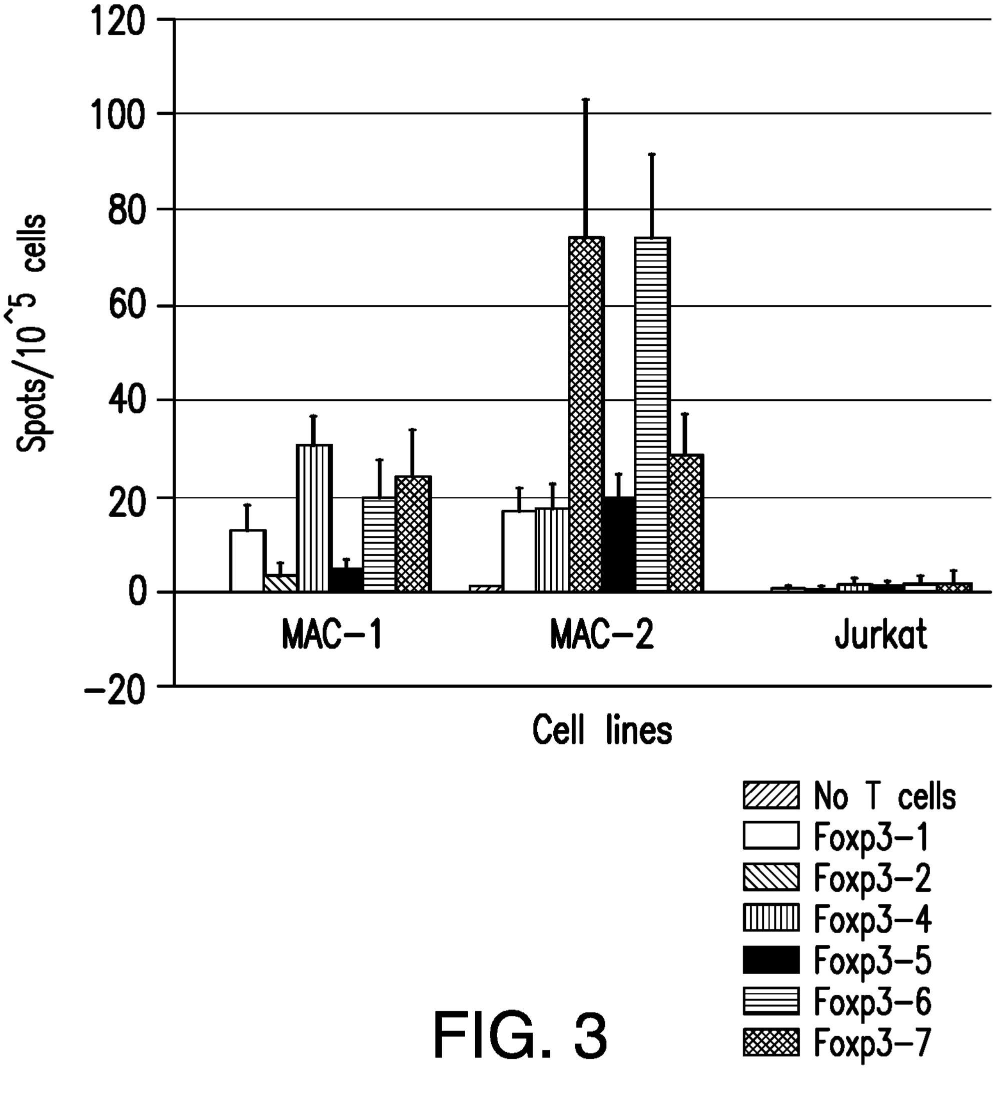
FIG. 3 represents epitope-specific T cell response of Foxp3 peptides. CD3 T cells from a HLA-A*02:01$^+$ donor were stimulated with the Foxp3-peptides 1, 2, 4, 5, 6 or 7 for 4 rounds and the recognition of Foxp3 is tested against Foxp3$^+$/HLA-A2$^+$ cell lines MAC-1, MAC-2A or Foxp3$^+$/HLA-A2-cell line Jurkat, by IFN-γ ELISPOT assay.
Figure 4A:
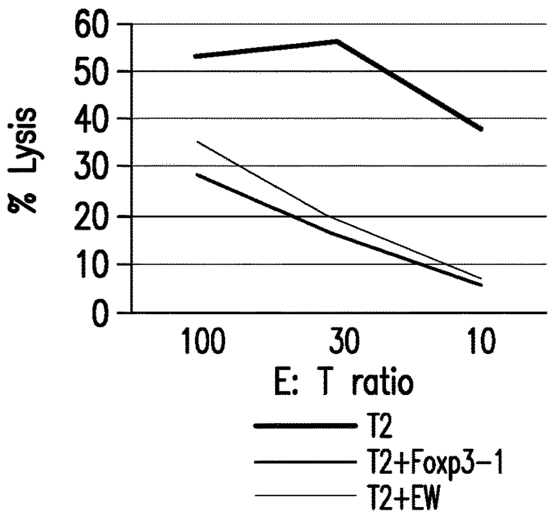
FIGS. 4A-4F represent peptide-specific T cell cytotoxicity of Foxp3 peptides. CD3 T cells from a HLA-A*02:01$^+$ donor were stimulated with Foxp3-derived peptides Foxp3-1, -2, -4, (A, C, and E)-5, -6 or -7 (B, D and F) for 5 rounds and the cytotoxicity against the stimulating peptides on T2 cells was measured by $^{51}$Cr-release assay. T2 cells alone or pulsed with EW were used as negative controls. Each data point represents average+/−SD from triplicate cultures.
Figure 4B:
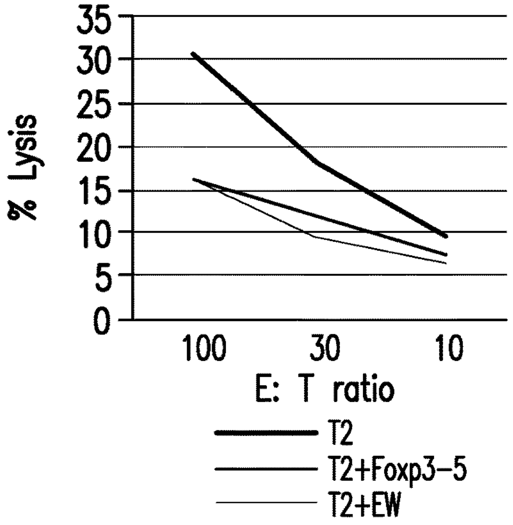
Figure 4C:
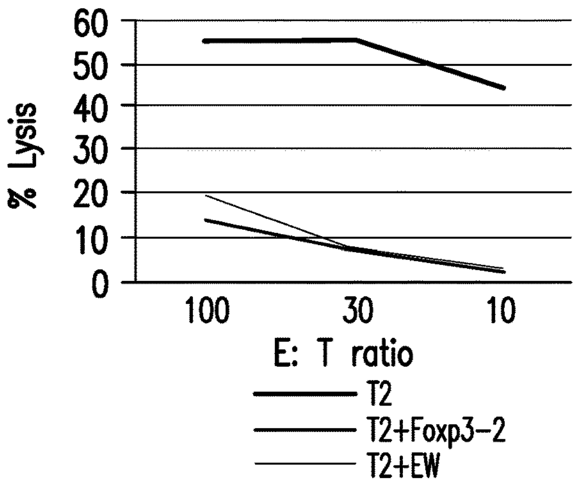
Figure 4D:
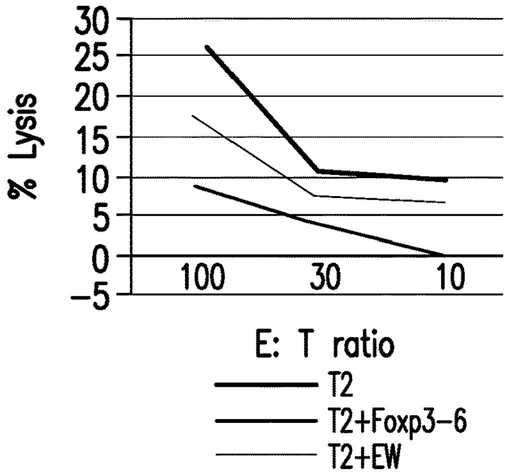
Figure 4E:
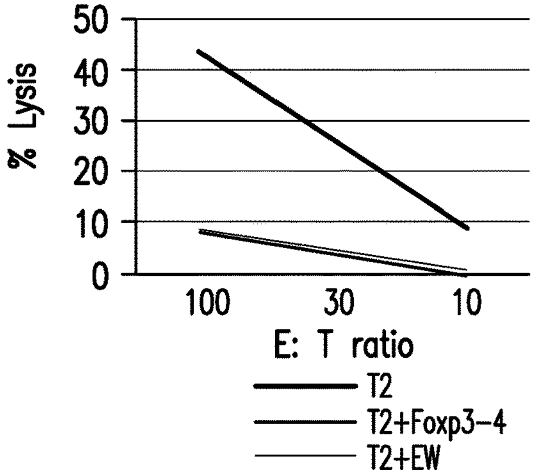
Figure 4F:
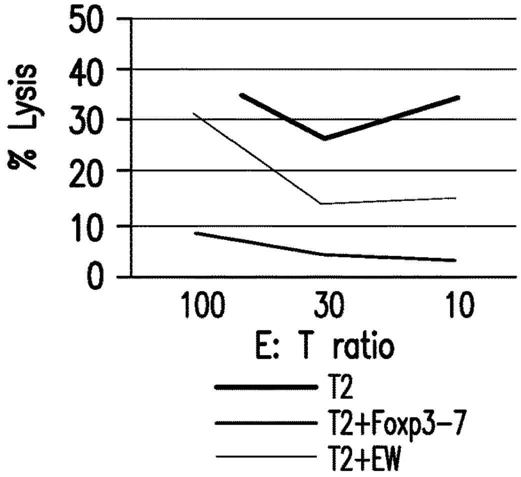

To test if the peptide-induced T cells can recognize naturally processed Foxp3 epitopes, T cell lymphoma cell lines MAC-1 and MAC2A that are Foxp3 and HLA-A*02:01$^+$ (FIG. 3) (14) and $Foxp3^+$ HLA-A*02:01$^-$ cell line Jurkat (FIG. 7C) were used as targets. T cells stimulated with Foxp3-4, -6 or -7 peptides were able to recognize MAC-1 and MAC-2A cell lines but not Jurkat. T cells stimulated with Foxp3-6 and -7 peptides also recognized the $Foxp3^+$ $CD4^+CD25$ Treg cells, generated from a HLA-A*02:01$^+$ donor, by stimulating the purified $CD4^+$ cells with anti-CD3 mAb, IL-2 and TGF-β.

Peptide-specific T cell cytotoxicity of Foxp3-derived peptides Foxp3-1, -2, -4, -5, -6 and -7 was also studied. CD3 T cells from a HLA-A*02:01$^+$ donor were stimulated with Foxp3-derived peptides Foxp3-1, -2, -4, -5, -6 or -7 and the cytotoxicity against the stimulating peptides on T2 cells was measured by $^{51}$Cr-release assay. As shown in FIGS. 4A-4F and FIGS. 5C and 5D, all tested Foxp3-derived peptides showed peptide-specific T cell cytotoxicity.

Figure 5A:
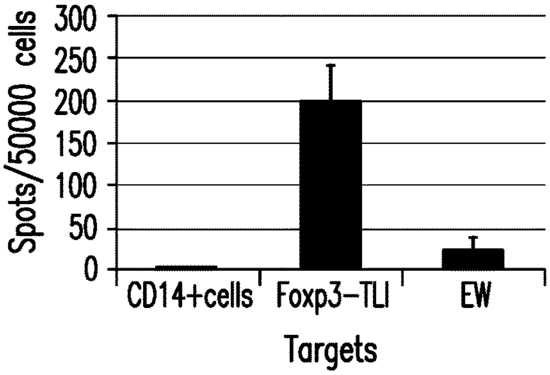
FIGS. 5A-5D represent induction of peptide-specific T cell response by Foxp3-TLI in the context of HLA-A0201 molecule. (A) CD3 T cells from HLA-A0*201$^+$ Foxp3 donors were stimulated with Foxp3-TLI peptide for four rounds and T cell response was tested against TLI peptide or with irrelevant peptide EW by IFN-γ elispot assay. CD14$^+$ APC serve as a negative control. (B) TLI-stimulated T cells also recognize HLA-A0201+ Treg-like cell lines MAC-1 and MAC-2A cells but not HLA-A0*201-Jurkat cells. (C and D) T cells from the same donor were stimulated for five rounds and the cytotoxicity was measured by $^{51}$Cr-release assay against the stimulating peptides pulsed onto T2 cells (C) or unpulsed target cells (D) by $^{51}$Cr-release assay. HLA-A0*201 negative AML cell line HL-60 were used as a negative control. (C) The T-cells were able to kill T2 cells pulsed with Foxp3 peptide, and (D) MAC-1 and MAC-2A cells but not HLA-A0201-HL-60 cells. Each data point represents average+/−SD from triplicate cultures.
Figure 5B:
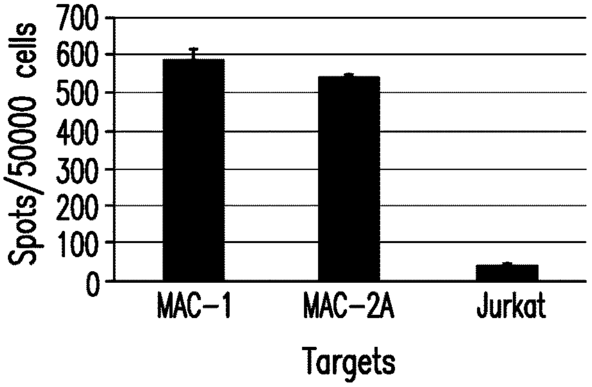
Figure 5C:
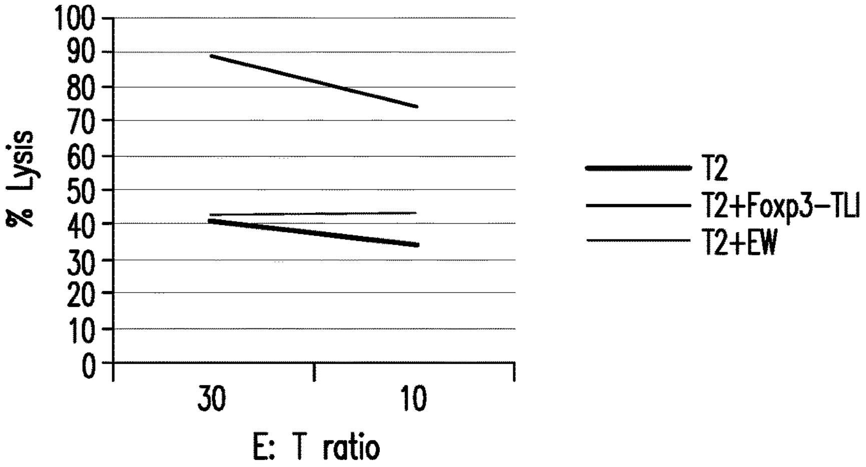
Figure 5D:
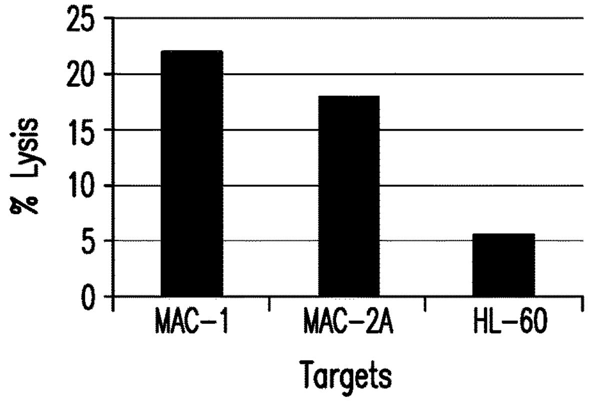

Additional experiments on Foxp3-7 (also denoted as TLI peptide or Foxp3-TLI peptide) shows that after four rounds of stimulation, T cells only recognize autologous $CD14^+$ monocytes pulsed with TLI peptide, but not $CD14^+$ APC alone or pulsed with an irrelevant HLA-A*0201-binding peptide EW, by IFN-γ elispot assay (FIG. 5A). Importantly, T cell response was also observed against HLA-A*0201$^+$ $Foxp3^+$ cutaneous T lymphoma cell lines MAC-1 and MAC-2A, but not the $Foxp3^+$ HLA-A*0201-T leukemia cell line Jurkat, suggesting that TLI-stimulated T cells could recognize the naturally processed Foxp3 TLI epitope presented by HLA-A*0201 molecule (FIG. 5B). Consistent with the results of IFN-γ secretion, TLI peptide-stimulated T cells killed T2 pulsed with the TLI peptide and unpulsed MAC-1 and MAC-2A cells, but not HLA-A*0201-negative, $Foxp3^+$ cell line HL-60 (FIGS. 5C and 5D). The above data demonstrated the identification of the Foxp3-derived epitopes in the context of HLA-A2 molecule and the generation of CTL responses against Foxp3 in both peptide-pulsed T2 cells and also T lymphoma cell lines expressing Foxp3/HLA-A2. This demonstrated that the native peptides are processed and presented in HLA on the cell surface for recognition by the T cell TCR. Based on these data, the Foxp3-7, Fox3-4 and Fox3-2 epitopes were selected to generate TCR-mimic monoclonal antibodies (mAbs) in the context of HLA-A*02:01 molecule.

Figure 6A:
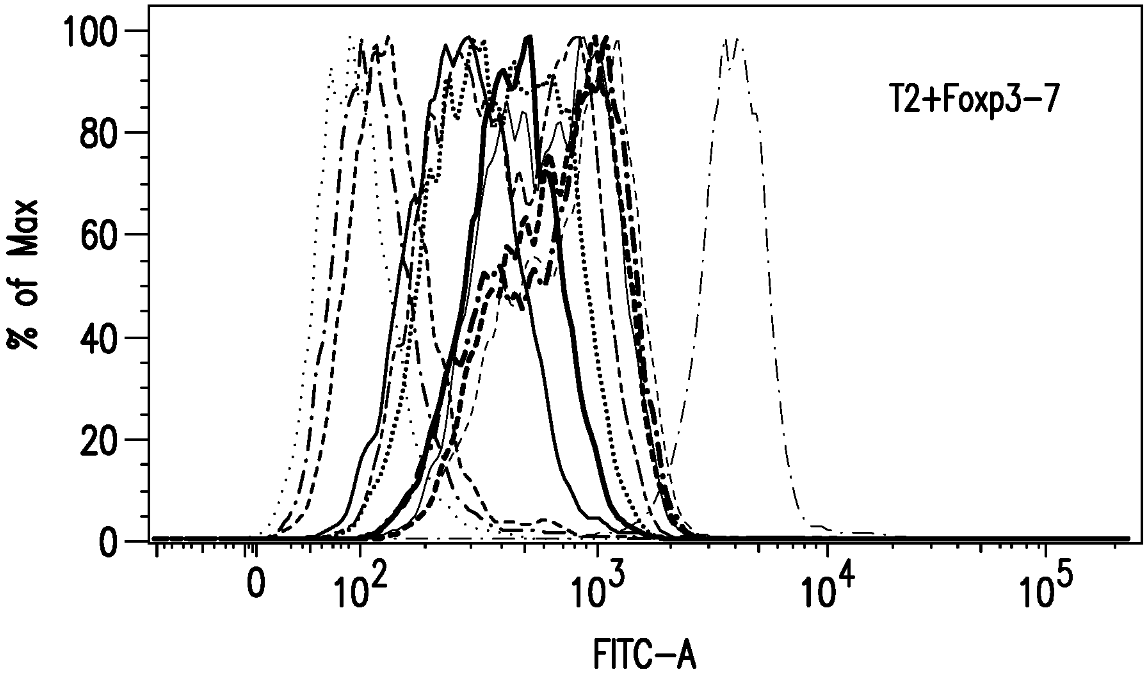
FIGS. 6A-6J represent binding of the phage scFv clones to T2 cells pulsed with Foxp3-7 peptide, Foxp3-2 peptide and Foxp3-4 peptide. (A) Representative data from flow cytometry analysis on T2 cells for phage clones specific for the Foxp3-7 peptide. Negative controls were no second antibody, no antibody, and an irrelevant antibody Pr435. T2 cells alone (B, D, F), pulsed with control peptide R3 (C, G), or pulsed with EW peptide (E, H). (I) Representative data from flow cytometry analysis on T2 cells for phage clones specific for the Foxp3-2 peptide. (J) Representative data from flow cytometry analysis on T2 cells for phage clones specific for the Foxp3-4 peptide. Phage clones #9, 11, 17, 18, 21, 26, 27, 28, 32 did not show any significant binding to T2 cells alone or pulsed with R3 peptide, but bound to the T2 cells pulsed with Foxp3-7 peptide, with the strongest binding of clone #32. The data represent the data from five similar experiments. Staining controls include unstained cells, secondary mAb (GAM) or irrelevant phage Pr435-#20.
Figure 6B:
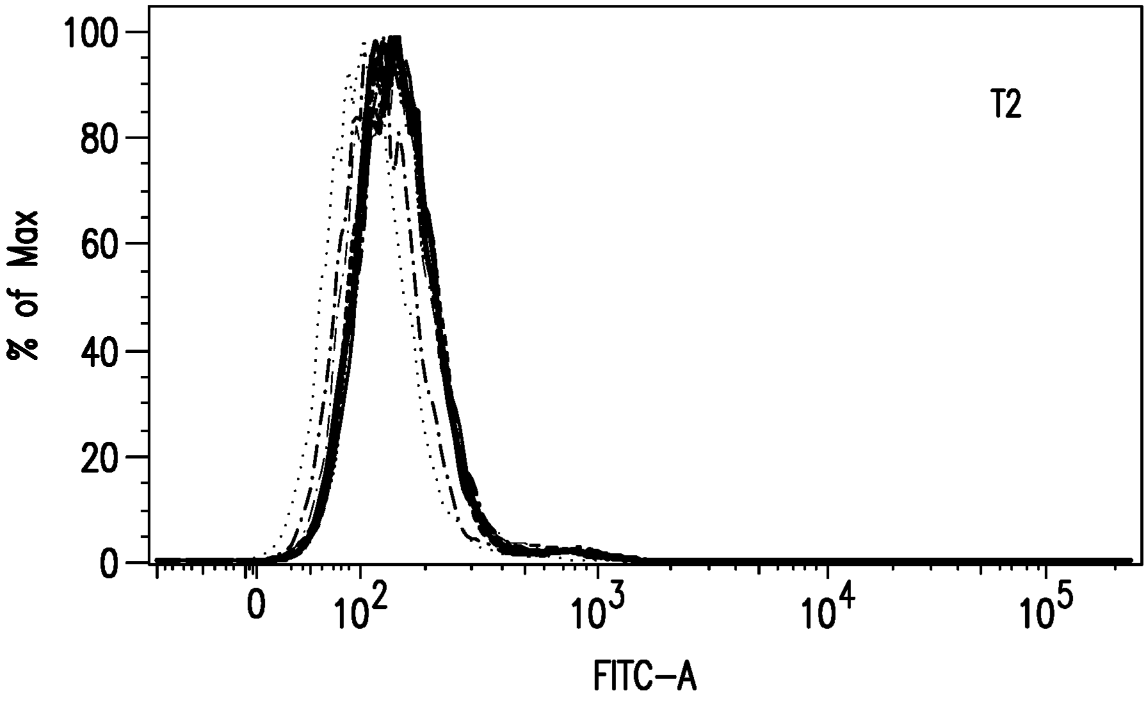
Figure 6C:
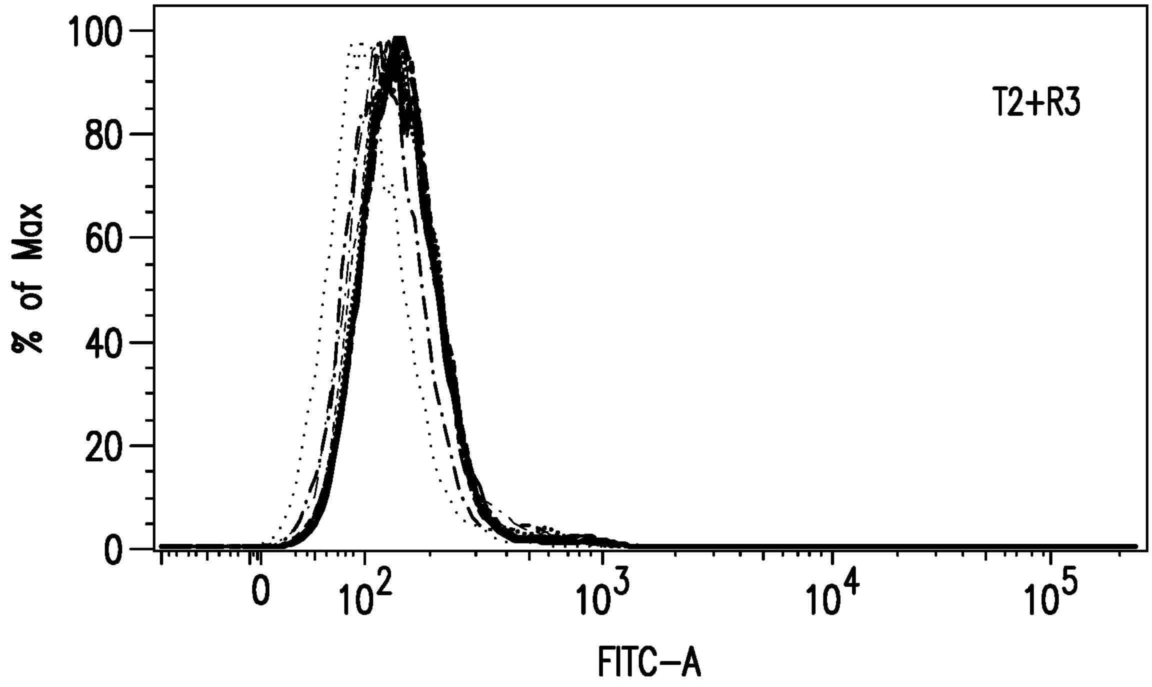
Figure 6D:
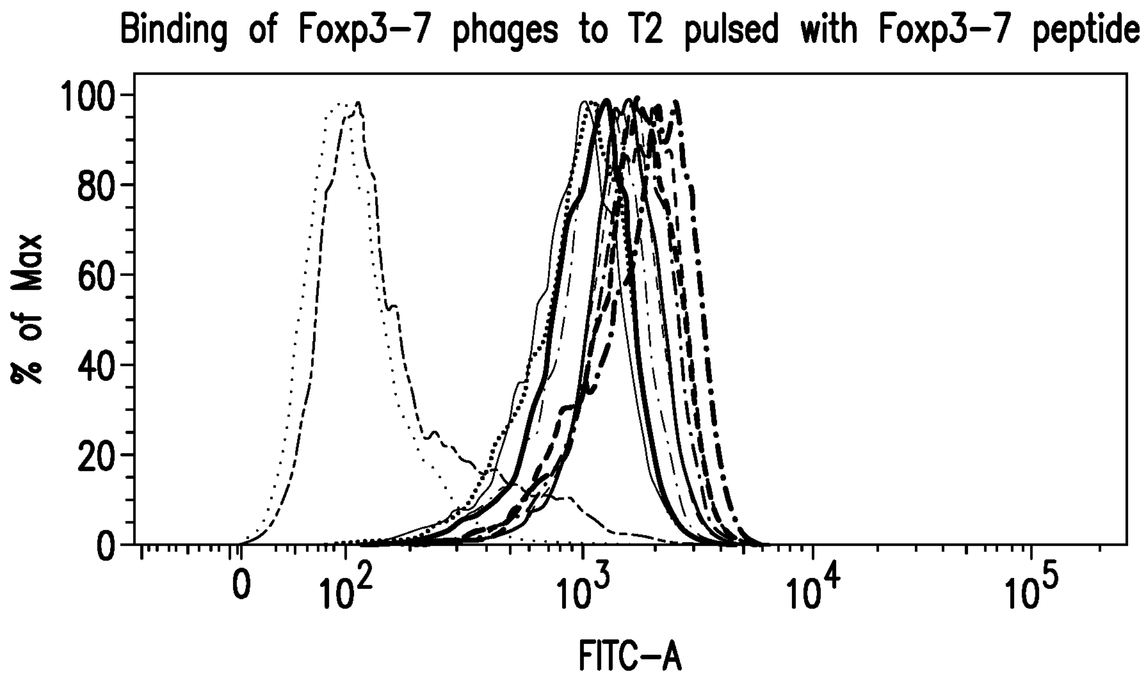
Figure 6E:
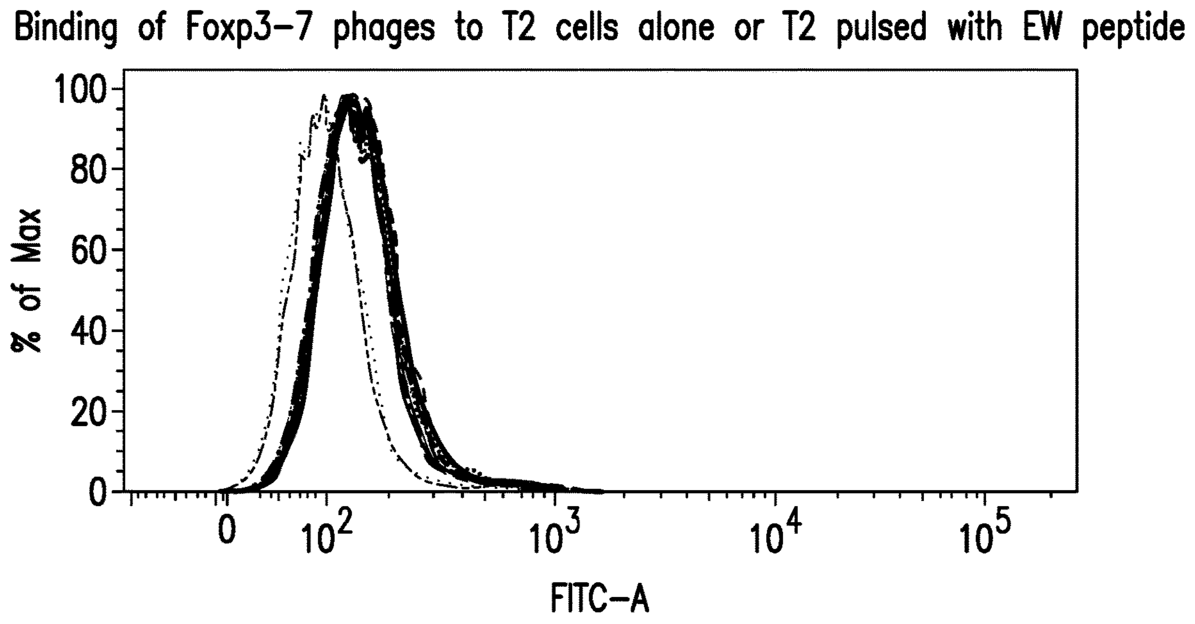
Figure 6E:
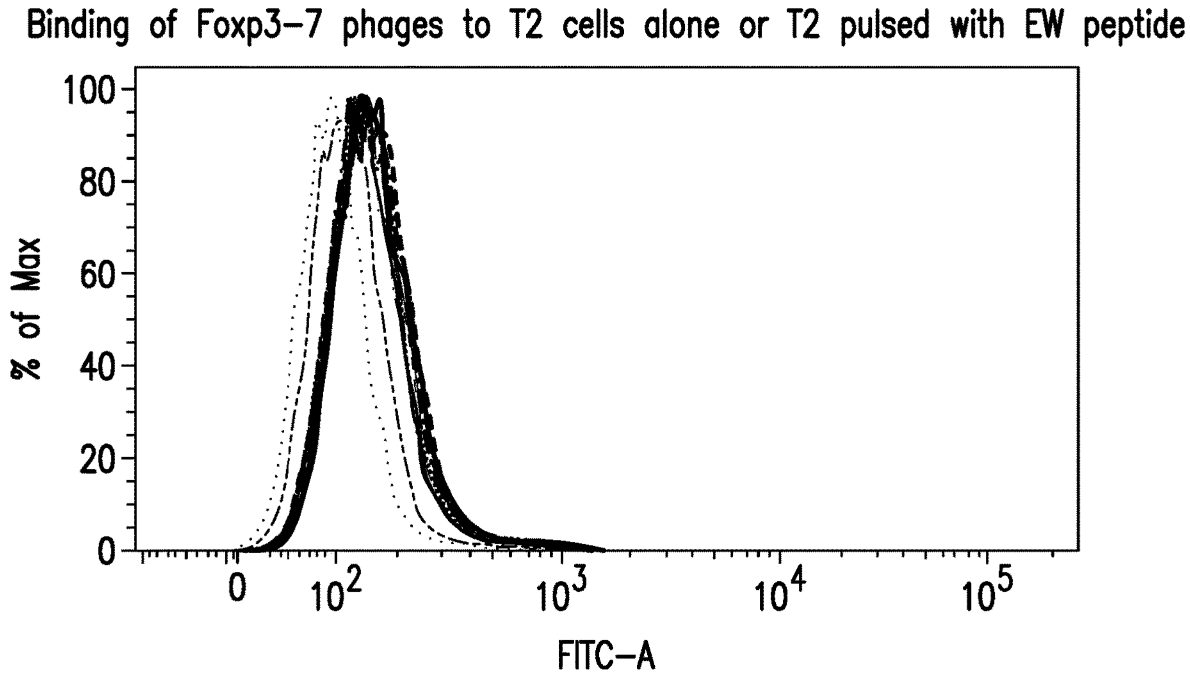
Figure 6F:
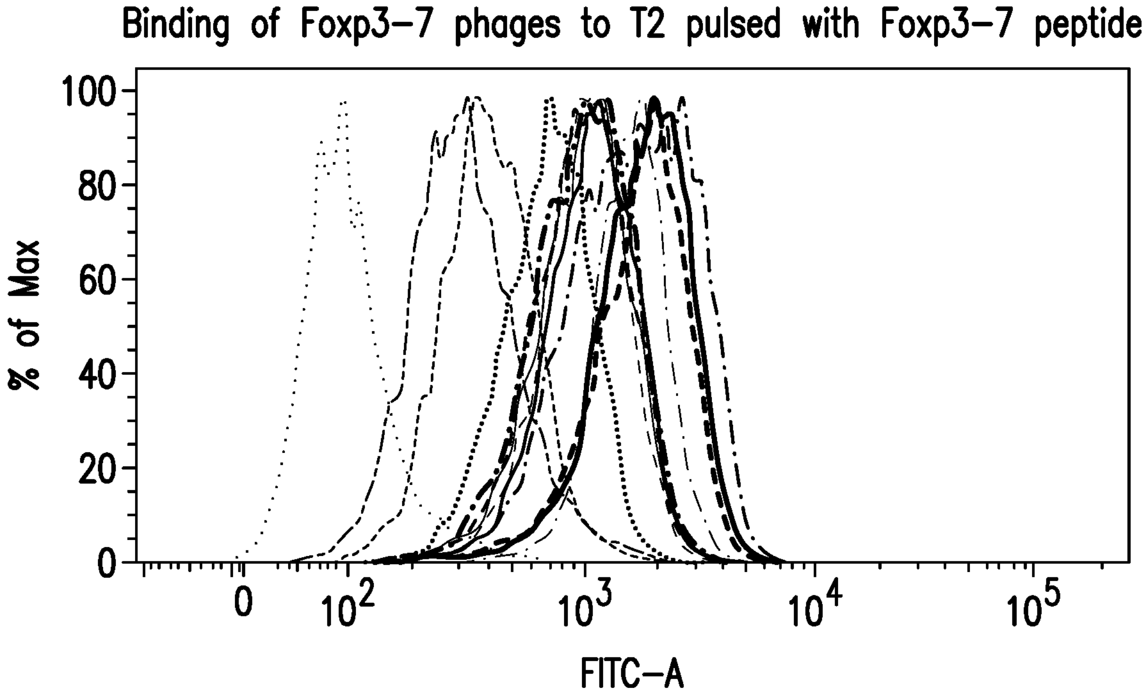
Figure 6G:
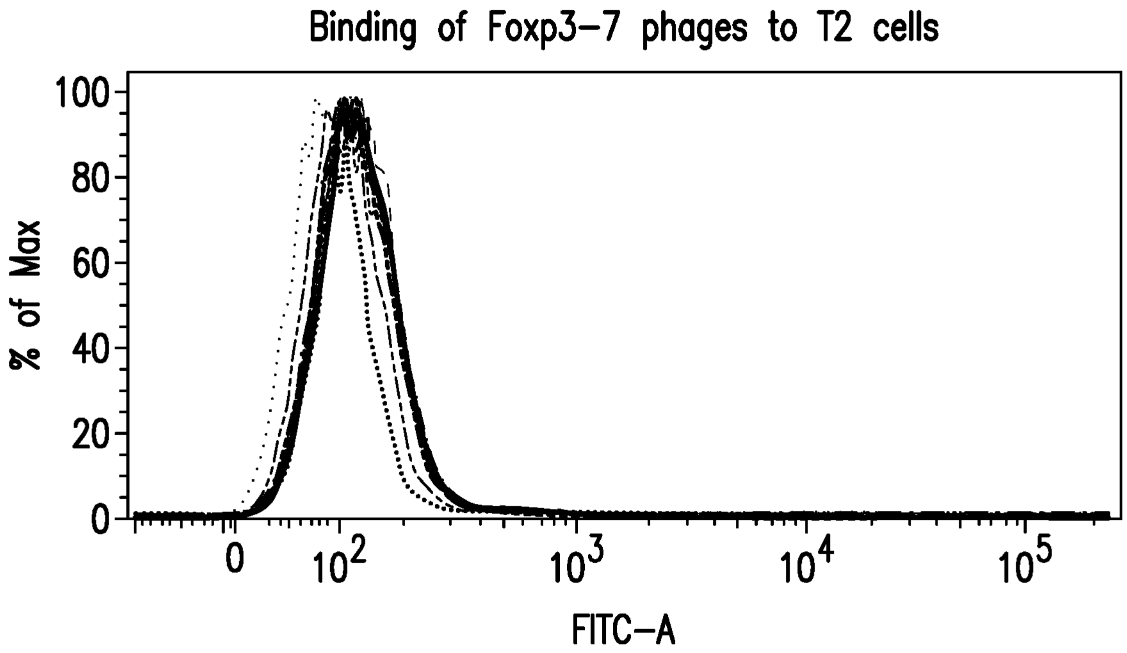
Figure 6G:
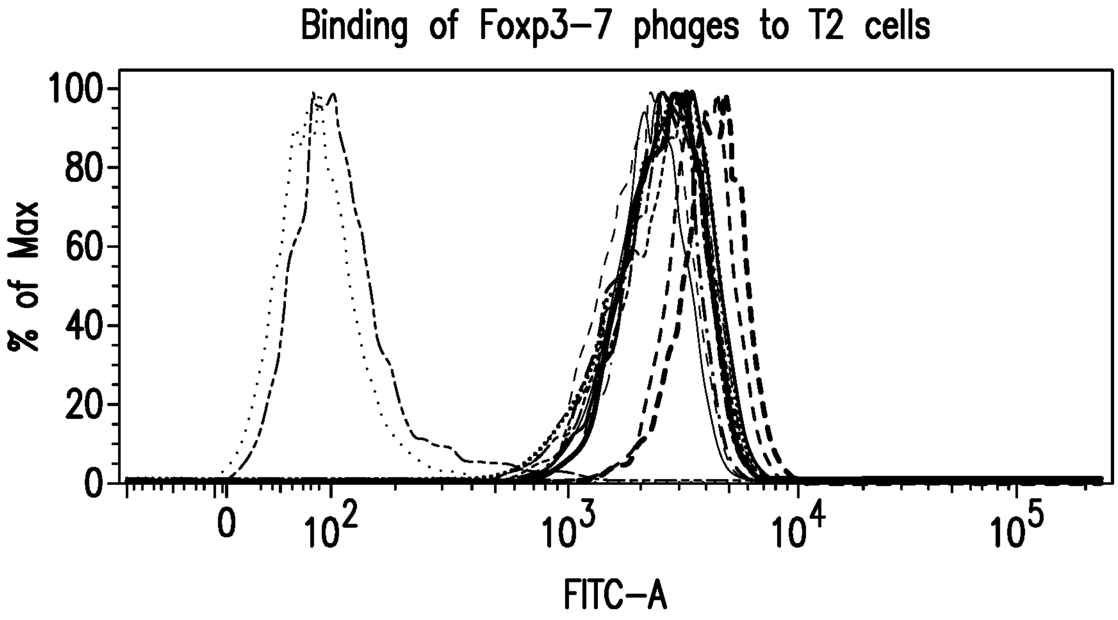
Figure 6G:
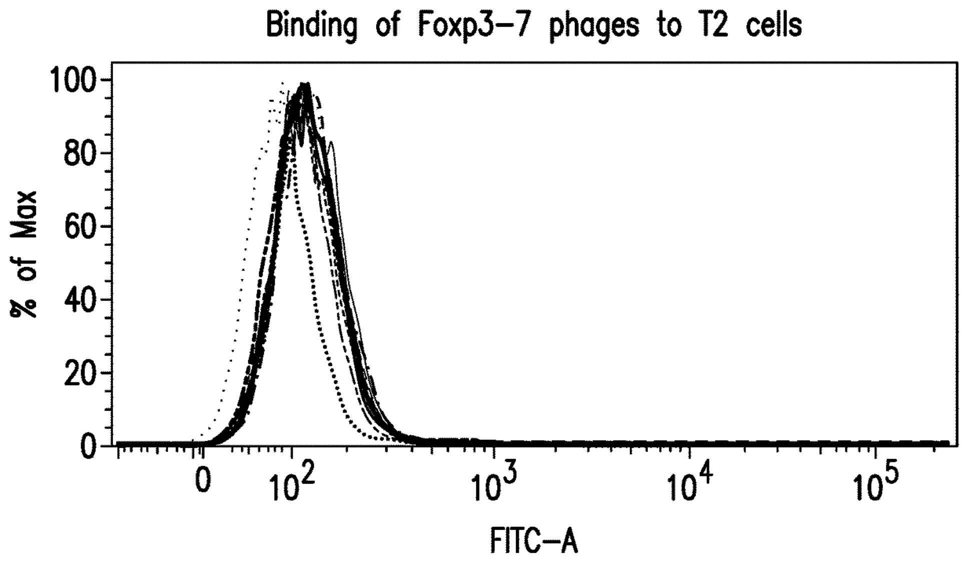
Figure 6H:
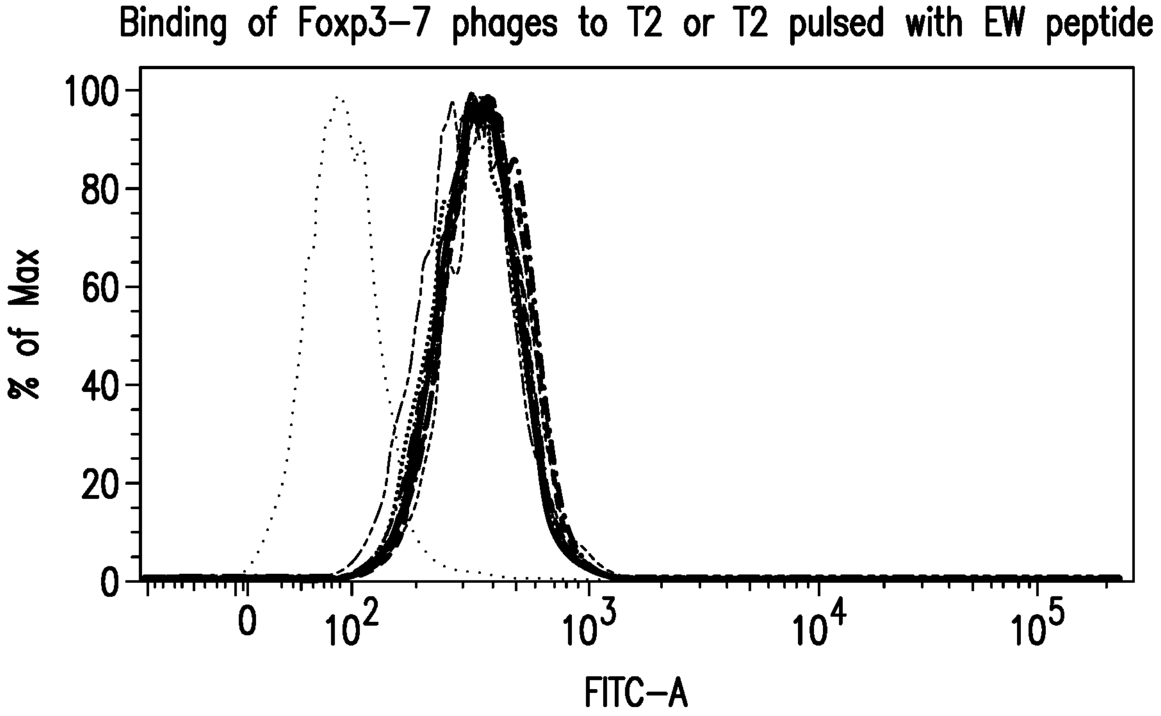
Figure 6H:
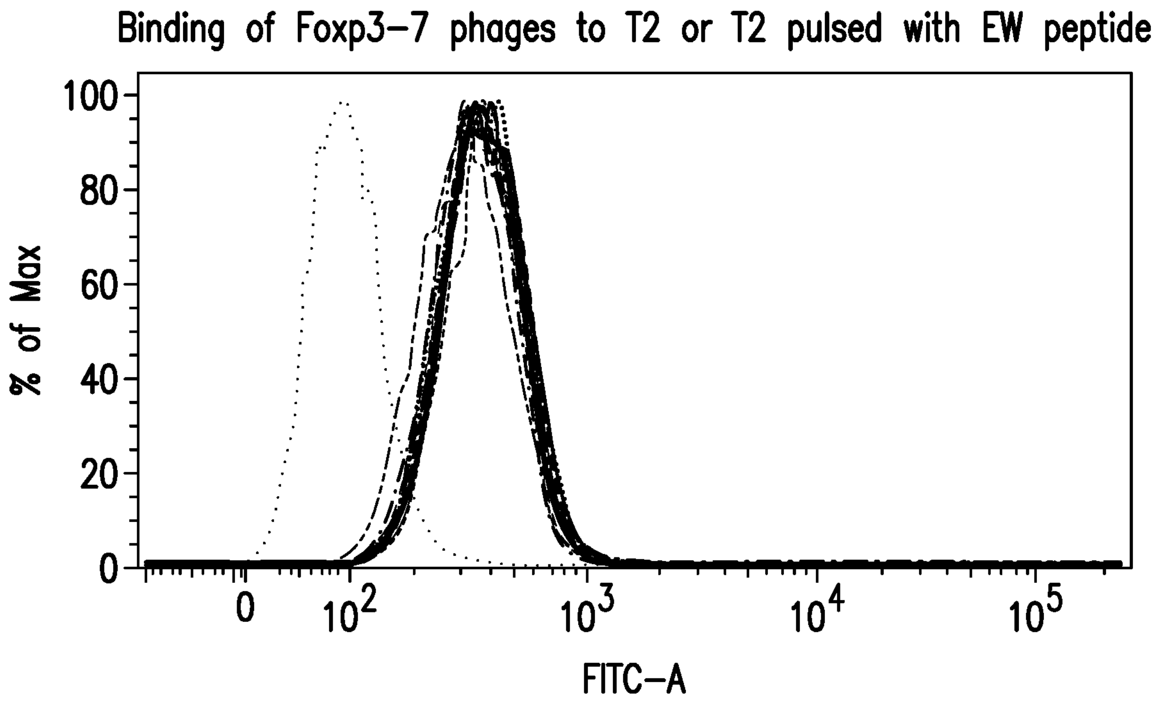
Figure 6I:
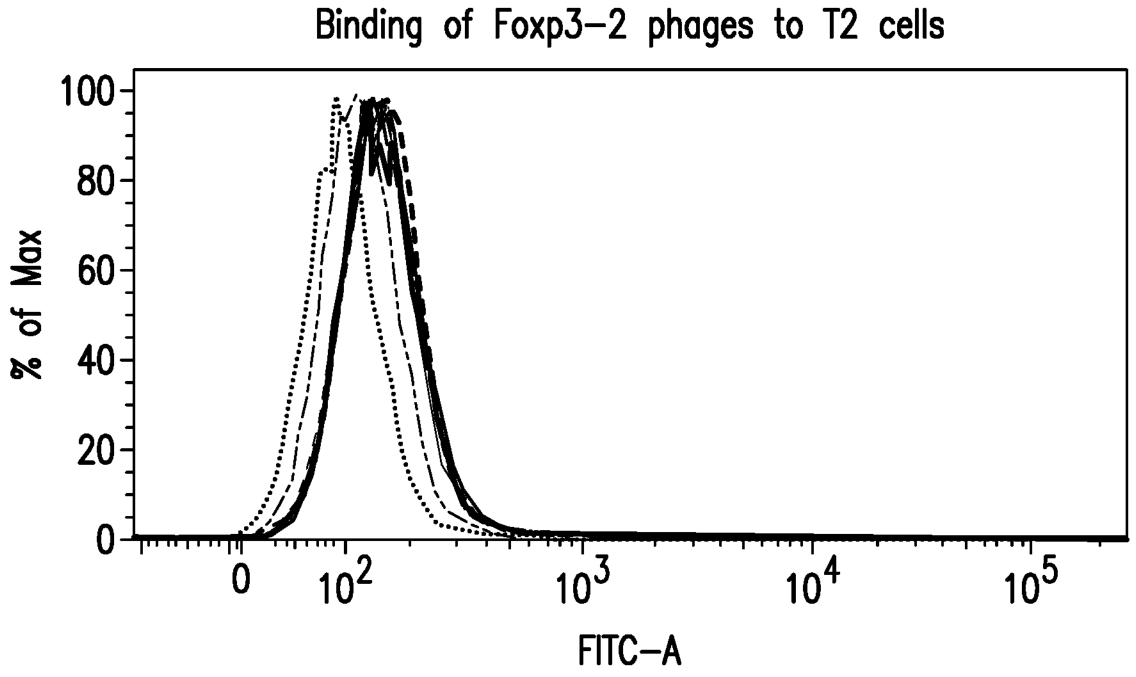
Figure 6I:
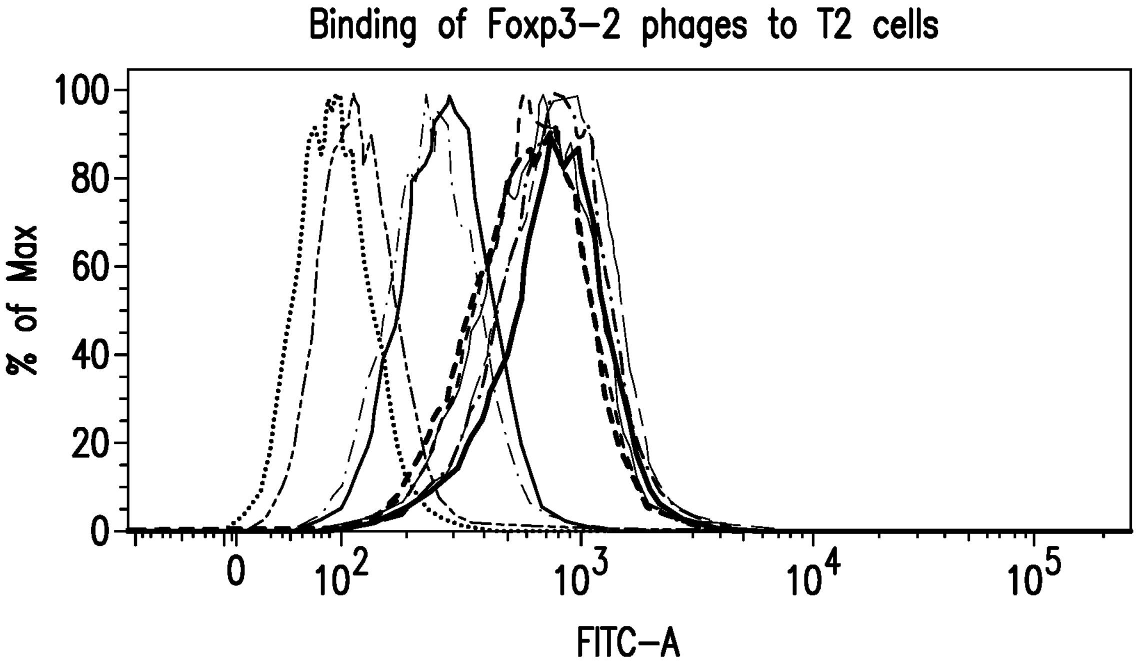
Figure 6I:
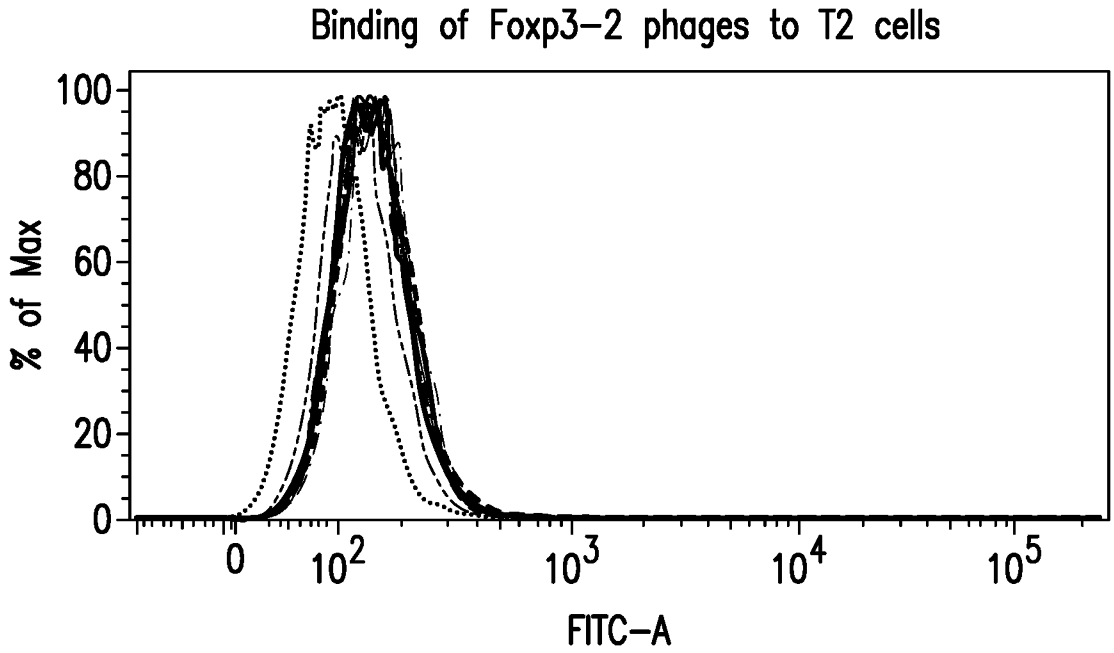
Figure 6J:
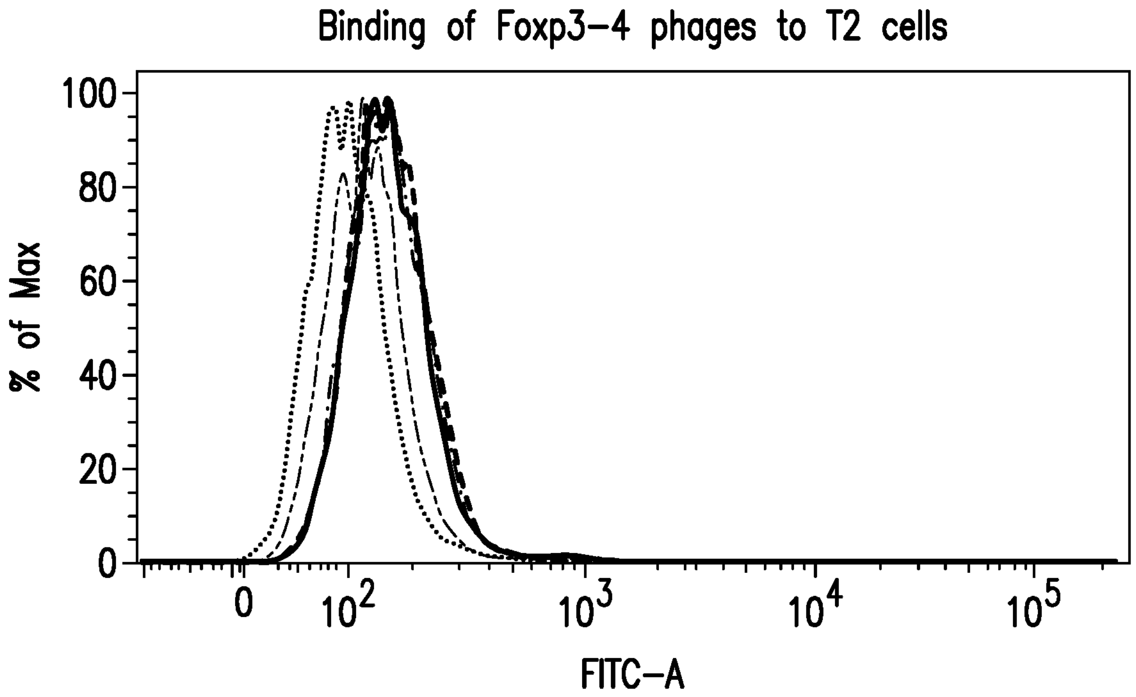
Figure 6J:
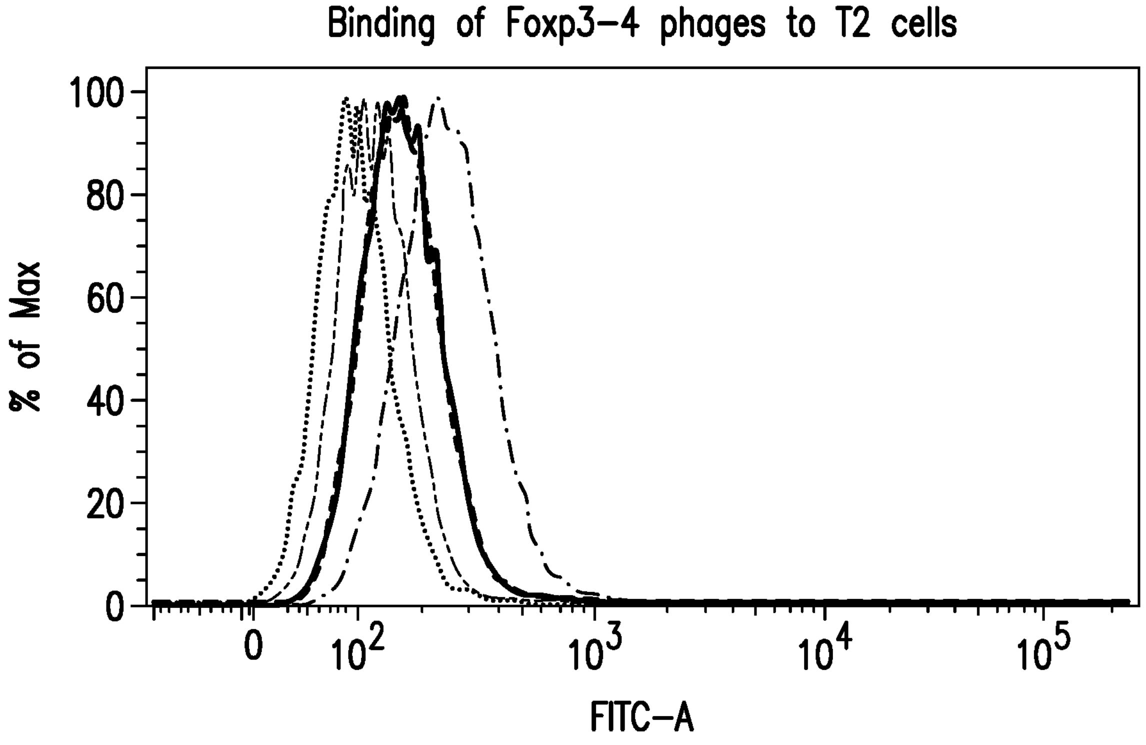
Figure 6J:
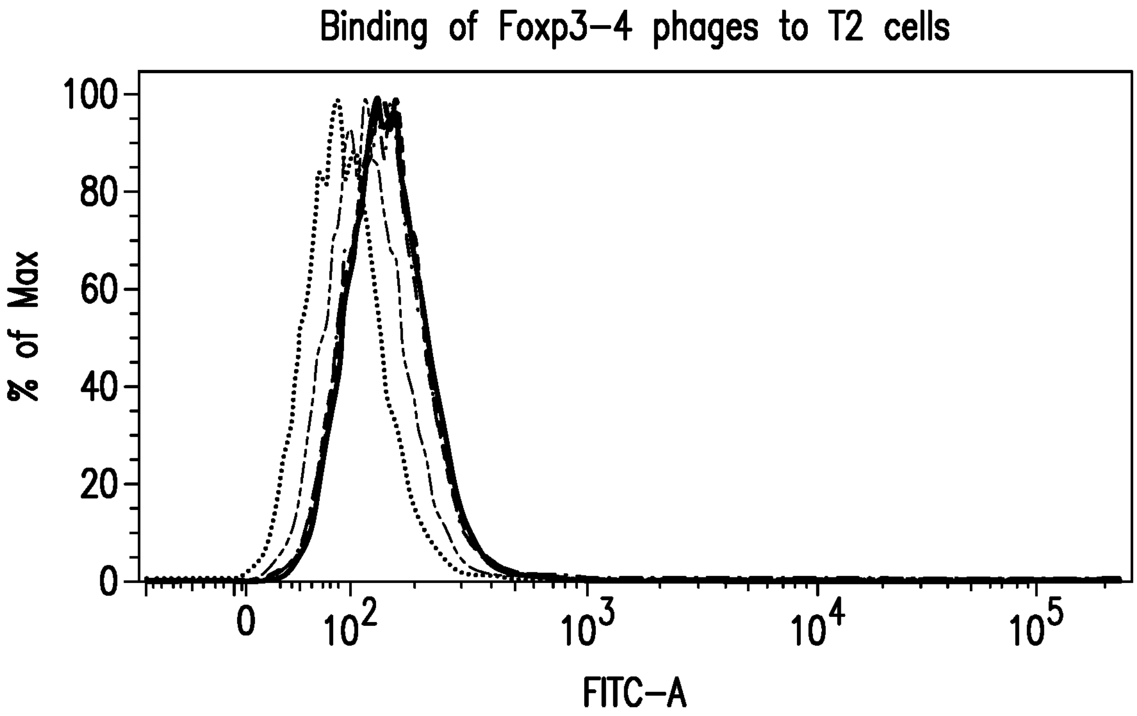

3. Generation of TCR-Mimic mAbs for the Foxp3 Peptides in the Context of HLA-A*02: 01 Molecule Using Phage Display Technology A total of 21 phage clones for Foxp3-7, 8 phage clones for Foxp3-2 (FIG. 6I) and 3 phage clones for Foxp3-4 (FIG. 6J) were screened for their ability to produce mAb specific for their respective Foxp3 peptide/A2 complex. FIGS. 6A-6H show the binding data of phage scFv clones to Fox3-7. FIG. 61 shows the binding data of phage scFv clones to Fox3-2. FIG. 6J shows the binding data of phage scFv clones to Fox3-4.

In particular, for Foxp3-7, by confirming that Foxp3-TLI peptide is able to induce epitope-specific T cell response which recognizes tumor cells expressing Foxp3 protein, a TCRm mAb specific for the TLI/HLA-A*0201 complex was generated, by using phage display technology as previously described[18]. In brief, single phage clones specific for the TLIp/A2 complex selected by screening of a phage library were further validated by ELISA. The selected clones were tested for their binding to live cells using T2 cells. Any clones that showed binding to T2 cells without the TLI peptide or with HLA-A*0201-binding irrelevant peptides were removed. After 5 rounds of screening, based on binding specificity to T2 cells pulsed with TLI peptide and live cells that express foxp3 and HLA-A*0201, eight scFv clones were selected for engineering into either full-length human IgG1 or bispecific T cell-engager mAb (T-BITE) for further characterization.

For Foxp3-7: Clone #32, 17, 28, 54, 18, 53, 27, 20

4. Characterization of BsAbs Specific for Foxp3-7/HLA-A*02:01 Complex

Mab killing functions can be enhanced in multiple ways. As a strategy to bring T cell cytotoxicity to the targets, eight bi-specific T cell engager constructs of the mAbs specific for the Foxp3-7 peptide/HLA-A2 complex were generated. The binding of the 8 BsAb (also referred to as "BITE") constructs specific for the Foxp3-7/HLA-A2 complex was tested on T2 cells pulsed with or without Foxp3-7 or irrelevant peptide and also on unpulsed T lymphoma cells MAC-1, MAC-2A and Jurkat cells.

Figure 7A:
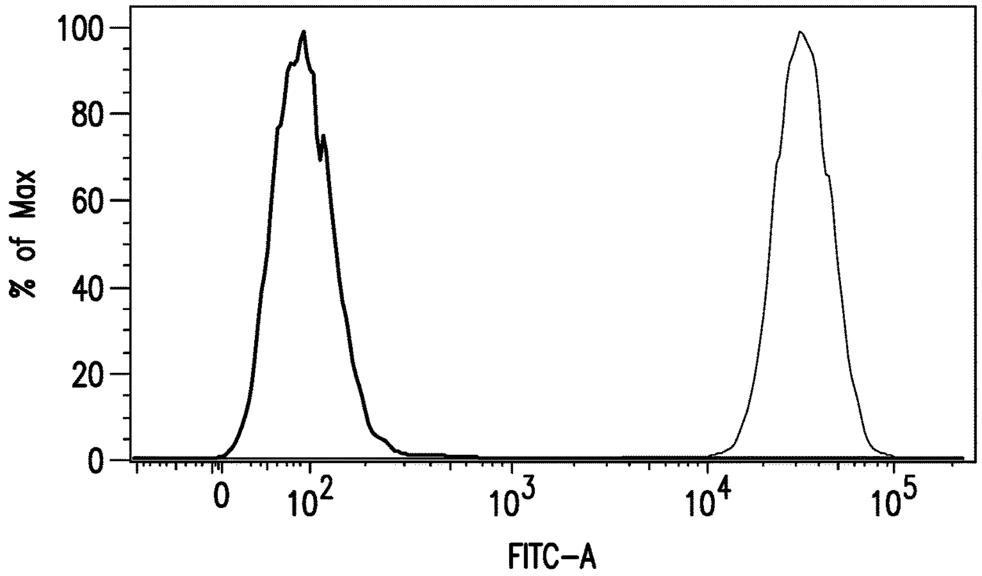
FIGS. 7A-7C represent binding of the indicated bi-specific antibody (BsAb) (also referred to as "BITE") constructs to Foxp3$^+$/HLA-A2$^+$ T lymphoma cell lines MAC-1, MAC-2A, and CD3$^+$ T cell line Jurkat. (A) Binding of the indicated BsAb constructs to Foxp3$^+$/HLA-A2$^+$ T lymphoma cell line MAC-1. Since the BsAb constructs were myc-tagged, the binding was tested by staining the cells with the BsAbs, followed by a secondary mAb, mouse anti-myc conjugated to FITC. Controls included unstained cell, control BsAb NC-16 or secondary mAb GA6×His ("6×His" is disclosed as SEQ ID NO: 143). HLA-A2 expression was measured by staining the cells with anti-A2 mAb BB7 and its isotype control mouse IgG2b, as indicated. Binding strength is shown by median fluorescent intensity. (B) Binding of the indicated BsAb constructs to Foxp3$^+$/HLA-A2$^+$ T lymphoma cell line MAC-2A. Controls included unstained cell, control BsAb NC-16 or secondary mAb GA6×His ("6×His" is disclosed as SEQ ID NO: 143). HLA-A2 expression was measured by staining the cells with anti-A2 mAb BB7 and its isotype control mouse IgG2b, as indicated. Binding strength is shown by median fluorescent intensity. (C) Similarly, the binding of the #32 BITE to CD3 arm was measured on CD3+ T cell line Jurkat, as described in (A). Controls included unstained cell, control BsAb NC-16 or secondary mAb GA6×His ("6×His" is disclosed as SEQ ID NO: 143). HLA-A2 expression was measured by staining the cells with anti-A2 mAb BB7 and its isotype control mouse IgG2b, as indicated. Binding strength is shown by median fluorescent intensity.
Figure 7B:
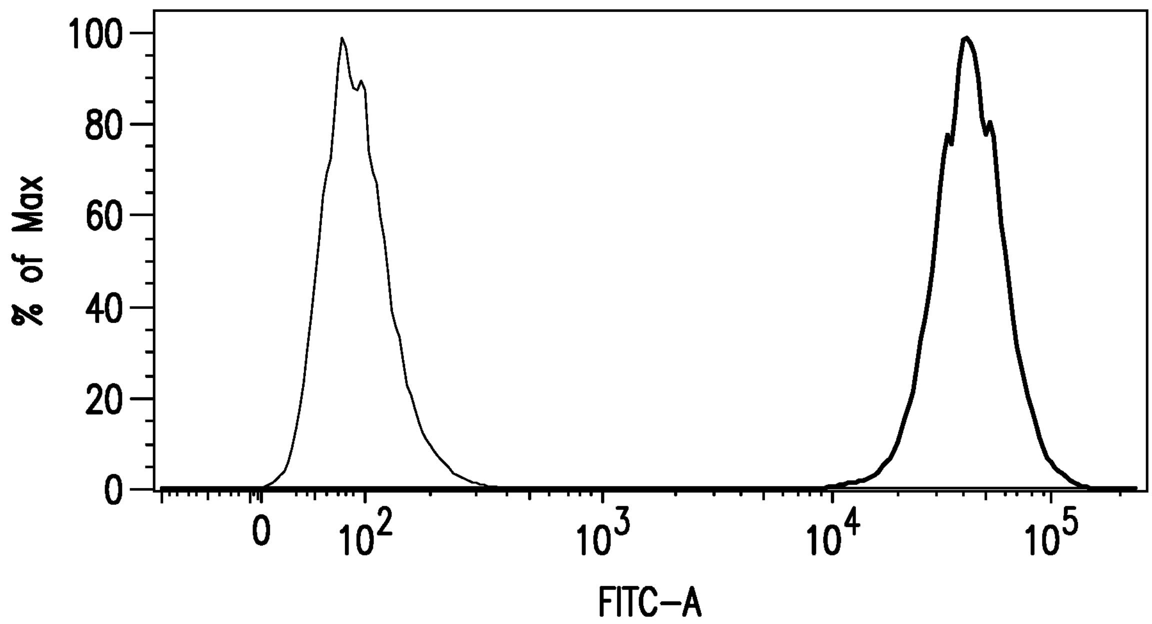
Figure 7C:
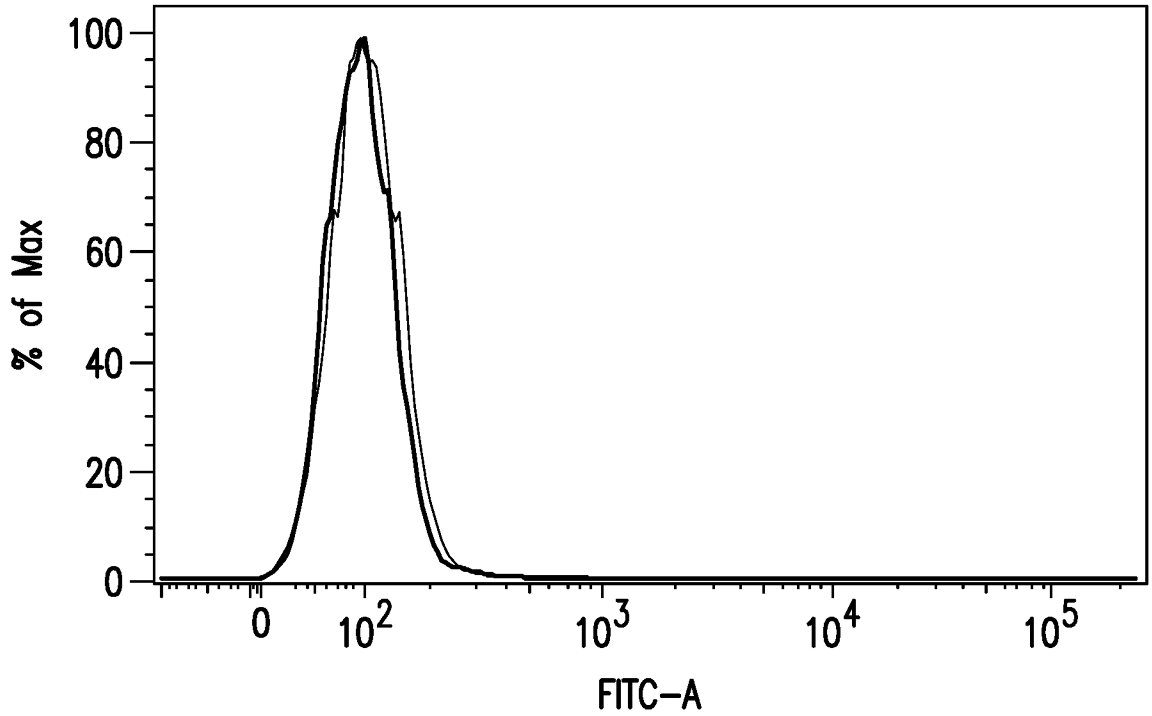

As shown in FIGS. 7A-7C, all the BsAb constructs #17, 18, 20, 27, 28, 32, 53, and 54 bound very well to T2 cells pulsed with Foxp3-7 peptide, but not the T2 cells alone or with control peptide. However, BsAb #32 bound to both MAC-1 and MAC-2A cells, demonstrating it had the sufficient avidity to recognize the naturally processed epitope (FIGS. 7A and 7B). #32 BITE also bound to $CD3^+$ T cell line Jurkat, demonstrating the binding to CD3 with anti-CD3 arm of the BITEs (FIG. 7C). All the BsAb constructs bound to $CD3^+$ T cell line Jurkat, demonstrating the binding of the anti-CD3 arm of the BsAbs.

Figure 8B:
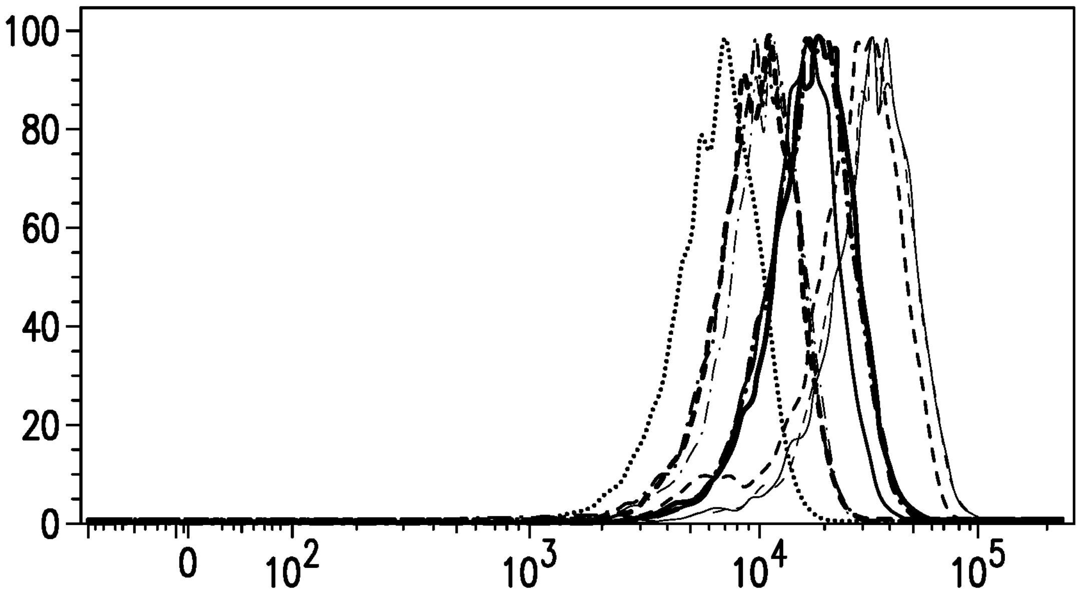

The specificity of the Foxp3-#32 mAb was further analyzed by use of binding of Foxp3-#32 BITE to T2 cells containing analog TLI peptides. TLI peptide was substituted with alanine at positionl, 2, 3, 4, 5, 7 and 8, or with glycine at position 10. Position 6 was already alanine and it was left intact. The mutant peptides were loaded onto T2 cells and tested for Foxp3-BITE binding. Alanine or glycine substitution at position 2, 8, 9 or 10 reduced the binding of foxp3-BITE, as compared to the native TLI peptide (FIG. 8A). The loss of the binding at position 2 and 9 could be due to the reduction of the peptide binding affinity to the HLA-A*02 molecule, as both peptides showed reduced binding in T2 stabilization assays (FIG. 8B). No significant reduction of mutant peptides TLI-A8 and G10 in HLA-A2 stabilization, suggesting amino acids at these positions could be specifically recognized by the mAb. These results further demonstrated the specificity of the foxp3-BITE against the TLI peptide/HLA-A*0201 complex and that binding to the HLA-A*0201 molecule alone was not sufficient.

5. Recognition of Foxp3-#32 mAb of Human Tregs and Tumor Cells Expressing Foxp3 and HLA-A*0201.

Figure 9A:
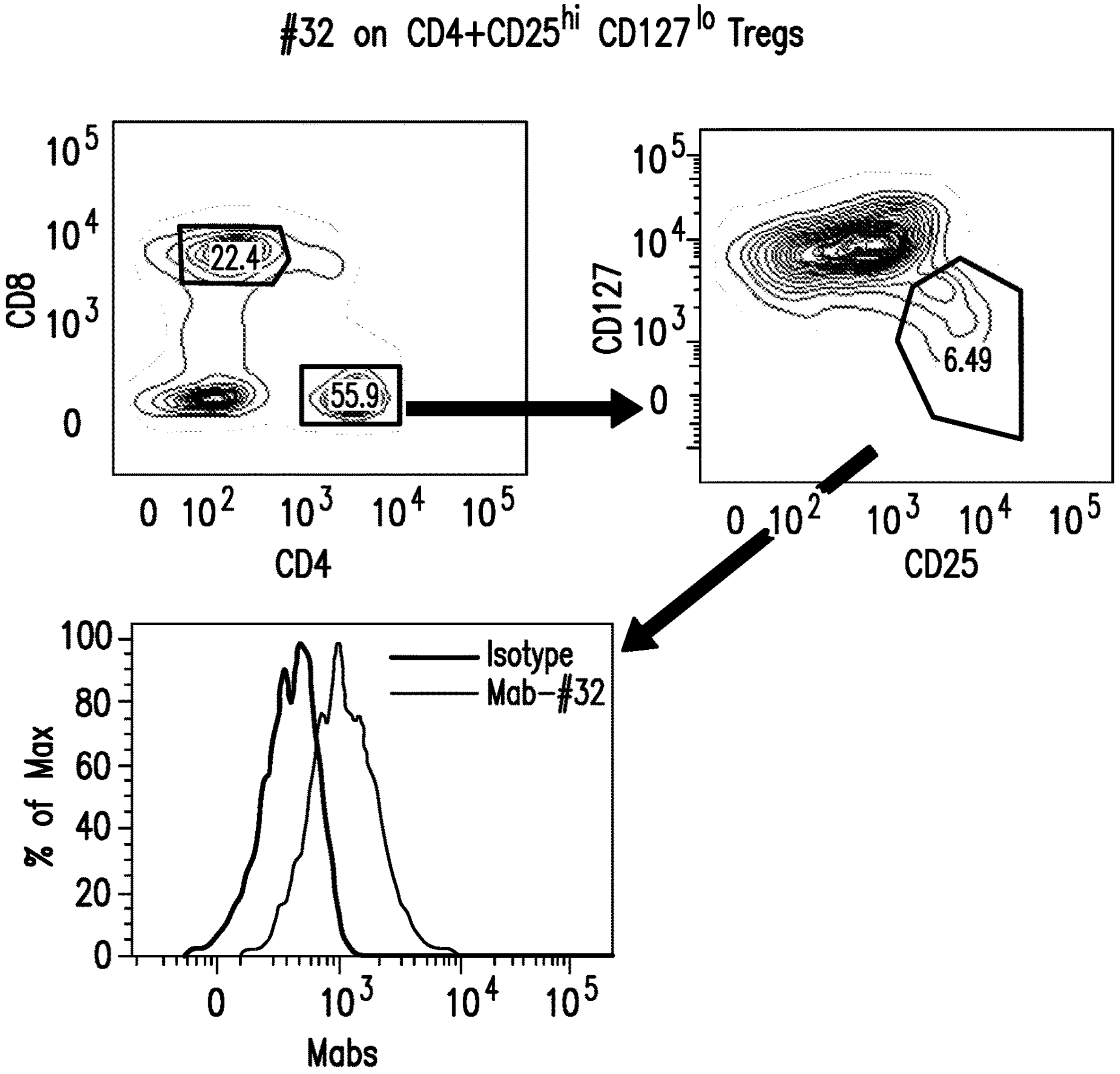
FIGS. 9A-9E represent specific binding of #32 mAb to natural Treg cells in PBMC in healthy donors. PBMCs were stained with mAbs specific for CD4, CD25 CD127 and mAb #32 mouse IgG1. Data show the binding of mAb #32 to $CD4^{+}CD25^{high}CD127^{low}$ Tregs (A), $CD4^{+}25^{high}CD127^{high}$ population (B), $CD8^{+}CD25^{high}CD127^{high}$ (C) from aHLA-A0*201$^{+}$ donor, or $CD4^{+}CD25^{high}CD127^{low}$ Tegs from a HLA-A-0*201 negative donor (D, E). Data show representative results from 3 sets of different individuals. #32 mAb recognizes $CD4^{+}CD25^{high}CD127^{low}$ Tregs from HLA-A0201$^{+}$ donor (A) but not HLA-A-0*201 negative donors (D, E).
Figure 9B:
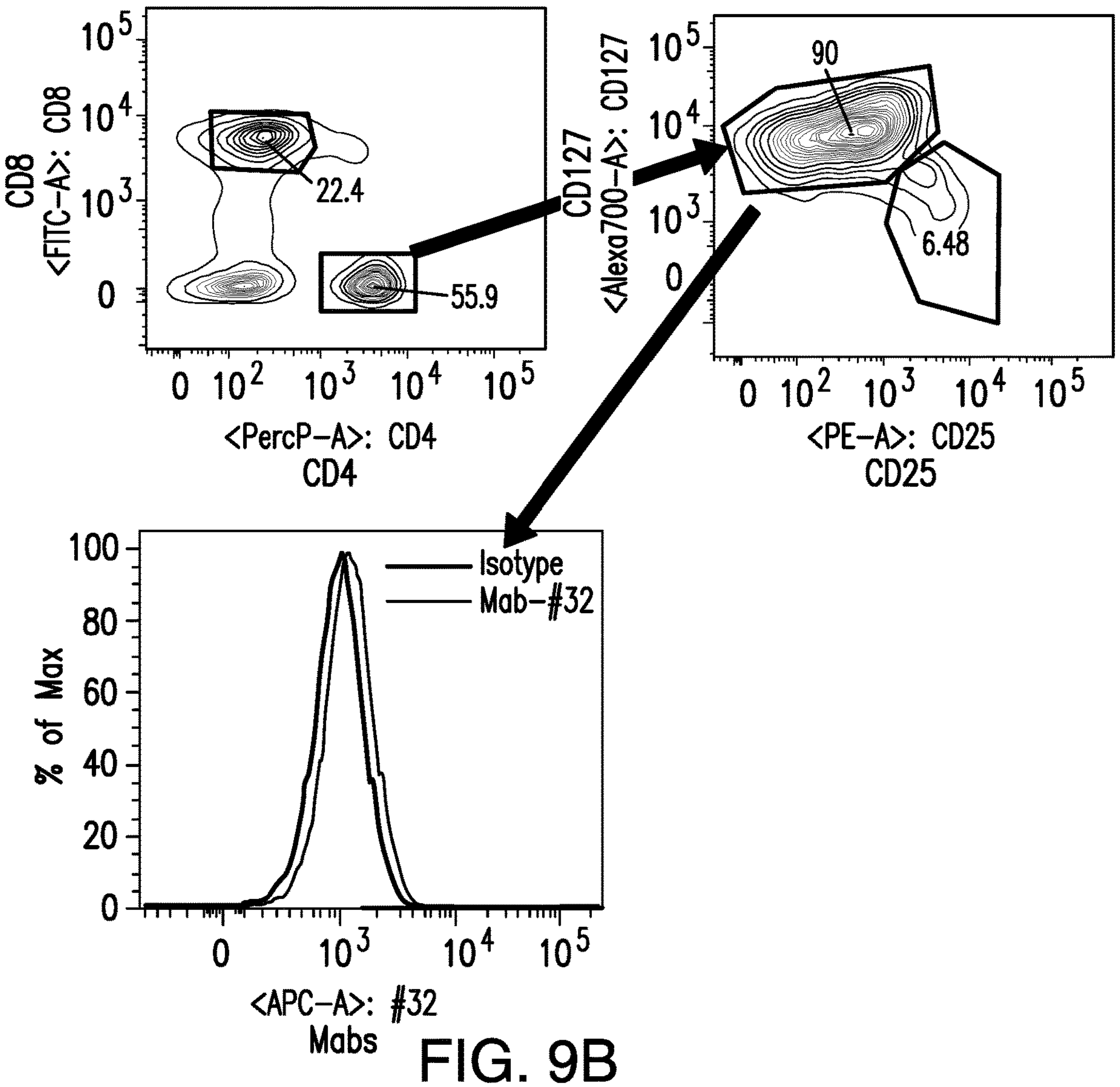
Figure 9C:
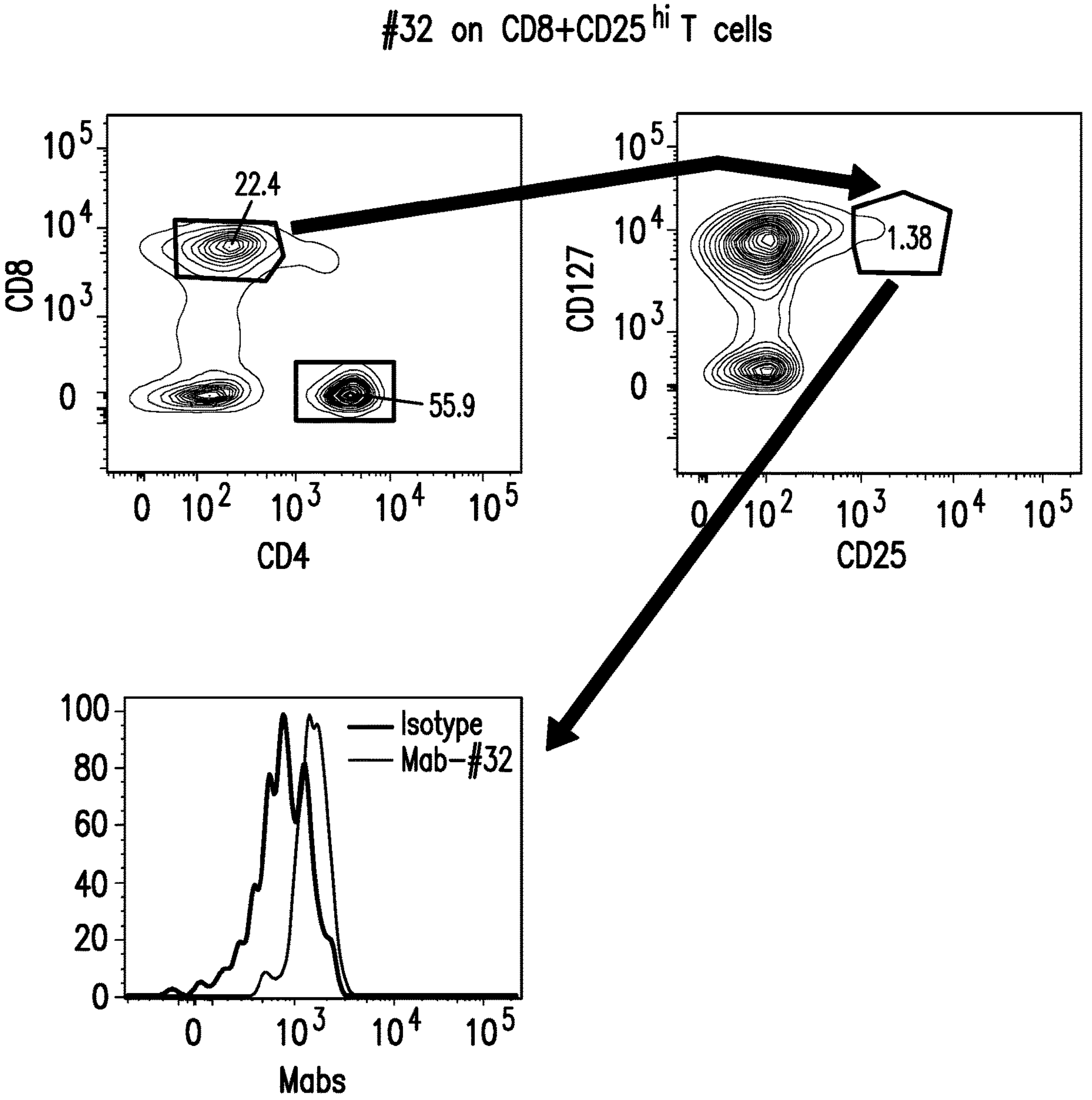
Figure 9D:
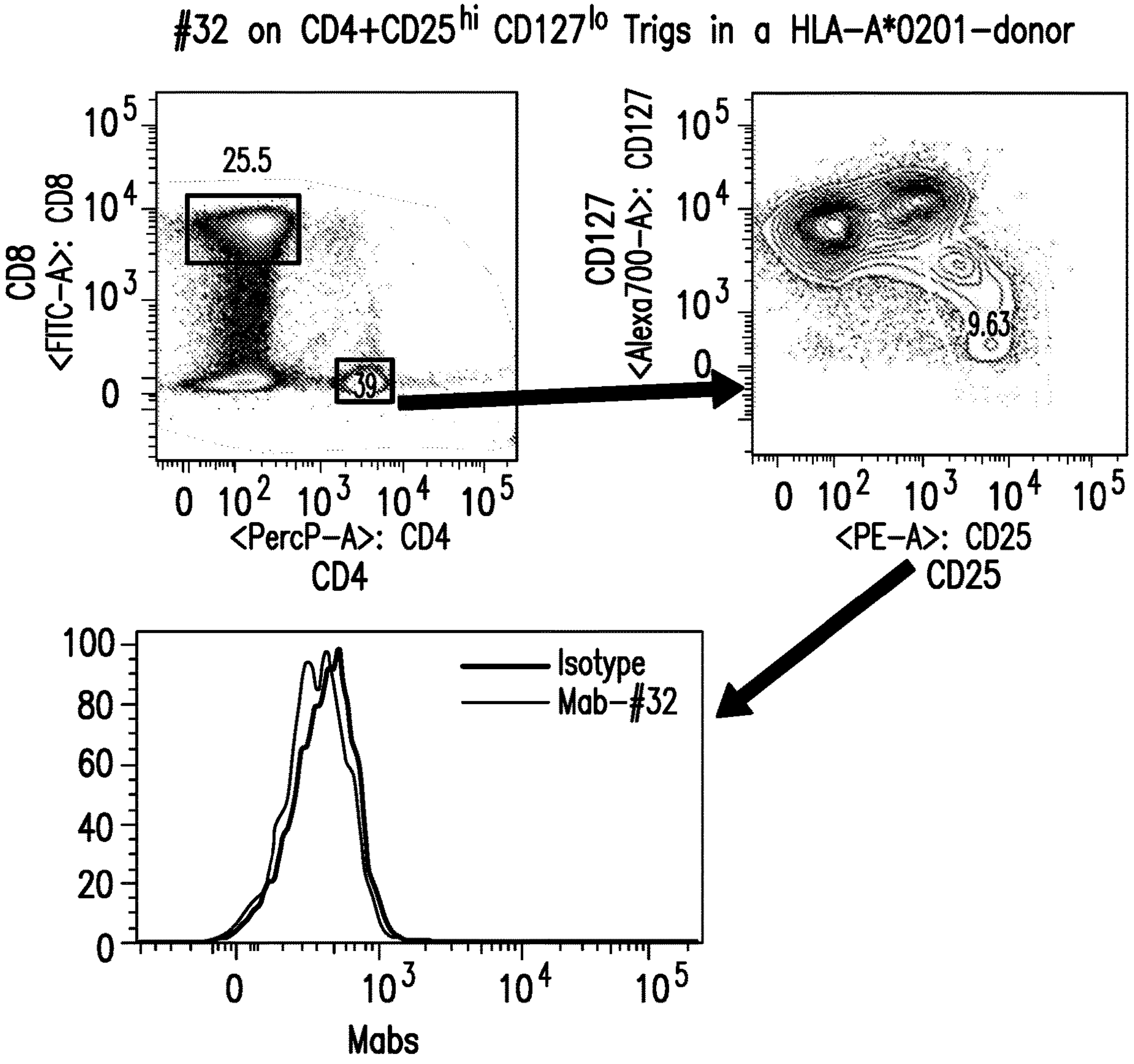
Figure 9E:
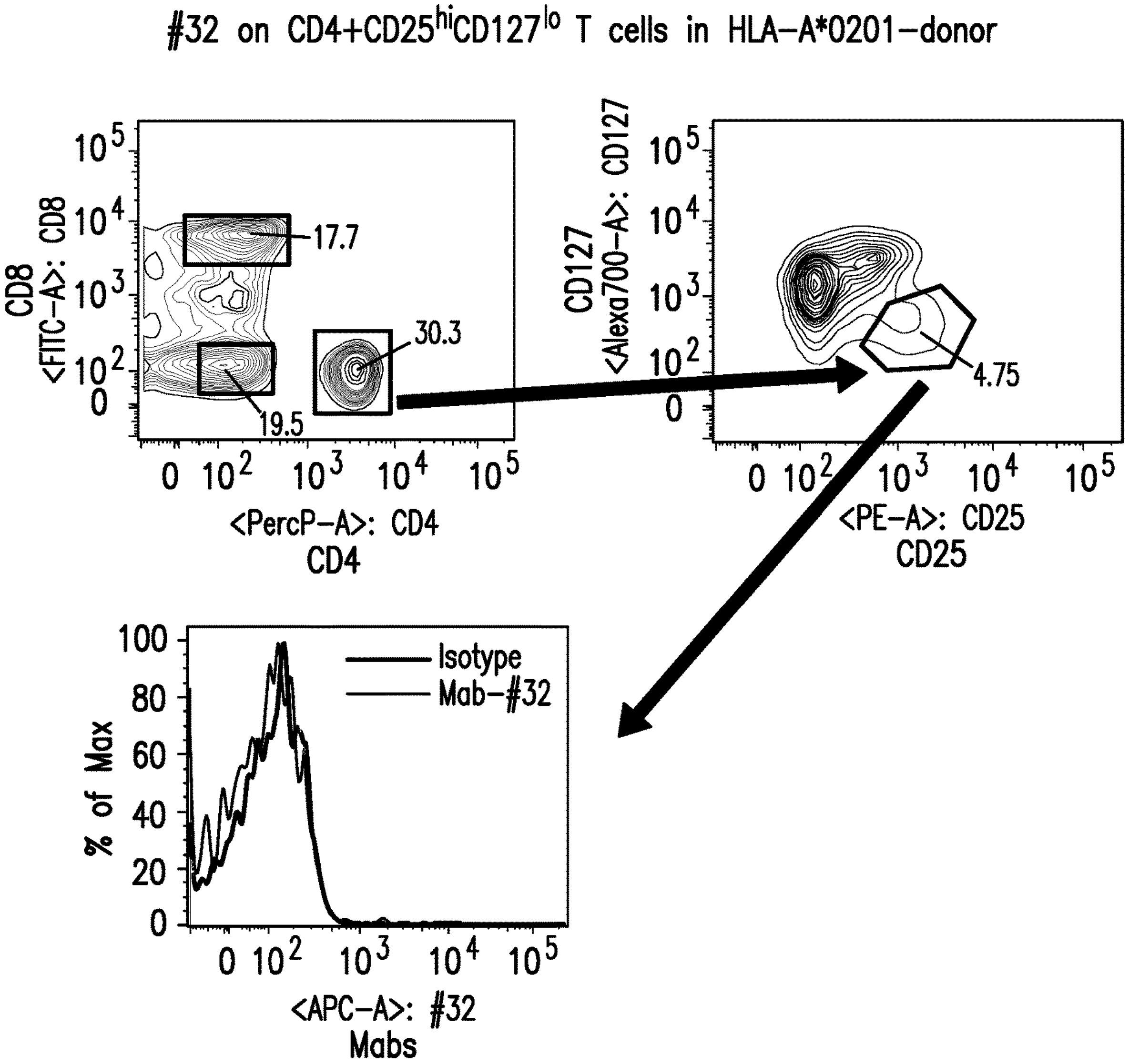

Although the Foxp3 mAb has demonstrated excellent specificity of binding to T2 cells pulsed with TLI peptide, it is crucial to test if the TLI epitope is processed and presented by HLA-A*0201 molecule in naturally occurring Tregs and inducible Tregs. A comparison was done on Foxp3 #32 mAb binding to Trges from HLA-A*0201 positive or negative PBMCs from healthy donors. $CD4^+$ T cells were gated on CD25 high and $CD127^{low}$ population, a characteristics of natural Tregs. Mab-#32 mAb showed a significant shift on this population compared to its isotype control in HLA-$A*0201^+$ donor (FIG. 9A). In contrast, mAb-#32 did not bind to either $CD4^+CD25^{low}CD127^{high}$, or $CD8^+$ $CD25^{high}CD127^{high}$ population (FIGS. 9B and 9C, respectively). Mab-#32 did not bind to the same $CD4^+$ $CD25^{high}CD127^{low}$ Treg population in a HLA-A*0201 negative donor (FIG. 9D).

Figure 10A:
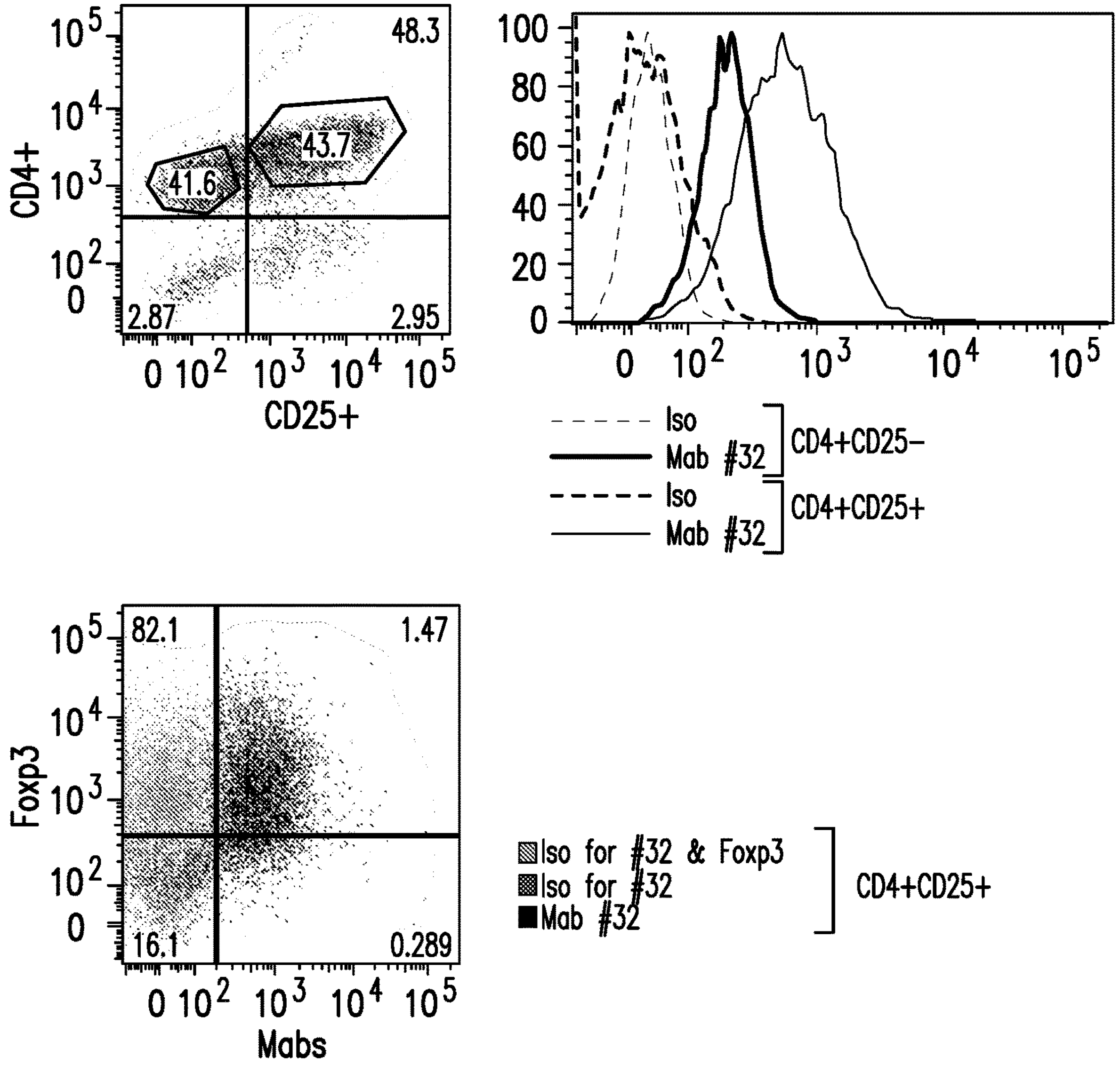
FIGS. 10A-10B represent specific binding of #32 mAb to Treg cells in vitro generated from a HLA-A*02:01$^{+}$ donor. The results were similar between Tregs generated by either (A) allo-PBMC or (B) MAC-2A cell stimulation. $CD4^{+}$ T cells were FACS sorted and stimulated with allo-PBMC or allo-tumor (MAC-2A) in the presence of IL-2 (100 unit) and TGF-β (long/ml) for a week. Cells were stained with mAbs to CD4, CD25, foxp3 and mAb #32/APC. Mab #32 binding was determined by gating on the DAPI-, CD4 and CD25 double positive cells. The data shows an overlay of mouse mAb #32 (red) and its isotype control mouse IgG1 (green) and rat isotype control for mAb to foxp3 (orange). #32 mAb only bound to $CD4^{+}CD25^{+}$ $Foxp3^{+}$ Tregs.
Figure 10B:
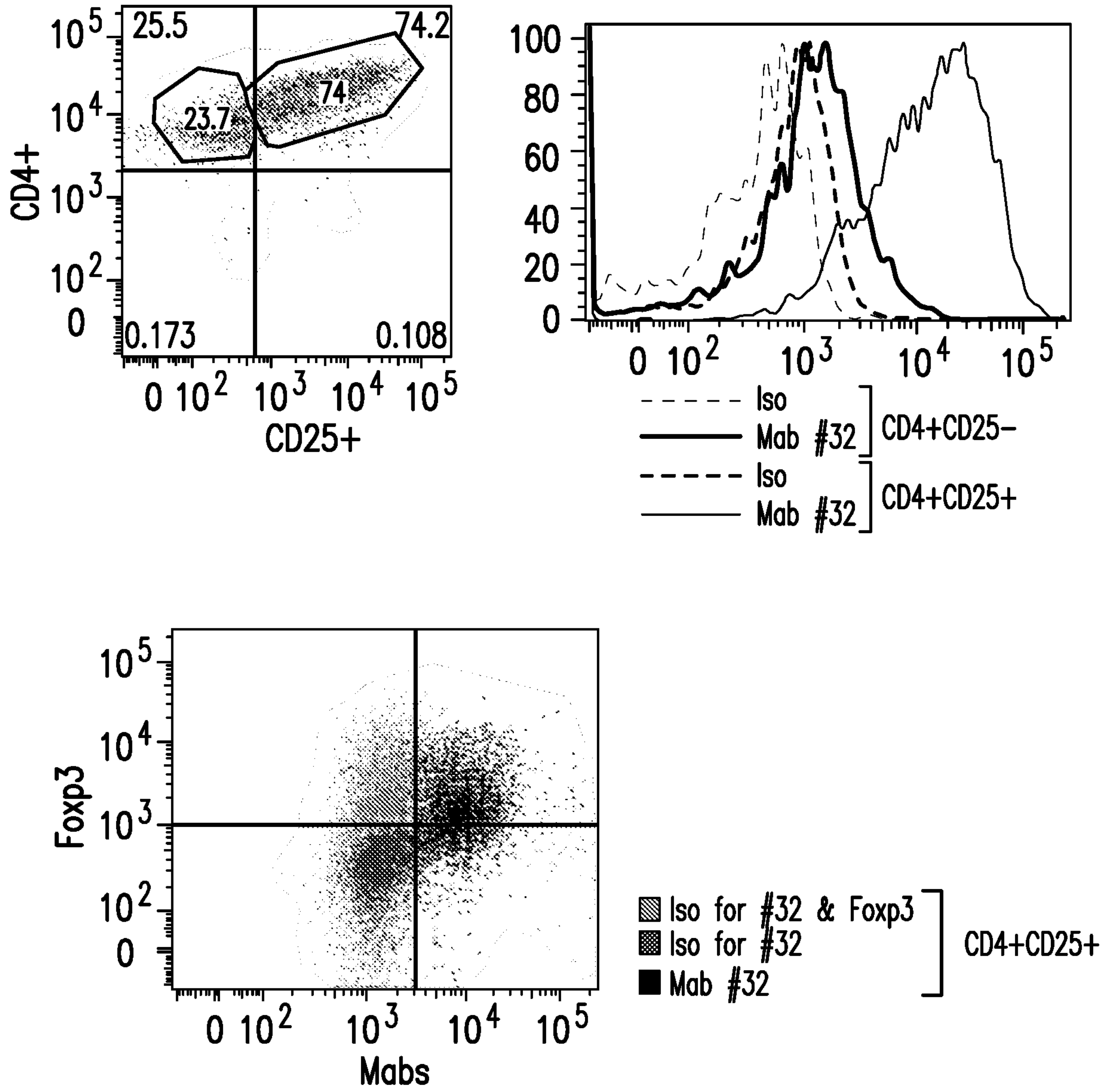

Next, to test if the #32 mAb also recognize inducible Tregs, Treg cell lines were generated by stimulating purified $CD4^+$T cells from a HLA-$A0201^+$ donors with either allo-PBMCs (HLA-A*0201 negative) or tumor cells MAC-2A in the presence of IL-2 and TGF-$\beta^{15-17}$. A typical staining pattern is shown in FIGS. 10A-10B. As shown in FIGS. 10A-10B, EXT017-32 specifically bound to HLA-A*02:$01^+$ Treg cells. Tregs were generated by stimulating $CD4^+$ T cells from a HLA-A*0201 positive donor with either HLA-A*0201 negative allo-PBMC (FIG. 10A) or MAC-2A tumor cells (FIG. 10B). Foxp3 #32 mAb bound strongly to $CD4^+$ $CD25^+$ T cells compare to the single $CD4^+$ T cell population (upper right), and that mAb-#32 only bound to $CD4^+CD25^+$ $Foxp3^+$ population but not $CD4^+CD25^+$ Foxp3 negative population (lower left panel). The results were similar between Tregs generated by either allo-PBMC (FIG. 10A) or MAC-2A cell stimulation (FIG. 10B). These results demonstrated that Foxp3-#32 mAb is able to specifically recognize Tregs expressing Foxp3 epitope in the context of HLA-A*0201 molecule.

It has been shown that may types of human cancer cells express Foxp3, which is associated with poor prognosis and distant metastasis. Therefor, the Foxp3 mAb could also directly attack tumor cells, expressing Foxp3.

6. Mab-#32 BITE-Mediated T Cell Cytotoxicity Against $Foxp3^+$ Tregs and Tumor Cells in the Context of HLA-A*0201

Figure 11A:
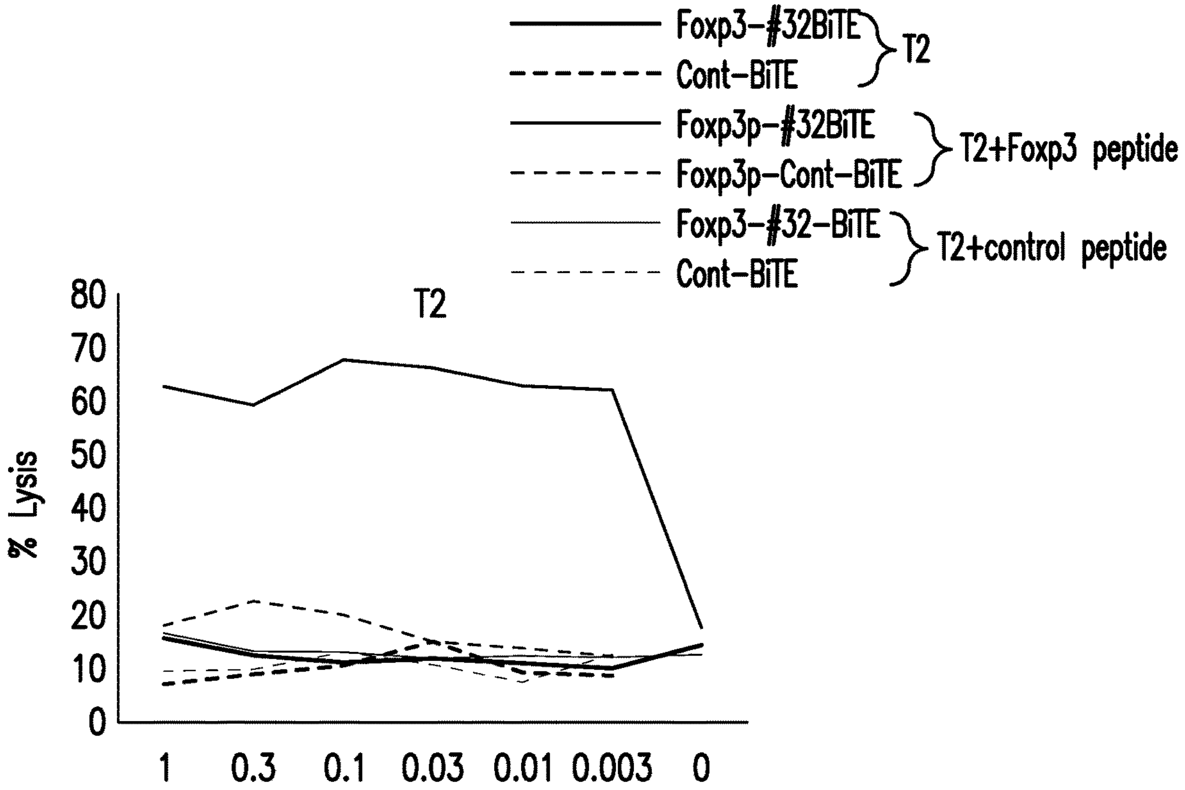
FIGS. 11A-11E represents BITE #32-mediated T cell killing against $Foxp3^{+}$ T lymphoma cells. PBMCs were incubated with TLI-pulsed T2 cells (A: blue line: #32 BITE against T2 alone; red: control BITE against T2 alone; green: #32 BITE against T2 pulsed with TLI peptide; purple: control BITE against T2 pulsed with TLI peptide; light blue: #32 BITE against T2 pulsed with EW peptide; orange: control BITE against T2 pulsed with control peptide), HL-60 (B), MAC-1 (C), MAC-2A (D), or Jurkat (E) target cells at an E: T ratio of 50:1, with or without BITEs at the concentrations ranging from 1 ug/ml to 0.0003 ug/ml. The cytotoxicity was measured by 5 hr $^{51}$Crelease assay. The data represent the mean value of triplicate microwell cultures.
Figure 11B:
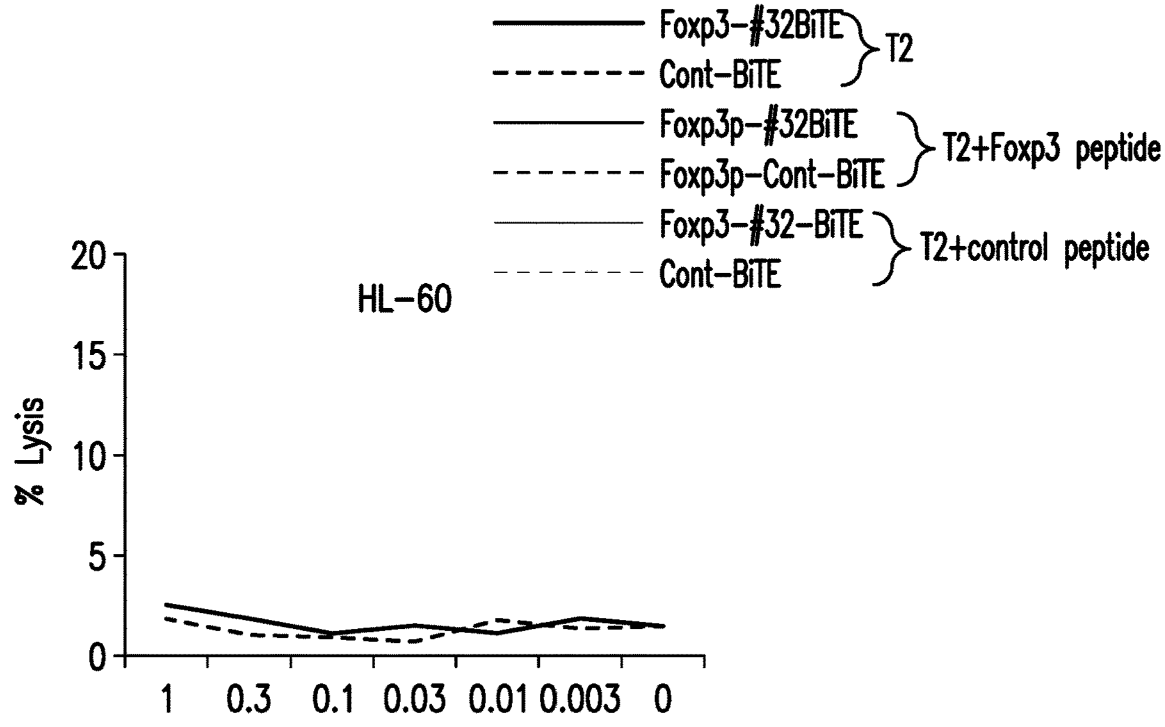
Figure 11C:
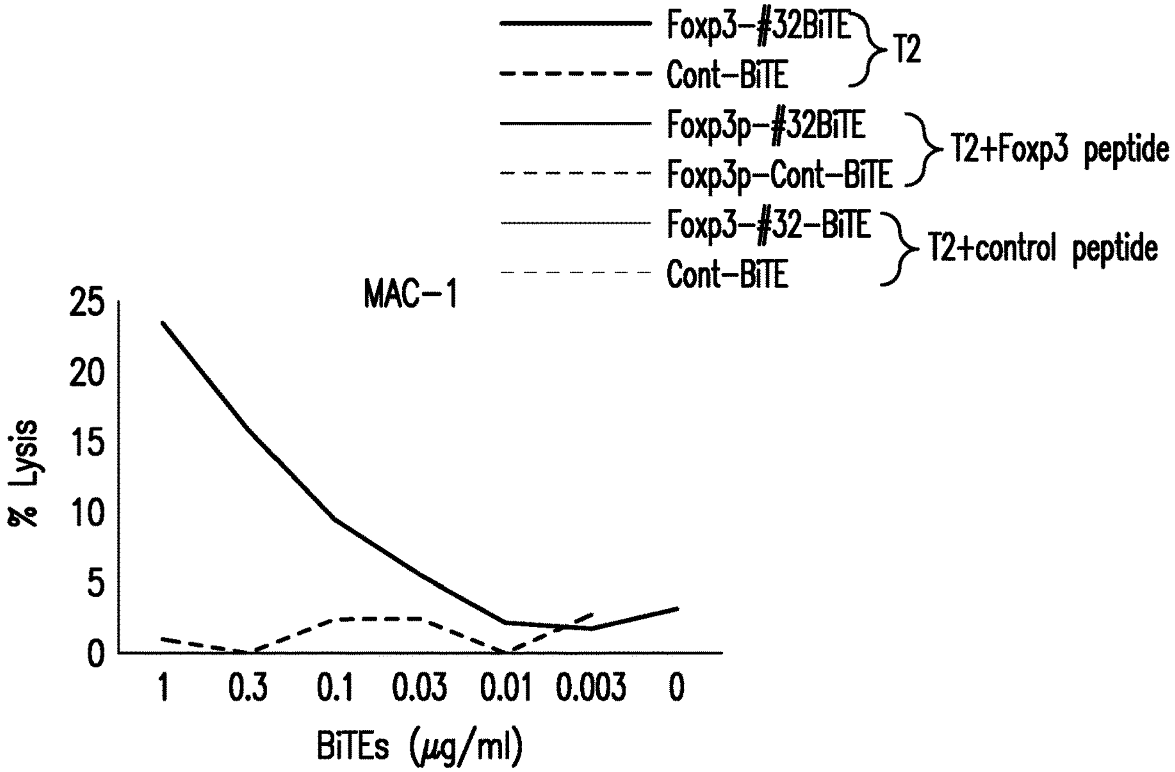
Figure 11D:
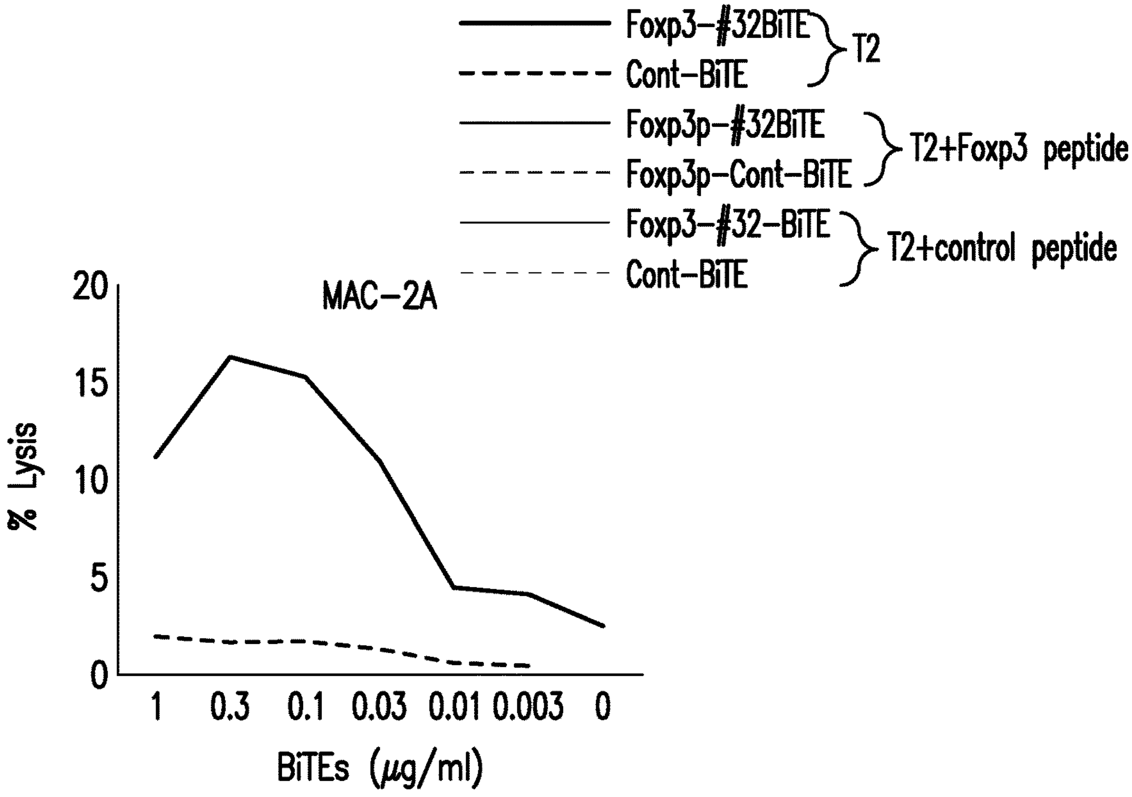
Figure 11E:
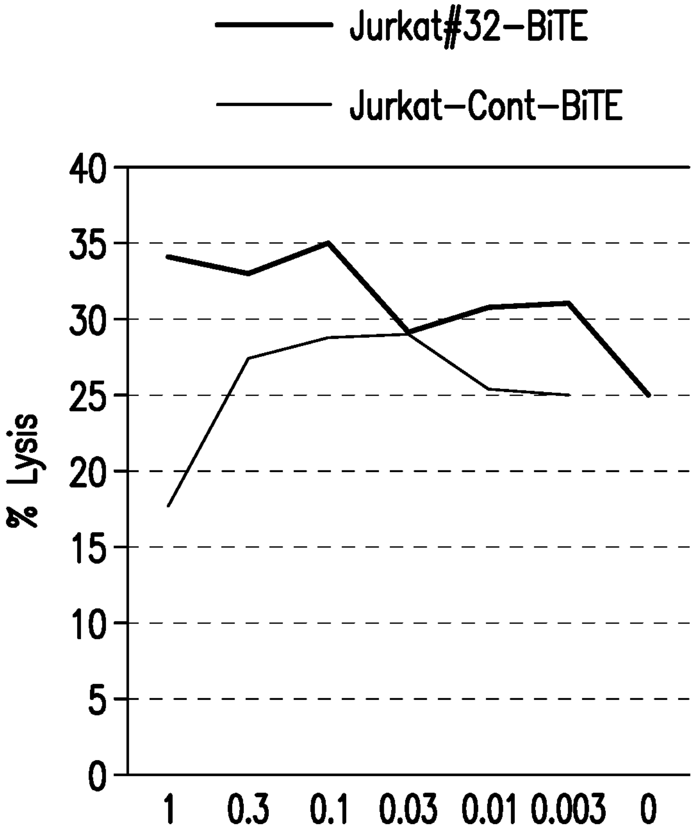

Experiments were done to test whether mAb-#32 BITE was able to mediate T cell killing against Foxp3 TLI epitope in the context of HLA-A*0201 molecule. PBMCs were used as effectors and the cytotoxicity was measured by standard $^{51}$Cr-release assay, in the presence or absence of the #32 BsAb and isotype-derived control BsAb. T2 cells were pulsed with TLI or control HLA-A0*201-binding peptide CT, and PBMCs were used as effectors, in the presence or absence of the mAb #32-BITE or isotype-derived control BITE. Mab-#32 BITE mediated a specific and strong killing activity against T2 cells pulsed with TLI peptide, but not T2 cells alone or pulsed with control peptide (FIG. 11A). Similarly, PBMCs in the presence of mAb-#32-BITE showed dose-dependent killing against Treg-like T lymphoma cell lines MAC-1 and MAC2A cells at the indicated concentrations (FIGS. 11C and 11D), but not $Foxp3^+$/HLA-A*0201 negative cell line HL-60 (FIG. 11B) or Jurkat cells (FIG. 11E). Both MAC-1 and MAC-2A cell lines do not express CD3, and T cell cytotoxicity against these cell lines are not mediated by scFv arm of anti-CD3 mAb. These data demonstrated that mAb-#32 BITE is able to kill the tumor cells expressing Foxp3 and HLA-A0*201, and demonstrated the specificity of killing for the cells expressing Foxp3.

Figure 12A:
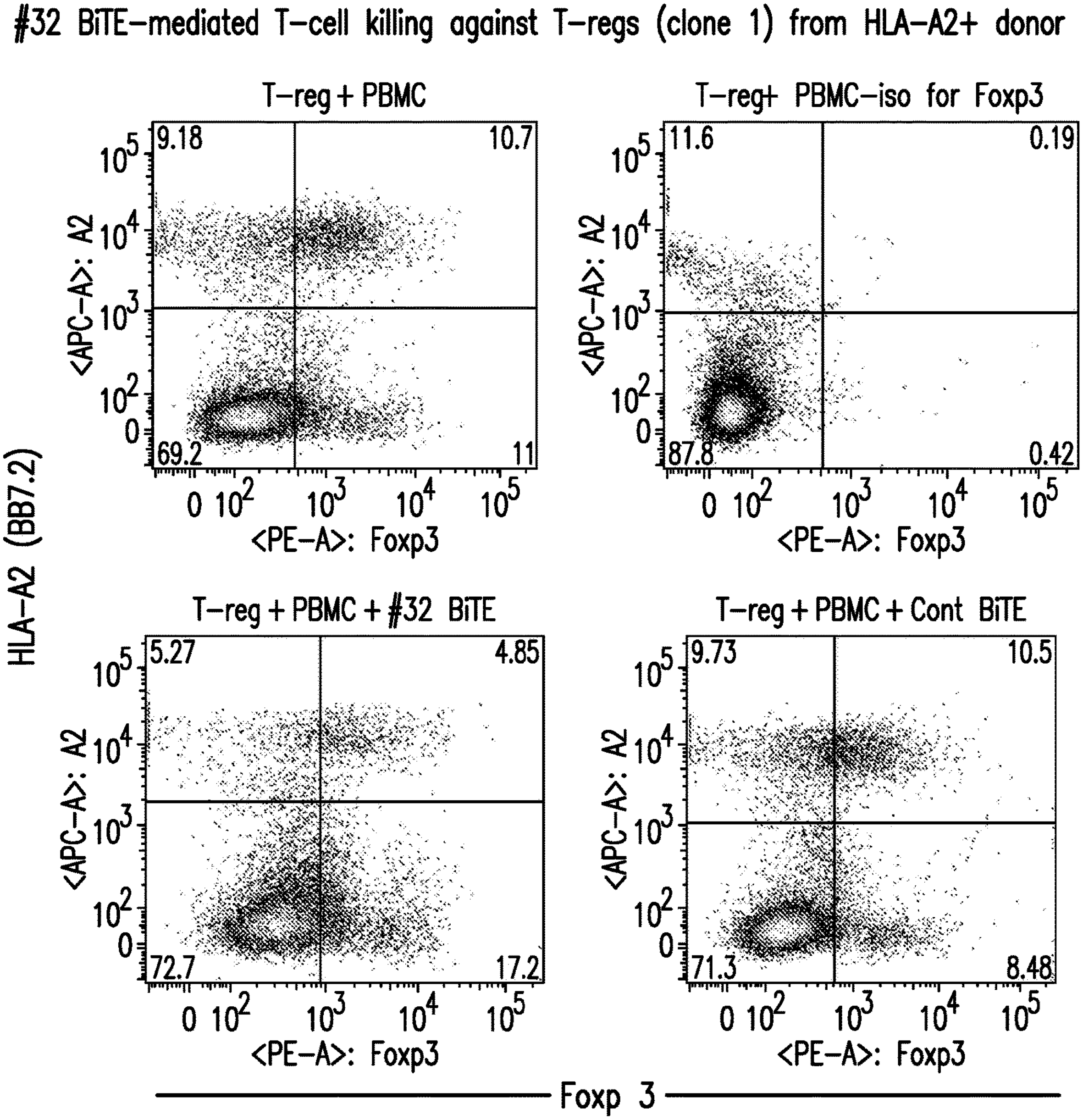
FIGS. 12A-12D represent #32 BsAb-mediated T cell killing against Treg from a HLA-A*02:01$^{+}$ donor. (A and B) Non HLA-A2 T cells were incubated with Treg clones (Treg clone 1 (A) and Treg clone 3 (B)) generated from a HLA-A*02:01$^{+}$ donor in the presence or absence of BsAb #32 or control BsAb (1 μg/ml) at an E: T ratio 5:1, overnight. The percentage of $Foxp3^{+}$ cells in $A2^{+}$ T cells was determined by flow cytometry. $Foxp3^{+}$ cells were gated on HLA-A2$^{+}$ (BB7.2). Reduction of the HLA-A2$^{+}$ $Foxp3^{+}$ cells indicated the #32 BsAb-mediated T cell killing. Data shows a representative data from duplicate cultures. (C) Flow cytometer data shown in FIGS. 12A and 12B was summarized as a bar graph to show the reduction of percent Treg cells. Each data point shows the average of duplicate cultures. (D) Treg cells lysis data of #32 BsAb, control-BsAb and No BsAb.
Figure 12B:
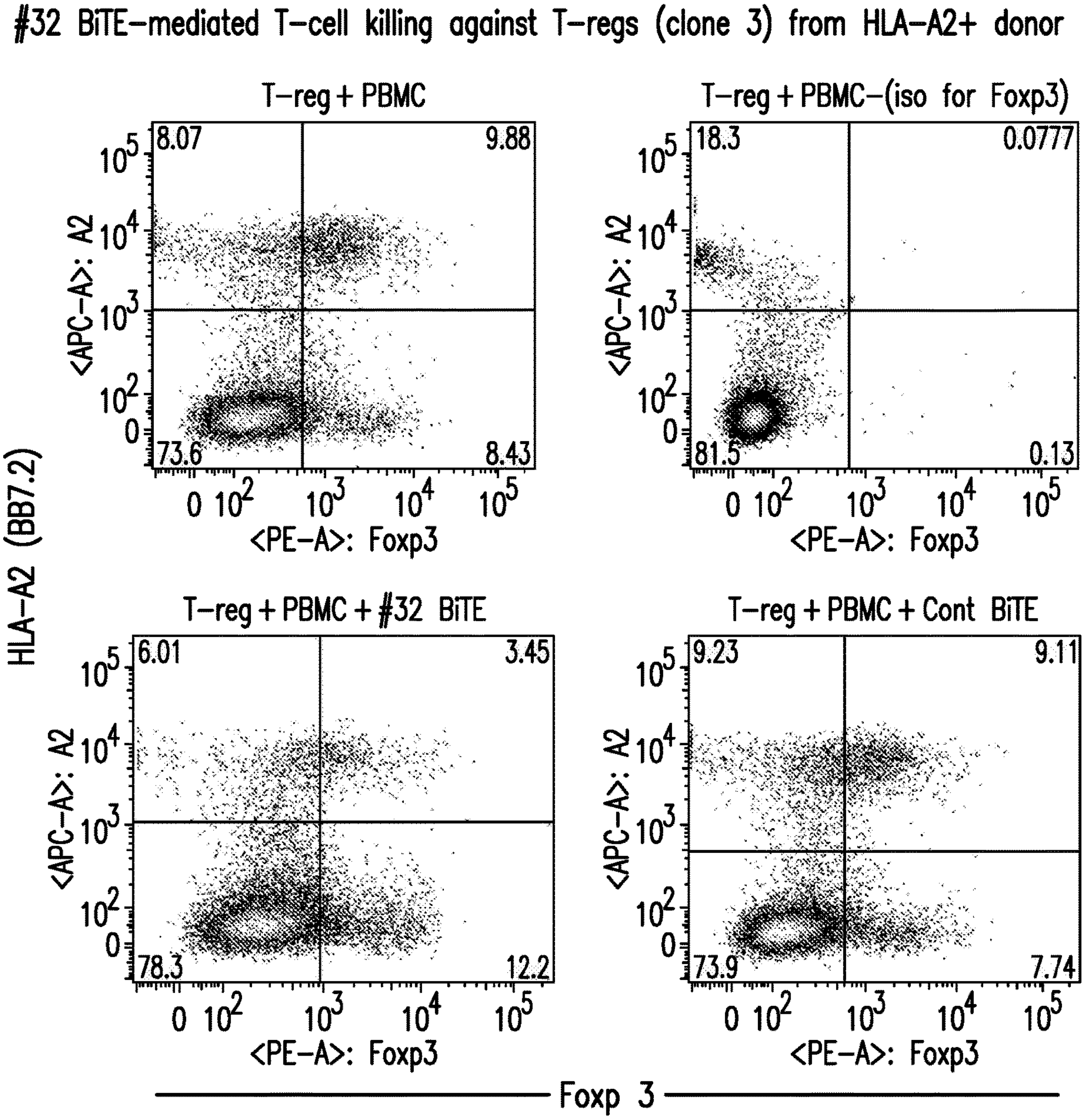
Figure 12C:
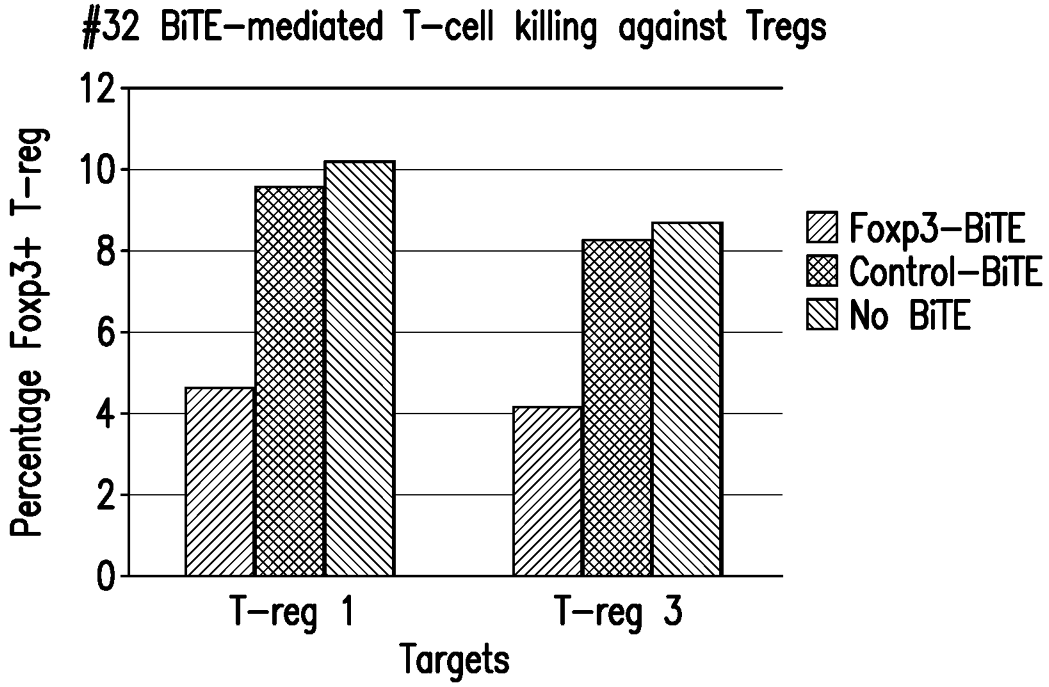
Figure 12D:
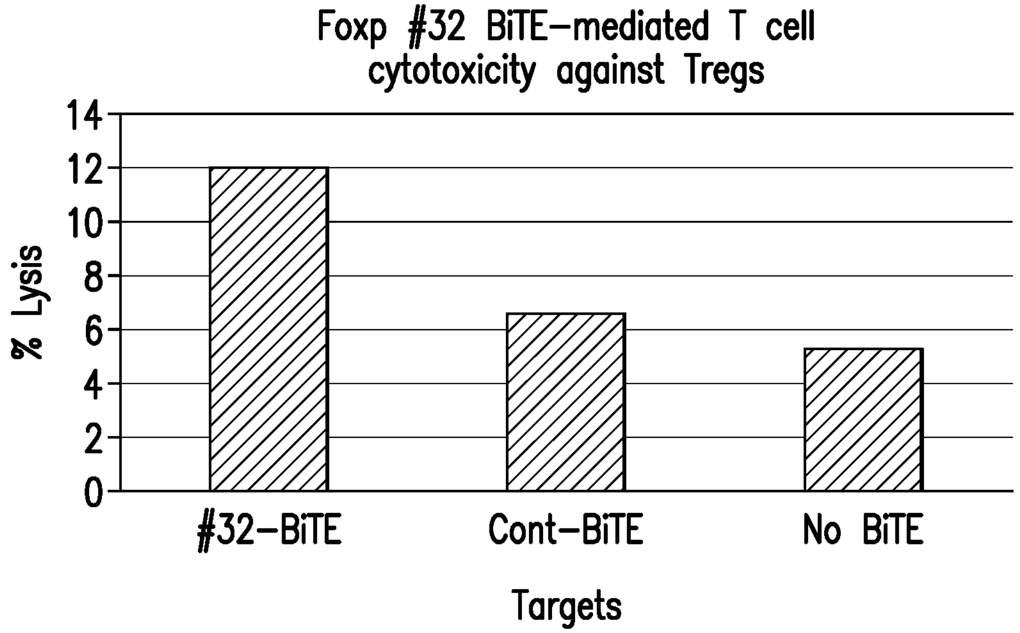
Figure 13A:
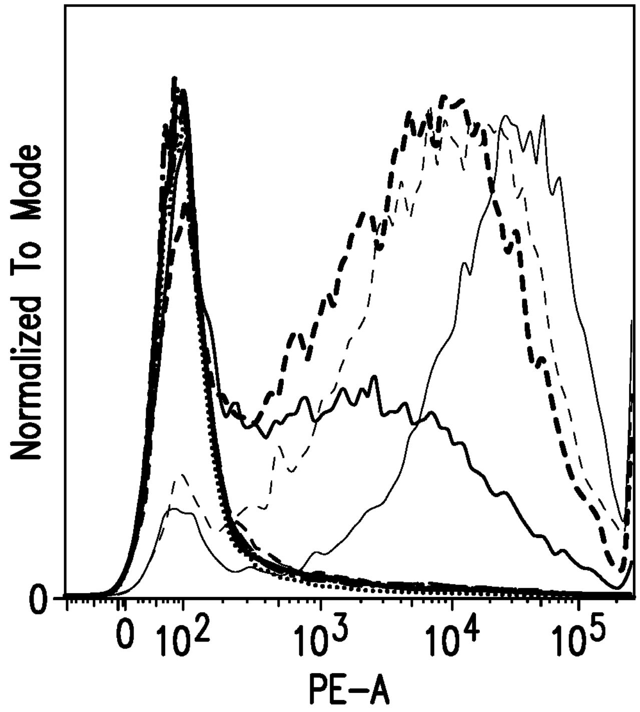
FIGS. 13A-13H represent histograms of the 8 EXT017-phage binding to T2 cells loaded with the panel of alanine mutants. (A) Histogram of EXT017-17 phage binding to T2 cells loaded with the panel of alanine mutants. (B) Histogram of EXT017-18 phage binding to T2 cells loaded with the panel of alanine mutants. (C) Histogram of EXT017-20 phage binding to T2 cells loaded with the panel of alanine mutants. (D) Histogram of EXT017-27 phage binding to T2 cells loaded with the panel of alanine mutants. (E) Histogram of EXT017-28 phage binding to T2 cells loaded with the panel of alanine mutants. (F) Histogram of EXT017-32 phage binding to T2 cells loaded with the panel of alanine mutants. (G) Histogram of EXT017-53 phage binding to T2 cells loaded with the panel of alanine mutants. (H) Histogram of EXT017-53 phage binding to T2 cells loaded with the panel of alanine mutants.
Figure 13B:
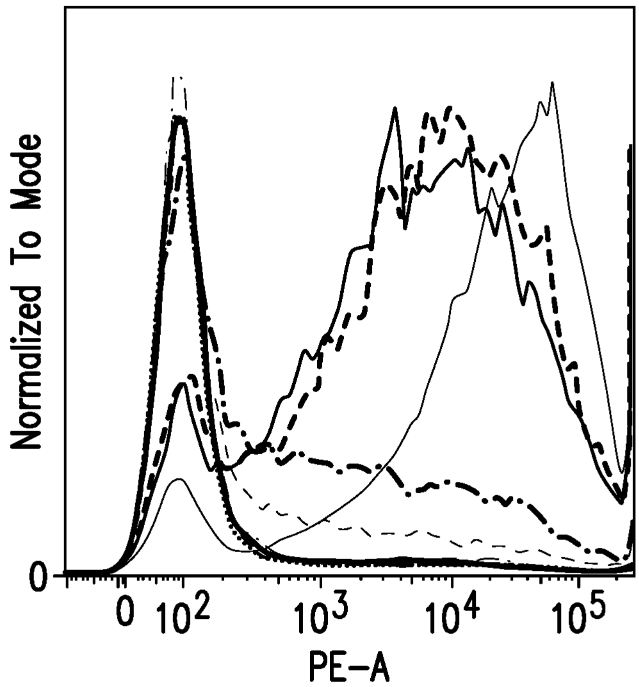
Figure 13C:
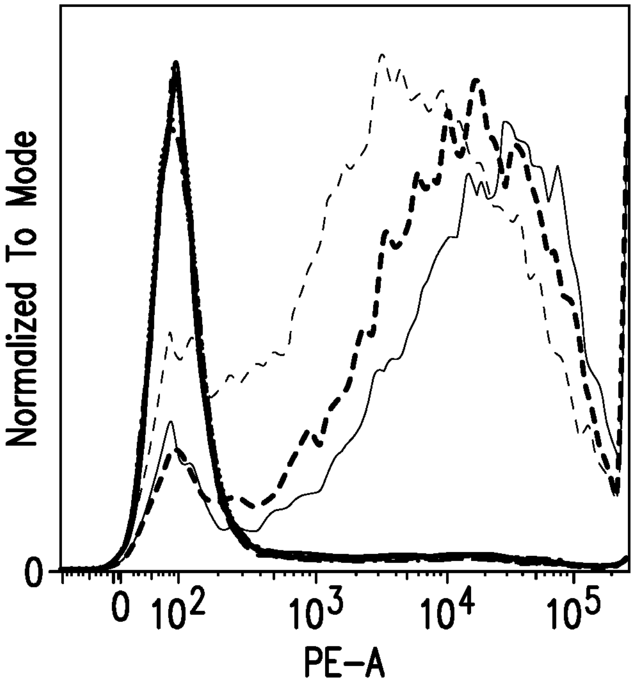
Figure 13D:
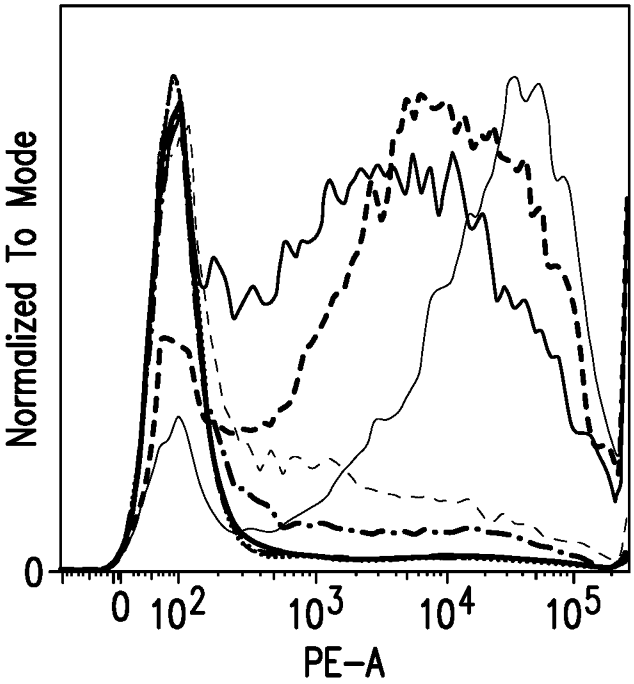
Figure 13E:
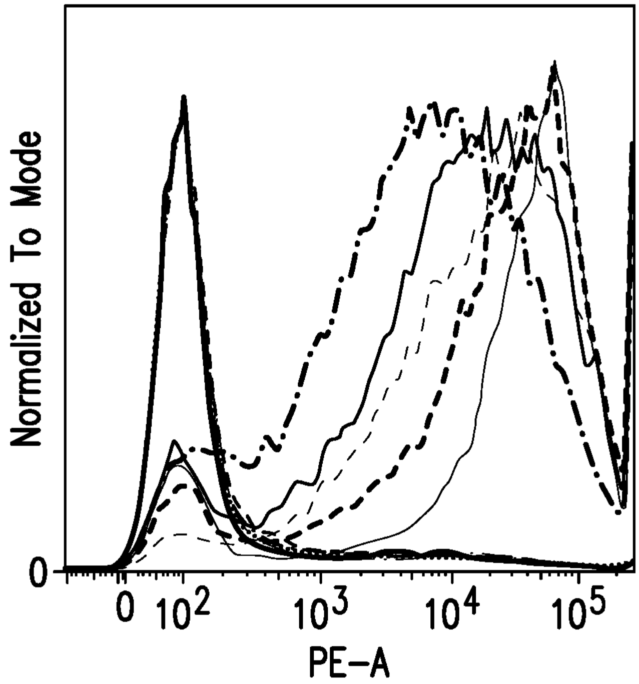
Figure 13F:
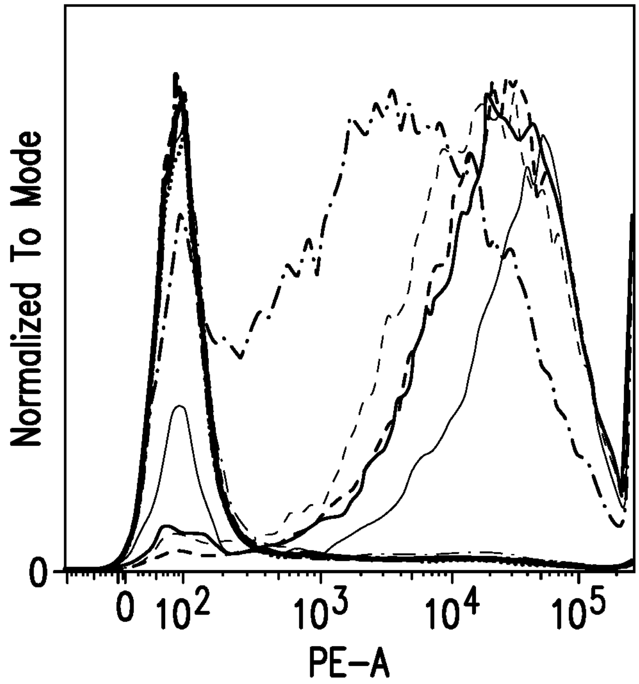
Figure 13G:
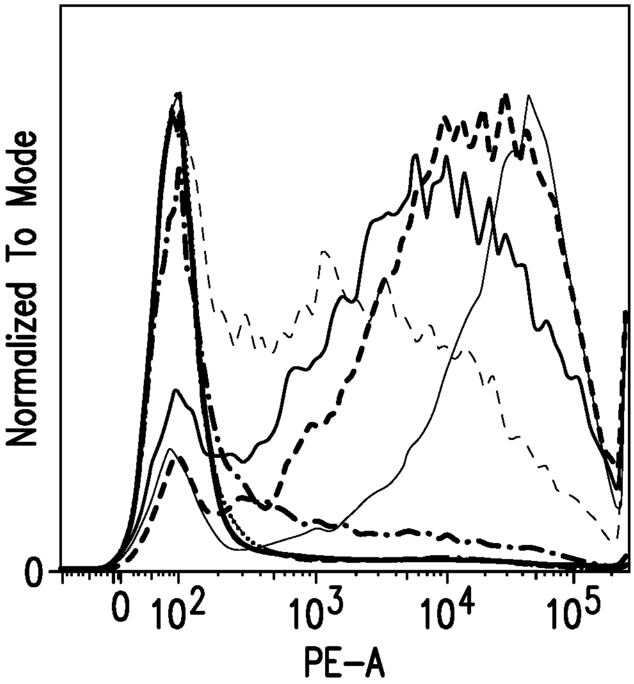
Figure 13H:
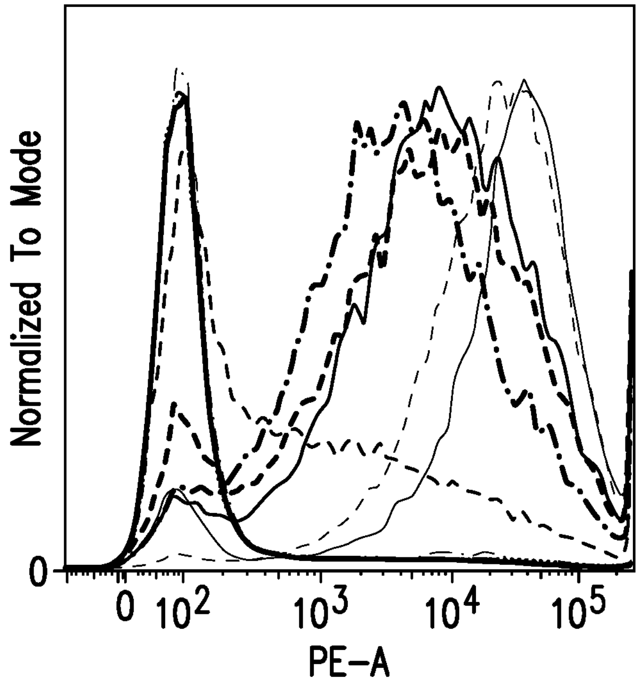

Since Treg population in healthy PBMCs might be too low to measure the cytotoxicity mediated by the BITE, Treg clones were generated from HLA-$A0201^+$ donor by allo-stimulation, followed by limiting dilution. Two different Treg clones were incubated with PBMCs from HLA-A*02-negative donor, in the presence or absence of Foxp3-BITE or control BITE for overnight. Then the percentage of $Foxp3^+$ cells in HLA-A*0201 T cells population (only from Treg clones) was measured by flow cytometry. Reduction of the HLA-A*$02^+$ $Foxp3^+$ cells indicates the Foxp3-BITE-mediated T cell killing. FIGS. 12A-12B show the results from two Treg clones respectively. Flow cytometer data shown in FIGS. 12A-12B was summarized as a bar graph in FIG. 12C to show the reduction of percent Treg cells. In clone 3, the percentage of HLA-A*$02^+$ $Foxp3^+$ T cells decreased about more than 60% in the presence of #32-BITE (3.45%), compared to controls with only effectors (PBMC: 9.88%) or effectors with control BITE (9.11%). The similar results were obtained from the other Treg clone.

These results demonstrated that the #32-BITE is able to recognize and mediates T cell cytotoxicity against Tregs in the context of HLA-A*0201 molecule.

7. Binding Affinity of the EXT017 Antibodies to Foxp3 Peptide/HLA-A*02:01 Complex The 8 EXT017-BsAbs were evaluated for binding affinity to EXT017 peptide/HLA-A*02:01 complex using biolayer interferometry (BLI), and the results are shown in Table 5.

TABLE 5

| Antibody | $k_d$ [1/s] | Error in $k_d$ [1/s] | $k_a$ [1/Ms] | $K_D$ [nM] |
|---|---|---|---|---|
| EXT-017-17 BsAb | 2.63E−3 | 5.46E−5 | 1.84E7 | 144 |
| EXT-017-18 BsAb | 1.88E−3 | 6.79E−5 | 5.31E7 | 35.4 |
| EXT-017-20 BsAb | 1.75E−3 | 4.84E−5 | 7.90E6 | 221 |
| EXT-017-27 BsAb | 2.08E−3 | 7.06E−5 | 4.28E7 | 48.5 |
| EXT-017-28 BsAb | 1.89E−3 | 6.79E−5 | 1.00E7 | 188 |
| EXT-017-32 BsAb | 2.27E−3 | 6.26E−5 | 3.15E7 | 72.2 |
| EXT-017-53 BsAb | 2.35E−3 | 6.98E−5 | 4.84E7 | 48.6 |
| EXT-017-54 BsAb | 1.05E−3 | 9.41E−5 | 3.19E7 | 32.9 |

The binding affinity of the EXT017-32-hIgG1 and mIgG1 to EXT017 peptide/HLA-A*02:01 complex was measured using surface plasmon resonance (SPR), and the results are shown in Table 6.

TABLE 6

| Antibody | $k_d$ [1/s] | $k_a$ [1/Ms] | $K_D$ [nM] |
|---|---|---|---|
| EXT017-32 mIgG | 1.12E$^+$07 | 0.005167 | 0.462 |
| EXT017-32 hIgG | 5.97E$^+$07 | 0.01222 | 0.205 |

DISCUSSION

Development of therapeutic strategies to deplete or interfere with the function of Tregs, without compromising anti-tumor immunity has been challenging, because there is no Treg-specific surface marker. One of the obstacle for specific depletion of Tregs is that both Tregs and effector T cells exhibit an activated phenotype, especially in expression patterns of cell surface molecules; both are high in CD25, cytotoxic T lymphocyte-associated antigens (CTLA)-4, OX40 and glucocorticoid-induced tumor necrosis factor receptor-related protein (GITR) expression. Depletion of Tregs alone or in combination of vaccination by anti-CD25 mAb has been shown to contribute to improved anti-tumor immune response in various animal models. However, clinically, targeting CD25 by using dacizumab (anti-CD25 mAb) or Denileukin diftitox, a recombinant protein composed of IL-2 and the active domain of diphtheria toxin, has shown less promising outcome. Although Tregs express CTLA-4, results from clinical studies suggest that the effects of anti-CTLA-4 treatment is due to increased activation of effector T cells, or there is a Treg-depletion effect early after initial administration which permits the optimal induction of effector cell responses. Most recently, Sakaguchi group has shown that C—C chemokine receptor 4 (CCR4) is predominantly expressed in effector Tregs (eTregs; CD45RA-Foxp3$^{hi}$ CD4$^+$) in TILs in melanoma patients. In vitro depletion of this population using anti-CCR4 mAb enhanced T cell responses when stimulated with NY-ESO-1 peptides. When the mAb was administered to a patient with T cell leukemia-lymphoma, the eTreg fraction is reduced and NY-ESO-1-specific CD8 T cell response is augmented. CCR-4 is the cognate receptor for CC chemokines CCL17 and CC122, and is expressed on functionally distinct subsets of immune cells. In addition to Tregs, it is also expressed in activated T cells, Th2 cells, platelets, NK cells, macrophages and dendritic cells (DCs). Similarly, targeting GITR using cognate ligand or agonistic mAb has been shown to be effective in anti-tumor response in murine models. However, the clinical efficacy of such strategy remains to be investigated in human trials.

Foxp3 is a transcription factor in the forkhead/winged-helix family and is predominantly found in CD4$^+$CD25$^+$ Treg cells, consisting of 2% to 5% of the total CD4$^+$ T cell population, but significantly enriched in the tumor mass, peripheral blood or ascites in cancer patients. Tumor cells not only recruit Tregs to tumor sites but also play a crucial role in the conversion of naïve and or effector T cells into Tregs by providing antigenic stimulation and cytokines directly or indirectly through tumor-infiltrating lymphocytes (TILs). In TILs, the ratio of effector T cells to Tregs determines disease outcome. There exists a strong correlation between tumor progress and Tregs, with increased numbers or frequency of Tregs associated with poor prognosis in a variety of cancers, including ovarian, breast, non-small cell lung, hepatocellular, renal cell, pancreatic and gastric carcinomas[1-7]. Although the precise mechanisms of Treg-mediated immune suppression is not fully understood, Tregs can act in part by secreting immunosuppressive cytokines and suppressing the activation and proliferation of T cells in a cell contact-dependent mechanism. In Tregs, the most important function of Foxp3 is that its ectopic expression in normal T cells can convert them to Treg-like cells functionally and phenotypically. Therefore, Foxp3 has been considered to be a master regulatory gene for lineage-commitment and developmental differentiation of Tregs.

Interestingly, immunosuppressive function of Foxp3 is not only limited in Tregs. Hinz et al have reported that Foxp3 expression was detected in majority of pancreatic cancer patients. Ectopic expression of Foxp3 in pancreatic adenocarcinoma cells induced complete inhibition of T cell proliferation in vitro, and this effect was partially abrogated by silencing Foxp3 gene expression using siRNA. The authors suggested that pancreatic cancer cells expressing Foxp3 mimic Treg function, which may represent a new mechanism of immune evasion in cancer patients. Immune suppressive function of Foxp3 has also been suggested in adult T leukemia (ATL) patients who are characterized by constitutive expression of CD4 and CD25 in leukemic cells and marked immune-deficient state. Subsequently, there have been numerous reports that many types of cancer cells express Foxp3, further support the important role of Foxp3 in tumor suppressive microenvironment.

Foxp3 has long been considered the most definitive marker for Tregs, and is an attractive target. However, there are no drugs or mAbs that inhibit Foxp3, because the protein is intracellular, inaccessible to traditional antibody therapy. While it is intracellular, certain proteasome-processed FOXp3 peptides can be expressed on the cell surface when presented by MHC class I molecules, to be recognized by CD8 T cells. Indeed, Anderson group has demonstrated that Foxp3-specific cytotoxic CD8 T cells are present in human PBMCs, especially in cancer patients. Such CTLs are able to recognize Tregs and kill malignant Treg-like cutaneous T lymphoma cells in a HLA-A*0201-restricted manner. The study has thus demonstrated the possibility of targeting intracellular Foxp3 by an approach of using peptide-specific CTLs. A novel approach in the instant application has been taken to develop a T cell receptor mimic mAb (TCRm), specific for the Foxp3 peptide in the context of HLA-A*02:01. A number of peptides were identified from Fopx3 protein that could induce specific CD8 T cell response in the context of HLA-A*0201 molecule. Because Foxp3 is a member of the large forkhead protein family, to avoid potential off targets, the peptide TLI was selected for mAb engineering, which has a minimal homology with other Foxp family members, such as Foxp1, 2 and 4. The mAb was successfully generated and is able to specifically bind to and kill Foxp3 positive cancer cell lines and Treg cells.

It is known that activated conventional T cells can transiently express Foxp3. However, activated CD4$^+$CD25$^+$ T cells and Tregs, can be distinguished by the expression of CD127, the alpha chain of IL-7 receptor. Tregs express low CD127 but activated T cells express high CD127. The TCRm Foxp3-#32 only bound to CD127 low CD25 high, Foxp3 high population of CD4$^+$ T cells in HLA-A*0201$^+$ healthy donors. When in vitro-induced Tregs were tested, the Foxp3 mAb only bound to CD4$^+$CD25hi population but not to CD25lo/negative population. In general, TCRm mAb recognizes a low density peptide/HLA complex, and low expression of either targeted proteins or HLA would be difficult for such a mAb to have effective recognition. Therefore, a Foxp3 TCRm mAb would only bind to the cells highly expressing Foxp3. In addition, in tumor microenvironment, T cells are profoundly in an inactivated state and CD25hiFoxp3hiCD4 T cells are most likely Tregs. This opens a therapeutic window of designing an effective combination therapies by depleting Treg first using the Foxp3-#32 mAb, followed by strategies that expand effector T cells or augment their effector activity, using approaches such as vaccination or check point blockade. Such strategy could avoid cocominatant depletion of Tregs and activated T cells, whereby achieving selective and more effective therapeutic outcome.

Example 2-Peptide Epitope Mapping for Foxp3-7 Top Phage Clones

Epitope mapping of the 8 EXT017 antibodies against Foxp3-7 peptide was performed to determine the epitope necessary for antibody binding. Briefly, mutant EXT017 peptides were generated with alanine substitutions at positions 1-9 and these were individually pulsed onto the surface of T2 cells. Peptide-loaded T2 cells were stained with EXT017-phage and binding was measured by flow cytometry. Table 7 lists the mutant EXT017 amino acid sequences used in the experiment. Table 8 summarizes the Mean Fluorescence Intensity (MFI) values of EXT017-phage FACS staining towards T2 cells loaded with the panel of alanine mutants shown in Table 7. As shown in Table 8, EXT017-mut2 was for anchor position. The histograms of the 8 EXT017-phage binding to T2 cells loaded with the panel of alanine mutants are shown in FIGS. 13A-13H. Table 7 discloses SEQID NOS: 8 and 144-152, respectively, in order of appearance.

TABLE 7

| | |
|---|---|
| EXT017: | TLIRWAILEA |
| 017-mut1: | ALIRWAILEA |
| 017-mut2: | TAIRWAILEA |
| 017-mut3: | TLARWAILEA |
| 017-mut4: | TLIAWAILEA |
| 017-mut5: | TLIRAAILEA |
| 017-mut7: | TLIRWAALEA |
| 017-mut8: | TLIRWAIAEA |
| 017-mut9: | TLIRWAILAA |
| G10: | TLIRWAILEG |

TABLE 8

| Phage Clone | T2 | EXT017 | 017-mut1 | 017-mut2 | 017-mut3 | 017-mut4 | 017-mut5 | 017-mut7 | 017-mut8 | 017-mut9 | Sensitive Position |
|---|---|---|---|---|---|---|---|---|---|---|---|
| EXT017-17 | 92.9 | 2.36E+04 | 7884 | 99.8* | 741 | 103* | 98.1* | 97.8* | 3587 | 94.7* | 4, 5, 7, 9 |
| EXT017-18 | 90.6 | 2.59E+04 | 143* | 97.3* | 5152 | 99.1* | 95.8* | 95.4* | 6603 | 386* | 1, 4, 5, 7, 9 |
| EXT017-20 | 91.3 | 1.71E+04 | 4074 | 96* | 96.4* | 93.7* | 95* | 94.9* | 1.11E+04 | 95.6* | 3, 4, 5, 7, 9 |
| EXT017-27 | 90.4 | 2.12E+04 | 222* | 98.2* | 2257 | 99* | 95.4* | 96.3* | 6405 | 131* | 1, 4, 5, 7, 9 |
| EXT017-28 | 93.9 | 3.95E+04 | 2.01E+04 | 102* | 1.34E+04 | 108* | 107* | 96.4* | 2.75E+04 | 5891 | 4, 5, 7 |
| EXT017-32 | 91.8 | 2.75E+04 | 1.51E+04 | 103* | 2.10E+04 | 2.08E+04 | 2713 | 99.6* | 96.7* | 93.6* | 7, 8, 9 |
| EXT017-53 | 89.5 | 2.58E+04 | 1102 | 95.3* | 5779 | 95.8* | 98.5* | 98.9* | 1.21E+04 | 149* | 4, 5, 7, 9 |
| EXT017-54 | 89.9 | 3.04E+04 | 2.35E+04 | 94.7* | 7776 | 374* | 91.2 | 91.1* | 5846 | 3535 | 4, 5, 7 |

Positions affecting antibody binding (binding MFI<20% of the wildtype peptide) are marked with *.

Example 3—CAR T Cell Targeting Foxp3

Adoptive transfer of CAR T cells has emerged as an effective therapy for B-cell ALL and other hematopoietic cancers. However, greater potency and mechanisms to defeat the immunosuppressive tumor microenvironment are still needed for many cancer types. One approach is to overcome tumor resistance by modifying CAR T cells to constitutively express a therapeutic TCRm CAR that can kill Treg cells, preferentially in the vicinity of the antigen directed CAR T cells. A T-cell receptor-mimic (TCRm) CAR that is reactive to a peptide fragment of Foxp3 is generated, that can kill Foxp3 expressed on the surface of the Treg cells and tumor cells in the context of HLA-A*02:01. T cells are modified to express this Foxp3-targeted CAR.

Generation of Retroviral Constructs and Transduction

A presently disclosed Foxp3 scFv sequence is used to generate a second generation CAR targeting Foxp3. The variable heavy and light chains (connected with a $(Gly_4Ser)_3$ linker) and a c-myc tag are added to allow detect CAR expression by flow cytometry. The CAR is optimized to include a spacer domain upstream of the CD28 transmembrane domain if required. This is cloned into the SFG retroviral vector containing the CD28 and CD3 zeta or 4-1BB or other similar signaling CAR forms that are well known in the art, e.g., Park (2016). Stable 293 viral producing cell lines are generated, and used to transduce primary human T cells as described previously (Rafiq (2017)). Following transduction, CAR expression is verified by flow cytometry, staining for the c-myc tag incorporated into the Foxp3-CAR. Retroviral transduction of primary human T cells has been previously described (Koneru (2015)).

Characterizing the Specificity and Activity of the Foxp3 CAR In Vitro and In Vivo.

The ability of the Foxp3-CAR to redirect T cell function is analyzed in vitro by detecting the Foxp3-specific cytotoxicity, cytokine secretion and proliferative function of PR20-transduced T cells, as previously described (Rafiq (2017)). Specific cytotoxicity is measured using a standard $^{51}$Chromium release assay against Tregs from HLA-A0201$^+$ donors or Foxp3$^+$ HLA-A*0201 positive or negative tumor cell lines. Specific cytokine secretion is measured by collecting supernatant from 24 hr cocultures of Foxp3T cells and Foxp3$^+$ or Foxp3$^-$ cells. The presence of cytokines is analyzed using Luminex technology. The ability of the foxp3 CAR to stimulate T cell proliferation is analyzed by coculturing transduced T cells with Foxp3$^+$ tumor cells and monitoring T cell expansion with flow cytometry using enumeration beads. T cells transduced to express a CAR targeted to an irrelevant antigen will be used as a control, as published previously (Rafiq (2017)).

Characterizing the Anti-Tumor Efficacy of the Foxp3 CAR In Vivo.

The ability of Foxp3-CAR T cells to eradicate Foxp3$^+$ tumor in vivo is assessed using preclinical xenogeneic murine models. SCID-Beige or NSG mice is inoculated (either systemically for hematological malignancies, or intraperitoneally for solid tumors) with tumor cells modified to express FireFly Luciferace (FFLuc) to allow bioluminescent imaging (Rafiq (2017)). Mice are subsequently treated with systemic infusion of foxp3− or control CAR T cells (expressing a CAR targeted to an irrelevant antigen). Disease progression is monitored both clinically and with bioluminescent imaging as described previously (Rafiq (2017)). Persistence of CART cells is determined by collecting peripheral blood from treated mice and flow cytometry to detect $CAR^+$ T cells. CAR function over time is determined by detection of cytokines in the serum of treated mice using Luminex technology.

Various patents and publications are cited herein, the contents of which are hereby incorporated by reference in their entireties.

REFERENCES

1. Wolf A M, Wolf D, Steurer M et al. Increase of regulatory T cells in the peripheral blood of cancer patients. *Clin. Cancer. Res.* 9: 606, 2003.
2. Liyanage U K, Moore T T, Joo H G et al. Prevalence of regulatory T cells is increased in peripheral blood and tumor microenvironment of patients with pancreas or breast adenocarcinoma. *J. Immunol.* 169: 2756, 2002.
3. Curiel T J, Coukos G, Zou L et al. Specific recruitment of regulatory T cells in ovarian carcinoma fosters immune privilege and predicts reduced survival. *Nat. Med.* 10: 942, 2004.
4. Baumgartner J, Wilson C, Palmer B et al. Melanoma induces immunosuppression by up-regulating $Foxp3^+$ regulatory T cells. I Surg. Res. 141: 72, 2007.
5. Dannull J. Su Z, Rizzieri D et al. Enhancement of vaccine-mediated antitumor immunity in cancer patients after depletion of regulator T cells. *J. Clin. Invest.* 115 (12): 3623
6. Bos P D, Plitas G. Rudra D et al. Transient regulatory T cell ablation deters oncogene-driven breast cancer and enhances radiotherapy. *J Exp. Med.* 210 (11): 2435, 2013.
7. Nair S, Boczkowski, Fassnacht M et al. Vaccination against the forkhead family transcription factor Foxp3 enhances tumor immunity. *Cancer Res.* 67 (1): 371, 2007.
8. Sugiyama D, Nishikawa H, Maeda Y et al. Anti-CCR4 mAb selectively depletes effector-type $Foxp3^+CD4^+$ regulator T cells, evoking antitumor immune responses in humans. *PNAS.* 110 (44): 17945, 2013.
9. Rech A J, Mick R, Martin S et al. CD25 blockade depletes and selectively reprogram regulatory T cells in concert with immunotherapy in cancer patients. *Sci. Transl. Med.* 4 (134): 134rd62, 2012.
10. Litzinger M T, Fermando R, Curiel T J et al. IL-2 immunotoxin denileukin diftitox reduces regulator T cells and enhances vaccine-mediated T-cell immunity. *Blood* 110 (9): 3192-201. 2007.
11. Heid J B, Schmidt A, Oberle N et al. $Foxp3^+CD25$-tumor cells with regulatory function in sezary syndrome. *J. Invest. Dermatol.* 129: 2875-2885, 2009.
12. Rena May, Tao Dao, Javier Pinilla-Ibarz et al. $CD4^+$ peptide epitopes from the WT1 oncoprotein stimulate $CD4^+$ and $CD8^+$ T cells that recognize and kill human malignant mesothelioma tumor cells. *Clin. Cancer Res.* 13: 4547-4555, 2007.
13. Tao Dao, Tatyana Koronsvit, Victoria Zakhaleva et al. Identification of a human cyclin D1-derived peptide that induces human cytotoxic CD4 T cells. *Plos One* 4 (8): e6730, 2009.
14. Larsen S K, Munir S, Woetmann A et al. Functional characterization of Foxp3-specific spontaneous immune responses. *Leukemia* 27: 2332-2340, 2013.
15. Lu L, Zhou X, Wang J etal. Characterization of protective human $CD4^+CD25^+$ $Foxp3^+$ regulatory T cells generated with IL-2, TGF-b and retinoic acid. *PLoSONE*5 (12): e15150. doi:10.1371/journal.pone.0015150, 2010.
16. Godfrey W R, Ge Y G, Spoden D J et al. In vitro-expanded human $CD4^+CD25^+$ regulatory T cells can markedly inhibit allogenic dendritic cell-stimulated MLR cultures. *Blood* 104: 453-461, 2004.
17. Levings M K, Sangregorio R, Sartirana C et al. Human $CD4^+CD25^+$ T suppressor cells clones produce transforming growth factor b, but not interleukin 10, and are distinct from type 1 T regulator cells. *J Exp Med.* 196 (10): 1335-1346, 2002.
18. Tao Dao, Su Yan, Nicholas Veomett, Dmitry Pankov, Liang Zhou, Tatyana Krontsvit, Andrew Scott, Joseph Witten, Peter Maslak, Emily Casey, Taochao Tan, Hong Liu, Victoria Zakhaleva, Michael Curcio, Ekaterina Doubrovina, Richard R. O'Reilly, Cheng Liu and David A. Scheinberg. Targeting the intracellular WT1 oncogene product with a therapeutic human antibody. *Sci Transl Med.* 5 (176) 176ra33, 2013.
19. Tao Dao, Dmitry Pankov, Andrew Scott, Tatyana Korontsvit, Victoriya Zakhaleva, Yiyang Xu, Jingyi Xiang, Su Yan, Manuel Direito de Morais Guerreiro, Nicholas Veomett, Leonid Dubrovsky, Michael Curcio, Ekaterina Doubrovina, Vladimir Ponomarev, Cheng Liu, Richard J O'Reilly & David A Scheinberg. Therapeutic bispecific T-cell engager antibody targeting the intracellular oncoprotein WT1. *Nat. Bio. Tech.* doi:10.1038/nbt.3349, 2015.
20. Koneru M, Purdon T J, Spriggs D, Koneru S, Brentjens R J. IL-12 secreting tumor-targeted chimeric antigen receptor T cells eradicate ovarian tumors. Oncoimmunology 2015; 4: e994446.
21. Rafiq S, Purdon T J, Daniyan A F et al. Optimized T-cell receptor-mimic chimeric antigen receptor T cells directed toward the intracellular Wilms tumor 1 antigen. Leukemia, doi: 10.1038/1eu.2016.373. 2017.
22. Park R I, Geyer M B, Brentjens R J. Blood. 2016 Jun. 30; 127(26):3312-20. doi: 10.1182/blood-2016-02-629063.

APPENDIX A

Linker (underlined)
His tag + HA tag (italicized)
#17
Lv(lamda)
DNA sequence
cagtctgtgttgacgcagccgccctcagtgtctggggccccagggcagagggtcaccatctcctgcactgg
gagcagctccaacatcggggcaggttatgatgtacactggtaccagcagcttccaggaacagcccccaaac
tcctcatctatggtaacagcaatcggccctcaggggtccctgaccgattctctggctccaagtctggcacctc
agcctccctggccatcactgggctccaggctgaggatgaggctgattattactgccagtcctatgacagcag
cctgagtggttatgtcttcggaactgggaccaaggtcaccgtcctaggt (SEQ ID NO: 153)

APPENDIX A-continued

AA sequence
QSVLTQPPSVSGAPGQRVTISCTGSSSNIGAGYDVHWYQQLPGTAPK
LLIYGNSNRPSGVPDRFSGSKSGTSASLAITGLQAEDEADYYCQSYD
SSLSGYVFGTGTKVTVLG [SEQ ID NO: 94]

Hv
DNA sequence
gaagtgcagctggtgcagtctggggctgaggtgaagaagcctgggtcctcggtgaaggtctcctgcaagg
cttctggagacaccttcagcaggtatgctatcagctgggtgcgacaggcccctggacaagggcttgagtgg
atgggaaggatcatccctatctttggtacaccaaactacgcacagaagttccagggcagagtcacgattacc
gcggacgaattcacgagcacagcctacatggagctgagcagcctgagatctgaggacaccgccatgtatta
ctgtgcgcgctctatctaccgttactctgaatacgatcattggggtcaaggtactctggtgaccgtctcctca
(SEQ ID NO: 154)

AA sequence
EVQLVQSGAEVKKPGSSVKVSCKASGDTFSRYAISWVRQAPGQGLE
WMGRIIPIFGTPNYAQKFQGRVTITADEFTSTAYMELSSLRSEDTAM
YYCARSIYRYSEYDHWGQGTLVTVSS [SEQ ID NO: 93]

Full-length AA sequence
QSVLTQPPSVSGAPGQRVTISCTGSSSNIGAGYDVHWYQQLPGTAPK
LLIYGNSNRPSGVPDRFSGSKSGTSASLAITGLQAEDEADYYCQSYD
SSLSGYVFGTGTKVTVLGSRGGGGSGGGGSGGGGSLEMAEVQLVQ
SGAEVKKPGSSVKVSCKASGDTFSRYAISWVRQAPGQGLEWMGRII
PIFGTPNYAQKFQGRVTITADEFTSTAYMELSSLRSEDTAMYYCARS
IYRYSEYDHWGQGTLVTVSST*SGQAGQHHHHHHGAYPYDVPDYAS*
[SEQ ID NO: 121]

Full-length DNA sequence
cagtctgtgttgacgcagccgccctcagtgtctggggccccagggcagagggtcaccatctcctgcactgg
gagcagctccaacatcggggcaggttatgatgtacactggtaccagcagcttccaggaacagcccccaaac
tcctcatctatggtaacagcaatcggccctcaggggtccctgaccgattctctggctccaagtctggcacctc
agcctccctggccatcactgggctccaggctgaggatgaggctgattattactgccagtcctatgacagcag
cctgagtggttatgtcttcggaactgggaccaaggtcaccgtcctaggttctagaggtggtggtggtagcgg
cggcggcggctctggtggtggtggatccctcgagatggccgaagtgcagctggtgcagtctggggctgag
gtgaagaagcctgggtcctcggtgaaggtctcctgcaaggcttctggagacaccttcagcaggtatgctatc
agctgggtgcgacaggcccctggacaagggcttgagtggatgggaaggatcatccctatctttggtacacc
aaactacgcacagaagttccagggcagagtcacgattaccgcggacgaattcacgagcacagcctacatg
gagctgagcagcctgagatctgaggacaccgccatgtattactgtgcgcgctctatctaccgttactctgaata
cgatcattggggtcaaggtactctggtgaccgtctcctca*actagtggccaggccggccagcaccatcacc*
*atcaccatggcgcatacccgtacgacgttccggactacgcttct* (SEQ ID NO: 155)

#18
Lv(lamda)
DNA sequence
caggctgtgctgactcagccaccctcagcgtctgggacccgcgggcagagggtcaccatctcttgttctgga
agcagctccaacatcggaagtaatactgtaaactggtaccagcagctcccaggaacggcccccaaactcct
catctatagtaataatcagcggccctcaggggtccctgaccgattctctggctccaagtctggcacctcagcc
tccctggccatcagtgggctccagtctgaagatgaggctgattattactgtgcagcatgggatgacagcctga
atggtcaggggtcttcggaactgggaccaaggtcaccgtcctaggt (SEQ ID NO: 156)

AA sequence
QAVLTQPPSASGTRGQRVTISCSGSSSNIGSNTVNWYQQLPGTAPKL
LIYSNNQRPSGVPDRFSGSKSGTSASLAISGLQSEDEADYYCAAWDD
SLNGQGVFGTGTKVTVLG [SEQ ID NO: 96]

Hv
DNA sequence
gaggtccagctggtgcagtctggggctgaggtgaagaagcctgggacctcagtgaaggtttcctgcaagg
catctggatacaccttcagcaactactatatacactgggtgcgacaggcccctggacaagggcttgagtgga
tgggagcgatcaaccctagtgttggtaccacaacctacgcacagaactttcagggcagagtcaccatgacc
agtgacacgtccacgagcacagtctacatggagttgagcagcctgacatctgaggacacggccgtgtatta
ctgtgcgcgcgactggtggggtcagatgatgtacgatggttggggtcaaggtactctggtgaccgtctcctca
(SEQ ID NO: 157)

AA sequence
EVQLVQSGAEVKKPGTSVKVSCKASGYTFSNYYIHWVRQAPGQGL
EWMGAINPSVGTTTYAQNFQGRVTMTSDTSTSTVYMELSSLTSEDT
AVYYCARDWWGQMMYDGWGQGTLVTVSS [SEQ ID NO: 95]

Full-length AA sequence
QAVLTQPPSASGTRGQRVTISCSGSSSNIGSNTVNWYQQLPGTAPKL
LIYSNNQRPSGVPDRFSGSKSGTSASLAISGLQSEDEADYYCAAWDD
SLNGQGVFGTGTKVTVLGSRGGGGSGGGGSGGGGSLEMAEVQLVQ
SGAEVKKPGTSVKVSCKASGYTFSNYYIHWVRQAPGQGLEWMGAI
NPSVGTTTYAQNFQGRVTMTSDTSTSTVYMELSSLTSEDTAVYYCA
RDWWGQMMYDGWGQGTLVTVSS*TSGQAGQHHHHHHGAYPYDVP*
*DYAS* [SEQ ID NO: 122]

APPENDIX A-continued

Full-length DNA sequence
CAGGCTGTGCTGACTCAGCCACCCTCAGCGTCTGGGACCCGCGG
GCAGAGGGTCACCATCTCTTGTTCTGGAAGCAGCTCCAACATCGG
AAGTAATActgtaaactggtaccagcagctcccaggaacggcccccaaactcctcatctatagtaat
aatcagcggccctcaggggtccctgaccgattctctggctccaagtctggcacctcagcctccctggccatc
agtgggctccagtctgaagatgaggctgattattactgtgcagcatgggatgacagcctgaatggtcagggg
gtcttcggaactgggaccaaggtcaccgtcctaggttctagaggtggtggtggtagcggcggcggcggctc
tggtggtggtggatccctcgagatggccgaggtccagctggtgcagtctggggctgaggtgaagaagcct
gggacctcagtgaaggtttcctgcaaggcatctggatacaccttcagcaactactatatacactgggtgcgac
aggcccctggacaagggcttgagtggatgggagcgatcaaccctagtgttggtaccacaacctacgcaca
gaactttcagggcagagtcaccatgaccagtgacacgtccacgagcacagtctacatggagttgagcagcc
tgacatctgaggacacggccgtgtattactgtgcgcgcgactggtggggtcagatgatgtacgatggttggg
gtcaaggtactctggtgaccgtctcctca*actagtggccaggccggccagcaccatcaccatcaccatgg*
*cgcatacccgtacgacgttccggactacgcttct* (SEQ ID NO: 158)

#20
Lv(lamda)
DNA sequence
cagtctgtcgtgacgcagccgccctcagtgtctgcggccccaggacagaaggtcaccatctcctgctctgg
aagcagctccaacatcggggcaggttatgatgtacactggtaccagcagcttccaggaacagcccccaaac
tcctcatctatggtaacagcaatcggccctcaggggtccctgaccgattctctggctccaagtctggcacctc
agcctccctggccatcactgggctccaggctgaggatgaggctgattattactgccagtcctatgacagcag
cctgagtggttcggtgttcggcggagggaccaagctgaccgtcctaggt (SEQ ID NO: 159)

AA sequence
QSVVTQPPSVSAAPGQKVTISCSGSSSNIGAGYDVHWYQQLPGTAP
KLLIYGNSNRPSGVPDRFSGSKSGTSASLAITGLQAEDEADYYCQSY
DSSLSGSVFGGGTKLTVLG [SEQ ID NO: 98]

Hv
DNA sequence
gaggtccagctggtgcagtctggggctgaggtgaagaagcctgggtcctcggtgaaggtctcctgcaagg
cttctggaggcaccttcagcagctatgctatcagctgggtgcgacaggcccctggacaagggcttgagtgg
atgggagggatcatccctatctttggtacagcaaactacgcacagaagttccagggcagagtcacgattacc
gcggacgaatccacgagcacagcctacatggagctgagcagcctgagatctgaggacacggccgtgtatt
actgtgcgcgctactcttacaaatacggtgaactggatacttggggtcaaggtactctggtgaccgtctcctca
(SEQ ID NO: 160)

AA sequence
EVQLVQSGAEVKKPGSSVKVSCKASGGTFSSYAISWVRQAPGQGLE
WMGGIIPIFGTANYAQKFQGRVTITADESTSTAYMELSSLRSEDTAV
YYCARYSYKYGELDTWGQGTLVTVSS [SEQ ID NO: 97]

Full-length AA sequence
QSVVTQPPSVSAAPGQKVTISCSGSSSNIGAGYDVHWYQQLPGTAP
KLLIYGNSNRPSGVPDRFSGSKSGTSASLAITGLQAEDEADYYCQSY
DSSLSGSVFGGGTKLTVLGSRGGGGSGGGGSGGGGSLEMAEVQLV
QSGAEVKKPGSSVKVSCKASGGTFSSYAISWVRQAPGQGLEWMGGI
IPIFGTANYAQKFQGRVTITADESTSTAYMELSSLRSEDTAVYYCAR
YSYKYGELDTWGQGTLVTVSS*TSGQAGQHHHHHHGAYPYDVPDYAS*
[SEQ ID NO: 123]

Full-length DNA sequence
cagtctgtcgtgacgcagccgccctcagtgtctgcggccccaggacagaaggtcaccatctcctgctctgg
aagcagctccaacatcggggcaggttatgatgtacactggtaccagcagcttccaggaacagcccccaaac
tcctcatctatggtaacagcaatcggccctcaggggtccctgaccgattctctggctccaagtctggcacctc
agcctccctggccatcactgggctccaggctgaggatgaggctgattattactgccagtcctatgacagcag
cctgagtggttcggtgttcggcggagggaccaagctgaccgtcctaggttctagaggtggtggtggtagcg
gcggcggcggctctggtggtggtggatccctcgagatggccgaggtccagctggtgcagtctggggctga
ggtgaagaagcctgggtcctcggtgaaggtctcctgcaaggcttctggaggcaccttcagcagctatgctat
cagctgggtgcgacaggcccctggacaagggcttgagtggatgggagggatcatccctatctttggtacag
caaactacgcacagaagttccagggcagagtcacgattaccgcggacgaatccacgagcacagcctacat
ggagctgagcagcctgagatctgaggacacggccgtgtattactgtgcgcgctactcttacaaatacggtga
actggatacttggggtcaaggtactctggtgaccgtctcctca*actagtggccaggccggccagcaccatc*
*accatcaccatggcgcatacccgtacgacgttccggactacgcttct* (SEQ ID NO: 161)

#27
Lv(lamda)
DNA sequence
caggctgtgctgactcagccaccctcggtgtcagtggccccaggaaagacggccagacttacctgtgggg
gaaacaacattggaagtgaaagtgtacattggtaccagcagaagccaggccaggcccctttactggtcgtct
atgatgatgacgaccggccctccgggatccctgagcgattctctggctccaactctgggaacacggccacc
ctgaccatcagcagggtcgaggccggcgatgaggccgactattactgtcaggtgtgggatcgaagtagtga
tcattggtttttcggcggagggaccaagctgaccgtcctaggt (SEQ ID NO: 162)

AA sequence
QAVLTQPPSVSVAPGKTARLTCGGNNIGSESVHWYQQKPGQAPLLV
VYDDDDRPSGIPERFSGSNSGNTATLTISRVEAGDEADYYCQVWDR
SSDHWFFGGGTKLTVLG[SEQ ID NO: 100]

APPENDIX A-continued

Hv
DNA sequence
caggtgcagctggtgcaatctggggctgaggtgaagaagcctggggcctctgtgaaggtttcctgcaaggc
atctggatacaccttcaccaattactatattcactgggtgcgacaggcccccggacaagggcttgagtggatg
ggaataatcagacctagtggtggtatcacaaactacgcacagaagttccagggcagggtcagcatgaccag
ggacacgtccacgagcacagtctacatggagctgagcagcctgagatctgaggacactgccgtgtattact
gtgcgcgctcttgggactacttcgcttctaacgatttctggggtcaaggtactctggtgaccgtctcctca
(SEQ ID NO: 163)

AA sequence
QVQLVQSGAEVKKPGASVKVSCKASGYTFTNYYIHWVRQAPGQGL
EWMGIIRPSGGITNYAQKFQGRVSMTRDTSTSTVYMELSSLRSEDTA
VYYCARSWDYFASNDFWGQGTLVTVSS [SEQ ID NO: 99]

Full-length AA sequence
QAVLTQPPSVSVAPGKTARLTCGGNNIGSESVHWYQQKPGQAPLLV
VYDDDDRPSGIPERFSGSNSGNTATLTISRVEAGDEADYYCQVWDR
SSDHWFFGGGTKLTVLGSRGGGGSGGGGSGGGGSLEMAQVQLVQS
GAEVKKPGASVKVSCKASGYTFTNYYIHWVRQAPGQGLEWMGIIR
PSGGITNYAQKFQGRVSMTRDTSTSTVYMELSSLRSEDTAVYYCAR
SWDYFASNDFWGQGTLVTVSS*TSGQAGQHHHHHHGAYPYDVPDYAS*
[SEQ ID NO: 124]

Full-length DNA sequence
caggctgtgctgactcagccaccctcggtgtcagtggccccaggaaagacggccagacttacctgtgggg
gaaacaacattggaagtgaaagtgtacattggtaccagcagaagccaggccaggcccctttactggtcgtct
atgatgatgacgaccggccctccgggatccctgagcgattctctggctccaactctgggaacacggccacc
ctgaccatcagcagggtcgaggccggcgatgaggccgactattactgtcaggtgtgggatcgaagtagtga
tcattggtttttcggcggagggaccaagctgaccgtcctaggttctagaggtggtggtggtagcggcggcgg
cggctctggtggtggtggatccctcgagatggcccaggtgcagctggtgcaatctggggctgaggtgaag
aagcctggggcctctgtgaaggtttcctgcaaggcatctggatacaccttcaccaattactatattcactgggt
gcgacaggcccccggacaagggcttgagtggatgggaataatcagacctagtggtggtatcacaaactac
gcacagaagttccagggcagggtcagcatgaccagggacacgtccacgagcacagtctacatggagctg
agcagcctgagatctgaggacactgccgtgtattactgtgcgcgctcttgggactacttcgcttctaacgatttc
tggggtcaaggtactctggtgaccgtctcctca*actagtggccaggccggccagcaccatcaccatcacc*
*atggcgcatacccgtacgacgttccggactacgcttct* (SEQ ID NO: 164)

#28
Lv(lamda)
DNA sequence
cagtctgtgctgacgcagccgccctcagtgtctggggccccagggcagagggtcaccatctcctgcactgg
gagcagctccaacatcggggcaggttatgatgtgcactggtaccagcagcttccaggaacagcccccaaa
ctcctcatctatggtaacagcgatcggccctccggggtccctgaccgattctctggctccaagtctggcacct
cagcctccctggccatcactgggctccaggctgaggatgaggctgattattactgccagtcctatgacagca
gcctgagtggttatgtcttcggaactgggaccaaggtcaccgtcctaggt
tctagaggtggtggtggtagcggcggcggcggctctggtggtggtggatccctcgagatggcc
(SEQ ID NO: 165)

AA sequence
QSVLTQPPSVSGAPGQRVTISCTGSSSNIGAGYDVHWYQQLPGTAPK
LLIYGNSDRPSGVPDRFSGSKSGTSASLAITGLQAEDEADYYCQSYD
SSLSGYVFGTGTKVTVLG [SEQ ID NO: 102]

Hv
DNA sequence
cagatgcagctggtgcagtctggggctgaggtgaagaagcctgggtcctcggtgaaggtctcctgcaagg
cttctggaggcaccttcagcacctacgctatcagctgggtgcgacaggcccctggacaagggcttgagtgg
atgggagggatcatccctatatttggacagcaaactacgcacagaagttccagggcagggtcacgattac
cgcggacaaatccacgagcacagcctacatggaggtgaggaacctgagatctgaggacacggccgtgtat
tactgtgcgcgcgctgaatacgtttacggtgaatacgatcagtggggtcaaggtactctggtgaccgtctcct
ca (SEQ ID NO: 166)

AA sequence
QMQLVQSGAEVKKPGSSVKVSCKASGGTFSTYAISWVRQAPGQGL
EWMGGIIPIFGTANYAQKFQGRVTITADKSTSTAYMEVRNLRSEDTA
VYYCARAEYVYGEYDQWGQGTLVTVSS [SEQ ID NO: 101]

Full-length AA sequence
QSVLTQPPSVSGAPGQRVTISCTGSSSNIGAGYDVHWYQQLPGTAPK
LLIYGNSDRPSGVPDRFSGSKSGTSASLAITGLQAEDEADYYCQSYD
SSLSGYVFGTGTKVTVLGSRGGGGSGGGGSGGGGSLEMAQMQLVQ
SGAEVKKPGSSVKVSCKASGGTFSTYAISWVRQAPGQGLEWMGGII
PIFGTANYAQKFQGRVTITADKSTSTAYMEVRNLRSEDTAVYYCAR
AEYVYGEYDQWGQGTLVTVSS*TSGQAGQHHHHHHGAYPYDVPDYA*
*S* [SEQ ID NO: 125]

Full-length DNA sequence
cagtctgtgctgacgcagccgccctcagtgtctggggccccagggcagagggtcaccatctcctgcactgg
gagcagctccaacatcggggcaggttatgatgtgcactggtaccagcagcttccaggaacagcccccaaa
ctcctcatctatggtaacagcgatcggccctccggggtccctgaccgattctctggctccaagtctggcacct APPENDIX A-continued cagcctccctggccatcactgggctccaggctgaggatgaggctgattattactgccagtcctatgacagca
gcctgagtggttatgtcttcggaactgggaccaaggtcaccgtcctaggttctagaggtggtggtggtagca
gcggcggcggctctggtggtggtggatccctcgagatggcccagatgcagctggtgcagtctggggctga
ggtgaagaagcctgggtcctcggtgaaggtctcctgcaaggcttctggaggcaccttcagcacctacgctat
cagctgggtgcgacaggcccctggacaagggcttgagtggatgggagggatcatccctatatttgggaca
gcaaactacgcacagaagttccagggcagggtcacgattaccgcggacaaatccacgagcacagcctaca
tggaggtgaggaacctgagatctgaggacacggccgtgtattactgtgcgcgcgctgaatacgtttacggtg
aatacgatcagtggggtcaaggtactctggtgaccgtctcctca*actagtggccaggccggccagcaccat*
*caccatcaccatggcgcatacccgtacgacgttccggactacgcttct* (SEQ ID NO: 167)

#32
Lv(lamda)
DNA sequence
cagtctgtgttgactcagccaccctcagtgtcagtggccccaggaaagacggccaggattacctgtggggg
aaacaacattggaagtaaaagtgtgcactggtaccagcagaagccaggccaggcccctgtgctggtcatct
attatgatagcgaccggccctcagggatccctgagcgattctctggctccaactctgggaacacggccaccc
tgaccatcagcagggtcgaagccggggatgaggccgactattactgtcaggtgtgggatagtagtagtgat
cattatgtcttcggaactgggaccaaggtcaccgtcctaggt (SEQ ID NO: 168)

AA sequence
QSVLTQPPSVSVAPGKTARITCGGNNIGSKSVHWYQQKPGQAPVLVI
YYDSDRPSGIPERFSGSNSGNTATLTISRVEAGDEADYYCQVWDSSS
DHYVFGTGTKVTVLG [SEQ ID NO: 104]

Hv
DNA sequence
gaggtgcagctggtggagtccgggggaggcgtggtccagcctgggaggtccctgagactctcctgtgcag
cctctgggttcaccttcaataatcatgctatgcactgggtccgccaggctccaggcaaggggctggagtggg
tggcagttatatcatttgatggagacgataaattctacgcagactccgtgaagggccgattcaccatctccaga
gacaattccaggaacacactgtttctgcaaatgaacaacctgagacctgaggacacggctgtgtattactgtt
cgagagatccatatcactttgcctcggggagttattcctactttgactactggggccagggaaccctggtcac
cgtctcctca (SEQ ID NO: 169)

AA sequence
EVQLVESGGGVVQPGRSLRLSCAASGFTFNNHAMHWVRQAPGKGL
EWVAVISFDGDDKFYADSVKGRFTISRDNSRNTLFLQMNNLRPEDT
AVYYCSRDPYHFASGSYSYFDYWGQGTLVTVSS [SEQ ID NO: 103]

Full-length AA sequence
QSVLTQPPSVSVAPGKTARITCGGNNIGSKSVHWYQQKPGQAPVLVI
YYDSDRPSGIPERFSGSNSGNTATLTISRVEAGDEADYYCQVWDSSS
DHYVFGTGTKVTVLGSRGGGGSGGGGSGGGGSLEMAEVQLVESGG
GVVQPGRSLRLSCAASGFTFNNHAMHWVRQAPGKGLEWVAVISFD
GDDKFYADSVKGRFTISRDNSRNTLFLQMNNLRPEDTAVYYCSRDP
YHFASGSYSYFDYWGQGTLVTVSS*TSGQAGQHHHHHHGAYPYDVPD*
*YAS* [SEQ ID NO: 126]

Full-length DNA sequence
cagtctgtgttgactcagccaccctcagtgtcagtggccccaggaaagacggccaggattacctgtggggg
aaacaacattggaagtaaaagtgtgcactggtaccagcagaagccaggccaggcccctgtgctggtcatct
attatgatagcgaccggccctcagggatccctgagcgattctctggctccaactctgggaacacggccaccc
tgaccatcagcagggtcgaagccggggatgaggccgactattactgtcaggtgtgggatagtagtagtgat
cattatgtcttcggaactgggaccaaggtcaccgtcctaggttctagaggtggtggtggtagcggcggcggc
ggctctggtggtggtggatccctcgagatggccgaggtgcagctggtggagtccgggggaggcgtggtcc
agcctgggaggtccctgagactctcctgtgcagcctctgggttcaccttcaataatcatgctatgcactgggtc
cgccaggctccaggcaaggggctggagtgggtggcagttatatcatttgatggagacgataaattctacgca
gactccgtgaagggccgattcaccatctccagagacaattccaggaacacactgtttctgcaaatgaacaac
ctgagacctgaggacacggctgtgtattactgttcgagagatccatatcactttgcctcggggagttattcctac
tttgactactggggccagggaaccctggtcaccgtctcctca*actagtggccaggccggccagcaccatc*
*accatcaccatggcgcatacccgtacgacgttccggactacgcttct* (SEQ ID NO: 170)

#53
Lv(lamda)
DNA sequence
aattttatgctgactcagccccactctgtgtcggagtctccggggaagacggtgaccatctcctgcacccgca
gcagtggcagcattgccagccactatgtgcagtggtaccagcagcgcccgggcagttcccccaccactgtg
atctatgagaataaccaaagaccctctggggtccctgatcggttctctggctccatcgacagttcctccaactc
tgcctccctcaccatctctggactgaagactgaggacgaggctgactactactgtcaatcttatgatcgcagc
aatcatgtggtattcggcggagggaccaagctgaccgtcctaggt (SEQ ID NO: 171)

AA sequence
NFMLTQPHSVSESPGKTVTISCTRSSGSIASHYVQWYQQRPGSSPTT
VIYENNQRPSGVPDRFSGSIDSSSNSASLTISGLKTEDEADYYCQSYD
RSNHVVFGGGTKLTVLG [SEQ ID NO: 106]

Hv
DNA sequence
caggtgcagctggtgcagtctggggctgaggtgaagaagcctggggcctcagtgaaggtctcctgcaagg
catctggatacaccttcaccaactactatatccactgggtgcgacaggcccctggagaagggcttgagtgga
tgggaataatcagacctagtggcggtaacacaaactacgcacagaagttccagggcagagtcaccatgacc APPENDIX A-continued agggacacgtccacgcgcacggtctatatggagttgagtagcctgagatctgaggacacggccgtgtatta
ctgtgcgcgctcttggaactctcgtgacgttgattcttggggtcaaggtactctggtgaccgtctcctca
(SEQ ID NO: 172)

AA sequence
QVQLVQSGAEVKKPGASVKVSCKASGYTFTNYYIHWVRQAPGEGL
EWMGIIRPSGGNTNYAQKFQGRVTMTRDTSTRTVYMELSSLRSEDT
AVYYCARSWNSRDVDSWGQGTLVTVSS [SEQ ID NO: 105]

Full-length AA sequence
NFMLTQPHSVSESPGKTVTISCTRSSGSIASHYVQWYQQRPGSSPTT
VIYENNQRPSGVPDRFSGSIDSSSNSASLTISGLKTEDEADYYCQSYD
RSNHVVFGGGTKLTVLGSRGGGGSGGGGSGGGGSLEMAQVQLVQS
GAEVKKPGASVKVSCKASGYTFTNYYIHWVRQAPGEGLEWMGIIRP
SGGNTNYAQKFQGRVTMTRDTSTRTVYMELSSLRSEDTAVYYCAR
SWNSRDVDSWGQGTLVTVSS*TSGQAGQHHHHHHGAYPYDVPDYAS*
[SEQ ID NO: 127]

Full-length DNA sequence
aattttatgctgactcagccccactctgtgtcggagtctccggggaagacggtgaccatctcctgcacccgca
gcagtggcagcattgccagccactatgtgcagtggtaccagcagcgcccgggcagttcccccaccactgtg
atctatgagaataaccaaagaccctctggggtccctgatcggttctctggctccatcgacagttcctccaactc
tgcctccctcaccatctctggactgaagactgaggacgaggctgactactactgtcaatcttatgatcgcagc
aatcatgtggtattcggcggagggaccaagctgaccgtcctaggttctagaggtggtggtggtagcggcgg
cggcggctctggtggtggtggatccctcgagatggcccaggtgcagctggtgcagtctggggctgaggtg
aagaagcctggggcctcagtgaaggtctcctgcaaggcatctggatacaccttcaccaactactatatccact
gggtgcgacaggcccctggagaagggcttgagtggatgggaataatcagacctagtggcggtaacacaaa
ctacgcacagaagttccagggcagagtcaccatgaccagggacacgtccacgcgcacggtctatatggag
ttgagtagcctgagatctgaggacacggccgtgtattactgtgcgcgctcttggaactctcgtgacgttgattc
ttggggtcaaggtactctggtgaccgtctcctca*actagtggccaggccggccagcaccatcaccatcac*
*catggcgcatacccgtacgacgttccggactacgcttct* (SEQ ID NO: 173)

#54
Lv(lamda)
DNA sequence
caggctgtgctgactcagccaccctcgctgtctggaggccccaggcagagggtcaccatctcctgttctgga
agcacctccaacatcggaaaaaatggtgtgagctggtaccagcagctcccaggaaaggctcccaaactcct
catctataatgatcatctgttgtcctcaggggtctctgaccgcttttctggctccaagtctggcacgtcagcctcc
ctggccatcagtggactccagtctgacgatgaagctgattattactgtgcgacatgggacgacactttggatct
tccgctattcggcggagggaccaaggtcaccgtcctaggt (SEQ ID NO: 174)

AA sequence
QAVLTQPPSLSGGPRQRVTISCSGSTSNIGKNGVSWYQQLPGKAPKL
LIYNDHLLSSGVSDRFSGSKSGTSASLAISGLQSDDEADYYCATWDD
TLDLPLFGGGTKVTVLG [SEQ ID NO: 108]

Hv
DNA sequence
cagatgcagctggtgcagtctggggctgaggtggagaagcctggggcctcagtgaagctctcctgcaagg
cttctggaggcaccttcagcagctatgctatcagctgggtgcgacaggcccctggacaagggcttgagtgg
atgggagggatcatccctatctttggtacagcaaactacgcacagaagttccagggcagagtcacgattacc
gcggacgaatccacgagcacagcctacatggagctgagcagcctgagatctgaggacacggccgtgtatt
actgtgcgcgcccgtcttactactctatcaaatctgcttgggatcattggggtcaaggtactctggtgaccgtct
cctca (SEQ ID NO: 175)

AA sequence
QMQLVQSGAEVEKPGASVKLSCKASGGTFSSYAISWVRQAPGQGLE
WMGGIIPIFGTANYAQKFQGRVTITADESTSTAYMELSSLRSEDTAV
YYCARPSYYSIKSAWDHWGQGTLVTVSS [SEQ ID NO: 107]

Full-length AA sequence
QAVLTQPPSLSGGPRQRVTISCSGSTSNIGKNGVSWYQQLPGKAPKL
LIYNDHLLSSGVSDRFSGSKSGTSASLAISGLQSDDEADYYCATWDD
TLDLPLFGGGTKVTVLGSRGGGGSGGGGSGGGGSLEMAQMQLVQS
GAEVEKPGASVKLSCKASGGTFSSYAISWVRQAPGQGLEWMGGIIPI
FGTANYAQKFQGRVTITADESTSTAYMELSSLRSEDTAVYYCARPS
YYSIKSAWDHWGQGTLVTVSS*TSGQAGQHHHHHHGAYPYDVPDYAS*
[SEQ ID NO: 128]

Full-length DNA sequence
Caggctgtgctgactcagccaccctcgctgtctggaggccccaggcagagggtcaccatctcctgttctgg
aagcacctccaacatcggaaaaaatggtgtgagctggtaccagcagctcccaggaaaggctcccaaactc
ctcatctataatgatcatctgttgtcctcaggggtctctgaccgcttttctggctccaagtctggcacgtcagcct
ccctggccatcagtggactccagtctgacgatgaagctgattattactgtgcgacatgggacgacactttgga
tcttccgctattcggcggagggaccaaggtcaccgtcctaggttctagaggtggtggtggtagcggcggcg
gcggctctggtggtggtggatccctcgagatggcccagatgcagctggtgcagtctggggctgaggtgga
gaagcctggggcctcagtgaagctctcctgcaaggcttctggaggcaccttcagcagctatgctatcagctg
ggtgcgacaggcccctggacaagggcttgagtggatgggagggatcatccctatctttggtacagcaaact
acgcacagaagttccagggcagagtcacgattaccgcggacgaatccacgagcacagcctacatggagct
gagcagcctgagatctgaggacacggccgtgtattactgtgcgcgcccgtcttactactctatcaaatctgctt APPENDIX A-continued gggatcattggggtcaaggtactctggtgaccgtctcctca*actagtggccaggccggccagcaccatca*
*ccatcaccatggcgcatacccgtacgacgttccggactacgcttc* (SEQ ID NO: 176)

APPENDIX B

| Clone no. | HCDR1 | HCDR2 | HCDR3 | LCDR1 | LCDR2 | LCDR3 |
|---|---|---|---|---|---|---|
| #5 | RYTFTNYY (SEQ ID NO: 177) | INPSGGST (SEQ ID NO: 185) | ARGWSGYDPGDF (SEQ ID NO: 191) | SSDVGGYNY (SEQ ID NO: 203) | EVS (SEQ ID NO: 211) | SSYAGSNTHVV (SEQ ID NO: 218) |
| #9 | RYTFTNYY (SEQ ID NO: 177) | INPSGGST (SEQ ID NO: 185) | ARGWSGYDPGDF (SEQ ID NO: 191) | SSDVGGYNY (SEQ ID NO: 203) | EVS (SEQ ID NO: 211) | SSYAGSNNVV (SEQ ID NO: 219) |
| #10 | GYSFTSYY (SEQ ID NO: 178) | IDPSDSYT (SEQ ID NO: 186) | VRHGFSNSPRLWFDT (SEQ ID NO: 192) | SSNIGVNP (SEQ ID NO: 204) | ANY (SEQ ID NO: 212) | STWDDSLNAWL (SEQ ID NO: 220) |
| #11 | GYTFNNYY (SEQ ID NO: 179) | INPSGGST (SEQ ID NO: 185) | ARSFDKQDIDY (SEQ ID NO: 193) | SGSIASNY (SEQ ID NO: 205) | EDN (SEQ ID NO: 213) | QSYDTNNYGVI (SEQ ID NO: 221) |
| #21 | GYTFTNTYY (SEQ ID NO: 180) | IRPSGGIT (SEQ ID NO: 28) | ARSWMSDSYYDG (SEQ ID NO: 194) | NIGSKS (SEQ ID NO: 42) | DDS (SEQ ID NO: 214) | QVWDSSSDHVI (SEQ ID NO: 222) |
| #23 | GYTFTNYG (SEQ ID NO: 181) | ISPYNGNT (SEQ ID NO: 187) | ARYWDSGYAYDE (SEQ ID NO: 195) | NIGSKS (SEQ ID NO: 66) | DDS (SEQ ID NO: 214) | QVWDSSSDRWV (SEQ ID NO: 223) |
| #24 | GYTFTNYY (SEQ ID NO: 182) | IRPSGGIT (SEQ ID NO: 28) | ARSWSNKLSWYNDG (SEQ ID NO: 196) | SSNIGNNY (SEQ ID NO: 206) | DNN (SEQ ID NO: 215) | GTWDSSLNAVV (SEQ ID NO: 224) |
| #25 | GYTFTNYY (SEQ ID NO: 182) | INPSGGST (SEQ ID NO: 185) | ARSWSKTEGSDR (SEQ ID NO: 197) | SSNIGNNY (SEQ ID NO: 206) | DNN (SEQ ID NO: 215) | GTWDNSLSAAV (SEQ ID NO: 225) |
| #26 | GYTFTNYY (SEQ ID NO: 182) | IRPSGGNT (SEQ ID NO: 46) | ARSWDTFSDE (SEQ ID NO: 198) | DIRRKT (SEQ ID NO: 207) | DDS (SEQ ID NO: 214) | QVWDNDNDHYV (SEQ ID NO: 226) |
| #29 | GYTFTNYY (SEQ ID NO: 182) | INPSIGST (SEQ ID NO: 188) | ARSFGDSDGADS (SEQ ID NO: 199) | SSNIGNNY (SEQ ID NO: 206) | DDN (SEQ ID NO: 216) | GTWDSSLSAVV (SEQ ID NO: 227) |
| #30 | GYTFTNYY (SEQ ID NO: 182) | IRPSGGIT (SEQ ID NO: 28) | ARSWHENSGVDS (SEQ ID NO: 200) | NLGSKS (SEQ ID NO: 208) | DDS (SEQ ID NO: 214) | QVWHSSSDHYV (SEQ ID NO: 228) |
| #34 | GGTFSSYA (SEQ ID NO: 183) | IIPILGIA (SEQ ID NO: 189) | ARGGDYVESWFDP (SEQ ID NO: 201) | SSDVGAYNY (SEQ ID NO: 209) | EVS (SEQ ID NO: 211) | SSYAGSNNFV (SEQ ID NO: 229) |
| #55 | GYTFDNFG (SEQ ID NO: 184) | INTYDGYT (SEQ ID NO: 190) | ARSVPHQISYGDL (SEQ ID NO: 202) | TSDFNDYLF (SEQ ID NO: 210) | DVT (SEQ ID NO: 217) | GSKTGRTTYV (SEQ ID NO: 230) |

APPENDIX C

Linker (underlined)
His tag + HA tag (italicized)

#5
DNA Sequence:
caatctgccctgactcagcctccctccgcgtccgggtctcctggacagtcagtcaccatctcctgcactggaaccagcagtgac
gttggtggttataactatgtctcctggtaccaacagcacccaggcaaagcccccaaactcatgatttatgaggtcagtaagcggc
cctcaggggtccctgatcgcttctctggctccaagtctggcaacacggcctccctgaccgtctctgggctccaggctgaggatg
aggctgattattactgcagctcatatgcaggcagcaacacccatgtggtattcggcggagggaccaagctgaccgtcctaggtt
ctagaggtggtggtggtagcggcggcggcggctctggtggtggtggatccctcgagatggccgaagtgcagctggtgcagtc
tggggctgaggtgaagaagcctggggcctcagtgaaaatttcctgcaaggcatctagatacaccttcaccaactactatatacac
tgggtgcgacaggcccctggacaagggcttgagtggatgggaataatcaaccctagtggtggtagcacaacctacccacaga
acttccagggcagactcaccatgaccagggacacgtccacgagcacagtctacatggagctgagcagcctgagatctgagga
cacggccatgtattactgtgcgagaggttggagtggctacgatccaggggacttctggggccagggaaccctggtcaccgtct
cctca*actagtggccaggccggccagcaccatcaccatcaccatggcgcatacccgtacgacgttccggactacgcttct*
(SEQ ID NO: 231)

Amino Acid Sequence:
QSALTQPPSASGSPGQSVTISCTGTSSDVGGYNYVSWYQQHPGKAPKLMIYEVS
KRPSGVPDRFSGSKSGNTASLTVSGLQAEDEADYYCSSYAGSNTHVVFGGGTKL
TVLGSRGGGGSGGGGSGGGGSLEMAEVQLVQSGAEVKKPGASVKISCKASRYT
FTNYYIHWVRQAPGQGLEWMGIINPSGGSTTYPQNFQGRLTMTRDTSTSTVYME
LSSLRSEDTAMYYCARGWSGYDPGDFWGQGTLVTVSS*TSGQAGQHHHHHHGA*
*YPYDVPDYAS* (SEQ ID NO: 232)

Light chain DNA Sequence:
caatctgccctgactcagcctccctccgcgtccgggtctcctggacagtcagtcaccatctcctgcactggaaccagcagtgac
gttggtggttataactatgtctcctggtaccaacagcacccaggcaaagcccccaaactcatgatttatgaggtcagtaagcggc
cctcaggggtccctgatcgcttctctggctccaagtctggcaacacggcctccctgaccgtctctgggctccaggctgaggatg
aggctgattattactgcagctcatatgcaggcagcaacacccatgtggtattcggcggagggaccaagctgaccgtcctaggt
(SEQ ID NO: 233)

Light Chain Amino Acid Sequence:
QSALTQPPSASGSPGQSVTISCTGTSSDVGGYNYVSWYQQHPGKAPKLMIYEVS
KRPSGVPDRFSGSKSGNTASLTVSGLQAEDEADYYCSSYAGSNTHVVFGGGTKL
TVLG (SEQ ID NO: 234)

Heavy Chain DNA Sequence:
gaagtgcagctggtgcagtctggggctgaggtgaagaagcctggggcctcagtgaaaatttcctgcaaggcatctagatacac
cttcaccaactactatatacactgggtgcgacaggcccctggacaagggcttgagtggatgggaataatcaaccctagtggtgg
tagcacaacctacccacagaacttccagggcagactcaccatgaccagggacacgtccacgagcacagtctacatggagctg
agcagcctgagatctgaggacacggccatgtattactgtgcgagaggttggagtggctacgatccaggggacttctggggcca
gggaaccctggtcaccgtctcctca (SEQ ID NO: 235)

Heavy Chain Amino Acid Sequience:
EVQLVQSGAEVKKPGASVKISCKASRYTFTNYYIHWVRQAPGQGLEWMGIINPS
GGSTTYPQNFQGRLTMTRDTSTSTVYMELSSLRSEDTAMYYCARGWSGYDPGD
FWGQGTLVTVSS (SEQ ID NO: 236)

#9
DNA Sequence:
caatctgccctgactcagcctgcctccgcgtccgggtctcctggacagtcagtcaccatctcctgcactggaaccagcagtgac
gttggtggttataactatgtctcctggtaccaacagcacccaggcaaagcccccaaactcatgatttatgaggtcagtaagcggc
cctcaggggtccctgatcgcttctctggctccaagtctggcaacacggcctccctgaccgtctctgggctccaggctgaggatg
aggctgattattactgcagctcatatgcaggcagcaacaatgtggtattcggcggagggaccaagctgaccgtcctaggttctag
aggtggtggtggtagcggcggcggcggctctggtggtggtggatccctcgagatggccgaggtccagctggtgcagtctggg
gctgaggtgaagaagcctggggcctcagtgaaaatttcctgcaaggcatctagatacaccttcaccaactactatatacactggg
tgcgacaggcccctggacaagggcttgagtggatgggaataatcaaccctagtggtggtagcacaacctacccacagaacttc
cagggcagactcaccatgaccagggacacgtccacgagcacagtctacatggagctgagcagcctgagatctgaggacacg
gccatgtattactgtgcgagaggttggagtggctacgatccaggggacttctggggccagggaaccctggtcaccgtctcctca
*actagtggccaggccggccagcaccatcaccatcaccatggcgcatacccgtacgacgttccggactacgcttct*
(SEQ ID NO: 237)

Amino Acid Sequence:
QSALTQPASASGSPGQSVTISCTGTSSDVGGYNYVSWYQQHPGKAPKLMIYEVS
KRPSGVPDRFSGSKSGNTASLTVSGLQAEDEADYYCSSYAGSNNVVFGGGTKLT
VLG
SRGGGGSGGGGSGGGGSLEMAEVQLVQSGAEVKKPGASVKISCKASRYTFTNY
YIHWVRQAPGQGLEWMGIINPSGGSTTYPQNFQGRLTMTRDTSTSTVYMELSSL
RSEDTAMYYCARGWSGYDPGDFWGQGTLVTVSS*TSGQAGQHHHHHHGAYPYD*
*VPDYAS* (SEQ ID NO: 238)

Light Chain DNA Sequence:
caatctgccctgactcagcctgcctccgcgtccgggtctcctggacagtcagtcaccatctcctgcactggaaccagcagtgac
gttggtggttataactatgtctcctggtaccaacagcacccaggcaaagcccccaaactcatgatttatgaggtcagtaagcggc
cctcaggggtccctgatcgcttctctggctccaagtctggcaacacggcctccctgaccgtctctgggctccaggctgaggatg
aggctgattattactgcagctcatatgcaggcagcaacaatgtggtattcggcggagggaccaagctgaccgtcctaggt
(SEQ ID NO: 239)

Light Chain Amino Acid Sequence:
QSALTQPASASGSPGQSVTISCTGTSSDVGGYNYVSWYQQHPGKAPKLMIYEVS
KRPSGVPDRFSGSKSGNTASLTVSGLQAEDEADYYCSSYAGSNNVVFGGGTKLT
VLG (SEQ ID NO: 240)

Heavy Chain DNA Sequence:
gaggtccagctggtgcagtctggggctgaggtgaagaagcctggggcctcagtgaaaatttcctgcaaggcatctagatacac
cttcaccaactactatatacactgggtgcgacaggcccctggacaagggcttgagtggatgggaataatcaaccctagtggtgg
tagcacaacctacccacagaacttccagggcagactcaccatgaccagggacacgtccacgagcacagtctacatggagctg
agcagcctgagatctgaggacacggccatgtattactgtgcgagaggttggagtggctacgatccaggggacttctggggcca
gggaaccctggtcaccgtctcctca (SEQ ID NO: 241)

Heavy Chain Amino Acid Sequence:
EVQLVQSGAEVKKPGASVKISCKASRYTFTNYYIHWVRQAPGQGLEWMGIINPS
GGSTTYPQNFQGRLTMTRDTSTSTVYMELSSLRSEDTAMYYCARGWSGYDPGD
FWGQGTLVTVSS (SEQ ID NO: 242)

#10
DNA Sequence:
caggctgtgctgactcagccaccctcagcgtctgggacccccgggcagagggtcaccatctcttgttctggaggcagctccaa
catcggagttaatcctgtaaactggtaccagcaactcccaggaacggcccccaaactcctcatctttgctaattatcagcggccct
caggggtccctgaccgattctctggctccaagtctggcacctcagcctccctggccatcagtggactccagtctgatgatgagg
ctcattattattgttcgacatgggatgacagcctgaatgcttggctgttcggcggagggaccaagctgaccgtcctaggttctaga
ggtggtggtggtagcggcggcggcggctctggtggtggtggatccctcgagatggccgaggtgcagctggtgcagtctgga
gcagaggtgaaaaagccgggggactctctgaggatctcctgtcagggttctggatacagctttaccagttactacatcagctgg
gtgcgccagatgcccgggaaaggcctggagtggatggggaacattgatcctagtgactcttacaccaactacagcccgtccttc
caaggccacgtcaccatgtcagttgacaagtccatcagcactgcctacctgcagtggagcagcctgaaggcctcggacatcgc
catatattactgtgtgagacatgggtttagcaactcgcctagattgtggttcgacacctggggccagggaaccctggtcaccgtct
cctca*actagtggccaggccggccagcaccatcaccatcaccatggcgcatacccgtacgacgttccggactacgcttct*
(SEQ ID NO: 243)

Amino Acid Sequence:
QAVLTQPPSASGTPGQRVTISCSGGSSNIGVNPVNWYQQLPGTAPKLLIFANYQR
PSGVPDRFSGSKSGTSASLAISGLQSDDEAHYYCSTWDDSLNAWLFGGGTKLTV
LG
SRGGGGSGGGGSGGGGSLEMAEVQLVQSGAEVKKPGDSLRISCQGSGYSFTSY
YISWVRQMPGKGLEWMGNIDPSDSYTNYSPSFQGHVTMSVDKSISTAYLQWSS
LKASDIAIYYCVRHGFSNSPRLWFDTWGQGTLVTVSS*TSGQAGQHHHHHHGAYP*
*YDVPDYAS* (SEQ ID NO: 244)

Light Chain DNA Sequence:
caggctgtgctgactcagccaccctcagcgtctgggacccccgggcagagggtcaccatctcttgttctggaggcagctccaa
catcggagttaatcctgtaaactggtaccagcaactcccaggaacggcccccaaactcctcatctttgctaattatcagcggccct
caggggtccctgaccgattctctggctccaagtctggcacctcagcctccctggccatcagtggactccagtctgatgatgagg
ctcattattattgttcgacatgggatgacagcctgaatgcttggctgttcggcggagggaccaagctgaccgtcctaggt
(SEQ ID NO: 245)

Light Chain Amino Acid Sequence:
QAVLTQPPSASGTPGQRVTISCSGGSSNIGVNPVNWYQQLPGTAPKLLIFANYQR
PSGVPDRFSGSKSGTSASLAISGLQSDDEAHYYCSTWDDSLNAWLFGGGTKLTV
LG (SEQ ID NO: 246)

Heavy Chain DNA Sequence:
gaggtgcagctggtgcagtctggagcagaggtgaaaaagccgggggactctctgaggatctcctgtcagggttctggatacag
ctttaccagttactacatcagctgggtgcgccagatgcccgggaaaggcctggagtggatggggaacattgatcctagtgactc
ttacaccaactacagcccgtccttccaaggccacgtcaccatgtcagttgacaagtccatcagcactgcctacctgcagtggagc
agcctgaaggcctcggacatcgccatatattactgtgtgagacatgggtttagcaactcgcctagattgtggttcgacacctggg
gccagggaaccctggtcaccgtctcctca (SEQ ID NO: 247)

Heavy Chain Amino Acid Sequence:
EVQLVQSGAEVKKPGDSLRISCQGSGYSFTSYYISWVRQMPGKGLEWMGNIDPS
DSYTNYSPSFQGHVTMSVDKSISTAYLQWSSLKASDIAIYYCVRHGFSNSPRLWF
DTWGQGTLVTVSS (SEQ ID NO: 248)

#11
DNA Sequence:
aattttatgctgactcagccccactctgtgtcggagtctccggggaagacggtaaccatctcctgcacccgcagcagtggcagc
attgccagcaactatgtgcagtggtaccagcagcgcccgggcagtgcccccaccactgtgatctatgaggataaccaaagacc
ctctggggtccctgatcggttctctggctccatcgacagctcctccaactctgcctccctcaccatctctggactgaagactgagg
acgaggctgattactactgtcagtcttatgataccaacaattatggggttatattcggcggagggaccaagctgaccgtcctaggt
tctagaggtggtggtggtagcggcggcggcggctctggtggtggtggatccctcgagatggcccagatgcagctggtgcagt
ctggggctgaggtgaagaagcctggggcctcagtgaaggtttcctgcaagacatctggatacaccttcaacaactactatatgc
actgggtgcgacaggcccctggacaagggcttgagtggatgggaataatcaaccctagtggtggtagcacaaactacgcaca
gaagttccagggcagagtcaccatgaccagggacacgtccacgagcacagtctacatggagctgagcagcctgagatctgag
gacactgccgtgtattactgtgcgcgctctttcgacaaacaggacatcgattactggggtcaaggtactctggtgaccgtctcctc
*aactagtggccaggccggccagcaccatcaccatcaccatggcgcatacccgtacgacgttccggactacgcttct*
(SEQ ID NO: 249)

APPENDIX C-continued

Amino Acid Sequence:
NFMLTQPHSVSESPGKTVTISCTRSSGSIASNYVQWYQQRPGSAPTTVIYEDNQR
PSGVPDRFSGSIDSSSNSASLTISGLKTEDEADYYCQSYDTNNYGVIFGGGTKLTV
LGSRGGGGSGGGGSGGGGSLEMAQMQLVQSGAEVKKPGASVKVSCKTSGYTF
NNYYMHWVRQAPGQGLEWMGIINPSGGSTNYAQKFQGRVTMTRDTSTSTVYM
ELSSLRSEDTAVYYCARSFDKQDIDYWGQGTLVTVSS*TSGQAGQHHHHHHGAYP*
*YDVPDYAS* (SEQ ID NO: 250)

Light Chain DNA Sequence:
aattttatgctgactcagccccactctgtgtcggagtctccggggaagacggtaaccatctcctgcacccgcagcagtggcagc
attgccagcaactatgtgcagtggtaccagcagcgcccgggcagtgcccccaccactgtgatctatgaggataaccaaagacc
ctctggggtccctgatcggttctctggctccatcgacagctcctccaactctgcctccctcaccatctctggactgaagactgagg
acgaggctgattactactgtcagtcttatgataccaacaattatggggttatattcggcggagggaccaagctgaccgtcctaggt
(SEQ ID NO: 251)

Light Chain Amino Acid Sequence:
NFMLTQPHSVSESPGKTVTISCTRSSGSIASNYVQWYQQRPGSAPTTVIYEDNQR
PSGVPDRFSGSIDSSSNSASLTISGLKTEDEADYYCQSYDTNNYGVIFGGGTKLTV
LG (SEQ ID NO: 252)

Heavy Chain DNA Sequence:
cagatgcagctggtgcagtctggggctgaggtgaagaagcctggggcctcagtgaaggtttcctgcaagacatctggatacac
cttcaacaactactatatgcactgggtgcgacaggcccctggacaagggcttgagtggatgggaataatcaaccctagtggtgg
tagcacaaactacgcacagaagttccagggcagagtcaccatgaccagggacacgtccacgagcacagtctacatggagctg
agcagcctgagatctgaggacactgccgtgtattactgtgcgcgctctttcgacaaacaggacatcgattactggggtcaaggta
ctctggtgaccgtctcctca (SEQ ID NO: 253)

Heavy Chain Amino Acid Sequence:
QMQLVQSGAEVKKPGASVKVSCKTSGYTFNNYYMHWVRQAPGQGLEWMGIIN
PSGGSTNYAQKFQGRVTMTRDTSTSTVYMELSSLRSEDTAVYYCARSFDKQDID
YWGQGTLVTVSS (SEQ ID NO: 254)

#21
DNA Sequence:
tcctatgagctgactcagccaccctcggtgtcagtggccccaggacagacggccagcatgacctgtggggaaacaacattg
gaagtaaaagtgtgcactggtaccagcagaagccaagccaggcccctgtgatggtcgtccatgatgatagcgagcggccctc
agggatccctgagcgaatctctggctccaagtctgggaacacggccaccctgaccatcagcagggtcgaagccggggatga
ggccgactattactgtcaggtgtgggatagtagtagtgatcatgtgatattcggcggagggaccaagctgaccgtcctaggttct
agaggtggtggtggtagcggcggcggcggctctggtggtggtggatccctcgagatggcccaggtgcagctggtgcaatctg
gggctgaggtgaagaagccgggggcctctgtgaaggtttcctgcaaggcatctggatacaccttcaccaactactatattcactg
ggtgcgacaggcccccggacaagggcttgagtggatgggaataatcagacctagtggtggtatcacaaactacgcacagaag
ttccagggcagggtcagcatgaccagagacacgtccacgagcacagtctacatggagctgagcagcctgagatctgaggaca
cggccgtgtattactgtgcgcgctcttggatgtctgactcttactacgatggttggggtcaaggtactctggtgaccgtctcctcaa
*ctagtggccaggccggccagcaccatcaccatcaccatggcgcatacccgtacgacgttccggactacgcttct*
(SEQ ID NO: 255)

Amino Acid Sequence:
SYELTQPPSVSVAPGQTASMTCGGNNIGSKSVHWYQQKPSQAPVMVVHDDSER
PSGIPERISGSKSGNTATLTISRVEAGDEADYYCQVWDSSSDHVIFGGGTKLTVL
GSRGGGGSGGGGSGGGGSLEMAQVQLVQSGAEVKKPGASVKVSCKASGYTFT
NYYIHWVRQAPGQGLEWMGIIRPSGGITNYAQKFQGRVSMTRDTSTSTVYMEL
SSLRSEDTAVYYCARSWMSDSYYDGWGQGTLVTVSS*TSGQAGQHHHHHHGAY*
*PYDVPDYAS* (SEQ ID NO: 256)

Light Chain DNA Sequence:
tcctatgagctgactcagccaccctcggtgtcagtggccccaggacagacggccagcatgacctgtggggaaacaacattg
gaagtaaaagtgtgcactggtaccagcagaagccaagccaggcccctgtgatggtcgtccatgatgatagcgagcggccctc
agggatccctgagcgaatctctggctccaagtctgggaacacggccaccctgaccatcagcagggtcgaagccggggatga
ggccgactattactgtcaggtgtgggatagtagtagtgatcatgtgatattcggcggagggaccaagctgaccgtcctaggt
(SEQ ID NO: 257)

Light Chain Amino Acid Sequence:
SYELTQPPSVSVAPGQTASMTCGGNNIGSKSVHWYQQKPSQAPVMVVHDDSER
PSGIPERISGSKSGNTATLTISRVEAGDEADYYCQVWDSSSDHVIFGGGTKLTVLG
(SEQ ID NO: 258)

Heavy Chain DNA Sequence:
caggtgcagctggtgcaatctggggctgaggtgaagaagccgggggcctctgtgaaggtttcctgcaaggcatctggatacac
cttcaccaactactatattcactgggtgcgacaggcccccggacaagggcttgagtggatgggaataatcagacctagtggtgg
tatcacaaactacgcacagaagttccagggcagggtcagcatgaccagagacacgtccacgagcacagtctacatggagctg
agcagcctgagatctgaggacacggccgtgtattactgtgcgcgctcttggatgtctgactcttactacgatggttggggtcaag
gtactctggtgaccgtctcctca (SEQ ID NO: 259)

Heavy Chain Amino Acid Sequence:
QVQLVQSGAEVKKPGASVKVSCKASGYTFTNYYIHWVRQAPGQGLEWMGIIRP
SGGITNYAQKFQGRVSMTRDTSTSTVYMELSSLRSEDTAVYYCARSWMSDSYY
DGWGQGTLVTVSS (SEQ ID NO: 260)

APPENDIX C-continued

#23

DNA Sequence:

tcctatgagctgactcagccaccctcggtgtcagtggctccaggacagacggcctggattacctgtggggaaacaacattgg
aagtaaaagtgtgcactggtaccagcagaagccaggccaggcccctatactggtcgtctatgatgatagcgaccggccctcag
ggatccctgagagagtctctggctccaactctgggaacacggccaccctgaccatcagcagggtcgaagccggggatgagg
ccgactattactgtcaggtgtgggatagtagtagtgatcgttgggtgttcggcggagggaccaagctgaccgtcctaggttctag
aggtggtggtggtagcggcggcggcggctctggtggtggtggatccctcgagatggcccagatgcagctggtgcagtctgga
gctgaggtgaagaagcctggggcctcagtgaaggtctcctgcaaggcttctggttacacctttaccaactatggtatcagctggg
tgcgacaggcccctggacaagggcttgagtggatgggatggatcagcccttacaatggtaacacaaactacgcacagaagct
ccagggcagagtcaccatgaccacagacacatccacgagcacagcctacatggagctgaggaacctgagatctgacgacac
tgccgtgtattactgtgcgcgctactgggactctggttacgcttacgatgaatggggtcaaggtactctggtgaccgtctcctcaa
*ctagtggccaggccggccagcaccatcaccatcaccatggcgcatacccgtacgacgttccggactacgcttct*
(SEQ ID NO: 261)

Amino Acid Sequence:

SYELTQPPSVSVAPGQTAWITCGGNNIGSKSVHWYQQKPGQAPILVVYDDSDRP
SGIPERVSGSNSGNTATLTISRVEAGDEADYYCQVWDSSSDRWVFGGGTKLTVL
GSRGGGGSGGGGSGGGGSLEMAQMQLVQSGAEVKKPGASVKVSCKASGYTFT
NYGISWVRQAPGQGLEWMGWISPYNGNTNYAQKLQGRVTMTTDTSTSTAYME
LRNLRSDDTAVYYCARYWDSGYAYDEWGQGTLVTVSS*TSGQAGQHHHHHHGA*
*YPYDVPDYAS* (SEQ ID NO: 262)

Light Chain DNA Sequence:

tcctatgagctgactcagccaccctcggtgtcagtggctccaggacagacggcctggattacctgtggggaaacaacattgg
aagtaaaagtgtgcactggtaccagcagaagccaggccaggcccctatactggtcgtctatgatgatagcgaccggccctcag
ggatccctgagagagtctctggctccaactctgggaacacggccaccctgaccatcagcagggtcgaagccggggatgagg
ccgactattactgtcaggtgtgggatagtagtagtgatcgttgggtgttcggcggagggaccaagctgaccgtcctaggt
(SEQ ID NO: 263)

Light Chain Amino Acid Sequence:

SYELTQPPSVSVAPGQTAWITCGGNNIGSKSVHWYQQKPGQAPILVVYDDSDRP
SGIPERVSGSNSGNTATLTISRVEAGDEADYYCQVWDSSSDRWVFGGGTKLTVLG (SEQ ID NO: 264)

Heavy Chain DNA Sequence:

cagatgcagctggtgcagtctggagctgaggtgaagaagcctggggcctcagtgaaggtctcctgcaaggcttctggttacac
ctttaccaactatggtatcagctgggtgcgacaggcccctggacaagggcttgagtggatgggatggatcagcccttacaatgg
taacacaaactacgcacagaagctccagggcagagtcaccatgaccacagacacatccacgagcacagcctacatggagct
gaggaacctgagatctgacgacactgccgtgtattactgtgcgcgctactgggactctggttacgcttacgatgaatggggtcaa
ggtactctggtgaccgtctcctca (SEQ ID NO: 265)

Heavy Chain Amino Acid Sequence:

QMQLVQSGAEVKKPGASVKVSCKASGYTFTNYGISWVRQAPGQGLEWMGWIS
PYNGNTNYAQKLQGRVTMTTDTSTSTAYMELRNLRSDDTAVYYCARYWDSGY
AYDEWGQGTLVTVSS (SEQ ID NO: 266)

#24

DNA Sequence:

caggctgtgctgactcagccgccctcagtgtctgcggccccaggacagaaggtcaccatctcctgctctggaagcagctccaa
cattgggaataattatgtatcctggtaccagcagctcccaggaacagcccccaaactcctcatttatgacaataataagcgaccct
ccggtcttcctgaccgattctctggctccaagtctggcacgtcagccaccctgggcatcaccggactccagactggggacgag
gccgattattactgcggaacatgggatagcagcctgaatgccgtggtattcggcggagggacccagctcaccgttttaagttcta
gaggtggtggtggtagcggcggcggcggctctggtggtggtggatccctcgagatggcccaggtgcagctggtgcagtctgg
ggctgaggtgaagaagccggggcctctgtgaaggtttcctgcaaggcatctggatacaccttcaccaactactatattcactgg
gtgcgacaggcccccggacaagggcttgagtggatgggaataatcagacctagtggtggtatcacaaactacgcacagaagtt
ccagggcagggtcaccatgaccagagacacgtccacgagcacagtctacatggagctgagcagcctgagatctgaggacac
ggccgtgtattactgtgcgcgctcttggtctaacaaactgtcttggtacaacgatggttggggtcaaggtactctggtgaccgtctc
ctca*actagtggccaggccggccagcaccatcaccatcaccatggcgcatacccgtacgacgttccggactacgcttct*
(SEQ ID NO: 267)

Amino Acid Sequence:

QAVLTQPPSVSAAPGQKVTISCSGSSSNIGNNYVSWYQQLPGTAPKLLIYDNNKR
PSGLPDRFSGSKSGTSATLGITGLQTGDEADYYCGTWDSSLNAVVFGGGTQLTV
LSSRGGGGSGGGGSGGGGSLEMAQVQLVQSGAEVKKPGASVKVSCKASGYTFT
NYYIHWVRQAPGQGLEWMGIIRPSGGITNYAQKFQGRVTMTRDTSTSTVYMEL
SSLRSEDTAVYYCARSWSNKLSWYNDGWGQGTLVTVSS*TSGQAGQHHHHHHG*
*AYPYDVPDYAS* (SEQ ID NO: 268)

Light Chain DNA Sequence:

caggctgtgctgactcagccgccctcagtgtctgcggccccaggacagaaggtcaccatctcctgctctggaagcagctccaa
cattgggaataattatgtatcctggtaccagcagctcccaggaacagcccccaaactcctcatttatgacaataataagcgaccct
ccggtcttcctgaccgattctctggctccaagtctggcacgtcagccaccctgggcatcaccggactccagactggggacgag
gccgattattactgcggaacatgggatagcagcctgaatgccgtggtattcggcggagggacccagctcaccgttttaagt
(SEQ ID NO: 269)

Light Chain Amino Acid Sequence:

QAVLTQPPSVSAAPGQKVTISCSGSSSNIGNNYVSWYQQLPGTAPKLLIYDNNKR
PSGLPDRFSGSKSGTSATLGITGLQTGDEADYYCGTWDSSLNAVVFGGGTQLTV
LS (SEQ ID NO: 270)

APPENDIX C-continued

Heavy Chain DNA Sequence:
caggtgcagctggtgcagtctggggctgaggtgaagaagccgggggcctctgtgaaggtttcctgcaaggcatctggatacac
cttcaccaactactatattcactgggtgcgacaggcccccggacaagggcttgagtggatgggaataatcagacctagtggtgg
tatcacaaactacgcacagaagttccagggcagggtcaccatgaccagagacacgtccacgagcacagtctacatggagctg
agcagcctgagatctgaggacacggccgtgtattactgtgcgcgctcttggtctaacaaactgtcttggtacaacgatggttggg
gtcaaggtactctggtgaccgtctcctca (SEQ ID NO: 271)

Heavy Chain Amino Acid Sequence:
QVQLVQSGAEVKKPGASVKVSCKASGYTFTNYYIHWVRQAPGQGLEWMGIIRP
SGGITNYAQKFQGRVTMTRDTSTSTVYMELSSLRSEDTAVYYCARSWSNKLSW
YNDGWGQGTLVTVSS (SEQ ID NO: 272)

#25
DNA Sequence:
cagtctgtgttgacgcagccgccctcagtgtctgcggccccaggacagaaggtcaccatctcctgctctggaagcagctccaa
cattgggaataattatgtatcctggtaccagttcctcccaggaacagcccccaaacttctcatttatgacaataatcagcgaccctc
aggcattcctgaccgattctctggcttcaagtctggcacgtcagccaccctggacatcaccggactccagactggggacgagg
ccgattattactgcggaacatgggataacagcctgagtgctgcagtgttcggcagagggaccaagctgaccgtcctaggttcta
gaggtggtggtggtagcggcggcggcggctctggtggtggtggatccctcgagatggcccagatgcagctggtgcagtctgg
gactgaggtgaagagggctggggcctcagtgaaggtttcctgcaaggcatctggatacaccttcaccaactactatatgcactg
ggtgcgacaggcccctggacaagggcttgagtggatgggaataatcaaccctagtggtggtagcacaacctacgcacagaag
ttccagggcagagtcaccatgaccagggacacgtccacgagcacagtctatatggagctgagcgacctgggatctgaggaca
cggccgtgtattactgtgcgcgctcttggtctaaaactgaaggttctgatcgttggggtcaaggtactctggtgaccgtctcctcaa
*ctagtggccaggccggccagcaccatcaccatcaccatggcgcatacccgtacgacgttccggactacgcttct*
(SEQ ID NO: 273)

Amino Acid Sequence:
QSVLTQPPSVSAAPGQKVTISCSGSSSNIGNNYVSWYQFLPGTAPKLLIYDNNQR
PSGIPDRFSGFKSGTSATLDITGLQTGDEADYYCGTWDNSLSAAVFGRGTKLTVLG
SRGGGGSGGGGSGGGGSLEMAQMQLVQSGTEVKRAGASVKVSCKASGYTFTN
YYMHWVRQAPGQGLEWMGIINPSGGSTTYAQKFQGRVTMTRDTSTSTVYMEL
SDLGSEDTAVYYCARSWSKTEGSDRWGQGTLVTVSS*TSGQAGQHHHHHHGAYP*
*YDVPDYAS* (SEQ ID NO: 274)

Light Chain DNA Sequence:
cagtctgtgttgacgcagccgccctcagtgtctgcggccccaggacagaaggtcaccatctcctgctctggaagcagctccaa
cattgggaataattatgtatcctggtaccagttcctcccaggaacagcccccaaacttctcatttatgacaataatcagcgaccctc
aggcattcctgaccgattctctggcttcaagtctggcacgtcagccaccctggacatcaccggactccagactggggacgagg
ccgattattactgcggaacatgggataacagcctgagtgctgcagtgttcggcagagggaccaagctgaccgtcctaggt
(SEQ ID NO: 275)

Light Chain Amino Acid Sequence:
QSVLTQPPSVSAAPGQKVTISCSGSSSNIGNNYVSWYQFLPGTAPKLLIYDNNQR
PSGIPDRFSGFKSGTSATLDITGLQTGDEADYYCGTWDNSLSAAVFGRGTKLTVLG (SEQ ID NO: 276)

Heavy Chain DNA Sequence:
cagatgcagctggtgcagtctgggactgaggtgaagagggctggggcctcagtgaaggtttcctgcaaggcatctggatacac
cttcaccaactactatatgcactgggtgcgacaggcccctggacaagggcttgagtggatgggaataatcaaccctagtggtgg
tagcacaacctacgcacagaagttccagggcagagtcaccatgaccagggacacgtccacgagcacagtctatatggagctg
agcgacctgggatctgaggacacggccgtgtattactgtgcgcgctcttggtctaaaactgaaggttctgatcgttggggtcaag
gtactctggtgaccgtctcctca (SEQ ID NO: 277)

Heavy Chain Amino Acid Sequence:
QMQLVQSGTEVKRAGASVKVSCKASGYTFTNYYMHWVRQAPGQGLEWMGIIN
PSGGSTTYAQKFQGRVTMTRDTSTSTVYMELSDLGSEDTAVYYCARSWSKTEG
SDRWGQGTLVTVSS (SEQ ID NO: 278)

#26
DNA Sequence:
tcctatgtgctgactcagccaccctcggtgtcagtggccccaggacagacggccaggatcacctgtgggggaaccgacatca
gacgtaaaactgtccactggtaccagcagaagccaggcctggccctgtgctggtcctctatgatgatagcgaccggccctca
gggatccctgagcgattctctggctccaactctggtaacacggccaccctgaccatcagcagggtcgaaggcggggatgagg
ccgactattactgtcaggtgtgggataacgataatgatcattatgtctttggacctgggaccaaggtcaccgtcctaggttctagag
gtggtggtggtagcggcggcggcggctctggtggtggtggatccctcgagatggccgaggtccagctggtgcagtctggggc
tgaggtgaagaagcctggggcctcagtaaaggtctcctgcaaggcatctggatacaccttcaccaactactatatccactgggtg
cgacagacccctggagaagggcttgagtggatgggaataatcagacctagtggcggtaacacaaactacgcacagaagttcc
agggcagagtcaccatgaccagggacacgtccacgcgcacggtctatatggagttgagtagcctgagatctgaggacacggc
cgtgtattactgtgcgcgctcttgggacactttctctgatgaatggggtcaaggtactctggtgaccgtctcctca*actagtggcca*
*ggccggccagcaccatcaccatcaccatggcgcatacccgtacgacgttccggactacgcttct* (SEQ ID NO: 279)

Amino Acid Sequence:
SYVLTQPPSVSVAPGQTARITCGGTDIRRKTVHWYQQKPGLAPVLVLYDDSDRP
SGIPERFSGSNSGNTATLTISRVEGGDEADYYCQVWDNDNDHYVFGPGTKVTVL
GSRGGGGSGGGGSGGGGSLEMAEVQLVQSGAEVKKPGASVKVSCKASGYTFT
NYYIHWVRQTPGEGLEWMGIIRPSGGNTNYAQKFQGRVTMTRDTSTRTVYMEL
SSLRSEDTAVYYCARSWDTFSDEWGQGTLVTVSS*TSGQAGQHHHHHHGAYPYD*
*VPDYAS* (SEQ ID NO: 280)

Light Chain DNA Sequence:
tcctatgtgctgactcagccaccctcggtgtcagtggccccaggacagacggccaggatcacctgtgggggaaccgacatca
gacgtaaaactgtccactggtaccagcagaagccaggcctggcccctgtgctggtcctctatgatgatagcgaccggccctca
gggatccctgagcgattctctggctccaactctggtaacacggccaccctgaccatcagcagggtcgaaggcggggatgagg
ccgactattactgtcaggtgtgggataacgataatgatcattatgtctttggacctgggaccaaggtcaccgtcctaggt
(SEQ ID NO: 281)

Light Chain Amino Acid Sequence:
SYVLTQPPSVSVAPGQTARITCGGTDIRRKTVHWYQQKPGLAPVLVLYDDSDRP
SGIPERFSGSNSGNTATLTISRVEGGDEADYYCQVWDNDNDHYVFGPGTKVTVLG (SEQ ID NO: 282)

Heavy Chain DNA Sequence:
gaggtccagctggtgcagtctggggctgaggtgaagaagcctggggcctcagtaaaggtctcctgcaaggcatctggataca
ccttcaccaactactatatccactgggtgcgacagacccctggagaagggcttgagtggatgggaataatcagacctagtggcg
gtaacacaaactacgcacagaagttccagggcagagtcaccatgaccagggacacgtccacgcgcacggtctatatggagtt
gagtagcctgagatctgaggacacggccgtgtattactgtgcgcgctcttgggacactttctctgatgaatggggtcaaggtact
ctggtgaccgtctcctca (SEQ ID NO: 283)

Heavy Chain Amino Acid Sequence:
EVQLVQSGAEVKKPGASVKVSCKASGYTFTNYYIHWVRQTPGEGLEWMGIIRPS
GGNTNYAQKFQGRVTMTRDTSTRTVYMELSSLRSEDTAVYYCARSWDTFSDE
WGQGTLVTVSS (SEQ ID NO: 284)

#29
DNA Sequence:
cagtctgtgttgacgcagccgccctcagtgtctgcggccccaagacagaaggtcaccatctcctgctctggaagcagctccaac
attgggaataattatgtatcctggtaccagcagctcccaggaacagcccccaaactcctcatttatgacgataataagcgaccctc
agggattcctgaccgattctctggctccaagtctggcacgtcagccaccctgggcatcaccggactccagactggggacgagg
ccgattattactgcggaacatgggatagcagcctgagtgctgtggtattcggcggagggaccaagctgaccgtcctaggttcta
gaggtggtggtggtagcggcggcggcggctctggtggtggtggatccctcgagatggcccaggtgcagctggtgcagtctgg
gactgaggtgaagagggctggggcctcagtgaaggtttcctgcaaggcatctggatacaccttcaccaactactatatgcactg
ggtgcgacaggcccctggacaagggctggaatggatgggaataatcaaccctagtattggtagcacaaactacgcacagaag
ttccagggcagagtcaccatgaccagagacacgtccacgagcacagtcttcatggaactgagcagcctcagatctgacgacac
ggccgtgtattactgtgcgcgctctttcggtgactctgacggtgctgattcttggggtcaaggtactctggtgaccgtctcctc*aac*
*tagtggccaggccggccagcaccatcaccatcaccatggcgcatacccgtacgacgttccggactacgcttct*
(SEQ ID NO: 285)

Amino Acid Sequence:
QSVLTQPPSVSAAPRQKVTISCSGSSSNIGNNYVSWYQQLPGTAPKLLIYDDNKR
PSGIPDRFSGSKSGTSATLGITGLQTGDEADYYCGTWDSSLSAVVFGGGTKLTVLG
SRGGGGSGGGGSGGGGSLEMA
QVQLVQSGTEVKRAGASVKVSCKASGYTFTNYYMHWVRQAPGQGLEWMGIIN
PSIGSTNYAQKFQGRVTMTRDTSTSTVFMELSSLRSDDTAVYYCARSFGDSDGA
DSWGQGTLVTVSS
*TSGQAGQHHHHHHGAYPYDVPDYAS* (SEQ ID NO: 286)

Light Chain DNA Sequence:
cagtctgtgttgacgcagccgccctcagtgtctgcggccccaagacagaaggtcaccatctcctgctctggaagcagctccaac
attgggaataattatgtatcctggtaccagcagctcccaggaacagcccccaaactcctcatttatgacgataataagcgaccctc
agggattcctgaccgattctctggctccaagtctggcacgtcagccaccctgggcatcaccggactccagactggggacgagg
ccgattattactgcggaacatgggatagcagcctgagtgctgtggtattcggcggagggaccaagctgaccgtcctaggt
(SEQ ID NO: 287)

Light Chain Amino Acid Sequence:
QSVLTQPPSVSAAPRQKVTISCSGSSSNIGNNYVSWYQQLPGTAPKLLIYDDNKR
PSGIPDRFSGSKSGTSATLGITGLQTGDEADYYCGTWDSSLSAVVFGGGTKLTVLG (SEQ ID NO: 288)

Heavy Chain DNA Sequence:
caggtgcagctggtgcagtctgggactgaggtgaagagggctggggcctcagtgaaggtttcctgcaaggcatctggatacac
cttcaccaactactatatgcactgggtgcgacaggcccctggacaagggctggaatggatgggaataatcaaccctagtattgg
tagcacaaactacgcacagaagttccagggcagagtcaccatgaccagagacacgtccacgagcacagtcttcatggaactg
agcagcctcagatctgacgacacggccgtgtattactgtgcgcgctctttcggtgactctgacggtgctgattcttggggtcaag
gtactctggtgaccgtctcctca (SEQ ID NO: 289)

Heavy Chain Amino Acid Sequence:
QVQLVQSGTEVKRAGASVKVSCKASGYTFTNYYMHWVRQAPGQGLEWMGIIN
PSIGSTNYAQKFQGRVTMTRDTSTSTVFMELSSLRSDDTAVYYCARSFGDSDGA
DSWGQGTLVTVSS (SEQ ID NO: 290)

#30
DNA Sequence:
tcctatgtgctgactcagccaccctcggtgtcagtggccccaggacagacggccaggatgacctgtgaaggaagcaaccttgg
aagtaaaagtgtgcattggtaccagcagaagccaggccaggcccctgtgctggtcgtccatgatgatagcgaccggccctcag
ggatccctgaccgattctctggctccaagtctgggaacacggccaccctgaccatcagcagggtcgaagccggggatgaggc
cgactattactgtcaggtgtggcatagtagtagtgatcattatgtcttcggaactgcgaccaaggtcaccgtcctaggt
tctagaggtggtggtggtagcggcggcggcggctctggtggtggtggatccctcgagatggcc
caggtgcagctggtgcaatctggggctgaggtgaagaagcctggggcctctgtgaaggtttcctgcaaggcatctggatacac
cttcaccaattactatattcactgggtgcgacaggcccccggacaagggcttgagtggatgggaataatcagacctagtggtggt
atcacaaactacgcacagaagttccagggcagggtcagcatgaccagggacacgtccacgagcacagtctacatggagctga APPENDIX C-continued gcagcctgagatctgaggacactgccgtgtattactgtgcgcgctcttggcatgaaaactctggtgttgattcttggggtcaaggt
actctggtgaccgtctcctca
*actagtggccaggccggccagcaccatcaccatcaccatggcgcatacccgtacgacgttccggactacgcttct*
(SEQ ID NO: 291)

Amino Acid Sequence:
QSVLTQPPSVSVAPGKTARITCGGNNIGSKSVHWYQQKPGQAPVLVIYYDSDRP
SGIPERFSGSNSGNTATLTISRVEAGDEADYYCQVWDSSSDHYVFGTGTKVTVL
GSRGGGGSGGGGSGGGGSLEMAEVQLVESGGGVVQPGRSLRLSCAASGFTFNN
HAMHWVRQAPGKGLEWVAVISFDGDDKFYADSVKGRFTISRDNSRNTLFLQM
NNLRPEDTAVYYCSRDPYHFASGSYSYFDYWGQGTLVTVSS*TSGQAGQHHHHH*
*HGAYPYDVPDYAS* (SEQ ID NO: 292)

Light Chain DNA Sequence:
tcctatgtgctgactcagccaccctcggtgtcagtggccccaggacagacggccaggatgacctgtgaaggaagcaaccttgg
aagtaaaagtgtgcattggtaccagcagaagccaggccaggcccctgtgctggtcgtccatgatgatagcgaccggccctcag
ggatccctgaccgattctctggctccaagtctgggaacacggccaccctgaccatcagcagggtcgaagccggggatgaggc
cgactattactgtcaggtgtggcatagtagtagtgatcattatgtcttcggaactgcgaccaaggtcaccgtcctaggt
(SEQ ID NO: 293)

Light Chain Amino Acid Sequence:
QSVLTQPPSVSVAPGKTARITCGGNNIGSKSVHWYQQKPGQAPVLVIYYDSDRP
SGIPERFSGSNSGNTATLTISRVEAGDEADYYCQVWDSSSDHYVFGTGTKVTVLG (SEQ ID NO: 294)

Heavy Chain DNA Sequence:
caggtgcagctggtgcaatctggggctgaggtgaagaagcctggggcctctgtgaaggtttcctgcaaggcatctggatacac
cttcaccaattactatattcactgggtgcgacaggcccccggacaagggcttgagtggatgggaataatcagacctagtggtggt
atcacaaactacgcacagaagttccagggcagggtcagcatgaccagggacacgtccacgagcacagtctacatggagctga
gcagcctgagatctgaggacactgccgtgtattactgtgcgcgctcttggcatgaaaactctggtgttgattcttggggtcaaggt
actctggtgaccgtctcctca (SEQ ID NO: 295)

Heavy Chain Amino Acid Sequence:
EVQLVESGGGVVQPGRSLRLSCAASGFTFNNHAMHWVRQAPGKGLEWVAVISF
DGDDKFYADSVKGRFTISRDNSRNTLFLQMNNLRPEDTAVYYCSRDPYHFASGS
YSYFDYWGQGTLVTVSS (SEQ ID NO: 296)

#34
DNA Sequence:
caatctgccctgactcagcctccctccgcgtccgggtctcctggacagtcagtcaccatctcctgcactggaaccagcagtgac
gttggtgcttataactatgtctcctggtaccaacactacccaggcaaagcccccaaactcatgatttatgaggtcagtgagcggcc
ctcaggggtccctgatcgcttctctggctccaagtctggcaacacggcctccctgaccgtctctgggctccaggctgaggatga
ggctgattatttctgcagctcatatgcgggcagcaacaattttgtcttcggaactgggaccaaggtcaccgtcctaggttctagag
gtggtggtggtagcggcggcggcggctctggtggtggtggatccctcgagatggccgaggtccagctggtgcagtctggggc
tgaggtgaagaagcctgggtcctcggtgaaggtctcctgcaaggcttctggaggcaccttcagcagctatgctatcagctgggt
gcgacaggcccctggacaagggcttgagtggatgggaaggatcatccctatccttggtatagcaaactacgcacagaagttcc
agggcagagtcacgattaccgcggacaaatcctcgagcacagcctacatggcgctgagcagcctgacatctgaggacacgg
ccgtgtattactgtgcgagagggggtgactacgtcgagtcctggttcgacccctggggccagggaaccctggtcaccgtctcct
ca*actagtggccaggccggccagcaccatcaccatcaccatggcgcatacccgtacgacgttccggactacgcttct*
(SEQ ID NO: 297)

Amino Acid Sequence:
QSALTQPPSASGSPGQSVTISCTGTSSDVGAYNYVSWYQHYPGKAPKLMIYEVS
ERPSGVPDRFSGSKSGNTASLTVSGLQAEDEADYFCSSYAGSNNFVFGTGTKVT
VLGSRGGGGSGGGGSGGGGSLEMAEVQLVQSGAEVKKPGSSVKVSCKASGGTF
SSYAISWVRQAPGQGLEWMGRIIPILGIANYAQKFQGRVTITADKSSSTAYMALS
SLTSEDTAVYYCARGGDYVESWFDPWGQGTLVTVSS*TSGQAGQHHHHHHGAYP*
*YDVPDYAS* (SEQ ID NO: 298)

Light Chain DNA Sequence:
caatctgccctgactcagcctccctccgcgtccgggtctcctggacagtcagtcaccatctcctgcactggaaccagcagtgac
gttggtgcttataactatgtctcctggtaccaacactacccaggcaaagcccccaaactcatgatttatgaggtcagtgagcggcc
ctcaggggtccctgatcgcttctctggctccaagtctggcaacacggcctccctgaccgtctctgggctccaggctgaggatga
ggctgattatttctgcagctcatatgcgggcagcaacaattttgtcttcggaactgggaccaaggtcaccgtcctaggt
(SEQ ID NO: 299)

Light Chain Amino Acid Sequence:
QSALTQPPSASGSPGQSVTISCTGTSSDVGAYNYVSWYQHYPGKAPKLMIYEVS
ERPSGVPDRFSGSKSGNTASLTVSGLQAEDEADYFCSSYAGSNNFVFGTGTKVT
VLG (SEQ ID NO: 300)

Heavy Chain DNA Sequence:
gaggtccagctggtgcagtctggggctgaggtgaagaagcctgggtcctcggtgaaggtctcctgcaaggcttctggaggca
ccttcagcagctatgctatcagctgggtgcgacaggcccctggacaagggcttgagtggatgggaaggatcatccctatccttg
gtatagcaaactacgcacagaagttccagggcagagtcacgattaccgcggacaaatcctcgagcacagcctacatggcgct
gagcagcctgacatctgaggacacggccgtgtattactgtgcgagagggggtgactacgtcgagtcctggttcgacccctggg
gccagggaaccctggtcaccgtctcctca (SEQ ID NO: 301)

APPENDIX C-continued

Heavy Chain Amino Acid Sequence:
EVQLVQSGAEVKKPGSSVKVSCKASGGTFSSYAISWVRQAPGQGLEWMGRIIPI
LGIANYAQKFQGRVTITADKSSSTAYMALSSLTSEDTAVYYCARGGDYVESWF
DPWGQGTLVTVSS (SEQ ID NO: 302)

#55
DNA Sequence:
caatctgccctgactcagcctgcctccgtgtctgggtctcctggacagtcgatcaccatctcctgcactggacccaccagtgactt
taatgattatctctttgtctcctggtaccaacaacacccaggcaaagcccccaaactcatcctttatgatgtcactcatcggccctca
ggggtttctggtcgcttctctggctccaagtctgccagcacggcctccctgaccatctctgggctccaggctgaggacgaggct
gattatttctgcggctcaaaaacaggcaggaccacttatgtcttcggaactgggaccaaggtcaccgtcctaggttctagaggtg
gtggtggtagcggcggcggcggctctggtggtggtggatccctcgagatggcccaggtgcagctggtgcaatctggagctga
ggtgaagaagcctggggcctcagtaaaggtctcctgcaaggcttctggttacacctttgacaactttggtatcagctgggtgcga
caggcccctggacaagggcttgagtggatgggatggatcaacacttacgatggttacacaaactatgtagagaaactccaggg
cagagtcaccatgaccacagacacatccacgggcacagcctacatggagctgaggggcctgagatctgacgacacggccgt
gtattactgtgcgcgctctgttccgcatcagatctcttacggtgatctgtggggtcaaggtactctggtgaccgtctcctca*actagt*
*ggccaggccggccagcaccatcaccatcaccatggcgcatacccgtacgacgttccggactacgcttct* (SEQ ID NO: 303)

Amino Acid Sequence:
QSALTQPASVSGSPGQSITISCTGPTSDFNDYLFVSWYQQHPGKAPKLILYDVTH
RPSGVSGRFSGSKSASTASLTISGLQAEDEADYFCGSKTGRTTYVFGTGTKVTVL
GSRGGGGSGGGGSGGGGSLEMAQVQLVQSGAEVKKPGASVKVSCKASGYTFD
NFGISWVRQAPGQGLEWMGWINTYDGYTNYVEKLQGRVTMTTDTSTGTAYME
LRGLRSDDTAVYYCARSVPHQISYGDLWGQGTLVTVSS*TSGQAGQHHHHHHGA*
*YPYDVPDYAS* (SEQ ID NO: 304)

Light Chain DNA Sequence:
caatctgccctgactcagcctgcctccgtgtctgggtctcctggacagtcgatcaccatctcctgcactggacccaccagtgactt
taatgattatctctttgtctcctggtaccaacaacacccaggcaaagcccccaaactcatcctttatgatgtcactcatcggccctca
ggggtttctggtcgcttctctggctccaagtctgccagcacggcctccctgaccatctctgggctccaggctgaggacgaggct
gattatttctgcggctcaaaaacaggcaggaccacttatgtcttcggaactgggaccaaggtcaccgtcctaggt
(SEQ ID NO: 305)

Light Chain Amino Acid Sequence:
QSALTQPASVSGSPGQSITISCTGPTSDFNDYLFVSWYQQHPGKAPKLILYDVTH
RPSGVSGRFSGSKSASTASLTISGLQAEDEADYFCGSKTGRTTYVFGTGTKVTVLG (SEQ ID NO: 306)

Heavy Chain DNA Sequence:
caggtgcagctggtgcaatctggagctgaggtgaagaagcctggggcctcagtaaaggtctcctgcaaggcttctggttacac
ctttgacaactttggtatcagctgggtgcgacaggcccctggacaagggcttgagtggatgggatggatcaacacttacgatggt
tacacaaactatgtagagaaactccagggcagagtcaccatgaccacagacacatccacgggcacagcctacatggagctga
ggggcctgagatctgacgacacggccgtgtattactgtgcgcgctctgttccgcatcagatctcttacggtgatctgtggggtca
aggtactctggtgaccgtctcctca (SEQ ID NO: 307)

Heavy Chain Amino Acid Sequence:
QVQLVQSGAEVKKPGASVKVSCKASGYTFDNFGISWVRQAPGQGLEWMGWIN
TYDGYTNYVEKLQGRVTMTTDTSTGTAYMELRGLRSDDTAVYYCARSVPHQIS
YGDLWGQGTLVTVSS (SEQ ID NO: 308)

APPENDIX D

EXT019-04
DNA Sequence (SEQ ID NO: 309)
(light chain variable region scFv linker heavy chain variable region His tag $^{+}$ HA tag)
CAGCCTGTGCTGACTCAGCCACCCTCAGTGTCAGTGGCCCCAGGAAAGACGGCCAGGATTACCTGTGGGGGAAACA
ACATTGGAAGTAAAAGTGTGCACTGGTACCAGCAGAAGCCAGGCCAGGCCCCTGTGCTGGTCATCTATTATGATAGC
GACCGGCCCTCAGGGATCCCTGAGCGATTCTCTGGCTCCAACTCTGGGAACACGGCCACCCTGACCATCAGCAGGG
TCGAAGCCGGGGATGAGGCCGACTATTACTGTCAGGTGTGGGATAGTAGTAGTGATCATCCGGTATTCGGCGGAGG
GACCAAGCTGACCGTCCTAGGT (light chain variable region)
TCTAGAGGTGGTGGTGGTAGCGGCGGCGGCGGCTCTGGTGGTGGTGGATCCCTCGAGATGGCC (scFv linker)
CAGGTGCAGCTGGTGCAGTCTGGGGCTGAGGTGAAGAAGCCTGGGTCCTCGGTGAAGGTCTCCTGCAAGGCTTCT
GGAGGCACCTTCAGCAGCTATGCTATCAGCTGGGTGCGACAGGCCCCTGGACAAGGGCTTGAGTGGATGGGAGGG
ATCATCCCTATCTTTGGTACAGCAAACTACGCACAGAAGTTCCAGGGCAGAGTCACGATTACCGCGGACGAATCCAC
GAGCACAGCCTACATGGAGCTGAGCAGCCTGAGATCTGAGGACACGGCCGTGTATTACTGTGCGCGCTCTTCTTAC
TGGTGGACTTCTGATCGTTGGGGTCAAGGTACTCTGGTGACCGTCTCCTCA (heavy chain variable region)
ACTAGTGGCCAGGCCGGCCAGCACCATCACCATCACCATGGCGCATACCCGTACGACGTTCCGGACTACGCTTCT
(His tag $^{+}$ HA tag)

Amino Acid Sequence (SEQ ID NO: 310)
(light chain variable region scFv linker heavy chain variable region His tag $^{+}$ HA tag)
QPVLTQPPSVSVAPGKTARITCGGNNIGSKSVHWYQQKPGQAPVLVIYYDSDRPSGIPERFSGSNSGNTATLTISRVEA
GDEADYYCQVWDSSSDHPVFGGGTKLTVLG (light chain variable region)
SRGGGGSGGGGSGGGGSLEMA (scFv linker)
QVQLVQSGAEVKKPGSSVKVSCKASGGTFSSYAISWVRQAPGQGLEWMGGIIPIFGTANYAQKFQGRVTITADESTST
AYMELSSLRSEDTAVYYCARSSYWWTSDRWGQGTLVTVSS (heavy chain variable region)
TSGQAGQHHHHHHGAYPYDVPDYAS (His tag $^{+}$ HA tag)

APPENDIX D-continued

EXT019-06
DNA Sequence (SEQ ID NO: 311)
(light chain variable region scFv linker heavy chain variable region His tag + HA tag)
CAGTCTGTCGTGACGCAGCCGCCCTCAGTGTCTGGGGCCCCAGGGCAGGGGGTCACCATCCCCTGCACTGGGAGC
AGCTCCAACATCGGGGCAGGTTATGATGTACACTGGTACCAGCAGCTTCCAGGGACAGCCCCCAAACTCCTCATCTA
TGGTAACAACAATCGGCCCTCAGGGGTCCCTGACCGCTTCTCTGGCTCCAGGTCTGGCTCCTCAGCCTCCCTGGCCA
TCACTGGGCTCCAGGCTGAGGATGAGGCTGATTATTACTGCCAGTCCTATGACAGCAGCCTGAGTGATGTGGTATTC
GGCGGAGGGACCAAGCTGACCGTCCTAGGT (light chain variable region)
TCTAGAGGTGGTGGTGGTAGCGGCGGCGGCGGCTCTGGTGGTGGTGGATCCCTCGAGATGGCC (scFv linker)
GAGGTGCAGCTGGTGCAGTCTGGAGCAGAGGTGAAAAAGCCGGGGGAGTCTCTGAAGATCTCCTGTAAGGGTTCT
GGATACAACTTTGCCAGCGAGTGGATCGGATGGGTCCGCCAGATGCCCGGGAAAGGCCTGGAGTGGATGGGACTG
ATCTATCCTGCTGAATCTGAAATCACATACAGCCCGTCCTTCCAAGGCCAGGTCACCATTTCAGTCGACAAGTCCATC
AGCACCGCCTACCTGCAGTGGAGCAGCCTGAAGGCCTCGGACACCGCCATGTATTACTGTGCGCGCGCTTGGGACG
CTAACTACATCTACATGGATATCTGGGGTCAAGGTACTCTGGTGACCGTCTCCTCA (heavy chain variable region)
ACTAGTGGCCAGGCCGGCCAGCACCATCACCATCACCATGGCGCATACCCGTACGACGTTCCGGACTACGCTTCT
(His tag + HA tag)

Amino Acid Sequence
(light chain variable region scFv linker heavy chain variable region His tag + HA tag)
QSVVTQPPSVSGAPGQGVTIPCTGSSSNIGAGYDVHWYQQLPGTAPKLLIYGNNNRPSGVPDRFSGSRSGSSASLAITG
LQAEDEADYYCQSYDSSLSDVVFGGGTKLTVLG [SEQ ID NO: 110]
SRGGGGSGGGGSGGGGSLEMA [SEQ ID NO: 135]
EVQLVQSGAEVKKPGESLKISCKGSGYNFASEWIGWVRQMPGKGLEWMGLIYPAESEITYSPSFQGQVTISVDKSISTA
YLQWSSLKASDTAMYYCARAWDANYIYMDIWGQGTLVTVSS [SEQ ID NO: 109]
TSGQAGQHHHHHHGAYPYDVPDYAS [SEQ ID NO: 141]
QSVVTQPPSVSGAPGQGVTIPCTGSSSNIGAGYDVHWYQQLPGTAPKLLIYGNNNRPSGVPDRFSGSRSGSSASLAITG
LQAEDEADYYCQSYDSSLSDVVFGGGTKLTVLGSRGGGGSGGGGSGGGGSLEMAEVQLVQSGAEVKKPGESLKISCK
GSGYNFASEWIGWVRQMPGKGLEWMGLIYPAESEITYSPSFQGQVTISVDKSISTAYLQWSSLKASDTAMYYCARAWD
ANYIYMDIWGQGTLVTVSSTSGQAGQHHHHHHGAYPYDVPDYAS [SEQ ID NO: 129]

EXT019-08
DNA Sequence (SEQ ID NO: 312)
(light chain variable region scFv linker heavy chain variable region His tag + HA tag)
CAGTCTGTGTTGACTCAGCCACCCTCGGTGTCTGAAGCCCCCAGGCAGAGGGTCACCATCTCCTGTTCTGGAAGCA
GCTCCAACATCGGAAATAATGCTGTAAACTGGTACCAGCAGCTCCCAGGAAAGGCTCCCAAACTCCTCATCTATTAT
GATGATCTGCTGCCCTCAGGGGTCTCTGACCGATTCTCTGGCTCCAAGTCTGGCACCTCAGCCTCCCTGGCCATCAG
TGGGCTCCAGTCTGAGGATGAGGCTGATTATTACTGTGCAGCATGGGATGACAGCCTGAATGGTCCTGTCTTCGGA
ACTGGGACCAAGGTCACCGTCCTAGGT (light chain variable region)
TCTAGAGGTGGTGGTGGTAGCGGCGGCGGCGGCTCTGGTGGTGGTGGATCCCTCGAGATGGCC (scFv linker)
GAGGTGCAGCTGGTGCAGTCTGGAGCTGAGGTGAAGAAGCCTGGGGCCTCAGTGAAGGTCTCCTGCAAGGCTTCT
GGTTACAACTTTACCAGTTATGGTATCAGCTGGGTGCGACAGGCCCCTGGACAAGGGCTTGAGTGGATGGGATGGA
TCAGCGCTTACAATGGTAACACAAACTATGCACAGAAGCTCCAGGGCAGAGTCACCATGACCACAGACACATCCACG
AGCACAGCCTACATGGAGTTGAGGAGCCTGAGATCTGACGACACGGCCGTGTATTACTGTGCGAGAGACTGGGATT
ACGATTTTTTGACTGGGTGGGACGGTATGGACGTCTGGGGCCAAGGGACCACGGTCACCGTCTCCTCA (heavy
chain variable region)
ACTAGTGGCCAGGCCGGCCAGCACCATCACCATCACCATGGCGCATACCCGTACGACGTTCCGGACTACGCTTCT
(His tag + HA tag)

Amino Acid Sequence (SEQ ID NO: 313)
(light chain variable region scFv linker heavy chain variable region His tag + HA tag)
QSVLTQPPSVSEAPRQRVTISCSGSSSNIGNNAVNWYQQLPGKAPKLLIYYDDLLPSGVSDRFSGSKSGTSASLAISGL
QSEDEADYYCAAWDDSLNGPVFGTGTKVTVLG (light chain variable region)
SRGGGGSGGGGSGGGGSLEMA (scFv linker)
EVQLVQSGAEVKKPGASVKVSCKASGYNFTSYGISWVRQAPGQGLEWMGWISAYNGNTNYAQKLQGRVTMTTDTSTS
TAYMELRSLRSDDTAVYYCARDWDYDFLTGWDGMDVWGQGTTVTVSS (heavy chain variable region)
TSGQAGQHHHHHHGAYPYDVPDYAS (His tag + HA tag)

EXT019-09
DNA Sequence (SEQ ID NO: 314)
(light chain variable region scFv linker heavy chain variable region His tag + HA tag)
TCCTATGAGCTGACTCAGCCACCCTCAGTGTCAGTGGCCCCAGGAAAGACGGCCAGGATTACCTGTGGGGGAAACA
ACATTGGAAGTAAAAGTGTGCACTGGTACCAGCAGAAGCCAGGCCAGGCCCCTGTGCTGGTCATCTATTATGATAGC
GACCGGCCCTCAGGGATCCCTGAGCGATTCTCTGGCTCCAACTCTGGGAACACGGCCACCCTGACCATCAGCAGGG
TCGAAGCCGGGGATGAGGCCGACTATTACTGTCAGGTGTGGGATAGTAGTAGTGATCATTGGGTGTTCGGCGGAGG
GACCAAGCTGACCGTCCTAGGT (light chain variable region)
TCTAGAGGTGGTGGTGGTAGCGGCGGCGGCGGCTCTGGTGGTGGTGGATCCCTCGAGATGGCC (scFv linker)
CAGGTGCAGCTGGTGCAATCTGGGGGAGGCTTGGTCCAGCCTGGGGGGTCCCTGAAACTCTCCTGTGCAGCCTCTG
GGTTCGCCTTCAGCGGCTCTTCTCTGCACTGGGTCCGCCAGGCTTCCGGGAAAGGGCTGGAGTGGGTTGGCCGTAT
TACAAGCAAAGCTTACAATTACGCGACACTATATGCTGCGTCGGTGAAAGGCAGGTTCACCATCTCCAGAGATGATT
CAAAGAACACGGCATATCTTCAGATGAACAGCCTGCAAACCGAGGACACGGCCGTGTATTACTGTACCCAGACTGG
GGACTCATCAGCCTACTGGGGCCAGGGAACCCTGGTCACCGTCTCCTCA (heavy chain variable region)
ACTAGTGGCCAGGCCGGCCAGCACCATCACCATCACCATGGCGCATACCCGTACGACGTTCCGGACTACGCTTCT
(His tag + HA tag)

Amino Acid Sequence
(light chain variable region scFv linker heavy chain variable region His tag + HA tag)
SYELTQPPSVSVAPGKTARITCGGNNIGSKSVHWYQQKPGQAPVLVIYYDSDRPSGIPERFSGSNSGNTATLTISRVEAG
DEADYYCQVWDSSSDHWVFGGGTKLTVLG [SEQ ID NO: 112]
SRGGGGSGGGGSGGGGSLEMA [SEQ ID NO: 135]
QVQLVQSGGGLVQPGGSLKLSCAASGFAFSGSSLHWVRQASGKGLEWVGRITSKAYNYATLYAASVKGRFTISRDDSK
NTAYLQMNSLQTEDTAVYYCTQTGDSSAYWGQGTLVTVSS [SEQ ID NO: 111]
TSGQAGQHHHHHHGAYPYDVPDYAS [SEQ ID NO: 141]
SYELTQPPSVSVAPGKTARITCGGNNIGSKSVHWYQQKPGQAPVLVIYYDSDRPSGIPERFSGSNSGNTATLTISRVEAG
DEADYYCQVWDSSSDHWVFGGGTKLTVLGSRGGGGSGGGGSGGGGSLEMAQVQLVQSGGGLVQPGGSLKLSCAAS
GFAFSGSSLHWVRQASGKGLEWVGRITSKAYNYATLYAASVKGRFTISRDDSKNTAYLQMNSLQTEDTAVYYCTQTGD
SSAYWGQGTLVTVSSTSGQAGQHHHHHHGAYPYDVPDYAS [SEQ ID NO: 130]

EXT019-12
DNA Sequence (SEQ ID NO: 315)
(light chain variable region scFv linker heavy chain variable region His tag + HA tag)
TCCTATGAGCTGACTCAGCCACCCTCAGTGTCAGTGGCCCCAGGAAAGACGGCCAGGATTACCTGTGGGGGAAACA
ACATTGGAAGTAAAAGTGTGCACTGGTACCAGCAGAAGCCAGGCCAGGCCCCTGTGCTGGTCATCTATTATGATAGC
GACCGGCCCTCAGGGATCCCTGAGCGATTCTCTGGCTCCAACTCTGGGAACACGGCCACCCTGACCATCAGCAGGG
TCGAAGCCGGGGATGAGGCCGACTATTACTGTCAGGTGTGGGATAGTAGTAGTGATCATCGAGTGTTCGGCGGAGG
GACCAAGGTCACCGTCCTAGGT (light chain variable region)
TCTAGAGGTGGTGGTGGTAGCGGCGGCGGCGGCTCTGGTGGTGGTGGATCCCTCGAGATGGCC (scFv linker)
GAGGTGCAGCTGGTGGAGTCTGGGGGAGGCTTGGTCCAGCCTGGGGGGTCCCTGAGACTCTCCTGTGCAGCCTCT
GGATTCACTTTTAGTAGTTATTGGATGAATTGGGTCCGCCAGGCTCCAGGGAAGGGGCTGGAGTGGGTGGCCAACA
TAAAGCAAGATGGAAGTGAGAAAAACTATGTGGACTCTGTGAAGGGCCGATTCACCATCTCCAGAGACAACGCCAA
GAATTCACTGTATCTGCAAATGAATAGCCTGAGAGGCGAGGACACGGCCGTATATTACTGTGCGCGCTACGGTGGT
GGTCCGTACGATTCTTGGGGTCAAGGTACTCTGGTGACCGTCTCCTCA (heavy chain variable region)
ACTAGTGGCCAGGCCGGCCAGCACCATCACCATCACCATGGCGCATACCCGTACGACGTTCCGGACTACGCTTCT
(His tag + HA tag)

Amino Acid Sequence
(light chain variable region scFv linker heavy chain variable region His tag + HA tag)
SYELTQPPSVSVAPGKTARITCGGNNIGSKSVHWYQQKPGQAPVLVIYYDSDRPSGIPERFSGSNSGNTATLTISRVEAG
DEADYYCQVWDSSSDHRVFGGGTKVTVLG [SEQ ID NO: 114]
SRGGGGSGGGGSGGGGSLEMA [SEQ ID NO: 135]
EVQLVESGGGLVQPGGSLRLSCAASGFTFSSYWMNWVRQAPGKGLEWVANIKQDGSEKNYVDSVKGRFTISRDNAKN
SLYLQMNSLRGEDTAVYYCARYGGGPYDSWGQGTLVTVSS [SEQ ID NO: 113]
TSGQAGQHHHHHHGAYPYDVPDYAS [SEQ ID NO: 141]
SYELTQPPSVSVAPGKTARITCGGNNIGSKSVHWYQQKPGQAPVLVIYYDSDRPSGIPERFSGSNSGNTATLTISRVEAG
DEADYYCQVWDSSSDHRVFGGGTKVTVLGSRGGGGSGGGGSGGGGSLEMAEVQLVESGGGLVQPGGSLRLSCAAS
GFTFSSYWMNWVRQAPGKGLEWVANIKQDGSEKNYVDSVKGRFTISRDNAKNSLYLQMNSLRGEDTAVYYCARYGGG
PYDSWGQGTLVTVSSTSGQAGQHHHHHHGAYPYDVPDYAS [SEQ ID NO: 131]

EXT019-13
DNA Sequence (SEQ ID NO: 316)
(light chain variable region scFv linker heavy chain variable region His tag + HA tag)
CTGCCTGTGCTGACTCAGCCACCCTCAGTGTCAGTGGCCCCAGGAAAGACGGCCAGGATTACCTGTGGGGGAAACA
ACATTGGAAGTAAAAGTGTGCACTGGTACCAGCAGAAGCCAGGCCAGGCCCCTGTGCTGGTCATCTATTATGATAGC
GACCGGCCCTCAGGGATCCCTGAGCGATTCTCTGGCTCCAACTCTGGGAACACGGCCACCCTGACCATCAGCAGGG
TCGAAGCCGGGGATGAGGCCGACTATTACTGTCAGGTGTGGGATAGTAGTAGTGCCTATGTCTTCGGAACTGGGAC
CAAGGTCACCGTCCTAGGT (light chain variable region)
TCTAGAGGTGGTGGTGGTAGCGGCGGCGGCGGCTCTGGTGGTGGTGGATCCCTCGAGATGGCC (scFv linker)
CAGGTACAGCTGCAGCAGTCAGGTCCAGGACTGGTGAAGCCCTCGCAGACCCTCTCACTCACCTGTGCCATCTCCG
GGGACAGTGTCTCTAGCAACAGTGCTGCTTGGAACTGGATCAGGCAGTCCCCATCGAGAGGCCTTGAGTGGCTGGG
AAGGACATACTACAGGTCCAAGTGGTATAATGATTATGCAGTATCTGTGAAAAGTCGAATAACCATCAACCCAGACA
CATCCAAGAACCAGTTCTCCCTGCAGCTGAACTCTGTGACTCCCGAGGACACGGCTGTGTATTACTGTGCGCGCTAC
TACTCTACTTCTCTGGATTCTTGGGGTCAAGGTACTCTGGTGACCGTCTCCTCA (heavy chain variable region)
ACTAGTGGCCAGGCCGGCCAGCACCATCACCATCACCATGGCGCATACCCGTACGACGTTCCGGACTACGCTTCT
(His tag + HA tag)

Amino Acid Sequence (SEQ ID NO: 317)
(light chain variable region scFv linker heavy chain variable region His tag + HA tag)
LPVLTQPPSVSVAPGKTARITCGGNNIGSKSVHWYQQKPGQAPVLVIYYDSDRPSGIPERFSGSNSGNTATLTISRVEAG
DEADYYCQVWDSSSAYVFGTGTKVTVLG (light chain variable region)
SRGGGGSGGGGSGGGGSLEMA (scFv linker)
QVQLQQSGPGLVKPSQTLSLTCAISGDSVSSNSAAWNWIRQSPSRGLEWLGRTYYRSKWYNDYAVSVKSRITINPDTS
KNQFSLQLNSVTPEDTAVYYCARYYSTSLDSWGQGTLVTVSS (heavy chain variable region)
TSGQAGQHHHHHHGAYPYDVPDYAS (His tag + HA tag)

EXT019-15
DNA Sequence (SEQ ID NO: 318)
(light chain variable region scFv linker heavy chain variable region His tag + HA tag)
TCCTATGTGCTGACTCAGCCACCCTCAGTGTCAGTGGCCCCGGGAGAGACGGCCAGTATTACCTGTGGGGCCAACA
ACATTGGAAGTGAGAGTGTGCACTGGTATCAGCAGAAGTCAGGCCAGGCCCCTGTGCTGGTCATCTATTATGATAGC APPENDIX D-continued GACCGGCCCTCAGGGATCCCTGAGCGATTCTCTGGGTCCAACTCTGACAACACGGCCACCCTGACCATCAGCAGGG
TCGAAGCCGGAGATGAGGCCGACTATTACTGTCAGGTTTGGGATCATATTAATGATCATTATGTCTTCGGAAGTGGG
ACCAAGGTCACCGTCCTAGGT (light chain variable region)
TCTAGAGGTGGTGGTGGTAGCGGCGGCGGCGGCTCTGGTGGTGGTGGATCCCTCGAGATGGCC (scFv linker)
GAGGTGCAGCTGGTGGAGTCTGGGGGAGGCTTGGCACAGCCTGGGGGGTCCCTGAGACTCTCCTGTGCAGCCTCC
GGATTCTCTTTTAGCAACTATGCCATGAGCTGGGTCCGCCAGGCTCCAGGGACGGGGCTGGAGTGGGTCGCAGGTA
TTAGCGGTAGAGGTGGGAGTATACATTACGCAGACTCCGTGAAGGGTCGGTTCACCATCTCCAGAGACAATTCCCA
GAGCACGGTCTTTCTGCAAATGAACAACCTGGGAGCCGAGGACACGGCCATATACTACTGTGCGAAATCGAGCGAG
GACTATTACTTCTATCACATGGACGCCTGGGGCATTGGGACCACGGTCACCGTCTCCTCA (heavy chain variable region)
ACTAGTGGCCAGGCCGGCCAGCACCATCACCATCACCATGGCGCATACCCGTACGACGTTCCGGACTACGCTTCT
(His tag + HA tag)

Amino Acid Sequence
(light chain variable region scFv linker heavy chain variable region His tag + HA tag)
SYVLTQPPSVSVAPGETASITCGANNIGSESVHWYQQKSGQAPVLVIYYDSDRPSGIPERFSGSNSDNTATLTISRVEAG
DEADYYCQVWDHINDHYVFGSGTKVTVLG [SEQ ID NO: 116]
SRGGGGSGGGGSGGGGSLEMA [SEQ ID NO: 135]
EVQLVESGGGLAQPGGSLRLSCAASGFSFSNYAMSWVRQAPGTGLEWVAGISGRGGSIHYADSVKGRFTISRDNSQS
TVFLQMNNLGAEDTAIYYCAKSSEDYYFYHMDAWGIGTTVTVSS [SEQ ID NO: 115]
TSGQAGQHHHHHHGAYPYDVPDYAS [SEQ ID NO: 141]
SYVLTQPPSVSVAPGETASITCGANNIGSESVHWYQQKSGQAPVLVIYYDSDRPSGIPERFSGSNSDNTATLTISRVEAG
DEADYYCQVWDHINDHYVFGSGTKVTVLGSRGGGGSGGGGSGGGGSLEMAEVQLVESGGGLAQPGGSLRLSCAASG
FSFSNYAMSWVRQAPGTGLEWVAGISGRGGSIHYADSVKGRFTISRDNSQSTVFLQMNNLGAEDTAIYYCAKSSEDYY
FYHMDAWGIGTTVTVSSTSGQAGQHHHHHHGAYPYDVPDYAS [SEQ ID NO: 132]

EXT019-20
DNA Sequence (SEQ ID NO: 319)
(light chain variable region scFv linker heavy chain variable region His tag + HA tag)
TCCTATGTGCTGACTCAGCCACCCTCAGTGTCAGTGGCCCCAGGAAAGACGGCCAGGATTACCTGTGGGGGAAACA
ACATTGGAAGTAAAAGTGTGCACTGGTACCAGCAGAAGCCAGGCCAGGCCCCTGTGCTGGTCATCTATTATGATAGC
GACCGGCCCTCAGGGATCCCTGAGCGATTCTCTGGCTCCAACTCTGGGAACACGGCCACCCTGACCATCAGCAGGG
TCGAAGCCGGGGATGAGGCCGACTATTACTGTCAGGTGTGGGATAGTAGTAGTGATCGTGTGGTATTCGGCGGAGG
GACCAAGCTGACCGTCCTAGGT (light chain variable region)
TCTAGAGGTGGTGGTGGTAGCGGCGGCGGCGGCTCTGGTGGTGGTGGATCCCTCGAGATGGCC (scFv linker)
CAGGTACAGCTGCAGCAGTCAGGTCCAGGACTGGTGAAGCCCTCGCAGACCCTCTCACTCACCTGTGCCATCTCCG
GGGACAGTATCTCTAGCAAAAGTGCTGCTTGGAACTGGATCAGGCAGTCCCCATCGAGAGGCCTAGAGTGGCTGGG
AAGGACATACTACAGGTCCAAGTGGTATTATGAATATGCACCATCTGTGAGAAGTCGAATAACCATCAACCGAGACA
CATCCAAGAACCAGTTCTCCCTGCAACTTAACTCTGTGACTCCCGAGGACACGGCTGTATATTATTGTGCAAGATCCA
CTGGGACCTTTGACTACTGGGGCCAGGGAACCCTGGTCACCGTCTCCTCA (heavy chain variable region)
ACTAGTGGCCAGGCCGGCCAGCACCATCACCATCACCATGGCGCATACCCGTACGACGTTCCGGACTACGCTTCT
(His tag + HA tag)

Amino Acid Sequence
(light chain variable region scFv linker heavy chain variable region His tag + HA tag)
SYVLTQPPSVSVAPGKTARITCGGNNIGSKSVHWYQQKPGQAPVLVIYYDSDRPSGIPERFSGSNSGNTATLTISRVEAG
DEADYYCQVWDSSSDRVVFGGGTKLTVLG [SEQ ID NO: 118]
SRGGGGSGGGGSGGGGSLEMA [SEQ ID NO: 135]
QVQLQQSGPGLVKPSQTLSLTCAISGDSISSKSAAWNWIRQSPSRGLEWLGRTYYRSKWYYEYAPSVRSRITINRDTSK
NQFSLQLNSVTPEDTAVYYCARSTGTFDYWGQGTLVTVSS [SEQ ID NO: 117]
TSGQAGQHHHHHHGAYPYDVPDYAS [SEQ ID NO: 141]
SYVLTQPPSVSVAPGKTARITCGGNNIGSKSVHWYQQKPGQAPVLVIYYDSDRPSGIPERFSGSNSGNTATLTISRVEAG
DEADYYCQVWDSSSDRVVFGGGTKLTVLGSRGGGGSGGGGSGGGGSLEMAQVQLQQSGPGLVKPSQTLSLTCAISG
DSISSKSAAWNWIRQSPSRGLEWLGRTYYRSKWYYEYAPSVRSRITINRDTSKNQFSLQLNSVTPEDTAVYYCARSTGT
FDYWGQGTLVTVSSTSGQAGQHHHHHHGAYPYDVPDYAS [SEQ ID NO: 133]

APPENDIX E

| | VH CDR1 | VHCDR2 | VH CDR3 | VL CDR1 | VL CDR2 | VL CDR3 |
|---|---|---|---|---|---|---|
| EXT019-04 | GGTFSSYA (SEQ ID NO: 21) | IIPIFGTA (SEQ ID NO: 22) | ARSSYWWTSDR (SEQ ID NO: 327) | NIGSKS (SEQ ID NO: 42) | YDS (SEQ ID NO: 43) | QVWDSSSDHPV (SEQ ID NO: 332) |
| EXT019-08 | GYNFTSYG (SEQ ID NO: 323) | ISAYNGNT (SEQ ID NO: 325) | ARDWDYD-FLTGWDGMDV (SEQ ID NO: 328) | SSNIGNNA (SEQ ID NO: 330) | YDD (SEQ ID NO: 331) | AAWDDSLNGPV (SEQ ID NO: 333) |

APPENDIX E-continued

| | VH CDR1 | VHCDR2 | VH CDR3 | VL CDR1 | VL CDR2 | VL CDR3 |
|---|---|---|---|---|---|---|
| EXT019-13 | VSSNSAAWN (SEQ ID NO: 324) | YRSKWYN (SEQ ID NO: 326) | ARYYSTSLDS (SEQ ID NO: 329) | NIGSKS (SEQ ID NO: 42) | YDS (SEQ ID NO: 43) | QVWDSSSAYV (SEQ ID NO: 334) |

APPENDIX F

EXT018-02
DNA Sequence (SEQ ID NO: 335)
(light chain variable region scFv linker heavy chain variable region His tag $^{+}$ HA tag)
CAGTCTGTCGTGACGCAGCCGCCCTCAGTGTCTGGGGCCCCAGGGCAGAGGGTCACCATCTCCTGCACTGGGAGC
AGCTCCAACATCGGGGCAGGTTTTGATGTACACTGGTACCAGCAGCTTCCAGGAACAGCCCCCAAACTCCTCATCTA
TGGTAACAGCAATCGGCCCTCAGGGGTCCCTGACCGATTCTCTGGCTCCAAGTCTGCCACCTCAGCCTCCCTGGCCA
TCACTGGGCTCCAGGCTGAGGATGAGGCTGATTATTACTGCCAGTCCTATGACAGCAGCCTGAGTGGTGTGGTATTC
GGCGGAGGGACCAAGCTGACCGTCCTAGGT (light chain variable region)
TCTAGAGGTGGTGGTGGTAGCGGCGGCGGCGGCTCTGGTGGTGGTGGATCCCTCGAGATGGCC (scFv linker)
CAGGTGCAGCTGGTGCAGTCTGGGGCTGAGGTGAAGAAGCCTGGGTCCTCGGTGAAGGTCTCCTGCAAGACTTCTG
GAGGCACCTTCAGCAGCTATGCTATCAGCTGGGTGCGACAGGCCCCTGGACAAGGGCTTGAGTGGATGGGAGGGA
TCATCCCTATCTTTGGTACAGCAAACTACGCACAGAGGTTCCAGGGCAGAGTCACGATTACCGCGGACGAATCCACA
AACACAGTCTACATGGAGCTGAGCAGCCTGAGATCTGAGGACACGGCCGTGTATTACTGTGCGCGCGAATCTTGGT
ACCTTGATGAATGGGGTCAAGGTACTCTGGTGACCGTCTCCTCA (heavy chain variable region)
ACTAGTGGCCAGGCCGGCCAGCACCATCACCATCACCATGGCGCATACCCGTACGACGTTCCGGACTACGCTTCT
(His tag $^{+}$ HA tag)

Amino Acid Sequence (SEQ ID NO: 336)
(light chain variable region scFv linker heavy chain variable region His tag $^{+}$ HA tag)
QSVVTQPPSVSGAPGQRVTISCTGSSSNIGAGFDVHWYQQLPGTAPKLLIYGNSNRPSGVPDRFSGSKSATSASLAITG
LQAEDEA DYYCQSYDSSLSGVVFGGGTKLTVLG (light chain variable region)
SRGGGGSGGGGSGGGGSLEMA (scFv linker)
QVQLVQSGAEVKKPGSSVKVSCKTSGGTFSSYAISWVRQAPGQGLEWMGGIIPIFGTANYAQRFQGRVTITADESTNT
VYMELSSLRSEDTAVYYCARESWYLDEWGQGTLVTVSS (heavy chain variable region)
TSGQAGQHHHHHHGAYPYDVPDYAS (His tag $^{+}$ HA tag)

EXT018-04
DNA Sequence (SEQ ID NO: 337)
(light chain variable region scFv linker heavy chain variable region His tag $^{+}$ HA tag)
CAGTCTGTGTTGACGCAGCCGCCCTCAGTGTCTGGGGCCCCAGGGCAGAGGGTCACCATCTCCTGCACTGGGAGCA
ACTCCAACATCGGGGCAGATTTTGATGTACACTGGTACCAGCAGCTTCCAGGAACAGCCCCCAAGCTCCTCATCTAT
GGTAACAACAATCGGCCCTCAGGGGTCCCTGACCGATTTTCTGGCTCCAAGTCTGACACCTCAGCCTCCCTGGCCAT
CACTGGGCTCCAGGCTGAGGATGAGGCTGATTACTACTGCCAGTCCTATGACATCAGCCTGAATGGTTATGTCTTCG
GAACTGGGACCAAGGTCACCGTCCTAGGT (light chain variable region)
TCTAGAGGTGGTGGTGGTAGCGGCGGCGGCGGCTCTGGTGGTGGTGGATCCCTCGAGATGGCC (scFv linker)
CAGGTGCAGCTACAGCAGTGGGGCGCAGGACTGTTGAAGCCTTCGGAGACCCTGTCCCTCACCTGCGCTGTCTCTG
GTGGGTCCTTCAGTGATTACTACTGGAGCTGGATCCGCCAGCCCCCAGGGAAGGGGCTGGAGTGGATTGGGGAAA
TCACTCATACTGGAAGCACCAACTACAACCCGTCCCTCAAGAGTCGAGTCACCATATCAGTAGACACGTCCAAGAAC
CATTTCTCCCTGAATCTGACCTCTGTGACCGCCGCGGACACGGCCGTGTATTACTGTGCGCGCTCTAACGGTTTCTA
CTACGATACTTGGGGTCAAGGTACTCTGGTGACCGTCTCCTCA (heavy chain variable region)
ACTAGTGGCCAGGCCGGCCAGCACCATCACCATCACCATGGCGCATACCCGTACGACGTTCCGGACTACGCTTCT
(His tag $^{+}$ HA tag)

Amino Acid Sequence (SEQ ID NO: 338)
(light chain variable region scFv linker heavy chain variable region His tag $^{+}$ HA tag)
QSVLTQPPSVSGAPGQRVTISCTGSNSNIGADFDVHWYQQLPGTAPKLLIYGNNNRPSGVPDRFSGSKSDTSASLAITG
LQAEDEADYYCQSYDISLNGYVFGTGTKVTVLG (light chain variable region)
SRGGGGSGGGGSGGGGSLEMA (scFv linker)
QVQLQQWGAGLLKPSETLSLTCAVSGGSFSDYYWSWIRQPPGKGLEWIGEITHTGSTNYNPSLKSRVTISVDTSKNHF
SLNLTSVTAADTAVYYCARSNGFYYDTWGQGTLVTVSS (heavy chain variable region)
TSGQAGQHHHHHHGAYPYDVPDYAS (His tag $^{+}$ HA tag)

EXT018-05
DNA Sequence (SEQ ID NO: 339)
(light chain variable region scFv linker heavy chain variable region His tag $^{+}$ HA tag)
CAGTCTGTGTTGACTCAGCCACCCTCAGTGTCAGTGGCCCCAGGAAAGACGGCCAAGATTACCTGTGGCGGAGACA
ACATTGGAAGTAAAACTGTGCACTGGTACCAGCAGAAGCCAGGCCAGGCCCCTGCACTTCTCATCTATTATGATAGT APPENDIX F-continued GACCGGCCCTCAGGGATCCCTGAGCGATTCTCTGGCTCCAATTCTGGAAATACGGCCACCCTGAGCATCAGCAGGG
TCGAGGCCGGGGATGAGGCCGGCTATTTCTGTCAGGTGTGGGATGGGAGTAGTGATCATGTGATCTTCGGCGGAG
GGACCAAGCTGACCGTCCTAGGT (light chain variable region)
TCTAGAGGTGGTGGTGGTAGCGGCGGCGGCGGCTCTGGTGGTGGTGGATCCCTCGAGATGGCC (scFv linker)
CAGATGCAGCTGGTGCAATCTGGGGGAGGCGTGGTCCAGCCTGGGAGGTCCCTGAGACTCTCCTGTGCAGCCTCT
GGATTCACCTTCAGTAGCTATGCTATGCACTGGGTCCGCCAGGCTCCAGGCAAGGGGCTGGAGTGGGTGGCAGTTA
TATCATATGATGGAAGTAATAAATACTACGCAGACTCCGTGAAGGGCCGATTCACCATCTCCAGAGACAATTCCAAG
AACACGCTGTATCTGCAAATGAACAGCCTGAGAGCTGAGGACACGGCTGTGTATTACTGTGCGAGAGATCGGCATG
ATTACGTTATGGACGTCTGGGGCAAAGGGACCACGGTCACCGTCTCCTCA (heavy chain variable region)
ACTAGTGGCCAGGCCGGCCAGCACCATCACCATCACCATGGCGCATACCCGTACGACGTTCCGGACTACGCTTCT
(His tag + HA tag)

Amino Acid Sequence
(light chain variable region scFv linker heavy chain variable region His tag + HA tag)
QSVLTQPPSVSVAPGKTAKITCGGDNIGSKTVHWYQQKPGQAPALLIYYDSDRPSGIPERFSGSNSGNTATLSISRVEA
GDEAGYFCQVWDGSSDHVIFGGGTKLTVLG [SEQ ID NO: 120]
SRGGGGSGGGGSGGGGSLEMA [SEQ ID NO: 135]
QMQLVQSGGGVVQPGRSLRLSCAASGFTFSSYAMHWVRQAPGKGLEWVAVISYDGSNKYYADSVKGRFTISRDNSKN
TLYLQMNSLRAEDTAVYYCARDRHDYVMDVWGKGTTVTVSS [SEQ ID NO: 119]
TSGQAGQHHHHHHGAYPYDVPDYAS [SEQ ID NO: 141]
QSVLTQPPSVSVAPGKTAKITCGGDNIGSKTVHWYQQKPGQAPALLIYYDSDRPSGIPERFSGSNSGNTATLSISRVEA
GDEAGYFCQVWDGSSDHVIFGGGTKLTVLGSRGGGGSGGGGSGGGGSLEMAQMQLVQSGGGVVQPGRSLRLSCAA
SGFTFSSYAMHWVRQAPGKGLEWVAVISYDGSNKYYADSVKGRFTISRDNSKNTLYLQMNSLRAEDTAVYYCARDRHD
YVMDVWGKGTTVTVSSTSGQAGQHHHHHHGAYPYDVPDYAS [SEQ ID NO: 134]

APPENDIX G

| | HCDR1 | HCDR2 | HCDR3 | LCDR1 | LCDR2 | LCDR3 |
|---|---|---|---|---|---|---|
| EXT018-02 | GGTFSSYA (SEQ ID NO: 21) | IIPIFGTA (SEQ ID NO: 22) | ARESWYLDE (SEQ ID NO: 342) | SSNIGAGFD (SEQ ID NO: 344) | GNS (SEQ ID NO: 13) | QSYDSSLSGVV (SEQ ID NO: 321) |
| EXT018-04 | GGSFSDYY (SEQ ID NO: 340) | ITHTGST (SEQ ID NO: 341) | ARSNGFYYDT (SEQ ID NO: 343) | NSNIGADFD (SEQ ID NO: 320) | GNN (SEQ ID NO: 61) | QSYDISLNGYV (SEQ ID NO: 322) |

What is claimed is:

1. A monoclonal antibody or an antigen-binding portion thereof, which binds to a Foxp3 peptide bound to a human major histocompatibility complex (MEW) molecule, wherein the antibody or antigen-binding portion thereof each comprises a heavy chain variable region that comprises a CDR1 comprising the amino acid sequence set forth in SEQ ID NO: 39, a CDR2 comprising the amino acid sequence set forth in SEQ ID NO: 40, and a CDR3 comprising the amino acid sequence set forth in SEQ ID NO: 41; and a light chain variable region that comprises a CDR1 comprising the amino acid sequence set forth in SEQ ID NO: 42, a CDR2 comprising the amino acid sequence set forth in SEQ ID NO: 43, and a CDR3 comprising the amino acid sequence set forth in SEQ ID NO: 44.

2. The antibody or antigen-binding portion thereof of claim 1, wherein the heavy chain variable region comprises the amino acid sequence set forth in SEQ ID NO: 103, and the light chain variable region comprises the amino acid sequence set forth in SEQ ID NO: 104.

3. The antibody or antigen-binding portion thereof of claim 1, wherein (a) the antibody comprises a human variable region framework region; (b) the antibody or antigen-binding portion thereof is a fully human antibody or an antigen-binding portion thereof; (c) the antigen-binding portion of the antibody is a Fab, a Fab', a $F(ab')_2$, a variable fragment (Fv), or a single chain variable fragment (scFv); (d) the antibody or antigen-binding portion thereof is of an IgG1, IgG2, IgG3, or IgG4 isotype; and/or (e) the antibody or antigen-binding portion thereof comprises one or more post-translational modifications.

4. An immunoconjugate comprising the antibody or antigen-binding portion thereof of claim 1 linked to a therapeutic agent.

5. A composition comprising the antibody or antigen-binding portion thereof of claim 1 and a pharmaceutically acceptable carrier.

6. A kit for inducing death of cancer cells, comprising the antibody or antigen-binding portion thereof of claim 1, wherein the cancer cells present the Foxp3 peptide bound to the MHC molecule.

7. The immunoconjugate of claim 4, wherein the therapeutic agent is a drug, a cytotoxin, or a radioactive isotope.

8. An immunoconjugate comprising the antibody or antigen-binding portion thereof of claim 2 linked to a therapeutic agent.

9. The immunoconjugate of claim 8, wherein the therapeutic agent is a drug, a cytotoxin, or a radioactive isotope.

10. A composition comprising the antibody or antigen-binding portion thereof of claim 2 and a pharmaceutically acceptable carrier.

11. A kit for inducing death of cancer cells, comprising the antibody or antigen-binding portion thereof of claim 2, wherein the cancer cells present the Foxp3 peptide bound to the MHC molecule.

* * * * *

SEQUENCE LISTING

<160> NUMBER OF SEQ ID NOS: 344

<210> SEQ ID NO 1
<211> LENGTH: 431
<212> TYPE: PRT
<213> ORGANISM: Homo sapiens

<400> SEQUENCE: 1

Met Pro Asn Pro Arg Pro Gly Lys Pro Ser Ala Pro Ser Leu Ala Leu
1 5 10 15

Gly Pro Ser Pro Gly Ala Ser Pro Ser Trp Arg Ala Ala Pro Lys Ala
20 25 30

Ser Asp Leu Leu Gly Ala Arg Gly Pro Gly Gly Thr Phe Gln Gly Arg
35 40 45

Asp Leu Arg Gly Gly Ala His Ala Ser Ser Ser Ser Leu Asn Pro Met
50 55 60

Pro Pro Ser Gln Leu Gln Leu Pro Thr Leu Pro Leu Val Met Val Ala
65 70 75 80

Pro Ser Gly Ala Arg Leu Gly Pro Leu Pro His Leu Gln Ala Leu Leu
85 90 95

Gln Asp Arg Pro His Phe Met His Gln Leu Ser Thr Val Asp Ala His
100 105 110

Ala Arg Thr Pro Val Leu Gln Val His Pro Leu Glu Ser Pro Ala Met

```
        115                 120                 125

Ile Ser Leu Thr Pro Pro Thr Thr Ala Thr Gly Val Phe Ser Leu Lys
    130                 135                 140

Ala Arg Pro Gly Leu Pro Pro Gly Ile Asn Val Ala Ser Leu Glu Trp
145                 150                 155                 160

Val Ser Arg Glu Pro Ala Leu Leu Cys Thr Phe Pro Asn Pro Ser Ala
                165                 170                 175

Pro Arg Lys Asp Ser Thr Leu Ser Ala Val Pro Gln Ser Ser Tyr Pro
            180                 185                 190

Leu Leu Ala Asn Gly Val Cys Lys Trp Pro Gly Cys Glu Lys Val Phe
        195                 200                 205

Glu Glu Pro Glu Asp Phe Leu Lys His Cys Gln Ala Asp His Leu Leu
    210                 215                 220

Asp Glu Lys Gly Arg Ala Gln Cys Leu Leu Gln Arg Glu Met Val Gln
225                 230                 235                 240

Ser Leu Glu Gln Gln Leu Val Leu Glu Lys Glu Lys Leu Ser Ala Met
                245                 250                 255

Gln Ala His Leu Ala Gly Lys Met Ala Leu Thr Lys Ala Ser Ser Val
            260                 265                 270

Ala Ser Ser Asp Lys Gly Ser Cys Cys Ile Val Ala Ala Gly Ser Gln
        275                 280                 285

Gly Pro Val Val Pro Ala Trp Ser Gly Pro Arg Glu Ala Pro Asp Ser
    290                 295                 300

Leu Phe Ala Val Arg Arg His Leu Trp Gly Ser His Gly Asn Ser Thr
305                 310                 315                 320

Phe Pro Glu Phe Leu His Asn Met Asp Tyr Phe Lys Phe His Asn Met
                325                 330                 335

Arg Pro Pro Phe Thr Tyr Ala Thr Leu Ile Arg Trp Ala Ile Leu Glu
            340                 345                 350

Ala Pro Glu Lys Gln Arg Thr Leu Asn Glu Ile Tyr His Trp Phe Thr
        355                 360                 365

Arg Met Phe Ala Phe Phe Arg Asn His Pro Ala Thr Trp Lys Asn Ala
    370                 375                 380

Ile Arg His Asn Leu Ser Leu His Lys Cys Phe Val Arg Val Glu Ser
385                 390                 395                 400

Glu Lys Gly Ala Val Trp Thr Val Asp Glu Leu Glu Phe Arg Lys Lys
                405                 410                 415

Arg Ser Gln Arg Pro Ser Arg Cys Ser Asn Pro Thr Pro Gly Pro
            420                 425                 430


<210> SEQ ID NO 2
<211> LENGTH: 9
<212> TYPE: PRT
<213> ORGANISM: Homo sapiens

<400> SEQUENCE: 2

Lys Leu Ser Ala Met Gln Ala His Leu
1               5


<210> SEQ ID NO 3
<211> LENGTH: 9
<212> TYPE: PRT
<213> ORGANISM: Homo sapiens

<400> SEQUENCE: 3

Ser Leu His Lys Cys Phe Val Arg Val
```

1 5

<210> SEQ ID NO 4
<211> LENGTH: 9
<212> TYPE: PRT
<213> ORGANISM: Homo sapiens

<400> SEQUENCE: 4

Ser Leu Phe Ala Val Arg Arg His Leu
1 5

<210> SEQ ID NO 5
<211> LENGTH: 9
<212> TYPE: PRT
<213> ORGANISM: Homo sapiens

<400> SEQUENCE: 5

Asn Leu Ser Leu His Lys Cys Phe Val
1 5

<210> SEQ ID NO 6
<211> LENGTH: 9
<212> TYPE: PRT
<213> ORGANISM: Homo sapiens

<400> SEQUENCE: 6

Leu Leu Gln Asp Arg Pro His Phe Met
1 5

<210> SEQ ID NO 7
<211> LENGTH: 9
<212> TYPE: PRT
<213> ORGANISM: Homo sapiens

<400> SEQUENCE: 7

Leu Gln Leu Pro Thr Leu Pro Leu Val
1 5

<210> SEQ ID NO 8
<211> LENGTH: 10
<212> TYPE: PRT
<213> ORGANISM: Homo sapiens

<400> SEQUENCE: 8

Thr Leu Ile Arg Trp Ala Ile Leu Glu Ala
1 5 10

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 9

Gly Asp Thr Phe Ser Arg Tyr Ala
1 5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 10

Ile Ile Pro Ile Phe Gly Thr Pro
1 5

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 11

Ala Arg Ser Ile Tyr Arg Tyr Ser Glu Tyr Asp His
1 5 10

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 12

Ser Ser Asn Ile Gly Ala Gly Tyr Asp
1 5

<210> SEQ ID NO 13
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 13

Gly Asn Ser
1

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 14

Gln Ser Tyr Asp Ser Ser Leu Ser Gly Tyr Val
1 5 10

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 15

Gly Tyr Thr Phe Ser Asn Tyr Tyr
1 5

<210> SEQ ID NO 16
<211> LENGTH: 8

<212> TYPE: PRT
<213> ORGANISM: Artificial Sequence
<220> FEATURE:
<223> OTHER INFORMATION: Description of Artificial Sequence: Synthetic peptide

<400> SEQUENCE: 16

Ile Asn Pro Ser Val Gly Thr Thr
1 5

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 17

Ala Arg Asp Trp Trp Gly Gln Met Met Tyr Asp Gly
1 5 10

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 18

Ser Ser Asn Ile Gly Ser Asn Thr
1 5

<210> SEQ ID NO 19
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 19

Ser Asn Asn
1

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 20

Ala Ala Trp Asp Asp Ser Leu Asn Gly Gln Gly Val
1 5 10

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 21

Gly Gly Thr Phe Ser Ser Tyr Ala 1 5

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 22

Ile Ile Pro Ile Phe Gly Thr Ala
1 5

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 23

Ala Arg Tyr Ser Tyr Lys Tyr Gly Glu Leu Asp Thr
1 5 10

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 24

Ser Ser Asn Ile Gly Ala Gly Tyr Asp
1 5

<210> SEQ ID NO 25
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 25

Gly Asn Ser
1

<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 26

Gln Ser Tyr Asp Ser Ser Leu Ser Gly Ser Val
1 5 10

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 27

Gly Tyr Thr Phe Thr Asn Tyr Tyr
1 5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 28

Ile Arg Pro Ser Gly Gly Ile Thr
1 5

<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 29

Ala Arg Ser Trp Asp Tyr Phe Ala Ser Asn Asp Phe
1 5 10

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 30

Asn Ile Gly Ser Glu Ser
1 5

<210> SEQ ID NO 31
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 31

Asp Asp Asp
1

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 32

Gln Val Trp Asp Arg Ser Ser Asp His Trp Phe
1 5 10

<210> SEQ ID NO 33

<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 33

Gly Gly Thr Phe Ser Thr Tyr Ala
1 5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 34

Ile Ile Pro Ile Phe Gly Thr Ala
1 5

<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 35

Ala Arg Ala Glu Tyr Val Tyr Gly Glu Tyr Asp Gln
1 5 10

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 36

Ser Ser Asn Ile Gly Ala Gly Tyr Asp
1 5

<210> SEQ ID NO 37
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 37

Gly Asn Ser
1

<210> SEQ ID NO 38
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 38

Gln Ser Tyr Asp Ser Ser Leu Ser Gly Tyr Val
1 5 10

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 39

Gly Phe Thr Phe Asn Asn His Ala
1 5

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 40

Ile Ser Phe Asp Gly Asp Asp Lys
1 5

<210> SEQ ID NO 41
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 41

Ser Arg Asp Pro Tyr His Phe Ala Ser Gly Ser Tyr Ser Tyr Phe Asp
1 5 10 15

Tyr

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 42

Asn Ile Gly Ser Lys Ser
1 5

<210> SEQ ID NO 43
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 43

Tyr Asp Ser
1

<210> SEQ ID NO 44
<211> LENGTH: 11
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 44

Gln Val Trp Asp Ser Ser Ser Asp His Tyr Val
1               5                   10

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Tyr Thr Phe Thr Asn Tyr Tyr
1               5

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ile Arg Pro Ser Gly Gly Asn Thr
1               5

<210> SEQ ID NO 47
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ala Arg Ser Trp Asn Ser Arg Asp Val Asp Ser
1               5                   10

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ser Gly Ser Ile Ala Ser His Tyr
1               5

<210> SEQ ID NO 49
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Glu Asn Asn
1

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 50

Gln Ser Tyr Asp Arg Ser Asn His Val Val
1 5 10

<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 51

Gly Gly Thr Phe Ser Ser Tyr Ala
1 5

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 52

Ile Ile Pro Ile Phe Gly Thr Ala
1 5

<210> SEQ ID NO 53
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 53

Ala Arg Pro Ser Tyr Tyr Ser Ile Lys Ser Ala Trp Asp His
1 5 10

<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 54

Thr Ser Asn Ile Gly Lys Asn Gly
1 5

<210> SEQ ID NO 55
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 55

Asn Asp His
1

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 56

Ala Thr Trp Asp Asp Thr Leu Asp Leu Pro Leu
1 5 10

<210> SEQ ID NO 57
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 57

Gly Tyr Asn Phe Ala Ser Glu Trp
1 5

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 58

Ile Tyr Pro Ala Glu Ser Glu Ile
1 5

<210> SEQ ID NO 59
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 59

Ala Arg Ala Trp Asp Ala Asn Tyr Ile Tyr Met Asp Ile
1 5 10

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 60

Ser Ser Asn Ile Gly Ala Gly Tyr Asp
1 5

<210> SEQ ID NO 61
<211> LENGTH: 3

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gly Asn Asn
1


<210> SEQ ID NO 62
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gln Ser Tyr Asp Ser Ser Leu Ser Asp Val Val
1               5                   10


<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gly Phe Ala Phe Ser Gly Ser Ser
1               5


<210> SEQ ID NO 64
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ile Thr Ser Lys Ala Tyr Asn Tyr Ala Thr
1               5                   10


<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Thr Gln Thr Gly Asp Ser Ser Ala Tyr
1               5


<210> SEQ ID NO 66
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Asn Ile Gly Ser Lys Ser
```

1 5

<210> SEQ ID NO 67
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 67

Tyr Asp Ser
1

<210> SEQ ID NO 68
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 68

Gln Val Trp Asp Ser Ser Ser Asp His Trp Val
1 5 10

<210> SEQ ID NO 69
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 69

Gly Phe Thr Phe Ser Ser Tyr Trp
1 5

<210> SEQ ID NO 70
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 70

Ile Lys Gln Asp Gly Ser Glu Lys
1 5

<210> SEQ ID NO 71
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 71

Ala Arg Tyr Gly Gly Gly Pro Tyr Asp Ser
1 5 10

<210> SEQ ID NO 72
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 72

Asn Ile Gly Ser Lys Ser
1 5

<210> SEQ ID NO 73
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 73

Tyr Asp Ser
1

<210> SEQ ID NO 74
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 74

Gln Val Trp Asp Ser Ser Ser Asp His Arg Val
1 5 10

<210> SEQ ID NO 75
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 75

Gly Phe Ser Phe Ser Asn Tyr Ala
1 5

<210> SEQ ID NO 76
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 76

Ile Ser Gly Arg Gly Gly Ser Ile
1 5

<210> SEQ ID NO 77
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 77

Ala Lys Ser Ser Glu Asp Tyr Tyr Phe Tyr His Met Asp Ala
1 5 10

<210> SEQ ID NO 78

<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 78

Asn Ile Gly Ser Glu Ser
1 5

<210> SEQ ID NO 79
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 79

Tyr Asp Ser
1

<210> SEQ ID NO 80
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 80

Gln Val Trp Asp His Ile Asn Asp His Tyr Val
1 5 10

<210> SEQ ID NO 81
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 81

Ser Ile Ser Ser Lys Ser Ala Ala Trp Asn
1 5 10

<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 82

Tyr Arg Ser Lys Trp Tyr Tyr
1 5

<210> SEQ ID NO 83
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 83

-continued

```
Ala Arg Ser Thr Gly Thr Phe Asp Tyr
1               5


<210> SEQ ID NO 84
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Asn Ile Gly Ser Lys Ser
1               5


<210> SEQ ID NO 85
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Tyr Asp Ser
1


<210> SEQ ID NO 86
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gln Val Trp Asp Ser Ser Ser Asp Arg Val Val
1               5                   10


<210> SEQ ID NO 87
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Gly Phe Thr Phe Ser Ser Tyr Ala
1               5


<210> SEQ ID NO 88
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ile Ser Tyr Asp Gly Ser Asn Lys
1               5


<210> SEQ ID NO 89
<211> LENGTH: 11
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 89

Ala Arg Asp Arg His Asp Tyr Val Met Asp Val
1               5                   10

<210> SEQ ID NO 90
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Asn Ile Gly Ser Lys Thr
1               5

<210> SEQ ID NO 91
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Tyr Asp Ser
1

<210> SEQ ID NO 92
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gln Val Trp Asp Gly Ser Ser Asp His Val Ile
1               5                   10

<210> SEQ ID NO 93
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Ser Arg Tyr
            20                  25                  30

Ala Ile Ser Trp Val Arg Gln Ala Pro Gly Gln Gly Leu Glu Trp Met
        35                  40                  45

Gly Arg Ile Ile Pro Ile Phe Gly Thr Pro Asn Tyr Ala Gln Lys Phe
    50                  55                  60

Gln Gly Arg Val Thr Ile Thr Ala Asp Glu Phe Thr Ser Thr Ala Tyr
65                  70                  75                  80

Met Glu Leu Ser Ser Leu Arg Ser Glu Asp Thr Ala Met Tyr Tyr Cys
                85                  90                  95

```
Ala Arg Ser Ile Tyr Arg Tyr Ser Glu Tyr Asp His Trp Gly Gln Gly
            100                 105                 110

Thr Leu Val Thr Val Ser Ser
        115


<210> SEQ ID NO 94
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Val Thr Val Leu Gly
            100                 105                 110


<210> SEQ ID NO 95
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Glu Val Gln Leu Val Gln Ser Gly Ala Glu Val Lys Lys Pro Gly Thr
1               5                   10                  15

Ser Val Lys Val Ser Cys Lys Ala Ser Gly Tyr Thr Phe Ser Asn Tyr
            20                  25                  30

Tyr Ile His Trp Val Arg Gln Ala Pro Gly Gln Gly Leu Glu Trp Met
        35                  40                  45

Gly Ala Ile Asn Pro Ser Val Gly Thr Thr Thr Tyr Ala Gln Asn Phe
    50                  55                  60

Gln Gly Arg Val Thr Met Thr Ser Asp Thr Ser Thr Ser Thr Val Tyr
65                  70                  75                  80

Met Glu Leu Ser Ser Leu Thr Ser Glu Asp Thr Ala Val Tyr Tyr Cys
                85                  90                  95

Ala Arg Asp Trp Trp Gly Gln Met Met Tyr Asp Gly Trp Gly Gln Gly
            100                 105                 110

Thr Leu Val Thr Val Ser Ser
        115


<210> SEQ ID NO 96
<211> LENGTH: 112
<212> TYPE: PRT
<213> ORGANISM: Artificial Sequence
<220> FEATURE:
```

<223> OTHER INFORMATION: Description of Artificial Sequence: Synthetic
polypeptide

<400> SEQUENCE: 96

Gln Ala Val Leu Thr Gln Pro Pro Ser Ala Ser Gly Thr Arg Gly Gln
1 5 10 15

Arg Val Thr Ile Ser Cys Ser Gly Ser Ser Ser Asn Ile Gly Ser Asn
20 25 30

Thr Val Asn Trp Tyr Gln Gln Leu Pro Gly Thr Ala Pro Lys Leu Leu
35 40 45

Ile Tyr Ser Asn Asn Gln Arg Pro Ser Gly Val Pro Asp Arg Phe Ser
50 55 60

Gly Ser Lys Ser Gly Thr Ser Ala Ser Leu Ala Ile Ser Gly Leu Gln
65 70 75 80

Ser Glu Asp Glu Ala Asp Tyr Tyr Cys Ala Ala Trp Asp Asp Ser Leu
85 90 95

Asn Gly Gln Gly Val Phe Gly Thr Gly Thr Lys Val Thr Val Leu Gly
100 105 110

<210> SEQ ID NO 97
<211> LENGTH: 119
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 97

Glu Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Tyr Ser Tyr Lys Tyr Gly Glu Leu Asp Thr Trp Gly Gln Gly
100 105 110

Thr Leu Val Thr Val Ser Ser
115

<210> SEQ ID NO 98
<211> LENGTH: 112
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 98

Gln Ser Val Val Thr Gln Pro Pro Ser Val Ser Ala Ala Pro Gly Gln
1 5 10 15

Lys Val Thr Ile Ser Cys Ser Gly Ser Ser Ser Asn Ile Gly Ala Gly
20 25 30

Tyr Asp Val His Trp Tyr Gln Gln Leu Pro Gly Thr Ala Pro Lys Leu

```
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Ser Val Phe Gly Gly Gly Thr Lys Leu Thr Val Leu Gly
            100                 105                 110


<210> SEQ ID NO 99
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile His Trp Val Arg Gln Ala Pro Gly Gln Gly Leu Glu Trp Met
        35                  40                  45

Gly Ile Ile Arg Pro Ser Gly Gly Ile Thr Asn Tyr Ala Gln Lys Phe
    50                  55                  60

Gln Gly Arg Val Ser Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Trp Asp Tyr Phe Ala Ser Asn Asp Phe Trp Gly Gln Gly
            100                 105                 110

Thr Leu Val Thr Val Ser Ser
        115


<210> SEQ ID NO 100
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Gln Ala Val Leu Thr Gln Pro Pro Ser Val Ser Val Ala Pro Gly Lys
1               5                   10                  15

Thr Ala Arg Leu Thr Cys Gly Gly Asn Asn Ile Gly Ser Glu Ser Val
            20                  25                  30

His Trp Tyr Gln Gln Lys Pro Gly Gln Ala Pro Leu Leu Val Val Tyr
        35                  40                  45

Asp Asp Asp Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Arg Ser Ser Asp His
                85                  90                  95

Trp Phe Phe Gly Gly Gly Thr Lys Leu Thr Val Leu Gly
```

100 105

<210> SEQ ID NO 101
<211> LENGTH: 119
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 101

Gln Met Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Thr Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

Gln Gly Arg Val Thr Ile Thr Ala Asp Lys Ser Thr Ser Thr Ala Tyr
65 70 75 80

Met Glu Val Arg Asn Leu Arg Ser Glu Asp Thr Ala Val Tyr Tyr Cys
85 90 95

Ala Arg Ala Glu Tyr Val Tyr Gly Glu Tyr Asp Gln Trp Gly Gln Gly
100 105 110

Thr Leu Val Thr Val Ser Ser
115

<210> SEQ ID NO 102
<211> LENGTH: 112
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 102

Gln Ser Val Leu Thr Gln Pro Pro Ser Val Ser Gly Ala Pro Gly Gln
1 5 10 15

Arg Val Thr Ile Ser Cys Thr Gly Ser Ser Ser Asn Ile Gly Ala Gly
20 25 30

Tyr Asp Val His Trp Tyr Gln Gln Leu Pro Gly Thr Ala Pro Lys Leu
35 40 45

Leu Ile Tyr Gly Asn Ser Asp Arg Pro Ser Gly Val Pro Asp Arg Phe
50 55 60

Ser Gly Ser Lys Ser Gly Thr Ser Ala Ser Leu Ala Ile Thr Gly Leu
65 70 75 80

Gln Ala Glu Asp Glu Ala Asp Tyr Tyr Cys Gln Ser Tyr Asp Ser Ser
85 90 95

Leu Ser Gly Tyr Val Phe Gly Thr Gly Thr Lys Val Thr Val Leu Gly
100 105 110

<210> SEQ ID NO 103
<211> LENGTH: 124
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 103

-continued

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Asn Asn His
            20                  25                  30

Ala Met His Trp Val Arg Gln Ala Pro Gly Lys Gly Leu Glu Trp Val
        35                  40                  45

Ala Val Ile Ser Phe Asp Gly Asp Asp Lys Phe Tyr Ala Asp Ser Val
    50                  55                  60

Lys Gly Arg Phe Thr Ile Ser Arg Asp Asn Ser Arg Asn Thr Leu Phe
65                  70                  75                  80

Leu Gln Met Asn Asn Leu Arg Pro Glu Asp Thr Ala Val Tyr Tyr Cys
                85                  90                  95

Ser Arg Asp Pro Tyr His Phe Ala Ser Gly Ser Tyr Ser Tyr Phe Asp
            100                 105                 110

Tyr Trp Gly Gln Gly Thr Leu Val Thr Val Ser Ser
        115                 120
```

<210> SEQ ID NO 104
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 104

```
Gln Ser Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Tyr Val Phe Gly Thr Gly Thr Lys Val Thr Val Leu Gly
            100                 105
```

<210> SEQ ID NO 105
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 105

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile His Trp Val Arg Gln Ala Pro Gly Glu Gly Leu Glu Trp Met
        35                  40                  45

Gly Ile Ile Arg Pro Ser Gly Gly Asn Thr Asn Tyr Ala Gln Lys Phe
    50                  55                  60
```

Gln Gly Arg Val Thr Met Thr Arg Asp Thr Ser Thr Arg Thr Val Tyr
65 70 75 80

Met Glu Leu Ser Ser Leu Arg Ser Glu Asp Thr Ala Val Tyr Tyr Cys
85 90 95

Ala Arg Ser Trp Asn Ser Arg Asp Val Asp Ser Trp Gly Gln Gly Thr
100 105 110

Leu Val Thr Val Ser Ser
115

<210> SEQ ID NO 106
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 106

Asn Phe Met Leu Thr Gln Pro His Ser Val Ser Glu Ser Pro Gly Lys
1 5 10 15

Thr Val Thr Ile Ser Cys Thr Arg Ser Ser Gly Ser Ile Ala Ser His
20 25 30

Tyr Val Gln Trp Tyr Gln Gln Arg Pro Gly Ser Ser Pro Thr Thr Val
35 40 45

Ile Tyr Glu Asn Asn Gln Arg Pro Ser Gly Val Pro Asp Arg Phe Ser
50 55 60

Gly Ser Ile Asp Ser Ser Ser Asn Ser Ala Ser Leu Thr Ile Ser Gly
65 70 75 80

Leu Lys Thr Glu Asp Glu Ala Asp Tyr Tyr Cys Gln Ser Tyr Asp Arg
85 90 95

Ser Asn His Val Val Phe Gly Gly Gly Thr Lys Leu Thr Val Leu Gly
100 105 110

<210> SEQ ID NO 107
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 107

Gln Met Gln Leu Val Gln Ser Gly Ala Glu Val Glu Lys Pro Gly Ala
1 5 10 15

Ser Val Lys Leu Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Pro Ser Tyr Tyr Ser Ile Lys Ser Ala Trp Asp His Trp Gly
100 105 110

Gln Gly Thr Leu Val Thr Val Ser Ser
115 120

<210> SEQ ID NO 108
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 108

```
Gln Ala Val Leu Thr Gln Pro Pro Ser Leu Ser Gly Gly Pro Arg Gln
1               5                   10                  15

Arg Val Thr Ile Ser Cys Ser Gly Ser Thr Ser Asn Ile Gly Lys Asn
            20                  25                  30

Gly Val Ser Trp Tyr Gln Gln Leu Pro Gly Lys Ala Pro Lys Leu Leu
        35                  40                  45

Ile Tyr Asn Asp His Leu Leu Ser Ser Gly Val Ser Asp Arg Phe Ser
    50                  55                  60

Gly Ser Lys Ser Gly Thr Ser Ala Ser Leu Ala Ile Ser Gly Leu Gln
65                  70                  75                  80

Ser Asp Asp Glu Ala Asp Tyr Tyr Cys Ala Thr Trp Asp Asp Thr Leu
                85                  90                  95

Asp Leu Pro Leu Phe Gly Gly Gly Thr Lys Val Thr Val Leu Gly
            100                 105                 110
```

<210> SEQ ID NO 109
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 109

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Asn Phe Ala Ser Glu
            20                  25                  30

Trp Ile Gly Trp Val Arg Gln Met Pro Gly Lys Gly Leu Glu Trp Met
        35                  40                  45

Gly Leu Ile Tyr Pro Ala Glu Ser Glu Ile Thr Tyr Ser Pro Ser Phe
    50                  55                  60

Gln Gly Gln Val Thr Ile Ser Val Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ala Trp Asp Ala Asn Tyr Ile Tyr Met Asp Ile Trp Gly Gln
            100                 105                 110

Gly Thr Leu Val Thr Val Ser Ser
        115                 120
```

<210> SEQ ID NO 110
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 110

```
Gln Ser Val Val Thr Gln Pro Pro Ser Val Ser Gly Ala Pro Gly Gln
1               5                   10                  15

Gly Val Thr Ile Pro Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Asn Asn Arg Pro Ser Gly Val Pro Asp Arg Phe
    50                  55                  60

Ser Gly Ser Arg Ser Gly Ser Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Asp Val Val Phe Gly Gly Gly Thr Lys Leu Thr Val Leu Gly
            100                 105                 110


<210> SEQ ID NO 111
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Gln Val Gln Leu Val Gln Ser Gly Gly Gly Leu Val Gln Pro Gly Gly
1               5                   10                  15

Ser Leu Lys Leu Ser Cys Ala Ala Ser Gly Phe Ala Phe Ser Gly Ser
            20                  25                  30

Ser Leu His Trp Val Arg Gln Ala Ser Gly Lys Gly Leu Glu Trp Val
        35                  40                  45

Gly Arg Ile Thr Ser Lys Ala Tyr Asn Tyr Ala Thr Leu Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Gln Thr Glu Asp Thr Ala Val Tyr
                85                  90                  95

Tyr Cys Thr Gln Thr Gly Asp Ser Ser Ala Tyr Trp Gly Gln Gly Thr
            100                 105                 110

Leu Val Thr Val Ser Ser
        115


<210> SEQ ID NO 112
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Ser Tyr Glu Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60
```

```
Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Gly
            100                 105


<210> SEQ ID NO 113
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Asn Trp Val Arg Gln Ala Pro Gly Lys Gly Leu Glu Trp Val
        35                  40                  45

Ala Asn Ile Lys Gln Asp Gly Ser Glu Lys Asn Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Gly Glu Asp Thr Ala Val Tyr Tyr Cys
                85                  90                  95

Ala Arg Tyr Gly Gly Gly Pro Tyr Asp Ser Trp Gly Gln Gly Thr Leu
            100                 105                 110

Val Thr Val Ser Ser
        115


<210> SEQ ID NO 114
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Ser Tyr Glu Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Arg Val Phe Gly Gly Gly Thr Lys Val Thr Val Leu Gly
            100                 105


<210> SEQ ID NO 115
<211> LENGTH: 121
```

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 115

Glu Val Gln Leu Val Glu Ser Gly Gly Gly Leu Ala Gln Pro Gly Gly
1 5 10 15

Ser Leu Arg Leu Ser Cys Ala Ala Ser Gly Phe Ser Phe Ser Asn Tyr
20 25 30

Ala Met Ser Trp Val Arg Gln Ala Pro Gly Thr Gly Leu Glu Trp Val
35 40 45

Ala Gly Ile Ser Gly Arg Gly Gly Ser Ile His Tyr Ala Asp Ser Val
50 55 60

Lys Gly Arg Phe Thr Ile Ser Arg Asp Asn Ser Gln Ser Thr Val Phe
65 70 75 80

Leu Gln Met Asn Asn Leu Gly Ala Glu Asp Thr Ala Ile Tyr Tyr Cys
85 90 95

Ala Lys Ser Ser Glu Asp Tyr Tyr Phe Tyr His Met Asp Ala Trp Gly
100 105 110

Ile Gly Thr Thr Val Thr Val Ser Ser
115 120

<210> SEQ ID NO 116
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 116

Ser Tyr Val Leu Thr Gln Pro Pro Ser Val Ser Val Ala Pro Gly Glu
1 5 10 15

Thr Ala Ser Ile Thr Cys Gly Ala Asn Asn Ile Gly Ser Glu Ser Val
20 25 30

His Trp Tyr Gln Gln Lys Ser Gly Gln Ala Pro Val Leu Val Ile Tyr
35 40 45

Tyr Asp Ser Asp Arg Pro Ser Gly Ile Pro Glu Arg Phe Ser Gly Ser
50 55 60

Asn Ser Asp Asn Thr Ala Thr Leu Thr Ile Ser Arg Val Glu Ala Gly
65 70 75 80

Asp Glu Ala Asp Tyr Tyr Cys Gln Val Trp Asp His Ile Asn Asp His
85 90 95

Tyr Val Phe Gly Ser Gly Thr Lys Val Thr Val Leu Gly
100 105

<210> SEQ ID NO 117
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 117

Gln Val Gln Leu Gln Gln Ser Gly Pro Gly Leu Val Lys Pro Ser Gln
1 5 10 15

Thr Leu Ser Leu Thr Cys Ala Ile Ser Gly Asp Ser Ile Ser Ser Lys

```
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Tyr Glu Tyr Ala
    50                  55                  60

Pro Ser Val Arg Ser Arg Ile Thr Ile Asn Arg Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Ser Thr Gly Thr Phe Asp Tyr Trp Gly Gln Gly
            100                 105                 110

Thr Leu Val Thr Val Ser Ser
        115


<210> SEQ ID NO 118
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp Arg
                85                  90                  95

Val Val Phe Gly Gly Gly Thr Lys Leu Thr Val Leu Gly
            100                 105


<210> SEQ ID NO 119
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Gln Met Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

```
                85                  90                  95

Ala Arg Asp Arg His Asp Tyr Val Met Asp Val Trp Gly Lys Gly Thr
            100                 105                 110

Thr Val Thr Val Ser Ser
        115


<210> SEQ ID NO 120
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Gln Ser Val Leu Thr Gln Pro Pro Ser Val Ser Val Ala Pro Gly Lys
1               5                   10                  15

Thr Ala Lys Ile Thr Cys Gly Gly Asp Asn Ile Gly Ser Lys Thr Val
            20                  25                  30

His Trp Tyr Gln Gln Lys Pro Gly Gln Ala Pro Ala Leu Leu Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Ser Ile Ser Arg Val Glu Ala Gly
65                  70                  75                  80

Asp Glu Ala Gly Tyr Phe Cys Gln Val Trp Asp Gly Ser Ser Asp His
                85                  90                  95

Val Ile Phe Gly Gly Gly Thr Lys Leu Thr Val Leu Gly
            100                 105


<210> SEQ ID NO 121
<211> LENGTH: 277
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Val Thr Val Leu Gly
            100                 105                 110

Ser Arg Gly Gly Gly Gly Ser Gly Gly Gly Gly Ser Gly Gly Gly Gly
        115                 120                 125

Ser Leu Glu Met Ala Glu Val Gln Leu Val Gln Ser Gly Ala Glu Val
    130                 135                 140

Lys Lys Pro Gly Ser Ser Val Lys Val Ser Cys Lys Ala Ser Gly Asp
```

```
145                 150                 155                 160

Thr Phe Ser Arg Tyr Ala Ile Ser Trp Val Arg Gln Ala Pro Gly Gln
                165                 170                 175

Gly Leu Glu Trp Met Gly Arg Ile Ile Pro Ile Phe Gly Thr Pro Asn
            180                 185                 190

Tyr Ala Gln Lys Phe Gln Gly Arg Val Thr Ile Thr Ala Asp Glu Phe
        195                 200                 205

Thr Ser Thr Ala Tyr Met Glu Leu Ser Ser Leu Arg Ser Glu Asp Thr
    210                 215                 220

Ala Met Tyr Tyr Cys Ala Arg Ser Ile Tyr Arg Tyr Ser Glu Tyr Asp
225                 230                 235                 240

His Trp Gly Gln Gly Thr Leu Val Thr Val Ser Ser Thr Ser Gly Gln
                245                 250                 255

Ala Gly Gln His His His His His His Gly Ala Tyr Pro Tyr Asp Val
            260                 265                 270

Pro Asp Tyr Ala Ser
        275


<210> SEQ ID NO 122
<211> LENGTH: 277
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Gln Ala Val Leu Thr Gln Pro Pro Ser Ala Ser Gly Thr Arg Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Gln Gly Val Phe Gly Thr Gly Thr Lys Val Thr Val Leu Gly
            100                 105                 110

Ser Arg Gly Gly Gly Gly Ser Gly Gly Gly Gly Ser Gly Gly Gly Gly
        115                 120                 125

Ser Leu Glu Met Ala Glu Val Gln Leu Val Gln Ser Gly Ala Glu Val
    130                 135                 140

Lys Lys Pro Gly Thr Ser Val Lys Val Ser Cys Lys Ala Ser Gly Tyr
145                 150                 155                 160

Thr Phe Ser Asn Tyr Tyr Ile His Trp Val Arg Gln Ala Pro Gly Gln
                165                 170                 175

Gly Leu Glu Trp Met Gly Ala Ile Asn Pro Ser Val Gly Thr Thr Thr
            180                 185                 190

Tyr Ala Gln Asn Phe Gln Gly Arg Val Thr Met Thr Ser Asp Thr Ser
        195                 200                 205

Thr Ser Thr Val Tyr Met Glu Leu Ser Ser Leu Thr Ser Glu Asp Thr
    210                 215                 220
```

-continued

```
Ala Val Tyr Tyr Cys Ala Arg Asp Trp Trp Gly Gln Met Met Tyr Asp
225                 230                 235                 240

Gly Trp Gly Gln Gly Thr Leu Val Thr Val Ser Ser Thr Ser Gly Gln
                245                 250                 255

Ala Gly Gln His His His His His His Gly Ala Tyr Pro Tyr Asp Val
            260                 265                 270

Pro Asp Tyr Ala Ser
        275


<210> SEQ ID NO 123
<211> LENGTH: 277
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Gln Ser Val Val Thr Gln Pro Pro Ser Val Ser Ala Ala Pro Gly Gln
1               5                   10                  15

Lys Val Thr Ile Ser Cys Ser Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Ser Val Phe Gly Gly Gly Thr Lys Leu Thr Val Leu Gly
            100                 105                 110

Ser Arg Gly Gly Gly Gly Ser Gly Gly Gly Gly Ser Gly Gly Gly Gly
        115                 120                 125

Ser Leu Glu Met Ala Glu Val Gln Leu Val Gln Ser Gly Ala Glu Val
    130                 135                 140

Lys Lys Pro Gly Ser Ser Val Lys Val Ser Cys Lys Ala Ser Gly Gly
145                 150                 155                 160

Thr Phe Ser Ser Tyr Ala Ile Ser Trp Val Arg Gln Ala Pro Gly Gln
                165                 170                 175

Gly Leu Glu Trp Met Gly Gly Ile Ile Pro Ile Phe Gly Thr Ala Asn
            180                 185                 190

Tyr Ala Gln Lys Phe Gln Gly Arg Val Thr Ile Thr Ala Asp Glu Ser
        195                 200                 205

Thr Ser Thr Ala Tyr Met Glu Leu Ser Ser Leu Arg Ser Glu Asp Thr
    210                 215                 220

Ala Val Tyr Tyr Cys Ala Arg Tyr Ser Tyr Lys Tyr Gly Glu Leu Asp
225                 230                 235                 240

Thr Trp Gly Gln Gly Thr Leu Val Thr Val Ser Ser Thr Ser Gly Gln
                245                 250                 255

Ala Gly Gln His His His His His His Gly Ala Tyr Pro Tyr Asp Val
            260                 265                 270

Pro Asp Tyr Ala Ser
        275


<210> SEQ ID NO 124
```

<211> LENGTH: 274
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 124

Gln Ala Val Leu Thr Gln Pro Pro Ser Val Ser Val Ala Pro Gly Lys
1 5 10 15

Thr Ala Arg Leu Thr Cys Gly Gly Asn Asn Ile Gly Ser Glu Ser Val
20 25 30

His Trp Tyr Gln Gln Lys Pro Gly Gln Ala Pro Leu Leu Val Val Tyr
35 40 45

Asp Asp Asp Asp Arg Pro Ser Gly Ile Pro Glu Arg Phe Ser Gly Ser
50 55 60

Asn Ser Gly Asn Thr Ala Thr Leu Thr Ile Ser Arg Val Glu Ala Gly
65 70 75 80

Asp Glu Ala Asp Tyr Tyr Cys Gln Val Trp Asp Arg Ser Ser Asp His
85 90 95

Trp Phe Phe Gly Gly Gly Thr Lys Leu Thr Val Leu Gly Ser Arg Gly
100 105 110

Gly Gly Gly Ser Gly Gly Gly Gly Ser Gly Gly Gly Gly Ser Leu Glu
115 120 125

Met Ala Gln Val Gln Leu Val Gln Ser Gly Ala Glu Val Lys Lys Pro
130 135 140

Gly Ala Ser Val Lys Val Ser Cys Lys Ala Ser Gly Tyr Thr Phe Thr
145 150 155 160

Asn Tyr Tyr Ile His Trp Val Arg Gln Ala Pro Gly Gln Gly Leu Glu
165 170 175

Trp Met Gly Ile Ile Arg Pro Ser Gly Gly Ile Thr Asn Tyr Ala Gln
180 185 190

Lys Phe Gln Gly Arg Val Ser Met Thr Arg Asp Thr Ser Thr Ser Thr
195 200 205

Val Tyr Met Glu Leu Ser Ser Leu Arg Ser Glu Asp Thr Ala Val Tyr
210 215 220

Tyr Cys Ala Arg Ser Trp Asp Tyr Phe Ala Ser Asn Asp Phe Trp Gly
225 230 235 240

Gln Gly Thr Leu Val Thr Val Ser Ser Thr Ser Gly Gln Ala Gly Gln
245 250 255

His His His His His His Gly Ala Tyr Pro Tyr Asp Val Pro Asp Tyr
260 265 270

Ala Ser

<210> SEQ ID NO 125
<211> LENGTH: 277
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 125

Gln Ser Val Leu Thr Gln Pro Pro Ser Val Ser Gly Ala Pro Gly Gln
1 5 10 15

Arg Val Thr Ile Ser Cys Thr Gly Ser Ser Ser Asn Ile Gly Ala Gly
20 25 30

Tyr Asp Val His Trp Tyr Gln Gln Leu Pro Gly Thr Ala Pro Lys Leu
35 40 45

Leu Ile Tyr Gly Asn Ser Asp Arg Pro Ser Gly Val Pro Asp Arg Phe
50 55 60

Ser Gly Ser Lys Ser Gly Thr Ser Ala Ser Leu Ala Ile Thr Gly Leu
65 70 75 80

Gln Ala Glu Asp Glu Ala Asp Tyr Tyr Cys Gln Ser Tyr Asp Ser Ser
85 90 95

Leu Ser Gly Tyr Val Phe Gly Thr Gly Thr Lys Val Thr Val Leu Gly
100 105 110

Ser Arg Gly Gly Gly Gly Ser Gly Gly Gly Gly Ser Gly Gly Gly Gly
115 120 125

Ser Leu Glu Met Ala Gln Met Gln Leu Val Gln Ser Gly Ala Glu Val
130 135 140

Lys Lys Pro Gly Ser Ser Val Lys Val Ser Cys Lys Ala Ser Gly Gly
145 150 155 160

Thr Phe Ser Thr Tyr Ala Ile Ser Trp Val Arg Gln Ala Pro Gly Gln
165 170 175

Gly Leu Glu Trp Met Gly Gly Ile Ile Pro Ile Phe Gly Thr Ala Asn
180 185 190

Tyr Ala Gln Lys Phe Gln Gly Arg Val Thr Ile Thr Ala Asp Lys Ser
195 200 205

Thr Ser Thr Ala Tyr Met Glu Val Arg Asn Leu Arg Ser Glu Asp Thr
210 215 220

Ala Val Tyr Tyr Cys Ala Arg Ala Glu Tyr Val Tyr Gly Glu Tyr Asp
225 230 235 240

Gln Trp Gly Gln Gly Thr Leu Val Thr Val Ser Ser Thr Ser Gly Gln
245 250 255

Ala Gly Gln His His His His His His Gly Ala Tyr Pro Tyr Asp Val
260 265 270

Pro Asp Tyr Ala Ser
275

<210> SEQ ID NO 126
<211> LENGTH: 279
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 126

Gln Ser Val Leu Thr Gln Pro Pro Ser Val Ser Val Ala Pro Gly Lys
1 5 10 15

Thr Ala Arg Ile Thr Cys Gly Gly Asn Asn Ile Gly Ser Lys Ser Val
20 25 30

His Trp Tyr Gln Gln Lys Pro Gly Gln Ala Pro Val Leu Val Ile Tyr
35 40 45

Tyr Asp Ser Asp Arg Pro Ser Gly Ile Pro Glu Arg Phe Ser Gly Ser
50 55 60

Asn Ser Gly Asn Thr Ala Thr Leu Thr Ile Ser Arg Val Glu Ala Gly
65 70 75 80

Asp Glu Ala Asp Tyr Tyr Cys Gln Val Trp Asp Ser Ser Ser Asp His
85 90 95

Tyr Val Phe Gly Thr Gly Thr Lys Val Thr Val Leu Gly Ser Arg Gly
100 105 110

```
Gly Gly Gly Ser Gly Gly Gly Gly Ser Gly Gly Gly Gly Ser Leu Glu
        115                 120                 125

Met Ala Glu Val Gln Leu Val Glu Ser Gly Gly Gly Val Val Gln Pro
    130                 135                 140

Gly Arg Ser Leu Arg Leu Ser Cys Ala Ala Ser Gly Phe Thr Phe Asn
145                 150                 155                 160

Asn His Ala Met His Trp Val Arg Gln Ala Pro Gly Lys Gly Leu Glu
                165                 170                 175

Trp Val Ala Val Ile Ser Phe Asp Gly Asp Asp Lys Phe Tyr Ala Asp
            180                 185                 190

Ser Val Lys Gly Arg Phe Thr Ile Ser Arg Asp Asn Ser Arg Asn Thr
        195                 200                 205

Leu Phe Leu Gln Met Asn Asn Leu Arg Pro Glu Asp Thr Ala Val Tyr
    210                 215                 220

Tyr Cys Ser Arg Asp Pro Tyr His Phe Ala Ser Gly Ser Tyr Ser Tyr
225                 230                 235                 240

Phe Asp Tyr Trp Gly Gln Gly Thr Leu Val Thr Val Ser Ser Thr Ser
                245                 250                 255

Gly Gln Ala Gly Gln His His His His His His Gly Ala Tyr Pro Tyr
            260                 265                 270

Asp Val Pro Asp Tyr Ala Ser
        275


<210> SEQ ID NO 127
<211> LENGTH: 276
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser His
            20                  25                  30

Tyr Val Gln Trp Tyr Gln Gln Arg Pro Gly Ser Ser Pro Thr Thr Val
        35                  40                  45

Ile Tyr Glu Asn Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Arg
                85                  90                  95

Ser Asn His Val Val Phe Gly Gly Gly Thr Lys Leu Thr Val Leu Gly
            100                 105                 110

Ser Arg Gly Gly Gly Gly Ser Gly Gly Gly Gly Ser Gly Gly Gly Gly
        115                 120                 125

Ser Leu Glu Met Ala Gln Val Gln Leu Val Gln Ser Gly Ala Glu Val
    130                 135                 140

Lys Lys Pro Gly Ala Ser Val Lys Val Ser Cys Lys Ala Ser Gly Tyr
145                 150                 155                 160

Thr Phe Thr Asn Tyr Tyr Ile His Trp Val Arg Gln Ala Pro Gly Glu
                165                 170                 175

Gly Leu Glu Trp Met Gly Ile Ile Arg Pro Ser Gly Gly Asn Thr Asn
```

```
            180                 185                 190

Tyr Ala Gln Lys Phe Gln Gly Arg Val Thr Met Thr Arg Asp Thr Ser
        195                 200                 205

Thr Arg Thr Val Tyr Met Glu Leu Ser Ser Leu Arg Ser Glu Asp Thr
    210                 215                 220

Ala Val Tyr Tyr Cys Ala Arg Ser Trp Asn Ser Arg Asp Val Asp Ser
225                 230                 235                 240

Trp Gly Gln Gly Thr Leu Val Thr Val Ser Ser Thr Ser Gly Gln Ala
                245                 250                 255

Gly Gln His His His His His His Gly Ala Tyr Pro Tyr Asp Val Pro
            260                 265                 270

Asp Tyr Ala Ser
        275


<210> SEQ ID NO 128
<211> LENGTH: 278
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Gln Ala Val Leu Thr Gln Pro Pro Ser Leu Ser Gly Gly Pro Arg Gln
1               5                   10                  15

Arg Val Thr Ile Ser Cys Ser Gly Ser Thr Ser Asn Ile Gly Lys Asn
            20                  25                  30

Gly Val Ser Trp Tyr Gln Gln Leu Pro Gly Lys Ala Pro Lys Leu Leu
        35                  40                  45

Ile Tyr Asn Asp His Leu Leu Ser Ser Gly Val Ser Asp Arg Phe Ser
    50                  55                  60

Gly Ser Lys Ser Gly Thr Ser Ala Ser Leu Ala Ile Ser Gly Leu Gln
65                  70                  75                  80

Ser Asp Asp Glu Ala Asp Tyr Tyr Cys Ala Thr Trp Asp Asp Thr Leu
                85                  90                  95

Asp Leu Pro Leu Phe Gly Gly Gly Thr Lys Val Thr Val Leu Gly Ser
            100                 105                 110

Arg Gly Gly Gly Gly Ser Gly Gly Gly Gly Ser Gly Gly Gly Gly Ser
        115                 120                 125

Leu Glu Met Ala Gln Met Gln Leu Val Gln Ser Gly Ala Glu Val Glu
    130                 135                 140

Lys Pro Gly Ala Ser Val Lys Leu Ser Cys Lys Ala Ser Gly Gly Thr
145                 150                 155                 160

Phe Ser Ser Tyr Ala Ile Ser Trp Val Arg Gln Ala Pro Gly Gln Gly
                165                 170                 175

Leu Glu Trp Met Gly Gly Ile Ile Pro Ile Phe Gly Thr Ala Asn Tyr
            180                 185                 190

Ala Gln Lys Phe Gln Gly Arg Val Thr Ile Thr Ala Asp Glu Ser Thr
        195                 200                 205

Ser Thr Ala Tyr Met Glu Leu Ser Ser Leu Arg Ser Glu Asp Thr Ala
    210                 215                 220

Val Tyr Tyr Cys Ala Arg Pro Ser Tyr Tyr Ser Ile Lys Ser Ala Trp
225                 230                 235                 240

Asp His Trp Gly Gln Gly Thr Leu Val Thr Val Ser Ser Thr Ser Gly
                245                 250                 255
```

Gln Ala Gly Gln His His His His His His Gly Ala Tyr Pro Tyr Asp
260 265 270

Val Pro Asp Tyr Ala Ser
275

<210> SEQ ID NO 129
<211> LENGTH: 278
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 129

Gln Ser Val Val Thr Gln Pro Pro Ser Val Ser Gly Ala Pro Gly Gln
1 5 10 15

Gly Val Thr Ile Pro Cys Thr Gly Ser Ser Ser Asn Ile Gly Ala Gly
20 25 30

Tyr Asp Val His Trp Tyr Gln Gln Leu Pro Gly Thr Ala Pro Lys Leu
35 40 45

Leu Ile Tyr Gly Asn Asn Asn Arg Pro Ser Gly Val Pro Asp Arg Phe
50 55 60

Ser Gly Ser Arg Ser Gly Ser Ser Ala Ser Leu Ala Ile Thr Gly Leu
65 70 75 80

Gln Ala Glu Asp Glu Ala Asp Tyr Tyr Cys Gln Ser Tyr Asp Ser Ser
85 90 95

Leu Ser Asp Val Val Phe Gly Gly Gly Thr Lys Leu Thr Val Leu Gly
100 105 110

Ser Arg Gly Gly Gly Gly Ser Gly Gly Gly Gly Ser Gly Gly Gly Gly
115 120 125

Ser Leu Glu Met Ala Glu Val Gln Leu Val Gln Ser Gly Ala Glu Val
130 135 140

Lys Lys Pro Gly Glu Ser Leu Lys Ile Ser Cys Lys Gly Ser Gly Tyr
145 150 155 160

Asn Phe Ala Ser Glu Trp Ile Gly Trp Val Arg Gln Met Pro Gly Lys
165 170 175

Gly Leu Glu Trp Met Gly Leu Ile Tyr Pro Ala Glu Ser Glu Ile Thr
180 185 190

Tyr Ser Pro Ser Phe Gln Gly Gln Val Thr Ile Ser Val Asp Lys Ser
195 200 205

Ile Ser Thr Ala Tyr Leu Gln Trp Ser Ser Leu Lys Ala Ser Asp Thr
210 215 220

Ala Met Tyr Tyr Cys Ala Arg Ala Trp Asp Ala Asn Tyr Ile Tyr Met
225 230 235 240

Asp Ile Trp Gly Gln Gly Thr Leu Val Thr Val Ser Ser Thr Ser Gly
245 250 255

Gln Ala Gly Gln His His His His His His Gly Ala Tyr Pro Tyr Asp
260 265 270

Val Pro Asp Tyr Ala Ser
275

<210> SEQ ID NO 130
<211> LENGTH: 273
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 130

Ser Tyr Glu Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Gly Ser Arg Gly
            100                 105                 110

Gly Gly Gly Ser Gly Gly Gly Gly Ser Gly Gly Gly Gly Ser Leu Glu
        115                 120                 125

Met Ala Gln Val Gln Leu Val Gln Ser Gly Gly Gly Leu Val Gln Pro
    130                 135                 140

Gly Gly Ser Leu Lys Leu Ser Cys Ala Ala Ser Gly Phe Ala Phe Ser
145                 150                 155                 160

Gly Ser Ser Leu His Trp Val Arg Gln Ala Ser Gly Lys Gly Leu Glu
                165                 170                 175

Trp Val Gly Arg Ile Thr Ser Lys Ala Tyr Asn Tyr Ala Thr Leu Tyr
            180                 185                 190

Ala Ala Ser Val Lys Gly Arg Phe Thr Ile Ser Arg Asp Asp Ser Lys
        195                 200                 205

Asn Thr Ala Tyr Leu Gln Met Asn Ser Leu Gln Thr Glu Asp Thr Ala
    210                 215                 220

Val Tyr Tyr Cys Thr Gln Thr Gly Asp Ser Ser Ala Tyr Trp Gly Gln
225                 230                 235                 240

Gly Thr Leu Val Thr Val Ser Ser Thr Ser Gly Gln Ala Gly Gln His
                245                 250                 255

His His His His His Gly Ala Tyr Pro Tyr Asp Val Pro Asp Tyr Ala
            260                 265                 270

Ser

<210> SEQ ID NO 131
<211> LENGTH: 272
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Ser Tyr Glu Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

```
Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Arg Val Phe Gly Gly Gly Thr Lys Val Thr Val Leu Gly Ser Arg Gly
            100                 105                 110

Gly Gly Gly Ser Gly Gly Gly Gly Ser Gly Gly Gly Gly Ser Leu Glu
        115                 120                 125

Met Ala Glu Val Gln Leu Val Glu Ser Gly Gly Gly Leu Val Gln Pro
    130                 135                 140

Gly Gly Ser Leu Arg Leu Ser Cys Ala Ala Ser Gly Phe Thr Phe Ser
145                 150                 155                 160

Ser Tyr Trp Met Asn Trp Val Arg Gln Ala Pro Gly Lys Gly Leu Glu
                165                 170                 175

Trp Val Ala Asn Ile Lys Gln Asp Gly Ser Glu Lys Asn Tyr Val Asp
            180                 185                 190

Ser Val Lys Gly Arg Phe Thr Ile Ser Arg Asp Asn Ala Lys Asn Ser
        195                 200                 205

Leu Tyr Leu Gln Met Asn Ser Leu Arg Gly Glu Asp Thr Ala Val Tyr
    210                 215                 220

Tyr Cys Ala Arg Tyr Gly Gly Gly Pro Tyr Asp Ser Trp Gly Gln Gly
225                 230                 235                 240

Thr Leu Val Thr Val Ser Ser Thr Ser Gly Gln Ala Gly Gln His His
                245                 250                 255

His His His His Gly Ala Tyr Pro Tyr Asp Val Pro Asp Tyr Ala Ser
            260                 265                 270


<210> SEQ ID NO 132
<211> LENGTH: 276
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Ser Tyr Val Leu Thr Gln Pro Pro Ser Val Ser Val Ala Pro Gly Glu
1               5                   10                  15

Thr Ala Ser Ile Thr Cys Gly Ala Asn Asn Ile Gly Ser Glu Ser Val
            20                  25                  30

His Trp Tyr Gln Gln Lys Ser Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Asp Asn Thr Ala Thr Leu Thr Ile Ser Arg Val Glu Ala Gly
65                  70                  75                  80

Asp Glu Ala Asp Tyr Tyr Cys Gln Val Trp Asp His Ile Asn Asp His
                85                  90                  95

Tyr Val Phe Gly Ser Gly Thr Lys Val Thr Val Leu Gly Ser Arg Gly
            100                 105                 110

Gly Gly Gly Ser Gly Gly Gly Gly Ser Gly Gly Gly Gly Ser Leu Glu
        115                 120                 125

Met Ala Glu Val Gln Leu Val Glu Ser Gly Gly Gly Leu Ala Gln Pro
    130                 135                 140

Gly Gly Ser Leu Arg Leu Ser Cys Ala Ala Ser Gly Phe Ser Phe Ser
145                 150                 155                 160
```

```
Asn Tyr Ala Met Ser Trp Val Arg Gln Ala Pro Gly Thr Gly Leu Glu
                165                 170                 175

Trp Val Ala Gly Ile Ser Gly Arg Gly Gly Ser Ile His Tyr Ala Asp
            180                 185                 190

Ser Val Lys Gly Arg Phe Thr Ile Ser Arg Asp Asn Ser Gln Ser Thr
        195                 200                 205

Val Phe Leu Gln Met Asn Asn Leu Gly Ala Glu Asp Thr Ala Ile Tyr
    210                 215                 220

Tyr Cys Ala Lys Ser Ser Glu Asp Tyr Tyr Phe Tyr His Met Asp Ala
225                 230                 235                 240

Trp Gly Ile Gly Thr Thr Val Thr Val Ser Ser Thr Ser Gly Gln Ala
                245                 250                 255

Gly Gln His His His His His His Gly Ala Tyr Pro Tyr Asp Val Pro
            260                 265                 270

Asp Tyr Ala Ser
        275


<210> SEQ ID NO 133
<211> LENGTH: 274
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp Arg
                85                  90                  95

Val Val Phe Gly Gly Gly Thr Lys Leu Thr Val Leu Gly Ser Arg Gly
            100                 105                 110

Gly Gly Gly Ser Gly Gly Gly Gly Ser Gly Gly Gly Gly Ser Leu Glu
        115                 120                 125

Met Ala Gln Val Gln Leu Gln Gln Ser Gly Pro Gly Leu Val Lys Pro
    130                 135                 140

Ser Gln Thr Leu Ser Leu Thr Cys Ala Ile Ser Gly Asp Ser Ile Ser
145                 150                 155                 160

Ser Lys Ser Ala Ala Trp Asn Trp Ile Arg Gln Ser Pro Ser Arg Gly
                165                 170                 175

Leu Glu Trp Leu Gly Arg Thr Tyr Tyr Arg Ser Lys Trp Tyr Tyr Glu
            180                 185                 190

Tyr Ala Pro Ser Val Arg Ser Arg Ile Thr Ile Asn Arg Asp Thr Ser
        195                 200                 205

Lys Asn Gln Phe Ser Leu Gln Leu Asn Ser Val Thr Pro Glu Asp Thr
    210                 215                 220

Ala Val Tyr Tyr Cys Ala Arg Ser Thr Gly Thr Phe Asp Tyr Trp Gly
```

```
225                 230                 235                 240

Gln Gly Thr Leu Val Thr Val Ser Ser Thr Ser Gly Gln Ala Gly Gln
                245                 250                 255

His His His His His His Gly Ala Tyr Pro Tyr Asp Val Pro Asp Tyr
            260                 265                 270

Ala Ser


<210> SEQ ID NO 134
<211> LENGTH: 273
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Gln Ser Val Leu Thr Gln Pro Pro Ser Val Ser Val Ala Pro Gly Lys
1               5                   10                  15

Thr Ala Lys Ile Thr Cys Gly Gly Asp Asn Ile Gly Ser Lys Thr Val
            20                  25                  30

His Trp Tyr Gln Gln Lys Pro Gly Gln Ala Pro Ala Leu Leu Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Ser Ile Ser Arg Val Glu Ala Gly
65                  70                  75                  80

Asp Glu Ala Gly Tyr Phe Cys Gln Val Trp Asp Gly Ser Ser Asp His
                85                  90                  95

Val Ile Phe Gly Gly Gly Thr Lys Leu Thr Val Leu Gly Ser Arg Gly
            100                 105                 110

Gly Gly Gly Ser Gly Gly Gly Gly Ser Gly Gly Gly Gly Ser Leu Glu
        115                 120                 125

Met Ala Gln Met Gln Leu Val Gln Ser Gly Gly Gly Val Val Gln Pro
    130                 135                 140

Gly Arg Ser Leu Arg Leu Ser Cys Ala Ala Ser Gly Phe Thr Phe Ser
145                 150                 155                 160

Ser Tyr Ala Met His Trp Val Arg Gln Ala Pro Gly Lys Gly Leu Glu
                165                 170                 175

Trp Val Ala Val Ile Ser Tyr Asp Gly Ser Asn Lys Tyr Tyr Ala Asp
            180                 185                 190

Ser Val Lys Gly Arg Phe Thr Ile Ser Arg Asp Asn Ser Lys Asn Thr
        195                 200                 205

Leu Tyr Leu Gln Met Asn Ser Leu Arg Ala Glu Asp Thr Ala Val Tyr
    210                 215                 220

Tyr Cys Ala Arg Asp Arg His Asp Tyr Val Met Asp Val Trp Gly Lys
225                 230                 235                 240

Gly Thr Thr Val Thr Val Ser Ser Thr Ser Gly Gln Ala Gly Gln His
                245                 250                 255

His His His His His Gly Ala Tyr Pro Tyr Asp Val Pro Asp Tyr Ala
            260                 265                 270

Ser


<210> SEQ ID NO 135
<211> LENGTH: 21
<212> TYPE: PRT
<213> ORGANISM: Artificial Sequence
```

<220> FEATURE:
<223> OTHER INFORMATION: Description of Artificial Sequence: Synthetic peptide

<400> SEQUENCE: 135

```
Ser Arg Gly Gly Gly Gly Ser Gly Gly Gly Gly Ser Gly Gly Gly Gly
1               5                   10                  15

Ser Leu Glu Met Ala
            20
```

<210> SEQ ID NO 136
<211> LENGTH: 63
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 136

```
tctagaggtg gtggtggtag cggcggcggc ggctctggtg gtggtggatc cctcgagatg     60

gcc                                                                   63
```

<210> SEQ ID NO 137
<211> LENGTH: 164
<212> TYPE: PRT
<213> ORGANISM: Homo sapiens

<400> SEQUENCE: 137

```
Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
        115                 120                 125

Lys Gly Glu Arg Arg Arg Gly Lys Gly His Asp Gly Leu Tyr Gln Gly
    130                 135                 140

Leu Ser Thr Ala Thr Lys Asp Thr Tyr Asp Ala Leu His Met Gln Ala
145                 150                 155                 160

Leu Pro Pro Arg
```

<210> SEQ ID NO 138
<211> LENGTH: 112
<212> TYPE: PRT
<213> ORGANISM: Homo sapiens

<400> SEQUENCE: 138

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
```

```
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110


<210> SEQ ID NO 139
<211> LENGTH: 107
<212> TYPE: PRT
<213> ORGANISM: Homo sapiens

<400> SEQUENCE: 139

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val Arg Ser Lys Arg Ser Arg Leu Leu His Ser Asp Tyr Met Asn
65                  70                  75                  80

Met Thr Pro Arg Arg Pro Gly Pro Thr Arg Lys His Tyr Gln Pro Tyr
                85                  90                  95

Ala Pro Pro Arg Asp Phe Ala Ala Tyr Arg Ser
            100                 105


<210> SEQ ID NO 140
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Gln Leu Gln Asn Pro Ser Tyr Asp Lys
1               5


<210> SEQ ID NO 141
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Thr Ser Gly Gln Ala Gly Gln His His His His His His Gly Ala Tyr
1               5                   10                  15

Pro Tyr Asp Val Pro Asp Tyr Ala Ser
            20                  25


<210> SEQ ID NO 142
```

<211> LENGTH: 74
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 142
ctagtggcca ggccggccag caccatcacc atcaccatgg cgcatacccg tacgacgttc 60
cggactacgc ttct 74

<210> SEQ ID NO 143
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 143

His His His His His His
1 5

<210> SEQ ID NO 144
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 144

Ala Leu Ile Arg Trp Ala Ile Leu Glu Ala
1 5 10

<210> SEQ ID NO 145
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 145

Thr Ala Ile Arg Trp Ala Ile Leu Glu Ala
1 5 10

<210> SEQ ID NO 146
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 146

Thr Leu Ala Arg Trp Ala Ile Leu Glu Ala
1 5 10

<210> SEQ ID NO 147
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 147

Thr Leu Ile Ala Trp Ala Ile Leu Glu Ala
1 5 10

<210> SEQ ID NO 148
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 148

Thr Leu Ile Arg Ala Ala Ile Leu Glu Ala
1 5 10

<210> SEQ ID NO 149
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 149

Thr Leu Ile Arg Trp Ala Ala Leu Glu Ala
1 5 10

<210> SEQ ID NO 150
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 150

Thr Leu Ile Arg Trp Ala Ile Ala Glu Ala
1 5 10

<210> SEQ ID NO 151
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 151

Thr Leu Ile Arg Trp Ala Ile Leu Ala Ala
1 5 10

<210> SEQ ID NO 152
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 152

Thr Leu Ile Arg Trp Ala Ile Leu Glu Gly
1 5 10

<210> SEQ ID NO 153
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 153
cagtctgtgt tgacgcagcc gccctcagtg tctggggccc cagggcagag ggtcaccatc 60
tcctgcactg ggagcagctc caacatcggg gcaggttatg atgtacactg gtaccagcag 120
cttccaggaa cagcccccaa actcctcatc tatggtaaca gcaatcggcc ctcaggggtc 180
cctgaccgat tctctggctc caagtctggc acctcagcct ccctggccat cactgggctc 240
caggctgagg atgaggctga ttattactgc cagtcctatg acagcagcct gagtggttat 300
gtcttcggaa ctgggaccaa ggtcaccgtc ctaggt 336

<210> SEQ ID NO 154
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 154
gaagtgcagc tggtgcagtc tggggctgag gtgaagaagc ctgggtcctc ggtgaaggtc 60
tcctgcaagg cttctggaga caccttcagc aggtatgcta tcagctgggt gcgacaggcc 120
cctggacaag ggcttgagtg gatgggaagg atcatcccta tctttggtac accaaactac 180
gcacagaagt tccagggcag agtcacgatt accgcggacg aattcacgag cacagcctac 240
atggagctga gcagcctgag atctgaggac accgccatgt attactgtgc gcgctctatc 300
taccgttact ctgaatacga tcattggggt caaggtactc tggtgaccgt ctcctca 357

<210> SEQ ID NO 155
<211> LENGTH: 831
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 155
cagtctgtgt tgacgcagcc gccctcagtg tctggggccc cagggcagag ggtcaccatc 60
tcctgcactg ggagcagctc caacatcggg gcaggttatg atgtacactg gtaccagcag 120
cttccaggaa cagcccccaa actcctcatc tatggtaaca gcaatcggcc ctcaggggtc 180
cctgaccgat tctctggctc caagtctggc acctcagcct ccctggccat cactgggctc 240
caggctgagg atgaggctga ttattactgc cagtcctatg acagcagcct gagtggttat 300
gtcttcggaa ctgggaccaa ggtcaccgtc ctaggttcta gaggtggtgg tggtagcggc 360
ggcggcggct ctggtggtgg tggatccctc gagatggccg aagtgcagct ggtgcagtct 420
ggggctgagg tgaagaagcc tgggtcctcg gtgaaggtct cctgcaaggc ttctggagac 480
accttcagca ggtatgctat cagctgggtg cgacaggccc ctggacaagg gcttgagtgg 540
atgggaagga tcatccctat ctttggtaca ccaaactacg cacagaagtt ccagggcaga 600
gtcacgatta ccgcggacga attcacgagc acagcctaca tggagctgag cagcctgaga 660
tctgaggaca ccgccatgta ttactgtgcg cgctctatct accgttactc tgaatacgat 720
cattggggtc aaggtactct ggtgaccgtc tcctcaacta gtggccaggc cggccagcac 780
catcaccatc accatggcgc atacccgtac gacgttccgg actacgcttc t 831

<210> SEQ ID NO 156
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 156
caggctgtgc tgactcagcc accctcagcg tctgggaccc gcgggcagag ggtcaccatc 60
tcttgttctg gaagcagctc caacatcgga agtaatactg taaactggta ccagcagctc 120
ccaggaacgg cccccaaact cctcatctat agtaataatc agcggccctc aggggtccct 180
gaccgattct ctggctccaa gtctggcacc tcagcctccc tggccatcag tgggctccag 240
tctgaagatg aggctgatta ttactgtgca gcatgggatg acagcctgaa tggtcagggg 300
gtcttcggaa ctgggaccaa ggtcaccgtc ctaggt 336

<210> SEQ ID NO 157
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 157
gaggtccagc tggtgcagtc tggggctgag gtgaagaagc ctgggacctc agtgaaggtt 60
tcctgcaagg catctggata caccttcagc aactactata tacactgggt gcgacaggcc 120
cctggacaag ggcttgagtg gatgggagcg atcaacccta gtgttggtac cacaacctac 180
gcacagaact ttcagggcag agtcaccatg accagtgaca cgtccacgag cacagtctac 240
atggagttga gcagcctgac atctgaggac acggccgtgt attactgtgc gcgcgactgg 300
tggggtcaga tgatgtacga tggttggggt caaggtactc tggtgaccgt ctcctca 357

<210> SEQ ID NO 158
<211> LENGTH: 831
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 158
caggctgtgc tgactcagcc accctcagcg tctgggaccc gcgggcagag ggtcaccatc 60
tcttgttctg gaagcagctc caacatcgga agtaatactg taaactggta ccagcagctc 120
ccaggaacgg cccccaaact cctcatctat agtaataatc agcggccctc aggggtccct 180
gaccgattct ctggctccaa gtctggcacc tcagcctccc tggccatcag tgggctccag 240
tctgaagatg aggctgatta ttactgtgca gcatgggatg acagcctgaa tggtcagggg 300
gtcttcggaa ctgggaccaa ggtcaccgtc ctaggttcta gaggtggtgg tggtagcggc 360
ggcggcggct ctggtggtgg tggatccctc gagatggccg aggtccagct ggtgcagtct 420
ggggctgagg tgaagaagcc tgggacctca gtgaaggttt cctgcaaggc atctggatac 480
accttcagca actactatat acactgggtg cgacaggccc ctggacaagg gcttgagtgg 540
atgggagcga tcaaccctag tgttggtacc acaacctacg cacagaactt tcagggcaga 600
gtcaccatga ccagtgacac gtccacgagc acagtctaca tggagttgag cagcctgaca 660
tctgaggaca cggccgtgta ttactgtgcg cgcgactggt ggggtcagat gatgtacgat 720
ggttggggtc aaggtactct ggtgaccgtc tcctcaacta gtggccaggc cggccagcac 780
catcaccatc accatggcgc atacccgtac gacgttccgg actacgcttc t 831

<210> SEQ ID NO 159
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 159
cagtctgtcg tgacgcagcc gccctcagtg tctgcggccc caggacagaa ggtcaccatc 60
tcctgctctg gaagcagctc caacatcggg gcaggttatg atgtacactg gtaccagcag 120
cttccaggaa cagcccccaa actcctcatc tatggtaaca gcaatcggcc ctcaggggtc 180
cctgaccgat tctctggctc caagtctggc acctcagcct ccctggccat cactgggctc 240
caggctgagg atgaggctga ttattactgc cagtcctatg acagcagcct gagtggttcg 300
gtgttcggcg gagggaccaa gctgaccgtc ctaggt 336

<210> SEQ ID NO 160
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 160
gaggtccagc tggtgcagtc tggggctgag gtgaagaagc ctgggtcctc ggtgaaggtc 60
tcctgcaagg cttctggagg caccttcagc agctatgcta tcagctgggt gcgacaggcc 120
cctggacaag ggcttgagtg gatgggaggg atcatcccta tctttggtac agcaaactac 180
gcacagaagt tccagggcag agtcacgatt accgcggacg aatccacgag cacagcctac 240
atggagctga gcagcctgag atctgaggac acggccgtgt attactgtgc gcgctactct 300
tacaaatacg gtgaactgga tacttggggt caaggtactc tggtgaccgt ctcctca 357

<210> SEQ ID NO 161
<211> LENGTH: 831
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 161
cagtctgtcg tgacgcagcc gccctcagtg tctgcggccc caggacagaa ggtcaccatc 60
tcctgctctg gaagcagctc caacatcggg gcaggttatg atgtacactg gtaccagcag 120
cttccaggaa cagcccccaa actcctcatc tatggtaaca gcaatcggcc ctcaggggtc 180
cctgaccgat tctctggctc caagtctggc acctcagcct ccctggccat cactgggctc 240
caggctgagg atgaggctga ttattactgc cagtcctatg acagcagcct gagtggttcg 300
gtgttcggcg gagggaccaa gctgaccgtc ctaggttcta gaggtggtgg tggtagcggc 360
ggcggcggct ctggtggtgg tggatccctc gagatggccg aggtccagct ggtgcagtct 420
ggggctgagg tgaagaagcc tgggtcctcg gtgaaggtct cctgcaaggc ttctggaggc 480
accttcagca gctatgctat cagctgggtg cgacaggccc ctggacaagg gcttgagtgg 540
atgggaggga tcatccctat ctttggtaca gcaaactacg cacagaagtt ccagggcaga 600
gtcacgatta ccgcggacga atccacgagc acagcctaca tggagctgag cagcctgaga 660
tctgaggaca cggccgtgta ttactgtgcg cgctactctt acaaatacgg tgaactggat 720
acttggggtc aaggtactct ggtgaccgtc tcctcaacta gtggccaggc cggccagcac 780
catcaccatc accatggcgc atacccgtac gacgttccgg actacgcttc t 831

<210> SEQ ID NO 162
<211> LENGTH: 327
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 162
caggctgtgc tgactcagcc accctcggtg tcagtggccc caggaaagac ggccagactt 60
acctgtgggg gaaacaacat tggaagtgaa agtgtacatt ggtaccagca gaagccaggc 120
caggcccctt tactggtcgt ctatgatgat gacgaccggc cctccgggat ccctgagcga 180
ttctctggct ccaactctgg gaacacggcc accctgacca tcagcagggt cgaggccggc 240
gatgaggccg actattactg tcaggtgtgg gatcgaagta gtgatcattg gtttttcggc 300
ggagggacca agctgaccgt cctaggt 327

<210> SEQ ID NO 163
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 163
caggtgcagc tggtgcaatc tggggctgag gtgaagaagc ctggggcctc tgtgaaggtt 60
tcctgcaagg catctggata caccttcacc aattactata ttcactgggt gcgacaggcc 120
cccggacaag ggcttgagtg gatgggaata atcagaccta gtggtggtat cacaaactac 180
gcacagaagt tccagggcag ggtcagcatg accagggaca cgtccacgag cacagtctac 240
atggagctga gcagcctgag atctgaggac actgccgtgt attactgtgc gcgctcttgg 300
gactacttcg cttctaacga tttctggggt caaggtactc tggtgaccgt ctcctca 357

<210> SEQ ID NO 164
<211> LENGTH: 822
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 164
caggctgtgc tgactcagcc accctcggtg tcagtggccc caggaaagac ggccagactt 60
acctgtgggg gaaacaacat tggaagtgaa agtgtacatt ggtaccagca gaagccaggc 120
caggcccctt tactggtcgt ctatgatgat gacgaccggc cctccgggat ccctgagcga 180
ttctctggct ccaactctgg gaacacggcc accctgacca tcagcagggt cgaggccggc 240
gatgaggccg actattactg tcaggtgtgg gatcgaagta gtgatcattg gtttttcggc 300

```
ggagggacca agctgaccgt cctaggttct agaggtggtg gtggtagcgg cggcggcggc    360

tctggtggtg gtggatccct cgagatggcc caggtgcagc tggtgcaatc tggggctgag    420

gtgaagaagc ctggggcctc tgtgaaggtt tcctgcaagg catctggata caccttcacc    480

aattactata ttcactgggt gcgacaggcc cccggacaag ggcttgagtg gatgggaata    540

atcagaccta gtggtggtat cacaaactac gcacagaagt tccagggcag ggtcagcatg    600

accagggaca cgtccacgag cacagtctac atggagctga gcagcctgag atctgaggac    660

actgccgtgt attactgtgc gcgctcttgg gactacttcg cttctaacga tttctggggt    720

caaggtactc tggtgaccgt ctcctcaact agtggccagg ccggccagca ccatcaccat    780

caccatggcg catacccgta cgacgttccg gactacgctt ct                      822
```

<210> SEQ ID NO 165
<211> LENGTH: 399
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 165

```
cagtctgtgc tgacgcagcc gccctcagtg tctggggccc cagggcagag ggtcaccatc     60

tcctgcactg ggagcagctc caacatcggg gcaggttatg atgtgcactg gtaccagcag    120

cttccaggaa cagcccccaa actcctcatc tatggtaaca gcgatcggcc ctccggggtc    180

cctgaccgat tctctggctc caagtctggc acctcagcct ccctggccat cactgggctc    240

caggctgagg atgaggctga ttattactgc cagtcctatg acagcagcct gagtggttat    300

gtcttcggaa ctgggaccaa ggtcaccgtc ctaggttcta gaggtggtgg tggtagcggc    360

ggcggcggct ctggtggtgg tggatccctc gagatggcc                           399
```

<210> SEQ ID NO 166
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 166

```
cagatgcagc tggtgcagtc tggggctgag gtgaagaagc ctgggtcctc ggtgaaggtc     60

tcctgcaagg cttctggagg caccttcagc acctacgcta tcagctgggt gcgacaggcc    120

cctggacaag ggcttgagtg gatgggaggg atcatcccta tatttgggac agcaaactac    180

gcacagaagt tccagggcag ggtcacgatt accgcggaca aatccacgag cacagcctac    240

atggaggtga ggaacctgag atctgaggac acggccgtgt attactgtgc gcgcgctgaa    300

tacgtttacg gtgaatacga tcagtggggt caaggtactc tggtgaccgt ctcctca       357
```

<210> SEQ ID NO 167
<211> LENGTH: 831
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 167

```
cagtctgtgc tgacgcagcc gccctcagtg tctggggccc cagggcagag ggtcaccatc     60
```

tcctgcactg ggagcagctc caacatcggg gcaggttatg atgtgcactg gtaccagcag 120
cttccaggaa cagcccccaa actcctcatc tatggtaaca gcgatcggcc ctccggggtc 180
cctgaccgat tctctggctc caagtctggc acctcagcct ccctggccat cactgggctc 240
caggctgagg atgaggctga ttattactgc cagtcctatg acagcagcct gagtggttat 300
gtcttcggaa ctgggaccaa ggtcaccgtc ctaggttcta gaggtggtgg tggtagcggc 360
ggcggcggct ctggtggtgg tggatccctc gagatggccc agatgcagct ggtgcagtct 420
ggggctgagg tgaagaagcc tgggtcctcg gtgaaggtct cctgcaaggc ttctggaggc 480
accttcagca cctacgctat cagctgggtg cgacaggccc ctggacaagg gcttgagtgg 540
atgggaggga tcatccctat atttgggaca gcaaactacg cacagaagtt ccagggcagg 600
gtcacgatta ccgcggacaa atccacgagc acagcctaca tggaggtgag gaacctgaga 660
tctgaggaca cggccgtgta ttactgtgcg cgcgctgaat acgtttacgg tgaatacgat 720
cagtggggtc aaggtactct ggtgaccgtc tcctcaacta gtggccaggc cggccagcac 780
catcaccatc accatggcgc atacccgtac gacgttccgg actacgcttc t 831

<210> SEQ ID NO 168
<211> LENGTH: 327
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 168
cagtctgtgt tgactcagcc accctcagtg tcagtggccc caggaaagac ggccaggatt 60
acctgtgggg gaaacaacat tggaagtaaa agtgtgcact ggtaccagca gaagccaggc 120
caggcccctg tgctggtcat ctattatgat agcgaccggc cctcagggat ccctgagcga 180
ttctctggct ccaactctgg gaacacggcc accctgacca tcagcagggt cgaagccggg 240
gatgaggccg actattactg tcaggtgtgg gatagtagta gtgatcatta tgtcttcgga 300
actgggacca aggtcaccgt cctaggt 327

<210> SEQ ID NO 169
<211> LENGTH: 372
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 169
gaggtgcagc tggtggagtc cgggggaggc gtggtccagc ctgggaggtc cctgagactc 60
tcctgtgcag cctctgggtt caccttcaat aatcatgcta tgcactgggt ccgccaggct 120
ccaggcaagg ggctggagtg ggtggcagtt atatcatttg atggagacga taaattctac 180
gcagactccg tgaagggccg attcaccatc tccagagaca attccaggaa cacactgttt 240
ctgcaaatga acaacctgag acctgaggac acggctgtgt attactgttc gagagatcca 300
tatcactttg cctcggggag ttattcctac tttgactact ggggccaggg aaccctggtc 360
accgtctcct ca 372

<210> SEQ ID NO 170
<211> LENGTH: 837
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 170
cagtctgtgt tgactcagcc accctcagtg tcagtggccc caggaaagac ggccaggatt 60
acctgtgggg gaaacaacat tggaagtaaa agtgtgcact ggtaccagca gaagccaggc 120
caggcccctg tgctggtcat ctattatgat agcgaccggc cctcagggat ccctgagcga 180
ttctctggct ccaactctgg gaacacggcc accctgacca tcagcagggt cgaagccggg 240
gatgaggccg actattactg tcaggtgtgg gatagtagta gtgatcatta tgtcttcgga 300
actgggacca aggtcaccgt cctaggttct agaggtggtg gtggtagcgg cggcggcggc 360
tctggtggtg gtggatccct cgagatggcc gaggtgcagc tggtggagtc cgggggaggc 420
gtggtccagc ctgggaggtc cctgagactc tcctgtgcag cctctgggtt caccttcaat 480
aatcatgcta tgcactgggt ccgccaggct ccaggcaagg ggctggagtg ggtggcagtt 540
atatcatttg atggagacga taaattctac gcagactccg tgaagggccg attcaccatc 600
tccagagaca attccaggaa cacactgttt ctgcaaatga acaacctgag acctgaggac 660
acggctgtgt attactgttc gagagatcca tatcactttg cctcggggag ttattcctac 720
tttgactact ggggccaggg aaccctggtc accgtctcct caactagtgg ccaggccggc 780
cagcaccatc accatcacca tggcgcatac ccgtacgacg ttccggacta cgcttct 837

<210> SEQ ID NO 171
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 171
aattttatgc tgactcagcc ccactctgtg tcggagtctc cggggaagac ggtgaccatc 60
tcctgcaccc gcagcagtgg cagcattgcc agccactatg tgcagtggta ccagcagcgc 120
ccgggcagtt cccccaccac tgtgatctat gagaataacc aaagaccctc tggggtccct 180
gatcggttct ctggctccat cgacagttcc tccaactctg cctccctcac catctctgga 240
ctgaagactg aggacgaggc tgactactac tgtcaatctt atgatcgcag caatcatgtg 300
gtattcggcg gagggaccaa gctgaccgtc ctaggt 336

<210> SEQ ID NO 172
<211> LENGTH: 354
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 172
caggtgcagc tggtgcagtc tggggctgag gtgaagaagc ctggggcctc agtgaaggtc 60
tcctgcaagg catctggata caccttcacc aactactata tccactgggt gcgacaggcc 120
cctggagaag ggcttgagtg gatgggaata atcagaccta gtggcggtaa cacaaactac 180
gcacagaagt tccagggcag agtcaccatg accagggaca cgtccacgcg cacggtctat 240
atggagttga gtagcctgag atctgaggac acggccgtgt attactgtgc gcgctcttgg 300
aactctcgtg acgttgattc ttggggtcaa ggtactctgg tgaccgtctc ctca 354

<210> SEQ ID NO 173
<211> LENGTH: 828
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 173
aattttatgc tgactcagcc ccactctgtg tcggagtctc cggggaagac ggtgaccatc 60
tcctgcaccc gcagcagtgg cagcattgcc agccactatg tgcagtggta ccagcagcgc 120
ccgggcagtt cccccaccac tgtgatctat gagaataacc aaagaccctc tggggtccct 180
gatcggttct ctggctccat cgacagttcc tccaactctg cctccctcac catctctgga 240
ctgaagactg aggacgaggc tgactactac tgtcaatctt atgatcgcag caatcatgtg 300
gtattcggcg gagggaccaa gctgaccgtc ctaggttcta gaggtggtgg tggtagcggc 360
ggcggcggct ctggtggtgg tggatccctc gagatggccc aggtgcagct ggtgcagtct 420
ggggctgagg tgaagaagcc tggggcctca gtgaaggtct cctgcaaggc atctggatac 480
accttcacca actactatat ccactgggtg cgacaggccc ctggagaagg gcttgagtgg 540
atgggaataa tcagacctag tggcggtaac acaaactacg cacagaagtt ccagggcaga 600
gtcaccatga ccagggacac gtccacgcgc acggtctata tggagttgag tagcctgaga 660
tctgaggaca cggccgtgta ttactgtgcg cgctcttgga actctcgtga cgttgattct 720
tggggtcaag gtactctggt gaccgtctcc tcaactagtg gccaggccgg ccagcaccat 780
caccatcacc atggcgcata cccgtacgac gttccggact acgcttct 828

<210> SEQ ID NO 174
<211> LENGTH: 333
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 174
caggctgtgc tgactcagcc accctcgctg tctggaggcc ccaggcagag ggtcaccatc 60
tcctgttctg gaagcacctc caacatcgga aaaaatggtg tgagctggta ccagcagctc 120
ccaggaaagg ctcccaaact cctcatctat aatgatcatc tgttgtcctc aggggtctct 180
gaccgctttt ctggctccaa gtctggcacg tcagcctccc tggccatcag tggactccag 240
tctgacgatg aagctgatta ttactgtgcg acatgggacg acactttgga tcttccgcta 300
ttcggcggag ggaccaaggt caccgtccta ggt 333

<210> SEQ ID NO 175
<211> LENGTH: 363
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 175
cagatgcagc tggtgcagtc tggggctgag gtggagaagc ctggggcctc agtgaagctc 60
tcctgcaagg cttctggagg caccttcagc agctatgcta tcagctgggt gcgacaggcc 120
cctggacaag ggcttgagtg gatgggaggg atcatcccta tctttggtac agcaaactac 180
gcacagaagt tccagggcag agtcacgatt accgcggacg aatccacgag cacagcctac 240
atggagctga gcagcctgag atctgaggac acggccgtgt attactgtgc gcgcccgtct 300
tactactcta tcaaatctgc ttgggatcat tggggtcaag gtactctggt gaccgtctcc 360
tca 363

<210> SEQ ID NO 176
<211> LENGTH: 833
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 176
caggctgtgc tgactcagcc accctcgctg tctggaggcc ccaggcagag ggtcaccatc 60
tcctgttctg gaagcacctc caacatcgga aaaaatggtg tgagctggta ccagcagctc 120
ccaggaaagg ctcccaaact cctcatctat aatgatcatc tgttgtcctc aggggtctct 180
gaccgctttt ctggctccaa gtctggcacg tcagcctccc tggccatcag tggactccag 240
tctgacgatg aagctgatta ttactgtgcg acatgggacg acactttgga tcttccgcta 300
ttcggcggag ggaccaaggt caccgtccta ggttctagag gtggtggtgg tagcggcggc 360
ggcggctctg gtggtggtgg atccctcgag atggcccaga tgcagctggt gcagtctggg 420
gctgaggtgg agaagcctgg ggcctcagtg aagctctcct gcaaggcttc tggaggcacc 480
ttcagcagct atgctatcag ctgggtgcga caggcccctg gacaagggct tgagtggatg 540
ggagggatca tccctatctt tggtacagca aactacgcac agaagttcca gggcagagtc 600
acgattaccg cggacgaatc cacgagcaca gcctacatgg agctgagcag cctgagatct 660
gaggacacgg ccgtgtatta ctgtgcgcgc ccgtcttact actctatcaa atctgcttgg 720
gatcattggg gtcaaggtac tctggtgacc gtctcctcaa ctagtggcca ggccggccag 780
caccatcacc atcaccatgg cgcatacccg tacgacgttc cggactacgc ttc 833

<210> SEQ ID NO 177
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 177

Arg Tyr Thr Phe Thr Asn Tyr Tyr
1 5

<210> SEQ ID NO 178
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 178

Gly Tyr Ser Phe Thr Ser Tyr Tyr
1 5

<210> SEQ ID NO 179

<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 179

Gly Tyr Thr Phe Asn Asn Tyr Tyr
1 5

<210> SEQ ID NO 180
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 180

Gly Tyr Thr Phe Thr Asn Tyr Tyr
1 5

<210> SEQ ID NO 181
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 181

Gly Tyr Thr Phe Thr Asn Tyr Gly
1 5

<210> SEQ ID NO 182
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 182

Gly Tyr Thr Phe Thr Asn Tyr Tyr
1 5

<210> SEQ ID NO 183
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 183

Gly Gly Thr Phe Ser Ser Tyr Ala
1 5

<210> SEQ ID NO 184
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 184

Gly Tyr Thr Phe Asp Asn Phe Gly
1               5

<210> SEQ ID NO 185
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Ile Asn Pro Ser Gly Gly Ser Thr
1               5

<210> SEQ ID NO 186
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Ile Asp Pro Ser Asp Ser Tyr Thr
1               5

<210> SEQ ID NO 187
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Ile Ser Pro Tyr Asn Gly Asn Thr
1               5

<210> SEQ ID NO 188
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Ile Asn Pro Ser Ile Gly Ser Thr
1               5

<210> SEQ ID NO 189
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Ile Ile Pro Ile Leu Gly Ile Ala
1               5

<210> SEQ ID NO 190
<211> LENGTH: 8
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 190

Ile Asn Thr Tyr Asp Gly Tyr Thr
1               5


<210> SEQ ID NO 191
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Ala Arg Gly Trp Ser Gly Tyr Asp Pro Gly Asp Phe
1               5                   10


<210> SEQ ID NO 192
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Val Arg His Gly Phe Ser Asn Ser Pro Arg Leu Trp Phe Asp Thr
1               5                   10                  15


<210> SEQ ID NO 193
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Ala Arg Ser Phe Asp Lys Gln Asp Ile Asp Tyr
1               5                   10


<210> SEQ ID NO 194
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Ala Arg Ser Trp Met Ser Asp Ser Tyr Tyr Asp Gly
1               5                   10


<210> SEQ ID NO 195
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Ala Arg Tyr Trp Asp Ser Gly Tyr Ala Tyr Asp Glu
1               5                   10
```

<210> SEQ ID NO 196
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 196

Ala Arg Ser Trp Ser Asn Lys Leu Ser Trp Tyr Asn Asp Gly
1 5 10

<210> SEQ ID NO 197
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 197

Ala Arg Ser Trp Ser Lys Thr Glu Gly Ser Asp Arg
1 5 10

<210> SEQ ID NO 198
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 198

Ala Arg Ser Trp Asp Thr Phe Ser Asp Glu
1 5 10

<210> SEQ ID NO 199
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 199

Ala Arg Ser Phe Gly Asp Ser Asp Gly Ala Asp Ser
1 5 10

<210> SEQ ID NO 200
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 200

Ala Arg Ser Trp His Glu Asn Ser Gly Val Asp Ser
1 5 10

<210> SEQ ID NO 201
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 201

```
Ala Arg Gly Gly Asp Tyr Val Glu Ser Trp Phe Asp Pro
1               5                   10


<210> SEQ ID NO 202
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Ala Arg Ser Val Pro His Gln Ile Ser Tyr Gly Asp Leu
1               5                   10


<210> SEQ ID NO 203
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Ser Ser Asp Val Gly Gly Tyr Asn Tyr
1               5


<210> SEQ ID NO 204
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Ser Ser Asn Ile Gly Val Asn Pro
1               5


<210> SEQ ID NO 205
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Ser Gly Ser Ile Ala Ser Asn Tyr
1               5


<210> SEQ ID NO 206
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Ser Ser Asn Ile Gly Asn Asn Tyr
1               5


<210> SEQ ID NO 207
<211> LENGTH: 6
<212> TYPE: PRT
<213> ORGANISM: Artificial Sequence
```

<220> FEATURE:
<223> OTHER INFORMATION: Description of Artificial Sequence: Synthetic
      peptide

<400> SEQUENCE: 207

Asp Ile Arg Arg Lys Thr
1               5

<210> SEQ ID NO 208
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Asn Leu Gly Ser Lys Ser
1               5

<210> SEQ ID NO 209
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Ser Ser Asp Val Gly Ala Tyr Asn Tyr
1               5

<210> SEQ ID NO 210
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Thr Ser Asp Phe Asn Asp Tyr Leu Phe
1               5

<210> SEQ ID NO 211
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Glu Val Ser
1

<210> SEQ ID NO 212
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Ala Asn Tyr
1

<210> SEQ ID NO 213
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 213

Glu Asp Asn
1

<210> SEQ ID NO 214
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 214

Asp Asp Ser
1

<210> SEQ ID NO 215
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 215

Asp Asn Asn
1

<210> SEQ ID NO 216
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 216

Asp Asp Asn
1

<210> SEQ ID NO 217
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 217

Asp Val Thr
1

<210> SEQ ID NO 218
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 218

Ser Ser Tyr Ala Gly Ser Asn Thr His Val Val
1 5 10

<210> SEQ ID NO 219
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 219

Ser Ser Tyr Ala Gly Ser Asn Asn Val Val
1 5 10

<210> SEQ ID NO 220
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 220

Ser Thr Trp Asp Asp Ser Leu Asn Ala Trp Leu
1 5 10

<210> SEQ ID NO 221
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 221

Gln Ser Tyr Asp Thr Asn Asn Tyr Gly Val Ile
1 5 10

<210> SEQ ID NO 222
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 222

Gln Val Trp Asp Ser Ser Ser Asp His Val Ile
1 5 10

<210> SEQ ID NO 223
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 223

Gln Val Trp Asp Ser Ser Ser Asp Arg Trp Val
1 5 10

<210> SEQ ID NO 224
<211> LENGTH: 11
<212> TYPE: PRT

<213> ORGANISM: Artificial Sequence
<220> FEATURE:
<223> OTHER INFORMATION: Description of Artificial Sequence: Synthetic peptide

<400> SEQUENCE: 224

Gly Thr Trp Asp Ser Ser Leu Asn Ala Val Val
1 5 10

<210> SEQ ID NO 225
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 225

Gly Thr Trp Asp Asn Ser Leu Ser Ala Ala Val
1 5 10

<210> SEQ ID NO 226
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 226

Gln Val Trp Asp Asn Asp Asn Asp His Tyr Val
1 5 10

<210> SEQ ID NO 227
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 227

Gly Thr Trp Asp Ser Ser Leu Ser Ala Val Val
1 5 10

<210> SEQ ID NO 228
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 228

Gln Val Trp His Ser Ser Ser Asp His Tyr Val
1 5 10

<210> SEQ ID NO 229
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 229

Ser Ser Tyr Ala Gly Ser Asn Asn Phe Val
1 5 10

<210> SEQ ID NO 230
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

```
Gly Ser Lys Thr Gly Arg Thr Thr Tyr Val
1               5                   10
```

<210> SEQ ID NO 231
<211> LENGTH: 831
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 231

```
caatctgccc tgactcagcc tccctccgcg tccgggtctc ctggacagtc agtcaccatc      60

tcctgcactg gaaccagcag tgacgttggt ggttataact atgtctcctg gtaccaacag     120

cacccaggca aagcccccaa actcatgatt tatgaggtca gtaagcggcc ctcaggggtc     180

cctgatcgct tctctggctc caagtctggc aacacggcct ccctgaccgt ctctgggctc     240

caggctgagg atgaggctga ttattactgc agctcatatg caggcagcaa cacccatgtg     300

gtattcggcg gagggaccaa gctgaccgtc ctaggttcta gaggtggtgg tggtagcggc     360

ggcggcggct ctggtggtgg tggatccctc gagatggccg aagtgcagct ggtgcagtct     420

ggggctgagg tgaagaagcc tggggcctca gtgaaaattt cctgcaaggc atctagatac     480

accttcacca actactatat acactgggtg cgacaggccc ctggacaagg gcttgagtgg     540

atgggaataa tcaaccctag tggtggtagc acaacctacc cacagaactt ccagggcaga     600

ctcaccatga ccagggacac gtccacgagc acagtctaca tggagctgag cagcctgaga     660

tctgaggaca cggccatgta ttactgtgcg agaggttgga gtggctacga tccaggggac     720

ttctggggcc agggaaccct ggtcaccgtc tcctcaacta gtggccaggc cggccagcac     780

catcaccatc accatggcgc atacccgtac gacgttccgg actacgcttc t              831
```

<210> SEQ ID NO 232
<211> LENGTH: 277
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232

```
Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80
```

```
Gln Ala Glu Asp Glu Ala Asp Tyr Tyr Cys Ser Ser Tyr Ala Gly Ser
                85                  90                  95

Asn Thr His Val Val Phe Gly Gly Gly Thr Lys Leu Thr Val Leu Gly
            100                 105                 110

Ser Arg Gly Gly Gly Gly Ser Gly Gly Gly Gly Ser Gly Gly Gly Gly
        115                 120                 125

Ser Leu Glu Met Ala Glu Val Gln Leu Val Gln Ser Gly Ala Glu Val
    130                 135                 140

Lys Lys Pro Gly Ala Ser Val Lys Ile Ser Cys Lys Ala Ser Arg Tyr
145                 150                 155                 160

Thr Phe Thr Asn Tyr Tyr Ile His Trp Val Arg Gln Ala Pro Gly Gln
                165                 170                 175

Gly Leu Glu Trp Met Gly Ile Ile Asn Pro Ser Gly Gly Ser Thr Thr
            180                 185                 190

Tyr Pro Gln Asn Phe Gln Gly Arg Leu Thr Met Thr Arg Asp Thr Ser
        195                 200                 205

Thr Ser Thr Val Tyr Met Glu Leu Ser Ser Leu Arg Ser Glu Asp Thr
    210                 215                 220

Ala Met Tyr Tyr Cys Ala Arg Gly Trp Ser Gly Tyr Asp Pro Gly Asp
225                 230                 235                 240

Phe Trp Gly Gln Gly Thr Leu Val Thr Val Ser Ser Thr Ser Gly Gln
                245                 250                 255

Ala Gly Gln His His His His His His Gly Ala Tyr Pro Tyr Asp Val
            260                 265                 270

Pro Asp Tyr Ala Ser
        275
```

<210> SEQ ID NO 233
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 233

```
caatctgccc tgactcagcc tccctccgcg tccgggtctc ctggacagtc agtcaccatc     60

tcctgcactg gaaccagcag tgacgttggt ggttataact atgtctcctg gtaccaacag    120

cacccaggca aagcccccaa actcatgatt tatgaggtca gtaagcggcc ctcaggggtc    180

cctgatcgct tctctggctc caagtctggc aacacggcct ccctgaccgt ctctgggctc    240

caggctgagg atgaggctga ttattactgc agctcatatg caggcagcaa cacccatgtg    300

gtattcggcg gagggaccaa gctgaccgtc ctaggt                              336
```

<210> SEQ ID NO 234
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 234

```
Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30
```

Asn Tyr Val Ser Trp Tyr Gln Gln His Pro Gly Lys Ala Pro Lys Leu
35 40 45

Met Ile Tyr Glu Val Ser Lys Arg Pro Ser Gly Val Pro Asp Arg Phe
50 55 60

Ser Gly Ser Lys Ser Gly Asn Thr Ala Ser Leu Thr Val Ser Gly Leu
65 70 75 80

Gln Ala Glu Asp Glu Ala Asp Tyr Tyr Cys Ser Ser Tyr Ala Gly Ser
85 90 95

Asn Thr His Val Val Phe Gly Gly Gly Thr Lys Leu Thr Val Leu Gly
100 105 110

<210> SEQ ID NO 235
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 235
gaagtgcagc tggtgcagtc tggggctgag gtgaagaagc ctggggcctc agtgaaaatt 60
tcctgcaagg catctagata caccttcacc aactactata tacactgggt gcgacaggcc 120
cctggacaag ggcttgagtg gatgggaata atcaacccta gtggtggtag cacaacctac 180
ccacagaact tccagggcag actcaccatg accagggaca cgtccacgag cacagtctac 240
atggagctga gcagcctgag atctgaggac acggccatgt attactgtgc gagaggttgg 300
agtggctacg atccagggga cttctggggc cagggaaccc tggtcaccgt ctcctca 357

<210> SEQ ID NO 236
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 236

Glu Val Gln Leu Val Gln Ser Gly Ala Glu Val Lys Lys Pro Gly Ala
1 5 10 15

Ser Val Lys Ile Ser Cys Lys Ala Ser Arg Tyr Thr Phe Thr Asn Tyr
20 25 30

Tyr Ile His Trp Val Arg Gln Ala Pro Gly Gln Gly Leu Glu Trp Met
35 40 45

Gly Ile Ile Asn Pro Ser Gly Gly Ser Thr Thr Tyr Pro Gln Asn Phe
50 55 60

Gln Gly Arg Leu Thr Met Thr Arg Asp Thr Ser Thr Ser Thr Val Tyr
65 70 75 80

Met Glu Leu Ser Ser Leu Arg Ser Glu Asp Thr Ala Met Tyr Tyr Cys
85 90 95

Ala Arg Gly Trp Ser Gly Tyr Asp Pro Gly Asp Phe Trp Gly Gln Gly
100 105 110

Thr Leu Val Thr Val Ser Ser
115

<210> SEQ ID NO 237
<211> LENGTH: 828
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 237
caatctgccc tgactcagcc tgcctccgcg tccgggtctc ctggacagtc agtcaccatc 60
tcctgcactg gaaccagcag tgacgttggt ggttataact atgtctcctg gtaccaacag 120
cacccaggca aagcccccaa actcatgatt tatgaggtca gtaagcggcc ctcaggggtc 180
cctgatcgct tctctggctc caagtctggc aacacggcct ccctgaccgt ctctgggctc 240
caggctgagg atgaggctga ttattactgc agctcatatg caggcagcaa caatgtggta 300
ttcggcggag ggaccaagct gaccgtccta ggttctagag gtggtggtgg tagcggcggc 360
ggcggctctg gtggtggtgg atccctcgag atggccgagg tccagctggt gcagtctggg 420
gctgaggtga agaagcctgg ggcctcagtg aaaatttcct gcaaggcatc tagatacacc 480
ttcaccaact actatataca ctgggtgcga caggcccctg gacaagggct tgagtggatg 540
ggaataatca accctagtgg tggtagcaca acctacccac agaacttcca gggcagactc 600
accatgacca gggacacgtc cacgagcaca gtctacatgg agctgagcag cctgagatct 660
gaggacacgg ccatgtatta ctgtgcgaga ggttggagtg gctacgatcc aggggacttc 720
tggggccagg gaaccctggt caccgtctcc tcaactagtg gccaggccgg ccagcaccat 780
caccatcacc atggcgcata cccgtacgac gttccggact acgcttct 828

<210> SEQ ID NO 238
<211> LENGTH: 276
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 238

Gln Ser Ala Leu Thr Gln Pro Ala Ser Ala Ser Gly Ser Pro Gly Gln
1 5 10 15

Ser Val Thr Ile Ser Cys Thr Gly Thr Ser Ser Asp Val Gly Gly Tyr
20 25 30

Asn Tyr Val Ser Trp Tyr Gln Gln His Pro Gly Lys Ala Pro Lys Leu
35 40 45

Met Ile Tyr Glu Val Ser Lys Arg Pro Ser Gly Val Pro Asp Arg Phe
50 55 60

Ser Gly Ser Lys Ser Gly Asn Thr Ala Ser Leu Thr Val Ser Gly Leu
65 70 75 80

Gln Ala Glu Asp Glu Ala Asp Tyr Tyr Cys Ser Ser Tyr Ala Gly Ser
85 90 95

Asn Asn Val Val Phe Gly Gly Gly Thr Lys Leu Thr Val Leu Gly Ser
100 105 110

Arg Gly Gly Gly Gly Ser Gly Gly Gly Gly Ser Gly Gly Gly Gly Ser
115 120 125

Leu Glu Met Ala Glu Val Gln Leu Val Gln Ser Gly Ala Glu Val Lys
130 135 140

Lys Pro Gly Ala Ser Val Lys Ile Ser Cys Lys Ala Ser Arg Tyr Thr
145 150 155 160

Phe Thr Asn Tyr Tyr Ile His Trp Val Arg Gln Ala Pro Gly Gln Gly
165 170 175

Leu Glu Trp Met Gly Ile Ile Asn Pro Ser Gly Gly Ser Thr Thr Tyr

```
            180                 185                 190

Pro Gln Asn Phe Gln Gly Arg Leu Thr Met Thr Arg Asp Thr Ser Thr
        195                 200                 205

Ser Thr Val Tyr Met Glu Leu Ser Ser Leu Arg Ser Glu Asp Thr Ala
    210                 215                 220

Met Tyr Tyr Cys Ala Arg Gly Trp Ser Gly Tyr Asp Pro Gly Asp Phe
225                 230                 235                 240

Trp Gly Gln Gly Thr Leu Val Thr Val Ser Ser Thr Ser Gly Gln Ala
                245                 250                 255

Gly Gln His His His His His His Gly Ala Tyr Pro Tyr Asp Val Pro
            260                 265                 270

Asp Tyr Ala Ser
        275
```

<210> SEQ ID NO 239
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 239

```
caatctgccc tgactcagcc tgcctccgcg tccgggtctc ctggacagtc agtcaccatc     60

tcctgcactg gaaccagcag tgacgttggt ggttataact atgtctcctg gtaccaacag    120

cacccaggca aagcccccaa actcatgatt tatgaggtca gtaagcggcc ctcaggggtc    180

cctgatcgct tctctggctc caagtctggc aacacggcct ccctgaccgt ctctgggctc    240

caggctgagg atgaggctga ttattactgc agctcatatg caggcagcaa caatgtggta    300

ttcggcggag ggaccaagct gaccgtccta ggt                                 333
```

<210> SEQ ID NO 240
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 240

```
Gln Ser Ala Leu Thr Gln Pro Ala Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Asn Asn Val Val Phe Gly Gly Gly Thr Lys Leu Thr Val Leu Gly
            100                 105                 110
```

<210> SEQ ID NO 241
<211> LENGTH: 357
<212> TYPE: DNA

<213> ORGANISM: Artificial Sequence
<220> FEATURE:
<223> OTHER INFORMATION: Description of Artificial Sequence: Synthetic
polynucleotide

<400> SEQUENCE: 241
gaggtccagc tggtgcagtc tggggctgag gtgaagaagc ctggggcctc agtgaaaatt 60
tcctgcaagg catctagata caccttcacc aactactata tacactgggt gcgacaggcc 120
cctggacaag ggcttgagtg gatgggaata atcaacccta gtggtggtag cacaacctac 180
ccacagaact tccagggcag actcaccatg accagggaca cgtccacgag cacagtctac 240
atggagctga gcagcctgag atctgaggac acggccatgt attactgtgc gagaggttgg 300
agtggctacg atccagggga cttctggggc cagggaaccc tggtcaccgt ctcctca 357

<210> SEQ ID NO 242
<211> LENGTH: 119
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 242

Glu Val Gln Leu Val Gln Ser Gly Ala Glu Val Lys Lys Pro Gly Ala
1 5 10 15

Ser Val Lys Ile Ser Cys Lys Ala Ser Arg Tyr Thr Phe Thr Asn Tyr
20 25 30

Tyr Ile His Trp Val Arg Gln Ala Pro Gly Gln Gly Leu Glu Trp Met
35 40 45

Gly Ile Ile Asn Pro Ser Gly Gly Ser Thr Thr Tyr Pro Gln Asn Phe
50 55 60

Gln Gly Arg Leu Thr Met Thr Arg Asp Thr Ser Thr Ser Thr Val Tyr
65 70 75 80

Met Glu Leu Ser Ser Leu Arg Ser Glu Asp Thr Ala Met Tyr Tyr Cys
85 90 95

Ala Arg Gly Trp Ser Gly Tyr Asp Pro Gly Asp Phe Trp Gly Gln Gly
100 105 110

Thr Leu Val Thr Val Ser Ser
115

<210> SEQ ID NO 243
<211> LENGTH: 837
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 243
caggctgtgc tgactcagcc accctcagcg tctgggaccc ccgggcagag ggtcaccatc 60
tcttgttctg gaggcagctc caacatcgga gttaatcctg taaactggta ccagcaactc 120
ccaggaacgg cccccaaact cctcatcttt gctaattatc agcggccctc aggggtccct 180
gaccgattct ctggctccaa gtctggcacc tcagcctccc tggccatcag tggactccag 240
tctgatgatg aggctcatta ttattgttcg acatgggatg acagcctgaa tgcttggctg 300
ttcggcggag ggaccaagct gaccgtccta ggttctagag gtggtggtgg tagcggcggc 360
ggcggctctg gtggtggtgg atccctcgag atggccgagg tgcagctggt gcagtctgga 420

```
gcagaggtga aaaagccggg ggactctctg aggatctcct gtcagggttc tggatacagc    480

tttaccagtt actacatcag ctgggtgcgc cagatgcccg ggaaaggcct ggagtggatg    540

gggaacattg atcctagtga ctcttacacc aactacagcc cgtccttcca aggccacgtc    600

accatgtcag ttgacaagtc catcagcact gcctacctgc agtggagcag cctgaaggcc    660

tcggacatcg ccatatatta ctgtgtgaga catgggttta gcaactcgcc tagattgtgg    720

ttcgacacct ggggccaggg aaccctggtc accgtctcct caactagtgg ccaggccggc    780

cagcaccatc accatcacca tggcgcatac ccgtacgacg ttccggacta cgcttct       837


<210> SEQ ID NO 244
<211> LENGTH: 279
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 244

Gln Ala Val Leu Thr Gln Pro Pro Ser Ala Ser Gly Thr Pro Gly Gln
1               5                   10                  15

Arg Val Thr Ile Ser Cys Ser Gly Gly Ser Ser Asn Ile Gly Val Asn
            20                  25                  30

Pro Val Asn Trp Tyr Gln Gln Leu Pro Gly Thr Ala Pro Lys Leu Leu
        35                  40                  45

Ile Phe Ala Asn Tyr Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Asp Asp Glu Ala His Tyr Tyr Cys Ser Thr Trp Asp Asp Ser Leu
                85                  90                  95

Asn Ala Trp Leu Phe Gly Gly Gly Thr Lys Leu Thr Val Leu Gly Ser
            100                 105                 110

Arg Gly Gly Gly Gly Ser Gly Gly Gly Gly Ser Gly Gly Gly Gly Ser
        115                 120                 125

Leu Glu Met Ala Glu Val Gln Leu Val Gln Ser Gly Ala Glu Val Lys
    130                 135                 140

Lys Pro Gly Asp Ser Leu Arg Ile Ser Cys Gln Gly Ser Gly Tyr Ser
145                 150                 155                 160

Phe Thr Ser Tyr Tyr Ile Ser Trp Val Arg Gln Met Pro Gly Lys Gly
                165                 170                 175

Leu Glu Trp Met Gly Asn Ile Asp Pro Ser Asp Ser Tyr Thr Asn Tyr
            180                 185                 190

Ser Pro Ser Phe Gln Gly His Val Thr Met Ser Val Asp Lys Ser Ile
        195                 200                 205

Ser Thr Ala Tyr Leu Gln Trp Ser Ser Leu Lys Ala Ser Asp Ile Ala
    210                 215                 220

Ile Tyr Tyr Cys Val Arg His Gly Phe Ser Asn Ser Pro Arg Leu Trp
225                 230                 235                 240

Phe Asp Thr Trp Gly Gln Gly Thr Leu Val Thr Val Ser Ser Thr Ser
                245                 250                 255

Gly Gln Ala Gly Gln His His His His His His Gly Ala Tyr Pro Tyr
            260                 265                 270

Asp Val Pro Asp Tyr Ala Ser
        275
```

<210> SEQ ID NO 245
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 245
caggctgtgc tgactcagcc accctcagcg tctgggaccc ccgggcagag ggtcaccatc 60
tcttgttctg gaggcagctc caacatcgga gttaatcctg taaactggta ccagcaactc 120
ccaggaacgg cccccaaact cctcatcttt gctaattatc agcggccctc aggggtccct 180
gaccgattct ctggctccaa gtctggcacc tcagcctccc tggccatcag tggactccag 240
tctgatgatg aggctcatta ttattgttcg acatgggatg acagcctgaa tgcttggctg 300
ttcggcggag ggaccaagct gaccgtccta ggt 333

<210> SEQ ID NO 246
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 246

Gln Ala Val Leu Thr Gln Pro Pro Ser Ala Ser Gly Thr Pro Gly Gln
1 5 10 15

Arg Val Thr Ile Ser Cys Ser Gly Gly Ser Ser Asn Ile Gly Val Asn
20 25 30

Pro Val Asn Trp Tyr Gln Gln Leu Pro Gly Thr Ala Pro Lys Leu Leu
35 40 45

Ile Phe Ala Asn Tyr Gln Arg Pro Ser Gly Val Pro Asp Arg Phe Ser
50 55 60

Gly Ser Lys Ser Gly Thr Ser Ala Ser Leu Ala Ile Ser Gly Leu Gln
65 70 75 80

Ser Asp Asp Glu Ala His Tyr Tyr Cys Ser Thr Trp Asp Asp Ser Leu
85 90 95

Asn Ala Trp Leu Phe Gly Gly Gly Thr Lys Leu Thr Val Leu Gly
100 105 110

<210> SEQ ID NO 247
<211> LENGTH: 366
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 247
gaggtgcagc tggtgcagtc tggagcagag gtgaaaaagc cgggggactc tctgaggatc 60
tcctgtcagg gttctggata cagctttacc agttactaca tcagctgggt gcgccagatg 120
cccgggaaag gcctggagtg gatggggaac attgatccta gtgactctta caccaactac 180
agcccgtcct tccaaggcca cgtcaccatg tcagttgaca agtccatcag cactgcctac 240
ctgcagtgga gcagcctgaa ggcctcggac atcgccatat attactgtgt gagacatggg 300
tttagcaact cgcctagatt gtggttcgac acctggggcc agggaaccct ggtcaccgtc 360
tcctca 366

-continued

<210> SEQ ID NO 248
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 248

```
Glu Val Gln Leu Val Gln Ser Gly Ala Glu Val Lys Lys Pro Gly Asp
1               5                   10                  15

Ser Leu Arg Ile Ser Cys Gln Gly Ser Gly Tyr Ser Phe Thr Ser Tyr
            20                  25                  30

Tyr Ile Ser Trp Val Arg Gln Met Pro Gly Lys Gly Leu Glu Trp Met
        35                  40                  45

Gly Asn Ile Asp Pro Ser Asp Ser Tyr Thr Asn Tyr Ser Pro Ser Phe
    50                  55                  60

Gln Gly His Val Thr Met Ser Val Asp Lys Ser Ile Ser Thr Ala Tyr
65                  70                  75                  80

Leu Gln Trp Ser Ser Leu Lys Ala Ser Asp Ile Ala Ile Tyr Tyr Cys
                85                  90                  95

Val Arg His Gly Phe Ser Asn Ser Pro Arg Leu Trp Phe Asp Thr Trp
            100                 105                 110

Gly Gln Gly Thr Leu Val Thr Val Ser Ser
        115                 120
```

<210> SEQ ID NO 249
<211> LENGTH: 831
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 249

```
aattttatgc tgactcagcc ccactctgtg tcggagtctc cggggaagac ggtaaccatc     60

tcctgcaccc gcagcagtgg cagcattgcc agcaactatg tgcagtggta ccagcagcgc    120

ccgggcagtg cccccaccac tgtgatctat gaggataacc aaagaccctc tggggtccct    180

gatcggttct ctggctccat cgacagctcc tccaactctg cctccctcac catctctgga    240

ctgaagactg aggacgaggc tgattactac tgtcagtctt atgataccaa caattatggg    300

gttatattcg gcggagggac caagctgacc gtcctaggtt ctagaggtgg tggtggtagc    360

ggcggcggcg gctctggtgg tggtggatcc ctcgagatgg cccagatgca gctggtgcag    420

tctggggctg aggtgaagaa gcctggggcc tcagtgaagg tttcctgcaa gacatctgga    480

tacaccttca acaactacta tatgcactgg gtgcgacagg cccctggaca agggcttgag    540

tggatgggaa taatcaaccc tagtggtggt agcacaaact acgcacagaa gttccagggc    600

agagtcacca tgaccaggga cacgtccacg agcacagtct acatggagct gagcagcctg    660

agatctgagg acactgccgt gtattactgt gcgcgctctt tcgacaaaca ggacatcgat    720

tactggggtc aaggtactct ggtgaccgtc tcctcaacta gtggccaggc cggccagcac    780

catcaccatc accatggcgc atacccgtac gacgttccgg actacgcttc t             831
```

<210> SEQ ID NO 250
<211> LENGTH: 277
<212> TYPE: PRT

<213> ORGANISM: Artificial Sequence
<220> FEATURE:
<223> OTHER INFORMATION: Description of Artificial Sequence: Synthetic
polypeptide

<400> SEQUENCE: 250

```
Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ala Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Thr
                85                  90                  95

Asn Asn Tyr Gly Val Ile Phe Gly Gly Gly Thr Lys Leu Thr Val Leu
            100                 105                 110

Gly Ser Arg Gly Gly Gly Gly Ser Gly Gly Gly Gly Ser Gly Gly Gly
        115                 120                 125

Gly Ser Leu Glu Met Ala Gln Met Gln Leu Val Gln Ser Gly Ala Glu
    130                 135                 140

Val Lys Lys Pro Gly Ala Ser Val Lys Val Ser Cys Lys Thr Ser Gly
145                 150                 155                 160

Tyr Thr Phe Asn Asn Tyr Tyr Met His Trp Val Arg Gln Ala Pro Gly
                165                 170                 175

Gln Gly Leu Glu Trp Met Gly Ile Ile Asn Pro Ser Gly Gly Ser Thr
            180                 185                 190

Asn Tyr Ala Gln Lys Phe Gln Gly Arg Val Thr Met Thr Arg Asp Thr
        195                 200                 205

Ser Thr Ser Thr Val Tyr Met Glu Leu Ser Ser Leu Arg Ser Glu Asp
    210                 215                 220

Thr Ala Val Tyr Tyr Cys Ala Arg Ser Phe Asp Lys Gln Asp Ile Asp
225                 230                 235                 240

Tyr Trp Gly Gln Gly Thr Leu Val Thr Val Ser Ser Thr Ser Gly Gln
                245                 250                 255

Ala Gly Gln His His His His His His Gly Ala Tyr Pro Tyr Asp Val
            260                 265                 270

Pro Asp Tyr Ala Ser
        275
```

<210> SEQ ID NO 251
<211> LENGTH: 339
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 251

```
aattttatgc tgactcagcc ccactctgtg tcggagtctc cggggaagac ggtaaccatc     60

tcctgcaccc gcagcagtgg cagcattgcc agcaactatg tgcagtggta ccagcagcgc    120

ccgggcagtg cccccaccac tgtgatctat gaggataacc aaagaccctc tggggtccct    180

gatcggttct ctggctccat cgacagctcc tccaactctg cctccctcac catctctgga    240
```

ctgaagactg aggacgaggc tgattactac tgtcagtctt atgataccaa caattatggg 300
gttatattcg gcggagggac caagctgacc gtcctaggt 339

<210> SEQ ID NO 252
<211> LENGTH: 113
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 252

Asn Phe Met Leu Thr Gln Pro His Ser Val Ser Glu Ser Pro Gly Lys
1 5 10 15

Thr Val Thr Ile Ser Cys Thr Arg Ser Ser Gly Ser Ile Ala Ser Asn
20 25 30

Tyr Val Gln Trp Tyr Gln Gln Arg Pro Gly Ser Ala Pro Thr Thr Val
35 40 45

Ile Tyr Glu Asp Asn Gln Arg Pro Ser Gly Val Pro Asp Arg Phe Ser
50 55 60

Gly Ser Ile Asp Ser Ser Ser Asn Ser Ala Ser Leu Thr Ile Ser Gly
65 70 75 80

Leu Lys Thr Glu Asp Glu Ala Asp Tyr Tyr Cys Gln Ser Tyr Asp Thr
85 90 95

Asn Asn Tyr Gly Val Ile Phe Gly Gly Gly Thr Lys Leu Thr Val Leu
100 105 110

Gly

<210> SEQ ID NO 253
<211> LENGTH: 354
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 253
cagatgcagc tggtgcagtc tggggctgag gtgaagaagc ctggggcctc agtgaaggtt 60
tcctgcaaga catctggata caccttcaac aactactata tgcactgggt gcgacaggcc 120
cctggacaag ggcttgagtg gatgggaata atcaacccta gtggtggtag cacaaactac 180
gcacagaagt tccagggcag agtcaccatg accagggaca cgtccacgag cacagtctac 240
atggagctga gcagcctgag atctgaggac actgccgtgt attactgtgc gcgctctttc 300
gacaaacagg acatcgatta ctggggtcaa ggtactctgg tgaccgtctc ctca 354

<210> SEQ ID NO 254
<211> LENGTH: 118
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 254

Gln Met Gln Leu Val Gln Ser Gly Ala Glu Val Lys Lys Pro Gly Ala
1 5 10 15

Ser Val Lys Val Ser Cys Lys Thr Ser Gly Tyr Thr Phe Asn Asn Tyr
20 25 30

-continued

```
Tyr Met His Trp Val Arg Gln Ala Pro Gly Gln Gly Leu Glu Trp Met
        35                  40                  45

Gly Ile Ile Asn Pro Ser Gly Gly Ser Thr Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Phe Asp Lys Gln Asp Ile Asp Tyr Trp Gly Gln Gly Thr
            100                 105                 110

Leu Val Thr Val Ser Ser
        115
```

<210> SEQ ID NO 255
<211> LENGTH: 822
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 255

```
tcctatgagc tgactcagcc accctcggtg tcagtggccc caggacagac ggccagcatg     60

acctgtgggg gaaacaacat tggaagtaaa agtgtgcact ggtaccagca gaagccaagc    120

caggcccctg tgatggtcgt ccatgatgat agcgagcggc cctcagggat ccctgagcga    180

atctctggct ccaagtctgg gaacacggcc accctgacca tcagcagggt cgaagccggg    240

gatgaggccg actattactg tcaggtgtgg gatagtagta gtgatcatgt gatattcggc    300

ggagggacca agctgaccgt cctaggttct agaggtggtg gtggtagcgg cggcggcggc    360

tctggtggtg gtggatccct cgagatggcc caggtgcagc tggtgcaatc tggggctgag    420

gtgaagaagc cgggggcctc tgtgaaggtt tcctgcaagg catctggata caccttcacc    480

aactactata ttcactgggt gcgacaggcc cccggacaag ggcttgagtg gatgggaata    540

atcagaccta gtggtggtat cacaaactac gcacagaagt tccagggcag ggtcagcatg    600

accagagaca cgtccacgag cacagtctac atggagctga gcagcctgag atctgaggac    660

acggccgtgt attactgtgc gcgctcttgg atgtctgact cttactacga tggttggggt    720

caaggtactc tggtgaccgt ctcctcaact agtggccagg ccggccagca ccatcaccat    780

caccatggcg catacccgta cgacgttccg gactacgctt ct                       822
```

<210> SEQ ID NO 256
<211> LENGTH: 274
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 256

```
Ser Tyr Glu Leu Thr Gln Pro Pro Ser Val Ser Val Ala Pro Gly Gln
1               5                   10                  15

Thr Ala Ser Met Thr Cys Gly Gly Asn Asn Ile Gly Ser Lys Ser Val
            20                  25                  30

His Trp Tyr Gln Gln Lys Pro Ser Gln Ala Pro Val Met Val Val His
        35                  40                  45

Asp Asp Ser Glu Arg Pro Ser Gly Ile Pro Glu Arg Ile Ser Gly Ser
    50                  55                  60
```

Lys Ser Gly Asn Thr Ala Thr Leu Thr Ile Ser Arg Val Glu Ala Gly
65 70 75 80

Asp Glu Ala Asp Tyr Tyr Cys Gln Val Trp Asp Ser Ser Ser Asp His
85 90 95

Val Ile Phe Gly Gly Gly Thr Lys Leu Thr Val Leu Gly Ser Arg Gly
100 105 110

Gly Gly Gly Ser Gly Gly Gly Gly Ser Gly Gly Gly Gly Ser Leu Glu
115 120 125

Met Ala Gln Val Gln Leu Val Gln Ser Gly Ala Glu Val Lys Lys Pro
130 135 140

Gly Ala Ser Val Lys Val Ser Cys Lys Ala Ser Gly Tyr Thr Phe Thr
145 150 155 160

Asn Tyr Tyr Ile His Trp Val Arg Gln Ala Pro Gly Gln Gly Leu Glu
165 170 175

Trp Met Gly Ile Ile Arg Pro Ser Gly Gly Ile Thr Asn Tyr Ala Gln
180 185 190

Lys Phe Gln Gly Arg Val Ser Met Thr Arg Asp Thr Ser Thr Ser Thr
195 200 205

Val Tyr Met Glu Leu Ser Ser Leu Arg Ser Glu Asp Thr Ala Val Tyr
210 215 220

Tyr Cys Ala Arg Ser Trp Met Ser Asp Ser Tyr Tyr Asp Gly Trp Gly
225 230 235 240

Gln Gly Thr Leu Val Thr Val Ser Ser Thr Ser Gly Gln Ala Gly Gln
245 250 255

His His His His His His Gly Ala Tyr Pro Tyr Asp Val Pro Asp Tyr
260 265 270

Ala Ser

<210> SEQ ID NO 257
<211> LENGTH: 327
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 257
tcctatgagc tgactcagcc accctcggtg tcagtggccc caggacagac ggccagcatg 60
acctgtgggg gaaacaacat tggaagtaaa agtgtgcact ggtaccagca gaagccaagc 120
caggcccctg tgatggtcgt ccatgatgat agcgagcggc cctcagggat ccctgagcga 180
atctctggct ccaagtctgg gaacacggcc accctgacca tcagcagggt cgaagccggg 240
gatgaggccg actattactg tcaggtgtgg gatagtagta gtgatcatgt gatattcggc 300
ggagggacca agctgaccgt cctaggt 327

<210> SEQ ID NO 258
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 258

Ser Tyr Glu Leu Thr Gln Pro Pro Ser Val Ser Val Ala Pro Gly Gln
1 5 10 15

```
Thr Ala Ser Met Thr Cys Gly Gly Asn Asn Ile Gly Ser Lys Ser Val
            20                  25                  30

His Trp Tyr Gln Gln Lys Pro Ser Gln Ala Pro Val Met Val Val His
        35                  40                  45

Asp Asp Ser Glu Arg Pro Ser Gly Ile Pro Glu Arg Ile Ser Gly Ser
    50                  55                  60

Lys Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Ile Phe Gly Gly Gly Thr Lys Leu Thr Val Leu Gly
            100                 105
```

<210> SEQ ID NO 259
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 259

```
caggtgcagc tggtgcaatc tggggctgag gtgaagaagc cgggggcctc tgtgaaggtt      60

tcctgcaagg catctggata caccttcacc aactactata ttcactgggt gcgacaggcc     120

cccggacaag ggcttgagtg gatgggaata atcagaccta gtggtggtat cacaaactac     180

gcacagaagt tccagggcag ggtcagcatg accagagaca cgtccacgag cacagtctac     240

atggagctga gcagcctgag atctgaggac acggccgtgt attactgtgc gcgctcttgg     300

atgtctgact cttactacga tggttggggt caaggtactc tggtgaccgt ctcctca        357
```

<210> SEQ ID NO 260
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 260

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile His Trp Val Arg Gln Ala Pro Gly Gln Gly Leu Glu Trp Met
        35                  40                  45

Gly Ile Ile Arg Pro Ser Gly Gly Ile Thr Asn Tyr Ala Gln Lys Phe
    50                  55                  60

Gln Gly Arg Val Ser Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Trp Met Ser Asp Ser Tyr Tyr Asp Gly Trp Gly Gln Gly
            100                 105                 110

Thr Leu Val Thr Val Ser Ser
        115
```

<210> SEQ ID NO 261
<211> LENGTH: 822

<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 261

```
tcctatgagc tgactcagcc accctcggtg tcagtggctc caggacagac ggcctggatt     60

acctgtgggg gaaacaacat tggaagtaaa agtgtgcact ggtaccagca gaagccaggc    120

caggcccta tactggtcgt ctatgatgat agcgaccggc cctcagggat ccctgagaga    180

gtctctggct ccaactctgg gaacacggcc accctgacca tcagcagggt cgaagccggg    240

gatgaggccg actattactg tcaggtgtgg gatagtagta gtgatcgttg ggtgttcggc    300

ggagggacca agctgaccgt cctaggttct agaggtggtg gtggtagcgg cggcggcggc    360

tctggtggtg gtggatccct cgagatggcc cagatgcagc tggtgcagtc tggagctgag    420

gtgaagaagc ctggggcctc agtgaaggtc tcctgcaagg cttctggtta cacctttacc    480

aactatggta tcagctgggt gcgacaggcc cctggacaag ggcttgagtg gatgggatgg    540

atcagccctt acaatggtaa cacaaactac gcacagaagc tccagggcag agtcaccatg    600

accacagaca catccacgag cacagcctac atggagctga ggaacctgag atctgacgac    660

actgccgtgt attactgtgc gcgctactgg gactctggtt acgcttacga tgaatggggt    720

caaggtactc tggtgaccgt ctcctcaact agtggccagg ccggccagca ccatcaccat    780

caccatggcg catacccgta cgacgttccg gactacgctt ct                      822
```

<210> SEQ ID NO 262
<211> LENGTH: 274
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 262

```
Ser Tyr Glu Leu Thr Gln Pro Pro Ser Val Ser Val Ala Pro Gly Gln
1               5                   10                  15

Thr Ala Trp Ile Thr Cys Gly Gly Asn Asn Ile Gly Ser Lys Ser Val
            20                  25                  30

His Trp Tyr Gln Gln Lys Pro Gly Gln Ala Pro Ile Leu Val Val Tyr
        35                  40                  45

Asp Asp Ser Asp Arg Pro Ser Gly Ile Pro Glu Arg Val Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp Arg
                85                  90                  95

Trp Val Phe Gly Gly Gly Thr Lys Leu Thr Val Leu Gly Ser Arg Gly
            100                 105                 110

Gly Gly Gly Ser Gly Gly Gly Gly Ser Gly Gly Gly Gly Ser Leu Glu
        115                 120                 125

Met Ala Gln Met Gln Leu Val Gln Ser Gly Ala Glu Val Lys Lys Pro
    130                 135                 140

Gly Ala Ser Val Lys Val Ser Cys Lys Ala Ser Gly Tyr Thr Phe Thr
145                 150                 155                 160

Asn Tyr Gly Ile Ser Trp Val Arg Gln Ala Pro Gly Gln Gly Leu Glu
                165                 170                 175
```

```
Trp Met Gly Trp Ile Ser Pro Tyr Asn Gly Asn Thr Asn Tyr Ala Gln
            180                 185                 190

Lys Leu Gln Gly Arg Val Thr Met Thr Thr Asp Thr Ser Thr Ser Thr
        195                 200                 205

Ala Tyr Met Glu Leu Arg Asn Leu Arg Ser Asp Asp Thr Ala Val Tyr
    210                 215                 220

Tyr Cys Ala Arg Tyr Trp Asp Ser Gly Tyr Ala Tyr Asp Glu Trp Gly
225                 230                 235                 240

Gln Gly Thr Leu Val Thr Val Ser Ser Thr Ser Gly Gln Ala Gly Gln
                245                 250                 255

His His His His His His Gly Ala Tyr Pro Tyr Asp Val Pro Asp Tyr
            260                 265                 270

Ala Ser


<210> SEQ ID NO 263
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 263

tcctatgagc tgactcagcc accctcggtg tcagtggctc caggacagac ggcctggatt      60

acctgtgggg gaaacaacat tggaagtaaa agtgtgcact ggtaccagca gaagccaggc     120

caggcccta tactggtcgt ctatgatgat agcgaccggc cctcagggat ccctgagaga     180

gtctctggct ccaactctgg gaacacggcc accctgacca tcagcagggt cgaagccggg     240

gatgaggccg actattactg tcaggtgtgg gatagtagta gtgatcgttg ggtgttcggc     300

ggagggacca agctgaccgt cctaggt                                        327


<210> SEQ ID NO 264
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 264

Ser Tyr Glu Leu Thr Gln Pro Pro Ser Val Ser Val Ala Pro Gly Gln
1               5                   10                  15

Thr Ala Trp Ile Thr Cys Gly Gly Asn Asn Ile Gly Ser Lys Ser Val
            20                  25                  30

His Trp Tyr Gln Gln Lys Pro Gly Gln Ala Pro Ile Leu Val Val Tyr
        35                  40                  45

Asp Asp Ser Asp Arg Pro Ser Gly Ile Pro Glu Arg Val Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp Arg
                85                  90                  95

Trp Val Phe Gly Gly Gly Thr Lys Leu Thr Val Leu Gly
            100                 105


<210> SEQ ID NO 265
<211> LENGTH: 357
```

<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 265

```
cagatgcagc tggtgcagtc tggagctgag gtgaagaagc ctggggcctc agtgaaggtc     60

tcctgcaagg cttctggtta cacctttacc aactatggta tcagctgggt gcgacaggcc    120

cctggacaag ggcttgagtg gatgggatgg atcagccctt acaatggtaa cacaaactac    180

gcacagaagc tccagggcag agtcaccatg accacagaca catccacgag cacagcctac    240

atggagctga ggaacctgag atctgacgac actgccgtgt attactgtgc gcgctactgg    300

gactctggtt acgcttacga tgaatggggt caaggtactc tggtgaccgt ctcctca      357
```

<210> SEQ ID NO 266
<211> LENGTH: 119
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 266

```
Gln Met Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Ile Ser Trp Val Arg Gln Ala Pro Gly Gln Gly Leu Glu Trp Met
        35                  40                  45

Gly Trp Ile Ser Pro Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Asn Leu Arg Ser Asp Asp Thr Ala Val Tyr Tyr Cys
                85                  90                  95

Ala Arg Tyr Trp Asp Ser Gly Tyr Ala Tyr Asp Glu Trp Gly Gln Gly
            100                 105                 110

Thr Leu Val Thr Val Ser Ser
        115
```

<210> SEQ ID NO 267
<211> LENGTH: 834
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 267

```
caggctgtgc tgactcagcc gccctcagtg tctgcggccc caggacagaa ggtcaccatc     60

tcctgctctg gaagcagctc caacattggg aataattatg tatcctggta ccagcagctc    120

ccaggaacag cccccaaact cctcatttat gacaataata agcgaccctc cggtcttcct    180

gaccgattct ctggctccaa gtctggcacg tcagccaccc tgggcatcac cggactccag    240

actggggacg aggccgatta ttactgcgga acatgggata gcagcctgaa tgccgtggta    300

ttcggcggag ggacccagct caccgtttta agttctagag gtggtggtgg tagcggcggc    360

ggcggctctg gtggtggtgg atccctcgag atggcccagg tgcagctggt gcagtctggg    420
```

```
gctgaggtga agaagccggg ggcctctgtg aaggtttcct gcaaggcatc tggatacacc    480

ttcaccaact actatattca ctgggtgcga caggcccccg gacaagggct tgagtggatg    540

ggaataatca gacctagtgg tggtatcaca aactacgcac agaagttcca gggcagggtc    600

accatgacca gagacacgtc cacgagcaca gtctacatgg agctgagcag cctgagatct    660

gaggacacgg ccgtgtatta ctgtgcgcgc tcttggtcta acaaactgtc ttggtacaac    720

gatggttggg gtcaaggtac tctggtgacc gtctcctcaa ctagtggcca ggccggccag    780

caccatcacc atcaccatgg cgcatacccg tacgacgttc cggactacgc ttct          834


<210> SEQ ID NO 268
<211> LENGTH: 278
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 268

Gln Ala Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Leu Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Asn Ala Val Val Phe Gly Gly Gly Thr Gln Leu Thr Val Leu Ser Ser
            100                 105                 110

Arg Gly Gly Gly Gly Ser Gly Gly Gly Gly Ser Gly Gly Gly Gly Ser
        115                 120                 125

Leu Glu Met Ala Gln Val Gln Leu Val Gln Ser Gly Ala Glu Val Lys
    130                 135                 140

Lys Pro Gly Ala Ser Val Lys Val Ser Cys Lys Ala Ser Gly Tyr Thr
145                 150                 155                 160

Phe Thr Asn Tyr Tyr Ile His Trp Val Arg Gln Ala Pro Gly Gln Gly
                165                 170                 175

Leu Glu Trp Met Gly Ile Ile Arg Pro Ser Gly Gly Ile Thr Asn Tyr
            180                 185                 190

Ala Gln Lys Phe Gln Gly Arg Val Thr Met Thr Arg Asp Thr Ser Thr
        195                 200                 205

Ser Thr Val Tyr Met Glu Leu Ser Ser Leu Arg Ser Glu Asp Thr Ala
    210                 215                 220

Val Tyr Tyr Cys Ala Arg Ser Trp Ser Asn Lys Leu Ser Trp Tyr Asn
225                 230                 235                 240

Asp Gly Trp Gly Gln Gly Thr Leu Val Thr Val Ser Ser Thr Ser Gly
                245                 250                 255

Gln Ala Gly Gln His His His His His His Gly Ala Tyr Pro Tyr Asp
            260                 265                 270

Val Pro Asp Tyr Ala Ser
        275
```

<210> SEQ ID NO 269
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 269
caggctgtgc tgactcagcc gccctcagtg tctgcggccc caggacagaa ggtcaccatc 60
tcctgctctg gaagcagctc caacattggg aataattatg tatcctggta ccagcagctc 120
ccaggaacag cccccaaact cctcatttat gacaataata agcgaccctc cggtcttcct 180
gaccgattct ctggctccaa gtctggcacg tcagccaccc tgggcatcac cggactccag 240
actggggacg aggccgatta ttactgcgga acatgggata gcagcctgaa tgccgtggta 300
ttcggcggag ggacccagct caccgtttta agt 333

<210> SEQ ID NO 270
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 270

Gln Ala Val Leu Thr Gln Pro Pro Ser Val Ser Ala Ala Pro Gly Gln
1 5 10 15

Lys Val Thr Ile Ser Cys Ser Gly Ser Ser Ser Asn Ile Gly Asn Asn
20 25 30

Tyr Val Ser Trp Tyr Gln Gln Leu Pro Gly Thr Ala Pro Lys Leu Leu
35 40 45

Ile Tyr Asp Asn Asn Lys Arg Pro Ser Gly Leu Pro Asp Arg Phe Ser
50 55 60

Gly Ser Lys Ser Gly Thr Ser Ala Thr Leu Gly Ile Thr Gly Leu Gln
65 70 75 80

Thr Gly Asp Glu Ala Asp Tyr Tyr Cys Gly Thr Trp Asp Ser Ser Leu
85 90 95

Asn Ala Val Val Phe Gly Gly Gly Thr Gln Leu Thr Val Leu Ser
100 105 110

<210> SEQ ID NO 271
<211> LENGTH: 363
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 271
caggtgcagc tggtgcagtc tggggctgag gtgaagaagc cgggggcctc tgtgaaggtt 60
tcctgcaagg catctggata caccttcacc aactactata ttcactgggt gcgacaggcc 120
cccggacaag ggcttgagtg gatgggaata atcagaccta gtggtggtat cacaaactac 180
gcacagaagt tccagggcag ggtcaccatg accagagaca cgtccacgag cacagtctac 240
atggagctga gcagcctgag atctgaggac acggccgtgt attactgtgc gcgctcttgg 300
tctaacaaac tgtcttggta caacgatggt tggggtcaag gtactctggt gaccgtctcc 360
tca 363

<210> SEQ ID NO 272
<211> LENGTH: 121
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 272

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asn Tyr
20 25 30

Tyr Ile His Trp Val Arg Gln Ala Pro Gly Gln Gly Leu Glu Trp Met
35 40 45

Gly Ile Ile Arg Pro Ser Gly Gly Ile Thr Asn Tyr Ala Gln Lys Phe
50 55 60

Gln Gly Arg Val Thr Met Thr Arg Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Arg Ser Trp Ser Asn Lys Leu Ser Trp Tyr Asn Asp Gly Trp Gly
100 105 110

Gln Gly Thr Leu Val Thr Val Ser Ser
115 120

<210> SEQ ID NO 273
<211> LENGTH: 828
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 273
cagtctgtgt tgacgcagcc gccctcagtg tctgcggccc caggacagaa ggtcaccatc 60
tcctgctctg gaagcagctc caacattggg aataattatg tatcctggta ccagttcctc 120
ccaggaacag cccccaaact tctcatttat gacaataatc agcgaccctc aggcattcct 180
gaccgattct ctggcttcaa gtctggcacg tcagccaccc tggacatcac cggactccag 240
actggggacg aggccgatta ttactgcgga acatgggata acagcctgag tgctgcagtg 300
ttcggcagag ggaccaagct gaccgtccta ggttctagag gtggtggtgg tagcggcggc 360
ggcggctctg gtggtggtgg atccctcgag atggcccaga tgcagctggt gcagtctggg 420
actgaggtga agagggctgg ggcctcagtg aaggtttcct gcaaggcatc tggatacacc 480
ttcaccaact actatatgca ctgggtgcga caggcccctg gacaagggct tgagtggatg 540
ggaataatca accctagtgg tggtagcaca acctacgcac agaagttcca gggcagagtc 600
accatgacca gggacacgtc cacgagcaca gtctatatgg agctgagcga cctgggatct 660
gaggacacgg ccgtgtatta ctgtgcgcgc tcttggtcta aaactgaagg ttctgatcgt 720
tggggtcaag gtactctggt gaccgtctcc tcaactagtg gccaggccgg ccagcaccat 780
caccatcacc atggcgcata cccgtacgac gttccggact acgcttct 828

<210> SEQ ID NO 274
<211> LENGTH: 276

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 274

Gln Ser Val Leu Thr Gln Pro Pro Ser Val Ser Ala Ala Pro Gly Gln
1 5 10 15

Lys Val Thr Ile Ser Cys Ser Gly Ser Ser Ser Asn Ile Gly Asn Asn
20 25 30

Tyr Val Ser Trp Tyr Gln Phe Leu Pro Gly Thr Ala Pro Lys Leu Leu
35 40 45

Ile Tyr Asp Asn Asn Gln Arg Pro Ser Gly Ile Pro Asp Arg Phe Ser
50 55 60

Gly Phe Lys Ser Gly Thr Ser Ala Thr Leu Asp Ile Thr Gly Leu Gln
65 70 75 80

Thr Gly Asp Glu Ala Asp Tyr Tyr Cys Gly Thr Trp Asp Asn Ser Leu
85 90 95

Ser Ala Ala Val Phe Gly Arg Gly Thr Lys Leu Thr Val Leu Gly Ser
100 105 110

Arg Gly Gly Gly Gly Ser Gly Gly Gly Gly Ser Gly Gly Gly Gly Ser
115 120 125

Leu Glu Met Ala Gln Met Gln Leu Val Gln Ser Gly Thr Glu Val Lys
130 135 140

Arg Ala Gly Ala Ser Val Lys Val Ser Cys Lys Ala Ser Gly Tyr Thr
145 150 155 160

Phe Thr Asn Tyr Tyr Met His Trp Val Arg Gln Ala Pro Gly Gln Gly
165 170 175

Leu Glu Trp Met Gly Ile Ile Asn Pro Ser Gly Gly Ser Thr Thr Tyr
180 185 190

Ala Gln Lys Phe Gln Gly Arg Val Thr Met Thr Arg Asp Thr Ser Thr
195 200 205

Ser Thr Val Tyr Met Glu Leu Ser Asp Leu Gly Ser Glu Asp Thr Ala
210 215 220

Val Tyr Tyr Cys Ala Arg Ser Trp Ser Lys Thr Glu Gly Ser Asp Arg
225 230 235 240

Trp Gly Gln Gly Thr Leu Val Thr Val Ser Ser Thr Ser Gly Gln Ala
245 250 255

Gly Gln His His His His His His Gly Ala Tyr Pro Tyr Asp Val Pro
260 265 270

Asp Tyr Ala Ser
275

<210> SEQ ID NO 275
<211> LENGTH: 333
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 275
cagtctgtgt tgacgcagcc gccctcagtg tctgcggccc caggacagaa ggtcaccatc 60
tcctgctctg gaagcagctc caacattggg aataattatg tatcctggta ccagttcctc 120
ccaggaacag cccccaaact tctcatttat gacaataatc agcgaccctc aggcattcct 180
gaccgattct ctggcttcaa gtctggcacg tcagccaccc tggacatcac cggactccag 240
actggggacg aggccgatta ttactgcgga acatgggata acagcctgag tgctgcagtg 300
ttcggcagag ggaccaagct gaccgtccta ggt 333

<210> SEQ ID NO 276
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 276

Gln Ser Val Leu Thr Gln Pro Pro Ser Val Ser Ala Ala Pro Gly Gln
1 5 10 15

Lys Val Thr Ile Ser Cys Ser Gly Ser Ser Ser Asn Ile Gly Asn Asn
20 25 30

Tyr Val Ser Trp Tyr Gln Phe Leu Pro Gly Thr Ala Pro Lys Leu Leu
35 40 45

Ile Tyr Asp Asn Asn Gln Arg Pro Ser Gly Ile Pro Asp Arg Phe Ser
50 55 60

Gly Phe Lys Ser Gly Thr Ser Ala Thr Leu Asp Ile Thr Gly Leu Gln
65 70 75 80

Thr Gly Asp Glu Ala Asp Tyr Tyr Cys Gly Thr Trp Asp Asn Ser Leu
85 90 95

Ser Ala Ala Val Phe Gly Arg Gly Thr Lys Leu Thr Val Leu Gly
100 105 110

<210> SEQ ID NO 277
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 277
cagatgcagc tggtgcagtc tgggactgag gtgaagaggg ctggggcctc agtgaaggtt 60
tcctgcaagg catctggata caccttcacc aactactata tgcactgggt gcgacaggcc 120
cctggacaag ggcttgagtg gatgggaata atcaacccta gtggtggtag cacaacctac 180
gcacagaagt tccagggcag agtcaccatg accagggaca cgtccacgag cacagtctat 240
atggagctga gcgacctggg atctgaggac acggccgtgt attactgtgc gcgctcttgg 300
tctaaaactg aaggttctga tcgttggggt caaggtactc tggtgaccgt ctcctca 357

<210> SEQ ID NO 278
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 278

Gln Met Gln Leu Val Gln Ser Gly Thr Glu Val Lys Arg Ala Gly Ala
1 5 10 15

Ser Val Lys Val Ser Cys Lys Ala Ser Gly Tyr Thr Phe Thr Asn Tyr
20 25 30

Tyr Met His Trp Val Arg Gln Ala Pro Gly Gln Gly Leu Glu Trp Met

```
        35                  40                  45

Gly Ile Ile Asn Pro Ser Gly Gly Ser Thr Thr Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Asp Leu Gly Ser Glu Asp Thr Ala Val Tyr Tyr Cys
                85                  90                  95

Ala Arg Ser Trp Ser Lys Thr Glu Gly Ser Asp Arg Trp Gly Gln Gly
            100                 105                 110

Thr Leu Val Thr Val Ser Ser
        115
```

<210> SEQ ID NO 279
<211> LENGTH: 816
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 279

```
tcctatgtgc tgactcagcc accctcggtg tcagtggccc caggacagac ggccaggatc     60

acctgtgggg gaaccgacat cagacgtaaa actgtccact ggtaccagca gaagccaggc    120

ctggcccctg tgctggtcct ctatgatgat agcgaccggc cctcagggat ccctgagcga    180

ttctctggct ccaactctgg taacacggcc accctgacca tcagcagggt cgaaggcggg    240

gatgaggccg actattactg tcaggtgtgg gataacgata atgatcatta tgtctttgga    300

cctgggacca aggtcaccgt cctaggttct agaggtggtg gtggtagcgg cggcggcggc    360

tctggtggtg gtggatccct cgagatggcc gaggtccagc tggtgcagtc tggggctgag    420

gtgaagaagc ctggggcctc agtaaaggtc tcctgcaagg catctggata caccttcacc    480

aactactata tccactgggt gcgacagacc cctggagaag ggcttgagtg gatgggaata    540

atcagaccta gtggcggtaa cacaaactac gcacagaagt tccagggcag agtcaccatg    600

accagggaca cgtccacgcg cacggtctat atggagttga gtagcctgag atctgaggac    660

acggccgtgt attactgtgc gcgctcttgg gacactttct ctgatgaatg gggtcaaggt    720

actctggtga ccgtctcctc aactagtggc caggccggcc agcaccatca ccatcaccat    780

ggcgcatacc cgtacgacgt tccggactac gcttct                              816
```

<210> SEQ ID NO 280
<211> LENGTH: 272
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 280

```
Ser Tyr Val Leu Thr Gln Pro Pro Ser Val Ser Val Ala Pro Gly Gln
1               5                   10                  15

Thr Ala Arg Ile Thr Cys Gly Gly Thr Asp Ile Arg Arg Lys Thr Val
            20                  25                  30

His Trp Tyr Gln Gln Lys Pro Gly Leu Ala Pro Val Leu Val Leu Tyr
        35                  40                  45

Asp Asp Ser Asp Arg Pro Ser Gly Ile Pro Glu Arg Phe Ser Gly Ser
    50                  55                  60
```

```
Asn Ser Gly Asn Thr Ala Thr Leu Thr Ile Ser Arg Val Glu Gly Gly
65                  70                  75                  80

Asp Glu Ala Asp Tyr Tyr Cys Gln Val Trp Asp Asn Asp Asn Asp His
                85                  90                  95

Tyr Val Phe Gly Pro Gly Thr Lys Val Thr Val Leu Gly Ser Arg Gly
            100                 105                 110

Gly Gly Gly Ser Gly Gly Gly Gly Ser Gly Gly Gly Gly Ser Leu Glu
        115                 120                 125

Met Ala Glu Val Gln Leu Val Gln Ser Gly Ala Glu Val Lys Lys Pro
    130                 135                 140

Gly Ala Ser Val Lys Val Ser Cys Lys Ala Ser Gly Tyr Thr Phe Thr
145                 150                 155                 160

Asn Tyr Tyr Ile His Trp Val Arg Gln Thr Pro Gly Glu Gly Leu Glu
                165                 170                 175

Trp Met Gly Ile Ile Arg Pro Ser Gly Gly Asn Thr Asn Tyr Ala Gln
            180                 185                 190

Lys Phe Gln Gly Arg Val Thr Met Thr Arg Asp Thr Ser Thr Arg Thr
        195                 200                 205

Val Tyr Met Glu Leu Ser Ser Leu Arg Ser Glu Asp Thr Ala Val Tyr
    210                 215                 220

Tyr Cys Ala Arg Ser Trp Asp Thr Phe Ser Asp Glu Trp Gly Gln Gly
225                 230                 235                 240

Thr Leu Val Thr Val Ser Ser Thr Ser Gly Gln Ala Gly Gln His His
                245                 250                 255

His His His His Gly Ala Tyr Pro Tyr Asp Val Pro Asp Tyr Ala Ser
            260                 265                 270
```

<210> SEQ ID NO 281
<211> LENGTH: 327
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 281

```
tcctatgtgc tgactcagcc accctcggtg tcagtggccc caggacagac ggccaggatc      60

acctgtgggg gaaccgacat cagacgtaaa actgtccact ggtaccagca gaagccaggc     120

ctggcccctg tgctggtcct ctatgatgat agcgaccggc cctcagggat ccctgagcga     180

ttctctggct ccaactctgg taacacggcc accctgacca tcagcagggt cgaaggcggg     240

gatgaggccg actattactg tcaggtgtgg gataacgata atgatcatta tgtctttgga     300

cctgggacca aggtcaccgt cctaggt                                         327
```

<210> SEQ ID NO 282
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 282

```
Ser Tyr Val Leu Thr Gln Pro Pro Ser Val Ser Val Ala Pro Gly Gln
1               5                   10                  15

Thr Ala Arg Ile Thr Cys Gly Gly Thr Asp Ile Arg Arg Lys Thr Val
            20                  25                  30
```

```
His Trp Tyr Gln Gln Lys Pro Gly Leu Ala Pro Val Leu Val Leu Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Gly Gly
65                  70                  75                  80

Asp Glu Ala Asp Tyr Tyr Cys Gln Val Trp Asp Asn Asp Asn Asp His
                85                  90                  95

Tyr Val Phe Gly Pro Gly Thr Lys Val Thr Val Leu Gly
            100                 105


<210> SEQ ID NO 283
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 283

gaggtccagc tggtgcagtc tggggctgag gtgaagaagc ctggggcctc agtaaaggtc      60

tcctgcaagg catctggata caccttcacc aactactata tccactgggt gcgacagacc     120

cctggagaag ggcttgagtg gatgggaata atcagaccta gtggcggtaa cacaaactac     180

gcacagaagt tccagggcag agtcaccatg accagggaca cgtccacgcg cacggtctat     240

atggagttga gtagcctgag atctgaggac acggccgtgt attactgtgc gcgctcttgg     300

gacactttct ctgatgaatg gggtcaaggt actctggtga ccgtctcctc a              351


<210> SEQ ID NO 284
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 284

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile His Trp Val Arg Gln Thr Pro Gly Glu Gly Leu Glu Trp Met
        35                  40                  45

Gly Ile Ile Arg Pro Ser Gly Gly Asn Thr Asn Tyr Ala Gln Lys Phe
    50                  55                  60

Gln Gly Arg Val Thr Met Thr Arg Asp Thr Ser Thr Arg Thr Val Tyr
65                  70                  75                  80

Met Glu Leu Ser Ser Leu Arg Ser Glu Asp Thr Ala Val Tyr Tyr Cys
                85                  90                  95

Ala Arg Ser Trp Asp Thr Phe Ser Asp Glu Trp Gly Gln Gly Thr Leu
            100                 105                 110

Val Thr Val Ser Ser
        115


<210> SEQ ID NO 285
<211> LENGTH: 828
<212> TYPE: DNA
<213> ORGANISM: Artificial Sequence
<220> FEATURE:
```

<223> OTHER INFORMATION: Description of Artificial Sequence: Synthetic polynucleotide

<400> SEQUENCE: 285
cagtctgtgt tgacgcagcc gccctcagtg tctgcggccc caagacagaa ggtcaccatc 60
tcctgctctg gaagcagctc caacattggg aataattatg tatcctggta ccagcagctc 120
ccaggaacag cccccaaact cctcatttat gacgataata agcgaccctc agggattcct 180
gaccgattct ctggctccaa gtctggcacg tcagccaccc tgggcatcac cggactccag 240
actggggacg aggccgatta ttactgcgga acatgggata gcagcctgag tgctgtggta 300
ttcggcggag ggaccaagct gaccgtccta ggttctagag gtggtggtgg tagcggcggc 360
ggcggctctg gtggtggtgg atccctcgag atggcccagg tgcagctggt gcagtctggg 420
actgaggtga agagggctgg ggcctcagtg aaggtttcct gcaaggcatc tggatacacc 480
ttcaccaact actatatgca ctgggtgcga caggcccctg gacaagggct ggaatggatg 540
ggaataatca accctagtat tggtagcaca aactacgcac agaagttcca gggcagagtc 600
accatgacca gagacacgtc cacgagcaca gtcttcatgg aactgagcag cctcagatct 660
gacgacacgg ccgtgtatta ctgtgcgcgc tctttcggtg actctgacgg tgctgattct 720
tggggtcaag gtactctggt gaccgtctcc tcaactagtg gccaggccgg ccagcaccat 780
caccatcacc atggcgcata cccgtacgac gttccggact acgcttct 828

<210> SEQ ID NO 286
<211> LENGTH: 276
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 286

Gln Ser Val Leu Thr Gln Pro Pro Ser Val Ser Ala Ala Pro Arg Gln
1 5 10 15

Lys Val Thr Ile Ser Cys Ser Gly Ser Ser Ser Asn Ile Gly Asn Asn
20 25 30

Tyr Val Ser Trp Tyr Gln Gln Leu Pro Gly Thr Ala Pro Lys Leu Leu
35 40 45

Ile Tyr Asp Asp Asn Lys Arg Pro Ser Gly Ile Pro Asp Arg Phe Ser
50 55 60

Gly Ser Lys Ser Gly Thr Ser Ala Thr Leu Gly Ile Thr Gly Leu Gln
65 70 75 80

Thr Gly Asp Glu Ala Asp Tyr Tyr Cys Gly Thr Trp Asp Ser Ser Leu
85 90 95

Ser Ala Val Val Phe Gly Gly Gly Thr Lys Leu Thr Val Leu Gly Ser
100 105 110

Arg Gly Gly Gly Gly Ser Gly Gly Gly Gly Ser Gly Gly Gly Gly Ser
115 120 125

Leu Glu Met Ala Gln Val Gln Leu Val Gln Ser Gly Thr Glu Val Lys
130 135 140

Arg Ala Gly Ala Ser Val Lys Val Ser Cys Lys Ala Ser Gly Tyr Thr
145 150 155 160

Phe Thr Asn Tyr Tyr Met His Trp Val Arg Gln Ala Pro Gly Gln Gly
165 170 175

Leu Glu Trp Met Gly Ile Ile Asn Pro Ser Ile Gly Ser Thr Asn Tyr
180 185 190

```
Ala Gln Lys Phe Gln Gly Arg Val Thr Met Thr Arg Asp Thr Ser Thr
        195                 200                 205

Ser Thr Val Phe Met Glu Leu Ser Ser Leu Arg Ser Asp Asp Thr Ala
    210                 215                 220

Val Tyr Tyr Cys Ala Arg Ser Phe Gly Asp Ser Asp Gly Ala Asp Ser
225                 230                 235                 240

Trp Gly Gln Gly Thr Leu Val Thr Val Ser Ser Thr Ser Gly Gln Ala
                245                 250                 255

Gly Gln His His His His His His Gly Ala Tyr Pro Tyr Asp Val Pro
            260                 265                 270

Asp Tyr Ala Ser
        275
```

<210> SEQ ID NO 287
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 287

```
cagtctgtgt tgacgcagcc gccctcagtg tctgcggccc caagacagaa ggtcaccatc     60

tcctgctctg gaagcagctc caacattggg aataattatg tatcctggta ccagcagctc    120

ccaggaacag cccccaaact cctcatttat gacgataata agcgaccctc agggattcct    180

gaccgattct ctggctccaa gtctggcacg tcagccaccc tgggcatcac cggactccag    240

actggggacg aggccgatta ttactgcgga acatgggata gcagcctgag tgctgtggta    300

ttcggcggag ggaccaagct gaccgtccta ggt                                 333
```

<210> SEQ ID NO 288
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 288

```
Gln Ser Val Leu Thr Gln Pro Pro Ser Val Ser Ala Ala Pro Arg Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asp Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Val Val Phe Gly Gly Gly Thr Lys Leu Thr Val Leu Gly
            100                 105                 110
```

<210> SEQ ID NO 289
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 289
caggtgcagc tggtgcagtc tgggactgag gtgaagaggg ctggggcctc agtgaaggtt 60
tcctgcaagg catctggata caccttcacc aactactata tgcactgggt gcgacaggcc 120
cctggacaag ggctggaatg gatgggaata atcaacccta gtattggtag cacaaactac 180
gcacagaagt tccagggcag agtcaccatg accagagaca cgtccacgag cacagtcttc 240
atggaactga gcagcctcag atctgacgac acggccgtgt attactgtgc gcgctctttc 300
ggtgactctg acggtgctga ttcttggggt caaggtactc tggtgaccgt ctcctca 357

<210> SEQ ID NO 290
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 290

Gln Val Gln Leu Val Gln Ser Gly Thr Glu Val Lys Arg Ala Gly Ala
1 5 10 15

Ser Val Lys Val Ser Cys Lys Ala Ser Gly Tyr Thr Phe Thr Asn Tyr
20 25 30

Tyr Met His Trp Val Arg Gln Ala Pro Gly Gln Gly Leu Glu Trp Met
35 40 45

Gly Ile Ile Asn Pro Ser Ile Gly Ser Thr Asn Tyr Ala Gln Lys Phe
50 55 60

Gln Gly Arg Val Thr Met Thr Arg Asp Thr Ser Thr Ser Thr Val Phe
65 70 75 80

Met Glu Leu Ser Ser Leu Arg Ser Asp Asp Thr Ala Val Tyr Tyr Cys
85 90 95

Ala Arg Ser Phe Gly Asp Ser Asp Gly Ala Asp Ser Trp Gly Gln Gly
100 105 110

Thr Leu Val Thr Val Ser Ser
115

<210> SEQ ID NO 291
<211> LENGTH: 822
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 291
tcctatgtgc tgactcagcc accctcggtg tcagtggccc caggacagac ggccaggatg 60
acctgtgaag gaagcaacct tggaagtaaa agtgtgcatt ggtaccagca gaagccaggc 120
caggcccctg tgctggtcgt ccatgatgat agcgaccggc cctcagggat ccctgaccga 180
ttctctggct ccaagtctgg gaacacggcc accctgacca tcagcagggt cgaagccggg 240
gatgaggccg actattactg tcaggtgtgg catagtagta gtgatcatta tgtcttcgga 300
actgcgacca aggtcaccgt cctaggttct agaggtggtg gtggtagcgg cggcggcggc 360
tctggtggtg gtggatccct cgagatggcc caggtgcagc tggtgcaatc tggggctgag 420
gtgaagaagc ctggggcctc tgtgaaggtt tcctgcaagg catctggata caccttcacc 480
aattactata ttcactgggt gcgacaggcc cccggacaag ggcttgagtg gatgggaata 540
atcagaccta gtggtggtat cacaaactac gcacagaagt tccagggcag ggtcagcatg 600
accagggaca cgtccacgag cacagtctac atggagctga gcagcctgag atctgaggac 660
actgccgtgt attactgtgc gcgctcttgg catgaaaact ctggtgttga ttcttggggt 720
caaggtactc tggtgaccgt ctcctcaact agtggccagg ccggccagca ccatcaccat 780
caccatggcg catacccgta cgacgttccg gactacgctt ct 822

<210> SEQ ID NO 292
<211> LENGTH: 279
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 292

Gln Ser Val Leu Thr Gln Pro Pro Ser Val Ser Val Ala Pro Gly Lys
1 5 10 15

Thr Ala Arg Ile Thr Cys Gly Gly Asn Asn Ile Gly Ser Lys Ser Val
20 25 30

His Trp Tyr Gln Gln Lys Pro Gly Gln Ala Pro Val Leu Val Ile Tyr
35 40 45

Tyr Asp Ser Asp Arg Pro Ser Gly Ile Pro Glu Arg Phe Ser Gly Ser
50 55 60

Asn Ser Gly Asn Thr Ala Thr Leu Thr Ile Ser Arg Val Glu Ala Gly
65 70 75 80

Asp Glu Ala Asp Tyr Tyr Cys Gln Val Trp Asp Ser Ser Ser Asp His
85 90 95

Tyr Val Phe Gly Thr Gly Thr Lys Val Thr Val Leu Gly Ser Arg Gly
100 105 110

Gly Gly Gly Ser Gly Gly Gly Gly Ser Gly Gly Gly Gly Ser Leu Glu
115 120 125

Met Ala Glu Val Gln Leu Val Glu Ser Gly Gly Gly Val Val Gln Pro
130 135 140

Gly Arg Ser Leu Arg Leu Ser Cys Ala Ala Ser Gly Phe Thr Phe Asn
145 150 155 160

Asn His Ala Met His Trp Val Arg Gln Ala Pro Gly Lys Gly Leu Glu
165 170 175

Trp Val Ala Val Ile Ser Phe Asp Gly Asp Asp Lys Phe Tyr Ala Asp
180 185 190

Ser Val Lys Gly Arg Phe Thr Ile Ser Arg Asp Asn Ser Arg Asn Thr
195 200 205

Leu Phe Leu Gln Met Asn Asn Leu Arg Pro Glu Asp Thr Ala Val Tyr
210 215 220

Tyr Cys Ser Arg Asp Pro Tyr His Phe Ala Ser Gly Ser Tyr Ser Tyr
225 230 235 240

Phe Asp Tyr Trp Gly Gln Gly Thr Leu Val Thr Val Ser Ser Thr Ser
245 250 255

Gly Gln Ala Gly Gln His His His His His His Gly Ala Tyr Pro Tyr
260 265 270

Asp Val Pro Asp Tyr Ala Ser
275

<210> SEQ ID NO 293
<211> LENGTH: 327
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 293
tcctatgtgc tgactcagcc accctcggtg tcagtggccc caggacagac ggccaggatg 60
acctgtgaag gaagcaacct tggaagtaaa agtgtgcatt ggtaccagca gaagccaggc 120
caggcccctg tgctggtcgt ccatgatgat agcgaccggc cctcagggat ccctgaccga 180
ttctctggct ccaagtctgg gaacacggcc accctgacca tcagcagggt cgaagccggg 240
gatgaggccg actattactg tcaggtgtgg catagtagta gtgatcatta tgtcttcgga 300
actgcgacca aggtcaccgt cctaggt 327

<210> SEQ ID NO 294
<211> LENGTH: 109
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 294

Gln Ser Val Leu Thr Gln Pro Pro Ser Val Ser Val Ala Pro Gly Lys
1 5 10 15

Thr Ala Arg Ile Thr Cys Gly Gly Asn Asn Ile Gly Ser Lys Ser Val
20 25 30

His Trp Tyr Gln Gln Lys Pro Gly Gln Ala Pro Val Leu Val Ile Tyr
35 40 45

Tyr Asp Ser Asp Arg Pro Ser Gly Ile Pro Glu Arg Phe Ser Gly Ser
50 55 60

Asn Ser Gly Asn Thr Ala Thr Leu Thr Ile Ser Arg Val Glu Ala Gly
65 70 75 80

Asp Glu Ala Asp Tyr Tyr Cys Gln Val Trp Asp Ser Ser Ser Asp His
85 90 95

Tyr Val Phe Gly Thr Gly Thr Lys Val Thr Val Leu Gly
100 105

<210> SEQ ID NO 295
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 295
caggtgcagc tggtgcaatc tggggctgag gtgaagaagc ctggggcctc tgtgaaggtt 60
tcctgcaagg catctggata caccttcacc aattactata ttcactgggt gcgacaggcc 120
cccggacaag ggcttgagtg gatgggaata atcagaccta gtggtggtat cacaaactac 180
gcacagaagt tccagggcag ggtcagcatg accagggaca cgtccacgag cacagtctac 240
atggagctga gcagcctgag atctgaggac actgccgtgt attactgtgc gcgctcttgg 300
catgaaaact ctggtgttga ttcttggggt caaggtactc tggtgaccgt ctcctca 357

<210> SEQ ID NO 296

<211> LENGTH: 124
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 296

Glu Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Asn Asn His
20 25 30

Ala Met His Trp Val Arg Gln Ala Pro Gly Lys Gly Leu Glu Trp Val
35 40 45

Ala Val Ile Ser Phe Asp Gly Asp Asp Lys Phe Tyr Ala Asp Ser Val
50 55 60

Lys Gly Arg Phe Thr Ile Ser Arg Asp Asn Ser Arg Asn Thr Leu Phe
65 70 75 80

Leu Gln Met Asn Asn Leu Arg Pro Glu Asp Thr Ala Val Tyr Tyr Cys
85 90 95

Ser Arg Asp Pro Tyr His Phe Ala Ser Gly Ser Tyr Ser Tyr Phe Asp
100 105 110

Tyr Trp Gly Gln Gly Thr Leu Val Thr Val Ser Ser
115 120

<210> SEQ ID NO 297
<211> LENGTH: 831
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 297
caatctgccc tgactcagcc tccctccgcg tccgggtctc ctggacagtc agtcaccatc 60
tcctgcactg gaaccagcag tgacgttggt gcttataact atgtctcctg gtaccaacac 120
tacccaggca aagcccccaa actcatgatt tatgaggtca gtgagcggcc ctcaggggtc 180
cctgatcgct tctctggctc caagtctggc aacacggcct ccctgaccgt ctctgggctc 240
caggctgagg atgaggctga ttatttctgc agctcatatg cgggcagcaa caattttgtc 300
ttcggaactg ggaccaaggt caccgtccta ggttctagag gtggtggtgg tagcggcggc 360
ggcggctctg gtggtggtgg atccctcgag atggccgagg tccagctggt gcagtctggg 420
gctgaggtga agaagcctgg gtcctcggtg aaggtctcct gcaaggcttc tggaggcacc 480
ttcagcagct atgctatcag ctgggtgcga caggcccctg gacaagggct tgagtggatg 540
ggaaggatca tccctatcct tggtatagca aactacgcac agaagttcca gggcagagtc 600
acgattaccg cggacaaatc ctcgagcaca gcctacatgg cgctgagcag cctgacatct 660
gaggacacgg ccgtgtatta ctgtgcgaga gggggtgact acgtcgagtc ctggttcgac 720
ccctggggcc agggaaccct ggtcaccgtc tcctcaacta gtggccaggc cggccagcac 780
catcaccatc accatggcgc atacccgtac gacgttccgg actacgcttc t 831

<210> SEQ ID NO 298
<211> LENGTH: 277
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 298

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Ala Tyr
            20                  25                  30

Asn Tyr Val Ser Trp Tyr Gln His Tyr Pro Gly Lys Ala Pro Lys Leu
        35                  40                  45

Met Ile Tyr Glu Val Ser Glu Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Phe Cys Ser Ser Tyr Ala Gly Ser
                85                  90                  95

Asn Asn Phe Val Phe Gly Thr Gly Thr Lys Val Thr Val Leu Gly Ser
            100                 105                 110

Arg Gly Gly Gly Gly Ser Gly Gly Gly Gly Ser Gly Gly Gly Gly Ser
        115                 120                 125

Leu Glu Met Ala Glu Val Gln Leu Val Gln Ser Gly Ala Glu Val Lys
    130                 135                 140

Lys Pro Gly Ser Ser Val Lys Val Ser Cys Lys Ala Ser Gly Gly Thr
145                 150                 155                 160

Phe Ser Ser Tyr Ala Ile Ser Trp Val Arg Gln Ala Pro Gly Gln Gly
                165                 170                 175

Leu Glu Trp Met Gly Arg Ile Ile Pro Ile Leu Gly Ile Ala Asn Tyr
            180                 185                 190

Ala Gln Lys Phe Gln Gly Arg Val Thr Ile Thr Ala Asp Lys Ser Ser
        195                 200                 205

Ser Thr Ala Tyr Met Ala Leu Ser Ser Leu Thr Ser Glu Asp Thr Ala
    210                 215                 220

Val Tyr Tyr Cys Ala Arg Gly Gly Asp Tyr Val Glu Ser Trp Phe Asp
225                 230                 235                 240

Pro Trp Gly Gln Gly Thr Leu Val Thr Val Ser Ser Thr Ser Gly Gln
                245                 250                 255

Ala Gly Gln His His His His His His Gly Ala Tyr Pro Tyr Asp Val
            260                 265                 270

Pro Asp Tyr Ala Ser
        275

<210> SEQ ID NO 299
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 299
caatctgccc tgactcagcc tccctccgcg tccgggtctc ctggacagtc agtcaccatc     60
tcctgcactg gaaccagcag tgacgttggt gcttataact atgtctcctg gtaccaacac    120
tacccaggca aagcccccaa actcatgatt tatgaggtca gtgagcggcc ctcaggggtc    180
cctgatcgct tctctggctc caagtctggc aacacggcct ccctgaccgt ctctgggctc    240
caggctgagg atgaggctga ttatttctgc agctcatatg cgggcagcaa caattttgtc    300
ttcggaactg ggaccaaggt caccgtccta ggt 333

<210> SEQ ID NO 300
<211> LENGTH: 111
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 300

Gln Ser Ala Leu Thr Gln Pro Pro Ser Ala Ser Gly Ser Pro Gly Gln
1 5 10 15

Ser Val Thr Ile Ser Cys Thr Gly Thr Ser Ser Asp Val Gly Ala Tyr
20 25 30

Asn Tyr Val Ser Trp Tyr Gln His Tyr Pro Gly Lys Ala Pro Lys Leu
35 40 45

Met Ile Tyr Glu Val Ser Glu Arg Pro Ser Gly Val Pro Asp Arg Phe
50 55 60

Ser Gly Ser Lys Ser Gly Asn Thr Ala Ser Leu Thr Val Ser Gly Leu
65 70 75 80

Gln Ala Glu Asp Glu Ala Asp Tyr Phe Cys Ser Ser Tyr Ala Gly Ser
85 90 95

Asn Asn Phe Val Phe Gly Thr Gly Thr Lys Val Thr Val Leu Gly
100 105 110

<210> SEQ ID NO 301
<211> LENGTH: 360
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 301
gaggtccagc tggtgcagtc tggggctgag gtgaagaagc ctgggtcctc ggtgaaggtc 60
tcctgcaagg cttctggagg caccttcagc agctatgcta tcagctgggt gcgacaggcc 120
cctggacaag ggcttgagtg gatgggaagg atcatcccta tccttggtat agcaaactac 180
gcacagaagt tccagggcag agtcacgatt accgcggaca aatcctcgag cacagcctac 240
atggcgctga gcagcctgac atctgaggac acggccgtgt attactgtgc gagagggggt 300
gactacgtcg agtcctggtt cgacccctgg ggccagggaa ccctggtcac cgtctcctca 360

<210> SEQ ID NO 302
<211> LENGTH: 120
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 302

Glu Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Arg Ile Ile Pro Ile Leu Gly Ile Ala Asn Tyr Ala Gln Lys Phe
50 55 60

```
Gln Gly Arg Val Thr Ile Thr Ala Asp Lys Ser Ser Ser Thr Ala Tyr
65                  70                  75                  80

Met Ala Leu Ser Ser Leu Thr Ser Glu Asp Thr Ala Val Tyr Tyr Cys
                85                  90                  95

Ala Arg Gly Gly Asp Tyr Val Glu Ser Trp Phe Asp Pro Trp Gly Gln
            100                 105                 110

Gly Thr Leu Val Thr Val Ser Ser
        115                 120


<210> SEQ ID NO 303
<211> LENGTH: 831
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 303

caatctgccc tgactcagcc tgcctccgtg tctgggtctc ctggacagtc gatcaccatc     60

tcctgcactg gacccaccag tgactttaat gattatctct ttgtctcctg gtaccaacaa    120

cacccaggca aagcccccaa actcatcctt tatgatgtca ctcatcggcc ctcaggggtt    180

tctggtcgct tctctggctc caagtctgcc agcacggcct ccctgaccat ctctgggctc    240

caggctgagg acgaggctga ttatttctgc ggctcaaaaa caggcaggac cacttatgtc    300

ttcggaactg ggaccaaggt caccgtccta ggttctagag gtggtggtgg tagcggcggc    360

ggcggctctg gtggtggtgg atccctcgag atggcccagg tgcagctggt gcaatctgga    420

gctgaggtga agaagcctgg ggcctcagta aaggtctcct gcaaggcttc tggttacacc    480

tttgacaact ttggtatcag ctgggtgcga caggcccctg gacaagggct tgagtggatg    540

ggatggatca acacttacga tggttacaca aactatgtag agaaactcca gggcagagtc    600

accatgacca cagacacatc cacgggcaca gcctacatgg agctgagggg cctgagatct    660

gacgacacgg ccgtgtatta ctgtgcgcgc tctgttccgc atcagatctc ttacggtgat    720

ctgtggggtc aaggtactct ggtgaccgtc tcctcaacta gtggccaggc cggccagcac    780

catcaccatc accatggcgc atacccgtac gacgttccgg actacgcttc t             831


<210> SEQ ID NO 304
<211> LENGTH: 277
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 304

Gln Ser Ala Leu Thr Gln Pro Ala Ser Val Ser Gly Ser Pro Gly Gln
1               5                   10                  15

Ser Ile Thr Ile Ser Cys Thr Gly Pro Thr Ser Asp Phe Asn Asp Tyr
            20                  25                  30

Leu Phe Val Ser Trp Tyr Gln Gln His Pro Gly Lys Ala Pro Lys Leu
        35                  40                  45

Ile Leu Tyr Asp Val Thr His Arg Pro Ser Gly Val Ser Gly Arg Phe
    50                  55                  60

Ser Gly Ser Lys Ser Ala Ser Thr Ala Ser Leu Thr Ile Ser Gly Leu
65                  70                  75                  80

Gln Ala Glu Asp Glu Ala Asp Tyr Phe Cys Gly Ser Lys Thr Gly Arg
```

```
                85                  90                  95

Thr Thr Tyr Val Phe Gly Thr Gly Thr Lys Val Thr Val Leu Gly Ser
            100                 105                 110

Arg Gly Gly Gly Gly Ser Gly Gly Gly Gly Ser Gly Gly Gly Gly Ser
        115                 120                 125

Leu Glu Met Ala Gln Val Gln Leu Val Gln Ser Gly Ala Glu Val Lys
    130                 135                 140

Lys Pro Gly Ala Ser Val Lys Val Ser Cys Lys Ala Ser Gly Tyr Thr
145                 150                 155                 160

Phe Asp Asn Phe Gly Ile Ser Trp Val Arg Gln Ala Pro Gly Gln Gly
                165                 170                 175

Leu Glu Trp Met Gly Trp Ile Asn Thr Tyr Asp Gly Tyr Thr Asn Tyr
            180                 185                 190

Val Glu Lys Leu Gln Gly Arg Val Thr Met Thr Thr Asp Thr Ser Thr
        195                 200                 205

Gly Thr Ala Tyr Met Glu Leu Arg Gly Leu Arg Ser Asp Asp Thr Ala
    210                 215                 220

Val Tyr Tyr Cys Ala Arg Ser Val Pro His Gln Ile Ser Tyr Gly Asp
225                 230                 235                 240

Leu Trp Gly Gln Gly Thr Leu Val Thr Val Ser Ser Thr Ser Gly Gln
                245                 250                 255

Ala Gly Gln His His His His His His Gly Ala Tyr Pro Tyr Asp Val
            260                 265                 270

Pro Asp Tyr Ala Ser
        275


<210> SEQ ID NO 305
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 305

caatctgccc tgactcagcc tgcctccgtg tctgggtctc ctggacagtc gatcaccatc      60

tcctgcactg gacccaccag tgactttaat gattatctct ttgtctcctg gtaccaacaa     120

cacccaggca aagcccccaa actcatcctt tatgatgtca ctcatcggcc ctcaggggtt     180

tctggtcgct tctctggctc caagtctgcc agcacggcct ccctgaccat ctctgggctc     240

caggctgagg acgaggctga ttatttctgc ggctcaaaaa caggcaggac cacttatgtc     300

ttcggaactg ggaccaaggt caccgtccta ggt                                  333


<210> SEQ ID NO 306
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 306

Gln Ser Ala Leu Thr Gln Pro Ala Ser Val Ser Gly Ser Pro Gly Gln
1               5                   10                  15

Ser Ile Thr Ile Ser Cys Thr Gly Pro Thr Ser Asp Phe Asn Asp Tyr
            20                  25                  30

Leu Phe Val Ser Trp Tyr Gln Gln His Pro Gly Lys Ala Pro Lys Leu
```

```
        35                  40                  45

Ile Leu Tyr Asp Val Thr His Arg Pro Ser Gly Val Ser Gly Arg Phe
    50                  55                  60

Ser Gly Ser Lys Ser Ala Ser Thr Ala Ser Leu Thr Ile Ser Gly Leu
65                  70                  75                  80

Gln Ala Glu Asp Glu Ala Asp Tyr Phe Cys Gly Ser Lys Thr Gly Arg
                85                  90                  95

Thr Thr Tyr Val Phe Gly Thr Gly Thr Lys Val Thr Val Leu Gly
            100                 105                 110


<210> SEQ ID NO 307
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 307

caggtgcagc tggtgcaatc tggagctgag gtgaagaagc ctggggcctc agtaaaggtc     60

tcctgcaagg cttctggtta cacctttgac aactttggta tcagctgggt gcgacaggcc    120

cctggacaag ggcttgagtg gatgggatgg atcaacactt acgatggtta cacaaactat    180

gtagagaaac tccagggcag agtcaccatg accacagaca catccacggg cacagcctac    240

atggagctga ggggcctgag atctgacgac acggccgtgt attactgtgc gcgctctgtt    300

ccgcatcaga tctcttacgg tgatctgtgg ggtcaaggta ctctggtgac cgtctcctca    360


<210> SEQ ID NO 308
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 308

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asp Asn Phe
            20                  25                  30

Gly Ile Ser Trp Val Arg Gln Ala Pro Gly Gln Gly Leu Glu Trp Met
        35                  40                  45

Gly Trp Ile Asn Thr Tyr Asp Gly Tyr Thr Asn Tyr Val Glu Lys Leu
    50                  55                  60

Gln Gly Arg Val Thr Met Thr Thr Asp Thr Ser Thr Gly Thr Ala Tyr
65                  70                  75                  80

Met Glu Leu Arg Gly Leu Arg Ser Asp Asp Thr Ala Val Tyr Tyr Cys
                85                  90                  95

Ala Arg Ser Val Pro His Gln Ile Ser Tyr Gly Asp Leu Trp Gly Gln
            100                 105                 110

Gly Thr Leu Val Thr Val Ser Ser
        115                 120


<210> SEQ ID NO 309
<211> LENGTH: 819
<212> TYPE: DNA
<213> ORGANISM: Artificial Sequence
<220> FEATURE:
<223> OTHER INFORMATION: Description of Artificial Sequence: Synthetic
```

polynucleotide

<400> SEQUENCE: 309
cagcctgtgc tgactcagcc accctcagtg tcagtggccc caggaaagac ggccaggatt 60
acctgtgggg gaaacaacat tggaagtaaa agtgtgcact ggtaccagca gaagccaggc 120
caggcccctg tgctggtcat ctattatgat agcgaccggc cctcagggat ccctgagcga 180
ttctctggct ccaactctgg gaacacggcc accctgacca tcagcagggt cgaagccggg 240
gatgaggccg actattactg tcaggtgtgg gatagtagta gtgatcatcc ggtattcggc 300
ggagggacca agctgaccgt cctaggttct agaggtggtg gtggtagcgg cggcggcggc 360
tctggtggtg gtggatccct cgagatggcc caggtgcagc tggtgcagtc tggggctgag 420
gtgaagaagc ctgggtcctc ggtgaaggtc tcctgcaagg cttctggagg caccttcagc 480
agctatgcta tcagctgggt gcgacaggcc cctggacaag ggcttgagtg gatgggaggg 540
atcatcccta tctttggtac agcaaactac gcacagaagt tccagggcag agtcacgatt 600
accgcggacg aatccacgag cacagcctac atggagctga gcagcctgag atctgaggac 660
acggccgtgt attactgtgc gcgctcttct tactggtgga cttctgatcg ttggggtcaa 720
ggtactctgg tgaccgtctc ctcaactagt ggccaggccg gccagcacca tcaccatcac 780
catggcgcat acccgtacga cgttccggac tacgcttct 819

<210> SEQ ID NO 310
<211> LENGTH: 273
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 310

Gln Pro Val Leu Thr Gln Pro Pro Ser Val Ser Val Ala Pro Gly Lys
1 5 10 15

Thr Ala Arg Ile Thr Cys Gly Gly Asn Asn Ile Gly Ser Lys Ser Val
20 25 30

His Trp Tyr Gln Gln Lys Pro Gly Gln Ala Pro Val Leu Val Ile Tyr
35 40 45

Tyr Asp Ser Asp Arg Pro Ser Gly Ile Pro Glu Arg Phe Ser Gly Ser
50 55 60

Asn Ser Gly Asn Thr Ala Thr Leu Thr Ile Ser Arg Val Glu Ala Gly
65 70 75 80

Asp Glu Ala Asp Tyr Tyr Cys Gln Val Trp Asp Ser Ser Ser Asp His
85 90 95

Pro Val Phe Gly Gly Gly Thr Lys Leu Thr Val Leu Gly Ser Arg Gly
100 105 110

Gly Gly Gly Ser Gly Gly Gly Gly Ser Gly Gly Gly Gly Ser Leu Glu
115 120 125

Met Ala Gln Val Gln Leu Val Gln Ser Gly Ala Glu Val Lys Lys Pro
130 135 140

Gly Ser Ser Val Lys Val Ser Cys Lys Ala Ser Gly Gly Thr Phe Ser
145 150 155 160

Ser Tyr Ala Ile Ser Trp Val Arg Gln Ala Pro Gly Gln Gly Leu Glu
165 170 175

Trp Met Gly Gly Ile Ile Pro Ile Phe Gly Thr Ala Asn Tyr Ala Gln
180 185 190

Lys Phe Gln Gly Arg Val Thr Ile Thr Ala Asp Glu Ser Thr Ser Thr
        195                 200                 205

Ala Tyr Met Glu Leu Ser Ser Leu Arg Ser Glu Asp Thr Ala Val Tyr
    210                 215                 220

Tyr Cys Ala Arg Ser Ser Tyr Trp Trp Thr Ser Asp Arg Trp Gly Gln
225                 230                 235                 240

Gly Thr Leu Val Thr Val Ser Ser Thr Ser Gly Gln Ala Gly Gln His
                245                 250                 255

His His His His His Gly Ala Tyr Pro Tyr Asp Val Pro Asp Tyr Ala
            260                 265                 270

Ser

<210> SEQ ID NO 311
<211> LENGTH: 834
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 311
cagtctgtcg tgacgcagcc gccctcagtg tctggggccc cagggcaggg ggtcaccatc     60
ccctgcactg ggagcagctc caacatcggg gcaggttatg atgtacactg gtaccagcag    120
cttccaggga cagcccccaa actcctcatc tatggtaaca acaatcggcc ctcaggggtc    180
cctgaccgct tctctggctc caggtctggc tcctcagcct ccctggccat cactgggctc    240
caggctgagg atgaggctga ttattactgc cagtcctatg acagcagcct gagtgatgtg    300
gtattcggcg gagggaccaa gctgaccgtc ctaggttcta gaggtggtgg tggtagcggc    360
ggcggcggct ctggtggtgg tggatccctc gagatggccg aggtgcagct ggtgcagtct    420
ggagcagagg tgaaaaagcc gggggagtct ctgaagatct cctgtaaggg ttctggatac    480
aactttgcca gcgagtggat cggatgggtc cgccagatgc ccgggaaagg cctggagtgg    540
atgggactga tctatcctgc tgaatctgaa atcacataca gcccgtcctt ccaaggccag    600
gtcaccattt cagtcgacaa gtccatcagc accgcctacc tgcagtggag cagcctgaag    660
gcctcggaca ccgccatgta ttactgtgcg cgcgcttggg acgctaacta catctacatg    720
gatatctggg gtcaaggtac tctggtgacc gtctcctcaa ctagtggcca ggccggccag    780
caccatcacc atcaccatgg cgcatacccg tacgacgttc cggactacgc ttct          834

<210> SEQ ID NO 312
<211> LENGTH: 843
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 312
cagtctgtgt tgactcagcc accctcggtg tctgaagccc ccaggcagag ggtcaccatc     60
tcctgttctg gaagcagctc caacatcgga aataatgctg taaactggta ccagcagctc    120
ccaggaaagg ctcccaaact cctcatctat tatgatgatc tgctgccctc aggggtctct    180
gaccgattct ctggctccaa gtctggcacc tcagcctccc tggccatcag tgggctccag    240
tctgaggatg aggctgatta ttactgtgca gcatgggatg acagcctgaa tggtcctgtc    300
ttcggaactg ggaccaaggt caccgtccta ggttctagag gtggtggtgg tagcggcggc    360

-continued

```
ggcggctctg gtggtggtgg atccctcgag atggccgagg tgcagctggt gcagtctgga    420

gctgaggtga agaagcctgg ggcctcagtg aaggtctcct gcaaggcttc tggttacaac    480

tttaccagtt atggtatcag ctgggtgcga caggcccctg gacaagggct tgagtggatg    540

ggatggatca gcgcttacaa tggtaacaca aactatgcac agaagctcca gggcagagtc    600

accatgacca cagacacatc cacgagcaca gcctacatgg agttgaggag cctgagatct    660

gacgacacgg ccgtgtatta ctgtgcgaga gactgggatt acgatttttt gactgggtgg    720

gacggtatgg acgtctgggg ccaagggacc acggtcaccg tctcctcaac tagtggccag    780

gccggccagc accatcacca tcaccatggc gcatacccgt acgacgttcc ggactacgct    840

tct                                                                  843
```

```
<210> SEQ ID NO 313
<211> LENGTH: 281
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 313

Gln Ser Val Leu Thr Gln Pro Pro Ser Val Ser Glu Ala Pro Arg Gln
1               5                   10                  15

Arg Val Thr Ile Ser Cys Ser Gly Ser Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Tyr Asp Asp Leu Leu Pro Ser Gly Val Ser Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Thr Gly Thr Lys Val Thr Val Leu Gly Ser
            100                 105                 110

Arg Gly Gly Gly Gly Ser Gly Gly Gly Gly Ser Gly Gly Gly Gly Ser
        115                 120                 125

Leu Glu Met Ala Glu Val Gln Leu Val Gln Ser Gly Ala Glu Val Lys
    130                 135                 140

Lys Pro Gly Ala Ser Val Lys Val Ser Cys Lys Ala Ser Gly Tyr Asn
145                 150                 155                 160

Phe Thr Ser Tyr Gly Ile Ser Trp Val Arg Gln Ala Pro Gly Gln Gly
                165                 170                 175

Leu Glu Trp Met Gly Trp Ile Ser Ala Tyr Asn Gly Asn Thr Asn Tyr
            180                 185                 190

Ala Gln Lys Leu Gln Gly Arg Val Thr Met Thr Thr Asp Thr Ser Thr
        195                 200                 205

Ser Thr Ala Tyr Met Glu Leu Arg Ser Leu Arg Ser Asp Asp Thr Ala
    210                 215                 220

Val Tyr Tyr Cys Ala Arg Asp Trp Asp Tyr Asp Phe Leu Thr Gly Trp
225                 230                 235                 240

Asp Gly Met Asp Val Trp Gly Gln Gly Thr Thr Val Thr Val Ser Ser
                245                 250                 255

Thr Ser Gly Gln Ala Gly Gln His His His His His His Gly Ala Tyr
            260                 265                 270
```

Pro Tyr Asp Val Pro Asp Tyr Ala Ser
        275                 280

<210> SEQ ID NO 314
<211> LENGTH: 819
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 314
tcctatgagc tgactcagcc accctcagtg tcagtggccc caggaaagac ggccaggatt 60
acctgtgggg gaaacaacat tggaagtaaa agtgtgcact ggtaccagca gaagccaggc 120
caggcccctg tgctggtcat ctattatgat agcgaccggc cctcagggat ccctgagcga 180
ttctctggct ccaactctgg gaacacggcc accctgacca tcagcagggt cgaagccggg 240
gatgaggccg actattactg tcaggtgtgg gatagtagta gtgatcattg ggtgttcggc 300
ggagggacca agctgaccgt cctaggttct agaggtggtg gtggtagcgg cggcggcggc 360
tctggtggtg gtggatccct cgagatggcc caggtgcagc tggtgcaatc tgggggaggc 420
ttggtccagc ctggggggtc cctgaaactc tcctgtgcag cctctgggtt cgccttcagc 480
ggctcttctc tgcactgggt ccgccaggct tccgggaaag ggctggagtg ggttggccgt 540
attacaagca aagcttacaa ttacgcgaca ctatatgctg cgtcggtgaa aggcaggttc 600
accatctcca gagatgattc aaagaacacg gcatatcttc agatgaacag cctgcaaacc 660
gaggacacgg ccgtgtatta ctgtacccag actggggact catcagccta ctggggccag 720
ggaaccctgg tcaccgtctc ctcaactagt ggccaggccg gccagcacca tcaccatcac 780
catggcgcat acccgtacga cgttccggac tacgcttct 819

<210> SEQ ID NO 315
<211> LENGTH: 816
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 315
tcctatgagc tgactcagcc accctcagtg tcagtggccc caggaaagac ggccaggatt 60
acctgtgggg gaaacaacat tggaagtaaa agtgtgcact ggtaccagca gaagccaggc 120
caggcccctg tgctggtcat ctattatgat agcgaccggc cctcagggat ccctgagcga 180
ttctctggct ccaactctgg gaacacggcc accctgacca tcagcagggt cgaagccggg 240
gatgaggccg actattactg tcaggtgtgg gatagtagta gtgatcatcg agtgttcggc 300
ggagggacca aggtcaccgt cctaggttct agaggtggtg gtggtagcgg cggcggcggc 360
tctggtggtg gtggatccct cgagatggcc gaggtgcagc tggtggagtc tgggggaggc 420
ttggtccagc ctggggggtc cctgagactc tcctgtgcag cctctggatt cacttttagt 480
agttattgga tgaattgggt ccgccaggct ccagggaagg ggctggagtg ggtggccaac 540
ataaagcaag atggaagtga gaaaaactat gtggactctg tgaagggccg attcaccatc 600
tccagagaca acgccaagaa ttcactgtat ctgcaaatga atagcctgag aggcgaggac 660
acggccgtat attactgtgc gcgctacggt ggtggtccgt acgattcttg gggtcaaggt 720
actctggtga ccgtctcctc aactagtggc caggccggcc agcaccatca ccatcaccat 780
ggcgcatacc cgtacgacgt tccggactac gcttct 816

<210> SEQ ID NO 316
<211> LENGTH: 822
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 316
ctgcctgtgc tgactcagcc accctcagtg tcagtggccc caggaaagac ggccaggatt 60
acctgtgggg gaaacaacat tggaagtaaa agtgtgcact ggtaccagca gaagccaggc 120
caggcccctg tgctggtcat ctattatgat agcgaccggc cctcagggat ccctgagcga 180
ttctctggct ccaactctgg gaacacggcc accctgacca tcagcagggt cgaagccggg 240
gatgaggccg actattactg tcaggtgtgg gatagtagta gtgcctatgt cttcggaact 300
gggaccaagg tcaccgtcct aggttctaga ggtggtggtg gtagcggcgg cggcggctct 360
ggtggtggtg gatccctcga gatggcccag gtacagctgc agcagtcagg tccaggactg 420
gtgaagccct cgcagaccct ctcactcacc tgtgccatct ccggggacag tgtctctagc 480
aacagtgctg cttggaactg gatcaggcag tccccatcga gaggccttga gtggctggga 540
aggacatact acaggtccaa gtggtataat gattatgcag tatctgtgaa aagtcgaata 600
accatcaacc cagacacatc caagaaccag ttctccctgc agctgaactc tgtgactccc 660
gaggacacgg ctgtgtatta ctgtgcgcgc tactactcta cttctctgga ttcttggggt 720
caaggtactc tggtgaccgt ctcctcaact agtggccagg ccggccagca ccatcaccat 780
caccatggcg catacccgta cgacgttccg gactacgctt ct 822

<210> SEQ ID NO 317
<211> LENGTH: 274
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 317

Leu Pro Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Ala Tyr
                85                  90                  95

Val Phe Gly Thr Gly Thr Lys Val Thr Val Leu Gly Ser Arg Gly Gly
            100                 105                 110

Gly Gly Ser Gly Gly Gly Gly Ser Gly Gly Gly Gly Ser Leu Glu Met
        115                 120                 125

Ala Gln Val Gln Leu Gln Gln Ser Gly Pro Gly Leu Val Lys Pro Ser
    130                 135                 140

Gln Thr Leu Ser Leu Thr Cys Ala Ile Ser Gly Asp Ser Val Ser Ser
145 150 155 160

Asn Ser Ala Ala Trp Asn Trp Ile Arg Gln Ser Pro Ser Arg Gly Leu
165 170 175

Glu Trp Leu Gly Arg Thr Tyr Tyr Arg Ser Lys Trp Tyr Asn Asp Tyr
180 185 190

Ala Val Ser Val Lys Ser Arg Ile Thr Ile Asn Pro Asp Thr Ser Lys
195 200 205

Asn Gln Phe Ser Leu Gln Leu Asn Ser Val Thr Pro Glu Asp Thr Ala
210 215 220

Val Tyr Tyr Cys Ala Arg Tyr Tyr Ser Thr Ser Leu Asp Ser Trp Gly
225 230 235 240

Gln Gly Thr Leu Val Thr Val Ser Ser Thr Ser Gly Gln Ala Gly Gln
245 250 255

His His His His His His Gly Ala Tyr Pro Tyr Asp Val Pro Asp Tyr
260 265 270

Ala Ser

<210> SEQ ID NO 318
<211> LENGTH: 828
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 318
tcctatgtgc tgactcagcc accctcagtg tcagtggccc cgggagagac ggccagtatt 60
acctgtgggg ccaacaacat tggaagtgag agtgtgcact ggtatcagca gaagtcaggc 120
caggcccctg tgctggtcat ctattatgat agcgaccggc cctcagggat ccctgagcga 180
ttctctgggt ccaactctga caacacggcc accctgacca tcagcagggt cgaagccgga 240
gatgaggccg actattactg tcaggtttgg gatcatatta atgatcatta tgtcttcgga 300
agtgggacca aggtcaccgt cctaggttct agaggtggtg gtggtagcgg cggcggcggc 360
tctggtggtg gtggatccct cgagatggcc gaggtgcagc tggtggagtc tgggggaggc 420
ttggcacagc ctggggggtc cctgagactc tcctgtgcag cctccggatt ctcttttagc 480
aactatgcca tgagctgggt ccgccaggct ccagggacgg ggctggagtg ggtcgcaggt 540
attagcggta gaggtgggag tatacattac gcagactccg tgaagggtcg gttcaccatc 600
tccagagaca attcccagag cacggtcttt ctgcaaatga acaacctggg agccgaggac 660
acggccatat actactgtgc gaaatcgagc gaggactatt acttctatca catggacgcc 720
tggggcattg ggaccacggt caccgtctcc tcaactagtg gccaggccgg ccagcaccat 780
caccatcacc atggcgcata cccgtacgac gttccggact acgcttct 828

<210> SEQ ID NO 319
<211> LENGTH: 822
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 319
tcctatgtgc tgactcagcc accctcagtg tcagtggccc caggaaagac ggccaggatt 60

```
acctgtgggg gaaacaacat tggaagtaaa agtgtgcact ggtaccagca gaagccaggc    120

caggcccctg tgctggtcat ctattatgat agcgaccggc cctcagggat ccctgagcga    180

ttctctggct ccaactctgg gaacacggcc accctgacca tcagcagggt cgaagccggg    240

gatgaggccg actattactg tcaggtgtgg gatagtagta gtgatcgtgt ggtattcggc    300

ggagggacca agctgaccgt cctaggttct agaggtggtg gtggtagcgg cggcggcggc    360

tctggtggtg gtggatccct cgagatggcc caggtacagc tgcagcagtc aggtccagga    420

ctggtgaagc cctcgcagac cctctcactc acctgtgcca tctccgggga cagtatctct    480

agcaaaagtg ctgcttggaa ctggatcagg cagtccccat cgagaggcct agagtggctg    540

ggaaggacat actacaggtc caagtggtat tatgaatatg caccatctgt gagaagtcga    600

ataaccatca accgagacac atccaagaac cagttctccc tgcaacttaa ctctgtgact    660

cccgaggaca cggctgtata ttattgtgca agatccactg ggacctttga ctactggggc    720

cagggaaccc tggtcaccgt ctcctcaact agtggccagg ccggccagca ccatcaccat    780

caccatggcg catacccgta cgacgttccg gactacgctt ct                       822
```

```
<210> SEQ ID NO 320
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Asn Ser Asn Ile Gly Ala Asp Phe Asp
1               5


<210> SEQ ID NO 321
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Gln Ser Tyr Asp Ser Ser Leu Ser Gly Val Val
1               5                   10


<210> SEQ ID NO 322
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Gln Ser Tyr Asp Ile Ser Leu Asn Gly Tyr Val
1               5                   10


<210> SEQ ID NO 323
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323
```

Gly Tyr Asn Phe Thr Ser Tyr Gly
1 5

<210> SEQ ID NO 324
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 324

Val Ser Ser Asn Ser Ala Ala Trp Asn
1 5

<210> SEQ ID NO 325
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 325

Ile Ser Ala Tyr Asn Gly Asn Thr
1 5

<210> SEQ ID NO 326
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 326

Tyr Arg Ser Lys Trp Tyr Asn
1 5

<210> SEQ ID NO 327
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 327

Ala Arg Ser Ser Tyr Trp Trp Thr Ser Asp Arg
1 5 10

<210> SEQ ID NO 328
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 328

Ala Arg Asp Trp Asp Tyr Asp Phe Leu Thr Gly Trp Asp Gly Met Asp
1 5 10 15

Val

<210> SEQ ID NO 329
<211> LENGTH: 10
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 329

Ala Arg Tyr Tyr Ser Thr Ser Leu Asp Ser
1 5 10

<210> SEQ ID NO 330
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 330

Ser Ser Asn Ile Gly Asn Asn Ala
1 5

<210> SEQ ID NO 331
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 331

Tyr Asp Asp
1

<210> SEQ ID NO 332
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 332

Gln Val Trp Asp Ser Ser Ser Asp His Pro Val
1 5 10

<210> SEQ ID NO 333
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 333

Ala Ala Trp Asp Asp Ser Leu Asn Gly Pro Val
1 5 10

<210> SEQ ID NO 334
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 334

Gln Val Trp Asp Ser Ser Ser Ala Tyr Val
1 5 10

<210> SEQ ID NO 335
<211> LENGTH: 822
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 335

```
cagtctgtcg tgacgcagcc gccctcagtg tctggggccc cagggcagag ggtcaccatc     60

tcctgcactg ggagcagctc caacatcggg gcaggttttg atgtacactg gtaccagcag    120

cttccaggaa cagcccccaa actcctcatc tatggtaaca gcaatcggcc ctcaggggtc    180

cctgaccgat tctctggctc caagtctgcc acctcagcct ccctggccat cactgggctc    240

caggctgagg atgaggctga ttattactgc cagtcctatg acagcagcct gagtggtgtg    300

gtattcggcg gagggaccaa gctgaccgtc ctaggttcta gaggtggtgg tggtagcggc    360

ggcggcggct ctggtggtgg tggatccctc gagatggccc aggtgcagct ggtgcagtct    420

ggggctgagg tgaagaagcc tgggtcctcg gtgaaggtct cctgcaagac ttctggaggc    480

accttcagca gctatgctat cagctgggtg cgacaggccc ctggacaagg gcttgagtgg    540

atgggaggga tcatccctat ctttggtaca gcaaactacg cacagaggtt ccagggcaga    600

gtcacgatta ccgcggacga atccacaaac acagtctaca tggagctgag cagcctgaga    660

tctgaggaca cggccgtgta ttactgtgcg cgcgaatctt ggtaccttga tgaatggggt    720

caaggtactc tggtgaccgt ctcctcaact agtggccagg ccggccagca ccatcaccat    780

caccatggcg catacccgta cgacgttccg gactacgctt ct                       822
```

<210> SEQ ID NO 336
<211> LENGTH: 274
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 336

```
Gln Ser Val Val Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Phe Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Ala Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Val Val Phe Gly Gly Gly Thr Lys Leu Thr Val Leu Gly
            100                 105                 110

Ser Arg Gly Gly Gly Gly Ser Gly Gly Gly Gly Ser Gly Gly Gly Gly
        115                 120                 125

Ser Leu Glu Met Ala Gln Val Gln Leu Val Gln Ser Gly Ala Glu Val
    130                 135                 140

Lys Lys Pro Gly Ser Ser Val Lys Val Ser Cys Lys Thr Ser Gly Gly
```

```
                145                 150                 155                 160
            Thr Phe Ser Ser Tyr Ala Ile Ser Trp Val Arg Gln Ala Pro Gly Gln
                            165                 170                 175

            Gly Leu Glu Trp Met Gly Gly Ile Ile Pro Ile Phe Gly Thr Ala Asn
                        180                 185                 190

            Tyr Ala Gln Arg Phe Gln Gly Arg Val Thr Ile Thr Ala Asp Glu Ser
                    195                 200                 205

            Thr Asn Thr Val Tyr Met Glu Leu Ser Ser Leu Arg Ser Glu Asp Thr
                210                 215                 220

            Ala Val Tyr Tyr Cys Ala Arg Glu Ser Trp Tyr Leu Asp Glu Trp Gly
            225                 230                 235                 240

            Gln Gly Thr Leu Val Thr Val Ser Ser Thr Ser Gly Gln Ala Gly Gln
                            245                 250                 255

            His His His His His His Gly Ala Tyr Pro Tyr Asp Val Pro Asp Tyr
                        260                 265                 270

            Ala Ser

            <210> SEQ ID NO 337
            <211> LENGTH: 822
            <212> TYPE: DNA
            <213> ORGANISM: Artificial Sequence
            <220> FEATURE:
            <223> OTHER INFORMATION: Description of Artificial Sequence: Synthetic
                  polynucleotide

            <400> SEQUENCE: 337

            cagtctgtgt tgacgcagcc gccctcagtg tctggggccc cagggcagag ggtcaccatc     60

            tcctgcactg ggagcaactc caacatcggg gcagattttg atgtacactg gtaccagcag    120

            cttccaggaa cagcccccaa gctcctcatc tatggtaaca acaatcggcc ctcaggggtc    180

            cctgaccgat tttctggctc caagtctgac acctcagcct ccctggccat cactgggctc    240

            caggctgagg atgaggctga ttactactgc cagtcctatg acatcagcct gaatggttat    300

            gtcttcggaa ctgggaccaa ggtcaccgtc ctaggttcta gaggtggtgg tggtagcggc    360

            ggcggcggct ctggtggtgg tggatccctc gagatggccc aggtgcagct acagcagtgg    420

            ggcgcaggac tgttgaagcc ttcggagacc ctgtccctca cctgcgctgt ctctggtggg    480

            tccttcagtg attactactg gagctggatc cgccagcccc cagggaaggg gctggagtgg    540

            attggggaaa tcactcatac tggaagcacc aactacaacc cgtccctcaa gagtcgagtc    600

            accatatcag tagacacgtc caagaaccat ttctccctga atctgacctc tgtgaccgcc    660

            gcggacacgg ccgtgtatta ctgtgcgcgc tctaacggtt tctactacga tacttggggt    720

            caaggtactc tggtgaccgt ctcctcaact agtggccagg ccggccagca ccatcaccat    780

            caccatggcg catacccgta cgacgttccg gactacgctt ct                       822

            <210> SEQ ID NO 338
            <211> LENGTH: 274
            <212> TYPE: PRT
            <213> ORGANISM: Artificial Sequence
            <220> FEATURE:
            <223> OTHER INFORMATION: Description of Artificial Sequence: Synthetic
                  polypeptide

            <400> SEQUENCE: 338

            Gln Ser Val Leu Thr Gln Pro Pro Ser Val Ser Gly Ala Pro Gly Gln
            1               5                   10                  15

            Arg Val Thr Ile Ser Cys Thr Gly Ser Asn Ser Asn Ile Gly Ala Asp
```

20 25 30

Phe Asp Val His Trp Tyr Gln Gln Leu Pro Gly Thr Ala Pro Lys Leu
35 40 45

Leu Ile Tyr Gly Asn Asn Asn Arg Pro Ser Gly Val Pro Asp Arg Phe
50 55 60

Ser Gly Ser Lys Ser Asp Thr Ser Ala Ser Leu Ala Ile Thr Gly Leu
65 70 75 80

Gln Ala Glu Asp Glu Ala Asp Tyr Tyr Cys Gln Ser Tyr Asp Ile Ser
85 90 95

Leu Asn Gly Tyr Val Phe Gly Thr Gly Thr Lys Val Thr Val Leu Gly
100 105 110

Ser Arg Gly Gly Gly Gly Ser Gly Gly Gly Gly Ser Gly Gly Gly Gly
115 120 125

Ser Leu Glu Met Ala Gln Val Gln Leu Gln Gln Trp Gly Ala Gly Leu
130 135 140

Leu Lys Pro Ser Glu Thr Leu Ser Leu Thr Cys Ala Val Ser Gly Gly
145 150 155 160

Ser Phe Ser Asp Tyr Tyr Trp Ser Trp Ile Arg Gln Pro Pro Gly Lys
165 170 175

Gly Leu Glu Trp Ile Gly Glu Ile Thr His Thr Gly Ser Thr Asn Tyr
180 185 190

Asn Pro Ser Leu Lys Ser Arg Val Thr Ile Ser Val Asp Thr Ser Lys
195 200 205

Asn His Phe Ser Leu Asn Leu Thr Ser Val Thr Ala Ala Asp Thr Ala
210 215 220

Val Tyr Tyr Cys Ala Arg Ser Asn Gly Phe Tyr Tyr Asp Thr Trp Gly
225 230 235 240

Gln Gly Thr Leu Val Thr Val Ser Ser Thr Ser Gly Gln Ala Gly Gln
245 250 255

His His His His His His Gly Ala Tyr Pro Tyr Asp Val Pro Asp Tyr
260 265 270

Ala Ser

<210> SEQ ID NO 339
<211> LENGTH: 819
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 339
cagtctgtgt tgactcagcc accctcagtg tcagtggccc caggaaagac ggccaagatt 60
acctgtggcg gagacaacat tggaagtaaa actgtgcact ggtaccagca gaagccaggc 120
caggcccctg cacttctcat ctattatgat agtgaccggc cctcagggat ccctgagcga 180
ttctctggct ccaattctgg aaatacggcc accctgagca tcagcagggt cgaggccggg 240
gatgaggccg gctatttctg tcaggtgtgg gatgggagta gtgatcatgt gatcttcggc 300
ggagggacca agctgaccgt cctaggttct agaggtggtg gtggtagcgg cggcggcggc 360
tctggtggtg gtggatccct cgagatggcc cagatgcagc tggtgcaatc tgggggaggc 420
gtggtccagc ctgggaggtc cctgagactc tcctgtgcag cctctggatt caccttcagt 480
agctatgcta tgcactgggt ccgccaggct ccaggcaagg ggctggagtg ggtggcagtt 540
atatcatatg atggaagtaa taaatactac gcagactccg tgaagggccg attcaccatc 600
tccagagaca attccaagaa cacgctgtat ctgcaaatga acagcctgag agctgaggac 660
acggctgtgt attactgtgc gagagatcgg catgattacg ttatggacgt ctggggcaaa 720
gggaccacgg tcaccgtctc ctcaactagt ggccaggccg gccagcacca tcaccatcac 780
catggcgcat acccgtacga cgttccggac tacgcttct 819

<210> SEQ ID NO 340
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 340

Gly Gly Ser Phe Ser Asp Tyr Tyr
1 5

<210> SEQ ID NO 341
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 341

Ile Thr His Thr Gly Ser Thr
1 5

<210> SEQ ID NO 342
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 342

Ala Arg Glu Ser Trp Tyr Leu Asp Glu
1 5

<210> SEQ ID NO 343
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 343

Ala Arg Ser Asn Gly Phe Tyr Tyr Asp Thr
1 5 10

<210> SEQ ID NO 344
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 344

Ser Ser Asn Ile Gly Ala Gly Phe Asp
1 5